US007556938B1

(12) United States Patent  
Rhodes et al.

(10) Patent No.: US 7,556,938 B1  
(45) Date of Patent: Jul. 7, 2009

(54) NUCLEIC ACIDS ENCODING POTASSIUM CHANNEL INTERACTORS

(75) Inventors: Kenneth Rhodes, Neshanic Station, NJ (US); Maria Betty, Mt. Laurel, NJ (US); Huai-Ping Ling, Princeton Junction, NJ (US); Wenqian An, Wayland, MA (US)

(73) Assignees: Millennium Pharmaceuticals, Inc., Cambridge, MA (US); Wyeth, Madison, NJ (US)

( * ) Notice: Subject to any disclaimer, the term of this patent is extended or adjusted under 35 U.S.C. 154(b) by 689 days.

(21) Appl. No.: 09/703,094

(22) Filed: Oct. 31, 2000

Related U.S. Application Data

(60) Continuation of application No. 09/670,756, filed on Sep. 27, 2000, now Pat. No. 7,078,481, which is a continuation-in-part of application No. 09/399,913, filed on Sep. 21, 1999, now Pat. No. 6,361,971, which is a continuation-in-part of application No. 09/350,614, filed on Jul. 9, 1999, now Pat. No. 6,689,581, which is a continuation-in-part of application No. 09/298,731, filed on Apr. 23, 1999, now Pat. No. 6,369,197, application No. 09/703,094, which is a continuation-in-part of application No. 09/350,874, filed on Jul. 9, 1999, now abandoned, which is a division of application No. 09/298,731, filed on Apr. 23, 1999, now Pat. No. 6,369,197.

(60) Provisional application No. 60/110,277, filed on Nov. 30, 1998, provisional application No. 60/110,033, filed on Nov. 25, 1998, provisional application No. 60/109,333, filed on Nov. 20, 1998.

(51) Int. Cl.  
*C12N 15/12* (2006.01)  
*C12N 15/62* (2006.01)  
*C12N 15/63* (2006.01)  
*C12N 5/10* (2006.01)

(52) U.S. Cl. ............... 435/69.1; 435/320.1; 435/252.3; 435/254.2; 536/23.4; 536/23.5

(58) Field of Classification Search ............... 435/69.1, 435/6, 320.1, 325, 7.8; 536/23.5  
See application file for complete search history.

(56) References Cited

U.S. PATENT DOCUMENTS 5,786,451 A * 7/1998 Thirkill ........................ 530/350  
6,117,989 A * 9/2000 Bandman et al. ........... 536/23.1

FOREIGN PATENT DOCUMENTS

| WO | WO 97/31112 | 8/1997 |
| WO | WO 98/16185 | 4/1998 |
| WO | WO 99/49038 | 9/1999 |
| WO | WO 00/31133 A2 | 6/2000 |
| WO | WO 00/70049 A2 | 11/2000 |
| WO | WO 00/70049 A3 | 11/2000 |
| WO | WO 01/53312 A1 | 7/2001 |

OTHER PUBLICATIONS

Buxbaum JD et al. Calsenilin: a calcium-binding protein that interacts with the presenilins and regulates the levels of a presenil fragment.Nat Med. Oct. 1998;4(10):1177-81.*  
Stratagene catalog (1988, p. 39).*  
Voet et al. Biochemistry. 1990. John Wiley & Sons, pp. 126-128 and 228-234.*  
Eck & Wilson in Goodman & Gilman's The Pharmacological Basis of Therapeutics. Ninth Edition. McGraw Hill, New York, 199 pages 77-101.*  
Mickle JE et al. Genotype-phenotype relationships in cystic fibrosis. Med Clin North Am. May 2000;84(3):597-607.*  
Marshall "Gene Therapy's Growing Pains". Science, vol. 269 (1995), pp. 1050-1055.*  
Verma, I. M., et al. "Gene therapy-promises, problems, and prospects". Nature, vol. 389 (Sep. 1997), pp. 239-242.*  
Stratagene 1991 catalog, p. 66.*  
Alberts et al., 1994. Molecular Biology of the Cell, pp. 582-585.*  
Adachi, Y. et al., "Identification and characterization of SET, a nuclear phosphoprotein encoded by the translocation break point in acute undifferentiated leukemia," *J. Biol. Chem.*, 269:2258-2262 (1994).  
Bilbe,G., et al., "Restin: a novel intermediate filament-associated protein highly expressed in the Reed-Sternberg cells of Hodgkin's disease," *EMBO J.* 11 (6):2103-2113 (1992).  
Bonaldo et al., GenBank Accession No. AA859724 [online], "Calcium-binding protein NCS-1" (Mar. 14, 1998).  
Buxbaum, Joseph D. , et al., "Calsenilin: A calcium-binding protein that interacts with the presenilins and regulates the levels of a presenilin fragment", *Nature Medicine*, vol. 4, No. 10, pp. 1177-1181 (1998).  
Carrion, Angel M., et al., "DREAM is a $CA^{2+}$-regulated transcriptional repressor", *Nature*, vol. 398, pp. 80-84 (1999).  
Castagna, Michela et al. "Molecular Characteristics of Mammalian and Insect Amino Acid Transporters: Implications for Amino Acid Homeostatis" *The Journal of Experimental Biology* 200:269-286 (1997).  
Cunningham, E. et al., "Phosphatidylinositol transfer protein dictates the rate of inositol triphosphate production by promoting the synthesis of PIP2," *Curr Biol.* 5(7):775-83 (1995).  
DeCastro, E. et al., "Regulation of rhodopsin phosphorylation by a family of neuronal calcium sensors" *Biochem Biophys Res Commun.*; 216(1):133-40 1995).

(Continued)

*Primary Examiner*—Daniel E. Kolker  
(74) *Attorney, Agent, or Firm*—Drinker Biddle & Reath LLP

(57) ABSTRACT

The invention provides isolated nucleic acids molecules, designated PCIP nucleic acid molecules, which encode proteins that bind potassium channels and modulate potassium channel mediated activities. The invention also provides antisense nucleic acid molecules, recombinant expression vectors containing PCIP nucleic acid molecules, host cells into which the expression vectors have been introduced, and nonhuman transgenic animals in which a PCIP gene has been introduced or disrupted. The invention still further provides isolated PCIP proteins, fusion proteins, antigenic peptides and anti-PCIP antibodies. Diagnostic methods utilizing compositions of the invention are also provided.

18 Claims, 76 Drawing Sheets

OTHER PUBLICATIONS

Dickeson, S.K., et al., "Isolation and sequence of cDNA clones encoding rat phosphatidylinositol transfer protein," *J. Biol. Chem.* 264 (28):16557-16564 (1989).

Dixon, J., "Role of the Kv4.3 K+ channel in ventricular muscle. A molecular correlate for the transient outward current" *Circ Res.* ;79(4):659-68. (1996).

Endo, T.A. et al., "A new protein containing an SH2 domain that inhibits JAK kinase," *Nature.* 387(6636):921-4 (1997).

Fukuda, J. et al., "Breakdown of cytoskeletal filaments selectively reduces Na and Ca spikes in cultured mammal neurones," *Nature.* 294(5836):82-5 (1981).

Funkhouser, J.D.; Amino-terminal sequence of a phospholipid transfer protein from rat,lung, Biochem. Biophys. Res. Commun. 145:1310-1314 (1987).

Hoffman, D.A. et al., "K+ channel regulation of signal propagation in dendrites of hippocampal pyramidal neurons," *Nature.* 387(6636):869-75 (1997).

Hoffman, D.A. et al., "Downregulation of transient K+ channels in dendrites of hippocampal CA1 pyramidal neurons by activation of PKA and PKC," *J Neurosci.* 18(10):3521-8 (1998).

Honore, E. et al., "Different types of K+ channel current are generated by different levels of a single mRNA," *EMBO J.* 11(7):2465-71 (1992).

Hoppe-Seyler, "Purification and characterization of to putative HLA class II associated proteins: PHAPI and PHAPII," *Biol. Chem.*, 375:113-126 (1994).

Jan, L.Y. et al., "How might the diversity of potassium channels be generated?" *Trends Neurosci.* 13(10):415-9 (1990).

Johnson, B.D. et al., "A cytoskeletal mechanism for Ca2+ channel metabolic dependence and inactivation by intracellular Ca2+," *Neuron.* 10(5):797-804 (1993).

Kaab, S. et al., "Molecular basis of transient outward potassium current downregulation in human heart failure: a decrease in Kv4.3 mRNA correlates with a reduction in current density" *Circulation.* 98(14):1383-93 (1998).

Kim, E. et al. "Clustering of Shaker-type K+ channels by interaction with a family of membrane-associated guanylate kinases" *Nature* 378:85-88 (Nov. 2, 1995).

Levin, G. et al., "Phosphorylation of a K+ channel alpha subunit modulates the inactivation conferred by a beta subunit. Involvement of cytoskeleton," *J Biol Chem.* 271(46):29321-8 (1996).

Li, M., et al., "The myeloid leukemia-associated protein SET is a potent inhibitor of protein phosphatase 2A," *J. Biol. Chem.* 271 (19):11059-11062 (1996).

Lombardi, Stephen J. et al. "Structure-Activity Relationships of the $K_v\beta1$ Inactivation Domain and Its Putative Receptor Probed Using Peptide Analogs of Voltage-gated Potassium Channel α- and β-Supunits" *The Journal of Biological Chemistry* 273(46):30092-30096 (Nov. 13, 1998).

Masiakowski, P. et al., "Nerve growth factor induces the genes for two proteins related to a family of calcium-binding proteins in PC12 cells," *Proc Natl Acad Sci U S A.* 85(4):1277-81 (1988).

Nagase, T. et al., "Prediction of the coding sequences of unidentified human genes. XI. The complete sequences of 100 new cDNA clones from brain which code for large proteins in vitro," *DNA Res.* 5 (5):277-286 (1998).

Nagata, K. et al., "Replication factor encoded by a putative oncogene, set, associated with myeloid leukemogenesis," *Proc. Natl. Acad. Sci. U.S.A.*, 92:4279-4283 (1995).

Naka, T. et al., "Structure and function of a new STAT-induced STAT inhibitor," *Nature.* 387(6636):924-9 (1997).

Nakamura, T.Y. et al., "Modulation of Kv4 channels, key components of rat ventricular transient outward K+ current, by PKC," *Am J Physiol.* 273(4 Pt 2):H1775-86 (1997).

National Cancer Intsitute-Cancer Genome Aanatomy Project, GenBank Accession No. AI038858 [online], ". . . *Homo sapiens* cDNA clone IMAGE:1659605 3' similar to SW:VIS3_Rat P35333 Visinin-like Protein" (Jul. 1, 1998).

Nerbonne, J., "Regulation of voltage-gated K+ channel expression in the developing mammalian myocardium", *J Neurobiol.*;37(1):37-59. (1998)Review.

Panaretou, C. et al., "Characterization of p150, an adaptor protein for the human phosphatidylinositol (PtdIns) 3-kinase. Substrate presentation by phosphatidylinositol transfer protein to the p150.PtdIns 3-kinase complex," *J Biol Chem.* 272(4):2477-85 (1997).

Pierre, P., et al., "CLIP-170 links endocytic vesicles to microtubules," *Cell* 70 (6):887-900 (1992).

Pongs, O. et al., "Regulation of the activity of voltage-gated potassium channels by beta subunits" *Sem. Neurosci.* 7:137-146 (1995).

Prevarskaya, N.B. et al., "Role of tyrosine phosphorylation in potassium channel activation. Functional association with prolactin receptor and JAK2 tyrosine kinase," *J Biol Chem.* 270(41):24292-9 (1995).

Scannevin, R.H. and Trimmer, J.S. "Cytoplasmic Domains of Voltage-Sensitive K+ Channels Involved in Mediating Protein-Protein Interactions" *Biochemical and Biophysical Research Communications* 232:585-589 (1997).

Serodio, P. et al., "Cloning of a Novel Component of A-Type K+ Channels Operating at Subthreshold Potential with Unique Expression in Heart and Brian" *Journal of Neurophysiology*, vol. 75, No. 5, pp. 2174-2179 (1996).

Sheng, M. et al., "Subcellular segregation of two A-type K+ channel proteins in rat central neurons," *Neuron.* 9(2):271-84 (1992).

Sheng, M. and Kim, E. "Ion channel associated proteins" *Current Opinion in Neurobiology* 6:602-608 (1996).

Simon, H.U. et al., "Molecular characterization of hNRP, a cDNA encoding a human nucleosome-assembly-protein-I-related gene product involved in the induction of cell proliferation," *Biochem. J.*, 297:389-397 (1994).

Starr, R. et al., "A family of cytokine-inducible inhibitors of signaling," *Nature.* 387(6636):917-21 (1997).

Touchot, N. et al., "Four additional members of the ras gene superfamily isolated by an oligonucleotide strategy: molecular cloning of YPT-related cDNAs from a rat brain library," *Proc Natl Acad Sci U S A.* 84(23):8210-4 (1987).

Van Hille, B. et al., "Identification of two subunit A isoforms of the vacuolar H(+)-ATPase in human osteoclastoma," *J Biol Chem.* 268(10):7075-80 (1993).

Von Lindern, M. et al., "Can, a putative oncogene associated with myeloid leukemogenesis, may be activated by fusion of its 3' half to different genes: characterization of the set gene," *Mol Cell Biol.*, 12:3346-3355 (1992).

BLASTN Search in EST Database using the mouse p19 nucleic acid Sequence.

BLASTN Search in Nucleic Acid Database using the mouse p19 nucleic acid Sequence.

BLASTN Search using the human 1v protein sequence.

BLASTN Search in EST Database using the rat 1vl nucleic acid sequence.

BLASTN Search in Nucleic Acid Database using the rat 1vl nucleic acid sequence.

BLASTN Search in EST Database using the human 9ql nucleic acid sequence.

BLASTN Search in Nucleic Acid Database using the human 9ql nucleic acid sequence.

GenBank accession No. AB018264 for *Homo sapiens* mRNA for KIAA0721 protein, partial cds.

GenBank accession No. U51924 for Human phosphatase 2A inhibitor I2PP2A mRNA, complete cds.

GenBank accession No. P30622 for restin (cytoplasmic limker protein-170 alpha-2) (clip-170) (reed-Sternberg internediate filament associatedprotein).

GenBank accession No. P38606 for vacuolar ATP sunthase subunit A, ubiquitous isoform (V-atpase 69 KD subunit) (isoform VA68).

GenBank accession No. B46091 HS-1063-A1-C02-MR.abi CIT Human Genomic Sperm Library C *Homo sapiens* genomic clone Plate=CT 796 Col=3 Row=E, genomic survey sequence.

GenBank accession No. P05712 for ras-related protein RAB-2.

GenBank accession No. P16446 for phosphatidylinositol transfer protein alpha isoform (PTDINS transfer protein alpha) (PTDINSTP) (PI-TP-alpha).

GenBank accession No. M25758 for Rat phosphatidylinositol transfer protein mRNA, complete cds.

GenBank accession No. AA849706 for EST192473 Normalized rat muscle, *Bento Soares rattus* sp. cDNA clone RMUAH89 3' end, mRNA sequence.

GenBank accession No. AA757119 for ah53h07.s1 Soares_testis_NHT *Homo sapiens* cDNA clone 1309405 3', mRNA sequence.

GenBank accession No. AU035979 Sugano mouse brain mncb *Mus musculus* cDNA clone MNCb-7005, mRNA sequence.

An, W.F. et al. "Modulation of A-type potassium channels by a family of calcium sensors" *Nature* 403:553-556 (Feb. 3, 2000).

* cited by examiner

HUMAN IV DNA (CD:225-87)

GAATAGCCCCCTTTCACTTCTGAGTCCCTGCATGTGCGGGGCTGAAGAAGAAGCCAGAAGCCTCCTAGCCTCGCCTCCA
CGTTTGCTGAATACCAAGCTGCAGGCGAGCTGCCGGGCGCCGGGGCGCTTTTCTCCTCCAATTCAGAGTAGACAAACCACGGGGAT
TTCTTTCCAGGGTAGGGAGGGGCCGGGCCCGGGGTCCCAACTGCCACTCAAGTCTTCGCTGCCATGGGCCGTCATGG
GCACCTTCTCATCTCTGCAAACCAAAGGCGACCCTCGAAAGATAAGATTGAAGATGAGCTGGAGATGACCATGGTT
TGCCATCGGCCCGAGGGACTGGAGCAGCTCGAGGCCCAGAAGACCAACTTCACCAAGAGGAGCTGCAGGTCCTTATCGAGG
CTTCAAAAATGAGTGCCCCCAGTGGTGCTCAACGAGCACACATTCAAGACAGATCTATGCTCCAGTTTTCCCTCATGGAG
ATGCCAGCACGTATGCCGATTACCTTCGACACCACTAAGGTGGACATTTAATTGTATGACATCAACAAGGA
ACCGCTCTGTCGATTTTATTGAGAGGAACTGTCCACGAGAAACTAAGGTGGACATTTAATTGTATGACATCAACAAGGA
CGGATACATAAACAAAGAGGAGATGATGGACATTGGACGTCTCTTCCAGAAATACATAAGAATGATACATCTGTGC
TCAAAGAGACACTCCAAGGCAGCATGTGGACGTCTCTTCCAGAGGTCTCTCCAGCTGTTTCAAAATGTCATGTAACTGGT
GATGAATTTCTTGAATCATGTCAGGAGGACGACAGACATTGTACTAAACAACACCCTTAACACCCTGATCTGCCCTTGTCTGATTTTA
GACACTCAGCCATTC4GCTCTCAGAGACAAACACCTTTTACACTTTGGAAGAATTCTCTGCTGAGAGACAAGATGAAATTTGAGTTTGTTTG
CACACCAACTCTTGGGACAGAAACACCTTTTACACTTTGGAAGAATTCTCTGCTGAGAGACAAGATGAAATTTGAGTTTGTTTG
CATGTGCCTCAGTCTCTGATTGCCAATCTCCTCACACTGCTGCCCCAAGTCAGGCAGACCTTGGTGAATCTGGAAGCAGAAATCGGAAGTAGAAATATGC
GAAGCATGCTCATCTCGCCCACGTCCCTATGGAAGGTCCCTCTGCTTAAGCTTAAACTAGTGCACAAAATATGC
TGCTTACGTGCCCCCAGCCACTGCCTCCCAAACCAATGTGCCTGTTTCTCCTTGGTGGGAAGAATGAGAGTTATCAGAACA
CACACCATCTCTGATGGCCTCGATGACCAGATTGGGAGAGCCAGCACCTAACATATGTGGGATAGGACTGAATTATTAAGCATGACATT
ATTAGGATCTGTCATGACCAGATTGGGAGAGCCAGCACCTAACATATGTGGGATAGGACTGAATTATTAAGCATGACATT
GTCTGATGACCAAACTGCCCCG

HUMAN IV PROTEIN

MGAVMGTFSSLQTKQRRPSKDKIEDELEMTMVCHRPEGIEQLEAQTNFTKRELQVLYRGFKNECPSGVVNEDTFKQIYAQ

FFPHGDASTYAHYLFNAFDTTQTGSVKFEDFVTALSILLRGTVHEKLRWTFNLYDINKDGYINKEEMMDIVKAIYDMGK

YTYPVLKEDTPRQHVDVFFQKMDKNKDGIVTLDEFLESCQEDDNIMRSLQLFQNVM

FIG. 1

RAT 1vN (r1vN) DNA (CD: 339-1037)

GGCACACAACCCCTGGATTCTTCGGAGAATATGCCGTGAGGTGTTGCCAATTATTAGTTCTCTTGGCTAGCAGATGTTTA
GGGACTGGTtaaGCCTTTGGAGAAATTACCTTAGGAAAACGGGGAAATAAAAGCAAAGATTACCATGAATTGCAAGATTA
CCTAGCAATTGCAAGGtagGAGGAGAGAGGTGGAGGGCGGAGTAGACAGGAGGGAGGGAGAAAGtgaGAGGAAGCTAGGC
TGGTGGAAATAACCCTGCACTTGGAACAGCGGCAAAGAAGCGCGATTTTCCAGCTTtaaATGCCTGCCCGCGTTCTGCTT
GCCTACCCGGGAACGGAGATGTTGACCCAGGGCGAGTCTGAAGGGCTCCAGACCTTGGGGATAGTAGTGGTCCTGTGTTC
CTCTCTGAAACTACTGCACTACCTCGGGCTGATTGACTTGTCGGATGACAAGATCGAGGATGATCTGGAGATGACCATGG
TTTGCCATCGGCCTGAGGGACTGGAGCAGCTTGAGGCACAGACGAACTTCACCAAGAGAGAACTGCAAGTCCTTTACCGG
GGATTCAAAAACGAGTGCCCCAGTGGTGTGGTTAACGAAGAGACATTCAAGCAGATCTACGCTCAGTTTTTCCCTCATGG
AGATGCCAGCACATACGCACATTACCTCTTCAATGCCTTCGACACCACCCAGACAGGCTCTGTAAAGTTCGAGGACTTTG
TGACTGCTCTGTCGATTTTACTGAGAGGAACGGTCCATGAAAAACTGAGGTGGACGTTTAATTTGTACGACATCAATAAA
GACGGCTACATAAACAAAGAGGAGATGATGGACATAGTGAAAGCCATCTATGACATGATGGGGAAATACACCTATCCTGT
GCTCAAAGAGGACACTCCCAGGCAGCACGTGGACGTCTTCTTCCAGAAAATGGATAAAAATAAAGATGGCATTGTAACGT
TAGACGAATTTCTCGAGTCCTGTCAGGAGGATGACAACATCATGAGGTCTCTACAGCTGTTCCAAAATGTCATGTAACTG
AGGACACTGGCCATCCTGCTCTCAGAGACACTGACAAACACCTCAATGCCCTGATCTGCCCTTGTTCCAGTTTTACACAT
CAACTCTCGGGACAGAAATACCTTTTACACTTTGGAAGAATTCTCTGCTGAAGACTTTCTACAAAACCTGGCACCGAGTG
GCTCAGTCTCTGATTGCCAACTCTTCCTCCCTCCTCCTCTTGAGAGGGACGAGCTGAAATCCGAAGTTTGTTTTGGAAGC
ATGCCCATCTCTCCATGCTGCTGCTGCCCTGTGGAAGGCCCCTCTGCTTGAGCTTAAACAGTAGTGCACAGTTTTCTGCG
TATACAGATCCCCAACTCACTGCCTCTAAGTCAGGCAGACCCTGATCAATCTGAACCAAATGTGCACCATCCTCCGATGG
CCTCCCAAGCCAATGTGCCTGCTTCTCTTCCTCTGGTGGGAAGAAAGAACGCTCTACAGAGCACTTAGAGCTTACCATGA
AAATACTGGGAGAGGCAGCACCTAACACATGTAGAATAGGACTGAATTATTAAGCATGGTGGTATCAGATGATGCAAACA
GCCCATGTCATTTTTTTTTCCAGAGGTAGGGACTAATAATTCTCCCACACTAGCACCTACGATCATAGAACAAGTCTTTT
AACACATCCAGGAGGGAAACCGCTGCCCAGTGGTCTATCCCTTCTCTCCATCCCCTGCTCAAGCCCAGCACTGCATGTCT
CTCCCGGAAGGTCCAGAATGCCTGTGAAATGCTGTAACTTTTATACCCTGTTATAATCAATAAACAGAACTATTTCGTAC
AAAAAAAAAAAAAAAA RAT 1vN (r1vN) PROTEIN MLTQGESEGLQTLGIVVVLCSSLKLLHYLGLIDLSDDKIEDDLEMTMVCHRPEGLEQLEAQINFTKRELQVLYRGFKNEC
PSGVVNEETFKQIYAQFFPHGDASTYAHYLFNAFDTTQTGSVKFEDFVTALSILLRGTVHEKLRWTFNLYDINKDGYINK
EEMMDIVKAIYDMMGKYTYPVLKEDTPRQHVDVF

MOUSE 1V (CD:477-1127)
CGGCCCCCTGAGATCCAGCCCGAGCGCGGGCGGAGCGGCCGGGTGGCAGCAGGGGCGGGCGGGCGGAGCGCAGCTCCCG
CACCGCACGCGGCGCGGGCTCGGCAGCCTCGGCCGTGCGGGCACGCCGGCCCCGTGTCCAACATCAGGCAGGCTTTGGGG
CTCGGGGCTCGGGCCTCGGAGAAGCAGTGGCCCGGCTGGGTGCCCGCACCGGGGGGCGCCTGTCAAGGCTCCCGCGAGC
CTCTGGCCCTGGGAGTCAGTGCATGTGCCTGGCTGAAGAAGGCAGCAGCCACGAGCTCCAGGCGCCCCGGCCCCACGTTT
TCTGAATACCAAGCTGCAGGCGAGCTGCTCGGGGCTTTTTTGCTTTCTCGCTTTTCCTCTCCTCCAATTCAAAGTGGGCA
ATCCACACCGATTTCTTTTCAGGGGAGGGAAGAGACAGGGCCTGGGGTCCCAAGACGCACACAAGTCTTCGCTGCCATGG
GGGCCGTCATGGGCACTTTCTCCTCCCTGCAGACCAAACAAAGGCGACCCTCTAAAGACAAGATTGAGGATGAGCTAGAG
ATGACCATGGTTTGCCACCGGCCTGAGGGACTGGAGCAGCTTGAGGCACAGACGAACTTCACCAAGAGAGAACTGCAAGT
CTTGTACCGGGGATTCAAAAACGAGTGCCCTAGCGGTGTGGTCAATGAAGAAACATTCAAGCAGATCTACGCTCAGTTTT
TCCCTCACGGAGATGCCAGCACATATGCACATTACCTCTTCAATGCCTTCGACACCACCCAGACAGGCTCTGTAAAGTTC
GAGGACTTTGTGACTGCTCTGTCGATTTTACTGAGAGGGACAGTCCATGAAAAACTAAGGTGGACGTTTAATTTGTATGA
CATCAATAAAGACGGCTACATAAACAAAGAGGAGATGATGGACATAGTCAAAGCCATCTATGACATGATGGGGAAATACA
CCTATCCTGTGCTCAAAGAGGACACTCCCAGGCAGCATGTGGATGTCTTCTTCCAGAAAATGGATAAAAATAAAGATGGC
ATTGTAACGTTAGATGAATTTCTTGAATCATGTCAGGAGGATGACAACATCATGAGATCTCTACAGCTGTTCCAAAATGT
CATGTAACTGAGGACACTGGCCATTCTGCTCTCAGAGACACTGACAAACACCTTAATGCCCTGATCTGCCCTTGTTCCAA
TTTTACACACCAACTCTTGGGACAGAAATACCTTTTACACTTTGGAAGAATTCTCTGCTGAAGACTTTCTACAAAACCTG
GCACCACGTGGCTCTGTCTCTGAGGGACGAGCGGAGATCCGACTTTGTTTTGGAAGCATGCCCATCTCTTCATGCTGCTG
CCCTGTGGAAGGCCCCTCTGCTTGAGCTTAATCAATAGTGCACAGTTTTATGCTTACACATATCCCCAACTCACTGCCTC
CAAGTCAGGCAGACTCTGATGAATCTGAGCCAAATGTGCACCATCCTCCGATGGCCTCCCAAGCCAATGTGCCTGCTTCT
CTTCCTCTGGTGGGAAGAAAGAGTGTTCTACGGAACAATTAGAGCTTACCATGAAAATATTGGGAGAGGCAGCACCTAAC
ACATGTAGAATAGGACTGAATTATTAAGCATGGTGATATCAGATGATGCAAATTGCCCATGTCATTTTTTTCAAAGGTAG
GGACAAATGATTCTCCCACACTAGCACCTGTGGTCATAGAGCAAGTCTCTTAACATGCCCAGAAGGGGAACCACTGTCCA
GTGGTCTATCCCTCCTCTCCATCCCCTGCTCAAACCCAGCACTGCATGTCCCTCCAAGAAGGTCCAGAATGCCTGCGAAA
CGCTGTACTTTTATACCCTGTTCTAATCAATAAACAGAACTATTTCGTAAAAAAAAAAAAAAAAAAA

MOUSE 1V PROTEIN
MGAVMGTFSSLQTKQRRPSKDKIEDELEMIMVCHRPEGLEQLEAQTNFTKRELQVLYRGFKNECPSGVVNEETFKQIYAQ
FFPHGDASTYAHYLFNAFDTTQTGSVKFEDFVTALSILLRGTVHEKLRWTFNLYDINKDGYINKEEMMDIVKAIYDMMGK
VTYPVLKEDTPRQHVDVFFQKMDKNKDGIVTLDEFLESCQEDDNIMRSLQLFQNVM

FIG. 3

RAT 1VL DNA (CD:31-714)

GTCCCAAGTCGCACACAAGTCTTCGCTGCCATGGGGGCCGTCATGGGTACCTTCTCGTCCCTGCAGACCAAACAAAGGCG
ACCCTCTAAAGACATCGCCTGGTGGTATTACCAGTATCAGAGAGACAAGATCGAGGATGATCTGGAGATGACCATGGTTT
GCCATCGGCCTGAGGGACTGGAGCAGCTTGAGGCACAGACGAACTTCACCAAGAGAGAACTGCAAGTCCTTTACCGGGGA
TTCAAAAACGAGTGCCCCAGTGGTGTGGTTAACGAAGAGACATTCAAGCAGATCTACGCTCAGTTTTTCCCTCATGGAGA
TGCCAGCACATACGCACATTACCTCTTCAATGCCTTCGACACCACCCAGACAGGCTCTGTAAAGTTCGAGGACTTTGTGA
CTGCTCTGTCGATTTTACTGAGAGGAACGGTCCATGAAAAACTGAGGTGGACGTTTAATTTGTACGACATCAATAAAGAC
GGCTACATAAACAAAGAGGAGATGATGGACATAGTGAAAGCCATCTATGACATGATGGGGAAATACACCTATCCTGTGCT
CAAAGAGGACACTCCCAGGCAGCACGTGGACGTCTTCTTCCAGAAAATGGATAAAAATAAAGATGGCATTGTAACGTTAG
ACGAATTTCTCGAGTCCTGTCAGGAGGATGACAACATCATGAGGTCTCTACAGCTGTTCCAAAATGTCATGTAACTGAGG
ACACTGGCCATCCTGCTCTCAGAGACACTGACAAACACCTCAATGCCCTGATCTGCCCTTGTTCCAGTTTTACACATCAA
CTCTCGGGACAGAAATACCTTTTACACTTTGGAAGAATTCTCTGCTGAAGACTTTCTACAAAACCTGGCACCGCGTGGCT
CAGTCTCTGATTGCCAACTCTTCCTCCCTCCTCCTCTTGAGAGGGACGAGCTGAAATCCGAAGTTTGTTTTGGAAGCATG
CCCATCTCTCCATGCTGCTGCTGCCCTGTGGAAGGCCCCTCTGCTTGAGCTTAAACAGTAGTGCACAGTTTTCTGCGTAT
ACAGATCCCCAACTCACTGCCTCTAAGTCAGGCAGACCCTGATCAATCTGAACCAAATGTGCACCATCCTCCGATGGCCT
CCCAAGCCAATGTGCCTGCTTCTCTTCCTCTGGTGGGAAGAAAGAACGCTCTACAGAGCACTTAGAGCTTACCATGAAAA
TACTGGGAGAGGCAGCACCTAACACATGTAGAATAGGACTGAATTATTAAGCATGGTGGTATCAGATGATGCAAACAGCC
CATGTCATTTTTTTCCAGAGGTAGGGACTAATAATTCTCCCACACTAGCACCTACGATCATAGAACAAGTCTTTTAACA
CATCCAGGAGGGAAACCGCTGCCCAGTGGTCTATCCCTTCTCTCCATCCCCTGCTCAAGCCCAGCACTGCATGTCTCTCC
CGGAAGGTCCAGAATGCCTGTGAAATGCTGTAACTTTTATACCCTGTTATAATCAATAAACAGAACTATTTCGTACAAAA
AAAAAAAAAAAAAA

RAT 1VL PROTEIN

MGAVMGTFSSLQTKQRRPSKDIAWWYYQYQRDKIEDDLEMTMVCHRPEGLEQLEAQTNFTKRELQVLYRGFKNECPSGVV
NEETFKQIYAQFFPHGDASTYAHYLFNAFDTTQTGSVKFEDFVTALSILLRGTVHEKLRWTFNLYDINKDGYINKEEMMD
IVKAIYDMMGKYTYPVLKEDTPRQHVDVFFQKMDKNKDGIVTLDEFLESCQEDDNIMRSLQLFQNVM

FIG. 4

MOUSE 1VL DNA (CD:77-760)

ATCCACACCGATTTCTTTTCAGGGGAGGGAAGAGACAGGGCCTGGGGTCCCAAGACGCACACAAGTCTTCGCTGCCATGG
GGGCCGTCATGGGCACTTTCTCCTCCCTGCAGACCAAACAAAGGCGACCCTCTAAAGACATCGCCTGGTGGTATTACCAG
TATCAGAGAGACAAGATTGAGGATGAGCTAGAGATGACCATGGTTTGCCACCGGCCTGAGGGACTGGAGCAGCTTGAGGC
ACAGACGAACTTCACCAAGAGAGAACTGCAAGTCTTGTACCGGGGATTCAAAAACGAGTGCCCTAGCGGTGTGGTCAATG
AAGAAACATTCAAGCAGATCTACGCTCAGTTTTTCCCTCACGGAGATGCCAGCACATATGCACATTACCTCTTCAATGCC
TTCGACACCACCCAGACAGGCTCTGTAAAGTTCGAGGACTTTGTGACTGCTCTGTCGATTTTACTGAGAGGGACAGTCCA
TGAAAAACTAAGGTGGACGTTTAATTTGTATGACATCAATAAAGACGGCTACATAAACAAAGAGGAGATGATGGACATAG
TCAAAGCCATCTATGACATGATGGGGAAATACACCTATCCTGTGCTCAAAGAGGACACTCCCAGGCAGCATGTGGATGTC
TTCTTCCAGAAAATGGATAAAAATAAAGATGGCATTGTAACGTTAGATGAATTTCTTGAATCATGTCAGGAGGATGACAA
CATCATGAGATCTCTACAGCTGTTCCAAAATGTCATGTAACTGAGGACACTGGCCATTCTGCTCTCAGAGACACTGACAA
ACACCTTAATGCCCTGATCTGCCCTTGTTCCAATTTTACACACCAACTCTTGGGACAGAAATACCTTTTACACTTTGGAA
GAATTCTCTGCTGAAGACTTTCTACAAAACCTGGCACCACGTGGCTCTGTCTCTGAGGGACGAGCGGAGATCCGACTTTG
TTTTGGAAGCATGCCCATCTCTTCATGCTGCTGCCCTGTGGAAGGCCCCTCTGCTTGAGCTTAATCAATAGTGCACAGTT
TTATGCTTACACATATCCCCAACTCACTGCCTCCAAGTCAGGCAGACTCTGATGAATCTGAGCCAAATGTGCACCATCCT
CCGATGGCCTCCCAAGCCAATGTGCCTGCTTCTCTTCCTCTGGTGGGAAGAAAGAGTGTTCTACGGAACAATTAGAGCTT
ACCATGAAAATATTGGGAGAGGCAGCACCTAACACATGTAGAATAGGACTGAATTATTAAGCATGGTGATATCAGATGAT
GCAAATTGCCCATGTCATTTTTTTCAAAGGTAGGGACAAATGATTCTCCCACACTAGCACCTGTGGTCATAGAGCAAGTC
TCTTAACATGCCCAGAAGGGGAACCACTGTCCAGTGGTCTATCCCTCCTCTCCATCCCCTGCTCAAACCCAGCACTGCAT
GTCCCTCCAAGAAGGTCCAGAATGCCTGCGAAACGCTGTACTTTTATACCCTGTTCTAATCAATAAACAGAACTATTTCG
TACAAAAAAAAAAAAAAAAA

MOUSE 1VL PROTEIN

MGAVMGTFSSLQTKQRRPSKDIAWWYYQYQRDKIEDELEMTMVCHRPEGLEQLEAQTNFTKRELQVLYRGFRNECPSGVV
NEETFKQIYAQFFPHGDASTYABYLFNAFDTTQTGSVKFEDFVTALSILLRGTVHEKLRWTFNLYDINKDGYINKEEMMD
IVKAIYDMMGKYTYPVLKEDTPRQHVDVFFQKMDKNKDGIVTLDEFLESCQEDDNIMRSLQLFQNVM

FIG. 5

RAT 1VN DNA (FIRST-PASS,PARTIAL;CD: 345-955)

GTCCGGGCACACAACCCCTGGATTCTTCGGAGAATATGCCGTGACGGTCTTGCCAATTATTAGTTCTCTTGGCTAGCAGA
TGTTTAGGGACTGGTTAAGCCTTTGGAGAAATTACCTTAGGAAAACGGGGAAATAAAAGCAAAGATTACCATGAATTGCA
AGATTACCTAGCAATTGCAAGGTAGGAGGAGAGAGGTGGAGGGCGGAGTAGACAGGAGGGAGGGAGAAAGTGAGAGGAAG
CTAGGCTGGTGGAAATAACCCTGCACTTGGAACAGCGGCAAAGAAGCGCGATTTTCCAGCTTTAAATGCCTGCCCGCGTT
CTGCTTGCCTACCCGGGAACGGAGATGTTGACCCAGGGCGAGTCTGAAGGGCTCCAGACCTTGGGGATAGTAGTGGTCCT
GTGTTCCTCTCTGAAACTACTGCACTACCTCGGGCTGATTGACTTGTCGGATGACAAGATCGAGGATGATCTGGAGATGA
CCATGGTTTGCCATCGGCCTGAGGGACTGGAGCAGCTTGAGGCACAGACGAACTTCACCAAGAGAGAACTGCAAGTCCTT
TACCGGGGATTCAAAAACGAGTGCCCCAGTGGTGTGGTTAACGAAGAGACATTCAAGCNGATCTACGCTCAGTTTTTCCC
TCATGGAGATGCCAGCACATACGCACATTACCTCTTCAATGCCTTCGACACCACCCAGACAGGCTCTGTAAAGTTCGAGG
ACTTTGTGACTGCTCTGTCGATTTTACTGAGAGGAACGGTCCATGAAAAACTGAAGTGGACGTTTAATTTGTACGACATC
AATAAAGACGGCTACATAAACAAAGAGGAGATGATGGACATAGTGAAAGCCATCTATGACATGATGGGAAATACACCTA
TCTTGTGCTCAAAGAGGACACTTCCAGGCAGCACGTGGACGTCTTCTTCCAGAAAATGGATAAAAATAAAGATGG

RAT 1VN PROTEIN (PARTIAL)

MLTQGESEGLQTLGIVVVLCSSLKLLHYLGLIDLSDDKIEDDLEMTMVCHRPEGLEQLEAQTNFTKRELQVLYRGFKNEC
PSGVVNEETFKXIYAQFFPHGDASTYAHYLFNAFDTTQTGSVKFEDFVTALSILLRGTVHEKLKWTFNLYDINKDGYINK
EEMMDIVKAIYDMMGKYTYLVLKEDTSRQHVDVFFQKMDKNKD

FIG. 6

HUMAN 9QL DNA (CD:207-1019)

CTCACCTGCTGCCTAGTGTTCCCTCTCCTGCTCCAGGACCTCCGGGTAGACCTCAGACCCCGGGCCCATTCCCAGACTCA
GCCTCAGCCCGGACTTCCCCAGCCCCGACAGCACAGTAGGCCGCCAGGGGCGCCGTGTGAGCGCCCTATCCCGGCCACC
CGGCGCCCCTCCCACGGCCCGGGCGGGAGCGGGGCGCCGGGGGCCATGCGGGGCCAGGGCCGCAAGGAGAGTTTGTCCG
ATTCCCGAGACCTGGACGGCTCCTACGACCAGCTCACGGGCCACCCTCCAGGGCCCACTAAAAAAGCGCTGAAGCAGCGA
TTCCTCAAGCTGCTGCCGTGCTGCGGGCCCCAAGCCCTGCCCTCAGTCAGTGAAACATTAGCCGCCCCAGCCTCCCTCCG
CCCCCACAGACCCCGCCTGCTGGACCCAGACAGCGTGGACGATGAATTTGAATTGTCCACCGTGTGTCACCGGCCTGAGG
GTCTGGAGCAGCTGCAGGAGCAAACCAAATTCACGCGCAAGGAGTTGCAGGTCCTGTACCGGGGCTTCAAGAACGAATGT
CCCAGCGGAATTGTCAATGAGGAGAACTTCAAGCAGATTTACTCCCAGTTCTTTCCTCAAGGAGACTCCAGCACCTATGC
CACTTTTCTCTTCAATGCCTTTGACACCAACCATGATGGCTCGGTCAGTTTTGAGGACTTTGTGGCTGGTTTGTCCGTGA
TTCTTCGGGGAACTGTAGATGACAGGCTTAATTGGGCCTTCAACCTGTATGACCTTAACAAGGACGGCTGCATCACCAAG
GAGGAAATGCTTGACATCATGAAGTCCATCTATGACATGATGGGCAAGTACACGTACCCTGCACTCCGGGAGGAGGCCCC
AAGGGAACACGTGGAGAGCTTCTTCCAGAAGATGGACAGAAACAAGGATGGTGTGGTGACCATTGAGGAATTCATTGAGT
CTTGTCAAAAGGATGAGAACATCATGAGGTCCATGCAGCTCTTTGACAATGTCATCTAGCCCCCAGGAGAGGGGGTCAGT
GTTTCCTGGGGGGACCATGCTCTAACCCTAGTCCAGGCGGACCTCACCCTTCTCTTCCCAGGTCTATCCTCATCCTACGC
CTCCCTGGGGGCTGGAGGGATCCAAGAGCTTGGGGATTCAGTAGTCCAGATCTCTGGAGCTGAAGGGCCAGAGAGTGGG
CAGAGTGCATCTCGGGGGGTGTTCCCAACTCCCACCAGCTCTCACCCCCTTCCTGCCTGACACCCAGTGTTGAGAGTGCC
CCTCCTGTAGGAATTGAGCGGTTCCCCACCTCCTACCCTACTCTAGAAACACACTAGAGCGATGTCTCCTGCTATGGTGC
TTCCCCCATCCCTGACCTCATAAACATTTCCCCTAAGACTCCCCTCTCAGAGAGAATGCTCCATTCTTGGCACTGGCTGG
CTTCTCAGACCAGCCATTGAGAGCCCTGTGGGAGGGGACAAGAATGTATAGGGAGAAATCTTGGGCCTGAGTCAATGGA
TAGGTCCTAGGAGGTGGGTGGGGTTGAGAATAGAAGGGCCTGGACAGATTATGATTGCTCAGGCATACCAGGTTATAGCT
CCAAGTTCCACAGGTCTGCTACCACAGGCCATCAAAATATAAGTTTCCAGGCTTTGCAGAAGACCTTGTCTCCTTAGAAA
TGCCCCAGAAATTTTCCACACCCTCCTCGGTATCCATGGAGAGCCTGGGGCCAGATATCTGGCTCATCTCTGGCATTGCT
TCCTCTCCTTCCTTCCTGCATGTGTTGGTGGTGGTTGTGGTGGGGAATGTGGATGGGGGATGTCCTGGCTGATGCCTGC
CAAAATTTCATCCCACCCTCCTTGCTTATCGTCCCTGTTTTGAGGGCTATGACTTGAGTTTTTGTTTCCCATGTTCTCTA
TAGACTTGGGACCTTCCTGAACTTGGGGCCTATCACTCCCCACAGTGGATGCCTTAGAAGGGAGAGGGAAGGAGGGAGGC
AGGCATAGC

HUMAN 9QL PROTEIN

MRGQGRKESLSDSRDLDGSYDQLTGHPPGPTKKALKQRFLKLLPCCGPQALPSVSETLAAPASLRPHRPRLLDPDSVDDE
FELSTVCHRPEGLEQLQEQTKFTRKELQVLYRGFKNECPSGIVNEENFKQIYSQFFPQGDSSTYATFLFNAFDTNHDGSV
SFEDFVAGLSVILRGTVDDRLNWAFNLYDLNKDGCITKEEMLDIMKSIYDMMGKYTYPALREEAPREHVESFFQKMDRNK
DGVVTIEEFIESCQKDENIMRSMQLFDNVI

FIG. 7

RAT 9QL DNA (PARTIAL; CD:2-775)

CCGAGATCTGGACGGCTCCTATGACCAGCTTACGGGCCACCCTCCAGGGCCCAGTAAAAAAGCCCTGAAGCAGCGTTTCC

TCAAGCTGCTGCCGTGCTGCGGGCCCCAAGCCCTGCCCTCAGTCAGTGAAACATTAGCTGCCCCAGCCTCCCTCCGCCCC

CACAGACCCCGCCCGCTGGACCCAGACAGCGTAGAGGATGAGTTTGAATTATCCACGGTGTGTCACCGACCTGAGGGCCT

GGAACAACTCCAGGAACAGACCAAGTTCACACGCAGAGAGCTGCAGGTCCTGTACCGAGGCTTCAAGAACGAATGCCCCA

GTGGGATTGTCAACGAGGAGAACTTCAAGCAGATTTATTCTCAGTTCTTTCCCCAAGGAGACTCCAGCAACTATGCTACT

TTTCTCTTCAATGCCTTTGACACCAACCACGATGGCTCTGTCAGTTTTGAGGACTTTGTGGCTGGTTTGTCGGTGATTCT

TCGGGGACCATAGATGATAGACTGAGCTGGGCTTTCAACTTATATGACCTCAACAAGGACGGCTGTATCACAAAGGAGG

AAATGCTTGACATTATGAAGTCCATCTATGACATGATGGGCAAGTACACATACCCTGCCCTCCGGGAGGAGGCCCCAAGA

GAACACGTGGAGAGCTTCTTCCAGAAGATGGACAGGAACAAGGACGGCGTGGTGACCATCGAGGAATTCATCGAGTCTTG

TCAACAGGACGAGAACATCATGAGGTCCATGCAGCTCTTTGATAATGTCATCTAGCTCCCCAGGGAGAGGGGTTAGTGTG

TCCTAGGGTGACCAGGCTGTAGTCCTAGTCCAGACGAACCTAACCCTCTCTCTCCAGGCCTGTCCTCATCTTACCTGTAC

CCTGGGGGCTGTAGGGATTCAATATCCTGGGGCTTCAGTAGTCCAGATCCCTGAGCTAAGTCACAAAAGTAGGCAAGAGT

AGGCAAGCTAAATCTGGGGGCTTCCCAACCCCCGACAGCTCTCACCCCTTCTCAACTGATACCTAGTGCTGAGGACACCC

CTGGTGTAGGGACCAAGTGGTTCTCCACCTTCTAGTCCCACTCTAGAAACCACATTAGACAGAAGGTCTCCTGCTATGGT

GCTTTCCCCATCCCTAATCTCTTAGATTTTCCTCAAGACTCCCTTCTCAGAGAACACGCTCTGTCCATGTCCCCAGCTGG

GGACATGGACAGAGCGTGTTCTCTAGTTCTAGATCGCGAGCGGCCGC

RAT 9QL PROTEIN (PARTIAL)

RDLDGSYDQLTGHPPGPSKKALKQRFLKLLPCCGPQALPSVSETLAAPASLRPHRPRPLDPDSVEDEFELSTVCHRPEGL

EQLQEQTKFTRRELQVLYRGFKNECPSGIVNEENFKQIYSQFFPQGDSSNYATFLFNAFDTNHDGSVSFEDFVAGLSVIL

RGTIDDRLSWAFNLYDLNKDGCITKEEMLDINKSIYDMKGKYTYPALREEAPREHVESFFQKMDRNKDGVVTIEEFIESC

QQDENIMRSMQLFDNVI

FIG. 8

MOUSE 9QL DNA (CD:181-993)

CGGGACTCTGAGGTGGGCCCTAAAATCCAGCGCTCCCCAGAGAAAAGCCTTGCCAGCCCCTACTCCCGGCCCCCAGCCCC
AGCAGGTCGCTGCGCCGCCAGGGGGCACTGTGTGAGCGCCCTATCCTGGCCACCCGGCGCCCCCTCCCACGGCCCAGGCG
GGAGCGGGGCGCCGGGGGCCATGCGGGGCCAAGGCCGAAAGGAGAGTTTGTCCGAATCCCGAGATTTGGACGGCTCCTAT
GACCAGCTTACGGGCCACCCTCCAGGGCCCAGTAAAAAAGCCCTGAAGCAGCGTTTCCTCAAGCTGCTGCCGTGCTGCGG
GCCCCAAGCCCTGCCCTCAGTCAGTGAAACATTAGCTGCCCCAGCCTCCCTCCGCCCCACAGACCCCGCCCGCTGGACC
CAGACAGCGTGGAGGATGAGTTTGAACTATCCACGGTGTGCCACCGGCCTGAGGGTCTGGAACAACTCCAGGAACAAACC
AAGTTCACACGCAGAGAGTTGCAGGTCCTGTACAGAGGCTTCAAGAACGAATGTCCCAGCGGAATTGTCAACGAGGAGAA
CTTCAAGCAAATTTATTCTCAGTTCTTTCCCCAAGGAGACTCCAGCAACTACGCTACTTTTCTCTTCAATGCCTTTGACA
CCAACCATGATGGCTCTGTCAGTTTTGAGGACTTTGTGGCTGGTTTGTCAGTGATTCTTCGGGGAACCATAGATGATAGA
CTGAACTGGGCTTTCAACTTATATGACCTCAACAAGGATGGCTGTATCACGAAGGAGGAAATGCTCGACATCATGAAGTC
CATCTATGACATGATGGGCAAGTACACCTACCCTGCCCTCCGGGAGGAGGCCCCGAGGGAACACGTGGAGAGCTTCTTCC
AGAAGATGGACAGAAACAAGGACGGCGTGGTGACCATTGAGGAATTCATTGAGTCTTGTCAACAGGACGAGAACATCATG
AGGTCCATGCAACTCTTTGATAATGTCATCTAGCTCCCCAGGGAGAGGGGTTAGTGTGTCCCAGGGTAACCATGCTGTAG
CCCTAGTCCAGGCAAACCTAACCCTCCTCTCCCCGGGTCTGTCCTCATCCTACCTGTACCCTGGGGGCTGTAGGGATTCA
ACATCCTGGCGCTTCAGTAGTCCAGATCCCTGAGCTAAGTGGCGAGAGTAGGCAAGCTAAGTCTTTGGAGGGTGGGTGGG
GGCGCGCAGATTCCCAACCCCGACGACTCTCACCCCTTTCTCGACTGATACCCAGTGCTGAGGCTACCCCTGGTGTCGG
GAACGACCAAAGTGGTTCTCTGCCTCCCCAGCCCACTCTAGAGACCCACACTAGACGGGAATATCTCCTGCTATGGTGCT
TTCCCCATCCCTGACCGCAGATTTTCCTCCTAAGACTCCCTTCTCAGAGAATATGCTTTTGTCCCTTGTCCCTGGCTGGC
TTTTCAGCCTAGCCTTTGAGGACCCTGTGGGAGGGGAGAATAAGAAAGCAGACAAAATCTTGGCCCTGAGCCAGTGGTTA
GGTCCTAGGAATCAGGCTGGAGTGGAGACCAGAAAGCCTGGGCAGGCTATGAGAGCCCCAGGTTGGCTTGTCACCGCCAG
GTTCCACAGGGCTGCTGCTCTGGGTCAGCAGAGTATGAGTTTCCAGACTTTCCAGAAGGCCTTATGTCCTTAGCAATGTC
CCAGAAATTCACCATACACTTCTCAGTGTCTTAGGATCCAGATGTCCGGTCCATCCCTGAAACCTCTCCCTCCTCCTTGC
TCCTATGGTGGGAGTGGTGGCCAGGGGACGATGAGTGAGCCGGTGTCCTGGATGATGCCTGTCAAGGTCCCACCTACCCT
CCGGCTGTCAAGCCGTTCTGGTGACCCTGTTTGATTCTCCATGACCCCTGTCTAGATGTAGAGGTGTGGAGTGAGTCTAG
TGGCAGCCTTAGGGGAATGGGAAGAACGAGAGGGGCACTCCATCTGAACCCAGTGTGGGGCATCCATTCGAATCTTTGC
CTGGCTCCCCACAATGCCCTAGGATCCTCTAGGGTCCCCACCCCCACTCTTTAGTCTACCCAGAGATGCTCCAGAGCTCA
CCTAGAGGGCAGGGACCATAGGATCCAGGTCCAACCTGTCATCAGCATCCGGCCATGCTGCTGCTGCTTATTAATAAACC
TGCTTGTCGTTCAGCGCCCCTTCCCAGTCAGCCAGGGTCTGAGGGGAAGGCCCCCACTTTCCCGCCTCCTGTCAGACATT
GTTGACTGCTTTGCATTTTGGGCTCTTCTACCTATATTTTGTATAATAAGAAAGACACCAGATCCAATAAAACACATGGC
TATGCACAAAAAAAAAAAAAAAA

MOUSE 9QL PROTEIN

MRGQGRKESLSESRDLDGSYDQLTGHPPGPSKKALKQRFLKLLPCCGPQALPSVSETLAAPASLRPHRPRPLDPDSVEDE
FELSTVCHRPEGLEQLQEQTKFTRRELQVLYRGFKNECPSGIVNEENFKQIYSQFFPQGDSSNYATFLFNAFDTNHDGSV
SFEDFVAGLSVILRGTIDDRLNWAFNLYDLNKDGCITKEEMLDIMKSIYDMMGKYTYPALREEAPREHVESFFQKNDRNK
DGVVTIEEFIESCQQDENIMRSMQLFDNVI

FIG. 9

HUMAN 9QM DNA (CD:207-965)

CTCACCTGCTGCCTAGTGTTCCCTCTCCTGCTCCAGGACCTCCGGGTAGACCTCAGACCCCGGGCCCATTCCCAGACTCA
GCCTCAGCCCCGACTTCCCCAGCCCCGACAGCACAGTAGGCCGCCAGGGGGCGCCGTGTGAGCGCCCTATCCCGGCCACC
CGGCGCCCCTCCCACGGCCCGGCCGGGAGCGGGGCGCCGGGGGCCATGCGGGGCCAGGGCCGCAAGGAGAGTTTGTCCG
ATTCCCGAGACCTGGACGGCTCCTACGACCAGCTCACGGGCCACCCTCCAGGGCCCACTAAAAAAGCGCTGAAGCAGCGA
TTCCTCAAGCTGCTGCCGTGCTGCGGGCCCCAAGCCCTGCCCTCAGTCAGTGAAAACAGCGTGGACGATGAATTTGAATT
GTCCACCGTGTGTCACCGGCCTGAGGGTCTGGAGCAGCTGCAGGAGCAAACCAAATTCACGCGCAAGGAGTTGCAGGTCC
TGTACCGGGGCTTCAAGAACGAATGTCCCAGCGGAATTGTCAATGAGGAGAACTTCAAGCAGATTTACTCCCAGTTCTTT
CCTCAAGGAGACTCCAGCACCTATGCCACTTTTCTCTTCAATGCCTTTGACACCAACCATGATGGCTCGGTCAGTTTTGA
GGACTTTGTGGCTGGTTTGTCCGTGATTCTTCGGGAACTGTAGATGACAGGCTTAATTGGGCCTTCAACCTGTATGACC
TTAACAAGGACGGCTGCATCACCAAGGAGGAAATGCTTGACATCATGAAGTCCATCTATGACATGATGGGCAAGTACACG
TACCCTGCACTCCGGGAGGAGGCCCCAAGGGAACACGTGGAGAGCTTCTTCCAGAAGATGGACAGAAACAAGGATGGTGT
GGTGACCATTGAGGAATTCATTGAGTCTTGTCAAAAGGATGAGAACATCATGAGGTCCATGCAGCTCTTTGACAATGTCA
TCTAGCCCCAGGAGAGGGGGTCAGTGTTTCCTGGGGGACCATGCTCTAACCCTAGTCCAGGCGGACCTCACCCTTCTC
TTCCCAGGTCTATCCTCATCCTACGCCTCCCTGGGGCTGGAGGGATCCAAGAGCTTGGGGATTCAGTAGTCCAGATCTC
TGGAGCTGAAGGGGCCAGAGAGTGGGCAGAGTGCATCTCGGGGGGTGTTCCCAACTCCCACCAGCTCTCACCCCCTTCCT
GCCTGACACCCAGTGTTGAGAGTGCCCCTCCTGTAGGAATTGAGCGGTTCCCCACCTCCTACCCTACTCTAGAAACACAC
TAGAGCGATGTCTCCTGCTATGGTGCTTCCCCCATCCCTGACCTCATAAACATTTCCCCTAAGACTCCCCTCTCAGAGAG
AATGCTCCATTCTTGGCACTGGCTGGCTTCTCAGACCAGCCATTGAGAGCCCTGTGGGAGGGGGACAAGAATGTATAGGG
AGAAATCTTGGGCCTGAGTCAATGGATAGGTCCTAGGAGGTGGGTGGGGTTGAGAATAGAAGGGCCTGGACAGATTATGA
TTGCTCAGGCATACCAGGTTATAGCTCCAAGTTCCACAGGTCTGCTACCACAGGCCATCAAAATATAAGTTTCCAGGCTT
TGCAGAAGACCTTGTCTCCTTAGAAATGCCCCAGAAATTTTCCACACCCTCCTCGGTATCCATGGAGAGCCTGGGGCCAG
ATATCTGGCTCATCTCTGGCATTGCTTCCTCTCCTTCCTTCCTGCATGTGTTGGTGGTGGTTGTGGTGGGGAATGTGGA
TGGGGGATGTCCTGGCTGATGCCTGCCAAAATTTCATCCCACCCTCCTTGCTTATCGTCCCTGTTTTGAGGGCTATGACT
TGAGTTTTTGTTTCCCATGTTCTCTATAGACTTGGGACCTTCCTGAACTTGGGGCCTATCACTCCCCACAGTGGATGCCT
TAGAAGGGAGAGGGAAGGAGGGAGGCAGGCATAGC

FIG. 10A

HUMAN 9QM PROTEIN

MRGQGRKESLSDSRDLDGSYDQLTGHPPGPTKKALKQRFLKLLPCCGPQALPSVSENSVDDEFELSTVCHRPEGLEQLQE
QTKFTRKELQVLYRGFKNECPSGIVNEENFKQIYSQFFPQGDSSTYATFLFNAFDTNHDGSVSFEDFVAGLSVILRGTVD
DRLNWAFNLYDLNKDGCITKEEMLDIMKSIYDMMGKYTYPALREFAPREHVESFFQKMDRNKDGVVTIEEFIESCQKDEN
IMRSMQLFDNVI

FIG. 10B

RAT 9QM DNA (CD:214-972)

CTCACTTGCTGCCCAAGGCTCCTGCTCCTGCCCCAGGACTCTGAGGTGGGCCCTAAAACCCAGCGCTCTCTAAAGAAAAG
CCTTGCCAGCCCCTACTCCCGGCCCCCAACCCCAGCAGGTCGCTGCGCCGCCAGGGGGCGCTGTGTGAGCGCCCTATTCT
GGCCACCCGGCGCCCCCTCCCACGGCCCAGGCGGGAGCGGGGCGCCGGGGGCCATGCGGGGCCAAGGCAGAAAGGAGAGT
TTGTCCGAATCCCGAGATCTGGACGGCTCCTATGACCAGCTTACGGGCCACCCTCCAGGGCCCAGTAAAAAAGCCCTGAA
GCAGCGTTTCCTCAAGCTGCTGCCGTGCTGCGGGCCCCAAGCCCTGCCCTCAGTCAGTGAAAACAGCGTAGAGGATGAGT
TTGAATTATCCACGGTGTGTCACCGACCTGAGGGCCTGGAACAACTCCAGGAACAGACCAAGTTCACACGCAGAGAGCTG
CAGGTCCTGTACCGAGGCTTCAAGAACGAATGCCCCAGTGGGATTGTCAACGAGGAGAACTTCAAGCAGATTTATTCTCA
GTTCTTTCCCCAAGGAGACTCCAGCAACTATGCTACTTTTCTCTTCAATGCCTTTGACACCAACCACGATGGCTCTGTCA
GTTTTGAGGACTTTGTGGCTGGTTTGTCGGTGATTCTTCGGGGACCATAGATGATAGACTGAGCTGGGCTTTCAACTTA
TATGACCTCAACAAGGACGGCTGTATCACAAAGGAGGAAATGCTTGACATTATGAAGTCCATCTATGACATGATGGGCAA
GTACACATACCCTGCCCTCCGGGAGGAGGCCCCAAGAGAACACGTGGAGAGCTTCTTCCAGAAGATGGACAGGAACAAGG
ACGGCGTGGTGACCATCGAGGAATTCATCGAGTCTTGTCAACAGGACGAGAACATCATGAGGTCCATGCAGCTCTTTGAT
AATGTCATCTAGCTCCCCAGGGAGAGGGGTTAGTGTGTCCTAGGGTGACCAGGCTGTAGTCCTAGTCCAGACGAACCTAA
CCCTCTCTCTCCAGGCCTGTCCTCATCTTACCTGTACCCTGGGGCTGTAGGGATTCAATATCCTGGGCTTCAGTAGTC
CAGATCCCTGAGCTAAGTCACAAAAGTAGGCAAGAGTAGGCAAGCTAAATCTGGGGCTTCCCAACCCCCGACAGCTCTC
ACCCCTTCTCAACTGATACCTAGTGCTGAGGACACCCCTGGTGTAGGGACCAAGTGGTTCTCCACCTTCTAGTCCCACTC
TAGAAACCACATTAGACAGAAGGTCTCCTGCTATGGTGCTTTCCCCATCCCTAATCTCTTAGATTTTCCTCAAGACTCCC
TTCTCAGAGAACACGCTCTGTCCATGTCCCCAGCTGGCTTCTCAGCCTAGCCTTTGAGGGCCCTGTGGGGAGGCGGGAC
AAGAAAGCAGAAAAGTCTTGGCCCCGAGCCAGTGGTTAGGTCCTAGGAATTGGCTGGAGTGGAGGCCAGAAAGCCTGGC
AGATGATGAGAGCCCAGCTGGGCTGTCACTGCAGGTTCCGGGCCTACAGCCCTGGGTCAGCAGAGTATGAGTTCCCAGA
CTTTCCAGAAGGTCCTTAGCAATGTCCCAGAAATTCACCGTACACTTCTCAGTGTCTTAGGAGGGCCCGGGATCCAGATG
TCTGGTTCATCCCTGAATCCTCTCCCTCCTTCTTGCTCGTATGGTGGGAGTGGTGGCCAGGGGAAGATGAGTGGTGTCCC
GGATGATGCCTGTCAAGGTCCCACCTCCCCTCCGGCTGTTCTCATGACAGCTGTTTGGTTCTCCATGACCCCTATCTAGA
TGTAGAGGCATGGAGTGAGTCAGGGATTTCCCGAACTTGAGTTTTACCACTCCTCCTAGTGGCTGCCTTAGGGAATGGG
AAGAACCCAGTGTGGGGCACCCATTAGAATCTTTGCCCGGCTCCTCACAATGCCCTAGGGTCCCCTAGGGTACCCGCTC
CCTCTGTTTAGTCTACCCAGAGATGCTCCTGAGCTCACCTAGAGGGTAGGGACGGTAGGCTCCAGGTCCAACCTCTCCAG
GTCAGCACCCTGCCATGCTGCTGCTCCTCATTAACAAACCTGCTTGTCTCCTCCTGCCGCCCCTTCTCAGTCAGCCAGGGT
CTGAGGGGAAGGGCCTCCCGTTTCCCCATCCGTCAGACATGGTTGACTGCTTTGCATTTTGGGCTCTTCTATCTATTTTG
TAAAATAAGACATCAGATCCAATAAAACACACGGCTATGCACAAAAAAAAAAAAAAAAA

RAT 9QM PROTEIN

MRGQGRKESLSESRDLDGSYDQLTGHPPGPSKKALKQRFLKLLPCCGPQALPSVSENSVEDEFELSTVCHRPEGLEQLQE
QTKFTRRELQVLYRGFKNECPSGIVNEENFKQIYSQFFPQGDSSNYATFLFNAFDTNHDGSVSFEDFVAGLSVILRGTID
DRLSWAFNLYDLNKDGCITKEEMLDIMKSIYDMMGKYTYPALREEAPREHVESFFQKMDRNKDGVVTIEEFIESCQQDEN
IMRSMQLFDNVI

FIG. 11

HUMAN 9QS DNA (CD:207-869)

CTCACCTGCTGCCTAGTGTTCCCTCTCCTGCTCCAGGACCTCCGGGTAGACCTCAGACCCCGGGCCCATTCCCAGACTCA
GCCTCAGCCCGGACTTCCCCAGCCCCGACAGCACAGTAGGCCGCCAGGGGGCGCCGTGTGAGCGCCCTATCCCGGCCACC
CGGCGCCCCCTCCCACGGCCCGGGCGGGAGCGGGGCGCCGGGGGCCATGCGGGCCAGGGCCGCAAGGAGAGTTTGTCCG
ATTCCCGAGACCTGGACGGCTCCTACGACCAGCTCACGGACAGCGTGGACGATGAATTTGAATTGTCCACCGTGTGTCAC
CGGCCTGAGGGTCTGGAGCAGCTGCAGGAGCAAACCAAATTCACGCGCAAGGAGTTGCAGGTCCTGTACCGGGGCTTCAA
GAACGAATGTCCCAGCGGAATTGTCAATGAGGAGAACTTCAAGCAGATTTACTCCCAGTTCTTTCCTCAAGGAGACTCCA
GCACCTATGCCACTTTTCTCTTCAATGCCTTTGACACCAACCATGATGGCTCGGTCAGTTTTGAGGACTTTGTGGCTGGT
TTGTCCGTGATTCTTCGGGGAACTGTAGATGACAGGCTTAATTGGGCCTTCAACCTGTATGACCTTAACAAGGACGGCTG
CATCACCAAGGAGGAAATGCTTGACATCATGAAGTCCATCTATGACATGATGGGCAAGTACACGTACCCTGCACTCCGGG
AGGAGGCCCCAAGGGAACACGTGGAGAGCTTCTTCCAGAAGATGGACAGAAACAAGGATGGTGTGGTGACCATTGAGGAA
TTCATTGAGTCTTGTCAAAAGGATGAGAACATCATGAGGTCCATGCAGCTCTTTGACAATGTCATCTAGCCCCCAGGAGA
GGGGGTCAGTGTTTCCTGGGGGACCATGCTCTAACCCTAGTCCAGGCGGACCTCACCCTTCTCTTCCCAGGTCTATCCT
CATCCTACGCCTCCCTGGGGGCTGGAGGGATCCAAGAGCTTGGGGATTCAGTAGTCCAGATCTCTGGAGCTGAAGGGGCC
AGAGAGTGGGCAGAGTGCATCTCGGGGGGTGTTCCCAACTCCCACCAGCTCTCACCCCCTTCCTGCCTGACACCCAGTGT
TGAGAGTGCCCCTCCTGTAGGAATTGAGCGGTTCCCCACCTCCTACCCTACTCTAGAAACACACTAGAGCGATGTCTCCT
GCTATGGTGCTTCCCCCATCCCTGACCTCATAAACATTTCCCCTAAGACTCCCCTCTCAGAGAGAATGCTCCATTCTTGG
CACTGGCTGGCTTCTCAGACCAGCCATTGAGAGCCCTGTGGGAGGGGACAAGAATGTATAGGGAGAAATCTTGGGCCTG
AGTCAATGGATAGGTCCTAGGAGGTGGGTGGGGTTGAGAATAGAAGGGCCTGGACAGATTATGATTGCTCAGGCATACCA
GGTTATAGCTCCAAGTTCCACAGGTCTGCTACCACAGGCCATCAAAATATAAGTTTCCAGGCTTTGCAGAAGACCTTGTC
TCCTTAGAAATGCCCCAGAAATTTTCCACACCCTCCTCGGTATCCATGGAGAGCCTGGGGCCAGATATCTGGCTCATCTC
TGGCATTGCTTCCTCTCCTTCCTTCCTGCATGTGTTGGTGGTGGTTGTGGTGGGGAATGTGGATGGGGATGTCCTGGC
TGATGCCTGCCAAAATTTCATCCCACCCTCCTTGCTTATCGTCCCTGTTTTGAGGGCTATGACTTGAGTTTTTGTTTCCC
ATGTTCTCTATAGACTTGGGACCTTCCTGAACTTGGGGCCTATCACTCCCCACAGTGGATGCCTTAGAAGGGAGAGGGAA
GGAGGGAGGCAGGCATAGC

FIG. 12

MONKEY 9QS DNA (CD:133-795)

CCCACGCGTCCGCCCACGCGTCCGCGGACGCGTGGGGTGCACTAGGCCGCCAGGGGGCGCCGTGTGAGCGCCCTATCCCG
GCCACCCGGCGCCCCCTCCCACGGACCGGGCGGGAGCGGGGCGCCGGGGGCCATGCGGGGCCAGGGCCGCAAGGAGAGTT
TGTCCGATTCCCGAGACCTGGACGGATCCTACGACCAGCTCACGGACAGCGTGGAGGATGAATTTGAATTGTCCACCGTG
TGTCACCGGCCTGAGGGTCTGGAGCAGCTGCAGGAGCAAACCAAATTCACGCGCAAGGAGTTGCAGGTCCTGTACCGGGG
CTTCAAGAACGAATGTCCGAGCGGAATTGTCAATGAGGAGAACTTCAAGCAAATTTACTCCCAGTTCTTTCCTCAAGGAG
ACTCCAGCACCTATGCCACTTTTCTCTTCAATGCCTTTGACACCAACCATGATGGCTCGGTCAGTTTTGAGGACTTTGTG
GCTGGTTTGTCCGTGATTCTTCGGGGAACTGTAGATGACAGGCTTAATTGGGCCTTCAACTTGTATGACCTCAACAAGGA
CGGCTGCATCACCAAGGAGGAAATGCTTGACATCATGAAGTCCATCTATGACATGATGGGCAAGTACACATACCCTGCAC
TCCGGGAGGAGGCCCCAAGGGAACATGTGGAGAACTTCTTCCAGAAGATGGACAGAAACAAGGATGGCGTGGTGACCATT
GAGGAATTCATTGAGTCTTGTCAAAAGGATGAGAACATCATGAGGTCCATGCAGCTCTTTGACAATGTCATCTAGCCCCC
AGGAGAGGGGGTCAGTGTTTCCTGGGGGGACCATGCTCTAACCCTAGTCCAGGTGGACCTCACCCTTCTCTTCCCAGGTC
TATCCTTGTCCTAGGCCTCCCTGGGGGCTGGAGGGATCCAAGAGCTTGGGGATTCAGTAGTCCAGATCTCTGGAGCTGAA
GGGGCCAGAGAGTGGGCAGAGTGCATCTTGGGGGGTGTTCCCAACTCCCACCAGCTTTCACCCGCTTCCTGCCTGACACC
CAGTGTTGAGAGTGCCCCTCCTGTAGGAACTGAGTGGTTCCCCACCTCCTACCCCCACTCTAGAAACACACTAGACAGAT
GTCTCGTGCTATGGTGCTTCCCCCATCCCTGACTTCATAAACATTTCCCCTAAAACTCCCTTCTCAGAGAGAATGCTCCA
TTCTTGGCACTGGCTGGCTTCTCAGACCAGCCTTTGAGAGCCCTGTGGGAGGGGGACAAGAATGTATAGGGGAGAAATCT
TGGGCCTGAGTCAATGGATAGGTCCTAGGAGGTGGCTGGGGTTGAGAATAGAAAGGCCTGGACACAATGTGATTGCTCAG
GCATACCAAGTTATAGCTCCAAGTTCCACAGGTCTGCTACCACAGGCCATCAAAATATAAGTTTCCAGGCTTTGCAGAAG
ACCTTGTCTCCTTGGAAATGCCCCAGATATTTTCCATACCCTCCTCGATATCCATGGAGAGCCTGGGGCTAGATATCTGG
CATATCCCTGGCATTGCTTCCTCTCCTTCCTTCCTGCATGTGTTGGTGGTGGTTGTGGCAGGGGAATGTGGATAGGAGAT
GTCCTGGCAGATGCCTGCCAAAGTTTCATCCCACCCTCCCTGCTCATCGCCCCTGTTTTGAGGGCTGTGACTTGAGTTTT
TGTTTCCCATGTTCTCTATAGACTTGGGACCTTCCTGAACTTGGGGCCTATCACTCCCCACAGTGGATGCCTTAGAAGGG
AGAGGGAAGGAGGGAGGCAGGCATAGCATCTGAACCCAGTGTGGGGGCATTCACTAGGATCTTCAATCAACCCGGGCTCT
CCCCAACCCCCCAGATAACCTCCTCAGTTCCCTAGAGTCTCCTCTTGCTCTACTCAATCTACCCAGAGATGCCCCTTAGC
ACACTCAGAGGGCAGGGACCATAGGACCCAGGTTCCAACCCCATTGTCAGCACCCCAGCCATGCTGCCATCCCTTAGCAC
ACCTGCTCGTCCCATTCAGCTTACCCTCCCAGTCAGCCAGAATCTGAGGGGAGGGCCCCAGAGAGCCCCCTTCCCCATC
AGAAGACTGTTGACTGCTTTGCATTTTGGGCTCTTCTATATATTTTGTAAAATAAGAACTATACCAGATCTAATAAAACA
CAATGGCTATGCAAAAAAAAAAAAAAAAAAAA

MONKEY 9QS PROTEIN

MRGQGRKESLSDSRDLDGSYDQLTDSVEDEFELSTVCHRPEGLEQLQEQTKFTRKELQVLYRGFKNECPSGIVNEENFKQ
IYSQFFPQGDSSTYATFLFNAFDINHDGSVSFEDFVAGLSVILRGTVDDRLNWAFNLYDLNKDGCITKEEMLDIMKSIYD
MMGKYTYPALREEAPREHVENFFQKMDRNKDGVVTIEEFIESCQKDENIMRSMQLFDNVI

FIG. 13

RAT 9QC DNA (CD:208-966)

TGCTGCCCAAGGCTCCTGCTCCTGCCCCAGGACTCTGAGGTGGGCCCTAAAACCCAGCGCTCTCTAAAGAAAAGCCTTGC
CAGCCCCTACTCCCGGCCCCCAACCCCAGCAGGTCGCTGCGCCGCCAGGGGGCGCTGTGTGAGCGCCCTATTCTGGCCAC
CCGGCGCCCCCTCCCACGGCCCAGGCGGGAGCGGGGCGCCGGGGGCCATGCGGGGCCAAGGCAGAAAGGAGAGTTTGTCC
GAATCCCGAGATCTGGACGGCTCCTATGACCAGCTTACGGGCCACCCTCCAGGGCCCAGTAAAAAAGCCCTGAAGCAGCG
TTTCCTCAAGCTGCTGCCGTGCTGCGGGCCCCAAGCCCTGCCCTCAGTCAGTGAAAACAGCGTAGAGGATGAGTTTGAAT
TATCCACGGTGTGTCACCGACCTGAGGGCCTGGAACAACTCCAGGAACAGACCAAGTTCACACGCAGAGAGCTGCAGGTC
CTGTACCGAGGCTTCAAGAACGAATGCCCCAGTGGGATTGTCAACGAGGAGAACTTCAAGCAGATTTATTCTCAGTTCTT
TCCCCAAGGAGACTCCAGCAACTATGCTACTTTTCTCTTCAATGCCTTTGACACCAACCACGATGGCTCTGTCAGTTTTG
AGGACTTTGTGGCTGGTTTGTCGGTGATTCTTCGGGGACCATAGATGATAGACTGAGCTGGGCTTTCAACTTATATGAC
CTCAACAAGGACGGCTGTATCACAAAGGAGGAAATGCTTGACATTATGAAGTCCATCTATGACATGATGGGCAAGTACAC
ATACCCTGCCCTCCGGGAGGAGGCCCCAAGAGAACACGTGGAGAGCTTCTTCCAGAAGATGGACAGGAACAAGGACGGCG
TGGTGACCATCGAGGAATTCATCGAGTCTTGTCAACAGGACGAGAACATCATGAGGTCCATGCAGCTCTCACCCCTTCTC
AACTGATACCTAGTGCTGAGGACACCCCTGGTGTAGGGACCAAGTGGTTCTCCACCTTCTAGTCCCACTCTAGAAACCAC
ATTAGACAGAAGGTCTCCTGCTATGGTGCTTTCCCCATCCCTAATCTCTTAGATTTTCCTCAAGACTCCCTTCTCAGAGA
ACACGCTCTGTCCATGTCCCCAGCTGGCTTCTCAGCCTAGCCTTTGAGGGCCCTGTGGGGAGGCGGGGACAAGAAAGCAG
AAAAGTCTTGGCCCCGAGCCAGTGGTTAGGTCCTAGGAATTGGCTGGAGTGGAGGCCAGAAAGCCTGGGCAGATGATGAG
AGCCCAGCTGGGCTGTCACTGCAGGTTCCGGGGCCTACAGCCCTGGGTCAGCAGAGTATGAGTTCCCAGACTTTCCAGAA
GGTCCTTAGCAATGTCCCAGAAATTCACCGTACACTTCTCAGTGTCTTAGGAGGGCCCGGGATCCAGATGTCTGGTTCAT
CCCTGAATCCTCTCCCTCCTTCTTGCTCGTATGGTGGGAGTGGTGGCCAGGGGAAGATGAGTGGTGTCCCGGATGATGCC
TGTCAAGGTCCCACCTCCCCTCCGGCTGTTCTCATGACAGCTGTTTGGTTCTCCATGACCCCTATCTAGATGTAGAGGCA
TGGAGTGAGTCAGGGATTTCCCGAACTTGAGTTTTACCACTCCTCCTAGTGGCTGCCTTAGGGGAATGGGAAGAACCCAG
TGTGGGGGCACCCATTAGAATCTTTGCCCGGCTCCTCACAATGCCCTAGGGTCCCCTAGGGTACCCGCTCCCTCTGTTTA
GTCTACCCAGAGATGCTCCTGAGCTCACCTAGAGGGTAGGGACGGTAGGCTCCAGGTCCAACCTCTCCAGGTCAGCACCC
TGCCATGCTGCTGCTCCTCATTAACAAACCTGCTTGTCTCCTCCTGCGCCCCTTCTCAGTCAGCCAGGGTCTGAGGGGAA
GGGCCTCCCGTTTCCCCATCCGTCAGACATGGTTGACTGCTTTGCATTTTGGGCTCTTCTATCTATTTTGTAAAATAAGA
CATCAGATCCAATAAAACACACGGCTATGCACAAAAAAAAAAAAAAAAAAAAAAAAA

RAT 9QC PROTEIN

MRGQGRIESLSESRDLDGSYDQLTGHPPGPSKKALKQRFLKLLPCCGPQALPSVSENSVEDEFELSTVCHRPEGLEQLQE
QTKFTRRELQVLYRGFKNECPSGIVNEENFKQIYSQFFPQGDSSNYATFLFNAFDTNHDGSVSFEDFVAGLSVILRGTID
DRLSWAFNLYDLNKDGCITKEEMLDIMKSIYDMMGKYTYPALREEAPREHVESFFQKMDRNKDGVVTIEEFIESCQQDEN
IMRSMQLSPLLN

FIG. 14

RAT 8T (9Q SPLICE VARAIANT) DNA (MAY NOT BE FULL LENGTH, CD: 1-678)

ATGAACCACTGCCCTCGCAGGTGCCGGAGCCCGTTGGGGCAGGCAGCTCGATCTCTCTACCAGTTGGTAACTGGGTCGCT
GTCGCCAGACAGCGTAGAGGATGAGTTTGAATTATCCACGGTGTGTCACCGACCTGAGGGCCTGGAACAACTCCAGGAAC
AGACCAAGTTCACACGCAGAGAGCTGCAGGTCCTGTACCGAGGCTTCAAGAACGAATGCCCCAGTGGGATTGTCAACGAG
GAGAACTTCAAGCAGATTTATTCTCAGTTCTTTCCCCAAGGAGACTCCAGCAACTATGCTACTTTTCTCTTCAATGCCTT
TGACACCAACCACGATGGCTCTGTCAGTTTTGAGGACTTTGTGGCTGGTTTGTCGGTGATTCTTCGGGGACCATAGATG
ATAGACTGAGCTGGGCTTTCAACTTATATGACCTCAACAAGGACGGCTGTATCACAAAGGAGGAAATGCTTGACATTATG
AAGTCCATCTATGACATGATGGGCAAGTACACATACCCTGCCCTCCGGGAGGAGGCCCCAAGAGAACACGTGGAGAGCTT
CTTCCAGAAGATGGACAGGAACAAGGACGGCGTGGTGACCATCGAGGAATTCATCGAGTCTTGTCAACAGGACGAGAACA
TCATGAGGTCCATGCAGCTCTTTGATAATGTCATCTAGCTCCCCAGGGAGAGGGGTTAGTGTGTCCTAGGGTGACCAGGC
TGTAGTCCTAGTCCAGACGAACCTAACCCTCTCTCTCCAGGCCTGTCCTCATCTTACCTGTACCCTGGGGCTGTAGGGA
TTCAATATCCTGGGGCTTCAGTAGTCCAGATCCCTGAGCTAAGTCACAAAAGTAGGCAAGAGTAGGCAAGCTAAATCTGG
GGGCTTCCCAACCCCCGACAGCTCTCACCCCTTCTCAACTGATACCTAGTGCTGAGGACACCCCTGGTGTAGGGACCAAG
TGGTTCTCCACCTTCTAGTCCCACTCTAGAAACCACATTAGACAGAAGGTCTCCTGCTATGGTGCTTTCCCCATCCCTAA
TCTCTTAGATTTTCCTCAAGACTCCCTTCTCAGAGAACACGCTCTGTCCATGTCCCCAGCTGGCTTCTCAGCCTAGCCTT
TGAGGGCCCTGTGGGAGGCGGGGACAAGAAAGCAGAAAAGTCTTGGCCCCGAGCTAGTGGTTAGGTCCTAGGAATTGGC
TGGAGTGGAGGCCAGAAAGCCTGGGCAGATGATGAGAGCCCAGCTGGGCTGTCACTGCAGGTTCCAGGGCCTACAGCCCT
GGGTCAGCAGAGTATGAGTTCCCAGACTTTCCAGAAGGTCCTTAGCAATGTCCCAGAAATTCACCATACACTTCTCAGTG
TCCCGGATGATGCCTGTCAAGGTCCCACCTCCCCTCCGGCTGTTCTCATGACAGCTGTTTGGTTCTCCATGACCCCTATC
TAGATGTAGAGGCATGGAGTGAGTCAGGGATTTCCCGAACTTGAGTTTTACCACTCCTCCTAGTGGCTGCCTTAGGGGAA
TGGGAAGAACCCAGTGTGGGGGCACCCATTAGAATCTTTGCCCGGTTCCTCACAATGCCCTAGGGTCCCCTAGGGTACCC
GCTCCCTCTGTTTAGTCTACCCAGAGATGCTCCTGAGCTCACCTAGAGGGTAGGGACGGTAGGCTCCAGGTCCAACCTCT
CCAGGTCAGCACCCTGCCATGCTGCTGCTCCTCATTAACAAACCTGCTTGTCTCCTCCTGCGCCCCTTCTCAGTCAGCCA
GGGTCTGAGGGGAAGGGCCTCCCGTTTCCCCATCCGTCAGACATGGTTGACTGCTTTGCATTTTGGGCTCTTCTATCTAT
TTTGTAAAATAAGACATCAGATCCAATAAAACACACGGCTATGCACAAAAAAAAAAAAAAAAA

RAT 8T (9Q SPLICE VARAIANT) PROTEIN (MAY NOT BE FULL LENGTH)

MNHCPRRCRSPLGQAARSLYQLVTGSLSPDSVEDEFELSTVCHRPEGLEQLQEQTKFTRRELQVLYRGFKNECPSGIVNE
ENFKQIYSQFFPQGDSSNYATFLFNAFDTNHDGSVSFEDFVAGLSVILRGTIDDRLSWAFNLYDLNKDGCITKEEMLDIM
KSIYDMMGKYTYPALREEAPREHVESFFQKMDRNKDGVVTIEEFIESCQQDENIMRSMQLFDNVI

FIG. 15

>human KChIP3 cds=1-7:

ATGCAGCCGGCTAAGGAAGTGACAAAGGCGTCGGACGGCAGCCTCCTGGGGGACCTCGGGC
ACACACCACTTAGCAAGAA
GGAGGGTATCAAGTGGCAGAGGCCGAGGCTCAGCCGCCAGGCTTTGATGAGATGCTGCCTG
GTCAAGTGGATCCTGTCCA
GCACAGCCCCACAGGGCTCAGATAGCAGCGACAGTGAGCTGGAGCTGTCCACGGTGCGCCA
CCAGCCAGAGGGGCTGGAC
CAGCTGCAGGCCCAGACCAAGTTCACCAAGAAGGAGCTGCAGTCTCTCTACAGGGGCTTTA
AGAATGAGTGTCCCACGGG
CCTGGTGGACGAAGACACCTTCAAACTCATTTACGCGCAGTTCTTCCCTCAGGGAGATGCCA
CCACCTATGCACACTTCC
TCTTCAACGCCTTTGATGCGGACGGGAACGGGGCCATCCACTTTGAGGACTTTGTGGTTGGC
CTCTCCATCCTGCTGCGG
GGCACAGTCCACGAGAAGCTCAAGTGGGCCTTTAATCTCTACGACATTAACAAGGATGGCT
ACATCACCAAAGAGGAGAT
GCTGGCCATCATGAAGTCCATCTATGACATGATGGCCGCCACACCTACCCCATCCTGCGGG
AGGACGCGCCGGCGGAGC
ACGTGGAGAGGTTCTTCGAGAAAATGGACCGGAACCAGGATGGGGTAGTGACCATTGAAGA
GTTCCTGGAGGCCTGTCAG
AAGGATGAGAACATCATGAGCTCCATGCAGCTGTTTGAGAATGTCATCTAGgacacgtccaaaggagt
gcatggccacag
ccacctccaccccaagaaacctccatcctgccaggagcagcctccaagaaacttttaaaaaatagatttgcaaaaagtg
aacagattgctacacacacacacacacacacacacacacacacacacacacacagccattcatctgggctggcagaggggac
agagttcagggaggggctgagtctggctaggggccgagtccaggagccccagccagcccttccaggccagcgaggcgag
gctgcctctgggtgagtggctgacagagcaggtctgcaggccaccagctgctggatgtcaccaagaagggctcgagtgc
ccctgcaggggagggtccaatctccggtgtgagcccacctcgtcccgttctccattctgctttcttgccacacagtgggc
cggcccaggctcccctggtctcctcccgtagccactctctgcccactacctatgcttctagaaagcccctcacctcag
gaccccagagggaccagctgggggcaggggggagaggggtaatggaggccaagcctgcagctttctggaaattcttcc
ctggggtcccaggatcccctgctactccactgacctggaagagctgggtaccaggccaccactgtggggcaagcctga
gtggtgaggggccactgggccccattctccctccatggcaggaaggcgggggatttcaagtttagggatttgggtcgtggt
ggagaatctgagggcactctctgccagctccacaggggtgggatgagcctctccttgcccagtcctggttcagtgggaat
gcagtgggtggggctgtacacaccctccagcacagactgttccctccaaggtcctcttaggtcccgggaggaacgtggtt
cagagactggcagccagggagcccggggcagagctcagaggagtctgggaaggggcgtgtccctcctcttcctgtagtgc
ccctccatggccagcagcttaggctgagccccctctcctgaagcagtgtcgccgtcctctgccttgcacaaaaagcac
aagcattccttagcagctcaggcgcagccctagtgggagcccagcacactgcttctcggaggccaggccctcctgctggc
tgaggcttgggcccagtagccccaatatggtggccctggggaagaggccttggggggtctgctctgtgcctgggatcagtg
gggcccaaagccagcccggctgaccaacattcaaaagcacaaacctggggactctgcttggctgtcccctccatctg
gggatggagaatgccagcccaaagctggagccaatggtgagggctgagagggctgtggctgggtggtcagcagaaacccc
caggaggagagagatgctgctcccgcctgattggggcctcacccagaaggaacccggtcccaggccgcatggcccctcca
ggaacattcccacataatacattccatcacagccagcccagctccactcagggctggccggggagtcccgtgtgccc
aagaggctagcccagggtgagcagggccctcagaggaaaggcagtatggcggaggccatgggggcccctcggcattcac
acacagcctggcctcccctgcggagctgcatggacgcctggctccaggctccaggctgactgggggcctctgcctccagg
agggcatcagctttcctggctcaggatcttctccctccctcacccgctgcccagccctccagctggtgtcactctg
cctctaaggccaaggcctcaggagagcatcaccaccacaccctgccggccttggccttggggccagactggctgcacag
cccaaccaggagggtctgcctcccacgctgggacacagaccggccgcatgtctgcatggcagaagcgtctcccaggcc
acggcctgggaggtggttcctgttctcagcatccactaatattcagtcctgtatattttaataaaataaacttgacaaa
ggaaaaaaaaaaaaaaaaaaattcctgcggccgcgttctcca

FIG. 16A

>human KChIP3

MQPAKEVTKASDGSLLGDLGHTPLSKKEGIKWQRPRLSRQALMRCCLVKWILSSTAPQGSDSSD
SELELSTVRHQPEGLD
QLQAQTKFTKKELQSLYRGFKNECPTGLVDEDTFKLIYAQFFPQGDATTYAHFLFNAFDADGNG
AIHFEDFVVGLSILLR
GTVHEKLKWAFNLYDINKDGYITKEEMLAIMKSIYDMMGRHTYPILREDAPAEHVERFFEKMD
RNQDGVVTIEEFLEACQ
KDENIMSSMQLFENVI

FIG. 16B

RAT P19 DNA (FIRST PASS, PARTIAL; CD:1-330)

TTTGAGGACTTTGTGGTTGGGCTCTCCATCCTGCTTCGAGGGACCGTCCATGAGAAGCTCAAGTGGGCCTTCAATCTCTA
CGACATCAACAAGGACGGTTACATCACCAAAGAGGAGATGCTGGCCATCATGAAGTCCATCTACGACATGATGGGCCGCC
ACACCTACCCTATCCTGCGGGAGGACGCACCTCTGGAGCATGTGGAGAGGTTCTTCCAGAAAATGGACAGGAACCAGGAT
GGAGTAGTGACTATTGATGAATTTCTGGAGACTTGTCAGAAGGACGAGAACATCATGAGCTCCATGCAGCTGTTTGAGAA
CGTCATCTAGGACATGTAGGAGGGGACCCTGGGTGGCCATGGGTTCTCAACCCAGAGAAGCCTCAATCCTGACAGGAGAA
GCCTCTATGAGAAACATTTTTCTAATATATTTGCAAAAAGTG

RAT P19 PROTEIN (PARTIAL)

FEDFVVGLSILLRGTVREKLKWAFNLYDINKDGYITKEEMLAIMKSIYDMMGRHTYPILREDAPLEHVERFFQKMDRNQD
GVVTIDEFLETCQKDENIMSSMQLFENVI

FIG. 17

MOUSE P19 DNA (CD: 49-819)

CGGGCTGCAAAGCGGGAAGSTTAGTGACGGTCCCTTTCAGCAGCAGAGATGCAGAGGACCAAGGAAGCCGTGAAGGCATC
AGATGGCAACCTCCTGGGAGATCCTGGGCGCATACCACTGAGCAAGAGGGAAAGCATCAAGTGGCAAAGGCCACGGTTCA
CCCGCCAGGCCCTGATGCGTTGCTGCTTAATCAAGTGGATCCTGTCCAGTGCTGCCCCACAAGGCTCAGACAGCAGTGAC
AGTGAACTGGAGTTATCCACGGTGCGCCATCAGCCAGAGGGCTTGGACCAGCTACAAGCTCAGACCAAGTTCACCAAGAA
GGAGCTGCAGTCCCTTTACCGAGGCTTCAAGAATGAGTGTCCCACAGGCCTGGTGGATGAAGACACCTTCAAACTCATTT
ATTCCCAGTTCTTCCCTCAGGGAGATGCCACCACCTATGCACACTTCCTCTTCAATGCCTTTGATGCTGATGGGAACGGG
GCCATCCACTTTGAGGACTTTGTGGTTGGGCTCTCCATCCTGCTTCGAGGGACGGTCCATGAGAAGCTCAAGTGGGCCTT
CAATCTCTATGACATTAACAAGGATGGTTGCATCACCAAGGAGGAGATGCTGGCCATCATGAAGTCCATCTACGACATGA
TGGGCCGCCACACCTACCCCATCCTGCGGGAGGATGCACCCCTGGAGCATGTGGAGAGGTTCTTTCAGAAAATGGACAGG
AACCAGGATGGAGTGGTGACCATTGATGTATTTCTGGAGACTTGTCAGAAGGATGAGAACATCATGAACTCCATGCAGCT
GTTTGAGAACGTCATCTAGGACATGTGGGAGGGGACCCCAGTGGTCATTGCTTCTCAACCCAGAGSAGCCTCAATCCTGA
CAGGAGAAGCCTCTATGAGAAACATTTTTCTAATATATTTGCAAAAAGTGAGCAGTTTACTTCCAAGACACAGCCACCGT
CACACACAGACACAGACATACAGACACACACACACACACACACACATGGTTCCTCTGGCTTGGCCAAGGAAGTGGCAGCC
AGAAGGCACCCCCGCCTATTCCTAGGTCAATAAAAAAGGCTGCCTCTGGGATGGCCAGCCCTGGCTAGATGTTACCCACA
AGGAACTCAGAGATCGAGAGGACCAGGTCTACAAAGCTAAGGTCCCTGTGTCTTTTCTACCACTCGGGAGATCAAACTAC
TCCCTGCCTATGGACCCATGCTCTTAGGAAGCTCCCAGAAACTCCAAGGGGACAAAGAGGGGAGAGGTCTATAGGAAGAA
ATGGTTTTGGAAGCTGGGCTTGCAGCCTTATGCTAATGATCACCTGGGGTCCTGGAACCCGAGTGCCAGGCTACCTACTA
TGCCGTGAGCTTAGATAGTGAGGGGCCATTGGACTAAGACCTCCTGTAAGAGTGGGGCAGGATTGAGGTTTTTGGAGAAA
CTGAGGAAACAATTTGTCCATACCACTGGGTGAAGACTGCTGGCCAGTGGGAATGTGGCTGGTGGAGATTTCCCAACTTC
CAGCACCAGGATGGCCTCTCCAAGGTCCTCTTTGATTCCCTGGGGAGATCACCTGGCTCATAGACTGACAACCAGGGAAC
TGGGCTGAAATGGGACGTCTGGTAGGGGGCATCCCCCTCCTTTTCCCTGGCCACTTGCCACCCAGTTCCTTAACACAGTG
GATCGGCCACACCTCTGTGGCTGCCCTTGAACAGACTCATCCCGACCAAGACAAAAAAGCACTAACTCCTAGCAGCTCAG
GCCAAGCCCACAAGGGAAGGCCTGGGTCCCTGCAGCCCTGATTCAGTGGCCGAGGAAGACGCTCAGACATCCATCCTGTA
CCTCGGAGCCTTGGGGGTCTCACAGCCCTTTCCCAGCCCAGCTCGCCAACATTCTAAAGCACAAACCTGCGGATTCTGCT
TGCTTGGGCTGCGCCCTGGGGATTGAAGGCCACTGTTAACCCTAAGCTGGAGCTAGCCCTGAGGGCTGGGGACCTGTGAC
CAGGCAACAGGTCAGCAGACCCTCAGGAGGAGAGAGAGCTGTTCCTGCCTCCCCAGGCCTCGCCCAGAAGGAACAGTGTC
CCAAGAAGCATGTTTCCTGGAGGAACATCCCCACAAAAGTACATTCCATCATCTGAAGCCCGGTCTCTGCTCAGGCCTGC
CTCTGAAAGTCCACGTGTGTTCCCCAGAAGGCCAGCCCAAGATAAGGGAGGTCCTTAGAGGAAGGACAGGGTGACAACA
CCCCTATACACAGGTGGACCCCCCCTCTGAGGACTGTACTGACCCCATCTCCATCCTGACCGGGGCCTTCCTTTACCCGA
TCTACAGACCACCAGTTCTCCCTGGCTCAGGGACCCCCTGTCCCCAGTCTGACTCTTCCCATCGAGGTCCCTGTCTTGT
GAAAAGCCAAGGCCACGGGAAAAGGCCACCACTCTAACCTGCTGCATCCCTTAGCCTCTGGCTGCACGCCCAACCTGGAG
GGGTCTGTCCCCTTTGCAGGGACACAGACTGGCCGCATGTCCGCATGGCAGAAGCGTCTCCCTTGGGTGCAGCCTGGAAG
GGTGGTTTCTGTCTCAGCGCCCACCAATATTCAGTCCTATATATTTTAATAAAAGAAACTTGACAAAGGAAAAAAAAAAA
AAAA

FIG. 18

>AI 352454 (partial) cds = 1-339

CACGAGGTGGAAAGCATTTCGGCTCAGCTGGAGGAGGCCAGCTCTACAGGCGGTTTCCTGT
ACGCTCAGAACAGCACCAA
GCGCAGCATTAAAGAGCGGCTCATGAAGCTCTTGCCCTGCTCAGCTGCCAAAACGTCGTCTC
CTGCTATTCAAAACAGCG
TGGAAGATGAACTGGAGATGGCCACCGTCAGGCATCGGCCCGAAGCCCTTGAGCTTCTGGA
AGCCCAGAGCAAATTTACC
AAGAAAGAGCTTCAGATCCTTTACAGAGGATTTAAGAACGTAAGAACTTTCTTTTTGACTTT
ACCTTCACACAATTCCCA
GAGGAGCATTGAGAAATGAgaggaaaaggggaaaatatcccattctatgagaagccccatcatatgtatatttcatact
gatccttcccagataggaatataatcagtatctgtggactttgaatctctgtggcacacccatgctggcatactgtaatt
gcccattaaacaaanagttttgagaaaaaaaaaaaaaaaaaaaaaaaaa

>AI352454

HEVESISAQLEEASSTGGFLYAQNSTKRSIKERLMKLLPCSAAKTSSPAIQNSVEDELEMATVRHR
PEALELLEAQSKFT
KKELQILYRGFKNVRTFFLTLPSHNSQRSIEK

FIG. 19

P193 (AA349365) DNA (CD:2-127, patial)

```
TGAAAGGTTCTTCGAGAAAATGGACCGGAACCAGGATGGGGTAGTGACCATTGAAGAGPTCCTGGAGG
CTGTCAGAAGGATGAGAACATCATGAGCTCCATGCAGCTGTTTGAGAATGTCATCTAGGACACGTCCAAA
GGAGTGCATGGCCACAGCCACCTCCACCCCCAAGAAACCTCCATCCTGCCAGGAGCAGCCTCCAAGAAA
CTTTTAAAAAATAGATTTGCAAAAAGTGAACAGATTGCTACACACACACACACACACACACACACACAC
ACACACACACAGCCATTCATCTGGGCTGGCAGAGGGGACAGAGTTCAGGGAGGGGCTGAGTCTGGCTAG
GGGCCGAGTCCAGGAGCCCCAGCCAGCCCTTCCCAGGCCAGCGAGGCGAGGCTGCCTCTGGGTGAGTGG
CTGACAGAGCAGGTCTGCAGGCCACCAGCTGCTGGATGTCACCAAGAAGGGGCTCGAGTGCCCCTGCAG
GGGAGGGTCCAATCTCCGGTGTGAGCCCACCTCGTCCCGTTCTCCATTCTGCTTTCTTGCCACACAGTGGG
CCGGCCCCAGGCTCCCCTGGTCTCCTCCCCGTAGCCACTCTCTGCCCACTACCTATGCTTCTAGAAAGCCC
CTCACCTCAGGACCCCAGAGGGACCAGCTGGGGGCAGGGGGGAGAGGGGGTAATGGAGGCCAAGCCT
GCAGCTTTCTGGAAATTCTTCCCTGGGGGTCCCAGGATCCCCTGCTACTCCACTNACCTGGAAGAGCTGG
GTACCAGGCCACCCACTGTGGGGCAAGCCTGAGTGGTGAGGGGCCACTGGGCCCCATTCTCCCTCCATGG
CAGGAAGGCGGGGATTTCAAGTTTAGGGATTGGGTCGTGGTGGAGAATCTGAGGGCACTCTCTGCCAG
CTCCACAGGGTGGGATGAGCCTCTCCTTGCCCCAGTCCTGGTTCAGTGGGAATGCAGTGGGTGGGGCIGT
ACACACCCTCCAGCACAGACTGTTCCCTCCAAGGTCCTCTTAGGTCCCGGGAGGAACGTGGTTCAGAGAC
TGGCAGCCAGGGAGCCCGGGGCAGAGCTCAGAGGAGTCTGGGAAGGGGCGTGTCCCTCCTCTTCCTGTA
GTGCCCCTCCCATGGCCCAGCAGCTTGGCTGAGCCCCCTCCTGAAGCAGTGTCGCCGTCCCTCTGCCTT
GCACAAAAAGCACAAGCATTCCTTAGCAGCTCAGGCGCAGCCCTAGTGGGAGCCCAGCACACTGCTTCT
CGGAGGCCAGGCCCTCCTGCTGGCTGAGGCTTGGGCCCAGTAGCCCCAATATGGTGGCCCTGGGGAAGA
GGCCTTGGGGGTCTGCTCTGTGCCTGGGATCAGTGGGGCCCCAAAGCCCAGCCCGGCTGACCAACATTCA
AAAGCACAAACCCTGGGGACTCTGCTTGGCTGTCCCCTCCATCTGGGGATGGAGAATGCCAGCCCAAAG
CTGGAGCCAATGGTGAGGGCTGAGAGGGCTGTGGCTGGGTGGTCAGCAGAAACCCCCAGGAGGAGAGA
GATGCTGCTCCCGCCTGATTGGGGCCTCACCCAGAAGGAACCCGGTCCCAGGCCGCATGGCCCCTCCAGG
AACATTCCCACATAATACATTCCATCACAGCCAGCCCAGCTCCACTCAGGGCTGGCCCGGGGAGTCCCCG
TGTGCCCCAAGAGGCTAGCCCCAGGGTGAGCAGGGCCCTCAGAGGAAAGGCAGTATGGCGGAGGCCATG
GGGGCCCCTCGGCATTCACACACAGCCTGGCCTCCCCTGCGGAGCTGCATGGACGCCTGGCTCCAGGCTC
CAGGCTGACTGGGGCCTCTGCCTCCAGGAGGGCATCAGCTTTCCCTGGCTCAGGGATCTTCTCCCTCCC
CTCACCCGCTGCCCAGCCCTCCCAGCTGGTGTCACTCTGCCTCTAAGGCCAAGGCCTCAGGAGAGCATCA
CCACCACACCCCTGCCGGCCTTGGCCTTGGGGCCAGACTGGCTGCACAGCCCAACCAGGAGGGGTCTGC
CTCCCACGCTGGGACACAGACCGGCCGCATGTCTGCATGGCAGAAGCGTCTCCCTTGGCCACGGCCTGGG
AGGGTGGTTCCTGTTCTCAGCATCCACTAATATTCAGTCCTGTATATTTTAATAAAATAAACTTGACAAAG
GAAAAAAAAAAAAAAAAAA
```

P193 PROTEIN (PARTIAL)

ERFFEKKDRNQDGVVTIEEFLEACQKDENIMSSMQLFENVI

FIG. 20

Human 9q genomic DNA sequences:

A. exon1 sequence (with introns included):

CGGGAGGAGAGAGGCAGCTCGGCTCGGCTCCGCGCTCAGCTCCGCTCTGCCTCCGGCTCTGCGCTCACCTGCTGCCT
AGTGTTCCCTCTCCTGCTCCAGGACCTCCGGGTAGACCTCAGACCCCGGGCCCATTCCCAGACTCAGCCTCAGCCCG
GACTTCCCCAGCCCCGACAGCACAGTAGGCCGCCAGGGGGCGCCGTGTGAGCGCCCTATCCCGGCCACCCGGCGCCC
CCTCCCACGGCCCGGGCGGGAGCGGGGCGCCGGGGGCCATGCGGGGCCAGGGCCGCAAGGAGAGTTTGTCCGATTCC
CGAGACCTGGACGGCTCCTACGACCAGCTCACGGGTGAGTCAGTGACGTGGGGGTCGCGGGAGGGAGGGTGGATTCC
ATTCCTCCAGACCCTTCCGCCTCTCCGACCCCGGCCTGGCCCGCACCAACACTCTGCCCCATTCCCAGGCACTCTTA
TGGCCGGTCTGGGCGGCAGGACACTGGGGGTTCAAAGCCTTGGGTCCCGCAGGGGTTGGGGAGGAACAGAAGAGGCA
GGTGTGGAGAGGCAGCAGGTGTGGGCGTATGTGACACAGGGCTGAGAGGGTGTCTGGAGTGGGAGGTGTTACCGTGC
GTGAGCACCTGTCATTCTGTGTGTGTGTGTGTGTGCGCGCGCACCTCCCACAGCTGGTTGCCATGTGCCCTGGGC
TTGGTGACAGCTAGGGTGAGTGTGATTGTATGTGGCAGTGCAATTGTATGGTCTCGTCAGATGTTTGAGTTTGCGTA
GGACCCTGGTTGTACTGATGAAGTTGTTTTGACCATGTGTCTYTATGTGCAACGATGTGTTGTGAGTGTGTAATTCT
GTATGAAAGTGGTGTGTAACTACCAGAATGTGTCAGGGCTCTACTTTAGGGTGGCTTGTCTCTTTG

B. Exon 2-11 sequence (with introns included):

AGCCNANTGGGTCNCCATGTGTATGCATCCTGTTTACTTAGGTCACATTTGTATATGTTGTGTAAGGAGTACCAGGT
CAATGTGTGTGTGTGTGTGAGCATGNATAAACGCCANCAGGTGTGAGTTANTGAATATCAAGCTGTCACTGGCACCC
ATCACTGTGATGTATTGTTCATACATGTCACNAACACGGCCTGTCACTGTAGGTGTGTGTATRAGAGAGGTGTTCTT
ACCCAGGCAATCCTTGGGTTGGACATCATCNTGAGAGGTCCAGCCATGGCACTTGAGCCAAGGGTACTAGGTCAGCA
AAGACATTGAGGCCACTGCCACCTCATCCTTGCCGCCTCGCTGTCACCGGCCACGTCCCATTAAACCAAGTGCNTGA
GCCTCACCTCTATGGACTCACTGGGCTCCCCTAACCCGATTCCAACCACCCTTGCCATTCCTTTCCTCCCCTTAATT
CCTCCCCCAGCCCGGTCCCCAGATGGGGTTGATTTGTGACTGGCGGGGAGGGGACAGGGAACAGAGGGACCCCGGGA
GTTAATGTGCCTTCCTGGGGTCTTCTCTCTTCNCAGGCCACCCTCCAGGGCCCACTAAAAAAGCGCTGAAGCAGCGA
TTCCTCAAGCTGCTGCCGAGCTGCGGGCCCCAAGCCCTGCCCTCAGTCAGTGAAAGCAAGTGCCTCTCATGTGCTTC
CCGGGGCGGGGCTCGATGTGTGCGTGCGTGTCTGTGCATGANTGTGTGCGCGTGTGCCCCAGGCCTGCRAGTGTKCS
CATGYTCCAGGCTTGCATGTGTGGGGGGGCGTGCCCCAAGCCTKSGTGTTTGGGGGTGGGGCCTGCCCCAVGCCTGT
GCGTGTGTATGTGTGTGCATGTGCGCRCGAGCGTRCCCCAGACCGGCGTGTGTGTGTGGGGGCGTGCCCTACCCC
TGCATGTGTGTGGAGGGCGTGCCCCAKGCCCKCGGCGNGTTGTTTGTTGTATGGGAAGGCGTACCGCACGCCTGC
GTGTGGGGGAGGGGCGTGCCCCAGAGCCTGCGTGCGTGTGTGTGTGTGTGTGTGTGTGTGTGGGCGTGACCAGCG
TGGCGAGGGCGGGTGCTGGCAAGGCTGGAGCATAAGNGGGCGNGGCTACATGTGTGNGTGTACGNCTGAAGCCAGCG
TGTGTGGGCGTGGTCAGTTGGNAGCGGGTGTGTGTCACCGCTCCCGCAAAACTGTGGGACCCGAGAGTGTGGGTGTG
ACCATTGTGACCAGGNTGAGGCCTGAGCCTGTGTAGCTGTGGCGGCCTGTGTAGACCAGGCGGCCGTGAGGGTCTGT
ATGTGGCTTAGCTGGGTTAGTGTCTTCAACTCCGTGCGGCCGCCCCCTTCCCCACCGTGTTTTGGACCCCTGATGTG
TGTTGCCTATGCCCCGACAGGATGGTGACAGGTGTAGAGGATGGCGCCTGCCCTCCTCCAGACGCCAGGGTATTTGG
GTTTTCTGTGCCAGCCTGGTCCCCTGCTGAAGTGATCTCCAGTTGAGTGACCTCGCTTTGTCTCTAGGTCTCCATTT
CCTCAGTTGGGCCTTGCCCACCTCATAGGATCATACTGCATTTTGCAAACCATAAAGGCCCGCTTTGTAGTTATTTG
AGCATGCTGTTGTGTTGGACTTAGATGGGTCCCACACGGGGGTGGATTCGGARAAGGACAGGCGTGAGTCCCGCAAG
CTTGTGTGCATGGGGTCCGTTTCGTGTGTGTCTGTCTGGTTGGGTGTGCCTTTGCACGGGCTGGGTTGTCAGGTTT
GCTCTGAGTGTGAGGGGCCAGGTGTGTGTATGCAGTTGGCCGGGTCTTCCGCTTTCTCGGTGWCAGTTCGCTCCCTT
CAGCATTAGCCGCCCCAGCCTCCCTCCGCCCCCACAGACCCCGCCTGCTGGACCCAGGTGACTTACGCTCCTGGTGG
GGGCGGGGCGGGGCAGGGCGGCTTTGCCATCTTGGGGTGGGGGGCACTTGCCTGGGGCTGGACGTTGGGGCGGGG
CAGGATTGAGATGGGGCTGGGCGGGGCGAGGGGAGGGGCTGGGTGGGACGAGGGGAGGGTTTGGGCGGGGCAAGGCT
GGGATAGATGGGGCTGGGCGGGGCGAGGGGAGGGGCTGGGTGGGACGAGGGGAGGGTTTGGGCGGGGCAAGCCTGGG
GCTGGGCGGATCTGAGTTGGTCCCCGAAGGCCCGGAGCTCTGACCCTCAGACGCCCCTCTTGAACTGGCTTTTCCC
ACTCCTCCCTTTCTAAAACGAAGATGCGGCTGGGGCCTTCCCCTCCAACGAGGGATCGAGGGCCGCGGGGCGAGCA
CTGAGTCGGATCCCTGGCTCTGGGCCAGGCCAGGCCTTGGCCCGCTGATAGACCTCGAAGATGGCCATCATCTTTT
CTCCTTACCTCAGTGTCCTTGGCTCGGGCCCAGGGAACTGGCAGCCTGGTCTCCGGCATCGGATGGGACCGGGGGG
CGGGGAGGGCGTGAATGGGCAGTGATTTGAAGAGGGGTCGCGGAGGCTGGGCATGAGGCGCGGCTGTCCTCACCGC
TCCCGCAGACAGCGTGGACGATGAATTTGAATTGTCCACCGTGTGTCACCGGCCTGAGGGTCTGGAGCAGCTGCAGG
AGCAAACCAAATTCACGCGCAAGGAGTTGCAGGTCCTGTACCGGGGCTTCAAGAACGTGAGTGCNGGGCGAGGCCAA

FIG. 22A

```
ACTCAGCGNGGGTGGGACAGGAGGACCCAANCCGGTCCANATTTTTCCCANAAAGCATGGCTTNGATGCTTGAGGNG
CGGGCGGAAGGGAGGCAAGGCCCTGAGACTGAACTTCTAGCTGGAGGTTCTGGGGCGGGGCCAGAACGRAAGTGGCG
CCTGTAGACTGTCAGTTTCGTTCCATGTTTTTTATTTGTGCACTGGGAAAGAAGTCTTCCCTCCCATCACATGAGCC
ACGTGGTGAGTCCTCTGGAGGCTTGAAGATTATCCCCCTCCCTGGGAGTCTTGGGCCATGGAGGGTGGGGCGGTGA
ACGGAAGGGGATTTTGTCTCTGCCCTCAGCCTGGTGCCCTCTCCTTCCAGGAATGTCCCAGCGGAATTGTCAATGAG
GAGAACTTCAAGCAGATTTACTCCCAGTTCTTTCCTCAAGGAGGTGAGGGGACAAGGCCCAAGGGGAAGCAGTTGTC
CTTCTCTAGGCTGAGGGAGGGAGGGATTCTGGAGGAGCTGGGAATGCCAAGGTGATGGGGGGTATGGGGAGCTCCTT
AGAGGGAGGAAGTCCTCTCCTGTGTGGAAGCCAACTTCTCCACACTCACCCTGCAGACTCCAGCACCTATGCCACTT
TTCTCTTCAATGCCTTTGACACCAACCATGATGGCTCGGTCAGTTTTGAGGTGAGCTGGGCGAGGTGGGCCAGGGAA
GCCTGTTTCCTGGAGTTCAGGGCCAGGATCTCCAGGCCAAACCCAGAGAAGGAGTTGGGTGAAGAGKACCCGAGGAC
ACAGCTCCCTNCTGCCTTCTTCCCAGGACTTTGTGGCTGGTTTGYCCGTGATTCTTCGGGAACTGTAGATGACAGG
CTTAATTGGGCCTTCAACCTGTATGACCTTAACAAGGACGGCTGCATCACCAAGGAGGTGCAGGGCAACTGAAGGGC
TGGGGGTCTGTGGCGGTGATGGGGGTGGCGTGCAKAGGGTGATGGGAGGGAAATATGACCCACATATGCCCACAAGC
AATGGGATCAAGGGAGGCTGGAGGCTCTGAGGAAGGATCCTCTTCTCTCTTGGCCTAACAGGAAATGCTTGACATCA
TGAAGTCCATCTATGACATGATGGGCAAGTACACGTACCCTGCACTCCGGGAGGAGGCCCCAAGGGAACACGTGGAG
AGCTTCTTCCAGGTACTTGGGAGTGGGTATGGCTGGAGGGCCCTGGAGTGAAGGGAAGAAGGCCAAGAACCAGCAGG
GAACTCACCTGACTTCTGTCTGCCTCTCTCTTGCCATCCCTCCTGTTCTCCCTGCCTGACCACCTTCTTGCAGAAGA
TGGACAGAAACAAGGATGGTGTGGTGACCATTGAGGAATTCATTGAGTCTTGTCAAAAGGTACAGCTCCCTGCCCTC
TACATTACCCTGACCTGGACTCAGGCCTGATTTAGTAATGCAGGGAAAAGCTTCTTTGGGAAGAATACCACCTTCCC
ACCTCACCCCCATATTTCAATCCTATTCCTTTGTGGGAGGCTTACCCCTTCCCTACCTCAGGTCTCTCTGGGCATCT
CCTTCCTCTGTGCTTTTGAATGTCCCCGTCTGTGACTCAAGTGTCCCTCTCACTGTCTCTGATAAAGCTCCTTCTCT
TTCTCTCTCTTCAATCTGCCTCGCTCACATCATGGCCACAGGATGAGAACATCATGAGGTCCATGCAGCTCTTTGAC
AATGTCATCTAGCCCCCAGGAGAGGGGGTCAGTGTTTCCTGGGGGGACCATGCTCTAACCCTAGTCCAGGCGGACCT
CACCCTTCTCTTCCCAGGTCTATCCTCATCCTACGCCTCCCTGGGGGCTGGAGGGATCCAAGAGCTTGGGGATTCAG
TAGTCCAGATCTCTGGAGCTGAAGGGGCCAGAGAGTGGGCAGAGTGCATCTCGGGGGGTGTTCCCAACTCCCACCAG
CTCTCACCCCCTTCCTGCCTGACACCCAGTGTTGAGAGTGCCCCTCCTGTAGGAATTGAGCGGTTCCCCACCTCCTA
CCCCTACTCTAGAAACACACTAGACAGATGTCTCCTGCTATGGTGCTTCCCCCATCCCTGACCTCATAAACATTTCC
CCTAAGACTCCCCTCTCAGAGAATGCTCCATTCTTGGCACTGGCTGGCTTCTCAGACCAGCCATTGAGAGCCCTG
TGGGAGGGGGACAAGAATGTATAGGGAGAAATCTTGGGCCTGAGTCAATGGATAGGTCCTAGRAGGTGGCTGGGGTT
GAGAATAGAAGGGCCTGGACAGATTATGATTGCTCAGGCATACCAGGTTATAGCTCCAAGTTCCACAGGTCTGCTAC
CACAGGCCATCAAAATATAAGTTTCCAGGCTTTGCAGAAGACCTTGTCTCCTTAGAAATGCCCCAGAAATTTTCCAC
ACCCTCCTCGGTATCCATGGAGAGCCTGGGGCCAGATATCTGGCTCATCTCTGGCATTGCTTCCTCTCCTTCTTTCC
TGCATGTGTTGGTGGTGGTTGTGGTGGGGGAATGTGAATGGGGGATGTCCTGGCTGATGCCTGCCAAAATTTCATCC
CACCCTCCTTGCTTATCGTCCCTGTTTTGAGGGCTATGACTTGAGTTTTTGTTTCCCATGTTCTCTATAGACTTGGG
ACCTTCCTGAACTTGGGGCCTATCACTCCCCACAGTGGATGCCTTAGAAGGGAGAGGGAAGGAGGGAGGCAGGCATA
GCATCTGAACCCAGTGTGGGGCATTCACTAGAATCTTCAATCAACCTGGGCTCTCCCCACCCCACCCCAGATAACC
TCCTCAGKTCCCTAGGGTCTCTTCTYGCTTGACTCAATCTACCCAGAGATGCCCCTTAGCACACCTAGAGGGCAGGG
ACCATAGGACCCAGGTTCCAACCCCATTGTCAGCACCCCAGCCATGCGGCCACCCCTTAGCACACCTGCTCGTCCCA
TTTAGCTTACCCTCCCAGTTGGCCAGAATCTGAGGGGAGAGCCCCAGAGAGCCCCCTTCCCCATCAGAAGACTGTT
GACTGCTTTGCATTTTGGGCTCTTCTATATATTTTGTAAAGTAAGAAATATACCAGATC:TAATAAAACACAATGGC
TATGCACAGGCTGCCGTCTCTGCCTTTTGTCCCTCCCACCTACAAATACTACACAACCCCTAACGAATGCACCTGCA
GCCTTTTAGATCCCCAAGAAAGTGGCTTTCTTTTCCATAGTTGGCCATACCTTGGCATGAGACTGAGACACAGGCTC
TGGAATGGTTGGAAACCCACCCAACCTCAGGCCCCCACATGAATCTCCCTCCCACACAGCCTGAGAGGAGACAAGGA
AGGAAGGACAGGACACTGATGTCCCGAAGACTGTGCCAAGCAAGCTGTTTTTTAGCTGACATTCTTACAAGTTGAAT
CACAGATTTCTAATTTACAGACTTTTTAGTTAATCTCAAAGTGCTTTCTTTTGAGGGGCCTCCTTTAAGTTCYTTCT
TTTTTTTTTTTTTTT
```

FIG. 22B

>monkey KChIP4 cds = 265 gtcgacccacgcgtccggtgcgctgtggagcgggggggagccccgccagccaaatgccaggatcagcatgagaggctgg
actttagtccaggtctgtcctcaccccgggggaccgccggcttttgcagggtgcagctgcgaggaactgctcacttttttc
cccttgcaagtctttgttccaagcctgacgttgctacgattctgtaattaactccctccactccaaagcgggtctggagcc
tgggatgctctgccagctcagaggATGTTGACTCTGGAGTGGGAGTCCGAAGGACTGCAAACAGTGGGTA
TTGTTGTGAT
TATATGTGCATCTCTGAAGCTGCTTCATTTGCTGGGACTGATTGATTTTTCGGAAGACAGCGT
GGAAGATGAACTGGAGA
TGGCCACTGTCAGGCATCGGCCTGAGGCCCTTGAGCTTCTGGAAGCCCAGAGCAAATTTACC
AAGAAAGAGCTTCAGATC
CTTTACAGAGGATTTAAGAACGAATGCCCCAGTGGTGTTGTTAATGAAGAAACCTTCAAAGA
GATTTACTCGCAGTTCTT
TCCACAGGGAGACTCTACAACATATGCACATTTTCTGTTCAATGCGTTTGATACGGACCACA
ATGGAGCTGTGAGTTTCG
AGGATTTCATCAAAGGTCTTTCCATTTTGCTCCGGGGACAGTACAAGAAAAACTCAATTGG
GCATTTAATCTGTATGAT
ATAAATAAAGATGGCTACATCACTAAAGAGGAAATGCTTGATATAATGAAAGCAATATACG
ACATGATGGGTAAATGTAC
ATATCCTGTCCTCAAAGAAGATGCACCCAGACAACACGTCGAAACATTTTTTCAGAAAATGG
ACAAAAATAAAGATGGGG
TTGTTACCATAGATGAGTTCATTGAAAGCTGCCAAAAAGATGAAAACATAATGCGCTCCATG
CAGCTCTTTGAAAATGTG
ATTTAActtgtcaactagatcctgaatccaacagacaaatgtgaactattctaccacccttaaagtcggagctaccactt
ttagcatagattgctcagcttgacactgaagcatattatgcaaacaagctttgttttaatataaagcaatcccaaaaga
tttgagtttctcagttataaatttgcatcctttccataatgccactgagttcatgggatgttctaactcatttcatactc
tgtgaatattcaaaagtaataaatctggcatatagtttattgattccttagccatgggattattgaggctttcacata
tcagtgattttaaaataccagtgtttttgctctcatttgtatgtattcagtcctaggattttgaatggttttttctaatat
actgacatctgcatttaatttccagaaattaaattaattttcatgtctgaatgctgtaattccatttatatactttaagt
aaacaaataagattactacaattaaacacatagttccagtttctatggccttccctccaccttctattataaattaat
tttatctggtatttttaaacatttaaaaatttatcatcagatatcagcatgcctaatatgcctaatgaaacttaata
agcatttaattttccatcatacattatagccaaggcctatatactatatataattttggatttgtttaatcttcaggct
gttttccattgtatcatcaagtggaagttcaagacggcatcaaacaaaacaaggatgtttacagacatatgcaaagggtc
aggatatctatcctccagtatatgttaatgcttaataacaagtaatcctaacagcattaaaggccaaatctgtcctctt
ccctgacttccttacagcatgtttatattacaagccattcagggacaaagaaaccttgactaccccactgtctactagg
aacaaacaaacagcaagcaaaattcactttgaaagcaccagtggttccattacattgacaactactaccaagattcagta
gaaaataagtgctcaacaactaatccagattacaatatgatttagtgcatcataaaattccaacaattcagattattttt
aatcatctcagccacaactgtaaagttgccacattactaaagacacacacatcgtccctgttttgtagaaatatcacaaa
gaccaagaggctacagaaggaggaaatttgcaactgtctttgcaacaataaatcaggtatctattctggtgtagagatag
gatgttgaaagctgccctgctatcaccagtgtagaaattaagagtagtacaatacatgtacactgaaatttgccatcgcg
tgtttgtgtaaactcaatgtgcacattttgtatttcaaaaagaaaaaataaaagcaaaataaaatgttwawaamwmwaaa
aaaaaaaaaaaa >monkey KChIP4

MLTLEWESEGLQTVGIVVIICASLKLLHLLGLIDFSEDSVEDELEMATVRHRPEALELLEAQSKFT
KKELQILYRGFKNE
CPSGVVNEETFKEIYSQFFPQGDSTTYAHFLFNAFDTDHNGAVSFEDFIKGLSILLRGTVQEKLNW
AFNLYDINKDGYIT
KEEMLDIMKAIYDMMGKCTYPVLKEDAPRQHVETFFQKMDKNKDGVVTIDEFIESCQKDENIM
RSMQLFENVI

FIG. 23

>monkey KChIP4 C terminal splice variant cds = 265-966 gtcgacccacgcgtccggtgcgctgtggttgcggggggagccccgccagccaaatgccaggatcagcatgagaggctgg
actttagtccaggtctgtcctcaccccggggaccgccggctttgcaggtgcagctgcgaggaactgctcactttttc
cccttgcaagtctttgttccaagcctgacgttgctacgattctgtaattaactccctccactccaaagggtctggaggc
tgggatgctctgccagctcagaggATGTTGACTCTGGAGTGGGAGTCCGAAGGACTGCAAACAGTGGGTA
TTGTTGTGAT
TATATGTGCATCTCTGAAGCTGCTTCATTTGCTGGGACTGATTGATTTTTCGGAAGACAGCGT
GGAAGATGAACTGGAGA
TGGCCACTGTCAGGCATCGGCCTGAGGCCCTTGAGCTTCTGGAAGCCCAGAGCAAATTTACC
AAGAAAGAGCTTCAGATC
CTTTACAGAGGATTTAAGAACGAATGCCCCAGTGGTGTTGTTAATGAAGAAACCTTCAAAGA
GATTTACTCGCAGTTCTT
TCCACAGGGAGACTCTACAACATATGCACATTTTCTGTTCAATGCGTTTGATACGGACCACA
ATGGAGCTGTGAGTTTCG
AGGATTTCATCAAAGGTCTTTCCATTTTGCTCCGGGGACAGTACAAGAAAAACTCAATTGG
GCATTTAATCTGTATGAT
ATAAATAAAGATGGCTACATCACTAAAGAGGAAATGCTTGATATAATGAAAGCAATATACG
ACATGATGGGTAAATGTAC
ATATCCTGTCCTCAAAGAAGATGCACCCAGACAACACGTCGAAACATTTTTTCAGGCTGTTT
TCCATTGTATCATCAAGT
GGAAGTTCAAGACGGCATCAAACAAAACAAGGATGTTTACAGACATATGCAAAGGGTCAGG
ATATCTATCCTCCAGTATA
TGTTAAtgcttaataacaagtaatcctaacagcattaaaggccaaatctgtcctctttcccctgacttccttacagcatg
tttatattacaagccattcagggacaaagaaaccttgactaccccactgtctactaggaacaaacaaacagcaagcaaaa
ttcactttgaaagcaccagtggttccattacattgacaactactaccaagattcagtagaaaataagtgctcaacaacta
atccagattacaatatgatttagtgcatcataaaattccaacaattcagattattttaatcatctcagccacaactgta
aagttgccacattactaaagacacacacatcgtccctgttttgtagaaatatcacaaagaccaagaggctacagaaggag
gaaatttgcaactgtctttgcaacaataaatcaggtatctattctggtgtagagataggatgttgaaagctgccctgcta
tcaccagtgtagaaattaagagtagtacaatacatgtacactgaaatttgccatcgcgtgtttgtgtaaactcaatgtgc
acattttgtatttcaaaaagaaaaaataaaagcaaaataaaatgttwawaamwmwaaaaaaaaaaaaaaaa >monkey KChIP4 C terminal splice variant MLTLEWESEGLQTVGIVVIICASLKLLHLLGLIDFSEDSVEDELEMATVRHRPEALELLEAQSKFT
KKELQILYRGFKNE
CPSGVVNEETFKEIYSQFFPQGDSTTYARFLFNAFDTDHNGAVSFEDFIKGLSILLRGTVQEKLNW
AFNLYDINKDGYIT
KEEMLDIMKAIYMMGKCTYPVLKEDAPRQHVETFFQAVFHCIIKWKFKTASNKTRMFTDICK
GSGYLSSSIC

```
Kchip1_1v    ------------------------------------------------------------
Kchip2_9q1   MRGQGRKESLSDSRDLDGSVDQLIGHPPGETKKAIKQRFLKLLPCCGPQALPSVSETLAA
Kchip3_p19   --MQPAKEVTKAS----DGSLLGDIGH---TPLSKKEGIKWQRPRLSRQALMRCCLVKWI
Kchip4_352   ---MLTLFWESEGLQTVGIVVIICAS----IKLLHLLGLIDFSE----------------
Kchip4_231   ---MLTLFWESEGLQTVGIVVIICAS----IKLLHLLGLIDFSE----------------
hsncspara    ----HEVESISAQLEAASSTGFLYAQN-STKRSIKERLMKLLECS---------------

KChip1_1v    ------------SKDKIEDELEMTVCHRPEGLEQLEAQTNFTKRELQVLYRGFKNECPS-
Kchip2_9q1   PASLRPHRPRLLDPDSVDDEFEISTVCHRPEGLEQIQEQTKFTKRELQVLYRGFKNECPS
Kchip3_p19   LSSTAPQ-----GSDSDSELEISTVRHQPEGLDQIQAQTKFTKKELQSLYRGFKNECPT
KChip4_352   ---------------DSVEDELEMATVRHRPEALELLEAQSKFTKKELQILYRGFKNECPS
KChip4_231   ---------------DSVEDELEMATVRHRPEALELLEAQSKFTKKELQILYRGFKNECPS
hsncspara    -AAKTSSP---AIQNSVEDELEMATVRHRPEALELLEAQSKFTKKELQILYRGFKNVRTF KChip1_1v    GVVNEDTFKQIYAQFFPHGDASTYAHYLENAFDTTQTGSVKFEDFVTALSILLRGTVHEK
KChip2_9q1   GIVNEENFKQIYSQFFPQGDSSTYATFLFNAFDINHDGSVSFEDFVAGLSVILRGTVDDR
KChip3_p19   GLVDEDTFKLIYAQFFPQGDATTYAHFLFNAFDADGNGAIHFEDFVVGLSILLRGTVHEK
KChip4_352   GVVNEETFKEIYSQFFPQGDSTTYAHFLFNAFDTDHNGAVSFEDFIKGLSILLRGTVQEK
KChip4_231   GVVNEETFKEIYSQFFPQGDSTTYAHFLFNAFDTDHNGAVSFEDFIKGLSILLRGTVQEK
hsncspara    FLTLPSHNSQRSIEK---------------------------------------------

KChip1_1v    LRMIFNLYDINKDGYINKEEMMDIVKAIYDMMGKYTYPVLKEDTPRQHVDVFFQKMD---
KChip2_9q1   LNWAFNLYDLNKDGCITKEEMLDIMKSIYDMMGKYTYPALREEAPREHVESFFQKMD---
KChip3_p19   IKWAFNLYDINKDGYITKEEMLAIMKSIYDMMGRHTYPILREDAPAEHVERFFEKMD---
KChip4_352   LNWAFNLYDINKDGYITKEEMLDIMKAIYDMMGKCTYPVLKEDAPRQHVETFFQKMD---
KChip4_231   LNWAFNLYDINKDGYITKEEMLDIMKAIYDMMGKCTYPVLKEDAPRQHVETFFAVFHCI
hsncspara    ------------------------------------------------------------

KChip1_1v    ----KNKDGIVTLDEFLESCQEDDNIMRSLQLFQNVM-----------------------
KChip2_9q1   ----RNKDGVVTIEEFIESCQKDENIMRSMQLFDNVI-----------------------
KChip3_p19   ----RNQDGVVTIEEFLEFLEACQKDENIMSMQLFENVI--------------------
KChip4_352   ----KNKDGVVTIDEFIESCQKDENIMRSMQLFENVI-----------------------
KChip4_231   IKWKFKTASNKTRMFTDICKGSGYLSSSIC-----------------------------
Hsncspara    ------------------------------------------------------------
```

Rat 33b07 protein

MNGVEGNNELPLANTSTSALVPEDLDLKQDQPLSEETDTVREMEAAGEAGAEGGASPDSEHCDPQLCLRVAENGCAAAAG
EGLEDGLSSSKCGDAPLASVAANDSNKNGCQLAGPLSPAKPKTLEASGAVGLGSQMMPGPKKTKVMTTKGAISATTGKEG
EAGAAMQEKKGVQKEKKAAGGGKDETRPRAPKINNCMDSLEAIDQELSNVNAQADRAFLQLERKFGRMRRLHMQRRSFII
QNIPGFWVTAFRNHPQLSPMISGQDEDMMRYMINLEVEELKHPRAGCKFKFIFQSNPYFRNEGLVKEYERRSSGRVVSLS
TPIRWHRGQEPQAHIHRNREGNTIPSFFNWFSDHSLLEFDRIAEIIKGELWSNPLQYYLMGDGPRRGVRVPPRQPVESPR
SFRFQSG.

Rat 33b07 DNA (coding: 85-1308)

GGTGGAGCTAAGCACTCACTGCGGTGCTGCCCTGCGTCTGCAGAGAACAAGGAAAGCTTCTCTGCAGGGCTGTCAGCTGC
CAAAATGAACGGCGTGGAAGGGAACAACGAGCTCCCTCTCGCTAACACCTCGACCTCCGCCCTTGTCCCGGAAGATCTGG
ATCTGAAGCAAGACCAGCCGCTCAGCGAGGAAACTGACACGGTGCGGGAGATGGAGGCTGCAGGTGAGGCCGGTGCGGAG
GGAGGCGCGTCCCCCGATTCGGAGCACTGCGACCCCCAGCTCTGCCTCCGAGTGGCTGAGAATGGCTGTGCTGCCGCAGC
GGGAGAGGGGCTGGACGATGGTCTGTCTTCATCAAAGTGTGGGGACGCACCCTTGGCGTCTGTGGCAGCCAACGACAGCA
ATAAAAATGGCTGTCAGCTTGCAGGGCCGCTCAGCCCTGCTAAGCCAAAAACTCTGGAAGCCAGTGGTGCAGTGGGCCTG
GGGTCGCAGATGATGCCAGGGCCGAAGAAGACCAAGGTAATGACTACCAAGGGCGCCATCTCTGCGACTACAGGCAAGA
AGGAGAAGCAGGGGCGGCAATGCAGGAAAAGAAGGGGGTGCAGAAAGAAAAAAGGCAGCTGGAGGAGGGAAAGACGAGA
CTCGTCCTAGAGCCCCTAAGATCAATAACTGCATGGACTCCCTGGAAGCCATCGATCAAGAGCTGTCAAATGTAAATGCG
CAAGCTGACAGGGCCTTCCTCCAGCTGGAACGAAATTTGGGCGGATCAGAAGGCTCCACATGCAGCGCCGAAGTTTCAT
CATCCAAAACATCCCAGGTTTCTGGGTCACAGCGTTTCGGAACCACCCGCAACTGTCACCGATGATCAGTGGCCAAGATG
AAGACATGATGAGGTACATGATCAATTTAGAGGTGGAGGAGCTTAAGCACCCAAGAGCAGGGTGCAAATTTAAGTTCATC
TTCCAAAGCAACCCCTACTTCCGAAATGAGGGGCTGGTCAAAGAGTACGAGCGCAGATCCTCAGGTCGAGTGGTGTCGCT
CTCTACGCCAATCCGCTGGCACCGGGGTCAAGAACCCCAGGCCCATATCCACAGGAATAGAGAGGGGAACACGATTCCCA
GTTTCTTCAATTGGTTCTCAGACCACAGCCTCCTAGAATTCGACAGAATAGCTGAAATTATCAAAGGGGAGCTTTGGTCC
AATCCCCTACAATACTACCTGATGGGCGATGGCCACGCAGAGGAGTTCGAGTCCCACCAAGGCAGCCAGTGGAGAGTCC
CAGGTCCTTCAGGTTCCAGTCTGGCTAAGCTCTGCCCTCGTGAGAAGCTCTTACAGAAGAGTCCTTACCACCTTCTCAGC
TTGGCTAGCAGCATGCAGCCTTCTGTCTGCTTCTCTTCCTTGGATTGTGTCCTTTGGTTCTTCTAAGTCTCCGGTAGTT
TCAAGGTTGTGGCTTCCAAGTCTTTGCTCTTCTTTCTCTTGGCCATCACGATGTCCTGCATAGTGTTAATGGTGTTCCAA
GTGCATGGCCTCCAAACTGCTTCTATGCCAAGCTCACGTGCTGTAGTTTGTACTGCTTTTCTTTCCATGGCTTGGTTCCT
GTCTGTGATCTTCTAGGTTTTTTGTTTTCTTTTTTAAAAGTTGGTTCTCTATCAAAAGAAAGCTTGACATATCCTTACCAA
GAACTAGCCAGATTTCATACTGTGTTCCCGATATCTATGTACTGTGAAGAACTGTGAGTTTCGCCACTGCAAGATGGGAC
TGTATCCCAATCCAGCCATCAGCCCAACAGGACATTCCAAGCTGTCACCAACTGATCCTAGCTGTCTTCCTGGGCCTTTG
CCATTTACCCTGCTTTTTATCTATAGAATGAGCAGGTGGCTGGTAGGTGACTACTAGGTAAGAGTGAAGTATTAGGTGAG
GAGTGTTTTCTGTCACCACATTGTTCTTGTACCAATGCATCATGATCAGCTTGGATCAGCTACTGACTGTCTGATATTTC
TAACCCCCAACACAAAAAAAAAAAAAAAAAAAAAAAAAAAAAAAAAAAA

FIG. 26

Human 33b7 (106d5) DNA (coding: 88-1332)

```
GGGGTGGTGCTAGACGTTTCGGGCAGAGCTCGGCCGCTGCGGAGGACAAGGAACTCTCCCTCTCCCACTAGTCTGACTTC
TTCCAAAATGAGCGGCCTGGATGGGGGCAACAAGCTCCCTCTCGCCCAAACCGGCGGCCTGGCTGCTCCCGACCATGCCT
CAGGAGATCCGGACCTAGACCAGTGCCAAGGGCTCCGTGAAGAAACCGAGGCGACACAGGTGATGGCGAACACAGGTGGG
GGCAGCCTGGAGACCGTTGCCGAGGGGGGTGCATCCCAGGATCCTGTCGACTGTGGCCCCGCGCTCCGCGTCCCAGTTGC
CGGGAGTCGCGGCGGTGCAGCGACCAAAGCCGGGCAGGAGGATGCTCCACCTTCTACGAAAGGTCTGGAAGCAGCCTCTG
CCGCCGAGGCTGCTGACAGCAGCCAGAAAAATGGCTGTCAGCTTGGAGAGCCCCGTGGCCCTGCTGGGCAGAAGGCTCTA
GAAGCCTGTGGCGCAGGGGGCTTGGGGTCTCAGATGATACCGGGGAAGAAGGCCAAGGAAGTGACGACTAAAAAACGCGC
CATCTCGGCAGCAGTGGAAAAGGAGGGAGAAGCAGGGGCGGCGATGGAGGAAAAGAAGGTAGTGCAGAAGGAAAAAAAGG
TGGCAGGAGGGGTGAAAGAGGAGACACGGCCCAGGGCCCCGAAGATCAATAACTGCATGGACTCACTGGAGGCCATCGAT
CAAGAGTTGTCAAACGTAAATGCCCAGGCTGACAGGGCCTTCCTTCAGCTTGAGCGCAAGTTTGGCCGCATGCGAAGGCT
CCACATGCAGCGCAGAAGTTTCATTATCCAGAATATCCCAGGTTTCTGGGTTACTGCCTTTCGAAACCACCCCCAGCTGT
CACCTATGATCAGTGGCCAAGATGAAGACATGCTGAGGTACATGATCAATTTGGAGGTGGAGGAGCTTAAACACCCCAGA
GCAGGCTGCAAATTCAAGTTCATCTTTCAGGGCAACCCCTACTTCCGAAATGAGGGGCTTGTCAAGGAATATGAACGCAG
ATCCTCTGGCCGGGTGGTGTCTCTTTCCACTCCAATCCGCTGGCACCGAGGCCAAGACCCCCAGGCTCATATCCACAGAA
ACCGGGAAGGGAACACTATCCCTAGTTTCTTCAACTGGTTTTCAGACCACAGCCTTCTAGAATTCGACAGAATTGCAGAG
ATTATCAAAGGAGAACTGTGGCCCAATCCCTACAATACTACCTGATGGGTGAAGGGCCCCGTAGAGGAATTCGAGGCCC
ACCAAGGCAGCCAGTGGAGAGCGCCAGATCCTTCAGGTTCCAGTCTGGCTAATCTCTGTCCTGTGAGAAGCTTCTGCACA
AGTTTCCTTACCACCTCCTCTTGGACCTATGCTTGGCCAACAGCATGCAGTCTTCCATCTGCTTTCTCTTCATACTGTGG
ATTATCTTTTCCTTTGGTTCTAAATCTTCAGTAATCGGTTGCAAGATTGTTGGCTTACCTGCCTGTGCCATTCTTCCTCT
GGGCCTTCATGCTTTTCTGCATTGTGTTAACATGTTTCAAGTGCATGGCCTTCTACGGCTTCTATGCCAAGCGTATGATA
CTATAGATATAGTGTACCATACTGCCTTTCTTTGCATGGCTTGGACCCTATCTGTGACCATGCTCTTCTCCCAATTTAAG
TGGTTCTGTACCACAAAGAATCTTGATACATTTTCACAAATAACTGATTGGGCTTCATACTTTATGCTGGCTGTGTCCTG
ATACCCATGTACTTATGGTAAGCTATTTGGGTATTACCACTGCAAGACAAAACTGATATCTTAACCCGGCCATCAACCCA
AATTGGACATTCCAGACTACCACCAACTGGATCCCAGCTGCCTTCCTGGGCTTGTGCCATCCACCCTACTGGTTATCTGA
TAGAACAAGCTGGTGGCTGATGGGTGACTGCTAGGCGTGACTGAGGTAATAGATGAAAAGTGTTCTATGTTATCACATTG
GTTTTCCTGTACCTTTGGTTACTCTACGTCATGACCAGCTGCTGGTGAGTATGAAGCCTGTGCTATAGCCCACCCCTACT
CACTCTCACCTTCTGGTTGAACTTTGCTTAGGCCACCATTGTCTGCCTCATCAGGAACTATCTGTAGACGTAGCTCCCAG
GGAGCTCACAGCAACACCCCCTACCACCAGGATGGGCAGTAATATGTGACAGAGCCCAAAGCAAGGCTGGAACGCAGTCC
CTTCCAGCTTAGTCTTTCTGACTCCTAGCCAACAAACCATCCTTAATGTGAGCAACTTCTTTAGGCATTTCCTCTTTTCC
CCGCCTGCACCCACTCTGAACATGACAAAAGTTGCCAGAGTTGGGCATTGAGGAAGAGATATTTCTGGAATGTGAGACT
TGTTATGCCTCTGTCTCTTTCTCTCCCTCCCCCTCCCCTCTCCCTCCCCCTCTCCCTCCCATCCCTTTTCTTCCCTTTCA
CTCTGAAGCAGTTTTAGCTTATTAACAGAAAACAAAACTGGCAAAGCAGGCTTTTTGTTTAATTTGCTCTTTCCCTGATT
GTGTTCAGAGAGAAAGGTTATGATTAAATGGGCTCCAGATCTCTTATTGCCCTTATTCCTCCACCCCACTTCTTTTAGCA
AGGTCTGAAAGTTTCAAAGGGAGACCTATAGGTTAATTGTTTAGTTATAGGCAGTGTTAAATTAGGCAGATTTTGACATA
TTTATCTTTTTACCCCATCCATTCTACCAAAACCTGTGTATTTCTTGAGTTTTTAGTTTGAGAAGCTGGAAAGAGAGAGA
AGGGCCTCACAGTGATGGGTTCAGGACGGGTCAAAGGCAAAGGCCTTTGTGATGTGAGCAAAGGCAACCAAAACTTAGCC
TCACTCCACTTTTCTAAAGATGGAAATTCTTTTTTGGGCCTTGGACTGCTTCTAGGGTAGCATTTTGTAGGTCACTCTTC
TCCTTTGTACTATTTTGTTTCTGCCCTGATGTCCCTTGGGTCTCCATCCTACTGCCTGGCTTTCTTGGCCCTCATTTCTC
AGCTTCTGCATTTCCTTCCCTGCTCCTAACAAATGAAGAAGCAGGCTGCAGCCTGCATTGTGAAGATCTCCAGCCTCCT
TGTAGGGGATAAGGGGATGTGTAGCATCTGTGTGGATTTTCACGGACAAGTTCCAGTAGGTGGGACAGTGATGCCGTCAA
GGCTTAGTTATGATCATGTGTGGTGATAAAGACCATCCACCATCACCCTTTTCCCCTTTGGTTTTGAAGGCCTTGCCCTA
AGCTACCTGAGGGTTTAGGAGGTCTGAACACACACAGTGGAGAGGTTAATCTAGGTTGGGAAACTGAGTAAAAGTCCAGA
GCAGGAATGAGCCTGCTGTGGCGTGGGTTTGGAAAGGCTCACAGGAAAGAACCTGCAGGATCAGGGGTGGGAGGGGAGGC
CCCTGAGGTGCTCTCCAGGGAAGAGGGGCTGGGGTTTAAATAGCATGCTTGGAGGAAGATTTTCCTTCAATTTTTCCTAA
GTCCTTGAATTCACCAGTAGATTTTTGTAAACAAAATGTAAGTCGATGTTTTCTCTCAATTATCCTAGGAGTGACCTTTA
TATGTGTGGAAGATTAATGGTATATGCTCCTTATGTCACTGTTTTTCAGTAAAATCCATTTCCTTTCTCTGTTTCAGCCT
ATGACAAAATTGATGTTTACAGGCCTGCTTTTTGCTTATAATTGACAACATGTGCAAAAATACCAAATTTGTGTCCTGTG
CAGTATGAAGAATTCAGTGAATATTCATTAATGTATTAGCTTGTTTTGCTCTCTGTTCATATATGGCTCTATTCTTAGAA
ATATAATTTGAATGTGATCTTTCAATAGTCTGAATATTTTACAAATTATAGCTATGTCTTGTGAAAATAAACCTCAAAAG
AAAAATACGACTCTGTTGTCTTACTTGATATTTCTTGCCCTAGTAATGTACTTGACATTTATGTTCCTAAGCAGTGTAAG
TACCAGTAGAATTTCTCTGTCAAACTCAATGATCATTTAGTACTTTTGTCTTCTCCCATGTGCTTGAAGGAAAAATAAAG
TGTCACTACCGTATTTCTTGTTTTCATCAAAAAATAAAAATAATTTAAAAAACAAAAAAAAAAAAAAA
```

FIG. 27A

Human 33b7 (106d5) protein

MSGLDGGNKLPLAQTGGLAAPDHASGDPDLDQCQGLREETEATQVMANTGGGSLETVAEGGASQDPVDCGPALRVPVAGS
RGGAATKAGQEDAPPSTKGLEAASAAEAADSSQKNGCQLGEPRGPAGQKALEACGAGGLGSQMIPGKKAKEVTTKKRAIS
AAVEKEGEAGAAMEEKKVVQKEKKVAGGVKEETRPRAPKINNCMDSLEAIDQELSNVNAQADRAFLQLERKFGRMRRLHM
QRRSFIIQNIPGFWVTAFRNHPQLSPMISGQDEDMLRYMINLEVEELKHPRAGCKFKFIFQGNPYFRNEGLVKEYERRSS
GRVVSLSTPIRWHRGQDPQAHIHRNREGNTIPSFFNWFSDHSLLEFDRIAEIIKGELWPNPLQYYLMGEGPRRGIRGPPR
QPVESARSFRFQSG

FIG. 27B

Rat 1p protein (partial)

LKGARPRVVNSTCSDFNHGSALHIAASNLCLGAAKCLLEHGANPALRNRKGQVPAEVVPDPMDMSLDKAEAALVAKELRT
LLEEAVPLSCTLPKVTLPNYDNVPGNLMLSALGLRLGDRVLLDGQKTGTLRFCGTTEFASGQWVGVELDEPEGKNDGSVG
GVRYFICPPKQGLFASVSKVSKAVDAPPSSVTSTPRTPRMDFSRVTGKGRREHKGKKKSPSSPSLGSIQQREGAKAEVGD
QVLVAGQNRDCAFLWEDRLCSRLLVWH

Rat 1p DNA (partial, coding:1-804)

CTGAAAGGGGCGAGGCCCAGGGTGGTGAACTCCACCTGCAGTGACTTCAACCATGGCTCAGCTCTGCACATCGCTGCCTC
GAATCTGTGCCTGGGCGCCGCCAAATGTTTACTGGAGCATGGTGCCAACCCAGCGCTGAGGAATCGAAAAGGACAGGTAC
CAGCGGAAGTGGTCCCAGACCCCATGGACATGTCCCTTGACAAGGCAGAGGCAGCCCTGGTGGCCAAGGAATTGCGGACG
CTGCTAGAAGAGGCTGTGCCACTGTCCTGCACCCTTCCTAAAGTCACACTACCCAACTATGACAACGTCCCAGGCAATCT
CATGCTCAGCGCGCTGGGCCTGCGTCTAGGAGACCGAGTGCTCCTCGATGGCCAGAAGACGGGCACGCTGAGGTTCTGCG
GGACCACCGAGTTCGCCAGTGGCCAGTGGGTGGGCGTGGAGCTAGATGAACCGGAAGGCAAGAACGACGGCAGCGTTGGG
GGTGTCCGGTACTTCATCTGCCCTCCCAAGCAGGGTCTCTTTGCATCTGTGTCCAAGGTCTCCAAGGCAGTGGATGCACC
CCCCTCATCTGTTACCTCCACGCCCCGCACTCCCCGGATGGACTTCTCCCGTGTAACGGGCAAAGGCCGGAGGGAACACA
AAGGGAAGAAGAAGTCCCCATCTTCCCCATCTCTGGGCAGCCTGCAGCAGCGTGAAGGGGCCAAAGCTGAAGTTGGAGAC
CAAGTCCTTGTGGCAGGCCAGAACAGGGATTGTGCGTTTCTATGGAAGACAGACTTTGCTCCAGGTTACTGGTATGGCA
TTGAACTGGACCAGCCCACGGGCAAGCATGACGGCTCTGTGTTCGGTGTCCGGTACTTTACCTGTGCCCGAGGCACGGG
GTCTTTGCACCAGCATCTCGTATCCAGAGGATTGGTGGATCCACTGATCCCCCTGGAGACAGTGTTGGAGCAAAAAAGT
GCATCAAGTGACAATGACACAGCCCAAACGCACCTTCACAACAGTCCGGACCCCAAAGGACATTGCATCAGAGAACTCTA
TCTCCAGGTTACTCTTCTGCTGCTGGTTTCCTTGGATGCTGAGGGCGGAGATGCAGTCTTAGAGACCTGGATACCTGACA
CAGAGACAGAGTCCCCTCTAGCATCTCCTGACACAAGGAGACCCCAGTCACCCTAAGATAGAGATTCCCAGTGACACCTC
CAGAATAGAAACCCCGTTAGCCAGCCCTCGATTACTGAGGTCCCATTATTAACAGATCTCCCATGACGACTCCCCCAAAT
ACAGACCTCATGTTACCCCAAAAGAGATTCCCTGAGTAGCACCTTCAGGCTAGTCCCTGTCCCTACCCCTCAGAGCAGA
TTTCCCCCAATAAACATTTTCCACATCACCCAAGGGATGCTGACCCTCTCCACGACAGGACGTTCTTGAGTTACCAGTGG
ATTAGAGTCCCATGAATGAAGACCCCCCCCACCCCGGTTCTCCTTAAGCATAGGTCATACCTCCAGAATAGCCAGCCACA
TCACTATCCCCATGTAACATCAGTCTCCTCAAAATGGCGTGAGGTCACTAGAAAGACCTTATACTCTCCTCTCCTTCTCA
GAGATGCCCTCCATTCACTTAAGTCCCTGTTCTCACCCCTGAACAAGACACCTAATTAACCGGCCCACTCACCTCAATTA
CAAACACCAAAATCGTCCTGGAAGCATGAATTACAGGACAGCAAGTCTTCCTGCCCTCTGCACCCTTGAGAAACCCCCAG
TGCCTTGTATGAAGCCCACCCCACATGGCCCACAGTCCCTGTGCTGGCCAAGGCTCCCAGAAAATTCTCTATTTTTTAAA
GTAATAACTTCCCCCCCTTTGGGGGATCCCCAAATTTGGAGACCCCATTCTAGAACACTGGGGAGTTCAAATTCCAGAG
AGAATATATATTATATATAATCCCCAATTCCCCATGCTTCCAAGCCCTACAATCTCTAGAAGACCCCAAATTTCTAATTC
CCAGGACTTCCCCTACCCAAGTCACAGAATCTTCAAATCCCCAGGGAATCCCAAACTTAAGATACCAATCCCAAACCCTC
AGGAAATCCCCCAACACAAGGTCCTTAGGACCGGGAGGAAGGAACCTGTTGCCAGGAGAACATCCCAGGCTCTCAGGGCA
TCTCAAACCTGACTCCCAGGCACCAGGAGACCCCAAACAGAAAGTCCCATCTTTGGAACAAGGATAGGACTCTAATACCC
TTAGTCCATGGATCTTTAATTTCCCAACCTCCAAACTCCATGGGCCCCACCCTCAAGGGAACCCCAAGATCCAAATCTC
TGATAACTAATATGTGCAGGGCCCCAGGGCTCTAACAGGACCCCAAATCATGGAGTCCCTACTTCAATCTACCTTCTGGT
CACAGGTCCAAGACACTAAATCTGAGTCATTGGCCCCAAAGGACTTCACAGCACCTGGGCCAGACTAACAGCCTGAGGGA
GAACCTGAGGGCCCCGTGGGTCCAGAGCAGACCTGGGGCCCTGACCACCAAGGACAGCTCACGACTGCCCCTTCACTGCA
TGTCCCTAAACTCAGCATGACTCCTGTCCTCTTCAATAAAGACGTTTCTATGGCAAAAAAAAAAAAAAAAAAAAAAAAAA
AAA

FIG. 28

Rat 7s Protein (partial)

ADSTSRWAEALREISGRLAEMPADSGYPAYLGARLASFYERAGRVKCLGNPEREGSVSIVGAVSPPGGDFSDPVTSATLG
IVQVFWGLDKKLAQRKHFPSVNWLISYSKYMRALDEYYDKHFTEFVPLRTKAKEILQEEEDLAEIVQLVGKASLAETDKI
TLEVAKLIKDDFLQQNGYTPYDRFCPFYKTVGMLSNMISFYDMARRAVETTAQSDNKITWSIIREHMGEILYKLSSMKFK
DPVKDGEAKIKADYAQLLEDMQNAFRSLED

Rat 7s DNA (partial, coding: 1-813)

GCTGACTCTACCTCTAGATGGGCTGAGGCCCTCAGAGAAATCTCTGGTCGCTTAGCTGAAATGCCTGCAGATAGTGGATA
CCCTGCATACCTTGGTGCCCGACTGGCTTCTTTCTATGAGCGAGCAGGCAGAGTGAAATGTCTTGGAAACCCTGAGAGAG
AAGGGAGTGTCAGCATTGTAGGAGCAGTTTCTCCACCTGGTGGTGATTTTTCTGATCCAGTCACATCTGCTACTCTGGGT
ATTGTTCAGGTGTTCTGGGGCTTGGATAAGAAGCTAGCTCAGCGCAAGCACTTCCCGTCCGTCAACTGGCTCATTAGCTA
CAGCAAGTACATGCGCGCCCTGGACGAGTACTATGACAAACACTTCACAGAGTTCGTGCCTCTGGAGACCAAAGCTAAGG
AGATTCTGCAGGAAGAGGAGGATCTGGCGGAAATCGTGCAGCTCGTGGGAAAGGCGTCTTTAGCAGAGACAGATAAAATC
ACCCTGGAGGTAGCAAAACTTATCAAAGATGACTTCCTACAACAAAATGGGTACACTCCTTATGACAGGTTCTGTCCATT
CTATAAGACGGTGGGGATGCTGTCCAACATGATTTCATTCTATGATATGGCCCGCCGGGCTGTGGAGACCACCGCCCAGA
GTGACAATAAGATCACATGGTCCATTATCCGTGAGCACATGGGGGAGATTCTCTATAAACTTTCCTCCATGAAATTCAAG
GATCCAGTGAAGGATGGCGAGGCAAAGATCAAGGCCGACTACGCACAGCTTCTTGAAGATATGCAGAACGCATTCCGTAG
CCTGGAAGATTAGAACTGTGACTTCTCTCCTCCTCTTCCGCAGCTCATATGTGTATATTTTCCTGAATTTCTCATCTCCA
ACCCTTTGCTTCCATATTGTGCAGCTTTGAGACTAGTGCCTCGTGCGTTCTCGTTCATTTTGCTGTTTCTTGGTAGGTC
TTATAAAACACACATTCCTGTGCTCCGCTGTCTGAAGGAGCTCCTGACCTTTGTCTGAAGTGGTGAATGTAGTGCATATG
ATACACAGTGTAACATACACATTGTAACATATACGTTCTGTAAACTTGTATGTAAGGTGACTACCCCTTCCCTCCTCTCC
AGTAAACTGTAAACAGGACTACTGCATGTGCTCTATTGGGGATGGAAGGCCAGATCTCCATACCGTGGACAGGTACATAA
GGAAACTAGACCACTTGCAACTTAGTGTTTGTTGAGTAACCATTTTGCAGGAAGTATTTCCATTTAAAAAACAAAAGATT
AATGTTCCAATTATTTGTAGCTTCCCCAGTATCAATCAGGACTGTTTGTGGCGCACTTGGGAACTATTTTGTTTTCCTAA
CAGACGTTTGCAAGGCTGAACGTAATAGATAAATCAGTTCCCTCTGAAAGTGTGAAAGTAAAAGAGAGCTAGGTGGTCA
GACTTAAATTGACATCGTCTTGTTTAAGCATATTTTATTTCACTGAGAGATTTAATATCAAGGACTTTTATATACTCAAT
TACTAGGAAATCTTTTTTTAAGTACAATTTAAAAATCATTGAAAATGTGATCCACATCATAGCCATTTTCCTTATATTTA
GTCAGATGAGCTCAGAGTGGGGAGGGTGTGGGTTAGAATACCACAAGGACACGCAGCAGTGCCTGCAGGCAGTGTGGCCG
GGGGCCAGAGCGGCATTGTTTTCACGAGGTACGTGTGTGGCGTGTGTGTTTGCTTGTTGACACTCTGAAAACAGCAAGCT
TACCAGTTCCAGGAAATATTTTGTTTTCTTTCACTGGCTCAGAAAGCTCCTCAAAGTACCTGGTCCCTGAAGCTTCCTAT
CTGTTAATAGAGACGAGAGAGGTTCTTAAATTTAACTGGTGACAAAACAAAAGAAAAAAAAGATCGATTTTTGTCTTGC
TGTTTTGGTGTGTTTAAATAATAATTCCATATTTGCATAACGAGGCTCGCTTCTGAGAGCTTGGAGATCGTGCTCCCTCT
TCACTCTCCGGGGTGATAATGCTGGCGCCATGCTACCTCTTCAGGAGGGGAAGGGGATTGAACATGGCTAACACTCTCAA
GTACACAAGCGTAACGACAAAGTATTTATTTTAAGCCTTGGTATGTTGTTTAAATTATTAGGTGGTGCATTTCTTATGGT
CTTTTGGGTAGACATAGTATACACTTCAGATGTAATGTGTAAATCCTTGCTAGTGCATGTCTACACGATAGACTGCTATT
CAAGAAGGATATTCTTCCACATAACAATTTAAAAACTATTAAATCAGATATGGATTATGCAATGACTTGTTGAGAGGTGG
ATTAACGGTGCTGCTTAATCAGTTTGCTTCCAATATGGCTTCGTATCCAGAAGCCCTGACTAGTGGAGATGAGAAAGATT
TCAAAACCTGTCTGCCTACACCTACCAGCAACCTAGGCTTGTGATCAGAATGAATGATCCCAAGAAACTACTTGACCAAG
TGTGTTTTGTTGTCCTGGATTTGAGATGTGCGTTCTTCCTCCCTCTGAGACTGTTGATGTATGAGTGTGAAGAAGTTACA
GAAACAACGCTCAGATTTTCACGGTAACTTTCCCTCTGCCCACACTGTAGAGTTTCAGATTGTTCACTGATAGTGCTTCT
TTCGTAAGGATGTGTTAAAATATAGCAGTCTTTTTAAAAGATTATGCAGTTCTCTATTTATTGTGCTGTGCCTGGTCCTA
AGTGCAGCCGGTTAAACAAGTTTCATATGTATTTTTCCAGTGTTAAATCTCATACCTATGCCCTTTGGAAAGCTCCATCC
TGAACAATGAATAGAAGAGGCTATATAAATTGCCTCCTTATCCTTAAGCATTTCACTATCTTTATGTTAAGAGTAATGTAT
AATTATTAAAATCTATGAAAAATAAAAAGTGGATTTAAATTAAGAGATC

FIG. 29

Rat 29x protein

ARLPAPEHARQQPLLSGPEPGSSARVPVPGVASRRQPRGGKPPSGDGLESGPSPRPLLHARGEAGLHRQSGRVPHTGTAY
FADEPTEAQAPGGFCVSPSLLGVRWPACATRTPGSLPLSPPSAQPRTLWPTPPAGPSSRMVARNQVAADNAISPASEPRR
RPEPSSSSSSSSPAAPARPRPCPVVPAPAPGDTHFRTFRSHSDYRRITRTSALLDACGFYWGPLSVHGAHERLRAEPVGT
FLVRDSRQRNCFFALSVKMASGPTSIRVHFQAGRFHLDGSRETFDCLFELLEHYVAAPRRMLGAPLRQRRVRPLQELCRQ
RIVAAVGRENLARIPLNPVLRDYLSSFPFQI

Rat 29x DNA (coding: 433-1071)

GCACGGCTCCCGGCCCCGGAGCATGCGCGACAGCAGCCCCTCCTCtCCGGCCCTGAGCCCGGATCGTCCGCCCGGGTTCC
AGTTCCCGGCGTGGCCAGTAGGCGGCAGCCGCGAGGCGGCAAGCCACCCAGCGGGGACGGCCTGGAGTCGGGCCCCTCTC
CACGCCCCCTTCTCCACGCGCGCGGGAGGCAGGGCTCCACCGCCAGTCTGGAAGGGTTCCACATACAGGAACGGCCTAC
TTCGCAGATGAGCCCACCGAGGCTCAGGCTCCGGGCCGATTCTGCGTGTCACCCTCGCTCCTTGGGGTCCGCTGGCCGGC
CTGTGCCACCCGGACGCCCGGCTCACTGCCTCTGTCTCCCCCATCAGCGCAGCCCCGGACGCTATGGCCCACCCCTCCAG
CTGGCCCCTCGAGTAGGATGGTAGCACGTAACCAGGTGGCAGCCGACAATGCGATCTCCCCGGCATCAGAGCCCCGACGG
CGGCCAGAGCCATCCTCGTCCTCGTCTTCGTCCTCGCCGGCGGCCCCGGCGCGTCCCCGGCCCTGCCCGGTGGTCCCGGC
CCCGGCTCCGGCGACACTCACTTCCGCACCTTCCGCTCCCACTCTGATTACCGGCGCATCACGCGGACCAGCGCTCTCC
TGGACGCCTGCGGCTTCTACTGGGGACCCCTGAGCGTGCATGGGCGCACGAACGGCTGCGTGCCGAGCCCGTGGGCACC
TTCTTGGCGGCCGCCAGTCGCCAGCGGAACTGCTTCTTCGCGCTCAGCGTGAAGATGGCTTCGGGCCCCACGAGCATTCG
TGTGCACTTCCAGGCCGGCCGCTTCCACCTGGACGGCAGCCGCGAGACCTTCGACTGCCTCTTCGAGCTGCTGGAGCACT
ACGTGGCGGCGCCGTGGTGCATGTTGGGGGCCCCACTGCGCCAGCGCCGCGTGCGGCCGCTGCAGGAGCTGTGTCGCCAG
CGCATCGTGGCCGCCGTGGGTCGCGAGAACCTGGCACGCATCCCTCTTAACCCGGTACTCCGTGACTACCTGAGTTCCTT
CCCCTTCCAGATCTGACCGGCTGCCGCCGTGCCCGCAGCATTAAGTGGGAGCGCCTTATTATTTCTTATTATTAATTATT
ATTATTTTTcTGGAACCACGTGGGAGCCCTCCCCGCCTAGGTCGGAGGGAGTGGGTGTGGAGGGTGAGATGCCTCCCACT
TCTGGCTGGAGACCTTATCCCGCCTCCTGGGGGGCCTCCCCTCCTGGTGCTCCCTCCCGGTCCCCCTGGTTGTAGCAGCT
TGTGTCTGGGGCCAGGACCTGAACTCCACGCCTACCTCTCCATGTTTACATGTTCCCAGTATCTTTGCACAAACCAGGGG
TGGGGGAGGGTCTCTGGCTTCATTTTTCTGCTGTGCAGAATATTCTATTTTATATTTTTACATCCAGTTTAGATAATAAA
CTTTATTATGAAAGTTTTTTTTTTAAAGAAAAAAAAAAAAAAAAAAAAA

FIG. 30

Rat 25r DNA (coding 130-

```
GGCACGGCTCCCGGCCCCGGAGCATGCGCGACAGCAGCCCCGGAACCCCCAGCCGCGGCGCCCCGCGTCCCGCCGCCAGC
GCAGCCCCGGACGCTATGGCCCACCCCTCCAGCTGGCCCCTCGAGTAGGATGGTAGCACGTAACCAGGTGGCAGCCGACA
ATGCGATCTCCCCGGCATCAGAGCCCCGACGGCGGCCAGAGCCATCCTCGTCCTCGTCTTCGTCCTCGCCGGCGGCCCCG
GCGCGTCCCCGGCCCTGCCCGGTGGTCCCGGCCCCGGCTCCGGGCGACACTCACTTCCGCACCTTCCGCTCCCACTCTGA
TTACCGGCGCATCACGCGGACCAGCGCTCTCCTGGACGCCTGCGGCTTCTACTGGGGACCCCTGAGCGTGCATGGGCGC
ACGAACGGCTGCGTGCCGAGCCCGTGGGCACCTTCTTGGTGCGCGACAGTCGCCAGCGGAACTGCTTCTTCGCGCTCAGC
GTGAAGATGGCTTCGGGCCCCACGAGCATTCGTGTGCACTTCCAGGCCGGCCGCTTCCACCTGGACGGCAGCCGCGAGAC
CTTCGACTGCCTCTTCGAGCTGCTGGAGCACTACGTGGCGGCGCCGCGCCGCATGTTGGGGCCCCACTGCGCCAGCGCC
GCGTGCGGCCGCTGCAGGAGCTGTGTCGCCAGCGCATCGTGGCCGCCGTGGGTCGCGAGAACCTGGCACGCATCCCTCTT
AACCCGGTACTCCGTGACTACCTGAGTTCCTTCCCCTTCCAGATCTGACCGGCTGCCGCCGTGCCCGCAGCATTAAGTGG
GAGCGCCTTATTATTTCTTATTATTAATTATTATTATTTTTCTGGAACCACGTGGGAGCCCTCCCCGCCTAGGTCGGAGG
GAGTGGGTGTGGAGGGTGAGATGCCTCCCACTTCTGGCTGGAGACCTTATCCCGCCTCTCGGGGGCCTCCCCTCCTGGT
GCTCCCTCCCGGTCCCCCTGGTTGTAGCAGCTTGTGTCTGGGGCCAGGACCTGAACTCCACGCCTACCTCTCCATGTTTA
CATGTTCCCAGTATCTTTGCACAAACCAGGGGTGGGGGAGGGTCTCTGGCTTCATTTTTCTGCTGTGCAGAATATTCTAT
TTTATATTTTTACATCCAGTTTAGATAATAAACTTTATTATGAAAGTTTTTTTTTTAAAAAAAAAAAAAAAAAAA
```

FIG. 31

Rat 5p protein

MPSQMEHAMETMMLTFHRFAGEKNYLTKEDLRVLMEREFPGFLENQKDPLAVDKIDLDQCRDGKVGFQSFLSLVAGLI
IACNDYFVVHMKQKK

Rat 5p DNA (coding: 52-339)

CTTCCAAAGACTGCAGCGCCTCAGGGCCCAGGTTTCAACAGATTCTTCAAAATGCCATCCCAAATGGAGCATGCCATGGA
AACCATGATGCTTACATTTCACAGGTTTGCAGGGGAAAAAAACTACTTGACAAAGGAGGACCTGAGAGTGCTCATGGAAA
GGGAGTTCCCTGGGTTTTTGGAAAATCAAAAGGACCCTCTGGCTGTGGACAAAATAATGAAAGACCTGGACCAGTGCCGA
GATGGAAAAGTGGGCTTCCAGAGCTTTCTATCACTAGTGGCGGGGCTCATCATTGCATGCAATGACTATTTTGTAGTACA
CATGAAGCAGAAGAAGTAGGCCAACTGGAGCCCTGGTACCCACACCTTGATGCGTCCTCTCCCATGGGGTCAACTGAGGA
ATCTGCCCCACTGCTTCCTGTGAGCAGATCAGGACCCTTAGGAAATGTGCAAATAACATCCAACTCCAATTCGACAAGCA
GAGAAAGAAAAGTTAATCCAATGACAGAGGAGCTTTCGAGTTTTATATTGTTTGCATCCGGTTGCCCTCAATAAAGAAAG
TCTTTTTTTTTAAGTTCCGAAAAAAAAAAAAAAAAAAAAAA

FIG. 32

Rat 7q protein

MAYAYLFKYIIIGDTGVGKSCLLLQFTDKRFQPVHDLTIGVEFGARMITIDGKQIKLQIWDTAGQESFRSITRSYYRGAA
GALLVYDITRRDTFNHLTTWLEDARQHSNSNMVIMLIGNKSDLESRREVKKEEGEAFAREHGLIFMETSAKTASNVEEAF
INTAKEIYEKIQEGVFDINNEANGIKIGPQHAATNASHGGNQGGQQAGGGCC

Rat 7q DNA (coding 1-639)

ATGGCGTACGCCTATCTCTTCAAGTACATCATCATCGGCGACACAGGTGTTGGTAAATCGTGCTTATTGCTACAGTTTAC
AGACAAGAGGTTTCAGCCGGTGCATGACCTCACAATTGGTGTAGAGTTTGGTGCTCGAATGATAACCATTGATGGAAAC
AGATAAAACTCCAGATCTGGGATACAGCAGGGCAGGAGTCCTTTCGTTCTATCACAAGGTCATATTACAGAGGTGCAGCG
GGGGCTTTACTAGTGTATGATATTACAAGGAGAGACACGTTCAACCACTTGACAACCTGGTTAGAAGACGCCCGTCAGCA
TTCCAATTCCAACATGGTCATCATGCTTATTGGAAATAAAAGTGACTTAGAATCTAGGAGAGAAGTGAAAAAGGAAGAAG
GTGAAGCTTTTGCACGAGAGCATGGACTTATCTTCATGGAAACTTCTGCCAAGACTGCTTCTAATGTAGAGGAGGCATTT
ATTAACACAGCAAAAGAAATTTATGAAAAAATCCAAGAAGGGGTCTTTGACATTAATAATGAGGCAAACGGCATCAAAAT
TGGCCCTCAGCATGCTGCTACCAATGCATCTCACGGAGGCAACCAAGGAGGGCAGCAGGCAGGGGGAGGCTGCTGCTGA

FIG. 33

Rat 19r protein

MVLLKEYRVILPVSVDEYQVGQLYSVAEASKNETGGGEGVEVLVNEPYEKDDGEKGQYTHKIYHLQSKVPTFVRMLAPEG
ALNIHEKAWNAYPYCRTVITNEYMKEDFLIKIETWHKPDLGTQENVHKLEPEAWKHVEAIYIDIADRSQVLSKDYKAEED
PAKFKSIKTGRGPLGPNWKQELVNQKDCPYMCAYKLVTVKFKWWGLQNKVENFIHKQEKRLFTNFHRQLFCWLDKWVDLT
MDDIRRMEEETKRQLDEMRQKDPVKGMTADD

Rat 19r DNA (coding 1-816)

ATGGTGCTGCTCAAGGAATATCGGGTCATCCTGCCTGTGTCTGTAGATGAGTATCAAGTGGGGCAGCTGTACTCTGTGGC
TGAAGCCAGTAAAAATGAAACTGGTGGTGGGGAAGGTGTGGAGGTCCTGGTGAACGAGCCCTACGAGAAGGATGATGGCG
AGAAAGGCCAGTACACACACAAGATCTACCACTTACAGAGCAAAGTTCCCACGTTTGTTCGAATGCTGGCCCCAGAAGGC
GCCCTGAATATACATGAGAAAGCCTGGAATGCCTACCCTTACTGCAGAACCGTTATTACAAATGAGTACATGAAGGAAGA
CTTTCTCATTAAAATTGAAACCTGGCACAAGCCAGACCTTGGCACCCAGGAGAATGTGCATAAACTGGAGCCTGAGGCAT
GGAAACATGTGGAAGCTATATATATAGACATCGCTGATCGAAGCCAAGTACTTAGCAAGGATTACAAGGCAGAGGAAGAC
CCAGCAAAATTTAAATCTATCAAAACAGGACGAGGACCATTGGGCCCGAATTGGAAGCAAGAACTTGTCAATCAGAAGGA
CTGCCCATATATGTGTGCATACAAACTGGTTACTGTCAAGTTCAAGTGGTGGGGCTTGCAGAACAAAGTGGAAAACTTTA
TACATAAGCAAGAGAAGCGTCTGTTTACAAACTTTCACAGGCAGCTGTTCTGTTGGCTTGATAAATGGGTTGATCTGACT
ATGGATGACATTCGGAGGATGGAAGAAGAGACGAAGAGACAGCTGGATGAGATGAGACAAAAGGACCCCGTGAAAGGAAT
GACAGCAGATGACTAG

FIG. 34

Monkey KChIP4c (jlkxa053cO2) DNA sequence (CD: 122-811)

```
CGCTCTCCTCCTCCCCTTTCTCTAGCAGTAGCCTTCTTAATGTAGTTTAATGGCTTTACAAAGAAAGCCAGGCAGAGGAG
CACTTCTCAGTGGCTGTGGTCGGACCATGACCTAGCTGACCATGAACTTGGAAGGGCTTGAAATGATAGCAGTTCTGATC
GTCATTGTGCTTTTTGTTAAATTATTGGAACAGTTTGGGCTGATTGAAGCAGGTTTAGAAGACAGCGTGGAAGATGAACT
GGAGATGGCCACTGTCAGGCATCGGCCTGAGGCCCTTGAGCTTCTGGAAGCCCAGAGCAAATTTACCAAGAAAGAGCTTC
AGATCCTTTACAGAGGATTTAAGAACGAATGCCCCAGTGGTGTTGTTAATGAAGAAACCTTCAAAGAGATTTACTCGCAG
TTCTTTCCACAGGGAGACTCTACAACATATGCACATTTTCTGTTCAATGCGTTTGATACGGACCACAATGGAGCTGTGAG
TTTCGAGGATTTCATCAAAGGTCTTTCCATTTTGCTCCGGGGACAGTACAAGAAAAACTCAATTGGGCATTTAATCTGT
ATGATATAAATAAAGATGGCTACATCACTAAAGAGGAAATGCTTGATATAATGAAAGCAATATACGACATGATGGGTAAA
TGTACATATCCTGTCCTCAAAGAAGATGCACCCAGACAACACGTCGAAACATTTTTTCAGAAAATGGACAAAAATAAAGA
TGGGGTTGTTACCATAGATGAGTTCATTGAAAGCTGCCAAAAAGATGAAAACATAATGCGCTCCATGCAGCTCTTTGAAA
ATGTGATTTAACTTGTCAACTAGATCCTGAATCCAACAGACAAATGTGAACTATTCTACCACCCTTAAAGTCGGAGCTAC
CACTTTTAGCATAGATTGCTCAGCTTGACACTGAAGCATATTATGCAAACAAGCTTTGTTTTAATATAAAGCAATCCCCA
AAAGATTTGAGTTTCTCAGTTATAAATTTGCATCCTTTCCATAATGCCACTGAGTTCATGGGATGTTCTAACTCATTTCA
TACTCTGTGAATATTCAAAAGTAATAGAATCTGGCATATAGTTTTATTGATTCCTTAGCCATGGGATTATTGAGGCTTTC
ACATATCAGTGATTTTAAAATACCAGTGTTTTTTGCTACTCATTTGTATGTATTCAGTCCTAGGATTTTGAATGGTTTTC
TAATATACTGACATCTGCATTTAATTTCCAGAAATTAAATTAATTTTCATGTCTGAATGCTGTAATTCCATTTATATACT
TTAAGTAAACAAATAAGATTACTACAATTAAACACATAGTTCCAGTTTCTATGGCCTTCACTTCCCACCTTCTATTAGAA
ATTAATTTTATCTGGTATTTTTAAACATTTAAAAATTTATCATCAGATATCAGCATATGCCTAATTATGCCTAATGAAAC
TTAATAAGCATTTAATTTTCCATCATACATTATAGTCAAGGCCTATATACTATATATAATTTTGGATTTGTTTAATCTTA
CAGGCTGTTTTCCATTGTATCATCAAGTGGAAGTTCAAGACGGCATCAAACAAAACAAGGATGTTTACAGACATATGCAA
AGGGTCAGGATATCTATCCTCCAGTATATGTTAATGCTTAATAACAAGTAATCCTAACAGCATTAAAGGCCAAATCTGTC
CTCTTTCCCCTGACTTCCTTACAGCATGTTTATATTACAAGCCATTCAGGGACAAAGAAACCTTGACTACCCCACTGTCT
ACTAGGAACAAACAAACAGCAAGCAAAATTCACTTTGAAAGCACCAGTGGTTCCATTACATTGACAACTACTACCAAGAT
TCAGTAGAAAATAAGTGCTCAACAACTAATCCAGATTACAATATGATTTAGTGCATCATAAAATTCCAACAATTCAGATT
ATTTTTAATCACCTCAGCCACAACTGTAAAGTTGCCACATTACTAAAGACACACACATCGTCCCTGTTTTGTAGAAATAT
CACAAAGACCAAGAGGCTACAGAAGGAGGAAATTTGCAACTGTCTTTGCAACAATAAATCAGGTATCTATTCTGGTGTAG
AGATAGGATGTTGAAAGCTGCCCTGCTATCACCAGTGTAGAAATTAAGAGTAGTACAATACATGTACACTGAAATTTGCC
ATCGCGTGTTTGTGTAAACTCAATGTGCACATTTTGTATTTCAAAAAGAAAAAATAAAAGCAAAATAAAATGTTTATAAC
TCTAAAAAAAAAAAAAAAAAAA
```

Monkey KChIP4c protein sequence

```
MNLEGLEMIAVLIVIVLFVKLLEQFGLIEAGLEDSVEDELEMATVRERPEALELLEAQSKFTKKELQILYRGFKNECPSG
VVNEETFKEIYSQFFPQGDSTTYAHFLFNAFDTDRNGAVSFEDFIKGLSILLRGTVQEKLNWAFNLYDINKDGYITKEEM
LDIMKAIYDMMGKCTYPVLKEDAPRQHVETFFQKMDKNKDGVVTIDEFIESCQKDENIMRSMQLFENVI.
```

FIG. 35

Monkey KChIP4d (jlkx015b10) DNA sequence (CD:64-816)

```
GTCGACAGACGCCCCTGGCCGGTGGACTCCTGAGTCTTACTCCTGCACCCTGCGTCCCCAGACATGAATGTGAGGAGAGT
GGAAAGCATTTCGGCTCAGCTGGAGGAGGCCAGCTCCACAGGCGGTTTCCTGTATGCTCAGAACAGCACCAAGCGCAGCA
TTAAAGAGCGGCTCATGAAGCTCTTGCCCTGCTCAGCTGCCAAAACATCGTCTCCTGCTATTCAAAACAGCGTGGAAGAT
GAACTGGAGATGGCCACTGTCAGGCATCGGCCTGAGGCCCTTGAGCTTCTGGAAGCCCAGAGCAAATTTACCAAGAAAGA
GCTTCAGATCCTTTACAGAGGATTTAAGAACGAATGCCCCAGTGGTGTTGTTAATGAAGAAACCTTCAAAGAGATTTACT
CGCAGTTCTTTCCACAGGGAGACTCTACAACATATGCACATTTTCTGTTCAATGCGTTTGATACGGACCACAATGGAGCT
GTGAGTTTCGAGGATTTCATCAAAGGTCTTTCCATTTTGCTCCGGGGACAGTACAAGAAAAACTCAATTGGGCATTTAA
TCTGTATGATATAAATAAAGATGGCTACATCACTAAAGAGGAAATGCTTGATATAATGAAAGCAATATACGACATGATGG
GTAAATGTACATATCCTGTCCTCAAAGAAGATGCACCCAGACAACACGTCGAAACATTTTTTCAGAAAATGGACAAAAAT
AAAGATGGGGTTGTTACCATAGATGAGTTCATTGAAAGCTGCCAAAAAGATGAAAACATAATGCGCTCCATGCAGCTCTT
TGAAAATGTGATTTAACTTGTCAACTAGATCCTGAATCCAACAGACAAATGTGAACTATTCTACCACCCTTAAAGTCGGA
GCTACCACTTTTAGCATAGATTGCTCAGCTTGACACTGAAGCATATTATGCAAACAAGCTTTGTTTTAATATAAAGCAAT
CCCCAAAAGATTTGAGTTTCTCAGTTATAAATTTGCATCCTTTCCATAATGCCACTGAGTTCATGGATGTTCTGACTCA
TTTCATACTCTGTGAATATTCAAAAGTAATAGAATCTGGCATATAGTTTTATTGATTCCTTAGCCATGGGATTATTGAGG
CTTTCACATATCAGTGATTTTAAAATACCAGTGTTTTTTGCTACTCATTTGTATGTATTCAGTCCTAGGATTTTGAATGG
TTTTCTAATATACTGACATCTGCATTTAATTTCCAGAAATTAAATTAATTTTCATGTCTGAATGCTGTAATTCCATTTAT
ATACTTTAAGTAAACAAATAAGATTACTACAATTAAACACATAGTTCCAGTTTCTATGGCCTTCACTTCCCACCTTCTAT
TAGAAATTAATTTTATCTGGTATTTTTAAACATTTAAAAATTTATCATCAGATATCAGCATATGCCTAATTATGCCTAAT
GAAACTTAATAAGCATTTAATTTTCCATCATACATTATAGTCAAGGCCTATATACTATATATAATTTTGGATTTGTTTAA
TCTTACAGGCTGTTTTCCATTGTATCATCAAGTGGAAGTTCAAGACGGCATCAAACAAAACAAGGATGTTTACAGACATA
TGCAAAGGGTCAGGATATCTATCCTCCAGTATATGTTAATGCTTAATAACAAGTAATCCTAACAGCATTAAAGGCCAAAT
CTGTCCTCTTTCCCCTGACTTCCTTACAGCATGTTTATATTACAAGCCATTCAGGGACAAAGAAACCTTGACTACCCCAC
TGTCTACTAGGAACAAACAAACAGCAAGCAAAATTCACTTTGAAAGCACCAGTGGTTCCATTACATTGACAACTACTACC
AAGATTCAGTAGAAAATAAGTGCTCAACAACTAATCCAGATTACAATATGATTTAGTGCATCATAAAATTCCAACAATTC
AGATTATTTTTAATCACCTCAGCCACAACTGTAAAGTTGCCACATTACTAAAGACACACACATCGTCCCTGTTTTGTAGA
AATATCACAAAGACCAAGAGGCTACAGAAGGAGGAAATTTGCAACTGTCTTTGCAACAATAAATCAGGTATCTATTCTGG
TGTAGAGATAGGATGTTGAAAGCTGCCCTGCTATCACCAGTGTAGAAATTAAGAGTAGTACAATACATGTACACTGAAAT
TTGCCATCGCGTGTTTGTGTAAACTCAATGTGCACATTTTGTATTTCAAAAAGAAAAAATAAAAGCAAAATAAAATGTTA
AAAAAAAAAAAAAAAAAAAA
```

Monkey KChIP4d protein sequence

```
MNVRRVESISAQLEEASSTGGFLYAQNSTKRSIKERLMKLLPCSAAKTSSPAIQNSVEDELEMATVRHRPEALELLEAQS
KFTKKELQILYRGFKNECPSGVVNEETFKEIYSQFFPQGDSTTYAHFLFNAFDTDRNGAVSFEDFIKGLSILLRGTVQEK
LNWAFNLYDINKDGYITKEEMLDIMKAIYDMMGKCTYPVLKEDAPRQRVETFFQKMDKNKDGVVTIDEFIESCQKDENIM
RSMQLFENVI.
```

FIG. 36

Alignment of monkey KChIP4

```
                    10         20         30         40
    1  M..........LTLEWESEGLQTVGIVVIICASLKLLHLLG........LIDFS.EDSVEDE    KChIP4N1
    1  M..........LTLEWESEGLQTVGIVVIICASLKLLHLLG........LIDFS.EDSVEDE    KChIP4C
    1  M........NLEGLEMIAVLIVLFVKLLETFG........LIEAGLEDSVEDE            KChIP4N2
    1  MNVEEVESTSATLEEASSTTGFIVATNSTVESIKFSLYKLLFFSAAVTSSDAIPNSVEDE      KChIP4N3

70         80         90        100
   44  LEMATVRHRPEALELLLEAQSKFTKKELQILYRGFKNECPSGVVNEETFKEIYSQFFPQGD    KChIP4N1
   44  LEMATVRHRPEALELLLEAQSKFTKKELQILYRGFKNECPSGVVNEETFKEIYSQFFPQGD    KChIP4C
   40  LEMATVRHRPEALELLLEAQSKFTKKELQILYRGFKNECPSGVVNEETFKEIYSQFFPQGD    KChIP4N2
   61  LEMATVRHRPEALELLLEAQSKFTKKELQILYRGFKNECPSGVVNEETFKEIYSQFFPQGD    KChIP4N3

130        140        150        160
  104  STTYAHFLFNAFDTDHNGAVSFEDFIKGLSIILLRGTVQEKLNWAFNLYDINKDGYTKEE    KChIP4N1
  104  STTYAHFLFNAFDTDHNGAVSFEDFIKGLSIILLRGTVQEKLNWAFNLYDINKDGYTKEE    KChIP4C
  100  STTYAHFLFNAFDTDHNGAVSFEDFIKGLSIILLRGTVQEKLNWAFNLYDINKDGYTKEE    KChIP4N2
  121  STTYAHFLFNAFDTDHNGAVSFEDFIKGLSIILLRGTVQEKLNWAFNLYDINKDGYTKEE    KChIP4N3

190        200        210
  164  MLDIMKAIYDMMGKCTYPVLKEDAPRQHVETFFQKMD........KNKDGVVTIDEFIESCQ    KChIP4N1
  164  MLDIMKAIYDMMGKCTYPVLKEDAPRQHVETFFQKMDAVFHCIIKWKFKTASNKTSVFTDTC   KChIP4C
  160  MLDIMKAIYDMMGKCTYPVLKEDAPRQHVETFFQKMD........KNKDGVVTIDEFIESCQ    KChIP4N2
  181  MLDIMKAIYDMMGKCTYPVLKEDAPRQHVETFFQKMD........KNKDGVVTIDEFIESCQ    KChIP4N3

220        230
  218  KDENIMRSMQLFENVI    KChIP4N1
  223  KTSTVISISMQLFENVI   KChIP4C
  214  KDENIKRSMQLFENVI    KChIP4N2
  235  KDENINRSMQLFENVI    KChIP4N3
```

CTGAGTCCCTGCATGTGCGGGGCTGAAGAAGGAAGCCAGAAGCCTCCTAGCCTCGCCTCCACGTTTGCTGAATACCAAGC
TGCAGGCGAGCTGCCGGGCGCTTTTCTCTCCTCCAATTCAGAGTAGACAAACCACGGGGATTTCTTTCCAGGGTAGGGGA
GGGGCCGGGCCCGGGTCCCAACTCGCACTCAAGTCTTCGCTGCCATGGGGGCCGTCATGGGCACCTTCTCATCTCTGCA
AACCAAACAAAGGCGACCCTCGAAAGacatcgcctggtggtattaccagtatcagagagATAAGATTGAAGATGAGCTGG
AGATGACCATGGTTTGCCATCGGCCCGAGGGACTGGAGCAGCTCGAGGCCCAGACCAACTTCACCAAGAGGGAGCTGCAG
GTCCTTTATCGAGGCTTCAAAAATgagtgccccagtggtgtggtcaacgaagcacacattcaagcagatctatgctcagtt
tttccctcatggagATGCCAGCACGTATGCCCATTACCTCTTCAATGCCTTCGACACCACTCAGACAGGCTCCGTGAAGT
TCGAGgactttgtaaccgctctgtcgatttattgagaggaactgtccacgagaaactaaggtggacatttaatttgtat
gacatcaacaaggacggatacataaacaaagagGAGATGATGGACATTGTCAAAGCCATCTATGACATGATGGGGAAATA
CACATATCCTGTGCTCAAAGAGGACACTCCAAGGCAGCATGTGGACGTCTTCTTCCAGaaaatggacaaaaataaagatg
gcatcgtaactttagatgaatttcttgaatcatgtcaggagGACGACAACATCATGAGGTCTCTCCAGCTGTTCAAAAT
GTCATGTAACTGGTGACACTCAGCCATTCAGCTCTCAGAGACATTGTACTAAACAACCACCTTAACACCCTGATCTGCCC
TTGTTCTGATTTTACACACCAACTCTTGGGACAGAAACACCTTTTACACTTTGGAAGAATTCTCTGCTGAAGACTTTCTT
ATGGAACCCAGCATCATGTGGCTCAGTCTCTGATTGCCAACTCTTCCTCTTTCTTCTTCTTGAGAGAGACAAGATGAAAT
TTGAGTTTGTTTTGGAAGCATGCTCATCTCCTCACACTGCTGCCCTATGGAAGGTCCCTCTGCTTAAGCTTAAACAGTAG
TGCACAAAATATGCTGCTTACGTGCCCCCAGCCCACTGCCTCCAAGTCAGGCAGACCTTGGTGAATCTGGAAGCAAGAGG
ACCTGAGCCAGATGCACACCATCTCTGATGGCCTCCCAAACCAATGTGCCTGTTTCTCTTCCTTTGGTGGGAAGAATGAG
AGTTATCCAGAACAATTAGGATCTGTCATGACCAGATTGGGAGAGCCAGCACCTAACATATGTGGGATAGGACTGAATTA
TTAAGCATGACATTGTCTGATGACCCAAACTGCCCCG MGAVMGTFSSLQTKQRRPSKDIAWWYYQYQRDKIEDELEMTMVCHRPEGLEQLEAQTNFTKRELQVLYRGFKNECPSGVV
NEDTFKQIYAQFFPHGDASTYAHYLFNAFDTTQTGSVKFEDFVTALSILLRGTVHEKLRWTFNLYDINKDGYINKEEMMD
IVKAIYDMMGKYTYPVLKEDTPRQHVDVFFQKMDKNKDGIVTLDEFLESCQEDDNIMRSLQLFQNVM

FIG. 44

KChIP1N (1vn) DNA sequence (CD: 353-1051. Alternation of lower and upper cases indicates individual exons.

cacacgttttctctgagctgccgagagaatatgccatgagatgttgccagtgatggttacactcagctagcagaagatta
gggactggttaaacctttggagaaattgccttgggaaaagaggaaataaaagcaaatattactatgaaacatagagatta
ccaggtaggaggaggagagaggtggagggaggggtaggagtggaaggaaggyagggaggcagaaagaggaaggcagactg
gtggaaaataaaccgtgcactttagaacagcaggaaggyaggcttggaagcctggttttctggctttgaatgaccgccta
gcgcttgccggtgcgccagggatgctgtgaggatgtgggcagagggcgagtccgaagggctccagacactgggaatagtg
gtggtcgtgtgctcctccctgaaacttttgcactacctcggactgattgacttgtcagacgATAAGATTGAAGATGAGCT
GGAGATGACCATGGTTTGCCATCGGCCCGAGGGACTGGAGCAGCTCGAGGCCCAGACCAACTTCACCAAGAGGGAGCTGC
AGGTCCTTTATCGAGGCTTCAAAAATgagtgccccagtggtgtggtcaacgaagacacattcaagcagatctatgctcag
ttttccctcatggagATGCCAGCACGTATGCCCATTACCTCTTCAATGCCTTCGACACCACTCAGACAGGCTCCGTGAA
GTTCGAGgactttgtaaccgctctgtcgattttattgagaggaactgtccacgagaaactaaggtggacatttaatttgt
atgacatcaacaaggacggatacataaacaaagagGAGATGATGGACATTGTCAAAGCCATCTATGACATGATGGGGAAA
TACACATATCCTGTGCTCAAAGAGGACACTCCAAGGCAGCATGTGGACGTCTTCTTCCAGaaaatggacaaaaataaaga
tggcatcgtaactttagatgaatttcttgaatcatgtcaggagGACGACAACATCATGAGGTCTCTCCAGCTGTTTCAAA
ATGTCATGTAACTGGTGACACTCAGCCATTCAGCTCTCAGAGACATTGTACTAAACAACCACCTTAACACCCTGATCTGC
CCTTGTTCTGATTTTACACACCAACTCTTGGGACAGAAACACCTTTTACACTTTGGAAGAATTCTCTGCTGAAGACTTTC
TTATGGAACCCAGCATCATGTGGCTCAGTCTCTGATTGCCAACTCTTCCTCTTTCTTCTTCTTGAGAGAGACAAGATGAA
ATTTGAGTTTGTTTTGGAAGCATGCTCATCTCCTCACACTGCTGCCCTATGGAAGGTCCCTCTGCTTAAGCTTAAACAGT
AGTGCACAAAATATGCTGCTTACGTGCCCCCAGCCCACTGCCTCCAAGTCAGGCAGACCTTGGTGAATCTGGAAGCAAGA
GGACCTGAGCCAGATGCACACCATCTCTGATGGCCTCCCAAACCAATGTGCCTGTTTCTCTTCCTTTGGTGGGAAGAATG
AGAGTTATCCAGAACAATTAGGATCTGTCATGACCAGATTGGGAGAGCCAGCACCTAACATATGTGGGATAGGACTGAAT
TATTAAGCATGACATTGTCTGATGACCCAAACTGCCCCG KChIP1N (1vn) protein sequence MWAEGESEGLQTLGIVVVVCSSLKLLHYLGLIDLSDDKIEDELEMIMVCHRPEGLEQLEAQTNFTKRELQVLYRGFKNEC
PSGVVNEDTFKQIYAQFFPHGDASTYAHYLFNAFDTTQTGSVKFEDFVTALSILLRGTVHEKLRWTFNLYDINKDGYINK
EEMMDIVKAIYDMMGKYTYPVLKEDTPRQHVDVFFQKMDKNKDGIVTLDEFLESCQEDDNIMRSLQLFQNVM

FIG. 45

```
           10             20             30
M L T Q G E S E G L Q T L G I V V V L C S S L K L L H Y L G L I D L S D  rkchip1N
M W A E G E S E G L Q T L G I V V   V C S S L K L L H Y L G L I D L S D  NkphIP1N
      V                                                                 N.pep
```

Decoration 'Decoration #1': Shaded residues are the ones that differ from rkchip1N N.pep.

FIG. 46

Hkchip21,m,s,N genomic sequence

```
GCGCTCACCTGCTGCCTAGTGTTCCCTCTCCTGCTCCAGGACCTCCGGGTAGACCTCAGACCCCGGGCCCATTCCCAGAC
TCAGCCTCAGCCCGGACTTCCCCAGCCCCGACAGCACAGTAGGCCGCCAGGGGGCGCCGTGTGAGCGCCCTATCCCGGCC
ACCCGGCGCCCCTCCCACGGCCCGGGCGGGAGCGGGGCGCCGGGGGCCATGCGGGCCAGGGCCGCAAGGAGAGTTTGT
CCGATTCCCGAGACCTGGACGGCTCCTACGACCAGCTCACGGgtgagtcagtgacgtgggggtcgcggggagggagggtgg
attccattcctccagacccttccgcctctccgaccccggcctggccgcacccacactctgccccattcccaggcactct
tatggccggtctgggcggcaggacactgggggttcaaagccttgggtcccgcaggggttggggaggaacagaagaggcag
gtgtggagaggcagcaggtgtgggcgtatgtgacacagggctgagaggtgtgtctggagtgggaggtgttacgtgcgtgag
cacctgtcattctgtgtgtgtgtgtgtgcgcgcgcacctcccacagctggttgccatgtgccctgggcttggtgac
agctagggtgagtgtgattgtatgtggcagtgcaattgtatggtctcgtcagatgtttgagtttgcgtaggaccctggtt
gtactgatgaagttgttttgaccatgtgtctctatgtgcaacgatgtgttgtgagtgtgtaattctgtatgaagtggtgt
gtaactaccagaatgtgtcagggctctactttaggggtggcttgtctctttgtaagccttcatgaccataagccctctggg
caagaatttgttaaagtaggttgtgttgtgttttgtggttgtgagattagtgttcagtgctagttgtgtactttcatgtg
gtgatgtctgcagcggggctctgtgagtgtctatgacgtgtctcatccctgctgcctctctggcttcctggtacagatag
gggtctttagtacaccccactccttcaccaattttttccacaaatagcccaggtggacccaaggagggactttagtgttca
gctgcccagtctggtttccaagagaccttatggctccagcacctggccctgtagggaggctttagttagtgctgggtca
gccctctctcccacaccaaatcatgtactgagattattcttacaactgaatccttcaaccccaacaaaccttttcagaa
cttcactcaaacccaggaaaacacatcctcttccttcccctccagagacagagctagaagctctaggcctgggaagtgc
catgtggtgtcctgcatgtccaccaaaccacttggctgcccgggcatcctctctttcccacatggggaggtatgtgaggc
cagtacatctgtgcatgtgcatgttcctgggtttggtaggaagagccatgtgtttgtgtaggtgactgtgtcaccctggg
tacatttccatgtatgtgtttgtgtctctcattgtgcagcctgctctagaaagccagcagagtggggaggagggaggctgt
ctccctgaggccaaaacaaagctggggaggtggagggaggccatgatccttgtccttcctgagggagtgagattgagac
ctgggaagggggagggactaggatgaggtgccttgagcatgtgtcttccccatccccatcactgtccctaggaggc
cctagtcaggatcaggggagccactcaggctggccccagatgagagaccatgccagatgtgcctcagagctggatggaat
ccaaaggacccactgtccagctcttccatgaattctgttcccatcaccagcttaggattcttgagagtagtaagggccta
ggggccttcaatagtatcacattagtcagtgtttgcttccagctttaatgggttctcacccttagtgaaaccatcccttc
cccacttggctatttgaatgagattgggtgggggaagcatttgtatttggagatgccctgccccagttcagtcaggaatg
gaagtgtaccagctatgtgacttttgttctcttggcctcacctttctcatctgtaaagggaatgttacttcctgcctgc
ctgcctacctcccaaggaaaatggaaaggtcaaatgttgacaagtatcaagaattgtggtccgggtctacagcagcctag
ctgtagatagctccacacacgacttggaaagtagaaataggactaccaggagctctcctctcgaagggcggcttatttta
tagcgggagacaaatcgggttgggacgccagtgtcaacgaagactcccgggcgggcgggcggcgctgagctctgagcgct
gagagatgcctaagctgaagcatgaagggagtcgttgtccgcggtgctgaagcgcgcgcgcaggcttcgcctcccccttcc
ctgcagttgggattcctgggatcggatttagggtagtctgcagctcccgtcttcccggcccatcaggcttgcagggaagc
agctggaaagttacacctcagggcatcctgggtacctccgaacattttacttccccactcccaccccaagctcaaagggg
agctgggagagactctttaggaaaacaaaacaaaacaaaaaacagtccgagccccgcccggaccccctgtctaatccctca
ggtcttcccagcccggcggggccgctgggcagtgcggttccgaggggaaaggccgcgtttagcagcggccctgtctgagc
ggaagagagaaaggccaagagaagatgcggagagggttggagcctggctggctagccctgagctcggtcccccgactggg
atctcagtggagtccctccggccctgagtattgttgccggggcggggcgcccccgtgtggctgcgaggagccatgcgca
cggagctgctttgcggtggggatagtcgccgtcaagtggacaagatttgcccagagttaggaggtcattctcaccactta
aatgtagggttttcaaccaatcatgcgggatcccagtcgaaagagcgggactatatctctcccgtaggcttcccaggaa
ttttaaggcgttagagagtcctggaagtgttttacttggggtctaacctgatagagatgagtccggagtccaggaaaggg
cgcagcgggaccgaagtgggggggggggtgcgggggggggctcttctcgaagcattcggctgtagccagcgtatggtggtag
tctgtgaacctgccgcaccgagacaaacacaaatagaaacagttatgagagcaaggaatttggagccaggagacagaagg
cagtgggggcacaactctgctgcctcttctttgccaccccaatacactggcctcttctccttcctcctggcttcttcca
ttggcccaggaagtgtggggagttgccatgacaactctgtcctcttaccccttcggctctttatgccaaaatggtgggg
cgggtgcagggtgcggggaggagtgcgacaggcggagaaagggggggctgaaaggggggcaataaaagatacggttcattc
cccatccagctctttttctcaaaacccacatgtgcctgcctggcctccccgccagaacccagaaaaatgctccctgagaag
gctgagtccgcgccgccccctccccgccacccccccccccgtccaggaactttgggggcggctgcttcacatgatggggc
```

FIG. 47A

```
cagggtgagctcctctcgtgcggccaggagaacatgggaaggctccagggtttcgatcctatGcctgccgggccggccct
cccgcgccgcccacgcgggcctacccggtgagggcggagaccggaccgccccgggccctgggggtggagcttagacgcc
gagctcgccgccaaaccATGAACCGATGCCCCCGCAGGTGCCGGAGCCCGCTGGGGCAGGCAGCGCGATCCCTCTACCAG
CTGGTGACTGGGTCGCTGTCCCCAGgtatgatgaggaagggaagggagggcaggatccttcaaaaagtgagcgaagtgg
gttaggagctccgcagaggtagggagggaagggcccctcaaatagatggagggagcaacatccctccaaggaaagggctt
ccaagacgagatcctggacagaagcggagcaggggatgggcctccttactgagcaggaggaagacagcgctcttcaaaga
ggaaaggacaggggcatcaaggtccctcacaatggtggagggggcgggcttctcaccgaaggcagaggagggggcctta
actgaggggcagggcgcctcccagggatgaaggaggaggcctgcagcagagcagggaaaaagttcagtcctttcctgca
tttcttggctgaaggggtcttaagatgaaggttcagtgtccagaaggaaaaaacccctgagatgggcctagaccaacatg
aactcagctagcaagttcatacatgacatgggactgatagacttgtgtggcttaaggattgtatgtctctgttttctctc
tctctgggagtgtgtattaatgggattgtgcattactaagttgtgcatcactgggctatgtatggctgagtctgtgtctc
cctgggttgtgatcactgggattctgtgacactgagactgtgtgtacctggagttctgtacttaggactgggttgagg
gttcctgagcctctaagttggttgtgtagccttcgtgaggttgtaccttggtgtgaaatttgtggagtgtatgaggtgtg
gattgttgagtatcccacggcactgctgaggtatgcacatctccacttgcatttccttatgactgcttgggcagggcc
catagaacgcaacgtctcctctgtacctgacctcaaacagaccaaaacaacctggtcctgtggcattctgagatctgtca
ttttctggctctctccatgggtatccacttgagcccctggagtatagataggggcctgtggcctctccttgccatctgtcc
cccaaaaggagggtagatggatggtcctgagccagaaccatacctggaaatcttctggggagcatacaacctccaagccc
cctgcttgggcctgtctccagtgacagatggctggagccaggcagggccagctctcagtcattgcaggcatgacttccag
gacccaaaatagcccaacgtctaggaggtcattaatcactcgatgcagctgggggctgcagtgtctttggcctagctg
ggaatggtgtgggtctgggggactgagagaaggctttgaggtcttcactggctgggttaacagtggcggtgggggtgg
gacaaagctaaactggggaaggtgggacagttgcatagagtgggttccccacaaggcagtgttactcacatttgaactg
ggggagataaataaataaatgataggaatatctctgtggtaagatttgagggatctggggaaggcccacctcatgcctcg
agatggttttcccttgagttcccactctgccaaattgcttccacagagattttactttgagtgaagagctaaattcgtgg
cacagggatgcttggggaggatggatctggcaagtttctcactgaacccgaggacttgagaagtctctgagtggggagaa
gggacagcctggaaaaataactcatcctttcactcctgacagactctgccacaggatgcctggctgatttaggaccatga
gtcctggcaaggctgggtcaaggtctctgagagttgagagtgggagttaggaaaaggaggggccagggccagggccaggt
ccagggcaactggctgcaagttatcagtagcagggagcaagaaggggctgttgtggggccccttttccattcaaatagtct
ggcttggcattcaaggtttcatggaatttgaccctttttgattttattacccatagctcccttacctaaactaagctgta
ggccctaggattccttgacaccccgcacatattggagagactgcctgagggagctgacagatcactgactctggttaaac
aactcattattattatcattattattattgagacagagttttgctctttcagtcagactggagtgaagtagcgtgat
ctcagttcactgcaacctccgcctccaggttcaagcaattctgccttagcctcctgagtagctgggattacaggcaagc
accatcacgcctggctaattttgtattttagtagagacggggttcaccatgtgagtcaggctggtcttgaactcctg
accttgtgatccaccgcctcggcctcccaaagtgctgggattataggcgtgagccactgcacccagccaaactcattct
taattagcatgtcagctgttatcttggaaaaaaaatcactctttttcccaagataagcagggagcttatcttggcgggg
agcttcaattccttcatctgcaaaatgggtatactatcactcactctgaccatgtcagctgtaaaaacaggaataataga
tcctacctctcaggtttattatgaggactaagtgagatactacatgtaaagtatccaggacacaaaatgtgctggataaa
tattatctttgtttatttgtttatttgagatgggtctcactttgtcatctaggctgaagtacagtggcacaatcatgg
ctcattgcagcctcaaactccccaccttagcctccaggtagctgggactataggtgtgtgccaccacgccaggctaatt
attattattttttttttgagacagagtctcgctctgttgctcaggctggagtgcagtggcgtgatctcggctcactgcaa
cctccacctcctgggttcaagcacttctcctgcctcagcctcccaagtagctgggattacaggtgtgtgccaccacgccc
ggctaattttgtattttagtagagacaggtttcaccattttggccaggctggtctcaaactcctgacctcgtgatcc
acctgcctcgacctcccagagtgctgggattacaggcatgagccaccttgcccagcccaggctaattttttgtagagaca
gagtttcgccatgttgcccaggctggtctgggactcctgatccaacctttagggattggcaagcaatccctaaatagact
ttttcctaggggaaaggagtggaacagaccaagcctatttgaggccagacgcggtggcacacgcctggaattccagcact
ttgggatgccgacgggggcagatcacttcaggccaggagttcgagaccagcctggccagcatgacaaaacccctatttaaa
aatataaaaatcagctgggcgtggtggtgcacgcctgtaatcccagctattcggtggctgaggcacgagaatcgctagcg
ccaccgcactttagcctgggtgatagaacgagactctgtctcaaaaaaaaaaaaaaaaaaaaagagaaaaaaagcctgt
gtgaagcgtcatcttcccacctcttccctggatggggcaggtcgggagaaggaaggtgtatggtactgtgtgaggttgg
acgcgtgccccgggtggtggctgtatagaactgcagatcagccaacctcgactgggggccttagggactggccccaccc
cacaaattgggctgagacacagtcatcccagagctggacaagagggagggctccttctggggccaatcccctaaattgg
gcctcctggctgggccagcttctctaagaagggagccagtgtagtgtggtggtttagagtgaaggctgagtcagactgggt
```

FIG. 47B

```
taaaattgaagctctgatcttgaagatttgcttaacttctctttgacttagtttcaccacctgtaatatgaggataatag
tatgccttcataggcttattgtgaaaattcggtgttacaacacctgtaagcacatagtgcattatctagtacatagtgaa
tgctcagtcacgttagccagcagcggtagtaatggtgttactaacccagaggccctagtcttgtggctcattggctctg
taggcctctcccaccccttttacacacacaaacaccccaccaagaagaagcagggaagaggagggagggactccgggat
gctggctgggagggtggctcccttagaaggttcagatttccctcctacagcagctgggcttctccatcagctcaataac
agttcctaaggagcaggcagggcttagcatctcccggatgaggtcccagccacatacggagccagcacagtcccccctc
ctctcccaagaagcttgggtttcttgaccccaaaggcagctgcagtaagtcccctcccagagggtcctgatggggttaa
gtggcctttttctgcctaggctactactgtatcttatccccctcccttgggcctcagtttcactgcctgtggcctgtgg
gaagagagtgcttccctcctcacagtctccatggcaaccaaatcgatattggtgatatcctcctagcaggagaggtcact
gccttctccgccattattctcatacaattccatgccaatacaatgacaaaacagtagacccaccctccaaattatacaac
acatccatacctaacaaacttcagacccacatcctacaaccctactaaaacacaggaacctcactcccatgcacactca
caaatacttcaacacactcctacacatgcagaccatagacacccagctcacatacccatatacgcaagagtcaaaatgca
taaccatacgccaaacacacacctctgtgacaggtgcacagtcacgtgtaagcacacaaagacacacataagaggagaca
tatgcactgccatactgacaaacacaggaatatacacacaggaaaacacctggccaccacaacatattctgacccatgca
tctgattacttatacatgtgcagatggtggtttctcatgcacatacaccctgcccttccctgccttctccctaagctcag
ctcctccctctgccccttccctttggcacagagtagccacaggatgtctaggggaagcacttctcagggacagaggcggg
tcactgctccctccctctggcccatatcttggcaaaagttcccaaggaggtgccagtccaaaggctgaggtggccctgc
gaagaggaagaggcggcggctgtggttgggaggcttgtggggcagaggcggggtgatgggggagaggaaggagatcctgg
gagggagagtgggaggaggctgcaggcagtcctactcaggctggggagtctgaggggaggtggtgtgaggcggtgaac
cggcgtatctgaacctgggccctgtaggggccatgccccaggcccaccatgaacctggaaggctggagatggttgctgt
gctcgtggtcctcgctctgtttgtcaaggtcctggagcagtttggcctctttgagcctgtctccttggaaggtaatccag
gtgtcctggcatgtctgagctgctggctggtggggcagctgccccacagcactaggagggtgtttgtctgtcttcatga
ctggggcagggatgagcaggtgagtgatggcacagggatctgggaggtgagtagggtgcttgggggatacaacatctgg
gagggtgaagaggaggcctcaaggagtagatatggagggaggagggaatctgggggaccaaggtgtcaggaggtgatga
ggggtgcagtgtggaggactggggtgtggagatgaggaggtgagggattctgggcgataccaggagggtctggagat
agggaaggagtgtctagagtagaggagggaggttctagggatcctgagataacaacgatttctgggggtcctttttgg
agtcaggggcccaccacggtgcctgtgcatcctctccacacctccatctgtgcagtgtagcttatgggtgtgtgggcat
agtgtgtgagagacacagggtgtgactttgtgttcctgtatgtgagagagtacaaagtgtgtaactgtgagcctgtgtat
gggacagggatatgactgtatgtgtgagagtgacagggcatgtggctttgtgagaaggtggatgtggcaggcctgagtg
gcacagtatgtggctgagcctctgggtatcaggttgtgcatgtggctgtttccagaatttcctgaggatataccagctcc
atacccaaggcttggaggaggtgggttctgagggaagagtgtgaacattgtgaaggagacatttatagcccagctatg
attggggatgaggagtggatcagatcagggaccctgcttcccaagtccccttgcctctccaagctcctatcaggatccaa
gtgcagagtgatctccagggcctagacattgggagtggaaaatcaactcccctcccagcccaccccaaagtcagtaggg
agagtaatattggggtggagtggggagcacttctgcctccccttgggagttttgacctctccctcctcttcacggctag
aactgtgtaactccgtagcatggctgttcccagtaccaccagggacaggaagacagactagaaccatgatggaggactg
cagggtagatacctggaagaactggaaaaatatgaaggaaactgggaacaagaggaaggtgcatgaattgcctgctctag
ggttcagtaagagcagaaaactcctagctcaccctccatcctctgctgcatttattggggtggagtggggaacagggagt
tggacctagataaactgggacagctgggctgagcttgttctcattcaatctggaaaaggtgaagttgattgagctctaac
ttgccattcctttagatgggaaaggggaagagagggcatctggaaatcccaggagtcttgggctgaaggcagccattc
tgttctcacctttagaggagacagaggcttagaagcaggtaggggctgggtggggggcaggagagccaccccgagtc
gggcaactacaccattggaggccccaggcgcaatccagctttgggaaactagagtccaggctaatggagccctgggccag
aggccaggaatgccatcgatcccctgcctggcccactgcctcctcccacctctccatggctcctgggtgggagggag
gtaaggatgtgttgaaggagaggaggtggttactcacccagtcacctcctgagaacagggcctgatctggagggtgaagc
ctggattgggagggtgggtatatgaggggggagtaacctttaactaaaggaagttggacccctccaggaatggactgag
gccaactttagtcactgtgtcagatccagtgggatctgatccaggaatctggatgcagtgcagctgggagacacagacac
acacacacacacacacacacacacacacacacacacacagtaacactgagggtcctctgggggtgcaattagagctgt
agagcatgtgcagaaataaggggagaagaggggaaggggagccatgatcagtgggccatggatagcccacaatacaccag
aatactcgcctccaagatctcttattgccacaaagtttactattatttcaccctcaaagagcaagccatactggaagaga
ctgtgaagggccacagtttagggtagatgagttagctgatgaggaaccctgcccttttggcagaaagattctgggcacct
```

FIG. 47C

```
tggaatgaggaggggttacaggaaagaaaagtgggtgtacccaggaaaaatgaagcctctgtgggtgaggtattgaggta
cagccttagatatctgggtgccatggggacccaggtcacagtatgatatggatatgtgtcatgacaaccttgatatgtct
cataatgttataaggtcacaatgtcatagtgttctttgtagactcacatgtcatgatgtcccagaggcattgtgtgttct
tgtgtggtttgatcatgctgtgtgtgagatggcctatatgggtctccatgtgtatgcatcctgttttacttaggtcacat
ttgtatatgtttgtgttaaggagttagcaggtcattgtgtgtgtgtgtgagcatgcatattacgccatcaggtgtgag
ttactggatatcaagctgtcactggcacccatcactgtgatgtattgttctacatgtcactatacacgcctgtcactgta
ggtgtgtgtatgagagaggtgttcttacccaggcaatccttgggttggacatcatcctgagaggtccagccatggcactt
gagccaagggtactaggtcagcaaagacactgaggccactgccacctcatccttgccgcctcgctgtcaccggccacgtc
ccattaaaccaagtgcctgagcctcacctctatggactcactgggctcccctaacccgattccaaccacccttgccattc
ctttcctcccctiaattcctccccagcccggtccccagatggggttgatttgtgactggcggggagggacagggaaca
gagggacaatgggagttaatgtgccttcctggggtcttctctcttcccagGCCACCCTCCAGGGCCCACTAAAAAAGCGC
TGAAGCAGCGATTCCTCAAGCTGCTGCCGTGCTGCGGGCCCAAGCCCTGCCCTCAGTCAGTGAAAgcaagtgcctctca
tgtgcttccggggcggggctcgatgtgtgcgtgcgtgtctgtgcatgagtgtgtgcgcgtgtgccccaggcctgcgagt
gtgcgcatgctccaggcctgcatgtgtggggggcgtgccccaggcctgcgtgtgtgggggtggggcctgccccaggcct
gtgcgtgtgtatgtgtgtgcatgtgcgcgcgagcgtgccccaggccggcgtgtgtgtgtggggggcgtgccctacccct
gcatgtgtgtggagggcgtgccccaggcccgcgcgcgtgtgtgtgtgtatggggaggcgtgccgcacgcctgcgtgtggg
ggaggggcgtgccccaggcctgcgtgcgtgtgtgtgtgtgtgtgtgtgtgtgtgggcgtgaccagcgtggcgagggcg
ggtgctggcaaggctggagcataaggggcgtggctactgtgtgcgtgtgcggctgaagccagcgtgtgtgggcgtggtc
agttgggagcgggtgtgtgtcaccgctcccgcaaaactgtggggacccgagagtgtgggtgtgaccattgtgaccaggctg
aggcctgagcctgtgtagctgtggcggcctgtgtagaccaggcggccgtgagggtctgtatgtggcttagctgggttagt
gtcttcaactccgtgcggccgcccccttccccaccgtgttttggaccccctgatgtgtgttgcctatgccccgacaggatg
gtgacaggtgtagaggatggcgcctgccctcctccagacgccagggtatttgggttttctgtgccagcctggtcccctgc
tgagtgatctccagttgagtgacctcgctttgtctctaggtctccatttcctcagttgggccttgcccacctcataggat
catactgcattttgcaaaccataaaggcccgctttgtagttatttgagcatgctgttgtgttggacttagatgggtccca
cacggggtggattcggaaaaggacaggcgtgagtcccgcaagcttgtgtgcatggggtccgtttcgtgtgtgtctgtgc
tggttgggtgtgcctttgcacgggctggttgtgaggtttgctctgagtgtgaggggccaggtgtgtgtctgcagttggc
cgggtcttccgctttctcggtgacagttcgctcccttcagCATTAGCCGCCCCAGCCTCCCTCCGCCCCACAGACCCCG
CCTGCTGGACCCAGgtgacttacgctcctggtgggggcggggcggggcagggcggctttgccatcttgggtgggggca
cttgcctgggggctggacgttgggggcggggcaggattgagatgggccggggtggggtctggatggaggttggctgag
ctgggcggggcatggctcaggcatggctgggatagatgggctgggcggggcgaggggagggctggtgggacgacggg
agggtttgggcggggcaaggctggggctggcggatctgagttggtccccgaaggcccggagctctgaccctcagacgcc
ccctcttgaactggcttttcccactcctccctttctaaaacgaagatgcgctgggggccttccctccaacgagggatc
gagggccgcggggcgagcactgagtcggatccctggctctggggccaggccaggccttggcccgctgatagacctcgaag
atggccatcatctttctccttacctcagtgtccttggctcggggcccagggaactggcagcctggtctccggcatcgga
tgggaccggggggcggggaggggtgaatggggcagtgatttgaagaggggtcgcggaggctgggcctgaggcgcggctg
tcctcaccgctcccgcagACAGCGTGGACGATGAATTTGAATTGTCCACCGTGTGTCACCGGCCTGAGGGTCTGGAGCAG
CTGCAGGAGCAAACCAAATTCACGCGCAAGGAGTTGCAGGTCCTGTACCGGGGCTTCAAGAACgtgagtgcaagcgagg
ccaaaactcagcgagggtgggacaggaggacccaagccggtccacagcttcccagaaagcatggcttggatgcttgaggtg
tgggcggaagggaggcaaggcccctgagactgaacttctagctggaggttctggggcggggccagaacggaagtggcgcct
gtagactgtcagtttcgttccatgttttttatttgtgcactgggaaagaagtcttccctcccatcacatgagccacgtgg
tgagtcctctgaggcttgaagattatcccctccctgggagtcttgggccatggagggtggggcggtgaacgaaggg
gattttgtctctgccctcagcctggtgccctctccttccagGAATGTCCCAGCGGAATTGTCAATGAGGAGAACTTCAAG
CAGATTTACTCCCAGTTCTTTCCTCAAGGAGgtgagggggacaaggcccaagggggaagcagttgtccttctctaggctgag
ggagggagggattctggaggagctgggaatgccaaggtgatgggggtatggggagctccttagagggaggaagtcctct
cctgtgtggaagccaacttctccacactcaccctgcagACTCCAGCACCTATGCCACTTTTCTCTTCAATGCCTTTGACA
CCAACCATGATGGCTCGGTCAGTTTTGAGgtgagctgggcgaggtgggccagggaagcctgtttcctggagttcagggcc
aggatctccaggccaaacccagagaaggagttgggtgaagagtacccgaggacacagctccctcctgcctccttcccagG
ACTTTGTGGCTGGTTTGTCCGTGATTCTTCGGGGAACTGTAGATGACAGGCTTAATTGGGCCTTCAACCTGTATGACCTT
```

FIG. 47D

AACAAGGACGGCTGCATCACCAAGGAGgtgcagggcaactgaagggctgggggtctgtggcggtgatgggggtggcgtgc
agagggtgatgggagggaaatatgacccacatatgcccacaagcaagggatcaagggaggctggaggctctgaggaagga
tcctcttctctcttggcctaacagGAAATGCTTGACATCATGAAGTCCATCTATGACATGATGGGCAAGTACACGTACCC
TGCACTCCGGGAGGAGGCCCCAAGGGAACACGTGGAGAGCTTCTTCCAGgtacttgggagtgggtaggctggagggccct
ggagtgaaggGaagaaggccaagaaccagcaggGaactcacctgacttctgtctgcctctctcttgccatccctcctgtt
ctccctgcctgaccaccttcttgcagAAGATGGACAGAAACAAGGATGGTGTGGTGACCATTGAGGAATTCATTGAGTCT
TGTCAAAAGgtacagctccctgccctctacattaccctgacctggactcaggcctgatttagtaatgcaggGaaaagctt
ctttgggaagaataccaccttcccacctcaccccccatatttcaatcctattcctttgtgggaggcttacccctttccctac
ctcaggtctctctgggcatctccttcctctgtgcttttgaatgtccccgtctgtgactcagtgtccctctcactgtctct
gataagctccttctctttctctctcttcaatctgcctcgctcacatcatggccacagGATGAGAACATCATGAGGTCCAT
GCAGCTCTTTGACAATGTCATCTAGCCCCCAGGAGAGGGGGTCAGTGTTTCCTGGGGGGACCATGCTCTAACCCTAGTCC
AGGCGGACCTCACCCTTCTCTTCCCAGGTCTATCCTCATCCTACGCCTCCCTGGGGGCTGGAGGGATCCAAGAGCTTGGG
GATTCAGTAGTCCAGATCTCTGGAGCTGAAGGGGCCAGAGAGTGGGCAGAGTGCATCTCGGGGGGTGTTCCCAACTCCCA
CCAGCTCTCACCCCCCTTCCTGCCTGACACCCAGTGTTGAGAGTGCCCCTCCTGTAGGAATTGAGCGGTTCCCCACCTCCT
ACCCCTACTCTAGAAACACACTAGACAGATGTCTCCTGCTATGGTGCTTCCCCCATCCCTGACCTCATAAACATTTCCCC
TAAGACTCCCCTCTCAGAGAGAATGCTCCATTCTTGGCACTGGCTGGCTTCTCAGACCAGCCATTGAGAGCCCTGTGGGA
GGGGGACAAGAATGTATAGGGAGAAATCTTGGGCCTGAGTCAATGGATAGGTCCTAGGAGGTGGCTGGGGTTGAGAATAG
AAGGGCCTGGACAGATTATGATTGCTCAGGCATACCAGGTTATAGCTCCAAGTTCCACAGGTCTGCTACCACAGGCCATC
AAAATATAAGTTTCCAGGCTTTGCAGAAGACCTTGTCTCCTTAGAAATGCCCCAGAAATTTTCCACACCCTCCTCGGTAT
CCATGGAGAGCCTGGGGCCAGATATCTGGCTCATCTCTGGCATTGCTTCCTCTCCTTCCTTCCTGCATGTGTTGGTGGTG
GTTGTGGTGGGGAATGTGGATGGGGATGTCCTGGCTGATGCCTGCCAAAATTTCATCCCACCCTCCTTGCTTATCGTC
CCTGTTTTGAGGGCTATGACTTGAGTTTTTGTTTCCCATGTTCTCTATAGACTTGGGACCTTCCTGAACTTGGGGCCTAT
CACTCCCCACAGTGGATGCCTTAGAAGGGAGAGGGAAGGAGGGAGGCAGGCATAGCATCTGAACCCAGTGTGGGGCATT
CACTAGAATCTTCAATCAACCTGGGCTCTCCCCACCCCACCCCAGATAACCTCCTCAGTTCCCTAGGGTCTCTTCTTGCT
TGACTCAATCTACCCAGAGATGCCCCTTAGCACACCTAGAGGGCAGGGACCATAGGACCCAGGTTCCAACCCCATTGTCA
GCACCCCAGCCATGCGGCCACCCCTTAGCACACCTGCTCGTCCCATTTAGCTTACCCTCCCAGTTGGCCAGAATCTGAGG
GGAGAGCCCCCAGAGAGCCCCCTTCCCCATCAGAAGACTGTTGACTGCTTTGCATTTTGGGCTCTTCTATATATTTTGTA
AAGTAAGAAATATACCAGATCTAATAAAACACAATGGCTATGC

FIG. 47E

Rat kchip21 DNA (CD: 1-813)

ATGCGGGGCCAAGGCAGAAAGGAGAGTTTGTCCGAATCCCGAGATCTGGACGGCTCCTATGACCAGCTTACGGGCCACCC
TCCAGGGCCCAGTAAAAAAGCCCTGAAGCAGCGTTTCCTCAAGCTGCTGCCGTGCTGCGGGCCCCAAGCCCTGCCCTCAG
TCAGTGAAACATTAGCTGCCCCAGCCTCCCTCCGCCCCACAGACCCCGCCCGCTGGACCCAGACAGCGTAGAGGATGAG
TTTGAATTATCCACGGTGTGTCACCGACCTGAGGGCCTGGAACAACTCCAGGAACAGACCAAGTTCACACGCAGAGAGCT
GCAGGTCCTGTACCGAGGCTTCAAGAACGAATGCCCCAGTGGGATTGTCAACGAGGAGAACTTCAAGCAGATTTATTCTC
AGTTCTTTCCCCAAGGAGACTCCAGCAACTATGCTACTTTTCTCTTCAATGCCTTTGACACCAACCACGATGGCTCTGTC
AGTTTTGAGGACTTTGTGGCTGGTTTGTCGGTGATTCTTCGGGGACCATAGATGATAGACTGAGCTGGGCTTTCAACTT
ATATGACCTCAACAAGGACGGCTGTATCACAAAGGAGGAAATGCTTGACATTATGAAGTCCATCTATGACATGATGGGCA
AGTACACATACCCTGCCCTCCGGGAGGAGGCCCCAAGAGAACACGTGGAGAGCTTCTTCCAGAAGATGGACAGGAACAAG
GACGGCGTGGTGACCATCGAGGAATTCATCGAGTCTTGTCAACAGGACGAGAACATCATGAGGTCCATGCAGCTCTTTGA
TAATGTCATCTAGCTCCCCAGGGAGAGGGGTTAGTGTGTCCTAGGGTGACCAGGCTGTAGTCCTAGTCCAGACGAACCTA
ACCCTCTCTCTCCAGGCCTGTCCTCATCTTACCTGTACCCTGGGGGCTGTAGGGATTCAATATCCTGGGGCTTCAGTAGT
CCAGATCCCTGAGCTAAGTCACAAAAGTAGGCAAGAGTAGGCAAGCTAAATCTGGGGGCTTCCCAACCCCCGACAGCTCT
CACCCCTTCTCAACTGATACCTAGTGCTGAGGACACCCCTGGTGTAGGGACCAAGTGGTTCTCCACCTTCTAGTCCCACT
CTAGAAACCACATTAGACAGAAGGTCTCCTGCTATGGTGCTTTCCCCATCCCTAATCTCTTAGATTTTCCTCAAGACTCC
CTTCTCAGAGAACACGCTCTGTCCATGTCCCCAGCTGGGACATGGACAGAGCGTGTTCTCTAGTTCTAGATCGCGAGCG
GCCGC

Rat kchip21 protein

MRGQGRKESLSESRDLDGSYDQLTGHPPGPSKKALKQRFLKLLPCCGPQALPSVSETLAAPASLRPHRPRPLDPDSVEDE
FELSTVCHRPEGLEQLQEQTKFTRRELQVLYRGFKNECPSGIVNEENFKQIYSQFFPQGDSSNYATFLFNAFDTNHDGSV
SFEDFVAGLSVILRGTIDDRLSWAFNLYDLNKDGCITKEEMLDIMKSIYDMMGKYTYPALREEAPREHVESFFQKMDRNK
DGVVTIEEFIESCQQDENIMRSMQLFDNVI

FIG. 48 human kchip2N DNA (CD:1-678; 1a is added based on genomic sequence)

aTGAACCGATGCCCCCGCAGGTGCCGGAGCCCGCTGGGGCAGGCAGCGCGATCCCTCTACCAGCTGGTGACTGGGTCGCT
GTCCCCAGACAGCGTGGACGATGAATTTGAATTGTCCACCGTGTGTCACCGGCCTGAGGGTCTGGAGCAGCTGCAGGAGC
AAACCAAATTCACGCGCAAGGAGTTGCAGGTCCTGTACCGGGGCTTCAAGAACGAATGTCCCAGCGGAATTGTCAATGAG
GAGAACTTCAAGCAGATTTACTCCCAGTTCTTTCCTCAAGGAGACTCCAGCACCTATGCCACTTTTCTCTTCAATGCCTT
TGACACCAACCATGATGGCTCGGTCAGTTTTGAGGACTTTGTGGCTGGTTTGTCCGTGATTCTTCGGGGAACTGTAGATG
ACAGGCTTAATTGGGCCTTCAACCTGTATGACCTTAACAAGGACGGCTGCATCACCAAGGAGGAAATGCTTGACATCATG
AAGTCCATCTATGACATGATGGGCAAGTACACGTACCCTGCACTCCGGGAGGAGCCCCAAGGGAACACGTGGAGAGCTT
CTTCCAGAAGATGGACAGAAACAAGGATGGTGTGGTGACCATTGAGGAATTCATTGAGTCTTGTCAAAAGGATGAGAACA
TCATGAGGTCCATGCAGCTCTTTGACAATGTCATCTAGCCCCCAGGAGAGGGGGTCAGTGTTTCCTGGGGGGACCATGCT
CTAACCCTAGTCCAGGCGGACCTCACCCTTCTCTTCCCAGGTCTATCCTCATCCTACGCCTCCCTGGGGGCTGGAGGGAT
CCAAGAGCTTGGGGATTCAGTAGTCCAGATCTCTGGAGCTGAAGGGGCCAGAGAGTGGGCAGAGTGCATCTCGGGGCGTG
TTCCCAACTCCCACCAGCTCTCACCCCCTTCCTGCCTGACACCCAGTGTTGAGAGTGCCCCTCCTGTAGGAATTGAGCGG
TTCCCCACCTCCTACCCCTACTCTAGAAACACACTAGACAGATGTCTCCTGCTATGGTGCTTCCCCCATCCCTGACCTCA
TAAACATTTCCCCTAAGACTCCCCTCTCAGAGAGAATGCTCCATTCTTGGCACTGGCTGGCTTCTCAGACCAGCCATTGA
GAGCCCTGTGGGAGGGGGACAAGAATGTATAGGGAGAAATCTTGGGCCTGAGTCAATGGATAGGTCCTAGGAGGTGGCTG
GGGTTGAGAATAGAAGGGCCTGGACAGATTATGATTGCTCAGGCATACCAGGTTATAGCTCCAAGTTCCACAGGTCTGCT
ACCACAGGCCATCAAAATATAAGTTTCCAGGCTTTGCAGAAGACCTTGTCTCCTTAGAAATGCCCCAGAAATTTTCCACA
CCCTCCTCGTATCCATGGAGAGCCTGGGGCCAGATATCTGGCTCATCTCTGGCATTGCTTCCTCTCCTTCCTTCCTGCA
TGTGTTGGTGGTGGTTGTGGTGGGGAATGTGGATGGGGGATGTCCTGGCTGATGCCTGCCAAAATTTCATCCCACCCTC
CTTGCTTATCGTCCCTGTTTTGAGGGCTATGACTTGAGTTTTTGTTTCCCATGTTCTCTATAGACTTGGGACCTTCCTGA
ACTTGGGGCCTATCACTCCCCACAGTGGATGCCTTAAAAGGGAGAGGGAAGGAGGGAGGCAGGCATAGCATCTGAACCCA
GTGTGGGGGCATTCACTAGAATCTTCAATCAACCTGGGCTCTCCCCACCCCACCCCAGATAACCTCCTCAGTTCCCTAGG
GTCTCTTCTTGCTTGACTCAATCTACCCAGAGATGCCCCTTAGCACACCTAGAGGGCAGGGACCATAGGACCCAGGTTCC
AACCCCATTGTCAGCACCCCAGCCATGCGGCCACCCCTTAGCCTGCTCGTCCCATTTAGCTTACCCTCCCAGTTGG
CCAGAATCTGAGGGGAGAGCCCCCAGAGAGCCCCCTTCCCCATCAGAAGACTGTTGACTGCTTTGCATTTTGGGCTCTTC
TATATATTTTGTAAAGTAAGAAATATACCAGATCTAATAAAACACAATGGCTATGCACAGAAAAAAAAAAAAAAAA human kchip2N protein
MNRCPRRCRSPLGQAARSLYQLVTGSLSPDSVDDEFELSTVCHRPEGLEQLQEQTKFTRKELQVLYRGFKNECPSGIVNE
ENFKQIYSQFFPQGDSSTYATFLFNAFDTNHDGSVSFEDFVAGLSVILRGTVDDRLNWAFNLYDLNKDGCITKEEMLDIM
KSIYDMMGKYTYPALREEAPREHVESFFQKMDRNKDGVVTIEEFIESCQKDENIMRSMQLFDNVI

FIG. 49 full length human kchip3 cDNA sequence based on sequences of p19, p193 tctagagccgccaccatgcagccggctaagGAAGTGACAAAGGCGTCGGACGGCAGCCTCCTGGGGGACCTCGGGCACAC
ACCACTTAGCAAGAAGGAGGGTATCAAGTGGCAGAGGCCGAGGCTCAGCCGCCAGGCTTTGATGAGATGCTGCCTGGTCA
AGTGGATCCTGTCCAGCACAGCCCCACAGGGCTCAGatagcagcgacagtgagctggagctgtccacggtgcgccaccag
ccagagggctggaccagctgcaggcccagaccaagttcaccaagaaggagctgcagtctctctacaggggctttaagaa
tGAGTGTCCCACGGGCCTGGTGGACGAAGACACCTTCAAACTCATTTACGCGCAGTTCTTCCCTCAGGGAGatgccacca
cctatgcacacttcctcttcaacgcctttgatgcggacgggaacggggccatccactttgaGGACTTTGTGGTTGGCCTC
TCCATCCTGCTGCGGGGCACAGTCCACGAGAAGCTCAAGTGGGCCTTTAATCTCTACGACATTAACAAGGATGGCTACAT
CACCAAAGAGgagatgctggccatcatgaagtccatctatgacatgatgggccgccacacctaccccatcctgcgggagg
acgcgccggcgagcacgtggagacgttcttcgagAAAATGGACCGGAACCAGGATGGGGTAGTGACCATTGAAGAGTTC
CTGGAGGCCTGTCAGAAGgatgagaacatcatgagctccatgcagctgtttgagaatgtcatctaggacacgtccaaagg
agtgcatggccacagccacctccaccccaagaaacctccatcctgccaggagcagcctccaagaaacttttaaaaaata
gatttgcaaaaagtgaacagattgctacacacacacacacacacacacacacacacacacacacacacagccattcatctgg
gctggcagagggacagagttcaggagggggctgagtctggctaggggccgagtccaggagcccagccagcccttccca
ggccagcgagcgaggctgcctctgggtgagtggctgacagagcaggtctgcaggccaccagctgctggatgtcaccaag
aagggggctcgagtgccctgcagggagggtccaatctccggtgtgagcccacctcgtcccgttctccattctgctttct
tgccacacagtgggccggccccaggctcccctggtctcctcccgtagccactctctgccactacctatgcttctagaa
agcccctcacctcaggaccccagagggaccagctgggggcaggggggagagggggtaatgcaggccaagcctgcagctt
tctggaaattcttccctggggtcccaggatcccctgctactccactgacctggaagagctgggtaccaggccaccact
gtggggcaagcctgagtggtgaggggccactgggcccattctccctccatggcaggaaggcgggggatttcaagtttag
ggattgggtcgtggtggagaatctgagggcactctctgccagctccacagggtgggatgagcctctccttgcccagtcc
tggttcagtgggaatgcagtgggtgggctgtacacaccctccagcacagactgttccctccaaggtcctcttaggtccc
gggaggaacgtggttcagagactggcagccagggagcccggggcagagctcagaggagtctgggaaggggcgtgtccctc
ctcttcctgtagtgcccctcccatggccagcagctggctgcagccctctcctgaagcagtgtcgccgtccctctgcc
ttgcacaaaaagcacaagcattccttagcagctcaggcgcagccctagtgggagcccagcacactgcttctcggaggcca
ggccctcctgctggctgaggcttgggcccagtagccccaatatggtggccctggggaagaggccttgggggtctgctctg
tgcctgggatcagtggggccccaaagcccagcccggctgaccaacattcaaaagcacaaaccctggggactctgcttggc
tgtcccctccatctggggatggagaatgccagcccaaagctggagccaatggtgagggctgagagggctgtggctgggtg
gtcagcagaaaccccaggaggagagagatgctgctcccgcctgattggggcctcacccagaaggaaccggtcccaggc
cgcatgcccctccaggaacattcccacataatacattccatcacagccagcccagctccactcagggctggccgggga
gtccccgtgtgccccaagaggctagccccaggggtgagcagggccctcagaggaaaggcagtatggcggaggccatgggg
cccctcggcattcacacacagcctggcctcccctgcggagctgcatggacgcctggctccaggctccaggctgactgggg
gcctctgcctccaggagggcatcagctttccctggctcagggatcttctccctcccctcacccgctgcccagccctccca
gctggtgtcactctgcctctaaggccaaggcctcaggagagcatcaccaccacaccctgccggccttggccttggggcc
agactggctgcacagcccaaccaggaggggtctgcctccacgctgggacacagacggccgcatgtctgcatggcagaa
gcgtctcccttggccacggcctgggagggtggttcctgttctcagcatccactaatattcagtcctgtatattttaataa
aataaacttgacaaaggaaaaaaaaaaaaaaaaaaa human kchip3 protein MQPAKEVTKASDGSLLGDLGHTPLSKKEGIKWQRPRLSRQAIMRCCLVKWILSSTAPQGSDSSDSELELSTVRHQPEGLD
QLQAQTKFTKKELQSLYRGFKNECPTGLVDEDTFKLIYAQFFPQGDATTYAHFLFNAFDADGNGAIHFEDFVVGLSILLR
GTVHEKLKWAFNLYDINKDGYITKEEMLAIMKSIYDMMGRHTYPILREDAPAEHVERFFEKMDRNQDGVVTIEEFLEACQ
KDENIMSSMQLFENVI

FIG. 51

Rat kchip3 cDNA (CD(partial): 1-579)

agtgaactggagttgtccacggtgcgccatcagccagagggcttggaccagctacaggcccaaaccaagttcaccaagaa
ggagctgcagtccctgtaccgaggcttcaagaacgaatgtcccacgggcctggtcgatgaagataccttcaaactcattt
attcccagttcttcccccagggagatgccaccacctatgcacacttcctcttcaatgccttcgatgctgatgggaacggg
gccatccactttgaggactttgtggttgggctctccatcctgcttcgagggaccgtccatgagaagctcaagtgggcctt
caatctctacgacatcaacaaggacggttacatcaccaaagaggagatgctggccatcatgaagtccatctacgacatga
tgggccgccacacctaccctatcctgcgggaggacgcacctctggagcatgtggagaggttcttccagaaaatggacagg
aaccaggatggagtagtgactattgatgaatttctggagacttgtcagaaggacgagaacatcatgagctccatgcagct
gtttgagaacgtcatctagGACATGTAGGAGGGGACCCTGGGTGGCCATGGGTTCTCAACCCAGAGAAGCCTCAATCCTG
ACAGGAGAAGCCTCTATGAGAAACATTTTTCTAATATATTTGCAAAAAGTGAGCAGTTTACTTCCAAGCACAGACACAG
TCACACACACACACACACACACACACACACACACACACACACACACACACACACGGTTCCTCTAACTTGGTAATTGAA
GTGGCAGCCTGGAGGCACCCCCAGCTATTCCCAGGTCCTCTGGGATGGCCAGCCCAGGCTAGATGTTACGCACAAGGAGC
TCAGAGCCCAAGAGGGCCAGTTAAACAAAGATAAGGTCCCTGTGTCTTTTCTACCACTTGGGGGATCAAACTACTCCCTG
CCCATGGACCCATGCTCCTAGGGAGCTCCCAGAAACTTCTCAGGGGCCAGGAGGGGAGAGGTCTGGTAGGGAGAAGTGGT
GTTGGAAGCTGAGTCTGCAGCCTTATGCTAATGCTTACCTGGGACCCTGGAACCCCAGCATCAGGATAGCTAGTGGGGT
GAACTTAGTGAGGGGCACTGGGTTATGCTCTCCTTTAAGAGTAGGGAAGGATTGAGGGTTTTGGGGAAACCAAGAGAAC
AATTTGTCCATACCATCGGATGAAGACTGCTGGCCAATGGGAATGTGACTGGTGGAGATCTCCCAACTTCCAGCACCAGG
CTGGCCTTTCCAGGGTCCCCTTTGGTCTTCTCGGAGATCACCCGGCTCAGGGACTGATAACCAGGGAGCTAGACTGAAA
TGGGAGAGGTCTGGTAGGGGCATCCCCCTCTTTCTCCCTGGCCACTTGCCACCCAGTTCCTTAACATGGCAAATCGGCC
AGCCACACCTCTGCAGCTGTCCTTGAACAGGTTCATCCCAACCCAGACAAAAAGCACAAACATCCTAGCAGCTCAGGCCA
TGCCCACCGGGGAGGCAGGGGGCCCTGGGTGGGATGGGGGGTTGGGTCCATGCAGCCCTGATCCAGTGTTCGGGAAG
ATGCTCAGAAATCCATCCTGTACCTCGGAGCCTTGGGATCTCACAGACCTTTCCCAGCCTAGCTCGCCAACATTCTAAAG
CACAAACCTGTGGACTCTGCTTGCCTGGGCTGCACCCCGGGGATCGGTGTCTGTGTTAGCCCTAAGCTGGAGCTAGCCCT
GAGGGCTGGGGACTTGTGACCAGGCAGCAGGTCAACAGAGCCTCAGGAAGAGAGAGAGCTGTTCCTGCCTCCCCAGAAGG
GACAGTGACCCAGGCAGCATCTTCCTGGAGGAACAATCCCACGAAAGTACATTCCATCACCTGCAGCCCGGTCTCTGCTC
AGGCTTGCTCTGAGAGTCCATGCGTGTTCCCCAGAAGGCCAGCCCCAGGTTAAGGGAGGTCCTTAGAGGAAGAACGGGGT
GACAGTGCCCCTACACACAGGTGGGCCCCCCTCTCAGGGCTGCACTGACCCCATCTCCATCCTGACTGGGGCCTCCCTTG
ACCCTGTCAACAGACCATCAGCTCTCCCTGGCTCAGGGACCTCCCCTACCCCAGCCTGGCTCTCCCCATTGAGGTTCCTA
TCCTGTGAGAAGCCAAGGCCACGGGAAAAGGCTATCACTCGAAACCTACTGCGCCCCTTAGCCTCTGGCTGCACGCCCAA
CCTGGAGGGTCTGTCCCCTTGGCAGGGACCCAGACGGGCCGCATGTCTGCATGGCAGAAGCGTCTCCCTTGGGTGCAGC
CTGGAAGGGTGGTTCCTGTCTCGGCGCCCACCAATATTCAGTCCTATATATTTTAATAAAAGAAACTTGACAAAGGAAAA
AAAAAAAAAAAAAA rkchip3 protein (partial)

SELELSTVRHQPEGLDQLQAQTKFIKKELQSLYRGFKNECPTGLVDEDTFKLIYSQFFPQGDATTYAHFLFNAFDADGNG
AIHFEDFVVGLSILLRGTVHEKLKWAFNLYDINKDGYITKEEMLAIMKSIYDMMGRHTYPILREDAPLEHVERFFQKMDR
NQDGVVTIDEFLETCQKD

FIG. 52 monkey kchip4XC cDNA (partial, CD: 1-385)

ATATGCACATTTTCTGTTCAATGCGTTTGATACGGACCACAATGGAGCTGTGAGTTTCGAGGATTTCATCAAAGGTCTTT
CCATTTTGCTCCGGGGGACAGTACAAGAAAAACTCAATTGGGCATTTAATCTGTATGATATAAATAAAGATGGCTACATC
ACTAAAGAGGAAATGCTTGATATAATGAAAGCAATATACGACATGATGGGTAAATGTACATATCCTGTCCTCAAAGAAGA
TGCACCCAGACAACACGTCGAAACATTTTTTCAGGCTGTTTTCCATTGTATCATCAAGTGGAAGTTCAAGACGGCATCAA
ACAAAACAAGGATGTTTACAGACATATGCAAAGGGTCAGGATATCTATCCTCCAGTATATGTTAATGCTTAATAACAAGT
AATCCTAACAGCATTAAAGGCCAAATCTGTCCTCTTTCCCCTGACTTCCTTACAGCATGTTTATATTACAAGCCATTCAG
GGACAAAGAAACCTTGACTACCCACTGTCTACTAGGAACAAACAAACAGCAAGCAAAATTCACTTTGAAAGCACCAGTG
GTTCCATTACATTGACAACTACTACCAAGATTCAGTAGAAAATAAGTGCTCAACAACTAATCCAGATTACAATATGATTT
AGTGCATCATAAAATTCCAACAATTCAGATTATTTTTAATCATCTCAGCCACAACTGTAAAGTTGCCACATTACTAAAGA
CACACACATCGTCCCTGTTTTGTAGAAATATCACAAAGACCAAGAGGCTACAGAAGGAGGAAATTTGCAACTGTCTTTGC
AACAATAAATCAGGTATCTATTCTGGTGTAGAGATAGGATGTTGAAAGCTGCCCTGCTATCACCAGTGTAGAAATTAAGA
GTAGTACAATACATGTACACTGAAATTTGCCATCGCGTGTTTGTGTAAACTCAATGTGCACATTTTGTATTTCAAAAAGA
AAAAATAAAAGCAAAATAAAATGTTAAAAAAAAAAAAAAAAAAAA monkey kchip4C protein (partial)
YAHFLFNAFDTDHNGAVSFEDFIKGLSILLRGTVQEKLNWAFNLYDINKDGYITKEEMLDIMKAIYDMMGKCTYPVLKED
APRQHVETFFQAVFHCIIKWKFKTASNKTRMFTDICKGSGYLSSSIC

FIG. 53

Mouse kchip4c (kchip4N2) cDNA (CD:56-745)

```
GCCAGGGTGAGGAGCGCTTCTCAGTGGCTGTGGCTGGACCATGACCtagCTGACCATGAACTTGGAGGGGCTTGAAATGA
TAGCAGTTCTGATCGTCATTGTGCTTTTTGTTAAATTATTGGAACAGTTTGGGCTGATTGAAGCAGGTTTAGAAGACAGC
GTGGAAGATGAGCTGGAGATGGCTACTGTCAGGCATCGGCCTGAAGCCCTGGAGCTGCTGGAGGCCCAGAGCAAATTCAC
CAAGAAAGAGCTTCAGATTCTTTACAGAGGATTTAAGAATGAATGCCCCAGTGGTGTTGTTAATGAAGAAACTTTCAAGG
AGATTTACTCACAGTTCTTTCCACAGGGAGACTCCACCACATATGCACATTTTCTCTTCAATGCATTCGACACGGACCAC
AATGGAGCTGTGAGCTTTGAGGATTTCATCAAAGGTCTTTCCATTTTGCTTCGAGGGACAGTACAAGAAAAACTCAACTG
GGCATTTAATTTGTATGACATAAACAAAGATGGCTACATCACTAAAGAAGAAATGCTGGACATAATGAAAGCAATCTACG
ACATGATGGGGAAATGCACATACCCGGTCCTCAAGGAAGATGCTCCCCGACAGCATGTGGAGACGTTCTTCCAGAAGATG
GACAAAAATAAAGATGGTGTCGTTACCATAGATGAGTTCATTGAAAGTTGCCAAAAAGATGAAAACATAATGCGCTCCAT
GCAGCTCTTTGAAAATGTGATCTAGAATGTCAGCACCTCCTCGACCGAAGAGGCAAATGTGAACGACTACACACAAGTTG
AAGCCCCCACTTGTAGCATAGATAGCTCAGCTTTACACTGAGGCAGATTATGCAAACAGCTTTGTTTTAATAAAAAGCAA
CCCACCACCACCACCAAAATTAAGTTTTCCAGTTACAAATCTGCATCCATGTCACCGGGGTCATGAAATGTGCTAACTTA
TTTCATACTCAAAAGGCACAGAATCTGGAATAGCTTTGATCCTTAGCCACGTTATTATTGAGGTTTTTACAGTTCAGTGA
TTTTAAAACACCAGTGGGTTTTCCTACTTGTTTGTATGTATTCAGCCCTGGGTTTTAAATGTTTTCTAAAATACTTACA
TCTGCATTTAACTTCCAGAAAGTCAATGAACTTTCATTAAATTCGACTCATGTAACACTGAAAAATGAAACAAAGATTAC
TACAATTTAAATAGACCAAAAACACAGTCCCAATTTCTATGGCTTCTCCACCTGCTGTTAAAGATATTAATGTATTTGGC
ATTTTTTTAAAAGGACACTTAAAAAATTAGTTTATTATCAGATGTTAGCATATACCTAATAAAATTATTTTAGTATTTGT
TAATTTTCCATACTCAAGCCAAGGCTCTATATAATCCATGAAACTTTGGACCTGTTCAATCTTACATGTAGACTGTTTTG
TATTGTGTTATGAAGTAGAAATTCAAAGTGTCAAACAAACCAAGGATGTTTACAGACTTGCCAAGGGTCCGGATGTCTGT
CCTGCAATGCCTAGTGACGCTTATTAACAAGTAACCCTAACAGCAGTAAAGGGCAGTTCTTGCCACCCTCCAAGCCCCTT
AATGTTTTCACAGCATGTTTATCATACATAAGCCATTCAGGAACAGAGAATCCTTGACGCCCAAAGCCTACTAGGAATA
ATGATCAAGTAACATACTCTTTGAGAACACCCGTGATTCTATAGTATTGGAAATTATACACAAGAATGTATAGAAAATGA
CTGCAAACACTGACGGTTCATCTGAAATGCATTATGATTTAGCACATCATATAGCTCAAAGGATTCATAGTCCTTTCAGT
GGTCTTAAGCCAAAACTGTAGAGTTGCCACAACAGTACTATAGAGATACACATCTTCCCTGTTGCGCAGAAATACAAGAA
CCAAGAGGATACAGGAGGAGAAAATTTACGACTGTCTGCAACAATAAATCAGGTATCTATTCTGGTGTAGAGATAGGATG
TTGAAAGCTGCCCTGCTATCACCAGTGTAGGAATTAAGAGTAGTACAGTACATGTACAGAAATCTGCCATCGCGTGTTTG
TGTAAACTCAATGTGCACATTTTGTATCTCAAAACGGAAAAATAAAAGCAAAATAAAGTGTTTATTACTCTAAAAAAAAA
AAAAAAAAAAAAAAAAAAAAA
```

Mouse kchip4c (kchip4N2) protein

```
MNLEGLEMIAVLIVIVLFVKLLEQFGLIEAGLEDSVEDELEMATVRHRPEALELLEAQSKFTKKELQILYRGFKNECPSG
VVNEETFKEIYSQFFPQGDSTTYAHFLFNAFDTDHNGAVSFEDFIKGLSILLRGTVQEKLNWAFNLYDINKDGYITKEEM
LDIMKAIYDMMGKCTYPVLKEDAPRQHVETFFQKMDKNKDGVVTIDEFIESCQKDENIMRSMQLFENVI
```

FIG. 54

Rat kchip4 cDNA (CD: 1-597, partial)

TTAGAAGACAGTGTGGAAGATGAACTGGAGATGGCCACTGTCAGGCACCGGCCTGAAGCCCTGGAGCTGCTGGAGGCCCA
GAGCAAATTCACCAAGAAAGAGCTTCAGATCCTTTACAGAGGATTTAAGAATGAATGCCCCAGTGGTGTTGTTAATGAAG
AAACCTTCAAGGAGATTTACTCGCAGTTCTTCCCACAGGGAGACTCCACCACATATGCACATTTTCTCTTCAATGCATTC
GACACGGACCACAATGGAGCTGTGAGCTTTGAGGATTTCATCAAAGGTCTTTCCATTTTGCTTCGAGGGACAGTACAAGA
AAAACTGAACTGGGCATTTAATTTGTATGACATAAACAAAGATGGCTACATCACTAAAGAGGAAATGCTGGACATAATGA
AAGCAATTTACGACATGATGGGGAAATGCACATACCCTGTCCTCAAGGAAGATGCTCCCCGACAGCACGTGGAGACATTT
TTCCAGAAGATGGACAAGAATAAAGATGGTGTCGTTACCATAGACGAGTTCATTGAAAGTTGCCAAAAAGATGAAAACAT
AATGCGCTCCATGCAGCTCTTTGAAAATGTGATCTAGactgtcggtgccttgaccggaggcaaatgtggacgactacaca
cgagttgaagccaccatttctagcatagattgctcagctttacactgaggcatattatgcaaacagctttgttttaatat
aaagacccccgcgcccaaatttaagttttccagttacaaatccgcatccacgtcactggggtcccgaaatgtgctcactt
atttcatactctgagaacactcaaaaggcacagaatctggaacagctttgatcctcagccacgtgttacggggcttttta
cagatgagtgattttaaaacaccagtgggTTTTCCTACTTGTTTGTATTCAGCCCTGGATTTTAAGTGGTTTTCTAAAAT
ATTTACATCTGCATTTAACTTCCAGAAAGCCAATGACCTTTTCATTTAACTCAATTCATGTAATACTGAAAAAAGGAACA
AAGATTATTACAATTAAAAAAGACCAAAAACACAGTCCCGATTTCTATAGCTTCTCCACCTGCTGTTAAAGACAGTCATG
TATTTGGCTTTTTTTTTTTTTTAAAAAGAACACTTAAAAAATTAGTTTATTATCAGATGTTAGCATATACCTAATAAAA
TTATTTAGTATTTGTTAATTTTCCATATTCAAGCCAAGGCTCTATATAATCCATGTAACTTTGGACCTGTTCAATCTTA
CATGTAGACTGTTTTGTATTGTGTTCTGAAGTAGAAGTTCAAAGTGTCAAACAAACCAAGGATGTTTACAGACTTGCAAA
GGGTCCAGATGTCTGTCCTGCAATGCCTAGTGACGCTTATTAACCAGTAACCTGAAGAGCAGTAACTGGCAATTCTAGCC
ACCACCCCTCCCCAAGCCCTTCATGTTCTCACAGCATGTTTATCACACACAAGCCATTCAGGGACAGAGAATCCTTGAC
TGCCCCAAAGCCTACTAGGAATAAAGATCAAGCAAAATCTTCTTTGAAAACACCAGTGATTCTATCATATTGGAAATATA
CATAAGAGTGTATAGAAAACGAATGTAGACATTGGACAGTTCATCCGAATTGCATTATGATTTAGCACATCATGTAGTTC
AAAGGATTCACATTCCTTTCCGTGATCTTAAGCCAAAACTGCCACAACAGTACTAGATATACACACATTCCC
TGTTTCGTGGAAATCCAAGAACCAAGAGGATACGGGAAGAGAAAATTTGCGACTGTCTGCAACAATAAATCAGGTATCTA
TTCTGGTGTAGAGATAGGATGTTGAGAGCCGCCCTGCTATCACCAGTGTAGGAATTAAGAGTAGTACAGTACATGTACAG
AAATCTGCCATCGCGTGTTTGTGTAAACTCAATGTGCACATTTTGTATCTCAAAAAGGAAAAATAAAGCAAAATAAAGTG
TTAAAAAAAAAAAAAAAAAAAAAAA Rat kchip4 protein (partial)

LEDSVEDELEMATVRHRPEALELLEAQSKFTKKELQILYRGFKNECPSGVVNEETFKEIYSQFFPQGDSTTYAHFLFNAF
DTDHNGAVSFEDFIKGLSILLRGTVQEKLNWAFNLYDINKDGYITKEEMLDIMKAIYDMMGKCTYPVLKEDAPRQHVETF
FQKMDKNKDGVVTIDEFIESCQKDENIMRSMQLFENVI

FIG. 55 human kchip4N1S cDNA (CD: 319-885)

```
GAGAGGTCCGTGCGCTGTGGTAGCAGGGGGGAAGCCCCGCCAGCCAAATGCCAGGATCAGCATGAGAAGCTGGACTTTAG
CCCAGGTCTGTCCTCACCCCGGGGGGCCGCCGGCTTTGCAGGGTGCATCTGCCAGGAGCTGCTCACTTTTTCCCCTTGCA
AGTCTTTGTTCCAAGCCTGACGTTGCTACGATTCTGTAATTAACTCCCTCCACTCCAAAGGGGTCTGGAGGCTGGGATGC
TCTGCCAGCTCAGAGGATGTTGACTCTGGAGTGGGAGTCCGAAGGACTGCAAACAACAGCGTGGAAGATGAACTGGAGAT
GGCCACCGTCAGGCATCGGCCCGAAGCCCTTGAGCTTCTGGAAGCCCAGAGCAAATTTACCAAGAAAGAGCTTCAGATCC
TTTACAGAGGATTTAAGAACGAATGCCCCAGTGGTGTTGTTAATGAAGAAACCTTCAAAGAGATTTACTCGCAGTTCTTT
CCACAGGGAGACTCTACAACATATGCACATTTTCTGTTCAATGCATTTGATACAGACCACAATGGAGCTGTGAGTTTCGA
GGATTTCATCAAAGGTCTTTCCATTTTGCTCCGGGGGACAGTACAAGAAAAACTCAATTGGGCATTTAATCTGTATGACA
TAAATAAAGATGGCTACATCACTAAAGAGGAAATGCTTGATATAATGAAAGCAATATACGATATGATGGGTAAATGTACA
TATCCTGTCCTCAAAGAAGATGCTCCCAGACAACACGTTGAAACATTTTTTCAGAAAATGGACAAAAATAAAGATGGGT
TGTTACCATAGATGAGTTCATTGAAAGCTGCCAAAAAGATGAAAACATAATGCGCTCCATGCAGCTCTTTGAAAATGTGA
TTTAACTTGTCAAATAGATCCTGAATCCAACAGACAAATGTGAACTATTCTACCACCCTTAAAGTTGGAGCTACCACTTT
TAGCATAGATTGCTCAGCTTGACACTGAAGCATATTATGCAAACAAGCTTTGTTTTAATATAAAGCAATCCCCAAAAGAT
TTGAGCTTTCAGTTATAAATTTGCATCCTTTTCATAATGCCACTGAGTTCAGGGGATGGTCTAACTCATTTCATACTCTG
TGAATATTCAAAAGTAATAGAATCTGGCATATAGTTTTATTGGTTCCTTAGCCATGGGATTATTGAGGCTTTCACATATC
AGTGATTTTAAAATATCAGTGTTTTTTGCTACTCATTTGTATGTATTCAGTCCTAGGATTTTGAATGGTTTTCTAATATA
GTGACATCTGCATTTAATTTCCAGAAATTAAATTAATTTTCATGTTTGAATGCTGTAATTCCATTTAAATTCCATTTATA
TACTTTAAGGAAACAAGATTACAACAATTAAAAAAACACATAGTTCCAGTTTCTATGGCCTTCCCACCTTCTGTTAGAAA
TTAGTTTTATCTGGCATTTTTAAACATTTAAAAATTATTAAACATTTAAAAATTAGTTTATTATCAGATATCAGCATATG
CCTAATAAAACTTATTTTAATAAGCATTTAATTTTCCATAGTATGTTACAGCCAAGGCCTATATAATAATTTTGGATTTG
TTCAATCTTTCTTACAGGCTGTTTTCTATTGTATCAATCATTAGTATCAATCATTAAGTGGAAGTTGAAGAAGGCATCAA
ACAAAACAAGGATGTTTACAGACATATGCAAAGGGTCAGGATATCTATCCTCCAGTATATAGTAATGCTTAATAACAAGT
AATCCTAACAGCATTAAAGGCCAAATCTGTCCTCTTTCCCCTGACTTCCTTACAGCATGTTTATTTATATTACAAGCCAT
TCAGGGACAAAGAAAGAAACCTTGACTACCCCACTGTCTACTAAGAACAAACAGCAAGCAAAATTAGCAAGCAAAATTCA
CTTTGAAAGCACCAGTGGTTCCATTACATTGACAACTACTACCAAGATTTAGTAGAAAATAAGTGCTCAACAACTAATCC
AGATTACAGTATGATTTAGCTCATCATAATTCAGATTATTTTTAATCATCTTAGCCAAAACTGTAAAGTTGCCACATTAC
TAAAGCCACACACATCGTCCCTGTTTTGTAGAAATATCACAAAGACCAAGAGGCTACAGAAGGAGGAAATTTGCAACTGT
CTTTGCAACAATAAATCAGGTATCTATTCTGGTGTAGAGATAGGATGTTGAAAGCTGCCCTGCTATCACCAGTGTAGAAA
TTAAGAGTAGTACAATACATGTACACTGAAATTTGCCATCACGTGTTTGTGTAAACTCAATGTGCACATTTTGTATTTCA
AAAAGAAAAAATAAAAGCAAAATAAAATGTTAAAAAAAAAAAAAAAA
``` human kchip4N1S protein

```
MATVRHRPEALELLEAQSKFTKKELQILYRGFKNECPSGVVNEETFKEIYSQFFPQGDSTTYAHFLFNAFDTDHNGAVSF
EDFIKGLSILLRGTVQEKLNWAFNLYDINKDGYITKEEMLDIMKAIYDMMGKCTYPVLKEDAPRQHVETFFQKMDKNKDG
VVTIDEFIESCQKDENIMRSMQLFENVI
```

FIG. 56

Human kchip4N1 cDNA (by joining kchip4N1 N + 5'UT and kchip4C, CD: 248-949)
GTGCGCTGTGGTAGCAGGGGGGAAGCCCCGCCAGCCAAATGCCAGGATCAGCATGAGAAGCTGGACTTTAGCCCAGGTCT
GTCCTCACCCCGGGGGGCCGCCGGCTTTGCAGGGTGCATCTGCCAGGAGCTGCTCACTTTTTCCCCTTGCAAGTCTTTGT
TCCAAGCCTGACGTTGCTACGATTCTGTAATTAACTCCCTCCACTCCAAAGGGGTCTGGAGGCTGGGATGCTCTGCCAGC
TCAGAGGATGTTGACTCTGGAGTGGGAGTCCGAAGGACTGCAAACAGTGGGTATTGTTGTGATTATATGTGCATCTCTGA
AGCTTCTTCATTTGCTGGGACTGATTGATTTTTCGGAAGACAGCGTGGAAGATGAACTGGAGATGGCCACCGTCAGGCAT
CGGCCTGAAGCCCTTGAGCTTCTGGAAGCCCAGAGCAAATTTACCAAGAAAGAGCTTCAGATCCTTTACAGAGGATTTAA
GAATGAATGCCCCAGTGGTGTTGTTAATGAAGAAACCTTCAAAGAGATTTACTCGCAGTTCTTTCCACAGGGAGACTCTA
CAACATATGCACATTTTCTGTTCAATGCATTTGATACAGACCACAATGGAGCTGTGAGTTTCGAGGATTTCATCAAAGGT
CTTTCCATTTTGCTCCGGGGACAGTACAAGAAAAACTCAATTGGGCATTTAATCTGTATGACATAAATAAAGATGGCTA
CATCACTAAAGAGGAAATGCTTGATATAATGAAAGCAATATACGATATGATGGGTAAATGTACATATCCTGTCCTCAAAG
AAGATGCTCCCAGACAACACGTTGAAACATTTTTTCAGAAAATGGACAAAAATAAAGATGGGGTTGTTACCATAGATGAG
TTCATTGAAAGCTGCCAAAAAGATGAAAACATAATGCGCTCCATGCAGCTCTTTGAAAATGTGATTTAACTTGTCAAATA
GATCCTGAATCCAACAGACAAATGTGAACTATTCTACCACCCTTAAAGTTGGAGCTACCACTTTTAGCATAGATTGCTCA
GCTTGACACTGAAGCATATTATGCAAACAAGCTTTGTTTTAATATAAAGCAATCCCCAAAAGATTTGAGCTTTCAGTTAT
AAATTTGCATCCTTTTCATAATGCCACTGAGTTCAGGGGATGGTCTAACTCATTTCATACTCTGTGAATATTCAAAAGTA
ATAGAATCTGGCATATAGTTTTATTGGTTCCTTAGCCATGGGATTATTGAGGCTTTCACATATCAGTGATTTTAAAATAT
CAGTGTTTTTTGCTACTCATTTGTATGTATTCAGTCCTAGGATTTTGAATGGTTTTCTAATATAGTGACATCTGCATTTA
ATTTCCAGAAATTAAATTAATTTTCATGTTTGAATGCTGTAATTCCATTTAAATTCCATTTATATACTTTAAGGAAACAA
GATTACAACAATTAAAAAAACACATAGTTCCAGTTTCTATGCCTTCCCACCTTCTGTTAGAAATTAGTTTTATCTGGCA
TTTTTAAACATTTAAAAATTATTAAACATTTAAAAATTAGTTTATTATCAGATATCAGCATATGCCTAATAAAACTTATT
TTAATAAGCATTTAATTTTCCATAATATGTTACAGCCAAGGCCTATATAATAATTTTGGATTTGTTCAATCTTTCTTACA
GGCTGTTTTCTATTGTATCAATCATTAGTATCAATCATTAAGTGGAAGTTGAAGAAGGCATCAAACAAAACAAGGATGTT
TACAGACATATGCAAAGGGTCAGGATATCTATCCTCCAGTATATAGTAATGCTTAATAACAAGTAATCCTAACAGCATTA
AAGGCCAAATCTGTCCTCTTTCCCCTGACTTCCTTACAGCATGTTTATTTATATTACAAGCCATTCAGGGACAAAGAAAG
AAACCTTGACTACCCCACTGTCTACTAAGAACAAACAGCAAGCAAAATTAGCAAGCAAAATTCACTTTGAAAGCACCAGT
GGTTCCATTACATTGACAACTACTACCAAGATTTAGTAGAAAATAAGTGCTCAACAACTAATCCAGATTACAGTATGATT
TAGCTCATCATAATTCAGATTATTTTTAATCATCTTAGCCAAAACTGTAAAGTTGCCACATTACTAAAGCCACACACATC
GTCCCTGTTTTGTAGAAATATCACAAAGACCAAGAGGCTACAGAAGGAGGAAATTTGCAACTGTCTTTGCAACAATAAAT
CAGGTATCTATTCTGGTGTAGAGATAGGATGTTGAAAGCTGCCCTGCTATCACCAGTGTAGAAATTAAGAGTAGTACAAT
ACATGTACACTGAAATTTGCCATCACGTGTTTGTGTAAACTCAATGTGCACATTTTGTATTTCAAAAAGAAAAAATAAAA
GCAAAATAAAATGTTAAAAAAAAAAAAAAA Human kchip4N1 protein (by translation of hkchip4N1 cDNA)
MLTLEWESEGLQTVGIVVIICASLKLLHLLGLIDFSEDSVEDELEMATVRHRPEALELLEAQSKFTKKELQILYRGFKNE
CPSGVVNEETFKEIYSQFFPQGDSTTYAHFLFNAFDTDHNGAVSFEDFIKGLSILLRGTVQEKLNWAFNLYDINKDGYIT
KEEMLDIMKAIYDMMGKCTYPVLKEDAPRQHVETFFQKMDKNKDGVVTIDEFIESCQKDENIMRSMQLFENVI

FIG. 57

Human kchip4N2 cDNA (by joining kchip4N2 N + 5'UT and kchip4C, CD: 90-779)

CCTTCTTAAGGAGGTTTAAGGCCTTCCAAAGAAAGCCAGGCAGAGAGGCACTTCTCAGTGGCTGTGGTCGGACCATGACC
TAGCTGACCATGAACTTGGAAGGGCTTGAAATGATAGCAGTTCTGATCGTCATTGTGCTTTTTGTTAAATTATTGGAACA
GTTTGGGCTGATTGAAGCAGGTTTAGAAGACAGCGTGGAAGATGAACTGGAGATGGCCACCGTCAGGCATCGGCCTGAAG
CCCTTGAGCTTCTGGAAGCCCAGAGCAAATTTACCAAGAAAGAGCTTCAGATCCTTTACAGAGGATTTAAGAATGAATGC
CCCAGTGGTGTTGTTAATGAAGAAACCTTCAAAGAGATTTACTCGCAGTTCTTTCCACAGGGAGACTCTACAACATATGC
ACATTTCTGTTCAATGCATTTGATACAGACCACAATGGAGCTGTGAGTTTCGAGGATTTCATCAAAGGTCTTTCCATTT
TGCTCCGGGGACAGTACAAGAAAAACTCAATTGGGCATTTAATCTGTATGACATAAATAAAGATGGCTACATCACTAAA
GAGGAAATGCTTGATATAATGAAAGCAATATACGATATGATGGGTAAATGTACATATCCTGTCCTCAAAGAAGATGCTCC
CAGACAACACGTTGAAACATTTTTTCAGAAAATGGACAAAAATAAAGATGGGGTTGTTACCATAGATGAGTTCATTGAAA
GCTGCCAAAAAGATGAAAACATAATGCGCTCCATGCAGCTCTTTGAAAATGTGATTTAACTTGTCAAATAGATCCTGAAT
CCAACAGACAAATGTGAACTATTCTACCACCCTTAAAGTTGGAGCTACCACTTTTAGCATAGATTGCTCAGCTTGACACT
GAAGCATATTATGCAAACAAGCTTTGTTTTAATATAAAGCAATCCCCAAAAGATTTGAGCTTTCAGTTATAAATTTGCAT
CCTTTTCATAATGCCACTGAGTTCAGGGGATGGTCTAACTCATTTCATACTCTGTGAATATTCAAAAGTAATAGAATCTG
GCATATAGTTTTATTGGTTCCTTAGCCATGGGATTATTGAGGCTTTCACATATCAGTGATTTTAAAATATCAGTGTTTTT
TGCTACTCATTTGTATGTATTCAGTCCTAGGATTTTGAATGGTTTTCTAATATAGTGACATCTGCATTTAATTTCCAGAA
ATTAAATTAATTTTCATGTTTGAATGCTGTAATTCCATTTAAATTCCATTTATATACTTTAAGGAAACAAGATTACAACA
ATTAAAAAAACACATAGTTCCAGTTTCTATGGCCTTCCCACCTTCTGTTAGAAATTAGTTTTATCTGGCATTTTTAAACA
TTTAAAAATTATTAAACATTTAAAAATTAGTTTATTATCAGATATCAGCATATGCCTAATAAAACTTATTTTAATAAGCA
TTTAATTTTCCATAATATGTTACAGCCAAGGCCTATATAATAATTTTGGATTTGTTCAATCTTTCTTACAGGCTGTTTTC
TATTGTATCAATCATTAGTATCAATCATTAAGTGGAAGTTGAAGAAGGCATCAAACAAAACAAGGATGTTTACAGACATA
TGCAAAGGGTCAGGATATCTATCCTCCAGTATATAGTAATGCTTAATAACAAGTAATCCTAACAGCATTAAAGCCAAAT
CTGTCCTCTTTCCCCTGACTTCCTTACAGCATGTTTATTTATATTACAAGCCATTCAGGGACAAAGAAAGAAACCTTGAC
TACCCCACTGTCTACTAAGAACAAACAGCAAGCAAAATTAGCAAGCAAAATTCACTTTGAAAGCACCAGTGGTTCCATTA
CATTGACAACTACTACCAAGATTTAGTAGAAAATAAGTGCTCAACAACTAATCCAGATTACAGTATGATTTAGCTCATCA
TAATTCAGATTATTTTTAATCATCTTAGCCAAAACTGTAAAGTTGCCACATTACTAAAGCCACACACATCGTCCCTGTTT
TGTAGAAATATCACAAAGACCAAGAGGCTACAGAAGGAGGAAATTTGCAACTGTCTTTGCAACAATAAATCAGGTATCTA
TTCTGGTGTAGAGATAGGATGTTGAAAGCTGCCCTGCTATCACCAGTGTAGAAATTAAGAGTAGTACAATACATGTACAC
TGAAATTTGCCATCACGTGTTTGTGTAAACTCAATGTGCACATTTTGTATTTCAAAAAGAAAAAATAAAAGCAAAATAAA
ATGTTAAAAAAAAAAAAAAAA

Human kchip4N2 protein (by translation of hkchip4N2 cDNA)

MNLEGLEMIAVLIVIVLFVKLLEQFGLIEAGLEDSVEDELEMATVRHRPEALELLEAQSKFTKKELQILYRGFKNECPSG
VVNEETFKEIYSQFFPQGDSTTYAHFLFNAFDTDHNGAVSFEDFIKGLSILLRGTVQEKLNWAFNLYDINKDGYITKEEM
LDIMKAIYDMMGKCTYPVLKEDAPRQHVETFFQKMDKNKDGVVTIDEFIESCQKDENIMRSMQLFENVI

FIG. 58

Human kchip4N3 cDNA (by joining kchip4N3 N exon1,exon2, and kchip4C, CD:65-817)

```
GTGGACAGACGCNCCCTGGCGGTGGACTTCTCGAGTCTCGCTTCTGCACCCTGCGTCCCCAGACATGAATGTGAGGAGGG
TGGAGAGCATTTCGGCTCAGCTGGAGGAGGCCAGCTCTACAGGCGGTTTCCTGTACGCTCAGAACAGCACCAAGCGCAGC
ATTAAAGAGCGGCTCATGAAGCTCTTGCCCTGCTCAGCTGCCAAAACGTCGTCTCCTGCTATTCAAAACAGCGTGGAAGA
TGAACTGGAGATGGCCACCGTCAGGCATCGGCCTGAAGCCCTTGAGCTTCTGGAAGCCCAGAGCAAATTTACCAAGAAAG
AGCTTCAGATCCTTTACAGAGGATTTAAGAATGAATGCCCCAGTGGTGTTGTTAATGAAGAAACCTTCAAAGAGATTTAC
TCGCAGTTCTTTCCACAGGGAGACTCTACAACATATGCACATTTTCTGTTCAATGCATTTGATACAGACCACAATGGAGC
TGTGAGTTTCGAGGATTTCATCAAAGGTCTTTCCATTTTGCTCCGGGGACAGTACAAGAAAAACTCAATGGGCATTTA
ATCTGTATGACATAAATAAAGATGGCTACATCACTAAAGAGGAAATGCTTGATATAATGAAAGCAATATACGATATGATG
GGTAAATGTACATATCCTGTCCTCAAAGAAGATGCTCCCAGACAACACGTTGAAACATTTTTTCAGAAAATGGACAAAAA
TAAAGATGGGGTTGTTACCATAGATGAGTTCATTGAAAGCTGCCAAAAAGATGAAAACATAATGCGCTCCATGCAGCTCT
TTGAAAATGTGATTTAACTTGTCAAATAGATCCTGAATCCAACAGACAAATGTGAACTATTCTACCACCCTTAAAGTTGG
AGCTACCACTTTTAGCATAGATTGCTCAGCTTGACACTGAAGCATATTATGCAAACAAGCTTTGTTTTAATATAAAGCAA
TCCCCAAAAGATTTGAGCTTTCAGTTATAAATTTGCATCCTTTTCATAATGCCACTGAGTTCAGGGGATGGTCTAACTCA
TTTCATACTCTGTGAATATTCAAAAGTAATAGAATCTGGCATATAGTTTTATTGGTTCCTTAGCCATGGGATTATTGAGG
CTTTCACATATCAGTGATTTTAAAATATCAGTGTTTTTGCTACTCATTTGTATGTATTCAGTCCTAGGATTTTGAATGG
TTTTCTAATATAGTGACATCTGCATTTAATTTCCAGAAATTAAATTAATTTTCATGTTTGAATGCTGTAATTCCATTTAA
ATTCCATTTATATACTTTAAGGAAACAAGATTACAACAATTAAAAAAACACATAGTTCCAGTTTCTATGGCCTTCCCACC
TTCTGTTAGAAATTAGTTTTATCTGGCATTTTTAAACATTTAAAAATTATTAAACATTTAAAAATTAGTTTATTATCAGA
TATCAGCATATGCCTAATAAAACTTATTTTAATAAGCATTTAATTTTCCATAATATGTTACAGCCAAGCCTATATAATA
ATTTTGGATTTGTTCAATCTTTCTTACAGGCTGTTTTCTATTGTATCAATCATTAGTATCAATCATTAAGTGGAAGTTGA
AGAAGGCATCAAACAAAACAAGGATGTTACAGACATATGCAAAGGGTCAGGATATCTATCCTCCAGTATATAGTAATGC
TTAATAACAAGTAATCCTAACAGCATTAAAGGCCAAATCTGTCCTCTTTCCCCTGACTTCCTTACAGCATGTTTATTTAT
ATTACAAGCCATTCAGGGACAAAGAAAGAAACCTTGACTACCCCACTGTCTACTAAGAACAAACAGCAAGCAAAATTAGC
AAGCAAAATTCACTTTGAAAGCACCAGTGGTTCCATTACATTGACAACTACTACCAAGATTTAGTAGAAAATAAGTGCTC
AACAACTAATCCAGATTACAGTATGATTTAGCTCATCATAATTCAGATTATTTTTAATCATCTTAGCCAAAACTGTAAAG
TTGCCACATTACTAAAGCCACACACATCGTCCCTGTTTTGTAGAAATATCACAAAGACCAAGAGGCTACAGAAGGAGCAA
ATTTGCAACTGTCTTTGCAACAATAAATCAGGTATCTATTCTGGTGTAGAGATAGGATGTTGAAAGCTGCCCTGCTATCA
CCAGTGTAGAAATTAAGAGTAGTACAATACATGTACACTGAAATTTGCCATCACGTGTTTGTGTAAACTCAATGTGCACA
TTTTGTATTTCAAAAAGAAAAAATAAAAGCAAAATAAAATGTTAAAAAAAAAAAAAAAA
```

Human kchip4N3 protein (by translation of hkchip4N3 cDNA)

```
MNVRRVESISAQLEEASSTGGFLYAQNSTKRSIKERLMKLLPCSAAKTSSPAIQNSVEDELEMATVRHRPEALELLEAQS
KFTKKELQILYRGFKNECPSGVVNEETFKEIYSQFFPQGDSTTYAHFLFNAFDTDHNGAVSFEDFIKGLSILLRGTVQEK
LNWAFNLYDINKDGYITKEEMLDIMKAIYDMMGKCTYPVLKEDAPRQHVETFFQKMDKNKDGVVTIDEFIESCQKDENIM
RSMQLFENVI
```

FIG. 59 rat KChIP4N1x (contig of jTrba133c02t1 and rkchip4) cDNA (partial), orf: +3, coding: 1-821

CCCCTCGCCAGACGCCCCTGGGTCAAGTGGACTCTAAGAGTGTCGCTCCAGCATCTATCATCCCTAAAGATGAACGTGAG
AAGGGTGGAAAGCATCTCGGCTCAGCTGGAGGAGGCGAGCTCCACAGGCGGTTTCCTCTACCTCAGAACAACACCAAGCG
CAGCATTAAAGAGCGGCTCATGAAGCTCTTGCCCTGCTCAGCTGCCAAAACGTCGTCTCCTGCTATACAAAACAGTGTGG
AAGATGAACTGGAGATGGCCACTGTCAGGCACCGGCCTGAAGCCCTGGAGCTGCTGGAGGCCCAGAGCAAATTCACCAAG
AAAGAGCTTCAGATCCTTTACAGAGGATTTAAGAATGAATGCCCCAGTGGTGTTGTTAATGAAGAAACCTTCAAGGAGAT
TTACTCGCAGTTCTTCCCACAGGGAGACTCCACCACATATGCACATTTTCTCTTCAATGCATTCGACACGGACCACAATG
GAGCTGTGAGCTTTGAGGATTTCATCAAAGGTCTTTCCATTTTGCTTCGAGGGACAGTACAAGAAAAACTGAACTGGGCA
TTTAATTTGTATGACATAAACAAAGATGGCTACATCACTAAAGAGGAAATGCTGGACATAATGAAAGCAATTTACGACAT
GATGGGGAAATGCACATACCCTGTCCTCAAGGAAGATGCTCCCCGACAGCACGTGGAGACATTTTTCCAGAAGATGGACA
AGAATAAAGATGGTGTCGTTACCATAGACGAGTTCATTGAAAGTTGCCAAAAAGATGAAAACATAATGCGCTCCATGCAG
CTCTTTGAAAATGTGATCTAGactgtcggtgccttgaccggaggcaaatgtggacgactacacacgagttgaagccacca
tttctagcatagattgctcagctttacactgaggcatattatgcaaacagctttgttttaatataaagaccccccgcgccc
aaatttaagttttccagttacaaatccgcatccacgtcactggggtcccgaaatgtgctcacttatttcatactctgaga
acactcaaaaggcacagaatctggaacagctttgatcctcagccacgtgttacggggcttttacagatgagtgatttta
aaacaccagtgggTTTTCCTACTTGTTTGTATTCAGCCCTGGATTTTAAGTGGTTTTCTAAAATATTTACATCTGCATTT
AACTTCCAGAAAGCCAATGACCTTTTCATTTAACTCAATTCATGTAATACTGAAAAAAGGAACAAAGATTATTACAATTA
AAAAAGACCAAAAACACAGTCCCGATTTCTATAGCTTCTCCACCTGCTGTTAAAGACAGTCATGTATTTGGCTTTTTTTT
TTTTTTTAAAAAGAACACTTAAAAAATTAGTTTATTATCAGATGTTAGCATATACCTAATAAAATTATTTTAGTATTTGT
TAATTTTCCATATTCAAGCCAAGGCTCTATATAATCCATGTAACTTTGGACCTGTTCAATCTTACATGTAGACTGTTTTG
TATTGTGTTCTGAAGTAGAAGTTCAAAGTGTCAAACAAACCAAGGATGTTTACAGACTTGCAAAGGGTCCAGATGTCTGT
CCTGCAATGCCTAGTGACGCTTATTAACCAGTAACCTGAAGAGCAGTAACTGGCAATTCTAGCCACCACCCCTCCCCAAG
CCCCTTCATGTTCTCACAGCATGTTTATCACACACAAGCCATTCAGGGACAGAGAATCCTTGACTGCCCCAAAGCCTACT
AGGAATAAAGATCAAGCAAAATCTTCTTTGAAAACACCAGTGATTCTATCATATTGGAAATATACATAAGAGTGTATAGA
AAACGAATGTAGACATTGGACAGTTCATCCGAATTGCATTATGATTTAGCACATCATGTAGTTCAAAGGATTCACATTCC
TTTCCGTGATCTTAAGCCAAAACTGTAGAATTGCCACAACAGTACTAGATATACACACATTCCCTGTTTCGTGGAAATCC
AAGAACCAAGAGGATACGGGAAGAGAAAATTTGCGACTGTCTGCAACAATAAATCAGGTATCTATTCTGGTGTAGAGATA
GGATGTTGAGAGCCGCCCTGCTATCACCAGTGTAGGAATTAAGAGTAGTACAGTACATGTACAGAAATCTGCCATCGCGT
GTTTGTGTAAACTCAATGTGCACATTTTGTATCTCAAAAAGGAAAAATAAAGCAAAATAAAGTGTTAAAAAAAAAAAAAA
AAAAAA rat KChIP4N1x (contig of jTrba133c02t1 and rkchip4) protein (partial)

PRQTPLGQVDSKSVAPASIIPKDEREKGGKHLGSAGGGELHRRFPLPQNNTKRSIKERLMKLLPCSAAKTSSPAIQNSVE
DELEMATVRHRPEALELLEAQSKFTKKELQILYRGFKNECPSGVVNEETFKEIYSQFFPQGDSTTYAHFLFNAFDTDHNG
AVSFEDFIKGLSILLRGTVQEKLNWAFNLYDINKDGYITKEEMLDIMKAIYDMMGKCTYPVLKEDAPRQHVETFFQKMDK
NKDGVVTIDEFIESCQKDENIMRSMQLFENVI

FIG. 60

```
                      v10         v20         v30
hKChIP1N N.pep    GESEGLQTLGIVVVVCSSLKLLHYLGLIDLSD
                  : |||: :::::|:   :|||: :|||: :
mkchip4N2 N.pep   MNLEGLEMIAVLIVIVLFVKLLEQFGLIEAGL
                           ^10         ^20         ^30 v10         v20
h/rKChIP1 N.pep   MGAVMGTFSSLQTKQRRPSKDKIEDDLE
                  :. :   :    :    :     :||.:||
mkchip4N2 N.pep   LEMIAVLIVIVLFVKLLEQFGLIEAGLE
                         ^10         ^20         ^30
```

FIG. 62 rat KChIP1N (1vn) DNA sequence (CD: 339-1037)

GGCACACAACCCCTGGATTCTTCGGAGAATATGCCGTGAGGTGTTGCCAATTATTAGTTCT
CTTGGCTAGCAGATGTTTAGGGACTGGTTAAGCCTTTGGAGAAATTACCTTAGGAAAACG
GGGAAATAAAAGCAAAGATTACCATGAATTGCAAGATTACCTAGCAATTGCAAGGTAGG
AGGAGAGAGGTGGAGGGCGGAGTAGACAGGAGGGAGGGAGAAAGTGAGAGGAAGCTAG
GCTGGTGGAAATAACCCTGCACTTGGAACAGCGGCAAAGAAGCGCGATTTTCCAGCTTTA
AATGCCTGCCCGCGTTCTGCTTGCCTACCCGGGAACGGAGATGTTGACCCAGGGCGAGTC
TGAAGGGCTCCAGACCTTGGGGATAGTAGTGGTCCTGTGTTCCTCTCTGAAACTACTGCAC
TACCTCGGGCTGATTGACTTGTCGGATGACAAGATCGAGGATGATCTGGAGATGACCATG
GTTTGCCATCGGCCTGAGGGACTGGAGCAGCTTGAGGCACAGACGAACTTCACCAAGAGA
GAACTGCAAGTCCTTTACCGGGGATTCAAAAACGAGTGCCCCAGTGGTGTGGTTAACGAA
GAGACATTCAAGCAGATCTACGCTCAGTTTTTCCCTCATGGAGATGCCAGCACATACGCAC
ATTACCTCTTCAATGCCTTCGACACCACCCAGACAGGCTCTGTAAAGTTCGAGGACTTTGT
GACTGCTCTGTCGATTTTACTGAGAGGAACGGTCCATGAAAAACTGAGGTGGACGTTTAA
TTTGTACGACATCAATAAAGACGGCTACATAAACAAAGAGGAGATGATGGACATAGTGA
AAGCCATCTATGACATGATGGGGAAATACACCTATCCTGTGCTCAAAGAGGACACTCCCA
GGCAGCACGTGGACGTCTTCTTCCAGAAAATGGATAAAAATAAAGATGGCATTGTAACGT
TAGACGAATTTCTCGAGTCCTGTCAGGAGGATGACAACATCATGAGGTCTCTACAGCTGTT
CCAAAATGTCATGTAACTGAGGACACTGGCCATCCTGCTCTCAGAGACACTGACAAACAC
CTCAATGCCCTGATCTGCCCTTGTTCCAGTTTTACACATCAACTCTCGGGACAGAAATACC
TTTTACACTTTGGAAGAATTCTCTGCTGAAGACTTTCTACAAAACCTGGCACCGAGTGGCT
CAGTCTCTGATTGCCAACTCTTCCTCCCTCCTCCTCTTGAGAGGGACGAGCTGAAATCCGA
AGTTTGTTTTGGAAGCATGCCCATCTCTCCATGCTGCTGCTGCCCTGTGGAAGGCCCCTCT
GCTTGAGCTTAAACAGTAGTGCACAGTTTTCTGCGTATACAGATCCCCAACTCACTGCCTC
TAAGTCAGGCAGACCCTGATCAATCTGAACCAAATGTGCACCATCCTCCGATGGCCTCCC
AAGCCAATGTGCCTGCTTCTCTTCCTCTGGTGGGAAGAAAGAACGCTCTACAGAGCACTTA
GAGCTTACCATGAAAATACTGGGAGAGGCAGCACCTAACACATGTAGAATAGGACTGAAT
TATTAAGCATGGTGGTATCAGATGATGCAAACAGCCCATGTCATTTTTTTTCCAGAGGTA
GGGACTAATAATTCTCCCACACTAGCACCTACGATCATAGAACAAGTCTTTTAACACATCC
AGGAGGGAAACCGCTGCCCAGTGGTCTATCCCTTCTCTCCATCCCCTGCTCAAGCCCAGCA
CTGCATGTCTCTCCCGGAAGGTCCAGAATGCCTGTGAAATGCTGTAACTTTTATACCCTGT
TATAATCAATAAACAGAACTATTTCGTACAAAAAAAAAAAAAAAAAA rat KChIP1N (1vn) protein sequence MLTQGESEGLQTLGIVVVLCSSLKLLHYLGLIDLSDDKIEDDLEMTMVCHRPEGLEQLEAQTN
FTKRELQVLYRGFKNECPSGVVNEETFKQIYAQFFPHGDASTYAHYLFNAFDTTQTGSVKFED
FVTALSILLRGTVHEKLRWTFNLYDINKDGYINKEEMMDIVKAIYDMMGKYTYPVLKEDTPR
QHVDVFFQKMDKNKDGIVTLDEFLESCQEDDNIMRSLQLFQNVM

FIG. 63

SEQUENCE LISTING

<160> NUMBER OF SEQ ID NOS: 109

<210> SEQ ID NO 1
<211> LENGTH: 1463
<212> TYPE: DNA
<213> ORGANISM: Homo sapiens
<220> FEATURE:
<221> NAME/KEY: CDS
<222> LOCATION: (225)..(872)

<400> SEQUENCE: 1

```
gaatagcccc ctttcacttc tgagtccctg catgtgcggg gctgaagaag gaagccagaa        60
gcctcctagc ctcgcctcca cgtttgctga ataccaagct gcaggcgagc tgccgggcgc       120
ttttctctcc tccaattcag agtagacaaa ccacgggggat ttctttccag ggtaggggag      180
gggccgggcc cggggtccca actcgcactc aagtcttcgc tgcc atg ggg gcc gtc       236
                                                Met Gly Ala Val
                                                 1 atg ggc acc ttc tca tct ctg caa acc aaa caa agg cga ccc tcg aaa        284
Met Gly Thr Phe Ser Ser Leu Gln Thr Lys Gln Arg Arg Pro Ser Lys
 5                  10                  15                  20 gat aag att gaa gat gag ctg gag atg acc atg gtt tgc cat cgg ccc        332
Asp Lys Ile Glu Asp Glu Leu Glu Met Thr Met Val Cys His Arg Pro
                 25                  30                  35 gag gga ctg gag cag ctc gag gcc cag acc aac ttc acc aag agg gag        380
Glu Gly Leu Glu Gln Leu Glu Ala Gln Thr Asn Phe Thr Lys Arg Glu
             40                  45                  50 ctg cag gtc ctt tat cga ggc ttc aaa aat gag tgc ccc agt ggt gtg        428
Leu Gln Val Leu Tyr Arg Gly Phe Lys Asn Glu Cys Pro Ser Gly Val
         55                  60                  65 gtc aac gaa gac aca ttc aag cag atc tat gct cag ttt ttc cct cat        476
Val Asn Glu Asp Thr Phe Lys Gln Ile Tyr Ala Gln Phe Phe Pro His
     70                  75                  80 gga gat gcc agc acg tat gcc cat tac ctc ttc aat gcc ttc gac acc        524
Gly Asp Ala Ser Thr Tyr Ala His Tyr Leu Phe Asn Ala Phe Asp Thr
 85                  90                  95                 100 act cag aca ggc tcc gtg aag ttc gag gac ttt gta acc gct ctg tcg        572
Thr Gln Thr Gly Ser Val Lys Phe Glu Asp Phe Val Thr Ala Leu Ser
                105                 110                 115 att tta ttg aga gga act gtc cac gag aaa cta agg tgg aca ttt aat        620
Ile Leu Leu Arg Gly Thr Val His Glu Lys Leu Arg Trp Thr Phe Asn
            120                 125                 130 ttg tat gac atc aac aag gac gga tac ata aac aaa gag gag atg atg        668
Leu Tyr Asp Ile Asn Lys Asp Gly Tyr Ile Asn Lys Glu Glu Met Met
        135                 140                 145
```

-continued

```
gac att gtc aaa gcc atc tat gac atg atg ggg aaa tac aca tat cct      716
Asp Ile Val Lys Ala Ile Tyr Asp Met Met Gly Lys Tyr Thr Tyr Pro
    150             155                 160 gtg ctc aaa gag gac act cca agg cag cat gtg gac gtc ttc ttc cag      764
Val Leu Lys Glu Asp Thr Pro Arg Gln His Val Asp Val Phe Phe Gln
165             170                 175                 180 aaa atg gac aaa aat aaa gat ggc atc gta act tta gat gaa ttt ctt      812
Lys Met Asp Lys Asn Lys Asp Gly Ile Val Thr Leu Asp Glu Phe Leu
                185                 190                 195 gaa tca tgt cag gag gac gac aac atc atg agg tct ctc cag ctg ttt      860
Glu Ser Cys Gln Glu Asp Asp Asn Ile Met Arg Ser Leu Gln Leu Phe
            200                 205                 210 caa aat gtc atg taactggtga cactcagcca ttcagctctc agagacattg          912
Gln Asn Val Met
            215 tactaaacaa ccaccttaac accctgatct gcccttgttc tgattttaca caccaactct    972 tgggacagaa acacctttta cactttggaa gaattctctg ctgaagactt tcttatggaa   1032 cccagcatca tgtggctcag tctctgattg ccaactcttc ctctttcttc ttcttgagag   1092 agacaagatg aaatttgagt ttgttttgga agcatgctca tctcctcaca ctgctgccct   1152 atggaaggtc cctctgctta agcttaaaca gtagtgcaca aaatatgctg cttacgtgcc   1212 cccagcccac tgcctccaag tcaggcagac cttggtgaat ctggaagcaa gaggacctga   1272 gccagatgca caccatctct gatggcctcc caaaccaatg tgcctgtttc tcttcctttg   1332 gtgggaagaa tgagagttat ccagaacaat taggatctgt catgaccaga ttgggagagc   1392 cagcacctaa catatgtggg ataggactga attattaagc atgacattgt ctgatgaccc   1452 aaactgcccc g                                                        1463

<210> SEQ ID NO 2
<211> LENGTH: 216
<212> TYPE: PRT
<213> ORGANISM: Homo sapiens

<400> SEQUENCE: 2

Met Gly Ala Val Met Gly Thr Phe Ser Ser Leu Gln Thr Lys Gln Arg
 1               5                  10                  15

Arg Pro Ser Lys Asp Lys Ile Glu Asp Glu Leu Glu Met Thr Met Val
            20                  25                  30

Cys His Arg Pro Glu Gly Leu Glu Gln Leu Glu Ala Gln Thr Asn Phe
        35                  40                  45

Thr Lys Arg Glu Leu Gln Val Leu Tyr Arg Gly Phe Lys Asn Glu Cys
    50                  55                  60

Pro Ser Gly Val Val Asn Glu Asp Thr Phe Lys Gln Ile Tyr Ala Gln
65                  70                  75                  80

Phe Phe Pro His Gly Asp Ala Ser Thr Tyr Ala His Tyr Leu Phe Asn
                85                  90                  95

Ala Phe Asp Thr Thr Gln Thr Gly Ser Val Lys Phe Glu Asp Phe Val
            100                 105                 110

Thr Ala Leu Ser Ile Leu Leu Arg Gly Thr Val His Glu Lys Leu Arg
        115                 120                 125

Trp Thr Phe Asn Leu Tyr Asp Ile Asn Lys Asp Gly Tyr Ile Asn Lys
    130                 135                 140

Glu Glu Met Met Asp Ile Val Lys Ala Ile Tyr Asp Met Met Gly Lys
145                 150                 155                 160

Tyr Thr Tyr Pro Val Leu Lys Glu Asp Thr Pro Arg Gln His Val Asp
```

```
                165                 170                 175
Val Phe Phe Gln Lys Met Asp Lys Asn Lys Asp Gly Ile Val Thr Leu
        180                 185                 190

Asp Glu Phe Leu Glu Ser Cys Gln Glu Asp Asn Ile Met Arg Ser
            195                 200                 205

Leu Gln Leu Phe Gln Asn Val Met
        210                 215

<210> SEQ ID NO 3
<211> LENGTH: 1856
<212> TYPE: DNA
<213> ORGANISM: Rattus sp.
<220> FEATURE:
<221> NAME/KEY: CDS
<222> LOCATION: (300)..(1034)

<400> SEQUENCE: 3
ggcacacaac ccctggattc ttcggagaat atgccgtgag gtgttgccaa ttattagttc      60
tcttggctag cagatgttta gggactggtt aagcctttgg agaaattacc ttaggaaaac    120
ggggaaataa agcaaagat taccatgaat tgcaagatta cctagcaatt gcaaggtagg     180
aggagagagg tggagggcgg agtagacagg agggaggag aaagtgagag aagctaggc      240 tggtggaaat aaccctgcac ttggaacagc ggcaaagaag cgcgattttc cagctttaa    299 atg cct gcc cgc gtt ctg ctt gcc tac ccg gga acg gag atg ttg acc    347
Met Pro Ala Arg Val Leu Leu Ala Tyr Pro Gly Thr Glu Met Leu Thr
  1               5                  10                  15 cag ggc gag tct gaa ggg ctc cag acc ttg ggg ata gta gtg gtc ctg    395
Gln Gly Glu Ser Glu Gly Leu Gln Thr Leu Gly Ile Val Val Val Leu
             20                  25                  30 tgt tcc tct ctg aaa cta ctg cac tac ctc ggg ctg att gac ttg tcg    443
Cys Ser Ser Leu Lys Leu Leu His Tyr Leu Gly Leu Ile Asp Leu Ser
         35                  40                  45 gat gac aag atc gag gat gat ctg gag atg acc atg gtt tgc cat cgg    491
Asp Asp Lys Ile Glu Asp Asp Leu Glu Met Thr Met Val Cys His Arg
     50                  55                  60 cct gag gga ctg gag cag ctt gag gca cag acg aac ttc acc aag aga    539
Pro Glu Gly Leu Glu Gln Leu Glu Ala Gln Thr Asn Phe Thr Lys Arg
 65                  70                  75                  80 gaa ctg caa gtc ctt tac cgg gga ttc aaa aac gag tgc ccc agt ggt    587
Glu Leu Gln Val Leu Tyr Arg Gly Phe Lys Asn Glu Cys Pro Ser Gly
                 85                  90                  95 gtg gtt aac gaa gag aca ttc aag cag atc tac gct cag ttt ttc cct    635
Val Val Asn Glu Glu Thr Phe Lys Gln Ile Tyr Ala Gln Phe Phe Pro
            100                 105                 110 cat gga gat gcc agc aca tac gca cat tac ctc ttc aat gcc ttc gac    683
His Gly Asp Ala Ser Thr Tyr Ala His Tyr Leu Phe Asn Ala Phe Asp
        115                 120                 125 acc acc cag aca ggc tct gta aag ttc gag gac ttt gtg act gct ctg    731
Thr Thr Gln Thr Gly Ser Val Lys Phe Glu Asp Phe Val Thr Ala Leu
    130                 135                 140 tcg att tta ctg aga gga acg tca cat gaa aaa ctg agg tgg acg ttt    779
Ser Ile Leu Leu Arg Gly Thr Val His Glu Lys Leu Arg Trp Thr Phe
145                 150                 155                 160 aat ttg tac gac atc aat aaa gac ggc tac ata aac aaa gag gag atg    827
Asn Leu Tyr Asp Ile Asn Lys Asp Gly Tyr Ile Asn Lys Glu Glu Met
                165                 170                 175 atg gac ata gtg aaa gcc atc tat gac atg atg ggg aaa tac acc tat    875
Met Asp Ile Val Lys Ala Ile Tyr Asp Met Met Gly Lys Tyr Thr Tyr
            180                 185                 190
```

-continued

```
cct gtg ctc aaa gag gac act ccc agg cag cac gtg gac gtc ttc ttc      923
Pro Val Leu Lys Glu Asp Thr Pro Arg Gln His Val Asp Val Phe Phe
        195                 200                 205 cag aaa atg gat aaa aat aaa gat ggc att gta acg tta gac gaa ttt      971
Gln Lys Met Asp Lys Asn Lys Asp Gly Ile Val Thr Leu Asp Glu Phe
    210                 215                 220 ctc gag tcc tgt cag gag gat gac aac atc atg agg tct cta cag ctg     1019
Leu Glu Ser Cys Gln Glu Asp Asp Asn Ile Met Arg Ser Leu Gln Leu
225                 230                 235                 240 ttc caa aat gtc atg taactgagga cactggccat cctgctctca gagacactga     1074
Phe Gln Asn Val Met
                245 caaacacctc aatgccctga tctgcccttg ttccagtttt acacatcaac tctcgggaca   1134 gaaatacctt ttacactttg gaagaattct ctgctgaaga ctttctacaa aacctggcac   1194 cgagtggctc agtctctgat tgccaactct tcctccctcc tcctcttgag agggacgagc   1254 tgaaatccga agtttgtttt ggaagcatgc ccatctctcc atgctgctgc tgccctgtgg   1314 aaggcccctc tgcttgagct taaacagtag tgcacagttt tctgcgtata cagatcccca   1374 actcactgcc tctaagtcag gcagaccctg atcaatctga accaaatgtg caccatcctc   1434 cgatggcctc ccaagccaat gtgcctgctt ctcttcctct ggtgggaaga aagaacgctc   1494 tacagagcac ttagagctta ccatgaaaat actgggagag gcagcaccta acacatgtag   1554 aataggactg aattattaag catggtggta tcagatgatg caaacagccc atgtcatttt   1614 tttttccaga ggtagggact aataattctc ccacactagc acctacgatc atagaacaag   1674 tcttttaaca catccaggag ggaaaccgct gcccagtggt ctatcccttc tctccatccc   1734 ctgctcaagc ccagcactgc atgtctctcc cggaaggtcc agaatgcctg tgaaatgctg   1794 taacttttat accctgttat aatcaataaa cagaactatt tcgtacaaaa aaaaaaaaaa   1854 aa                                                                  1856

<210> SEQ ID NO 4
<211> LENGTH: 245
<212> TYPE: PRT
<213> ORGANISM: Rattus sp.

<400> SEQUENCE: 4

Met Pro Ala Arg Val Leu Leu Ala Tyr Pro Gly Thr Glu Met Leu Thr
  1               5                  10                  15

Gln Gly Glu Ser Glu Gly Leu Gln Thr Leu Gly Ile Val Val Val Leu
             20                  25                  30

Cys Ser Ser Leu Lys Leu Leu His Tyr Leu Gly Leu Ile Asp Leu Ser
         35                  40                  45

Asp Asp Lys Ile Glu Asp Asp Leu Glu Met Thr Met Val Cys His Arg
     50                  55                  60

Pro Glu Gly Leu Glu Gln Leu Glu Ala Gln Thr Asn Phe Thr Lys Arg
 65                  70                  75                  80

Glu Leu Gln Val Leu Tyr Arg Gly Phe Lys Asn Glu Cys Pro Ser Gly
                 85                  90                  95

Val Val Asn Glu Glu Thr Phe Lys Gln Ile Tyr Ala Gln Phe Phe Pro
            100                 105                 110

His Gly Asp Ala Ser Thr Tyr Ala His Tyr Leu Phe Asn Ala Phe Asp
        115                 120                 125

Thr Thr Gln Thr Gly Ser Val Lys Phe Glu Asp Phe Val Thr Ala Leu
    130                 135                 140
```

```
Ser Ile Leu Leu Arg Gly Thr Val His Glu Lys Leu Arg Trp Thr Phe
145                 150                 155                 160

Asn Leu Tyr Asp Ile Asn Lys Asp Gly Tyr Ile Asn Lys Glu Glu Met
            165                 170                 175

Met Asp Ile Val Lys Ala Ile Tyr Asp Met Met Gly Lys Tyr Thr Tyr
                180                 185                 190

Pro Val Leu Lys Glu Asp Thr Pro Arg Gln His Val Asp Val Phe Phe
            195                 200                 205

Gln Lys Met Asp Lys Asn Lys Asp Gly Ile Val Thr Leu Asp Glu Phe
        210                 215                 220

Leu Glu Ser Cys Gln Glu Asp Asp Asn Ile Met Arg Ser Leu Gln Leu
225                 230                 235                 240

Phe Gln Asn Val Met
                245

<210> SEQ ID NO 5
<211> LENGTH: 1907
<212> TYPE: DNA
<213> ORGANISM: Mus musculus
<220> FEATURE:
<221> NAME/KEY: CDS
<222> LOCATION: (477)..(1124)

<400> SEQUENCE: 5 cggcccctg agatccagcc cgagcgcggg gcggagcggc cgggtggcag caggggcggg      60
cgggcggagc gcagctcccg caccgcacgc ggcgcgggct cggcagcctc ggccgtgcgg     120
gcacgccggc cccgtgtcca acatcaggca ggctttgggg ctcggggctc gggcctcgga    180
gaagccagtg gcccggctgg gtgcccgcac cggggggcgc ctgtgaaggc tcccgcgagc    240
ctctggccct gggagtcagt gcatgtgcct ggctgaagaa ggcagcagcc acgagctcca    300
ggcgccccgg ccccacgttt tctgaatacc aagctgcagg cgagctgctc ggggcttttt    360
tgctttctcg cttttcctct cctccaattc aaagtgggca atccacaccg atttcttttc    420
aggggaggga agagacaggg cctggggtcc caagacgcac acaagtcttc gctgcc atg    479
                                                              Met
                                                                1 ggg gcc gtc atg ggc act ttc tcc tcc ctg cag acc aaa caa agg cga    527
Gly Ala Val Met Gly Thr Phe Ser Ser Leu Gln Thr Lys Gln Arg Arg
        5                   10                  15 ccc tct aaa gac aag att gag gat gag cta gag atg acc atg gtt tgc    575
Pro Ser Lys Asp Lys Ile Glu Asp Glu Leu Glu Met Thr Met Val Cys
        20                  25                  30 cac cgg cct gag gga ctg gag cag ctt gag gca cag acg aac ttc acc    623
His Arg Pro Glu Gly Leu Glu Gln Leu Glu Ala Gln Thr Asn Phe Thr
    35                  40                  45 aag aga gaa ctg caa gtc ttg tac cgg gga ttc aaa aac gag tgc cct    671
Lys Arg Glu Leu Gln Val Leu Tyr Arg Gly Phe Lys Asn Glu Cys Pro
50                  55                  60                  65 agc ggt gtg gtc aat gaa gaa aca ttc aag cag atc tac gct cag ttt    719
Ser Gly Val Val Asn Glu Glu Thr Phe Lys Gln Ile Tyr Ala Gln Phe
                70                  75                  80 ttc cct cac gga gat gcc agc aca tat gca cat tac ctc ttc aat gcc    767
Phe Pro His Gly Asp Ala Ser Thr Tyr Ala His Tyr Leu Phe Asn Ala
            85                  90                  95 ttc gac acc acc cag aca ggc tct gta aag ttc gag gac ttt gtg act    815
Phe Asp Thr Thr Gln Thr Gly Ser Val Lys Phe Glu Asp Phe Val Thr
        100                 105                 110
```

```
gct ctg tcg att tta ctg aga ggg aca gtc cat gaa aaa cta agg tgg      863
Ala Leu Ser Ile Leu Leu Arg Gly Thr Val His Glu Lys Leu Arg Trp
    115                 120                 125 acg ttt aat ttg tat gac atc aat aaa gac ggc tac ata aac aaa gag      911
Thr Phe Asn Leu Tyr Asp Ile Asn Lys Asp Gly Tyr Ile Asn Lys Glu
130                 135                 140                 145 gag atg atg gac ata gtc aaa gcc atc tat gac atg atg ggg aaa tac      959
Glu Met Met Asp Ile Val Lys Ala Ile Tyr Asp Met Met Gly Lys Tyr
                150                 155                 160 acc tat cct gtg ctc aaa gag gac act ccc agg cag cat gtg gat gtc     1007
Thr Tyr Pro Val Leu Lys Glu Asp Thr Pro Arg Gln His Val Asp Val
            165                 170                 175 ttc ttc cag aaa atg gat aaa aat aaa gat ggc att gta acg tta gat     1055
Phe Phe Gln Lys Met Asp Lys Asn Lys Asp Gly Ile Val Thr Leu Asp
        180                 185                 190 gaa ttt ctt gaa tca tgt cag gag gat gac aac atc atg aga tct cta     1103
Glu Phe Leu Glu Ser Cys Gln Glu Asp Asp Asn Ile Met Arg Ser Leu
    195                 200                 205 cag ctg ttc caa aat gtc atg taactgagga cactggccat tctgctctca        1154
Gln Leu Phe Gln Asn Val Met
210                 215 gagacactga caaacacctt aatgccctga tctgcccttg ttccaatttt acacaccaac   1214
tcttgggaca gaaatacctt ttacactttg gaagaattct ctgctgaaga ctttctacaa   1274
aacctggcac cacgtggctc tgtctctgag ggacgagcgg agatccgact tgttttgga    1334 agcatgccca tctcttcatg ctgctgccct gtggaaggcc cctctgcttg agcttaatca   1394
atagtgcaca gttttatgct tacacatatc cccaactcac tgcctccaag tcaggcagac   1454
tctgatgaat ctgagccaaa tgtgcaccat cctccgatgg cctcccaagc caatgtgcct   1514
gcttctcttc ctctggtggg aagaaagagt gttctacgga acaattagag cttaccatga   1574
aaatattggg agaggcagca cctaacacat gtagaatagg actgaattat taagcatggt   1634
gatatcagat gatgcaaatt gcccatgtca ttttttttcaa aggtagggac aaatgattct  1694
cccacactag cacctgtggt catagagcaa gtctcttaac atgcccagaa ggggaaccac   1754
tgtccagtgg tctatccctc ctctccatcc cctgctcaaa cccagcactg catgtccctc   1814
caagaaggtc cagaatgcct gcgaaacgct gtacttttat accctgttct aatcaataaa   1874
cagaactatt tcgtaaaaaa aaaaaaaaaa aaa                                1907
```

<210> SEQ ID NO 6
<211> LENGTH: 216
<212> TYPE: PRT
<213> ORGANISM: Mus musculus

<400> SEQUENCE: 6

```
Met Gly Ala Val Met Gly Thr Phe Ser Ser Leu Gln Thr Lys Gln Arg
1               5                   10                  15

Arg Pro Ser Lys Asp Lys Ile Glu Asp Glu Leu Glu Met Thr Met Val
                20                  25                  30

Cys His Arg Pro Glu Gly Leu Glu Gln Leu Glu Ala Gln Thr Asn Phe
            35                  40                  45

Thr Lys Arg Glu Leu Gln Val Leu Tyr Arg Gly Phe Lys Asn Glu Cys
        50                  55                  60

Pro Ser Gly Val Val Asn Glu Glu Thr Phe Lys Gln Ile Tyr Ala Gln
65                  70                  75                  80

Phe Phe Pro His Gly Asp Ala Ser Thr Tyr Ala His Tyr Leu Phe Asn
                85                  90                  95
```

```
Ala Phe Asp Thr Thr Gln Thr Gly Ser Val Lys Phe Glu Asp Phe Val
            100                 105                 110
Thr Ala Leu Ser Ile Leu Leu Arg Gly Thr Val His Glu Lys Leu Arg
        115                 120                 125
Trp Thr Phe Asn Leu Tyr Asp Ile Asn Lys Asp Gly Tyr Ile Asn Lys
130                 135                 140
Glu Glu Met Met Asp Ile Val Lys Ala Ile Tyr Asp Met Met Gly Lys
145                 150                 155                 160
Tyr Thr Tyr Pro Val Leu Lys Glu Asp Thr Pro Arg Gln His Val Asp
                165                 170                 175
Val Phe Phe Gln Lys Met Asp Lys Asn Lys Asp Gly Ile Val Thr Leu
            180                 185                 190
Asp Glu Phe Leu Glu Ser Cys Gln Glu Asp Asp Asn Ile Met Arg Ser
        195                 200                 205
Leu Gln Leu Phe Gln Asn Val Met
    210                 215

<210> SEQ ID NO 7
<211> LENGTH: 1534
<212> TYPE: DNA
<213> ORGANISM: Rattus sp.
<220> FEATURE:
<221> NAME/KEY: CDS
<222> LOCATION: (31)..(711)

<400> SEQUENCE: 7
gtcccaagtc gcacacaagt cttcgctgcc atg ggg gcc gtc atg ggt acc ttc       54
                                Met Gly Ala Val Met Gly Thr Phe
                                  1               5 tcg tcc ctg cag acc aaa caa agg cga ccc tct aaa gac atc gcc tgg      102
Ser Ser Leu Gln Thr Lys Gln Arg Arg Pro Ser Lys Asp Ile Ala Trp
     10                  15                  20 tgg tat tac cag tat cag aga gac aag atc gag gat gat ctg gag atg      150
Trp Tyr Tyr Gln Tyr Gln Arg Asp Lys Ile Glu Asp Asp Leu Glu Met
 25                  30                  35                  40 acc atg gtt tgc cat cgg cct gag gga ctg gag cag ctt gag gca cag      198
Thr Met Val Cys His Arg Pro Glu Gly Leu Glu Gln Leu Glu Ala Gln
                 45                  50                  55 acg aac ttc acc aag aga gaa ctg caa gtc ctt tac cgg gga ttc aaa      246
Thr Asn Phe Thr Lys Arg Glu Leu Gln Val Leu Tyr Arg Gly Phe Lys
             60                  65                  70 aac gag tgc ccc agt ggt gtg gtt aac gaa gag aca ttc aag cag atc      294
Asn Glu Cys Pro Ser Gly Val Val Asn Glu Glu Thr Phe Lys Gln Ile
         75                  80                  85 tac gct cag ttt ttc cct cat gga gat gcc agc aca tac gca cat tac      342
Tyr Ala Gln Phe Phe Pro His Gly Asp Ala Ser Thr Tyr Ala His Tyr
     90                  95                 100 ctc ttc aat gcc ttc gac acc acc cag aca ggc tct gta aag ttc gag      390
Leu Phe Asn Ala Phe Asp Thr Thr Gln Thr Gly Ser Val Lys Phe Glu
105                 110                 115                 120 gac ttt gtg act gct ctg tcg att tta ctg aga gga acg gtc cat gaa      438
Asp Phe Val Thr Ala Leu Ser Ile Leu Leu Arg Gly Thr Val His Glu
                125                 130                 135 aaa ctg agg tgg acg ttt aat ttg tac gac atc aat aaa gac ggc tac      486
Lys Leu Arg Trp Thr Phe Asn Leu Tyr Asp Ile Asn Lys Asp Gly Tyr
            140                 145                 150 ata aac aaa gag gag atg atg gac ata gtg aaa gcc atc tat gac atg      534
Ile Asn Lys Glu Glu Met Met Asp Ile Val Lys Ala Ile Tyr Asp Met
        155                 160                 165
```

```
atg ggg aaa tac acc tat cct gtg ctc aaa gag gac act ccc agg cag      582
Met Gly Lys Tyr Thr Tyr Pro Val Leu Lys Glu Asp Thr Pro Arg Gln
170                 175                 180 cac gtg gac gtc ttc ttc cag aaa atg gat aaa aat aaa gat ggc att      630
His Val Asp Val Phe Phe Gln Lys Met Asp Lys Asn Lys Asp Gly Ile
    185                 190                 195                 200 gta acg tta gac gaa ttt ctc gag tcc tgt cag gag gat gac aac atc      678
Val Thr Leu Asp Glu Phe Leu Glu Ser Cys Gln Glu Asp Asp Asn Ile
                205                 210                 215 atg agg tct cta cag ctg ttc caa aat gtc atg taactgagga cactggccat    731
Met Arg Ser Leu Gln Leu Phe Gln Asn Val Met
            220                 225 cctgctctca gagacactga caaacacctc aatgccctga tctgcccttg ttccagtttt    791
acacatcaac tctcgggaca gaaataccct ttacactttg gaagaattct ctgctgaaga    851
ctttctacaa aacctggcac cgcgtggctc agtctctgat tgccaactct cctccctcc    911
tcctcttgag agggacgagc tgaaatccga agtttgtttt ggaagcatgc ccatctctcc    971
atgctgctgc tgccctgtgg aaggcccctc tgcttgagct taaacagtag tgcacagttt   1031
tctgcgtata cagatcccca actcactgcc tctaagtcag gcagaccctg atcaatctga   1091
accaaatgtg caccatcctc cgatggcctc ccaagccaat gtgcctgctt ctcttcctct   1151
ggtgggaaga agaacgctc tacagagcac ttagagctta ccatgaaaat actgggagag   1211
gcagcaccta acacatgtag aataggactg aattattaag catggtggta tcagatgatg   1271
caaacagccc atgtcatttt ttttccgag gtagggacta ataattctcc cacactagca    1331
cctacgatca tagaacaagt cttttaacac atccaggagg gaaaccgctg cccagtggtc   1391
tatcccttct ctccatcccc tgctcaagcc cagcactgca tgtctctccc ggaaggtcca   1451
gaatgcctgt gaaatgctgt aacttttata ccctgttata atcaataaac agaactattt   1511
cgtacaaaaa aaaaaaaaaa aaa                                           1534

<210> SEQ ID NO 8
<211> LENGTH: 227
<212> TYPE: PRT
<213> ORGANISM: Rattus sp.

<400> SEQUENCE: 8

Met Gly Ala Val Met Gly Thr Phe Ser Ser Leu Gln Thr Lys Gln Arg
1               5                   10                  15

Arg Pro Ser Lys Asp Ile Ala Trp Trp Tyr Tyr Gln Tyr Gln Arg Asp
            20                  25                  30

Lys Ile Glu Asp Asp Leu Glu Met Thr Met Val Cys His Arg Pro Glu
        35                  40                  45

Gly Leu Glu Gln Leu Glu Ala Gln Thr Asn Phe Thr Lys Arg Glu Leu
    50                  55                  60

Gln Val Leu Tyr Arg Gly Phe Lys Asn Glu Cys Pro Ser Gly Val Val
65                  70                  75                  80

Asn Glu Glu Thr Phe Lys Gln Ile Tyr Ala Gln Phe Phe Pro His Gly
                85                  90                  95

Asp Ala Ser Thr Tyr Ala His Tyr Leu Phe Asn Ala Phe Asp Thr Thr
            100                 105                 110

Gln Thr Gly Ser Val Lys Phe Glu Asp Phe Val Thr Ala Leu Ser Ile
        115                 120                 125

Leu Leu Arg Gly Thr Val His Glu Lys Leu Arg Trp Thr Phe Asn Leu
    130                 135                 140
```

```
Tyr Asp Ile Asn Lys Asp Gly Tyr Ile Asn Lys Glu Met Met Asp
145                 150                 155                 160

Ile Val Lys Ala Ile Tyr Asp Met Met Gly Lys Tyr Thr Tyr Pro Val
                165                 170                 175

Leu Lys Glu Asp Thr Pro Arg Gln His Val Asp Val Phe Phe Gln Lys
            180                 185                 190

Met Asp Lys Asn Lys Asp Gly Ile Val Thr Leu Asp Glu Phe Leu Glu
        195                 200                 205

Ser Cys Gln Glu Asp Asn Ile Met Arg Ser Leu Gln Leu Phe Gln
    210                 215                 220

Asn Val Met
225

<210> SEQ ID NO 9
<211> LENGTH: 1540
<212> TYPE: DNA
<213> ORGANISM: Mus musculus
<220> FEATURE:
<221> NAME/KEY: CDS
<222> LOCATION: (77)..(757)

<400> SEQUENCE: 9
atccacaccg atttcttttc aggggaggga agagacaggg cctggggtcc caagacgcac      60
acaagtcttc gctgcc atg ggg gcc gtc atg ggc act ttc tcc tcc ctg cag    112
               Met Gly Ala Val Met Gly Thr Phe Ser Ser Leu Gln
                 1               5                  10 acc aaa caa agg cga ccc tct aaa gac atc gcc tgg tgg tat tac cag      160
Thr Lys Gln Arg Arg Pro Ser Lys Asp Ile Ala Trp Trp Tyr Tyr Gln
         15                  20                  25 tat cag aga gac aag att gag gat gag cta gag atg acc atg gtt tgc      208
Tyr Gln Arg Asp Lys Ile Glu Asp Glu Leu Glu Met Thr Met Val Cys
     30                  35                  40 cac cgg cct gag gga ctg gag cag ctt gag gca cag acg aac ttc acc      256
His Arg Pro Glu Gly Leu Glu Gln Leu Glu Ala Gln Thr Asn Phe Thr
 45                  50                  55                  60 aag aga gaa ctg caa gtc ttg tac cgg gga ttc aaa aac gag tgc cct      304
Lys Arg Glu Leu Gln Val Leu Tyr Arg Gly Phe Lys Asn Glu Cys Pro
                 65                  70                  75 agc ggt gtg gtc aat gaa gaa aca ttc aag cag atc tac gct cag ttt      352
Ser Gly Val Val Asn Glu Glu Thr Phe Lys Gln Ile Tyr Ala Gln Phe
             80                  85                  90 ttc cct cac gga gat gcc agc aca tat gca cat tac ctc ttc aat gcc      400
Phe Pro His Gly Asp Ala Ser Thr Tyr Ala His Tyr Leu Phe Asn Ala
         95                 100                 105 ttc gac acc acc cag aca ggc tct gta aag ttc gag gac ttt gtg act      448
Phe Asp Thr Thr Gln Thr Gly Ser Val Lys Phe Glu Asp Phe Val Thr
    110                 115                 120 gct ctg tcg att tta ctg aga ggg aca gtc cat gaa aaa cta agg tgg      496
Ala Leu Ser Ile Leu Leu Arg Gly Thr Val His Glu Lys Leu Arg Trp
125                 130                 135                 140 acg ttt aat ttg tat gac atc aat aaa gac ggc tac ata aac aaa gag      544
Thr Phe Asn Leu Tyr Asp Ile Asn Lys Asp Gly Tyr Ile Asn Lys Glu
                145                 150                 155 gag atg atg gac ata gtc aaa gcc atc tat gac atg atg ggg aaa tac      592
Glu Met Met Asp Ile Val Lys Ala Ile Tyr Asp Met Met Gly Lys Tyr
            160                 165                 170 acc tat cct gtg ctc aaa gag gac act ccc agg cag cat gtg gat gtc      640
Thr Tyr Pro Val Leu Lys Glu Asp Thr Pro Arg Gln His Val Asp Val
        175                 180                 185
```

-continued

```
ttc ttc cag aaa atg gat aaa aat aaa gat ggc att gta acg tta gat      688
Phe Phe Gln Lys Met Asp Lys Asn Lys Asp Gly Ile Val Thr Leu Asp
    190                 195                 200 gaa ttt ctt gaa tca tgt cag gag gat gac aac atc atg aga tct cta      736
Glu Phe Leu Glu Ser Cys Gln Glu Asp Asp Asn Ile Met Arg Ser Leu
205                 210                 215                 220 cag ctg ttc caa aat gtc atg taactgagga cactggccat tctgctctca         787
Gln Leu Phe Gln Asn Val Met
                225 gagacactga caaacacctt aatgccctga tctgcccttg ttccaatttt acacaccaac    847 tcttgggaca gaaataccct ttacactttg gaagaattct ctgctgaaga ctttctacaa    907 aacctggcac cacgtggctc tgtctctgag ggacgagcgg agatccgact ttgttttgga    967 agcatgccca tctcttcatg ctgctgccct gtggaaggcc cctctgcttg agcttaatca   1027 atagtgcaca gttttatgct tacacatatc cccaactcac tgcctccaag tcaggcagac   1087 tctgatgaat ctgagccaaa tgtgcaccat cctccgatgg cctcccaagc caatgtgcct   1147 gcttctcttc ctctggtggg aagaaagagt gttctacgga acaattagag cttaccatga   1207 aaatattggg agaggcagca cctaacacat gtagaatagg actgaattat taagcatggt   1267 gatatcagat gatgcaaatt gcccatgtca ttttttttcaa aggtagggac aaatgattct   1327 cccacactag cacctgtggt catagagcaa gtctcttaac atgcccagaa ggggaaccac   1387 tgtccagtgg tctatccctc ctctccatcc cctgctcaaa cccagcactg catgtccctc   1447 caagaaggtc cagaatgcct gcgaaacgct gtactttat accctgttct aatcaataaa    1507 cagaactatt tcgtacaaaa aaaaaaaaaa aaa                                 1540

<210> SEQ ID NO 10
<211> LENGTH: 227
<212> TYPE: PRT
<213> ORGANISM: Mus musculus

<400> SEQUENCE: 10

Met Gly Ala Val Met Gly Thr Phe Ser Ser Leu Gln Thr Lys Gln Arg
 1               5                  10                  15

Arg Pro Ser Lys Asp Ile Ala Trp Trp Tyr Gln Tyr Gln Arg Asp
            20                  25                  30

Lys Ile Glu Asp Glu Leu Glu Met Thr Met Val Cys His Arg Pro Glu
        35                  40                  45

Gly Leu Glu Gln Leu Glu Ala Gln Thr Asn Phe Thr Lys Arg Glu Leu
    50                  55                  60

Gln Val Leu Tyr Arg Gly Phe Lys Asn Glu Cys Pro Ser Gly Val Val
65                  70                  75                  80

Asn Glu Glu Thr Phe Lys Gln Ile Tyr Ala Gln Phe Phe Pro His Gly
                85                  90                  95

Asp Ala Ser Thr Tyr Ala His Tyr Leu Phe Asn Ala Phe Asp Thr Thr
            100                 105                 110

Gln Thr Gly Ser Val Lys Phe Glu Asp Phe Val Thr Ala Leu Ser Ile
        115                 120                 125

Leu Leu Arg Gly Thr Val His Glu Lys Leu Arg Trp Thr Phe Asn Leu
    130                 135                 140

Tyr Asp Ile Asn Lys Asp Gly Tyr Ile Asn Lys Glu Glu Met Met Asp
145                 150                 155                 160

Ile Val Lys Ala Ile Tyr Asp Met Met Gly Lys Tyr Thr Tyr Pro Val
                165                 170                 175
```

```
Leu Lys Glu Asp Thr Pro Arg Gln His Val Asp Val Phe Phe Gln Lys
        180                 185                 190

Met Asp Lys Asn Lys Asp Gly Ile Val Thr Leu Asp Glu Phe Leu Glu
        195                 200                 205

Ser Cys Gln Glu Asp Asp Asn Ile Met Arg Ser Leu Gln Leu Phe Gln
        210                 215                 220

Asn Val Met
225

<210> SEQ ID NO 11
<211> LENGTH: 955
<212> TYPE: DNA
<213> ORGANISM: Rattus sp.
<220> FEATURE:
<221> NAME/KEY: CDS
<222> LOCATION: (345)..(953)
<221> NAME/KEY: misc_feature
<222> LOCATION: (667)..(667)
<223> OTHER INFORMATION: n = any nucleotide
<221> NAME/KEY: unsure
<222> LOCATION: (92)..(92)
<223> OTHER INFORMATION: Xaa = any amino acid

<400> SEQUENCE: 11
gtccgggcac acaaccctg  gattcttcgg agaatatgcc gtgacggtgt tgccaattat       60
tagttctctt ggctagcaga tgtttaggga ctggttaagc ctttggagaa attaccttag      120
gaaaacgggg aaataaaagc aaagattacc atgaattgca agattaccta gcaattgcaa      180
ggtaggagga gagaggtgga gggcggagta gacaggaggg agggagaaag tgagaggaag      240
ctaggctggt ggaaataacc ctgcacttgg aacagcggca aagaagcgcg attttccagc      300
tttaaatgcc tgcccgcgtt ctgcttgcct acccgggaac ggag atg ttg acc cag       356
                                                Met Leu Thr Gln
                                                  1 ggc gag tct gaa ggg ctc cag acc ttg ggg ata gta gtg gtc ctg tgt       404
Gly Glu Ser Glu Gly Leu Gln Thr Leu Gly Ile Val Val Val Leu Cys
  5              10                  15                  20 tcc tct ctg aaa cta ctg cac tac ctc ggg ctg att gac ttg tcg gat       452
Ser Ser Leu Lys Leu Leu His Tyr Leu Gly Leu Ile Asp Leu Ser Asp
         25                  30                  35 gac aag atc gag gat gat ctg gag atg acc atg gtt tgc cat cgg cct       500
Asp Lys Ile Glu Asp Asp Leu Glu Met Thr Met Val Cys His Arg Pro
     40                  45                  50 gag gga ctg gag cag ctt gag gca cag acg aac ttc acc aag aga gaa       548
Glu Gly Leu Glu Gln Leu Glu Ala Gln Thr Asn Phe Thr Lys Arg Glu
 55                  60                  65 ctg caa gtc ctt tac cgg gga ttc aaa aac gag tgc ccc agt ggt gtg       596
Leu Gln Val Leu Tyr Arg Gly Phe Lys Asn Glu Cys Pro Ser Gly Val
         70                  75                  80 gtt aac gaa gag aca ttc aag cng atc tac gct cag ttt ttc cct cat       644
Val Asn Glu Glu Thr Phe Lys Xaa Ile Tyr Ala Gln Phe Phe Pro His
 85                  90                  95                 100 gga gat gcc agc aca tac gca cat tac ctc ttc aat gcc ttc gac acc       692
Gly Asp Ala Ser Thr Tyr Ala His Tyr Leu Phe Asn Ala Phe Asp Thr
                105                 110                 115 acc cag aca ggc tct gta aag ttc gag gac ttt gtg act gct ctg tcg       740
Thr Gln Thr Gly Ser Val Lys Phe Glu Asp Phe Val Thr Ala Leu Ser
            120                 125                 130 att tta ctg aga gga acg gtc cat gaa aaa ctg aag tgg acg ttt aat       788
Ile Leu Leu Arg Gly Thr Val His Glu Lys Leu Lys Trp Thr Phe Asn
        135                 140                 145
```

```
ttg tac gac atc aat aaa gac ggc tac ata aac aaa gag gag atg atg      836
Leu Tyr Asp Ile Asn Lys Asp Gly Tyr Ile Asn Lys Glu Glu Met Met
        150                 155                 160 gac ata gtg aaa gcc atc tat gac atg atg ggg aaa tac acc tat ctt      884
Asp Ile Val Lys Ala Ile Tyr Asp Met Met Gly Lys Tyr Thr Tyr Leu
165                 170                 175                 180 gtg ctc aaa gag gac act tcc agg cag cac gtg gac gtc ttc ttc cag      932
Val Leu Lys Glu Asp Thr Ser Arg Gln His Val Asp Val Phe Phe Gln
                185                 190                 195 aaa atg gat aaa aat aaa gat gg                                       955
Lys Met Asp Lys Asn Lys Asp
            200

<210> SEQ ID NO 12
<211> LENGTH: 203
<212> TYPE: PRT
<213> ORGANISM: Rattus sp.
<220> FEATURE:
<221> NAME/KEY: unsure
<222> LOCATION: (92)..(92)
<223> OTHER INFORMATION: Xaa = any amino acid

<400> SEQUENCE: 12

Met Leu Thr Gln Gly Glu Ser Glu Gly Leu Gln Thr Leu Gly Ile Val
 1               5                  10                  15

Val Val Leu Cys Ser Ser Leu Lys Leu Leu His Tyr Leu Gly Leu Ile
            20                  25                  30

Asp Leu Ser Asp Asp Lys Ile Glu Asp Leu Glu Met Thr Met Val
        35                  40                  45

Cys His Arg Pro Glu Gly Leu Glu Gln Leu Glu Ala Gln Thr Asn Phe
    50                  55                  60

Thr Lys Arg Glu Leu Gln Val Leu Tyr Arg Gly Phe Lys Asn Glu Cys
65                  70                  75                  80

Pro Ser Gly Val Val Asn Glu Gly Thr Phe Lys Xaa Ile Tyr Ala Gln
                85                  90                  95

Phe Phe Pro His Gly Asp Ala Ser Thr Tyr Ala His Tyr Leu Phe Asn
                100                 105                 110

Ala Phe Asp Thr Thr Gln Thr Gly Ser Val Lys Phe Glu Asp Phe Val
            115                 120                 125

Thr Ala Leu Ser Ile Leu Leu Arg Gly Thr Val His Glu Lys Leu Lys
130                 135                 140

Trp Thr Phe Asn Leu Tyr Asp Ile Asn Lys Asp Gly Tyr Ile Asn Lys
145                 150                 155                 160

Glu Glu Met Met Asp Ile Val Lys Ala Ile Tyr Asp Met Met Gly Lys
                165                 170                 175

Tyr Thr Tyr Leu Val Leu Lys Glu Asp Thr Ser Arg Gln His Val Asp
            180                 185                 190

Val Phe Phe Gln Lys Met Asp Lys Asn Lys Asp
            195                 200

<210> SEQ ID NO 13
<211> LENGTH: 2009
<212> TYPE: DNA
<213> ORGANISM: Homo sapiens
<220> FEATURE:
<221> NAME/KEY: CDS
<222> LOCATION: (207)..(1016)

<400> SEQUENCE: 13
```

```
ctcacctgct gcctagtgtt ccctctcctg ctccaggacc tccgggtaga cctcagaccc      60
cgggcccatt cccagactca gcctcagccc ggacttcccc agccccgaca gcacagtagg     120
ccgccagggg gcgccgtgtg agcgcccctat cccggccacc cggcgccccc tcccacggcc    180
cgggcgggag cggggcgccg ggggcc atg cgg ggc cag ggc cgc aag gag agt      233
                              Met Arg Gly Gln Gly Arg Lys Glu Ser
                                1               5 ttg tcc gat tcc cga gac ctg gac ggc tcc tac gac cag ctc acg ggc       281
Leu Ser Asp Ser Arg Asp Leu Asp Gly Ser Tyr Asp Gln Leu Thr Gly
 10              15                  20                  25 cac cct cca ggg ccc act aaa aaa gcg ctg aag cag cga ttc ctc aag       329
His Pro Pro Gly Pro Thr Lys Lys Ala Leu Lys Gln Arg Phe Leu Lys
                 30                  35                  40 ctg ctg ccg tgc tgc ggg ccc caa gcc ctg ccc tca gtc agt gaa aca       377
Leu Leu Pro Cys Cys Gly Pro Gln Ala Leu Pro Ser Val Ser Glu Thr
                 45                  50                  55 tta gcc gcc cca gcc tcc ctc cgc ccc cac aga ccc cgc ctg ctg gac       425
Leu Ala Ala Pro Ala Ser Leu Arg Pro His Arg Pro Arg Leu Leu Asp
         60                  65                  70 cca gac agc gtg gac gat gaa ttt gaa ttg tcc acc gtg tgt cac cgg       473
Pro Asp Ser Val Asp Asp Glu Phe Glu Leu Ser Thr Val Cys His Arg
     75                  80                  85 cct gag ggt ctg gag cag ctg cag gag caa acc aaa ttc acg cgc aag       521
Pro Glu Gly Leu Glu Gln Leu Gln Glu Gln Thr Lys Phe Thr Arg Lys
 90                  95                 100                 105 gag ttg cag gtc ctg tac cgg ggc ttc aag aac gaa tgt ccc agc gga       569
Glu Leu Gln Val Leu Tyr Arg Gly Phe Lys Asn Glu Cys Pro Ser Gly
                110                 115                 120 att gtc aat gag gag aac ttc aag cag att tac tcc cag ttc ttt cct       617
Ile Val Asn Glu Glu Asn Phe Lys Gln Ile Tyr Ser Gln Phe Phe Pro
                125                 130                 135 caa gga gac tcc agc acc tat gcc act ttt ctc ttc aat gcc ttt gac       665
Gln Gly Asp Ser Ser Thr Tyr Ala Thr Phe Leu Phe Asn Ala Phe Asp
         140                 145                 150 acc aac cat gat ggc tcg gtc agt ttt gag gac ttt gtg gct ggt ttg       713
Thr Asn His Asp Gly Ser Val Ser Phe Glu Asp Phe Val Ala Gly Leu
     155                 160                 165 tcc gtg att ctt cgg gga act gta gat gac agg ctt aat tgg gcc ttc       761
Ser Val Ile Leu Arg Gly Thr Val Asp Asp Arg Leu Asn Trp Ala Phe
170                 175                 180                 185 aac ctg tat gac ctt aac aag gac ggc tgc atc acc aag gag gaa atg       809
Asn Leu Tyr Asp Leu Asn Lys Asp Gly Cys Ile Thr Lys Glu Glu Met
                190                 195                 200 ctt gac atc atg aag tcc atc tat gac atg atg ggc aag tac acg tac       857
Leu Asp Ile Met Lys Ser Ile Tyr Asp Met Met Gly Lys Tyr Thr Tyr
                205                 210                 215 cct gca ctc cgg gag gag gcc cca agg gaa cac gtg gag agc ttc ttc       905
Pro Ala Leu Arg Glu Glu Ala Pro Arg Glu His Val Glu Ser Phe Phe
         220                 225                 230 cag aag atg gac aga aac aag gat ggt gtg gtg acc att gag gaa ttc       953
Gln Lys Met Asp Arg Asn Lys Asp Gly Val Val Thr Ile Glu Glu Phe
     235                 240                 245 att gag tct tgt caa aag gat gag aac atc atg agg tcc atg cag ctc      1001
Ile Glu Ser Cys Gln Lys Asp Glu Asn Ile Met Arg Ser Met Gln Leu
250                 255                 260                 265 ttt gac aat gtc atc tagccccag gagaggggt cagtgtttcc tgggggacc         1056
Phe Asp Asn Val Ile
                270 atgctctaac cctagtccag gcggacctca cccttctctt cccaggtcta tcctcatcct   1116
```

```
acgcctccct gggggctgga gggatccaag agcttgggga ttcagtagtc cagatctctg    1176
gagctgaagg ggccagagag tgggcagagt gcatctcggg gggtgttccc aactcccacc    1236
agctctcacc cccttcctgc ctgacaccca gtgttgagag tgcccctcct gtaggaattg    1296
agcggttccc cacctcctac cctactctag aaacacacta gagcgatgtc tcctgctatg    1356
gtgcttcccc catccctgac ctcataaaca tttcccctaa gactcccctc tcagagagaa    1416
tgctccattc ttggcactgg ctggcttctc agaccagcca ttgagagccc tgtgggaggg    1476
ggacaagaat gtatagggag aaatcttggg cctgagtcaa tggataggtc ctaggaggtg    1536
ggtggggttg agaatagaag ggcctggaca gattatgatt gctcaggcat accaggttat    1596
agctccaagt tccacaggtc tgctaccaca ggccatcaaa atataagttt ccaggctttg    1656
cagaagacct tgtctcctta gaaatgcccc agaaattttc cacaccctcc tcggtatcca    1716
tggagagcct ggggccagat atctggctca tctctggcat tgcttcctct ccttccttcc    1776
tgcatgtgtt ggtggtggtt gtggtggggg aatgtggatg ggggatgtcc tggctgatgc    1836
ctgccaaaat ttcatcccac cctccttgct tatcgtccct gttttgaggg ctatgacttg    1896
agtttttgtt tcccatgttc tctatagact tgggaccttc ctgaacttgg ggcctatcac    1956
tccccacagt ggatgcctta gaagggagag ggaaggaggg aggcaggcat agc           2009
```

<210> SEQ ID NO 14
<211> LENGTH: 270
<212> TYPE: PRT
<213> ORGANISM: Homo sapiens
<400> SEQUENCE: 14

```
Met Arg Gly Gln Gly Arg Lys Glu Ser Leu Ser Asp Ser Arg Asp Leu
 1               5                  10                  15

Asp Gly Ser Tyr Asp Gln Leu Thr Gly His Pro Pro Gly Pro Thr Lys
            20                  25                  30

Lys Ala Leu Lys Gln Arg Phe Leu Lys Leu Leu Pro Cys Cys Gly Pro
        35                  40                  45

Gln Ala Leu Pro Ser Val Ser Glu Thr Leu Ala Ala Pro Ala Ser Leu
    50                  55                  60

Arg Pro His Arg Pro Arg Leu Leu Asp Pro Asp Ser Val Asp Asp Glu
65                  70                  75                  80

Phe Glu Leu Ser Thr Val Cys His Arg Pro Glu Gly Leu Glu Gln Leu
                85                  90                  95

Gln Glu Gln Thr Lys Phe Thr Arg Lys Glu Leu Gln Val Leu Tyr Arg
           100                 105                 110

Gly Phe Lys Asn Glu Cys Pro Ser Gly Ile Val Asn Glu Glu Asn Phe
       115                 120                 125

Lys Gln Ile Tyr Ser Gln Phe Phe Pro Gln Gly Asp Ser Ser Thr Tyr
   130                 135                 140

Ala Thr Phe Leu Phe Asn Ala Phe Asp Thr Asn His Asp Gly Ser Val
145                 150                 155                 160

Ser Phe Glu Asp Phe Val Ala Gly Leu Ser Val Ile Leu Arg Gly Thr
                165                 170                 175

Val Asp Asp Arg Leu Asn Trp Ala Phe Asn Leu Tyr Asp Leu Asn Lys
            180                 185                 190

Asp Gly Cys Ile Thr Lys Glu Glu Met Leu Asp Ile Met Lys Ser Ile
        195                 200                 205

Tyr Asp Met Met Gly Lys Tyr Thr Tyr Pro Ala Leu Arg Glu Glu Ala
```

```
                    210                 215                 220
Pro Arg Glu His Val Glu Ser Phe Phe Gln Lys Met Asp Arg Asn Lys
225                 230                 235                 240

Asp Gly Val Val Thr Ile Glu Glu Phe Ile Glu Ser Cys Gln Lys Asp
                245                 250                 255

Glu Asn Ile Met Arg Ser Met Gln Leu Phe Asp Asn Val Ile
                260                 265                 270

<210> SEQ ID NO 15
<211> LENGTH: 1247
<212> TYPE: DNA
<213> ORGANISM: Rattus sp.
<220> FEATURE:
<221> NAME/KEY: CDS
<222> LOCATION: (2)..(772)

<400> SEQUENCE: 15 c cga gat ctg gac ggc tcc tat gac cag ctt acg ggc cac cct cca ggg    49
  Arg Asp Leu Asp Gly Ser Tyr Asp Gln Leu Thr Gly His Pro Pro Gly
   1               5                  10                  15 ccc agt aaa aaa gcc ctg aag cag cgt ttc ctc aag ctg ctg ccg tgc     97
Pro Ser Lys Lys Ala Leu Lys Gln Arg Phe Leu Lys Leu Leu Pro Cys
             20                  25                  30 tgc ggg ccc caa gcc ctg ccc tca gtc agt gaa aca tta gct gcc cca    145
Cys Gly Pro Gln Ala Leu Pro Ser Val Ser Glu Thr Leu Ala Ala Pro
         35                  40                  45 gcc tcc ctc cgc ccc cac aga ccc cgc ccg ctg gac cca gac agc gta    193
Ala Ser Leu Arg Pro His Arg Pro Arg Pro Leu Asp Pro Asp Ser Val
     50                  55                  60 gag gat gag ttt gaa tta tcc acg gtg tgt cac cga cct gag ggc ctg    241
Glu Asp Glu Phe Glu Leu Ser Thr Val Cys His Arg Pro Glu Gly Leu
 65                  70                  75                  80 gaa caa ctc cag gaa cag acc aag ttc aca cgc aga gag ctg cag gtc    289
Glu Gln Leu Gln Glu Gln Thr Lys Phe Thr Arg Arg Glu Leu Gln Val
                 85                  90                  95 ctg tac cga ggc ttc aag aac gaa tgc ccc agt ggg att gtc aac gag    337
Leu Tyr Arg Gly Phe Lys Asn Glu Cys Pro Ser Gly Ile Val Asn Glu
            100                 105                 110 gag aac ttc aag cag att tat tct cag ttc ttt ccc caa gga gac tcc    385
Glu Asn Phe Lys Gln Ile Tyr Ser Gln Phe Phe Pro Gln Gly Asp Ser
        115                 120                 125 agc aac tat gct act ttt ctc ttc aat gcc ttt gac acc aac cac gat    433
Ser Asn Tyr Ala Thr Phe Leu Phe Asn Ala Phe Asp Thr Asn His Asp
    130                 135                 140 ggc tct gtc agt ttt gag gac ttt gtg gct ggt ttg tcg gtg att ctt    481
Gly Ser Val Ser Phe Glu Asp Phe Val Ala Gly Leu Ser Val Ile Leu
145                 150                 155                 160 cgg ggg acc ata gat gat aga ctg agc tgg gct ttc aac tta tat gac    529
Arg Gly Thr Ile Asp Asp Arg Leu Ser Trp Ala Phe Asn Leu Tyr Asp
                165                 170                 175 ctc aac aag gac ggc tgt atc aca aag gag gaa atg ctt gac att atg    577
Leu Asn Lys Asp Gly Cys Ile Thr Lys Glu Glu Met Leu Asp Ile Met
            180                 185                 190 aag tcc atc tat gac atg atg ggc aag tac aca tac cct gcc ctc cgg    625
Lys Ser Ile Tyr Asp Met Met Gly Lys Tyr Thr Tyr Pro Ala Leu Arg
        195                 200                 205 gag gag gcc cca aga gaa cac gtg gag agc ttc ttc cag aag atg gac    673
Glu Glu Ala Pro Arg Glu His Val Glu Ser Phe Phe Gln Lys Met Asp
    210                 215                 220 agg aac aag gac ggc gtg gtg acc atc gag gaa ttc atc gag tct tgt    721
```

```
Arg Asn Lys Asp Gly Val Val Thr Ile Glu Glu Phe Ile Glu Ser Cys
225                 230                 235                 240 caa cag gac gag aac atc atg agg tcc atg cag ctc ttt gat aat gtc      769
Gln Gln Asp Glu Asn Ile Met Arg Ser Met Gln Leu Phe Asp Asn Val
                245                 250                 255 atc tagctcccca gggagagggg ttagtgtgtc ctagggtgac caggctgtag           822
Ile tcctagtcca gacgaaccta accctctctc tccaggcctg tcctcatctt acctgtaccc    882
tgggggctgt agggattcaa tatcctgggg cttcagtagt ccagatccct gagctaagtc    942
acaaaagtag gcaagagtag gcaagctaaa tctgggggct tcccaacccc cgacagctct   1002
caccccttct caactgatac ctagtgctga ggacacccct ggtgtaggga ccaagtggtt   1062
ctccaccttc tagtcccact ctagaaacca cattagacag aaggtctcct gctatggtgc   1122
tttccccatc cctaatctct tagattttcc tcaagactcc cttctcagag aacacgctct   1182
gtccatgtcc ccagctgggg acatggacag agcgtgttct ctagttctag atcgcgagcg   1242
gccgc                                                               1247
```

```
<210> SEQ ID NO 16
<211> LENGTH: 257
<212> TYPE: PRT
<213> ORGANISM: Rattus sp.

<400> SEQUENCE: 16

Arg Asp Leu Asp Gly Ser Tyr Asp Gln Leu Thr Gly His Pro Pro Gly
1               5                   10                  15

Pro Ser Lys Lys Ala Leu Lys Gln Arg Phe Leu Lys Leu Leu Pro Cys
                20                  25                  30

Cys Gly Pro Gln Ala Leu Pro Ser Val Ser Glu Thr Leu Ala Ala Pro
            35                  40                  45

Ala Ser Leu Arg Pro His Arg Pro Arg Pro Leu Asp Pro Asp Ser Val
        50                  55                  60

Glu Asp Glu Phe Glu Leu Ser Thr Val Cys His Arg Pro Gly Leu
65                  70                  75                  80

Glu Gln Leu Gln Glu Gln Thr Lys Phe Thr Arg Arg Glu Leu Gln Val
                85                  90                  95

Leu Tyr Arg Gly Phe Lys Asn Glu Cys Pro Ser Gly Ile Val Asn Glu
            100                 105                 110

Glu Asn Phe Lys Gln Ile Tyr Ser Gln Phe Phe Pro Gln Gly Asp Ser
        115                 120                 125

Ser Asn Tyr Ala Thr Phe Leu Phe Asn Ala Phe Asp Thr Asn His Asp
    130                 135                 140

Gly Ser Val Ser Phe Glu Asp Phe Val Ala Gly Leu Ser Val Ile Leu
145                 150                 155                 160

Arg Gly Thr Ile Asp Asp Arg Leu Ser Trp Ala Phe Asn Leu Tyr Asp
                165                 170                 175

Leu Asn Lys Asp Gly Cys Ile Thr Lys Glu Glu Met Leu Asp Ile Met
            180                 185                 190

Lys Ser Ile Tyr Asp Met Met Gly Lys Tyr Thr Tyr Pro Ala Leu Arg
        195                 200                 205

Glu Glu Ala Pro Arg Glu His Val Glu Ser Phe Gln Lys Met Asp
    210                 215                 220

Arg Asn Lys Asp Gly Val Val Thr Ile Glu Glu Phe Ile Glu Ser Cys
225                 230                 235                 240
```

```
Gln Gln Asp Glu Asn Ile Met Arg Ser Met Gln Leu Phe Asp Asn Val
                245                 250                 255
Ile

<210> SEQ ID NO 17
<211> LENGTH: 2343
<212> TYPE: DNA
<213> ORGANISM: Mus musculus
<220> FEATURE:
<221> NAME/KEY: CDS
<222> LOCATION: (181)..(990)

<400> SEQUENCE: 17
cgggactctg aggtgggccc taaaatccag cgctccccag agaaaagcct tgccagcccc      60
tactcccggc ccccagcccc agcaggtcgc tgcgccgcca gggggcactg tgtgagcgcc     120
ctatcctggc cacccggcgc ccctcccac ggcccaggcg ggagcgggc gccggggccc      180 atg cgg ggc caa ggc cga aag gag agt ttg tcc gaa tcc cga gat ttg      228
Met Arg Gly Gln Gly Arg Lys Glu Ser Leu Ser Glu Ser Arg Asp Leu
 1               5                  10                  15 gac ggc tcc tat gac cag ctt acg ggc cac cct cca ggg ccc agt aaa      276
Asp Gly Ser Tyr Asp Gln Leu Thr Gly His Pro Pro Gly Pro Ser Lys
             20                  25                  30 aaa gcc ctg aag cag cgt ttc ctc aag ctg ctg ccg tgc tgc ggg ccc      324
Lys Ala Leu Lys Gln Arg Phe Leu Lys Leu Leu Pro Cys Cys Gly Pro
         35                  40                  45 caa gcc ctg ccc tca gtc agt gaa aca tta gct gcc cca gcc tcc ctc      372
Gln Ala Leu Pro Ser Val Ser Glu Thr Leu Ala Ala Pro Ala Ser Leu
     50                  55                  60 cgc ccc cac aga ccc cgc ccg ctg gac cca gac agc gtg gag gat gag      420
Arg Pro His Arg Pro Arg Pro Leu Asp Pro Asp Ser Val Glu Asp Glu
 65                  70                  75                  80 ttt gaa cta tcc acg gtg tgc cac cgg cct gag ggt ctg gaa caa ctc      468
Phe Glu Leu Ser Thr Val Cys His Arg Pro Glu Gly Leu Glu Gln Leu
                 85                  90                  95 cag gaa caa acc aag ttc aca cgc aga gag ttg cag gtc ctg tac aga      516
Gln Glu Gln Thr Lys Phe Thr Arg Arg Glu Leu Gln Val Leu Tyr Arg
            100                 105                 110 ggc ttc aag aac gaa tgt ccc agc gga att gtc aac gag gag aac ttc      564
Gly Phe Lys Asn Glu Cys Pro Ser Gly Ile Val Asn Glu Glu Asn Phe
        115                 120                 125 aag caa att tat tct cag ttc ttt ccc caa gga gac tcc agc aac tac      612
Lys Gln Ile Tyr Ser Gln Phe Phe Pro Gln Gly Asp Ser Ser Asn Tyr
    130                 135                 140 gct act ttt ctc ttc aat gcc ttt gac acc aac cat gat ggc tct gtc      660
Ala Thr Phe Leu Phe Asn Ala Phe Asp Thr Asn His Asp Gly Ser Val
145                 150                 155                 160 agt ttt gag gac ttt gtg gct ggt ttg tca gtg att ctt cgg gga acc      708
Ser Phe Glu Asp Phe Val Ala Gly Leu Ser Val Ile Leu Arg Gly Thr
                165                 170                 175 ata gat gat aga ctg aac tgg gct ttc aac tta tat gac ctc aac aag      756
Ile Asp Asp Arg Leu Asn Trp Ala Phe Asn Leu Tyr Asp Leu Asn Lys
            180                 185                 190 gat ggc tgt atc acg aag gag gaa atg ctc gac atc atg aag tcc atc      804
Asp Gly Cys Ile Thr Lys Glu Glu Met Leu Asp Ile Met Lys Ser Ile
        195                 200                 205 tat gac atg atg ggc aag tac acc tac cct gcc ctc cgg gag gag gcc      852
Tyr Asp Met Met Gly Lys Tyr Thr Tyr Pro Ala Leu Arg Glu Glu Ala
    210                 215                 220 ccg agg gaa cac gtg gag agc ttc ttc cag aag atg gac aga aac aag      900
```

| | | | | | | | | | | | | | | |
|---|---|---|---|---|---|---|---|---|---|---|---|---|---|---|
| Pro | Arg | Glu | His | Val | Glu | Ser | Phe | Phe | Gln | Lys | Met | Asp | Arg | Asn | Lys |
| 225 | | | | 230 | | | | | 235 | | | | | 240 |

| gac | ggc | gtg | gtg | acc | att | gag | gaa | ttc | att | gag | tct | tgt | caa | cag | gac | 948 |
|---|---|---|---|---|---|---|---|---|---|---|---|---|---|---|---|---|
| Asp | Gly | Val | Val | Thr | Ile | Glu | Glu | Phe | Ile | Glu | Ser | Cys | Gln | Gln | Asp | |
| | | | | 245 | | | | | 250 | | | | | 255 | | |

| gag | aac | atc | atg | agg | tcc | atg | caa | ctc | ttt | gat | aat | gtc | atc | 990 |
|---|---|---|---|---|---|---|---|---|---|---|---|---|---|---|
| Glu | Asn | Ile | Met | Arg | Ser | Met | Gln | Leu | Phe | Asp | Asn | Val | Ile | |
| | | | 260 | | | | | 265 | | | | | 270 | |

```
tagctcccca gggagagggg ttagtgtgtc ccagggtaac catgctgtag ccctagtcca    1050
ggcaaaccta accctcctct ccccgggtct gtcctcatcc tacctgtacc ctggggctg     1110
tagggattca acatcctggc gcttcagtag tccagatccc tgagctaagt ggcgagagta    1170
ggcaagctaa gtctttggag ggtgggtggg ggcgcgcaga ttcccaaccc ccgacgactc    1230
tcaccccttt ctcgactgat acccagtgct gaggctaccc ctggtgtcgg aacgaccaa    1290
agtggttctc tgcctcccca gcccactcta gagacccaca ctagacggga atatctcctg    1350
ctatggtgct ttccccatcc ctgaccgcag attttcctcc taagactccc ttctcagaga    1410
atatgctttt gtcccttgtc cctggctggc ttttcagcct agcctttgag gaccctgtgg    1470
gaggggagaa taagaaagca gacaaaatct tggccctgag ccagtggtta ggtcctagga    1530
atcaggctgg agtggagacc agaaagcctg gcaggctat  gagagcccca ggttggcttg    1590
tcaccgccag gttccacagg gctgctgctc tgggtcagca gagtatgagt ttccagactt    1650
tccagaaggc cttatgtcct tagcaatgtc ccagaaattc accatacact tctcagtgtc    1710
ttaggatcca gatgtccggt ccatccctga aacctctccc tcctccttgc tcctatggtg    1770
ggagtggtgg ccaggggacg atgagtgagc cggtgtcctg gatgatgcct gtcaaggtcc    1830
cacctaccct ccggctgtca agccgttctg gtgaccctgt tgattctcc atgacccctg     1890
tctagatgta gaggtgtgga gtgagtctag tggcagcctt aggggaatgg gaagaacgag    1950
aggggcactc catctgaacc cagtgtgggg gcatccattc gaatctttgc ctggctcccc    2010
acaatgccct aggatcctct agggtcccca ccccactct  ttagtctacc cagagatgct    2070
ccagagctca cctagagggc agggaccata ggatccaggt ccaacctgtc atcagcatcc    2130
ggccatgctg ctgctgctta ttaataaacc tgcttgtcgt tcagcgcccc ttcccagtca    2190
gccagggtct gaggggaagg ccccccactt cccgcctcct gtcagacatt gttgactgct    2250
ttgcattttg ggctcttcta cctatatttt gtataataag aaagacacca gatccaataa    2310
aacacatggc tatgcacaaa aaaaaaaaaa aaa                                 2343
```

<210> SEQ ID NO 18
<211> LENGTH: 270
<212> TYPE: PRT
<213> ORGANISM: Mus musculus

<400> SEQUENCE: 18

| Met | Arg | Gly | Gln | Gly | Arg | Lys | Glu | Ser | Leu | Ser | Glu | Ser | Arg | Asp | Leu |
|---|---|---|---|---|---|---|---|---|---|---|---|---|---|---|---|
| 1 | | | | 5 | | | | | 10 | | | | | 15 | |

| Asp | Gly | Ser | Tyr | Asp | Gln | Leu | Thr | Gly | His | Pro | Pro | Gly | Pro | Ser | Lys |
|---|---|---|---|---|---|---|---|---|---|---|---|---|---|---|---|
| | | | 20 | | | | | 25 | | | | | 30 | | |

| Lys | Ala | Leu | Lys | Gln | Arg | Phe | Leu | Lys | Leu | Leu | Pro | Cys | Cys | Gly | Pro |
|---|---|---|---|---|---|---|---|---|---|---|---|---|---|---|---|
| | | 35 | | | | | 40 | | | | | 45 | | | |

| Gln | Ala | Leu | Pro | Ser | Val | Ser | Glu | Thr | Leu | Ala | Ala | Pro | Ala | Ser | Leu |
|---|---|---|---|---|---|---|---|---|---|---|---|---|---|---|---|
| | 50 | | | | | 55 | | | | | 60 | | | | |

| Arg | Pro | His | Arg | Pro | Arg | Pro | Leu | Asp | Pro | Asp | Ser | Val | Glu | Asp | Glu |
|---|---|---|---|---|---|---|---|---|---|---|---|---|---|---|---|
| 65 | | | | | 70 | | | | | 75 | | | | | 80 |

```
Phe Glu Leu Ser Thr Val Cys His Arg Pro Glu Gly Leu Glu Gln Leu
             85                  90                  95

Gln Glu Gln Thr Lys Phe Thr Arg Arg Glu Leu Gln Val Leu Tyr Arg
        100                 105                 110

Gly Phe Lys Asn Glu Cys Pro Ser Gly Ile Val Asn Glu Glu Asn Phe
    115                 120                 125

Lys Gln Ile Tyr Ser Gln Phe Phe Pro Gln Gly Asp Ser Ser Asn Tyr
    130                 135                 140

Ala Thr Phe Leu Phe Asn Ala Phe Asp Thr Asn His Asp Gly Ser Val
145                 150                 155                 160

Ser Phe Glu Asp Phe Val Ala Gly Leu Ser Val Ile Leu Arg Gly Thr
                165                 170                 175

Ile Asp Asp Arg Leu Asn Trp Ala Phe Asn Leu Tyr Asp Leu Asn Lys
                180                 185                 190

Asp Gly Cys Ile Thr Lys Glu Glu Met Leu Asp Ile Met Lys Ser Ile
            195                 200                 205

Tyr Asp Met Met Gly Lys Tyr Thr Tyr Pro Ala Leu Arg Glu Glu Ala
    210                 215                 220

Pro Arg Glu His Val Glu Ser Phe Phe Gln Lys Met Asp Arg Asn Lys
225                 230                 235                 240

Asp Gly Val Val Thr Ile Glu Glu Phe Ile Glu Ser Cys Gln Gln Asp
                245                 250                 255

Glu Asn Ile Met Arg Ser Met Gln Leu Phe Asp Asn Val Ile
                260                 265                 270

<210> SEQ ID NO 19
<211> LENGTH: 1955
<212> TYPE: DNA
<213> ORGANISM: Homo sapiens
<220> FEATURE:
<221> NAME/KEY: CDS
<222> LOCATION: (207)..(962)

<400> SEQUENCE: 19
ctcacctgct gcctagtgtt ccctctcctg ctccaggacc tccgggtaga cctcagaccc      60
cgggcccatt cccagactca gcctcagccc ggacttcccc agccccgaca gcacagtagg     120
ccgccagggg gcgccgtgtg agcgccctat cccggccacc cggcgccccc tcccacggcc     180
cgggcgggag cggggcgccg ggggcc atg cgg ggc cag ggc cgc aag gag agt     233
               Met Arg Gly Gln Gly Arg Lys Glu Ser
               1               5 ttg tcc gat tcc cga gac ctg gac ggc tcc tac gac cag ctc acg ggc     281
Leu Ser Asp Ser Arg Asp Leu Asp Gly Ser Tyr Asp Gln Leu Thr Gly
 10              15                  20                  25 cac cct cca ggg ccc act aaa aaa gcg ctg aag cag cga ttc ctc aag     329
His Pro Pro Gly Pro Thr Lys Lys Ala Leu Lys Gln Arg Phe Leu Lys
             30                  35                  40 ctg ctg ccg tgc tgc ggg ccc caa gcc ctg ccc tca gtc agt gaa aac     377
Leu Leu Pro Cys Cys Gly Pro Gln Ala Leu Pro Ser Val Ser Glu Asn
         45                  50                  55 agc gtg gac gat gaa ttt gaa ttg tcc acc gtg tgt cac cgg cct gag     425
Ser Val Asp Asp Glu Phe Glu Leu Ser Thr Val Cys His Arg Pro Glu
     60                  65                  70 ggt ctg gag cag ctg cag gag caa acc aaa ttc acg cgc aag gag ttg     473
Gly Leu Glu Gln Leu Gln Glu Gln Thr Lys Phe Thr Arg Lys Glu Leu
 75                  80                  85 cag gtc ctg tac cgg ggc ttc aag aac gaa tgt ccc agc gga att gtc     521
```

```
                Gln Val Leu Tyr Arg Gly Phe Lys Asn Glu Cys Pro Ser Gly Ile Val
                 90                  95                 100                 105 aat gag gag aac ttc aag cag att tac tcc cag ttc ttt cct caa gga         569
Asn Glu Glu Asn Phe Lys Gln Ile Tyr Ser Gln Phe Phe Pro Gln Gly
                110                 115                 120 gac tcc agc acc tat gcc act ttt ctc ttc aat gcc ttt gac acc aac         617
Asp Ser Ser Thr Tyr Ala Thr Phe Leu Phe Asn Ala Phe Asp Thr Asn
            125                 130                 135 cat gat ggc tcg gtc agt ttt gag gac ttt gtg gct ggt ttg tcc gtg         665
His Asp Gly Ser Val Ser Phe Glu Asp Phe Val Ala Gly Leu Ser Val
        140                 145                 150 att ctt cgg gga act gta gat gac agg ctt aat tgg gcc ttc aac ctg         713
Ile Leu Arg Gly Thr Val Asp Asp Arg Leu Asn Trp Ala Phe Asn Leu
    155                 160                 165 tat gac ctt aac aag gac ggc tgc atc acc aag gag gaa atg ctt gac         761
Tyr Asp Leu Asn Lys Asp Gly Cys Ile Thr Lys Glu Glu Met Leu Asp
170                 175                 180                 185 atc atg aag tcc atc tat gac atg atg ggc aag tac acg tac cct gca         809
Ile Met Lys Ser Ile Tyr Asp Met Met Gly Lys Tyr Thr Tyr Pro Ala
                190                 195                 200 ctc cgg gag gag gcc cca agg gaa cac gtg gag agc ttc ttc cag aag         857
Leu Arg Glu Glu Ala Pro Arg Glu His Val Glu Ser Phe Phe Gln Lys
                205                 210                 215 atg gac aga aac aag gat ggt gtg gtg acc att gag gaa ttc att gag         905
Met Asp Arg Asn Lys Asp Gly Val Val Thr Ile Glu Glu Phe Ile Glu
            220                 225                 230 tct tgt caa aag gat gag aac atc atg agg tcc atg cag ctc ttt gac         953
Ser Cys Gln Lys Asp Glu Asn Ile Met Arg Ser Met Gln Leu Phe Asp
        235                 240                 245 aat gtc atc tagcccccag gagagggggt cagtgtttcc tgggggggacc               1002
Asn Val Ile
250 atgctctaac cctagtccag gcggacctca cccttctctt cccaggtcta tcctcatcct      1062 acgcctccct gggggctgga gggatccaag agcttgggga ttcagtagtc cagatctctg      1122 gagctgaagg ggccagagag tgggcagagt gcatctcggg gggtgttccc aactcccacc      1182 agctctcacc cccttcctgc ctgacaccca gtgttgagag tgcccctcct gtaggaattg      1242 agcggttccc cacctcctac cctactctag aaacacacta gagcgatgtc tcctgctatg      1302 gtgcttcccc catccctgac ctcataaaca tttcccctaa gactcccctc tcagagagaa      1362 tgctccattc ttggcactgg ctggcttctc agaccagcca ttgagagccc tgtgggaggg      1422 ggacaagaat gtatagggag aaatcttggg cctgagtcaa tggataggtc ctaggaggtg      1482 ggtggggttg agaatagaag ggcctggaca gattatgatt gctcaggcat accaggttat      1542 agctccaagt tccacaggtc tgctaccaca ggccatcaaa atataagttt ccaggctttg      1602 cagaagacct tgtctcctta gaaatgcccc agaaattttc cacaccctcc tcggtatcca      1662 tggagagcct ggggccagat atctggctca tctctggcat tgcttcctct ccttccttcc      1722 tgcatgtgtt ggtggtggtt gtggtggggg aatgtggatg ggggatgtcc tggctgatgc      1782 ctgccaaaat ttcatcccac cctccttgct tatcgtccct gttttgaggg ctatgacttg      1842 agttttttgtt tccatgttc tctatagact tgggaccttc ctgaacttgg ggcctatcac       1902 tccccacagt ggatgcctta gaagggagag ggaaggaggg aggcaggcat agc             1955

<210> SEQ ID NO 20
<211> LENGTH: 252
<212> TYPE: PRT
```

-continued

<213> ORGANISM: Homo sapiens

<400> SEQUENCE: 20

Met Arg Gly Gln Gly Arg Lys Glu Ser Leu Ser Asp Ser Arg Asp Leu
1               5                   10                  15

Asp Gly Ser Tyr Asp Gln Leu Thr Gly His Pro Pro Gly Pro Thr Lys
            20                  25                  30

Lys Ala Leu Lys Gln Arg Phe Leu Lys Leu Leu Pro Cys Cys Gly Pro
        35                  40                  45

Gln Ala Leu Pro Ser Val Ser Glu Asn Ser Val Asp Asp Glu Phe Glu
    50                  55                  60

Leu Ser Thr Val Cys His Arg Pro Glu Gly Leu Glu Gln Leu Gln Glu
65              70                  75                  80

Gln Thr Lys Phe Thr Arg Lys Glu Leu Gln Val Leu Tyr Arg Gly Phe
                85                  90                  95

Lys Asn Glu Cys Pro Ser Gly Ile Val Asn Glu Glu Asn Phe Lys Gln
            100                 105                 110

Ile Tyr Ser Gln Phe Phe Pro Gln Gly Asp Ser Ser Thr Tyr Ala Thr
        115                 120                 125

Phe Leu Phe Asn Ala Phe Asp Thr Asn His Asp Gly Ser Val Ser Phe
    130                 135                 140

Glu Asp Phe Val Ala Gly Leu Ser Val Ile Leu Arg Gly Thr Val Asp
145                 150                 155                 160

Asp Arg Leu Asn Trp Ala Phe Asn Leu Tyr Asp Leu Asn Lys Asp Gly
                165                 170                 175

Cys Ile Thr Lys Glu Glu Met Leu Asp Ile Met Lys Ser Ile Tyr Asp
            180                 185                 190

Met Met Gly Lys Tyr Thr Tyr Pro Ala Leu Arg Glu Glu Ala Pro Arg
        195                 200                 205

Glu His Val Glu Ser Phe Phe Gln Lys Met Asp Arg Asn Lys Asp Gly
    210                 215                 220

Val Val Thr Ile Glu Glu Phe Ile Glu Ser Cys Gln Lys Asp Glu Asn
225                 230                 235                 240

Ile Met Arg Ser Met Gln Leu Phe Asp Asn Val Ile
                245                 250

<210> SEQ ID NO 21
<211> LENGTH: 2300
<212> TYPE: DNA
<213> ORGANISM: Rattus sp.
<220> FEATURE:
<221> NAME/KEY: CDS
<222> LOCATION: (214)..(969)

<400> SEQUENCE: 21
ctcacttgct gcccaaggct cctgctcctg ccccaggact ctgaggtggg ccctaaaacc      60
cagcgctctc taaagaaaag ccttgccagc ccctactccc ggccccaac cccagcaggt     120 cgctgcgccg ccaggggggcg ctgtgtgagc gccctattct ggccacccgg cgccccctcc     180
cacggcccag gcgggagcgg ggcgccgggg gcc atg cgg ggc caa ggc aga aag      234
                                    Met Arg Gly Gln Gly Arg Lys
                                    1               5 gag agt ttg tcc gaa tcc cga gat ctg gac ggc tcc tat gac cag ctt      282
Glu Ser Leu Ser Glu Ser Arg Asp Leu Asp Gly Ser Tyr Asp Gln Leu
        10                  15                  20 acg ggc cac cct cca ggg ccc agt aaa aaa gcc ctg aag cag cgt ttc      330
Thr Gly His Pro Pro Gly Pro Ser Lys Lys Ala Leu Lys Gln Arg Phe -continued

```
                  25                  30                  35
ctc aag ctg ctg ccg tgc tgc ggg ccc caa gcc ctg ccc tca gtc agt      378
Leu Lys Leu Leu Pro Cys Cys Gly Pro Gln Ala Leu Pro Ser Val Ser
 40                  45                  50                  55 gaa aac agc gta gag gat gag ttt gaa tta tcc acg gtg tgt cac cga      426
Glu Asn Ser Val Glu Asp Glu Phe Glu Leu Ser Thr Val Cys His Arg
                 60                  65                  70 cct gag ggc ctg gaa caa ctc cag gaa cag acc aag ttc aca cgc aga      474
Pro Glu Gly Leu Glu Gln Leu Gln Glu Gln Thr Lys Phe Thr Arg Arg
             75                  80                  85 gag ctg cag gtc ctg tac cga ggc ttc aag aac gaa tgc ccc agt ggg      522
Glu Leu Gln Val Leu Tyr Arg Gly Phe Lys Asn Glu Cys Pro Ser Gly
         90                  95                 100 att gtc aac gag gag aac ttc aag cag att tat tct cag ttc ttt ccc      570
Ile Val Asn Glu Glu Asn Phe Lys Gln Ile Tyr Ser Gln Phe Phe Pro
     105                 110                 115 caa gga gac tcc agc aac tat gct act ttt ctc ttc aat gcc ttt gac      618
Gln Gly Asp Ser Ser Asn Tyr Ala Thr Phe Leu Phe Asn Ala Phe Asp
120                 125                 130                 135 acc aac cac gat ggc tct gtc agt ttt gag gac ttt gtg gct ggt ttg      666
Thr Asn His Asp Gly Ser Val Ser Phe Glu Asp Phe Val Ala Gly Leu
                140                 145                 150 tcg gtg att ctt cgg ggg acc ata gat gat aga ctg agc tgg gct ttc      714
Ser Val Ile Leu Arg Gly Thr Ile Asp Asp Arg Leu Ser Trp Ala Phe
            155                 160                 165 aac tta tat gac ctc aac aag gac ggc tgt atc aca aag gag gaa atg      762
Asn Leu Tyr Asp Leu Asn Lys Asp Gly Cys Ile Thr Lys Glu Glu Met
        170                 175                 180 ctt gac att atg aag tcc atc tat gac atg atg ggc aag tac aca tac      810
Leu Asp Ile Met Lys Ser Ile Tyr Asp Met Met Gly Lys Tyr Thr Tyr
    185                 190                 195 cct gcc ctc cgg gag gag gcc cca aga gaa cac gtg gag agc ttc ttc      858
Pro Ala Leu Arg Glu Glu Ala Pro Arg Glu His Val Glu Ser Phe Phe
200                 205                 210                 215 cag aag atg gac agg aac aag gac ggc gtg gtg acc atc gag gaa ttc      906
Gln Lys Met Asp Arg Asn Lys Asp Gly Val Val Thr Ile Glu Glu Phe
                220                 225                 230 atc gag tct tgt caa cag gac gag aac atc atg agg tcc atg cag ctc      954
Ile Glu Ser Cys Gln Gln Asp Glu Asn Ile Met Arg Ser Met Gln Leu
            235                 240                 245 ttt gat aat gtc atc tagctcccca gggagagggg ttagtgtgtc ctagggtgac     1009
Phe Asp Asn Val Ile
            250 caggctgtag tcctagtcca gacgaaccta accctctctc tccaggcctg tcctcatctt   1069 acctgtaccc tgggggctgt agggattcaa tatcctgggg cttcagtagt ccagatccct   1129 gagctaagtc acaaaagtag gcaagagtag gcaagctaaa tctgggggct tcccaacccc   1189 cgacagctct caccccttct caactgatac ctagtgctga ggacacccct ggtgtaggga   1249 ccaagtggtt ctccaccttc tagtcccact ctagaaacca cattagacag aaggtctcct   1309 gctatggtgc tttccccatc cctaatctct tagattttcc tcaagactcc cttctcagag   1369 aacacgctct gtccatgtcc ccagctggct tctcagccta gcctttgagg gccctgtggg   1429 gaggcgggga caagaaagca gaaaagtctt ggccccgagc cagtggttag gtcctaggaa   1489 ttggctggag tggaggccag aaagcctggg cagatgatga gagcccagct gggctgtcac   1549 tgcaggttcc ggggcctaca gccctgggtc agcagagtat gagttcccag actttccaga   1609 aggtccttag caatgtccca gaaattcacc gtacacttct cagtgtctta ggagggcccg   1669
```

-continued

```
ggatccagat gtctggttca tccctgaatc ctctccctcc ttcttgctcg tatggtggga   1729
gtggtggcca ggggaagatg agtggtgtcc cggatgatgc ctgtcaaggt cccacctccc   1789
ctccggctgt tctcatgaca gctgtttggt tctccatgac ccctatctag atgtagaggc   1849
atggagtgag tcagggattt cccgaacttg agttttacca ctcctcctag tggctgcctt   1909 agggaatgg gaagaaccca gtgtggggc acccattaga atctttgccc ggctcctcac    1969
aatgccctag gtcccctag ggtacccgct ccctctgttt agtctaccca gagatgctcc    2029
tgagctcacc tagagggtag ggacggtagg ctccaggtcc aacctctcca ggtcagcacc   2089
ctgccatgct gctgctcctc attaacaaac ctgcttgtct cctcctgcgc cccttctcag   2149
tcagccaggg tctgagggga agggcctccc gtttccccat ccgtcagaca tggttgactg   2209
ctttgcattt tgggctcttc tatctatttt gtaaaataag acatcagatc caataaaaca   2269
cacggctatg cacaaaaaaa aaaaaaaaaa a                                   2300
```

<210> SEQ ID NO 22
<211> LENGTH: 252
<212> TYPE: PRT
<213> ORGANISM: Rattus sp.

<400> SEQUENCE: 22

```
Met Arg Gly Gln Gly Arg Lys Glu Ser Leu Ser Glu Ser Arg Asp Leu
  1               5                  10                  15

Asp Gly Ser Tyr Asp Gln Leu Thr Gly His Pro Pro Gly Pro Ser Lys
             20                  25                  30

Lys Ala Leu Lys Gln Arg Phe Leu Lys Leu Leu Pro Cys Cys Gly Pro
         35                  40                  45

Gln Ala Leu Pro Ser Val Ser Glu Asn Ser Val Glu Asp Glu Phe Glu
     50                  55                  60

Leu Ser Thr Val Cys His Arg Pro Glu Gly Leu Glu Gln Leu Gln Glu
 65                  70                  75                  80

Gln Thr Lys Phe Thr Arg Arg Glu Leu Gln Val Leu Tyr Arg Gly Phe
                 85                  90                  95

Lys Asn Glu Cys Pro Ser Gly Ile Val Asn Glu Glu Asn Phe Lys Gln
            100                 105                 110

Ile Tyr Ser Gln Phe Phe Pro Gln Gly Asp Ser Ser Asn Tyr Ala Thr
        115                 120                 125

Phe Leu Phe Asn Ala Phe Asp Thr Asn His Asp Gly Ser Val Ser Phe
    130                 135                 140

Glu Asp Phe Val Ala Gly Leu Ser Val Ile Leu Arg Gly Thr Ile Asp
145                 150                 155                 160

Asp Arg Leu Ser Trp Ala Phe Asn Leu Tyr Asp Leu Asn Lys Asp Gly
                165                 170                 175

Cys Ile Thr Lys Glu Glu Met Leu Asp Ile Met Lys Ser Ile Tyr Asp
            180                 185                 190

Met Met Gly Lys Tyr Thr Tyr Pro Ala Leu Arg Glu Glu Ala Pro Arg
        195                 200                 205

Glu His Val Glu Ser Phe Phe Gln Lys Met Asp Arg Asn Lys Asp Gly
    210                 215                 220

Val Val Thr Ile Glu Glu Phe Ile Glu Ser Cys Gln Gln Asp Glu Asn
225                 230                 235                 240

Ile Met Arg Ser Met Gln Leu Phe Asp Asn Val Ile
                245                 250
```

<210> SEQ ID NO 23
<211> LENGTH: 1859
<212> TYPE: DNA
<213> ORGANISM: Homo sapiens
<220> FEATURE:
<221> NAME/KEY: CDS
<222> LOCATION: (207)..(866)

<400> SEQUENCE: 23

```
ctcacctgct gcctagtgtt ccctctcctg ctccaggacc tccgggtaga cctcagaccc      60
cgggcccatt cccagactca gcctcagccc ggacttcccc agccccgaca gcacagtagg     120
ccgccagggg gcgccgtgtg agcgccctat cccggccacc cggcgccccc tcccacggcc     180
cgggcgggag cggggcgccg gggcc atg cgg ggc cag ggc cgc aag gag agt      233
                              Met Arg Gly Gln Gly Arg Lys Glu Ser
                                1               5 ttg tcc gat tcc cga gac ctg gac ggc tcc tac gac cag ctc acg gac      281
Leu Ser Asp Ser Arg Asp Leu Asp Gly Ser Tyr Asp Gln Leu Thr Asp
 10              15                  20                  25 agc gtg gac gat gaa ttt gaa ttg tcc acc gtg tgt cac cgg cct gag      329
Ser Val Asp Asp Glu Phe Glu Leu Ser Thr Val Cys His Arg Pro Glu
                 30                  35                  40 ggt ctg gag cag ctg cag gag caa acc aaa ttc acg cgc aag gag ttg      377
Gly Leu Glu Gln Leu Gln Glu Gln Thr Lys Phe Thr Arg Lys Glu Leu
             45                  50                  55 cag gtc ctg tac cgg ggc ttc aag aac gaa tgt ccc agc gga att gtc      425
Gln Val Leu Tyr Arg Gly Phe Lys Asn Glu Cys Pro Ser Gly Ile Val
         60                  65                  70 aat gag gag aac ttc aag cag att tac tcc cag ttc ttt cct caa gga      473
Asn Glu Glu Asn Phe Lys Gln Ile Tyr Ser Gln Phe Phe Pro Gln Gly
     75                  80                  85 gac tcc agc acc tat gcc act ttt ctc ttc aat gcc ttt gac acc aac      521
Asp Ser Ser Thr Tyr Ala Thr Phe Leu Phe Asn Ala Phe Asp Thr Asn
 90                  95                 100                 105 cat gat ggc tcg gtc agt ttt gag gac ttt gtg gct ggt ttg tcc gtg      569
His Asp Gly Ser Val Ser Phe Glu Asp Phe Val Ala Gly Leu Ser Val
                110                 115                 120 att ctt cgg gga act gta gat gac agg ctt aat tgg gcc ttc aac ctg      617
Ile Leu Arg Gly Thr Val Asp Asp Arg Leu Asn Trp Ala Phe Asn Leu
            125                 130                 135 tat gac ctt aac aag gac ggc tgc atc acc aag gag gaa atg ctt gac      665
Tyr Asp Leu Asn Lys Asp Gly Cys Ile Thr Lys Glu Glu Met Leu Asp
        140                 145                 150 atc atg aag tcc atc tat gac atg atg ggc aag tac acg tac cct gca      713
Ile Met Lys Ser Ile Tyr Asp Met Met Gly Lys Tyr Thr Tyr Pro Ala
    155                 160                 165 ctc cgg gag gag gcc cca agg gaa cac gtg gag agc ttc ttc cag aag      761
Leu Arg Glu Glu Ala Pro Arg Glu His Val Glu Ser Phe Phe Gln Lys
170                 175                 180                 185 atg gac aga aac aag gat ggt gtg gtg acc att gag gaa ttc att gag      809
Met Asp Arg Asn Lys Asp Gly Val Val Thr Ile Glu Glu Phe Ile Glu
                190                 195                 200 tct tgt caa aag gat gag aac atc atg agg tcc atg cag ctc ttt gac      857
Ser Cys Gln Lys Asp Glu Asn Ile Met Arg Ser Met Gln Leu Phe Asp
            205                 210                 215 aat gtc atc tagcccccag gagaggggt cagtgtttcc tgggggacc                906
Asn Val Ile
        220 atgctctaac cctagtccag gcggacctca cccttctctt cccaggtcta tcctcatcct    966
```

```
acgcctccct gggggctgga gggatccaag agcttgggga ttcagtagtc cagatctctg     1026
gagctgaagg ggccagagag tgggcagagt gcatctcggg gggtgttccc aactcccacc     1086
agctctcacc cccttcctgc ctgacaccca gtgttgagag tgcccctcct gtaggaattg     1146
agcggttccc cacctcctac cctactctag aaacacacta gagcgatgtc tcctgctatg     1206
gtgcttcccc catccctgac ctcataaaca tttcccctaa gactcccctc tcagagagaa     1266
tgctccattc ttggcactgg ctggcttctc agaccagcca ttgagagccc tgtgggaggg     1326
ggacaagaat gtatagggag aaatcttggg cctgagtcaa tggataggtc ctaggaggtg     1386
ggtggggttg agaatagaag ggcctggaca gattatgatt gctcaggcat accaggttat     1446
agctccaagt tccacaggtc tgctaccaca ggccatcaaa atataagttt ccaggctttg     1506
cagaagacct tgtctcctta gaaatgcccc agaaattttc cacaccctcc tcggtatcca     1566
tggagagcct ggggccagat atctggctca tctctggcat tgcttcctct ccttccttcc     1626
tgcatgtgtt ggtggtggtt gtggtggggg aatgtggatg ggggatgtcc tggctgatgc     1686
ctgccaaaat ttcatcccac cctccttgct tatcgtccct gttttgaggg ctatgacttg     1746 agttttgtt tcccatgttc tctatagact tgggaccttc ctgaacttgg ggcctatcac     1806
tccccacagt ggatgcctta aagggagag ggaaggaggg aggcaggcat agc             1859
```

<210> SEQ ID NO 24
<211> LENGTH: 220
<212> TYPE: PRT
<213> ORGANISM: Homo sapiens

<400> SEQUENCE: 24

```
Met Arg Gly Gln Gly Arg Lys Glu Ser Leu Ser Asp Ser Arg Asp Leu
 1               5                  10                  15

Asp Gly Ser Tyr Asp Gln Leu Thr Asp Ser Val Asp Asp Glu Phe Glu
            20                  25                  30

Leu Ser Thr Val Cys His Arg Pro Glu Gly Leu Glu Gln Leu Gln Glu
        35                  40                  45

Gln Thr Lys Phe Thr Arg Lys Glu Leu Gln Val Leu Tyr Arg Gly Phe
    50                  55                  60

Lys Asn Glu Cys Pro Ser Gly Ile Val Asn Glu Glu Asn Phe Lys Gln
65                  70                  75                  80

Ile Tyr Ser Gln Phe Phe Pro Gln Gly Asp Ser Ser Thr Tyr Ala Thr
                85                  90                  95

Phe Leu Phe Asn Ala Phe Asp Thr Asn His Asp Gly Ser Val Ser Phe
            100                 105                 110

Glu Asp Phe Val Ala Gly Leu Ser Val Ile Leu Arg Gly Thr Val Asp
        115                 120                 125

Asp Arg Leu Asn Trp Ala Phe Asn Leu Tyr Asp Leu Asn Lys Asp Gly
    130                 135                 140

Cys Ile Thr Lys Glu Glu Met Leu Asp Ile Met Lys Ser Ile Tyr Asp
145                 150                 155                 160

Met Met Gly Lys Tyr Thr Tyr Pro Ala Leu Arg Glu Glu Ala Pro Arg
                165                 170                 175

Glu His Val Glu Ser Phe Phe Gln Lys Met Asp Arg Asn Lys Asp Gly
            180                 185                 190

Val Val Thr Ile Glu Glu Phe Ile Glu Ser Cys Gln Lys Asp Glu Asn
        195                 200                 205

Ile Met Arg Ser Met Gln Leu Phe Asp Asn Val Ile
    210                 215                 220
```

```
<210> SEQ ID NO 25
<211> LENGTH: 2191
<212> TYPE: DNA
<213> ORGANISM: Simian sp.
<220> FEATURE:
<221> NAME/KEY: CDS
<222> LOCATION: (133)..(792)

<400> SEQUENCE: 25
cccacgcgtc cgcccacgcg tccgcggacg cgtggggtgc actaggccgc caggggggcgc      60 cgtgtgagcg ccctatcccg gccacccggc gcccccctccc acggaccggg cgggagcggg     120
gcgccggggg cc atg cgg ggc cag ggc cgc aag gag agt ttg tcc gat tcc     171
              Met Arg Gly Gln Gly Arg Lys Glu Ser Leu Ser Asp Ser
                1               5                  10 cga gac ctg gac gga tcc tac gac cag ctc acg gac agc gtg gag gat     219
Arg Asp Leu Asp Gly Ser Tyr Asp Gln Leu Thr Asp Ser Val Glu Asp
 15                  20                  25 gaa ttt gaa ttg tcc acc gtg tgt cac cgg cct gag ggt ctg gag cag     267
Glu Phe Glu Leu Ser Thr Val Cys His Arg Pro Glu Gly Leu Glu Gln
 30                  35                  40                  45 ctg cag gag caa acc aaa ttc acg cgc aag gag ttg cag gtc ctg tac     315
Leu Gln Glu Gln Thr Lys Phe Thr Arg Lys Glu Leu Gln Val Leu Tyr
                 50                  55                  60 cgg ggc ttc aag aac gaa tgt ccg agc gga att gtc aat gag gag aac     363
Arg Gly Phe Lys Asn Glu Cys Pro Ser Gly Ile Val Asn Glu Glu Asn
                 65                  70                  75 ttc aag caa att tac tcc cag ttc ttt cct caa gga gac tcc agc acc     411
Phe Lys Gln Ile Tyr Ser Gln Phe Phe Pro Gln Gly Asp Ser Ser Thr
             80                  85                  90 tat gcc act ttt ctc ttc aat gcc ttt gac acc aac cat gat ggc tcg     459
Tyr Ala Thr Phe Leu Phe Asn Ala Phe Asp Thr Asn His Asp Gly Ser
             95                 100                 105 gtc agt ttt gag gac ttt gtg gct ggt ttg tcc gtg att ctt cgg gga     507
Val Ser Phe Glu Asp Phe Val Ala Gly Leu Ser Val Ile Leu Arg Gly
110                 115                 120                 125 act gta gat gac agg ctt aat tgg gcc ttc aac ttg tat gac ctc aac     555
Thr Val Asp Asp Arg Leu Asn Trp Ala Phe Asn Leu Tyr Asp Leu Asn
                130                 135                 140 aag gac ggc tgc atc acc aag gag gaa atg ctt gac atc atg aag tcc     603
Lys Asp Gly Cys Ile Thr Lys Glu Glu Met Leu Asp Ile Met Lys Ser
                145                 150                 155 atc tat gac atg atg ggc aag tac aca tac cct gca ctc cgg gag gag     651
Ile Tyr Asp Met Met Gly Lys Tyr Thr Tyr Pro Ala Leu Arg Glu Glu
            160                 165                 170 gcc cca agg gaa cat gtg gag aac ttc ttc cag aag atg gac aga aac     699
Ala Pro Arg Glu His Val Glu Asn Phe Phe Gln Lys Met Asp Arg Asn
            175                 180                 185 aag gat ggc gtg gtg acc att gag gaa ttc att gag tct tgt caa aag     747
Lys Asp Gly Val Val Thr Ile Glu Glu Phe Ile Glu Ser Cys Gln Lys
190                 195                 200                 205 gat gag aac atc atg agg tcc atg cag ctc ttt gac aat gtc atc         792
Asp Glu Asn Ile Met Arg Ser Met Gln Leu Phe Asp Asn Val Ile
                210                 215                 220 tagcccccag gagaggggt cagtgtttcc tgggggacc atgctctaac cctagtccag       852
gtggacctca cccttctctt cccaggtcta tccttgtcct aggcctccct ggggcctgga     912
gggatccaag agcttgggga ttcagtagtc cagatctctg gagctgaagg ggccagagag     972
tgggcagagt gcatcttggg gggtgttccc aactcccacc agctttcacc cgcttcctgc    1032
```

```
ctgacaccca gtgttgagag tgccctcct gtaggaactg agtggttccc cacctcctac    1092
ccccactcta gaaacacact agacagatgt ctcctgctat ggtgcttccc ccatccctga    1152
cttcataaac atttccccta aaactcccct ctcagagaga atgctccatt cttggcactg    1212
gctggcttct cagaccagcc tttgagagcc ctgtgggagg gggacaagaa tgtataggg     1272 agaaatcttg ggcctgagtc aatggatagg tcctaggagg tggctggggt tgagaataga    1332
aaggcctgga cacaatgtga ttgctcaggc ataccaagtt atagctccaa gttccacagg    1392
tctgctacca caggccatca aaatataagt ttccaggctt tgcagaagac cttgtctcct    1452
tggaaatgcc ccagatattt tccatacct cctcgatatc catggagagc tggggctag     1512 atatctggca tatccctggc attgcttcct ctccttcctt cctgcatgtg ttggtggtgg    1572
ttgtggcagg ggaatgtgga taggagatgt cctggcagat gcctgccaaa gtttcatccc    1632
accctccctg ctcatcgccc ctgttttgag ggctgtgact tgagttttg tttcccatgt     1692 tctctataga cttgggacct tcctgaactt ggggcctatc actccccaca gtggatgcct    1752
tagaagggag agggaaggag ggaggcaggc atagcatctg aacccagtgt ggggcattc     1812 actaggatct tcaatcaacc cgggctctcc ccaaccccc agataacctc ctcagttccc     1872
tagagtctcc tcttgctcta ctcaatctac ccagagatgc cccttagcac actcagaggg    1932
cagggaccat aggacccagg ttccaacccc attgtcagca ccccagccat gctgccatcc    1992
cttagcacac ctgctcgtcc cattcagctt accctcccag tcagccagaa tctgagggga    2052 gggccccag agagcccct tccccatcag aagactgttg actgctttgc attttgggct      2112
cttctatata ttttgtaaaa taagaactat accagatcta ataaaacaca atggctatgc    2172
aaaaaaaaaa aaaaaaaaa                                                 2191
```

<210> SEQ ID NO 26
<211> LENGTH: 220
<212> TYPE: PRT
<213> ORGANISM: Simian sp.

<400> SEQUENCE: 26

```
Met Arg Gly Gln Gly Arg Lys Glu Ser Leu Ser Asp Ser Arg Asp Leu
 1               5                  10                  15

Asp Gly Ser Tyr Asp Gln Leu Thr Asp Ser Val Glu Asp Phe Glu
                20                  25                  30

Leu Ser Thr Val Cys His Arg Pro Glu Gly Leu Glu Gln Leu Gln Glu
            35                  40                  45

Gln Thr Lys Phe Thr Arg Lys Glu Leu Gln Val Leu Tyr Arg Gly Phe
        50                  55                  60

Lys Asn Glu Cys Pro Ser Gly Ile Val Asn Glu Glu Asn Phe Lys Gln
65                  70                  75                  80

Ile Tyr Ser Gln Phe Phe Pro Gln Gly Asp Ser Ser Thr Tyr Ala Thr
                85                  90                  95

Phe Leu Phe Asn Ala Phe Asp Thr Asn His Asp Gly Ser Val Ser Phe
            100                 105                 110

Glu Asp Phe Val Ala Gly Leu Ser Val Ile Leu Arg Gly Thr Val Asp
        115                 120                 125

Asp Arg Leu Asn Trp Ala Phe Asn Leu Tyr Asp Leu Asn Lys Asp Gly
    130                 135                 140

Cys Ile Thr Lys Glu Glu Met Leu Asp Ile Met Lys Ser Ile Tyr Asp
145                 150                 155                 160
```

```
Met Met Gly Lys Tyr Thr Tyr Pro Ala Leu Arg Glu Ala Pro Arg
                165                 170                 175

Glu His Val Glu Asn Phe Phe Gln Lys Met Asp Arg Asn Lys Asp Gly
            180                 185                 190

Val Val Thr Ile Glu Glu Phe Ile Glu Ser Cys Gln Lys Asp Glu Asn
        195                 200                 205

Ile Met Arg Ser Met Gln Leu Phe Asp Asn Val Ile
    210                 215                 220

<210> SEQ ID NO 27
<211> LENGTH: 2057
<212> TYPE: DNA
<213> ORGANISM: Simian sp.
<220> FEATURE:
<221> NAME/KEY: CDS
<222> LOCATION: (208)..(963)

<400> SEQUENCE: 27
tgctgcccaa ggctcctgct cctgccccag gactctgagg tgggccctaa acccagcgc         60 tctctaaaga aaagccttgc cagccccctac tcccggcccc caaccccagc aggtcgctgc      120
gccgccaggg ggcgctgtgt gagcgcccta ttctggccac ccggcgcccc ctcccacgg        180 ccaggcggga gcggggcgcc ggggcc atg cgg ggc caa ggc aga aag gag agt       234
               Met Arg Gly Gln Gly Arg Lys Glu Ser
                 1               5 ttg tcc gaa tcc cga gat ctg gac ggc tcc tat gac cag ctt acg ggc        282
Leu Ser Glu Ser Arg Asp Leu Asp Gly Ser Tyr Asp Gln Leu Thr Gly
 10              15                  20                  25 cac cct cca ggg ccc agt aaa aaa gcc ctg aag cag cgt ttc ctc aag        330
His Pro Pro Gly Pro Ser Lys Lys Ala Leu Lys Gln Arg Phe Leu Lys
                 30                  35                  40 ctg ctg ccg tgc tgc ggg ccc caa gcc ctg ccc tca gtc agt gaa aac        378
Leu Leu Pro Cys Cys Gly Pro Gln Ala Leu Pro Ser Val Ser Glu Asn
             45                  50                  55 agc gta gag gat gag ttt gaa tta tcc acg gtg tgt cac cga cct gag        426
Ser Val Glu Asp Glu Phe Glu Leu Ser Thr Val Cys His Arg Pro Glu
         60                  65                  70 ggc ctg gaa caa ctc cag gaa cag acc aag ttc aca cgc aga gag ctg        474
Gly Leu Glu Gln Leu Gln Glu Gln Thr Lys Phe Thr Arg Arg Glu Leu
     75                  80                  85 cag gtc ctg tac cga ggc ttc aag aac gaa tgc ccc agt ggg att gtc        522
Gln Val Leu Tyr Arg Gly Phe Lys Asn Glu Cys Pro Ser Gly Ile Val
 90                  95                 100                 105 aac gag gag aac ttc aag cag att tat tct cag ttc ttt ccc caa gga        570
Asn Glu Glu Asn Phe Lys Gln Ile Tyr Ser Gln Phe Phe Pro Gln Gly
                110                 115                 120 gac tcc agc aac tat gct act ttt ctc ttc aat gcc ttt gac acc aac        618
Asp Ser Ser Asn Tyr Ala Thr Phe Leu Phe Asn Ala Phe Asp Thr Asn
            125                 130                 135 cac gat ggc tct gtc agt ttt gag gac ttt gtg gct ggt ttg tcg gtg        666
His Asp Gly Ser Val Ser Phe Glu Asp Phe Val Ala Gly Leu Ser Val
        140                 145                 150 att ctt cgg ggg acc ata gat gat aga ctg agc tgg gct ttc aac tta        714
Ile Leu Arg Gly Thr Ile Asp Asp Arg Leu Ser Trp Ala Phe Asn Leu
    155                 160                 165 tat gac ctc aac aag gac ggc tgt atc aca aag gag gaa atg ctt gac        762
Tyr Asp Leu Asn Lys Asp Gly Cys Ile Thr Lys Glu Glu Met Leu Asp
170                 175                 180                 185 att atg aag tcc atc tat gac atg atg ggc aag tac aca tac cct gcc        810
Ile Met Lys Ser Ile Tyr Asp Met Met Gly Lys Tyr Thr Tyr Pro Ala
```

-continued

```
                       190                 195                 200
ctc cgg gag gag gcc cca aga gaa cac gtg gag agc ttc ttc cag aag      858
Leu Arg Glu Glu Ala Pro Arg Glu His Val Glu Ser Phe Phe Gln Lys
            205                 210                 215 atg gac agg aac aag gac ggc gtg gtg acc atc gag gaa ttc atc gag      906
Met Asp Arg Asn Lys Asp Gly Val Val Thr Ile Glu Glu Phe Ile Glu
        220                 225                 230 tct tgt caa cag gac gag aac atc atg agg tcc atg cag ctc tca ccc      954
Ser Cys Gln Gln Asp Glu Asn Ile Met Arg Ser Met Gln Leu Ser Pro
    235                 240                 245 ctt ctc aac tgataccctag tgctgaggac acccctggtg tagggaccaa            1003
Leu Leu Asn
250 gtggttctcc accttctagt cccactctag aaaccacatt agacagaagg tctcctgcta   1063
tggtgctttc cccatcccta atctcttaga tttccctcaa gactcccttc tcagagaaca   1123
cgctctgtcc atgtccccag ctggcttctc agcctagcct ttgagggccc tgtggggagg   1183
cggggacaag aaagcagaaa agtcttggcc ccgagccagt ggttaggtcc taggaattgg   1243
ctggagtgga ggccagaaag cctgggcaga tgatgagagc ccagctgggc tgtcactgca   1303
ggttccgggg cctacagccc tgggtcagca gagtatgagt tcccagactt ccagaaggt    1363
ccttagcaat gtcccagaaa ttcaccgtac acttctcagt gtcttaggag ggcccgggat   1423
ccagatgtct ggttcatccc tgaatcctct ccctccttct tgctcgtatg gtgggagtgg   1483
tggccagggg aagatgagtg gtgtcccgga tgatgcctgt caaggtccca cctcccctcc   1543
ggctgttctc atgacagctg tttggttctc catgacccct atctagatgt agaggcatgg   1603
agtgagtcag ggatttcccg aacttgagtt ttaccactcc tcctagtggc tgccttaggg   1663
gaatgggaag aacccagtgt gggggcaccc attagaatct ttgcccggct cctcacaatg   1723
ccctagggtc ccctagggta cccgctccct ctgtttagtc tacccagaga tgctcctgag   1783
ctcacctaga gggtagggac ggtaggctcc aggtccaacc tctccaggtc agcaccctgc   1843
catgctgctg ctcctcatta acaaacctgc ttgtctcctc ctgcgcccct tctcagtcag   1903
ccagggtctg aggggaaggg cctcccgttt ccccatccgt cagacatggt tgactgcttt   1963
gcattttggg ctcttctatc tattttgtaa aataagacat cagatccaat aaaacacacg   2023
gctatgcaca aaaaaaaaaa aaaaaaaaaa aaaa                               2057
```

<210> SEQ ID NO 28
<211> LENGTH: 252
<212> TYPE: PRT
<213> ORGANISM: Simian sp.

<400> SEQUENCE: 28

```
Met Arg Gly Gln Gly Arg Lys Glu Ser Leu Ser Glu Ser Arg Asp Leu
 1               5                  10                  15

Asp Gly Ser Tyr Asp Gln Leu Thr Gly His Pro Gly Pro Ser Lys
            20                  25                  30

Lys Ala Leu Lys Gln Arg Phe Leu Lys Leu Leu Pro Cys Cys Gly Pro
        35                  40                  45

Gln Ala Leu Pro Ser Val Ser Glu Asn Ser Val Glu Asp Glu Phe Glu
    50                  55                  60

Leu Ser Thr Val Cys His Arg Pro Glu Gly Leu Glu Gln Leu Gln Glu
65                  70                  75                  80

Gln Thr Lys Phe Thr Arg Arg Glu Leu Gln Val Leu Tyr Arg Gly Phe
                85                  90                  95
```

```
Lys Asn Glu Cys Pro Ser Gly Ile Val Asn Glu Glu Asn Phe Lys Gln
                100                 105                 110

Ile Tyr Ser Gln Phe Phe Pro Gln Gly Asp Ser Ser Asn Tyr Ala Thr
            115                 120                 125

Phe Leu Phe Asn Ala Phe Asp Thr Asn His Asp Gly Ser Val Ser Phe
130                 135                 140

Glu Asp Phe Val Ala Gly Leu Ser Val Ile Leu Arg Gly Thr Ile Asp
145                 150                 155                 160

Asp Arg Leu Ser Trp Ala Phe Asn Leu Tyr Asp Leu Asn Lys Asp Gly
                165                 170                 175

Cys Ile Thr Lys Glu Glu Met Leu Asp Ile Met Lys Ser Ile Tyr Asp
                180                 185                 190

Met Met Gly Lys Tyr Thr Tyr Pro Ala Leu Arg Glu Glu Ala Pro Arg
            195                 200                 205

Glu His Val Glu Ser Phe Phe Gln Lys Met Asp Arg Asn Lys Asp Gly
        210                 215                 220

Val Val Thr Ile Glu Glu Phe Ile Glu Ser Cys Gln Gln Asp Glu Asn
225                 230                 235                 240

Ile Met Arg Ser Met Gln Leu Ser Pro Leu Leu Asn
                245                 250

<210> SEQ ID NO 29
<211> LENGTH: 1904
<212> TYPE: DNA
<213> ORGANISM: Rattus sp.
<220> FEATURE:
<221> NAME/KEY: CDS
<222> LOCATION: (1)..(675)

<400> SEQUENCE: 29 atg aac cac tgc cct cgc agg tgc cgg agc ccg ttg ggg cag gca gct     48
Met Asn His Cys Pro Arg Arg Cys Arg Ser Pro Leu Gly Gln Ala Ala
1               5                   10                  15 cga tct ctc tac cag ttg gta act ggg tcg ctg tcg cca gac agc gta     96
Arg Ser Leu Tyr Gln Leu Val Thr Gly Ser Leu Ser Pro Asp Ser Val
                20                  25                  30 gag gat gag ttt gaa tta tcc acg gtg tgt cac cga cct gag ggc ctg    144
Glu Asp Glu Phe Glu Leu Ser Thr Val Cys His Arg Pro Glu Gly Leu
            35                  40                  45 gaa caa ctc cag gaa cag acc aag ttc aca cgc aga gag ctg cag gtc    192
Glu Gln Leu Gln Glu Gln Thr Lys Phe Thr Arg Arg Glu Leu Gln Val
        50                  55                  60 ctg tac cga ggc ttc aag aac gaa tgc ccc agt ggg att gtc aac gag    240
Leu Tyr Arg Gly Phe Lys Asn Glu Cys Pro Ser Gly Ile Val Asn Glu
65                  70                  75                  80 gag aac ttc aag cag att tat tct cag ttc ttt ccc caa gga gac tcc    288
Glu Asn Phe Lys Gln Ile Tyr Ser Gln Phe Phe Pro Gln Gly Asp Ser
                85                  90                  95 agc aac tat gct act ttt ctc ttc aat gcc ttt gac acc aac cac gat    336
Ser Asn Tyr Ala Thr Phe Leu Phe Asn Ala Phe Asp Thr Asn His Asp
            100                 105                 110 ggc tct gtc agt ttt gag gac ttt gtg gct ggt ttg tcg gtg att ctt    384
Gly Ser Val Ser Phe Glu Asp Phe Val Ala Gly Leu Ser Val Ile Leu
        115                 120                 125 cgg ggg acc ata gat gat aga ctg agc tgg gct ttc aac tta tat gac    432
Arg Gly Thr Ile Asp Asp Arg Leu Ser Trp Ala Phe Asn Leu Tyr Asp
130                 135                 140 ctc aac aag gac ggc tgt atc aca aag gag gaa atg ctt gac att atg    480
```

```
Leu Asn Lys Asp Gly Cys Ile Thr Lys Glu Glu Met Leu Asp Ile Met
145                 150                 155                 160 aag tcc atc tat gac atg atg ggc aag tac aca tac cct gcc ctc cgg         528
Lys Ser Ile Tyr Asp Met Met Gly Lys Tyr Thr Tyr Pro Ala Leu Arg
                165                 170                 175 gag gag gcc cca aga gaa cac gtg gag agc ttc ttc cag aag atg gac         576
Glu Glu Ala Pro Arg Glu His Val Glu Ser Phe Phe Gln Lys Met Asp
            180                 185                 190 agg aac aag gac ggc gtg gtg acc atc gag gaa ttc atc gag tct tgt         624
Arg Asn Lys Asp Gly Val Val Thr Ile Glu Glu Phe Ile Glu Ser Cys
        195                 200                 205 caa cag gac gag aac atc atg agg tcc atg cag ctc ttt gat aat gtc         672
Gln Gln Asp Glu Asn Ile Met Arg Ser Met Gln Leu Phe Asp Asn Val
    210                 215                 220 atc tagctcccca gggagagggg ttagtgtgtc ctagggtgac caggctgtag              725
Ile
225 tcctagtcca gacgaaccta accctctctc tccaggcctg tcctcatctt acctgtaccc      785
tgggggctgt agggattcaa tatcctgggg cttcagtagt ccagatccct gagctaagtc      845
acaaaagtag gcaagagtag gcaagctaaa tctgggggct tcccaacccc cgacagctct      905
cacccttct caactgatac ctagtgctga ggacacccct ggtgtaggga ccaagtggtt       965
ctccaccttc tagtcccact ctagaaacca cattagacag aaggtctcct gctatggtgc     1025
tttccccatc cctaatctct tagatttttcc tcaagactcc cttctcagag aacacgctct    1085
gtccatgtcc ccagctggct tctcagccta gcctttgagg gccctgtggg gaggcgggga     1145
caagaaagca gaaagtctt ggccccgagc tagtggttag gtcctaggaa ttggctggag      1205
tggaggccag aaagcctggg cagatgatga gagcccagct gggctgtcac tgcaggttcc     1265
agggcctaca gccctgggtc agcagagtat gagttcccag actttccaga aggtccttag    1325
caatgtccca gaaattcacc atacacttct cagtgtcccg gatgatgcct gtcaaggtcc    1385
cacctcccct ccggctgttc tcatgacagc tgtttggttc tccatgaccc ctatctagat    1445
gtagaggcat ggagtgagtc agggatttcc cgaacttgag ttttaccact cctcctagtg    1505
gctgccttag gggaatggga agaacccagt gtggggcac ccattagaat ctttgcccgg     1565
ttcctcacaa tgcccctaggg tccctaggg taccgctcc ctctgtttag tctacccaga     1625
gatgctcctg agctcaccta gagggtaggg acggtaggct ccaggtccaa cctctccagg    1685
tcagcaccct gccatgctgc tgctcctcat taacaaacct gcttgtctcc tcctgcgccc    1745
cttctcagtc agccagggtc tgaggggaag ggcctcccgt ttccccatcc gtcagacatg    1805
gttgactgct ttgcattttg ggctcttcta tctattttgt aaaataagac atcagatcca    1865
ataaaacaca cggctatgca caaaaaaaaa aaaaaaaaa                            1904

<210> SEQ ID NO 30
<211> LENGTH: 225
<212> TYPE: PRT
<213> ORGANISM: Rattus sp.

<400> SEQUENCE: 30

Met Asn His Cys Pro Arg Arg Cys Arg Ser Pro Leu Gly Gln Ala Ala
1               5                   10                  15

Arg Ser Leu Tyr Gln Leu Val Thr Gly Ser Leu Ser Pro Asp Ser Val
            20                  25                  30

Glu Asp Glu Phe Glu Leu Ser Thr Val Cys His Arg Pro Glu Gly Leu
        35                  40                  45
```

```
Glu Gln Leu Gln Glu Gln Thr Lys Phe Thr Arg Arg Glu Leu Gln Val
        50                  55                  60
Leu Tyr Arg Gly Phe Lys Asn Glu Cys Pro Ser Gly Ile Val Asn Glu
 65                  70                  75                  80
Glu Asn Phe Lys Gln Ile Tyr Ser Gln Phe Pro Gln Gly Asp Ser
                 85                  90                  95
Ser Asn Tyr Ala Thr Phe Leu Phe Asn Ala Phe Asp Thr Asn His Asp
                100                 105                 110
Gly Ser Val Ser Phe Glu Asp Phe Val Ala Gly Leu Ser Val Ile Leu
                115                 120                 125
Arg Gly Thr Ile Asp Asp Arg Leu Ser Trp Ala Phe Asn Leu Tyr Asp
        130                 135                 140
Leu Asn Lys Asp Gly Cys Ile Thr Lys Glu Glu Met Leu Asp Ile Met
145                 150                 155                 160
Lys Ser Ile Tyr Asp Met Met Gly Lys Tyr Thr Tyr Pro Ala Leu Arg
                165                 170                 175
Glu Glu Ala Pro Arg Glu His Val Glu Ser Phe Phe Gln Lys Met Asp
                180                 185                 190
Arg Asn Lys Asp Gly Val Val Thr Ile Glu Glu Phe Ile Glu Ser Cys
        195                 200                 205
Gln Gln Asp Glu Asn Ile Met Arg Ser Met Gln Leu Phe Asp Asn Val
        210                 215                 220
Ile
225

<210> SEQ ID NO 31
<211> LENGTH: 2841
<212> TYPE: DNA
<213> ORGANISM: Homo sapiens
<220> FEATURE:
<221> NAME/KEY: CDS
<222> LOCATION: (1)..(768)

<400> SEQUENCE: 31 atg cag ccg gct aag gaa gtg aca aag gcg tcg gac ggc agc ctc ctg      48
Met Gln Pro Ala Lys Glu Val Thr Lys Ala Ser Asp Gly Ser Leu Leu
  1               5                  10                  15 ggg gac ctc ggg cac aca cca ctt agc aag aag gag ggt atc aag tgg      96
Gly Asp Leu Gly His Thr Pro Leu Ser Lys Lys Glu Gly Ile Lys Trp
                 20                  25                  30 cag agg ccg agg ctc agc cgc cag gct ttg atg aga tgc tgc ctg gtc     144
Gln Arg Pro Arg Leu Ser Arg Gln Ala Leu Met Arg Cys Cys Leu Val
             35                  40                  45 aag tgg atc ctg tcc agc aca gcc cca cag ggc tca gat agc agc gac     192
Lys Trp Ile Leu Ser Ser Thr Ala Pro Gln Gly Ser Asp Ser Ser Asp
         50                  55                  60 agt gag ctg gag ctg tcc acg gtg cgc cac cag cca gag ggg ctg gac     240
Ser Glu Leu Glu Leu Ser Thr Val Arg His Gln Pro Glu Gly Leu Asp
 65                  70                  75                  80 cag ctg cag gcc cag acc aag ttc acc aag aag gag ctg cag tct ctc     288
Gln Leu Gln Ala Gln Thr Lys Phe Thr Lys Lys Glu Leu Gln Ser Leu
                 85                  90                  95 tac agg ggc ttt aag aat gag tgt ccc acg ggc ctg gtg gac gaa gac     336
Tyr Arg Gly Phe Lys Asn Glu Cys Pro Thr Gly Leu Val Asp Glu Asp
                100                 105                 110 acc ttc aaa ctc att tac gcg cag ttc ttc cct cag gga gat gcc acc     384
Thr Phe Lys Leu Ile Tyr Ala Gln Phe Phe Pro Gln Gly Asp Ala Thr
            115                 120                 125
```

| | | | | | | | | | | | | | | |
|---|---|---|---|---|---|---|---|---|---|---|---|---|---|---|
| acc | tat | gca | cac | ttc | ctc | ttc | aac | gcc | ttt | gat | gcg | gac | ggg | aac | ggg | 432 |
| Thr | Tyr | Ala | His | Phe | Leu | Phe | Asn | Ala | Phe | Asp | Ala | Asp | Gly | Asn | Gly |
| | 130 | | | | 135 | | | | | 140 | | | | |

```
acc tat gca cac ttc ctc ttc aac gcc ttt gat gcg gac ggg aac ggg       432
Thr Tyr Ala His Phe Leu Phe Asn Ala Phe Asp Ala Asp Gly Asn Gly
    130                 135                 140 gcc atc cac ttt gag gac ttt gtg gtt ggc ctc tcc atc ctg ctg cgg       480
Ala Ile His Phe Glu Asp Phe Val Val Gly Leu Ser Ile Leu Leu Arg
145                 150                 155                 160 ggc aca gtc cac gag aag ctc aag tgg gcc ttt aat ctc tac gac att       528
Gly Thr Val His Glu Lys Leu Lys Trp Ala Phe Asn Leu Tyr Asp Ile
            165                 170                 175 aac aag gat ggc tac atc acc aaa gag gag atg ctg gcc atc atg aag       576
Asn Lys Asp Gly Tyr Ile Thr Lys Glu Glu Met Leu Ala Ile Met Lys
        180                 185                 190 tcc atc tat gac atg atg ggc cgc cac acc tac ccc atc ctg cgg gag       624
Ser Ile Tyr Asp Met Met Gly Arg His Thr Tyr Pro Ile Leu Arg Glu
    195                 200                 205 gac gcg ccg gcg gag cac gtg gag agg ttc ttc gag aaa atg gac cgg       672
Asp Ala Pro Ala Glu His Val Glu Arg Phe Phe Glu Lys Met Asp Arg
210                 215                 220 aac cag gat ggg gta gtg acc att gaa gag ttc ctg gag gcc tgt cag       720
Asn Gln Asp Gly Val Val Thr Ile Glu Glu Phe Leu Glu Ala Cys Gln
225                 230                 235                 240 aag gat gag aac atc atg agc tcc atg cag ctg ttt gag aat gtc atc       768
Lys Asp Glu Asn Ile Met Ser Ser Met Gln Leu Phe Glu Asn Val Ile
            245                 250                 255
```

| | |
|---|---|
| taggacacgt ccaaaggagt gcatggccac agccacctcc accccaaga aacctccatc | 828 |
| ctgccaggag cagcctccaa gaaactttta aaaatatagat ttgcaaaaag tgaacagatt | 888 |
| gctacacaca cacacacaca cacacacaca cacacacaca cacagccatt catctgggct | 948 |
| ggcagagggg acagagttca gggagggggct gagtctggct aggggccgag tccaggagcc | 1008 |
| ccagccagcc cttcccaggc cagcgaggcg aggctgcctc tgggtgagtg gctgacagag | 1068 |
| caggtctgca ggccaccagc tgctggatgt caccaagaag gggctcgagt gcccctgcag | 1128 |
| gggagggtcc aatctccggt gtgagcccac ctcgtcccgt tctccattct gctttcttgc | 1188 |
| cacacagtgg gccggcccca ggctcccctg gtctcctccc cgtagccact ctctgcccac | 1248 |
| tacctatgct tctagaaagc ccctcacctc aggacccccag agggaccagc tggggggcag | 1308 |
| gggggagagg gggtaatgga ggccaagcct gcagctttct ggaaattctt ccctgggggt | 1368 |
| cccaggatcc cctgctactc cactgacctg gaagagctgg gtaccaggcc acccactgtg | 1428 |
| gggcaagcct gagtggtgag gggccactgg gccccattct ccctccatgg caggaaggcg | 1488 |
| ggggatttca gtttaggga ttgggtcgtg gtggagaatc tgagggcact ctctgccagc | 1548 |
| tccacagggt gggatgagcc tctccttgcc ccagtcctgg ttcagtggga atgcagtggg | 1608 |
| tggggctgta cacaccctcc agcacagact gttccctcca aggtcctctt aggtcccggg | 1668 |
| aggaacgtgg ttcagagact ggcagccagg gagcccgggg cagagctcag aggagtctgg | 1728 |
| gaaggggcgt gtccctcctc ttcctgtagt gcccctccca tgcccagca gcttggctga | 1788 |
| gccccctctc ctgaagcagt gtcgccgtcc ctctgccttg cacaaaaagc acaagcattc | 1848 |
| cttagcagct caggcgcagc cctagtggga gcccagcaca ctgcttctcg gaggccaggc | 1908 |
| cctcctgctg gctgaggctt gggcccagta gccccaatat ggtggccctg ggaagaggc | 1968 |
| cttgggggtc tgctctgtgc ctgggatcag tggggcccca aagcccagcc cggctgacca | 2028 |
| acattcaaaa gcacaaaccc tggggactct gcttggctgt ccctccatc tggggatgga | 2088 |
| gaatgccagc ccaaagctgg agccaatggt gagggctgag agggctgtgg ctgggtggtc | 2148 |

-continued

```
agcagaaacc cccaggagga gagagatgct gctcccgcct gattgggggcc tcacccagaa    2208
ggaacccggt cccaggccgc atggcccctc caggaacatt cccacataat acattccatc    2268
acagccagcc cagctccact cagggctggc ccggggagtc cccgtgtgcc ccaagaggct    2328
agccccaggg tgagcagggc cctcagagga aaggcagtat ggcggaggcc atggggggccc    2388
ctcggcattc acacacagcc tggcctcccc tgcggagctg catggacgcc tggctccagg    2448
ctccaggctg actgggggcc tctgcctcca ggagggcatc agctttccct ggctcaggga    2508
tcttctccct cccctcaccc gctgcccagc cctcccagct ggtgtcactc tgcctctaag    2568
gccaaggcct caggagagca tcaccaccac accctgccg gccttggcct tggggccaga    2628
ctggctgcac agcccaacca ggagggtct gcctcccacg ctgggacaca gaccggccgc    2688
atgtctgcat ggcagaagcg tctcccttgg ccacggcctg ggagggtggt tcctgttctc    2748
agcatccact aatattcagt cctgtatatt ttaataaaat aaacttgaca aggaaaaaa    2808
aaaaaaaaaa aattcctgcg gccgcgttct cca                                2841
```

<210> SEQ ID NO 32
<211> LENGTH: 256
<212> TYPE: PRT
<213> ORGANISM: Homo sapiens

<400> SEQUENCE: 32

```
Met Gln Pro Ala Lys Glu Val Thr Lys Ala Ser Asp Gly Ser Leu Leu
 1               5                  10                  15
Gly Asp Leu Gly His Thr Pro Leu Ser Lys Lys Glu Gly Ile Lys Trp
             20                  25                  30
Gln Arg Pro Arg Leu Ser Arg Gln Ala Leu Met Arg Cys Cys Leu Val
         35                  40                  45
Lys Trp Ile Leu Ser Ser Thr Ala Pro Gln Gly Ser Asp Ser Ser Asp
     50                  55                  60
Ser Glu Leu Glu Leu Ser Thr Val Arg His Gln Pro Glu Gly Leu Asp
 65                  70                  75                  80
Gln Leu Gln Ala Gln Thr Lys Phe Thr Lys Lys Glu Leu Gln Ser Leu
                 85                  90                  95
Tyr Arg Gly Phe Lys Asn Glu Cys Pro Thr Gly Leu Val Asp Glu Asp
            100                 105                 110
Thr Phe Lys Leu Ile Tyr Ala Gln Phe Phe Pro Gln Gly Asp Ala Thr
        115                 120                 125
Thr Tyr Ala His Phe Leu Phe Asn Ala Phe Asp Ala Asp Gly Asn Gly
    130                 135                 140
Ala Ile His Phe Glu Asp Phe Val Val Gly Leu Ser Ile Leu Leu Arg
145                 150                 155                 160
Gly Thr Val His Glu Lys Leu Lys Trp Ala Phe Asn Leu Tyr Asp Ile
                165                 170                 175
Asn Lys Asp Gly Tyr Ile Thr Lys Glu Met Leu Ala Ile Met Lys
            180                 185                 190
Ser Ile Tyr Asp Met Met Gly Arg His Thr Tyr Pro Ile Leu Arg Glu
        195                 200                 205
Asp Ala Pro Ala Glu His Val Glu Arg Phe Phe Glu Lys Met Asp Arg
    210                 215                 220
Asn Gln Asp Gly Val Val Thr Ile Glu Glu Phe Leu Glu Ala Cys Gln
225                 230                 235                 240
Lys Asp Glu Asn Ile Met Ser Ser Met Gln Leu Phe Glu Asn Val Ile
                245                 250                 255
```

```
<210> SEQ ID NO 33
<211> LENGTH: 442
<212> TYPE: DNA
<213> ORGANISM: Rattus sp.
<220> FEATURE:
<221> NAME/KEY: CDS
<222> LOCATION: (1)..(327)

<400> SEQUENCE: 33 ttt gag gac ttt gtg gtt ggg ctc tcc atc ctg ctt cga ggg acc gtc        48
Phe Glu Asp Phe Val Val Gly Leu Ser Ile Leu Leu Arg Gly Thr Val
  1               5                  10                  15 cat gag aag ctc aag tgg gcc ttc aat ctc tac gac atc aac aag gac        96
His Glu Lys Leu Lys Trp Ala Phe Asn Leu Tyr Asp Ile Asn Lys Asp
             20                  25                  30 ggt tac atc acc aaa gag gag atg ctg gcc atc atg aag tcc atc tac       144
Gly Tyr Ile Thr Lys Glu Glu Met Leu Ala Ile Met Lys Ser Ile Tyr
         35                  40                  45 gac atg atg ggc cgc cac acc tac cct atc ctg cgg gag gac gca cct       192
Asp Met Met Gly Arg His Thr Tyr Pro Ile Leu Arg Glu Asp Ala Pro
     50                  55                  60 ctg gag cat gtg gag agg ttc ttc cag aaa atg gac agg aac cag gat       240
Leu Glu His Val Glu Arg Phe Phe Gln Lys Met Asp Arg Asn Gln Asp
 65                  70                  75                  80 gga gta gtg act att gat gaa ttt ctg gag act tgt cag aag gac gag       288
Gly Val Val Thr Ile Asp Glu Phe Leu Glu Thr Cys Gln Lys Asp Glu
                 85                  90                  95 aac atc atg agc tcc atg cag ctg ttt gag aac gtc atc taggacatgt        337
Asn Ile Met Ser Ser Met Gln Leu Phe Glu Asn Val Ile
            100                 105 aggagggggac cctgggtggc catgggttct caacccagag aagcctcaat cctgacagga    397
gaagcctcta tgagaaacat ttttctaata tatttgcaaa aagtg                    442

<210> SEQ ID NO 34
<211> LENGTH: 109
<212> TYPE: PRT
<213> ORGANISM: Rattus sp.

<400> SEQUENCE: 34

Phe Glu Asp Phe Val Val Gly Leu Ser Ile Leu Leu Arg Gly Thr Val
  1               5                  10                  15

His Glu Lys Leu Lys Trp Ala Phe Asn Leu Tyr Asp Ile Asn Lys Asp
             20                  25                  30

Gly Tyr Ile Thr Lys Glu Glu Met Leu Ala Ile Met Lys Ser Ile Tyr
         35                  40                  45

Asp Met Met Gly Arg His Thr Tyr Pro Ile Leu Arg Glu Asp Ala Pro
     50                  55                  60

Leu Glu His Val Glu Arg Phe Phe Gln Lys Met Asp Arg Asn Gln Asp
 65                  70                  75                  80

Gly Val Val Thr Ile Asp Glu Phe Leu Glu Thr Cys Gln Lys Asp Glu
                 85                  90                  95

Asn Ile Met Ser Ser Met Gln Leu Phe Glu Asn Val Ile
            100                 105

<210> SEQ ID NO 35
<211> LENGTH: 2644
<212> TYPE: DNA
<213> ORGANISM: Mus musculus
<220> FEATURE:
```

```
<221> NAME/KEY: CDS
<222> LOCATION: (49)..(816)

<400> SEQUENCE: 35
cgggctgcaa agcgggaaga ttagtgacgg tcccttcag cagcagag atg cag agg      57
                                                    Met Gln Arg
                                                      1 acc aag gaa gcc gtg aag gca tca gat ggc aac ctc ctg gga gat cct     105
Thr Lys Glu Ala Val Lys Ala Ser Asp Gly Asn Leu Leu Gly Asp Pro
      5              10                  15 ggg cgc ata cca ctg agc aag agg gaa agc atc aag tgg caa agg cca     153
Gly Arg Ile Pro Leu Ser Lys Arg Glu Ser Ile Lys Trp Gln Arg Pro
 20              25                  30                  35 cgg ttc acc cgc cag gcc ctg atg cgt tgc tgc tta atc aag tgg atc     201
Arg Phe Thr Arg Gln Ala Leu Met Arg Cys Cys Leu Ile Lys Trp Ile
                 40                  45                  50 ctg tcc agt gct gcc cca caa ggc tca gac agc agt gac agt gaa ctg     249
Leu Ser Ser Ala Ala Pro Gln Gly Ser Asp Ser Ser Asp Ser Glu Leu
             55                  60                  65 gag tta tcc acg gtg cgc cat cag cca gag ggc ttg gac cag cta caa     297
Glu Leu Ser Thr Val Arg His Gln Pro Glu Gly Leu Asp Gln Leu Gln
         70                  75                  80 gct cag acc aag ttc acc aag aag gag ctg cag tcc ctt tac cga ggc     345
Ala Gln Thr Lys Phe Thr Lys Lys Glu Leu Gln Ser Leu Tyr Arg Gly
     85                  90                  95 ttc aag aat gag tgt ccc aca ggc ctg gtg gat gaa gac acc ttc aaa     393
Phe Lys Asn Glu Cys Pro Thr Gly Leu Val Asp Glu Asp Thr Phe Lys
100                 105                 110                 115 ctc att tat tcc cag ttc ttc cct cag gga gat gcc acc acc tat gca     441
Leu Ile Tyr Ser Gln Phe Phe Pro Gln Gly Asp Ala Thr Thr Tyr Ala
                120                 125                 130 cac ttc ctc ttc aat gcc ttt gat gct gat ggg aac ggg gcc atc cac     489
His Phe Leu Phe Asn Ala Phe Asp Ala Asp Gly Asn Gly Ala Ile His
            135                 140                 145 ttt gag gac ttt gtg gtt ggg ctc tcc atc ctg ctt cga ggg acg gtc     537
Phe Glu Asp Phe Val Val Gly Leu Ser Ile Leu Leu Arg Gly Thr Val
        150                 155                 160 cat gag aag ctc aag tgg gcc ttc aat ctc tat gac att aac aag gat     585
His Glu Lys Leu Lys Trp Ala Phe Asn Leu Tyr Asp Ile Asn Lys Asp
    165                 170                 175 ggt tgc atc acc aag gag gag atg ctg gcc atc atg aag tcc atc tac     633
Gly Cys Ile Thr Lys Glu Glu Met Leu Ala Ile Met Lys Ser Ile Tyr
180                 185                 190                 195 gac atg atg ggc cgc cac acc tac ccc atc ctg cgg gag gat gca ccc     681
Asp Met Met Gly Arg His Thr Tyr Pro Ile Leu Arg Glu Asp Ala Pro
                200                 205                 210 ctg gag cat gtg gag agg ttc ttt cag aaa atg gac agg aac cag gat     729
Leu Glu His Val Glu Arg Phe Phe Gln Lys Met Asp Arg Asn Gln Asp
            215                 220                 225 gga gtg gtg acc att gat gaa ttt ctg gag act tgt cag aag gat gag     777
Gly Val Val Thr Ile Asp Glu Phe Leu Glu Thr Cys Gln Lys Asp Glu
        230                 235                 240 aac atc atg aac tcc atg cag ctg ttt gag aac gtc atc taggacatgt      826
Asn Ile Met Asn Ser Met Gln Leu Phe Glu Asn Val Ile
    245                 250                 255 gggaggggac cccagtggtc attgcttctc aacccagaga agcctcaatc ctgacaggag    886
aagcctctat gagaaacatt tttctaatat atttgcaaaa agtgagcagt ttacttccaa    946
gacacagcca ccgtcacaca cagacacaga catacagaca cacacacaca cacacacaca   1006
```

```
tggttcctct ggcttggcca aggaagtggc agccagaagg cacccccgcc tattcctagg    1066
tcaataaaaa aggctgcctc tgggatggcc agccctggct agatgttacc cacaaggaac    1126
tcagagatcg agaggaccag gtctacaaag ctaaggtccc tgtgtctttt ctaccactcg    1186
ggagatcaaa ctactccctg cctatggacc catgctctta ggaagctccc agaaactcca    1246 agggacaaa gaggggagag gtctatagga gaaatggtt ttggaagctg ggcttgcagc     1306
cttatgctaa tgatcacctg gggtcctgga acccgagtgc caggctacct actatgccgt    1366
gagcttagat agtgaggggc cattggacta agacctcctg taagagtggg gcaggattga    1426 ggttttgga gaaactgagg aaacaatttg tccataccac tgggtgaaga ctgctggcca    1486
gtgggaatgt ggctggtgga gatttcccaa cttccagcac caggatggcc tctccaaggt    1546
cctctttgat tccctgggga gatcacctgg ctcatagact gacaaccagg gaactgggct    1606
gaaatgggag gtctggtagg gggcatcccc ctccttttcc ctggccactt gccacccagt    1666
tccttaacac agtggatcgg ccacacctct gtggctgccc ttgaacagac tcatcccgac    1726
caagacaaaa aagcacaaac tcctagcagc tcaggccaag cccacaaggg aaggcctggg    1786
tccctgcagc cctgattcag tggccgagga agacgctcag acatccatcc tgtacctcgg    1846
agccttgggg gtctcacagc cctttcccag cccagctcgc caacattcta aagcacaaac    1906
ctgcggattc tgcttgcttg ggctgcgccc tggggattga aggccactgt taaccctaag    1966
ctggagctag ccctgagggc tggggacctg tgaccaggca acaggtcagc agaccctcag    2026
gaggagagag agctgttcct gcctccccag gcctcgccca gaaggaacag tgtcccaaga    2086
agcatgtttc ctggaggaac atccccacaa aagtacattc catcatctga agcccggtct    2146
ctgctcaggc ctgcctctga aagtccacgt gtgttcccca gaaggccagc ccaagataa    2206 gggaggtcct tagaggaagg acagggtgac aacacccta tacacaggtg acccccccct    2266
ctgaggactg tactgacccc atctccatcc tgaccggggc cttcctttac ccgatctaca    2326
gaccaccagt tctccctggc tcagggaccc cctgtccccc agtctgactc ttcccatcga    2386
ggtccctgtc ttgtgaaaag ccaaggccac gggaaaaggc caccactcta acctgctgca    2446
tcccttagcc tctggctgca cgcccaacct ggaggggtct gtccccttg cagggacaca     2506 gactggccgc atgtccgcat ggcagaagcg tctcccttgg gtgcagcctg aagggtggt    2566 ttctgtctca gcgcccacca atattcagtc ctatatattt taataaaga aacttgacaa    2626 aggaaaaaa aaaaaaaa                                                  2644
```

<210> SEQ ID NO 36
<211> LENGTH: 256
<212> TYPE: PRT
<213> ORGANISM: Mus musculus

<400> SEQUENCE: 36

Met Gln Arg Thr Lys Glu Ala Val Lys Ala Ser Asp Gly Asn Leu Leu
 1               5                  10                  15

Gly Asp Pro Gly Arg Ile Pro Leu Ser Lys Arg Glu Ser Ile Lys Trp
            20                  25                  30

Gln Arg Pro Arg Phe Thr Arg Gln Ala Leu Met Arg Cys Cys Leu Ile
        35                  40                  45

Lys Trp Ile Leu Ser Ser Ala Ala Pro Gln Gly Ser Asp Ser Ser Asp
    50                  55                  60

Ser Glu Leu Glu Leu Ser Thr Val Arg His Gln Pro Glu Gly Leu Asp
65                  70                  75                  80

```
Gln Leu Gln Ala Gln Thr Lys Phe Thr Lys Lys Glu Leu Gln Ser Leu
                85                  90                  95

Tyr Arg Gly Phe Lys Asn Glu Cys Pro Thr Gly Leu Val Asp Glu Asp
            100                 105                 110

Thr Phe Lys Leu Ile Tyr Ser Gln Phe Phe Pro Gln Gly Asp Ala Thr
        115                 120                 125

Thr Tyr Ala His Phe Leu Phe Asn Ala Phe Asp Ala Asp Gly Asn Gly
    130                 135                 140

Ala Ile His Phe Glu Asp Phe Val Val Gly Leu Ser Ile Leu Leu Arg
145                 150                 155                 160

Gly Thr Val His Glu Lys Leu Lys Trp Ala Phe Asn Leu Tyr Asp Ile
                165                 170                 175

Asn Lys Asp Gly Cys Ile Thr Lys Glu Glu Met Leu Ala Ile Met Lys
            180                 185                 190

Ser Ile Tyr Asp Met Met Gly Arg His Thr Tyr Pro Ile Leu Arg Glu
        195                 200                 205

Asp Ala Pro Leu Glu His Val Glu Arg Phe Phe Gln Lys Met Asp Arg
    210                 215                 220

Asn Gln Asp Gly Val Val Thr Ile Asp Glu Phe Leu Glu Thr Cys Gln
225                 230                 235                 240

Lys Asp Glu Asn Ile Met Asn Ser Met Gln Leu Phe Glu Asn Val Ile
                245                 250                 255

<210> SEQ ID NO 37
<211> LENGTH: 531
<212> TYPE: DNA
<213> ORGANISM: Homo sapiens
<220> FEATURE:
<221> NAME/KEY: CDS
<222> LOCATION: (1)..(336)
<221> NAME/KEY: misc_feature
<222> LOCATION: (495)..(495)
<223> OTHER INFORMATION: n = any nucleotide

<400> SEQUENCE: 37 cac gag gtg gaa agc att tcg gct cag ctg gag gag gcc agc tct aca       48
His Glu Val Glu Ser Ile Ser Ala Gln Leu Glu Glu Ala Ser Ser Thr
  1               5                  10                  15 ggc ggt ttc ctg tac gct cag aac agc acc aag cgc agc att aaa gag      96
Gly Gly Phe Leu Tyr Ala Gln Asn Ser Thr Lys Arg Ser Ile Lys Glu
             20                  25                  30 cgg ctc atg aag ctc ttg ccc tgc tca gct gcc aaa acg tcg tct cct     144
Arg Leu Met Lys Leu Leu Pro Cys Ser Ala Ala Lys Thr Ser Ser Pro
         35                  40                  45 gct att caa aac agc gtg gaa gat gaa ctg gag atg gcc acc gtc agg     192
Ala Ile Gln Asn Ser Val Glu Asp Glu Leu Glu Met Ala Thr Val Arg
     50                  55                  60 cat cgg ccc gaa gcc ctt gag ctt ctg gaa gcc cag agc aaa ttt acc     240
His Arg Pro Glu Ala Leu Glu Leu Leu Glu Ala Gln Ser Lys Phe Thr
 65                  70                  75                  80 aag aaa gag ctt cag atc ctt tac aga gga ttt aag aac gta aga act     288
Lys Lys Glu Leu Gln Ile Leu Tyr Arg Gly Phe Lys Asn Val Arg Thr
                 85                  90                  95 ttc ttt ttg act tta cct tca cac aat tcc cag agg agc att gag aaa     336
Phe Phe Leu Thr Leu Pro Ser His Asn Ser Gln Arg Ser Ile Glu Lys
            100                 105                 110 tgagaggaaa aggggggaaaa tatcccattc tatgagaagc cccatcatat gtatatttca    396
tactgatcct tcccagatag gaatataatc agtatctgtg gactttgaat ctctgtggca    456
```

-continued

```
cacccatgct ggcatactgt aattgcccat taaacaaana gtttttgaga aaaaaaaaaa    516
aaaaaaaaaa aaaaa                                                     531
```

<210> SEQ ID NO 38
<211> LENGTH: 112
<212> TYPE: PRT
<213> ORGANISM: Homo sapiens

<400> SEQUENCE: 38

```
His Glu Val Glu Ser Ile Ser Ala Gln Leu Glu Ala Ser Ser Thr
 1               5                  10                  15

Gly Gly Phe Leu Tyr Ala Gln Asn Ser Thr Lys Arg Ser Ile Lys Glu
             20                  25                  30

Arg Leu Met Lys Leu Leu Pro Cys Ser Ala Ala Lys Thr Ser Ser Pro
         35                  40                  45

Ala Ile Gln Asn Ser Val Glu Asp Glu Leu Glu Met Ala Thr Val Arg
     50                  55                  60

His Arg Pro Glu Ala Leu Glu Leu Leu Glu Ala Gln Ser Lys Phe Thr
 65                  70                  75                  80

Lys Lys Glu Leu Gln Ile Leu Tyr Arg Gly Phe Lys Asn Val Arg Thr
                 85                  90                  95

Phe Phe Leu Thr Leu Pro Ser His Asn Ser Gln Arg Ser Ile Glu Lys
            100                 105                 110
```

<210> SEQ ID NO 39
<211> LENGTH: 2176
<212> TYPE: DNA
<213> ORGANISM: Homo sapiens
<220> FEATURE:
<221> NAME/KEY: CDS
<222> LOCATION: (2)..(124)

<400> SEQUENCE: 39

```
t gaa agg ttc ttc gag aaa atg gac cgg aac cag gat ggg gta gtg acc    49
  Glu Arg Phe Phe Glu Lys Met Asp Arg Asn Gln Asp Gly Val Val Thr
   1               5                  10                  15 att gaa gag ttc ctg gag gcc tgt cag aag gat gag aac atc atg agc    97
Ile Glu Glu Phe Leu Glu Ala Cys Gln Lys Asp Glu Asn Ile Met Ser
             20                  25                  30 tcc atg cag ctg ttt gag aat gtc atc taggacacgt ccaaggagt            144
Ser Met Gln Leu Phe Glu Asn Val Ile
         35                  40 gcatggccac agccacctcc accccaaga aacctccatc ctgccaggag cagcctccaa    204
gaaactttta aaaatagat ttgcaaaaag tgaacagatt gctacacaca cacacacaca    264
cacacacaca cacacacaca cacagccatt catctgggct ggcagagggg acagagttca    324 gggagggct gagtctggct aggggccgag tccaggagcc ccagccagcc cttcccaggc    384
cagcgaggcg aggctgcctc tgggtgagtg gctgacagag caggtctgca ggccaccagc    444
tgctggatgt caccaagaag gggctcgagt gcccctgcag ggagggtcc aatctccggt    504 gtgagcccac ctcgtcccgt tctccattct gctttcttgc cacacagtgg gccggcccca    564
ggctcccctg gtctcctccc cgtagccact ctctgcccac tacctatgct tctagaaagc    624
ccctcacctc aggaccccag agggaccagc tgggggcag gggggagagg gggtaatgga    684
ggccaagcct gcagcttcct ggaaattctt ccctgggggt cccaggatcc cctgctactc    744
cactgacctg gaagagctgg gtaccaggcc acccactgtg gggcaagcct gagtggtgag    804
gggccactgg gccccattct ccctccatgg caggaaggcg ggggatttca agtttaggga    864
```

-continued

```
ttgggtcgtg gtggagaatc tgagggcact ctctgccagc tccacagggt gggatgagcc   924
tctccttgcc ccagtcctgg ttcagtggga atgcagtggg tggggctgta cacaccctcc   984
agcacagact gttccctcca aggtcctctt aggtcccggg aggaacgtgg ttcagagact  1044
ggcagccagg gagcccgggg cagagctcag aggagtctgg aagggggcgt gtccctcctc  1104
ttcctgtagt gcccctccca tggcccagca gcttggctga gccccctctc ctgaagcagt  1164
gtcgccgtcc ctctgccttg cacaaaaagc acaagcattc cttagcagct caggcgcagc  1224
cctagtggga gcccagcaca ctgcttctcg gaggccaggc cctcctgctg gctgaggctt  1284
gggcccagta gccccaatat ggtggccctg gggaagaggc cttggggggtc tgctctgtgc  1344 ctgggatcag tggggcccca aagcccagcc cggctgacca acattcaaaa gcacaaaccc  1404 tgggactct gcttggctgt cccctccatc tggggatgga gaatgccagc ccaaagctgg   1464
agccaatggt gagggctgag agggctgtgg ctgggtggtc agcagaaacc cccaggagga  1524
gagagatgct gctcccgcct gattggggcc tcacccagaa ggaacccggt cccaggccgc  1584
atggcccctc caggaacatt cccacataat acattccatc acagccagcc cagctccact  1644
cagggctggc ccggggagtc cccgtgtgcc ccaagaggct agcccagggg tgagcagggc  1704
cctcagagga aaggcagtat ggcggaggcc atggggggccc ctcggcattc acacacagcc  1764
tggcctcccc tgcggagctg catggacgcc tggctccagg ctccaggctg actgggggcc  1824
tctgcctcca ggagggcatc agctttccct ggctcaggga tcttctccct ccctcaccc   1884 gctgccagc cctcccagct ggtgtcactc tgcctctaag gccaaggcct caggagagca   1944
tcaccaccac acccctgccg gccttggcct tggggccaga ctggctgcac agcccaacca  2004
ggaggggtct gcctcccacg ctgggacaca gaccggccgc atgtctgcat ggcagaagcg  2064
tctcccttgg ccacggcctg ggagggtggt tcctgttctc agcatccact aatattcagt  2124
cctgtatatt ttaataaaat aaacttgaca aaggaaaaaa aaaaaaaaaa aa          2176
```

<210> SEQ ID NO 40
<211> LENGTH: 41
<212> TYPE: PRT
<213> ORGANISM: Homo sapiens

<400> SEQUENCE: 40

Glu Arg Phe Phe Glu Lys Met Asp Arg Asn Gln Asp Gly Val Val Thr
1               5                   10                  15

Ile Glu Glu Phe Leu Glu Ala Cys Gln Lys Asp Glu Asn Ile Met Ser
            20                  25                  30

Ser Met Gln Leu Phe Glu Asn Val Ile
        35                  40

<210> SEQ ID NO 41
<211> LENGTH: 2057
<212> TYPE: DNA
<213> ORGANISM: Rattus sp.
<220> FEATURE:
<221> NAME/KEY: CDS
<222> LOCATION: (208)..(963)

<400> SEQUENCE: 41

```
tgctgcccaa ggctcctgct cctgccccag gactctgagg tgggccctaa aacccagcgc    60
tctctaaaga aaagccttgc cagccccctac tcccggcccc caaccccagc aggtcgctgc   120
gccgccaggg ggcgctgtgt gagcgcccta ttctggccac ccggcgcccc ctcccacggc   180
```

```
                                                                              -continued ccaggcggga gcggggcgcc gggggcc atg cgg ggc caa ggc aga aag gag agt            234
                                Met Arg Gly Gln Gly Arg Lys Glu Ser
                                 1               5 ttg tcc gaa tcc cga gat ctg gac ggc tcc tat gac cag ctt acg ggc              282
Leu Ser Glu Ser Arg Asp Leu Asp Gly Ser Tyr Asp Gln Leu Thr Gly
 10              15                  20                  25 cac cct cca ggg ccc agt aaa aaa gcc ctg aag cag cgt ttc ctc aag              330
His Pro Pro Gly Pro Ser Lys Lys Ala Leu Lys Gln Arg Phe Leu Lys
                 30                  35                  40 ctg ctg ccg tgc tgc ggg ccc caa gcc ctg ccc tca gtc agt gaa aac              378
Leu Leu Pro Cys Cys Gly Pro Gln Ala Leu Pro Ser Val Ser Glu Asn
             45                  50                  55 agc gta gag gat gag ttt gaa tta tcc acg gtg tgt cac cga cct gag              426
Ser Val Glu Asp Glu Phe Glu Leu Ser Thr Val Cys His Arg Pro Glu
         60                  65                  70 ggc ctg gaa caa ctc cag gaa cag acc aag ttc aca cgc aga gag ctg              474
Gly Leu Glu Gln Leu Gln Glu Gln Thr Lys Phe Thr Arg Arg Glu Leu
     75                  80                  85 cag gtc ctg tac cga ggc ttc aag aac gaa tgc ccc agt ggg att gtc              522
Gln Val Leu Tyr Arg Gly Phe Lys Asn Glu Cys Pro Ser Gly Ile Val
 90                  95                 100                 105 aac gag gag aac ttc aag cag att tat tct cag ttc ttt ccc caa gga              570
Asn Glu Glu Asn Phe Lys Gln Ile Tyr Ser Gln Phe Phe Pro Gln Gly
                110                 115                 120 gac tcc agc aac tat gct act ttt ctc ttc aat gcc ttt gac acc aac              618
Asp Ser Ser Asn Tyr Ala Thr Phe Leu Phe Asn Ala Phe Asp Thr Asn
            125                 130                 135 cac gat ggc tct gtc agt ttt gag gac ttt gtg gct ggt ttg tcg gtg              666
His Asp Gly Ser Val Ser Phe Glu Asp Phe Val Ala Gly Leu Ser Val
        140                 145                 150 att ctt cgg ggg acc ata gat gat aga ctg agc tgg gct ttc aac tta              714
Ile Leu Arg Gly Thr Ile Asp Asp Arg Leu Ser Trp Ala Phe Asn Leu
    155                 160                 165 tat gac ctc aac aag gac ggc tgt atc aca aag gag gaa atg ctt gac              762
Tyr Asp Leu Asn Lys Asp Gly Cys Ile Thr Lys Glu Glu Met Leu Asp
170                 175                 180                 185 att atg aag tcc atc tat gac atg atg ggc aag tac aca tac cct gcc              810
Ile Met Lys Ser Ile Tyr Asp Met Met Gly Lys Tyr Thr Tyr Pro Ala
                190                 195                 200 ctc cgg gag gag gcc cca aga gaa cac gtg gag agc ttc ttc cag aag              858
Leu Arg Glu Glu Ala Pro Arg Glu His Val Glu Ser Phe Phe Gln Lys
            205                 210                 215 atg gac agg aac aag gac ggc gtg gtg acc atc gag gaa ttc atc gag              906
Met Asp Arg Asn Lys Asp Gly Val Val Thr Ile Glu Glu Phe Ile Glu
        220                 225                 230 tct tgt caa cag gac gag aac atc atg agg tcc atg cag ctc tca ccc              954
Ser Cys Gln Gln Asp Glu Asn Ile Met Arg Ser Met Gln Leu Ser Pro
    235                 240                 245 ctt ctc aac tgatacctag tgctgaggac acccctggtg tagggaccaa                     1003
Leu Leu Asn
250 gtggttctcc accttctagt cccactctag aaaccacatt agacagaagg tctcctgcta           1063 tggtgctttc cccatcccta atctcttaga ttttcctcaa gactcccttc tcagagaaca           1123 cgctctgtcc atgtcccag ctggcttctc agcctagcct tgagggccc tgtggggagg             1183 cggggacaag aaagcagaaa agtcttggcc ccgagccagt ggttaggtcc taggaattgg           1243 ctggagtgga ggccagaaag cctgggcaga tgatgagagc ccagctggc tgtcactgca            1303 ggttccgggg cctacagccc tgggtcagca gagtatgagt tcccagactt tccagaaggt          1363
```

```
ccttagcaat gtcccagaaa ttcaccgtac acttctcagt gtcttaggag ggcccgggat    1423
ccagatgtct ggttcatccc tgaatcctct ccctccttct tgctcgtatg gtgggagtgg    1483
tggccagggg aagatgagtg gtgtcccgga tgatgcctgt caaggtccca cctcccctcc    1543
ggctgttctc atgacagctg tttggttctc catgacccct atctagatgt agaggcatgg    1603
agtgagtcag ggatttcccg aacttgagtt ttaccactcc tcctagtggc tgccttaggg    1663
gaatgggaag aacccagtgt gggggcaccc attagaatct ttgcccggct cctcacaatg    1723
ccctagggtc ccctagggta cccgctccct ctgtttagtc tacccagaga tgctcctgag    1783
ctcacctaga gggtagggac ggtaggctcc aggtccaacc tctccaggtc agcaccctgc    1843
catgctgctg ctcctcatta acaaacctgc ttgtctcctc ctgcgcccct tctcagtcag    1903
ccagggtctg aggggaaggg cctcccgttt ccccatccgt cagacatggt tgactgcttt    1963
gcatttgggg ctcttctatc tattttgtaa aataagacat cagatccaat aaaacacacg    2023
gctatgcaca aaaaaaaaaa aaaaaaaaaa aaaa                               2057
```

<210> SEQ ID NO 42
<211> LENGTH: 252
<212> TYPE: PRT
<213> ORGANISM: Rattus sp.

<400> SEQUENCE: 42

```
Met Arg Gly Gln Gly Arg Lys Glu Ser Leu Ser Glu Ser Arg Asp Leu
 1               5                  10                  15

Asp Gly Ser Tyr Asp Gln Leu Thr Gly His Pro Gly Pro Ser Lys
            20                  25                  30

Lys Ala Leu Lys Gln Arg Phe Leu Lys Leu Leu Pro Cys Cys Gly Pro
        35                  40                  45

Gln Ala Leu Pro Ser Val Ser Glu Asn Ser Val Glu Asp Glu Phe Glu
    50                  55                  60

Leu Ser Thr Val Cys His Arg Pro Glu Gly Leu Glu Gln Leu Gln Glu
 65                  70                  75                  80

Gln Thr Lys Phe Thr Arg Arg Glu Leu Gln Val Leu Tyr Arg Gly Phe
                85                  90                  95

Lys Asn Glu Cys Pro Ser Gly Ile Val Asn Glu Glu Asn Phe Lys Gln
            100                 105                 110

Ile Tyr Ser Gln Phe Phe Pro Gln Gly Asp Ser Ser Asn Tyr Ala Thr
        115                 120                 125

Phe Leu Phe Asn Ala Phe Asp Thr Asn His Asp Gly Ser Val Ser Phe
    130                 135                 140

Glu Asp Phe Val Ala Gly Leu Ser Val Ile Leu Arg Gly Thr Ile Asp
145                 150                 155                 160

Asp Arg Leu Ser Trp Ala Phe Asn Leu Tyr Asp Leu Asn Lys Asp Gly
                165                 170                 175

Cys Ile Thr Lys Glu Glu Met Leu Asp Ile Met Lys Ser Ile Tyr Asp
            180                 185                 190

Met Met Gly Lys Tyr Thr Tyr Pro Ala Leu Arg Glu Glu Ala Pro Arg
        195                 200                 205

Glu His Val Glu Ser Phe Phe Gln Lys Met Asp Arg Asn Lys Asp Gly
    210                 215                 220

Val Val Thr Ile Glu Glu Phe Ile Glu Ser Cys Gln Gln Asp Glu Asn
225                 230                 235                 240

Ile Met Arg Ser Met Gln Leu Ser Pro Leu Leu Asn
                245                 250
```

<210> SEQ ID NO 43
<211> LENGTH: 26
<212> TYPE: PRT
<213> ORGANISM: Artificial Sequence
<220> FEATURE:
<221> NAME/KEY: unsure
<222> LOCATION: 2,5,6,9,17,25 and 26
<223> OTHER INFORMATION: Xaa = Ile, Leu, Val or Met
<221> NAME/KEY: unsure
<222> LOCATION: 3,4,7,8,16,18,20,23 and 24
<223> OTHER INFORMATION: Xaa = any amino acid
<223> OTHER INFORMATION: Description of Artificial Sequence: consensus
      motif

<400> SEQUENCE: 43

Glu Xaa Xaa Xaa Xaa Xaa Xaa Xaa Xaa Asp Lys Asp Gly Asp Gly Xaa
 1               5                   10                  15

Xaa Xaa Xaa Xaa Glu Phe Xaa Xaa Xaa Xaa
            20                  25

<210> SEQ ID NO 44
<211> LENGTH: 40
<212> TYPE: DNA
<213> ORGANISM: Rattus sp.

<400> SEQUENCE: 44
taatacgact cactataggg actggccatc ctgctctcag                    40

<210> SEQ ID NO 45
<211> LENGTH: 40
<212> TYPE: DNA
<213> ORGANISM: Rattus sp.

<400> SEQUENCE: 45
attaaccctc actaaaggga cactactgtt taagctcaag                    40

<210> SEQ ID NO 46
<211> LENGTH: 40
<212> TYPE: DNA
<213> ORGANISM: Rattus sp.

<400> SEQUENCE: 46
taatacgact cactataggg cacctcccct ccggctgttc                    40

<210> SEQ ID NO 47
<211> LENGTH: 40
<212> TYPE: DNA
<213> ORGANISM: Rattus sp.

<400> SEQUENCE: 47
attaaccctc actaaaggga gagcagcagc atggcagggt                    40

<210> SEQ ID NO 48
<211> LENGTH: 2413
<212> TYPE: DNA
<213> ORGANISM: Simian sp.
<220> FEATURE:
<221> NAME/KEY: CDS
<222> LOCATION: (265)..(963)

<400> SEQUENCE: 48
gtcgacccac gcgtccggtg cgctgtggtt gcgggggggga gccccgccag ccaaatgcca     60
ggatcagcat gagaggctgg actttagtcc aggtctgtcc tcaccccggg ggaccgccgg    120

```
ctttgcaggg tgcagctgcg aggaactgct cacttttttc ccttgcaag tctttgttcc      180 aagcctgacg ttgctacgat tctgtaatta actccctcca ctccaaaggg gtctggaggc     240
tgggatgctc tgccagctca gagg atg ttg act ctg gag tgg gag tcc gaa       291
                           Met Leu Thr Leu Glu Trp Glu Ser Glu
                            1               5 gga ctg caa aca gtg ggt att gtt gtg att ata tgt gca tct ctg aag       339
Gly Leu Gln Thr Val Gly Ile Val Val Ile Ile Cys Ala Ser Leu Lys
 10              15                  20                  25 ctg ctt cat ttg ctg gga ctg att gat ttt tcg gaa gac agc gtg gaa       387
Leu Leu His Leu Leu Gly Leu Ile Asp Phe Ser Glu Asp Ser Val Glu
             30                  35                  40 gat gaa ctg gag atg gcc act gtc agg cat cgg cct gag gcc ctt gag       435
Asp Glu Leu Glu Met Ala Thr Val Arg His Arg Pro Glu Ala Leu Glu
         45                  50                  55 ctt ctg gaa gcc cag agc aaa ttt acc aag aaa gag ctt cag atc ctt       483
Leu Leu Glu Ala Gln Ser Lys Phe Thr Lys Lys Glu Leu Gln Ile Leu
     60                  65                  70 tac aga gga ttt aag aac gaa tgc ccc agt ggt gtt gtt aat gaa gaa       531
Tyr Arg Gly Phe Lys Asn Glu Cys Pro Ser Gly Val Val Asn Glu Glu
 75                  80                  85 acc ttc aaa gag att tac tcg cag ttc ttt cca cag gga gac tct aca       579
Thr Phe Lys Glu Ile Tyr Ser Gln Phe Phe Pro Gln Gly Asp Ser Thr
 90                  95                 100                 105 aca tat gca cat ttt ctg ttc aat gcg ttt gat acg gac cac aat gga       627
Thr Tyr Ala His Phe Leu Phe Asn Ala Phe Asp Thr Asp His Asn Gly
             110                 115                 120 gct gtg agt ttc gag gat ttc atc aaa ggt ctt tcc att ttg ctc cgg       675
Ala Val Ser Phe Glu Asp Phe Ile Lys Gly Leu Ser Ile Leu Leu Arg
         125                 130                 135 ggg aca gta caa gaa aaa ctc aat tgg gca ttt aat ctg tat gat ata       723
Gly Thr Val Gln Glu Lys Leu Asn Trp Ala Phe Asn Leu Tyr Asp Ile
     140                 145                 150 aat aaa gat ggc tac atc act aaa gag gaa atg ctt gat ata atg aaa       771
Asn Lys Asp Gly Tyr Ile Thr Lys Glu Glu Met Leu Asp Ile Met Lys
 155                 160                 165 gca ata tac gac atg atg ggt aaa tgt aca tat cct gtc ctc aaa gaa       819
Ala Ile Tyr Asp Met Met Gly Lys Cys Thr Tyr Pro Val Leu Lys Glu
170                 175                 180                 185 gat gca ccc aga caa cac gtc gaa aca ttt ttt cag aaa atg gac aaa       867
Asp Ala Pro Arg Gln His Val Glu Thr Phe Phe Gln Lys Met Asp Lys
             190                 195                 200 aat aaa gat ggg gtt gtt acc ata gat gag ttc att gaa agc tgc caa       915
Asn Lys Asp Gly Val Val Thr Ile Asp Glu Phe Ile Glu Ser Cys Gln
         205                 210                 215 aaa gat gaa aac ata atg cgc tcc atg cag ctc ttt gaa aat gtg att       963
Lys Asp Glu Asn Ile Met Arg Ser Met Gln Leu Phe Glu Asn Val Ile
     220                 225                 230 taacttgtca actagatcct gaatccaaca gacaaatgtg aactattcta ccacccttaa    1023
agtcggagct accacttttta gcatagattg ctcagcttga cactgaagca tattatgcaa   1083
acaagctttg ttttaatata aagcaatccc caaaagattt gagtttctca gttataaatt    1143
tgcatccttt ccataatgcc actgagttca tgggatgttc taactcattt catactctgt    1203
gaatattcaa aagtaataga atctggcata tagttttatt gattccttag ccatgggatt    1263
attgaggctt tcacatatca gtgattttaa aataccagtg ttttttgctc tcatttgtat    1323
gtattcagtc ctaggatttt gaatggtttt ctaatatact gacatctgca tttaatttcc    1383
```

-continued

```
agaaattaaa ttaattttca tgtctgaatg ctgtaattcc atttatatac tttaagtaaa    1443
caaataagat tactacaatt aaacacatag ttccagtttc tatggccttc ccttcccacc    1503
ttctattata aattaatttt atctggtatt tttaaacatt taaaaattta tcatcagata    1563
tcagcatatg cctaattatg cctaatgaaa cttaataagc atttaatttt ccatcataca    1623
ttatagccaa ggcctatata ctatatataa ttttggattt gtttaatctt acaggctgtt    1683
ttccattgta tcatcaagtg gaagttcaag acggcatcaa acaaacaag gatgtttaca     1743
gacatatgca aagggtcagg atatctatcc tccagtatat gttaatgctt aataacaagt    1803
aatcctaaca gcattaaagg ccaaatctgt cctctttccc ctgacttcct tacagcatgt    1863
ttatattaca agccattcag ggacaaagaa accttgacta ccccactgtc tactaggaac    1923
aaacaaacag caagcaaaat tcactttgaa agcaccagtg gttccattac attgacaact    1983
actaccaaga ttcagtagaa aataagtgct caacaactaa tccagattac aatatgattt    2043
agtgcatcat aaaattccaa caattcagat tattttttaat catctcagcc acaactgtaa   2103
agttgccaca ttactaaaga cacacacatc gtccctgttt tgtagaaata tcacaaagac    2163
caagaggcta cagaaggagg aaatttgcaa ctgtctttgc aacaataaat caggtatcta    2223
ttctggtgta gagataggat gttgaaagct gccctgctat caccagtgta gaaattaaga    2283
gtagtacaat acatgtacac tgaaatttgc catcgcgtgt ttgtgtaaac tcaatgtgca    2343
cattttgtat ttcaaaaaga aaaataaaa gcaaataaa atgttwawaa mwmwaaaaaa      2403
aaaaaaaaaa                                                           2413
```

<210> SEQ ID NO 49
<211> LENGTH: 233
<212> TYPE: PRT
<213> ORGANISM: Simian sp.

<400> SEQUENCE: 49

```
Met Leu Thr Leu Glu Trp Glu Ser Glu Gly Leu Gln Thr Val Gly Ile
 1               5                  10                  15

Val Val Ile Ile Cys Ala Ser Leu Lys Leu Leu His Leu Leu Gly Leu
            20                  25                  30

Ile Asp Phe Ser Glu Asp Ser Val Glu Asp Leu Glu Met Ala Thr
         35                  40                  45

Val Arg His Arg Pro Glu Ala Leu Glu Leu Leu Glu Ala Gln Ser Lys
     50                  55                  60

Phe Thr Lys Lys Glu Leu Gln Ile Leu Tyr Arg Gly Phe Lys Asn Glu
 65                  70                  75                  80

Cys Pro Ser Gly Val Val Asn Glu Glu Thr Phe Lys Glu Ile Tyr Ser
                 85                  90                  95

Gln Phe Phe Pro Gln Gly Asp Ser Thr Thr Tyr Ala His Phe Leu Phe
            100                 105                 110

Asn Ala Phe Asp Thr Asp His Asn Gly Ala Val Ser Phe Glu Asp Phe
        115                 120                 125

Ile Lys Gly Leu Ser Ile Leu Leu Arg Gly Thr Val Gln Glu Lys Leu
    130                 135                 140

Asn Trp Ala Phe Asn Leu Tyr Asp Ile Asn Lys Asp Gly Tyr Ile Thr
145                 150                 155                 160

Lys Glu Glu Met Leu Asp Ile Met Lys Ala Ile Tyr Asp Met Met Gly
                165                 170                 175

Lys Cys Thr Tyr Pro Val Leu Lys Glu Asp Ala Pro Arg Gln His Val
            180                 185                 190
```

```
Glu Thr Phe Phe Gln Lys Met Asp Lys Asn Lys Asp Gly Val Val Thr
            195                 200                 205

Ile Asp Glu Phe Ile Glu Ser Cys Gln Lys Asp Glu Asn Ile Met Arg
    210                 215                 220

Ser Met Gln Leu Phe Glu Asn Val Ile
225                 230

<210> SEQ ID NO 50
<211> LENGTH: 1591
<212> TYPE: DNA
<213> ORGANISM: Simian sp.
<220> FEATURE:
<221> NAME/KEY: CDS
<222> LOCATION: (265)..(963)

<400> SEQUENCE: 50
gtcgacccac gcgtccggtg cgctgtggtt gcggggggga gccccgccag ccaaatgcca      60
ggatcagcat gagaggctgg actttagtcc aggtctgtcc tcaccccggg ggaccgccgg     120
ctttgcaggg tgcagctgcg aggaactgct cactttttc cccttgcaag tctttgttcc     180
aagcctgacg ttgctacgat tctgtaatta actccctcca ctccaaaggg gtctggaggc     240
tgggatgctc tgccagctca gagg atg ttg act ctg gag tgg gag tcc gaa       291
                          Met Leu Thr Leu Glu Trp Glu Ser Glu
                           1               5 gga ctg caa aca gtg ggt att gtt gtg att ata tgt gca tct ctg aag      339
Gly Leu Gln Thr Val Gly Ile Val Val Ile Ile Cys Ala Ser Leu Lys
 10              15                  20                  25 ctg ctt cat ttg ctg gga ctg att gat ttt tcg gaa gac agc gtg gaa      387
Leu Leu His Leu Leu Gly Leu Ile Asp Phe Ser Glu Asp Ser Val Glu
             30                  35                  40 gat gaa ctg gag atg gcc act gtc agg cat cgg cct gag gcc ctt gag      435
Asp Glu Leu Glu Met Ala Thr Val Arg His Arg Pro Glu Ala Leu Glu
         45                  50                  55 ctt ctg gaa gcc cag agc aaa ttt acc aag aaa gag ctt cag atc ctt      483
Leu Leu Glu Ala Gln Ser Lys Phe Thr Lys Lys Glu Leu Gln Ile Leu
     60                  65                  70 tac aga gga ttt aag aac gaa tgc ccc agt ggt gtt gtt aat gaa gaa      531
Tyr Arg Gly Phe Lys Asn Glu Cys Pro Ser Gly Val Val Asn Glu Glu
 75                  80                  85 acc ttc aaa gag att tac tcg cag ttc ttt cca cag gga gac tct aca      579
Thr Phe Lys Glu Ile Tyr Ser Gln Phe Phe Pro Gln Gly Asp Ser Thr
 90                  95                 100                 105 aca tat gca cat ttt ctg ttc aat gcg ttt gat acg gac cac aat gga      627
Thr Tyr Ala His Phe Leu Phe Asn Ala Phe Asp Thr Asp His Asn Gly
             110                 115                 120 gct gtg agt ttc gag gat ttc atc aaa ggt ctt tcc att ttg ctc cgg      675
Ala Val Ser Phe Glu Asp Phe Ile Lys Gly Leu Ser Ile Leu Leu Arg
         125                 130                 135 ggg aca gta caa gaa aaa ctc aat tgg gca ttt aat ctg tat gat ata      723
Gly Thr Val Gln Glu Lys Leu Asn Trp Ala Phe Asn Leu Tyr Asp Ile
     140                 145                 150 aat aaa gat ggc tac atc act aaa gag gaa atg ctt gat ata atg aaa      771
Asn Lys Asp Gly Tyr Ile Thr Lys Glu Glu Met Leu Asp Ile Met Lys
 155                 160                 165 gca ata tac gac atg atg ggt aaa tgt aca tat cct gtc ctc aaa gaa      819
Ala Ile Tyr Asp Met Met Gly Lys Cys Thr Tyr Pro Val Leu Lys Glu
170                  175                 180                 185 gat gca ccc aga caa cac gtc gaa aca ttt ttt cag gct gtt ttc cat      867
Asp Ala Pro Arg Gln His Val Glu Thr Phe Phe Gln Ala Val Phe His
```

```
                  190               195               200
tgt atc atc aag tgg aag ttc aag acg gca tca aac aaa aca agg atg        915
Cys Ile Ile Lys Trp Lys Phe Lys Thr Ala Ser Asn Lys Thr Arg Met
            205               210               215 ttt aca gac ata tgc aaa ggg tca gga tat cta tcc tcc agt ata tgt        963
Phe Thr Asp Ile Cys Lys Gly Ser Gly Tyr Leu Ser Ser Ser Ile Cys
            220               225               230 taatgcttaa taacaagtaa tcctaacagc attaaaggcc aaatctgtcc tctttcccct     1023
gacttcctta cagcatgttt atattacaag ccattcaggg acaagaaac cttgactacc      1083 ccactgtcta ctaggaacaa acaaacagca agcaaaattc actttgaaag caccagtggt     1143
tccattacat tgacaactac taccaagatt cagtagaaaa taagtgctca acaactaatc     1203
cagattacaa tatgatttag tgcatcataa aattccaaca attcagatta tttttaatca     1263
tctcagccac aactgtaaag ttgccacatt actaagaca cacacatcgt ccctgttttg      1323
tagaaatatc acaagacca agaggctaca gaaggaggaa atttgcaact gtctttgcaa      1383
caataaatca ggtatctatt ctggtgtaga gataggatgt tgaaagctgc cctgctatca     1443
ccagtgtaga aattaagagt agtacaatac atgtacactg aaatttgcca tcgcgtgttt     1503
gtgtaaactc aatgtgcaca ttttgtattt caaaagaaa aataaaagc aaaataaaat       1563 gttwawaamw mwaaaaaaaa aaaaaaaa                                        1591
```

<210> SEQ ID NO 51
<211> LENGTH: 233
<212> TYPE: PRT
<213> ORGANISM: Simian sp.

<400> SEQUENCE: 51

```
Met Leu Thr Leu Glu Trp Glu Ser Glu Gly Leu Gln Thr Val Gly Ile
 1               5                  10                  15

Val Val Ile Ile Cys Ala Ser Leu Lys Leu Leu His Leu Leu Gly Leu
                20                  25                  30

Ile Asp Phe Ser Glu Asp Ser Val Glu Asp Glu Leu Glu Met Ala Thr
            35                  40                  45

Val Arg His Arg Pro Glu Ala Leu Glu Leu Leu Glu Ala Gln Ser Lys
        50                  55                  60

Phe Thr Lys Lys Glu Leu Gln Ile Leu Tyr Arg Gly Phe Lys Asn Glu
 65                  70                  75                  80

Cys Pro Ser Gly Val Val Asn Glu Glu Thr Phe Lys Glu Ile Tyr Ser
                85                  90                  95

Gln Phe Phe Pro Gln Gly Asp Ser Thr Thr Tyr Ala His Phe Leu Phe
           100                 105                 110

Asn Ala Phe Asp Thr Asp His Asn Gly Ala Val Ser Phe Glu Asp Phe
       115                 120                 125

Ile Lys Gly Leu Ser Ile Leu Leu Arg Gly Thr Val Gln Glu Lys Leu
   130                 135                 140

Asn Trp Ala Phe Asn Leu Tyr Asp Ile Asn Lys Asp Gly Tyr Ile Thr
145                 150                 155                 160

Lys Glu Glu Met Leu Asp Ile Met Lys Ala Ile Tyr Asp Met Met Gly
               165                 170                 175

Lys Cys Thr Tyr Pro Val Leu Lys Glu Asp Ala Pro Arg Gln His Val
           180                 185                 190

Glu Thr Phe Phe Gln Ala Val Phe His Cys Ile Ile Lys Trp Lys Phe
       195                 200                 205
```

```
                Lys Thr Ala Ser Asn Lys Thr Arg Met Phe Thr Asp Ile Cys Lys Gly
                    210                 215                 220

Ser Gly Tyr Leu Ser Ser Ser Ile Cys
                225                 230

<210> SEQ ID NO 52
<211> LENGTH: 2051
<212> TYPE: DNA
<213> ORGANISM: Rattus sp.
<220> FEATURE:
<221> NAME/KEY: CDS
<222> LOCATION: (85)..(1305)

<400> SEQUENCE: 52
ggtggagcta agcactcact gcggtgctgc cctgcgtctg cagagaacaa ggaaagcttc          60
tctgcagggc tgtcagctgc caaa atg aac ggc gtg gaa ggg aac aac gag           111
                          Met Asn Gly Val Glu Gly Asn Asn Glu
                            1               5 ctc cct ctc gct aac acc tcg acc tcc gcc ctt gtc ccg gaa gat ctg          159
Leu Pro Leu Ala Asn Thr Ser Thr Ser Ala Leu Val Pro Glu Asp Leu
 10              15                  20                  25 gat ctg aag caa gac cag ccg ctc agc gag gaa act gac acg gtg cgg          207
Asp Leu Lys Gln Asp Gln Pro Leu Ser Glu Glu Thr Asp Thr Val Arg
                 30                  35                  40 gag atg gag gct gca ggt gag gcc ggt gcg gag gga ggc gcg tcc ccc          255
Glu Met Glu Ala Ala Gly Glu Ala Gly Ala Glu Gly Gly Ala Ser Pro
             45                  50                  55 gat tcg gag cac tgc gac ccc cag ctc tgc ctc cga gtg gct gag aat          303
Asp Ser Glu His Cys Asp Pro Gln Leu Cys Leu Arg Val Ala Glu Asn
         60                  65                  70 ggc tgt gct gcc gca gcg gga gag ggg ctg gag gat ggt ctg tct tca          351
Gly Cys Ala Ala Ala Ala Gly Glu Gly Leu Glu Asp Gly Leu Ser Ser
     75                  80                  85 tca aag tgt ggg gac gca ccc ttg gcg tct gtg gca gcc aac gac agc          399
Ser Lys Cys Gly Asp Ala Pro Leu Ala Ser Val Ala Ala Asn Asp Ser
 90                  95                 100                 105 aat aaa aat ggc tgt cag ctt gca ggg ccg ctc agc cct gct aag cca          447
Asn Lys Asn Gly Cys Gln Leu Ala Gly Pro Leu Ser Pro Ala Lys Pro
                110                 115                 120 aaa act ctg gaa gcc agt ggt gca gtg ggc ctg ggg tcg cag atg atg          495
Lys Thr Leu Glu Ala Ser Gly Ala Val Gly Leu Gly Ser Gln Met Met
            125                 130                 135 cca ggg ccg aag aag acc aag gta atg act acc aag ggc gcc atc tct          543
Pro Gly Pro Lys Lys Thr Lys Val Met Thr Thr Lys Gly Ala Ile Ser
        140                 145                 150 gcg act aca ggc aag gaa gga gaa gca ggg gcg gca atg cag gaa aag          591
Ala Thr Thr Gly Lys Glu Gly Glu Ala Gly Ala Ala Met Gln Glu Lys
    155                 160                 165 aag ggg gtg cag aaa gaa aaa aag gca gct gga gga ggg aaa gac gag          639
Lys Gly Val Gln Lys Glu Lys Lys Ala Ala Gly Gly Gly Lys Asp Glu
170                 175                 180                 185 act cgt cct aga gcc cct aag atc aat aac tgc atg gac tcc ctg gaa          687
Thr Arg Pro Arg Ala Pro Lys Ile Asn Asn Cys Met Asp Ser Leu Glu
                190                 195                 200 gcc atc gat caa gag ctg tca aat gta aat gcg caa gct gac agg gcc          735
Ala Ile Asp Gln Glu Leu Ser Asn Val Asn Ala Gln Ala Asp Arg Ala
            205                 210                 215 ttc ctc cag ctg gaa cgc aaa ttt ggg cgg atg aga agg ctc cac atg          783
Phe Leu Gln Leu Glu Arg Lys Phe Gly Arg Met Arg Arg Leu His Met
        220                 225                 230
```

| | | |
|---|---|---|
| cag cgc cga agt ttc atc atc caa aac atc cca ggt ttc tgg gtc aca<br>Gln Arg Arg Ser Phe Ile Ile Gln Asn Ile Pro Gly Phe Trp Val Thr<br>235                    240                    245 | | 831 |
| gcg ttt cgg aac cac ccg caa ctg tca ccg atg atc agt ggc caa gat<br>Ala Phe Arg Asn His Pro Gln Leu Ser Pro Met Ile Ser Gly Gln Asp<br>250                    255                    260                    265 | | 879 |
| gaa gac atg atg agg tac atg atc aat tta gag gtg gag gag ctt aag<br>Glu Asp Met Met Arg Tyr Met Ile Asn Leu Glu Val Glu Glu Leu Lys<br>                  270                    275                    280 | | 927 |
| cac cca aga gca ggg tgc aaa ttt aag ttc atc ttc caa agc aac ccc<br>His Pro Arg Ala Gly Cys Lys Phe Lys Phe Ile Phe Gln Ser Asn Pro<br>              285                    290                    295 | | 975 |
| tac ttc cga aat gag ggg ctg gtc aaa gag tac gag cgc aga tcc tca<br>Tyr Phe Arg Asn Glu Gly Leu Val Lys Glu Tyr Glu Arg Arg Ser Ser<br>300                    305                    310 | | 1023 |
| ggt cga gtg gtg tcg ctc tct acg cca atc cgc tgg cac cgg ggt caa<br>Gly Arg Val Val Ser Leu Ser Thr Pro Ile Arg Trp His Arg Gly Gln<br>315                    320                    325 | | 1071 |
| gaa ccc cag gcc cat atc cac agg aat aga gag ggg aac acg att ccc<br>Glu Pro Gln Ala His Ile His Arg Asn Arg Glu Gly Asn Thr Ile Pro<br>330                    335                    340                    345 | | 1119 |
| agt ttc ttc aat tgg ttc tca gac cac agc ctc cta gaa ttc gac aga<br>Ser Phe Phe Asn Trp Phe Ser Asp His Ser Leu Leu Glu Phe Asp Arg<br>                  350                    355                    360 | | 1167 |
| ata gct gaa att atc aaa ggg gag ctt tgg tcc aat ccc cta caa tac<br>Ile Ala Glu Ile Ile Lys Gly Glu Leu Trp Ser Asn Pro Leu Gln Tyr<br>              365                    370                    375 | | 1215 |
| tac ctg atg ggc gat ggg cca cgc aga gga gtt cga gtc cca cca agg<br>Tyr Leu Met Gly Asp Gly Pro Arg Arg Gly Val Arg Val Pro Pro Arg<br>380                    385                    390 | | 1263 |
| cag cca gtg gag agt ccc agg tcc ttc agg ttc cag tct ggc<br>Gln Pro Val Glu Ser Pro Arg Ser Phe Arg Phe Gln Ser Gly<br>395                    400                    405 | | 1305 |
| taagctctgc cctcgtgaga agctcttaca gaagagtcct taccaccttc tcagcttggc | | 1365 |
| tagcagcatg cagccttctg tctgctttct cttccttgga ttgtgtcctt tggttcttct | | 1425 |
| aagtctccgg tagtttcaag gttgtggctt ccaagtcttt gctcttcttt ctcttggcca | | 1485 |
| tcacgatgtc ctgcatagtg ttaatggtgt tccaagtgca tggcctccaa actgcttcta | | 1545 |
| tgccaagctc acgtgctgta gtttgtactg cttttctttg catggcttgg ttcctgtctg | | 1605 |
| tgatcttcta ggttttttgt tttctttttt aaaagtggtt ctctatcaaa agaaagcttg | | 1665 |
| acatatcctt accaagaact agccagattt catactgtgt tcccgatatc tatgtactgt | | 1725 |
| gaagaactgt gagtttcgcc actgcaagat gggactgtat cccaatccag ccatcagccc | | 1785 |
| aacaggacat tccaagctgt caccaactga tcctagctgt cttcctgggc ctttgccatt | | 1845 |
| taccctgctt tttatctata gaatgagcag gtggctggta ggtgactact aggtaagagt | | 1905 |
| gaagtattag gtgaggagtg ttttctgtca ccacattgtt cttgtaccaa tgcatcatga | | 1965 |
| tcagcttgga tcagctactg actgtctgat atttctaacc cccaacacaa aaaaaaaaa | | 2025 |
| aaaaaaaaaa aaaaaaaaa aaaaa | | 2051 |

<210> SEQ ID NO 53
<211> LENGTH: 407
<212> TYPE: PRT
<213> ORGANISM: Rattus sp.

<400> SEQUENCE: 53

Met Asn Gly Val Glu Gly Asn Asn Glu Leu Pro Leu Ala Asn Thr Ser

```
  1               5                    10                   15
Thr Ser Ala Leu Val Pro Glu Asp Leu Asp Leu Lys Gln Asp Gln Pro
             20                  25                  30

Leu Ser Glu Glu Thr Asp Thr Val Arg Glu Met Glu Ala Ala Gly Glu
             35                  40                  45

Ala Gly Ala Glu Gly Gly Ala Ser Pro Asp Ser Glu His Cys Asp Pro
             50                  55                  60

Gln Leu Cys Leu Arg Val Ala Glu Asn Gly Cys Ala Ala Ala Ala Gly
 65              70                  75                      80

Glu Gly Leu Glu Asp Gly Leu Ser Ser Ser Lys Cys Gly Asp Ala Pro
                 85                  90                  95

Leu Ala Ser Val Ala Ala Asn Asp Ser Asn Lys Asn Gly Cys Gln Leu
             100                 105                 110

Ala Gly Pro Leu Ser Pro Ala Lys Pro Lys Thr Leu Glu Ala Ser Gly
             115                 120                 125

Ala Val Gly Leu Gly Ser Gln Met Met Pro Gly Pro Lys Lys Thr Lys
             130                 135                 140

Val Met Thr Thr Lys Gly Ala Ile Ser Ala Thr Thr Gly Lys Glu Gly
145              150                 155                 160

Glu Ala Gly Ala Ala Met Gln Glu Lys Lys Gly Val Gln Lys Glu Lys
             165                 170                 175

Lys Ala Ala Gly Gly Lys Asp Glu Thr Arg Pro Arg Ala Pro Lys
             180                 185                 190

Ile Asn Asn Cys Met Asp Ser Leu Glu Ala Ile Asp Gln Glu Leu Ser
             195                 200                 205

Asn Val Asn Ala Gln Ala Asp Arg Ala Phe Leu Gln Leu Glu Arg Lys
             210                 215                 220

Phe Gly Arg Met Arg Arg Leu His Met Gln Arg Arg Ser Phe Ile Ile
225              230                 235                 240

Gln Asn Ile Pro Gly Phe Trp Val Thr Ala Phe Arg Asn His Pro Gln
             245                 250                 255

Leu Ser Pro Met Ile Ser Gly Gln Asp Glu Asp Met Met Arg Tyr Met
             260                 265                 270

Ile Asn Leu Glu Val Glu Glu Leu Lys His Pro Arg Ala Gly Cys Lys
             275                 280                 285

Phe Lys Phe Ile Phe Gln Ser Asn Pro Tyr Phe Arg Asn Glu Gly Leu
             290                 295                 300

Val Lys Glu Tyr Glu Arg Arg Ser Ser Gly Arg Val Val Ser Leu Ser
305              310                 315                 320

Thr Pro Ile Arg Trp His Arg Gly Gln Glu Pro Gln Ala His Ile His
             325                 330                 335

Arg Asn Arg Glu Gly Asn Thr Ile Pro Ser Phe Phe Asn Trp Phe Ser
             340                 345                 350

Asp His Ser Leu Leu Glu Phe Asp Arg Ile Ala Glu Ile Ile Lys Gly
             355                 360                 365

Glu Leu Trp Ser Asn Pro Leu Gln Tyr Tyr Leu Met Gly Asp Gly Pro
             370                 375                 380

Arg Arg Gly Val Arg Val Pro Pro Arg Gln Pro Val Glu Ser Pro Arg
385              390                 395                 400

Ser Phe Arg Phe Gln Ser Gly
             405

<210> SEQ ID NO 54
```

```
<211> LENGTH: 4148
<212> TYPE: DNA
<213> ORGANISM: Homo sapiens
<220> FEATURE:
<221> NAME/KEY: CDS
<222> LOCATION: (88)..(1329)

<400> SEQUENCE: 54
ggggtggtgc tagacgtttc gggcagagct cggccgctgc ggaggacaag gaactctccc      60
tctcccacta gtctgacttc ttccaaa atg agc ggc ctg gat ggg ggc aac aag     114
                                Met Ser Gly Leu Asp Gly Gly Asn Lys
                                 1               5 ctc cct ctc gcc caa acc ggc ggc ctg gct gct ccc gac cat gcc tca       162
Leu Pro Leu Ala Gln Thr Gly Gly Leu Ala Ala Pro Asp His Ala Ser
 10              15                  20                  25 gga gat ccg gac cta gac cag tgc caa ggg ctc cgt gaa gaa acc gag       210
Gly Asp Pro Asp Leu Asp Gln Cys Gln Gly Leu Arg Glu Glu Thr Glu
             30                  35                  40 gcg aca cag gtg atg gcg aac aca ggt ggg ggc agc ctg gag acc gtt       258
Ala Thr Gln Val Met Ala Asn Thr Gly Gly Gly Ser Leu Glu Thr Val
         45                  50                  55 gcg gag ggg ggt gca tcc cag gat cct gtc gac tgt ggc ccc gcg ctc       306
Ala Glu Gly Gly Ala Ser Gln Asp Pro Val Asp Cys Gly Pro Ala Leu
     60                  65                  70 cgc gtc cca gtt gcc ggg agt cgc ggc ggt gca gcg acc aaa gcc ggg       354
Arg Val Pro Val Ala Gly Ser Arg Gly Gly Ala Ala Thr Lys Ala Gly
 75                  80                  85 cag gag gat gct cca cct tct acg aaa ggt ctg gaa gca gcc tct gcc       402
Gln Glu Asp Ala Pro Pro Ser Thr Lys Gly Leu Glu Ala Ala Ser Ala
 90                  95                 100                 105 gcc gag gct gct gac agc agc cag aaa aat ggc tgt cag ctt gga gag       450
Ala Glu Ala Ala Asp Ser Ser Gln Lys Asn Gly Cys Gln Leu Gly Glu
                 110                 115                 120 ccc cgt ggc cct gct ggg cag aag gct cta gaa gcc tgt ggc gca ggg       498
Pro Arg Gly Pro Ala Gly Gln Lys Ala Leu Glu Ala Cys Gly Ala Gly
             125                 130                 135 ggc ttg ggg tct cag atg ata ccg ggg aag aag gcc aag gaa gtg acg       546
Gly Leu Gly Ser Gln Met Ile Pro Gly Lys Lys Ala Lys Glu Val Thr
         140                 145                 150 act aaa aaa cgc gcc atc tcg gca gca gtg gaa aag gag gga gaa gca       594
Thr Lys Lys Arg Ala Ile Ser Ala Ala Val Glu Lys Glu Gly Glu Ala
     155                 160                 165 ggg gcg gcg atg gag gaa aag aag gta gtg cag aag gaa aaa aag gtg       642
Gly Ala Ala Met Glu Glu Lys Lys Val Val Gln Lys Glu Lys Lys Val
 170                 175                 180                 185 gca gga ggg gtg aaa gag gag aca cgg ccc agg gcc ccg aag atc aat       690
Ala Gly Gly Val Lys Glu Glu Thr Arg Pro Arg Ala Pro Lys Ile Asn
                 190                 195                 200 aac tgc atg gac tca ctg gag gcc atc gat caa gag ttg tca aac gta       738
Asn Cys Met Asp Ser Leu Glu Ala Ile Asp Gln Glu Leu Ser Asn Val
             205                 210                 215 aat gcc cag gct gac agg gcc ttc ctt cag ctt gag cgc aag ttt ggc       786
Asn Ala Gln Ala Asp Arg Ala Phe Leu Gln Leu Glu Arg Lys Phe Gly
         220                 225                 230 cgc atg cga agg ctc cac atg cag cgc aga agt ttc att atc cag aat       834
Arg Met Arg Arg Leu His Met Gln Arg Arg Ser Phe Ile Ile Gln Asn
     235                 240                 245 atc cca ggt ttc tgg gtt act gcc ttt cga aac cac ccc cag ctg tca       882
Ile Pro Gly Phe Trp Val Thr Ala Phe Arg Asn His Pro Gln Leu Ser
 250                 255                 260                 265
```

| | | | | | | | | | | | | | | | | |
|---|---|---|---|---|---|---|---|---|---|---|---|---|---|---|---|---|
| cct | atg | atc | agt | ggc | caa | gat | gaa | gac | atg | ctg | agg | tac | atg | atc | aat | 930 |
| Pro | Met | Ile | Ser | Gly | Gln | Asp | Glu | Asp | Met | Leu | Arg | Tyr | Met | Ile | Asn | |
| | | | 270 | | | | 275 | | | | | 280 | | | | |
| ttg | gag | gtg | gag | gag | ctt | aaa | cac | ccc | aga | gca | ggc | tgc | aaa | ttc | aag | 978 |
| Leu | Glu | Val | Glu | Glu | Leu | Lys | His | Pro | Arg | Ala | Gly | Cys | Lys | Phe | Lys | |
| | | 285 | | | | | 290 | | | | | 295 | | | | |
| ttc | atc | ttt | cag | ggc | aac | ccc | tac | ttc | cga | aat | gag | ggg | ctt | gtc | aag | 1026 |
| Phe | Ile | Phe | Gln | Gly | Asn | Pro | Tyr | Phe | Arg | Asn | Glu | Gly | Leu | Val | Lys | |
| | | 300 | | | | | 305 | | | | | | 310 | | | |
| gaa | tat | gaa | cgc | aga | tcc | tct | ggc | cgg | gtg | gtg | tct | ctt | tcc | act | cca | 1074 |
| Glu | Tyr | Glu | Arg | Arg | Ser | Ser | Gly | Arg | Val | Val | Ser | Leu | Ser | Thr | Pro | |
| | 315 | | | | | 320 | | | | | 325 | | | | | |
| atc | cgc | tgg | cac | cga | ggc | caa | gac | ccc | cag | gct | cat | atc | cac | aga | aac | 1122 |
| Ile | Arg | Trp | His | Arg | Gly | Gln | Asp | Pro | Gln | Ala | His | Ile | His | Arg | Asn | |
| 330 | | | | | 335 | | | | | 340 | | | | | 345 | |
| cgg | gaa | ggg | aac | act | atc | cct | agt | ttc | ttc | aac | tgg | ttt | tca | gac | cac | 1170 |
| Arg | Glu | Gly | Asn | Thr | Ile | Pro | Ser | Phe | Phe | Asn | Trp | Phe | Ser | Asp | His | |
| | | | 350 | | | | | 355 | | | | | 360 | | | |
| agc | ctt | cta | gaa | ttc | gac | aga | att | gca | gag | att | atc | aaa | gga | gaa | ctg | 1218 |
| Ser | Leu | Leu | Glu | Phe | Asp | Arg | Ile | Ala | Glu | Ile | Ile | Lys | Gly | Glu | Leu | |
| | | 365 | | | | | 370 | | | | | 375 | | | | |
| tgg | ccc | aat | ccc | cta | caa | tac | tac | ctg | atg | ggt | gaa | ggg | ccc | cgt | aga | 1266 |
| Trp | Pro | Asn | Pro | Leu | Gln | Tyr | Tyr | Leu | Met | Gly | Glu | Gly | Pro | Arg | Arg | |
| | | 380 | | | | | 385 | | | | | 390 | | | | |
| gga | att | cga | ggc | cca | cca | agg | cag | cca | gtg | gag | agc | gcc | aga | tcc | ttc | 1314 |
| Gly | Ile | Arg | Gly | Pro | Pro | Arg | Gln | Pro | Val | Glu | Ser | Ala | Arg | Ser | Phe | |
| | 395 | | | | | 400 | | | | | 405 | | | | | |
| agg | ttc | cag | tct | ggc | taatctctgt | | cctgtgagaa | | gcttctgcac | | aagtttcctt | | | | | 1369 |
| Arg | Phe | Gln | Ser | Gly | | | | | | | | | | | | |
| 410 | | | | | | | | | | | | | | | | |

| | | |
|---|---|---|
| accacctcct cttggaccta tgcttggcca acagcatgca gtcttccatc tgctttctct | 1429 |
| tcatactgtg gattatcttt ccttttggtt ctaaatcttc agtaatcggt tgcaagattg | 1489 |
| ttggcttacc tgcctgtgcc attcttcctc tgggccttca tgcttttctg cattgtgtta | 1549 |
| acatgtttca agtgcatggc cttctacggc ttctatgcca agcgtatgat actatagata | 1609 |
| tagtgtacca tactgccttt cttgcatgg cttggaccct atctgtgacc atgctcttct | 1669 |
| cccaatttaa gtggttctgt accacaaaga atcttgatac attttcacaa ataactgatt | 1729 |
| gggcttcata ctttatgctg gctgtgtcct gatacccatg tacttatggt aagctatttg | 1789 |
| ggtattacca ctgcaagaca aaactgtatat cttaacccgg ccatcaaccc aaattggaca | 1849 |
| ttccagacta ccaccaactg gatcccagct gccttcctgg gcttgtgcca tccaccctac | 1909 |
| tggttatctg atagaacaag ctggtggctg atgggtgact gctaggcgtg actgaggtaa | 1969 |
| tagatgaaaa gtgttctatg ttatcacatt ggttttcctg tacctttggt tactctacgt | 2029 |
| catgaccagc tgctggtgag tatgaagcct gtgctatagc ccaccctac tcactctcac | 2089 |
| cttctggttg aactttgctt aggccaccat tgtctgcctc atcaggaact atctgtagac | 2149 |
| gtagctccca gggagctcac agcaacaccc cctaccacca ggatgggcag taatatgtga | 2209 |
| cagagcccaa agcaaggctg gaacgcagtc ccttccagct tagtctttct gactcctagc | 2269 |
| caacaaacca tccttaatgt gagcaacttc tttaggcatt tcctcttttc ccgcctgca | 2329 |
| cccactctga acatgacaaa agttgccaga gttggggcat tgaggaagag atatttctgg | 2389 |
| aatgtgagac ttgttatgcc tctgtctctt tctctccctc cccctcccct ctccctcccc | 2449 |
| ctctccctcc catcccttt cttccctttc actctgaagc agtttttagct tattaacaga | 2509 |
| aaacaaaact ggcaaagcag gctttttgtt taatttgctc tttccctgat tgtgttcaga | 2569 |

-continued

```
gagaaaggtt atgattaaat gggctccaga tctcttattg cccttattcc tccaccccac    2629
ttcttttagc aaggtctgaa agtttcaaag ggagacctat aggttaattg tttagttata    2689
ggcagtgtta aattaggcag attttgacat atttatcttt ttaccccatc cattctacca    2749
aaacctgtgt atttcttgag tttttagttt gagaagctgg aaagagagag aagggcctca    2809
cagtgatggg ttcaggacgg gtcaaaggca aaggcctttg tgatgtgagc aaaggcaacc    2869
aaaacttagc ctcactccac ttttctaaag atggaaattc ttttttgggc cttggactgc    2929
ttctagggta gcattttgta ggtcactctt ctcctttgta ctattttgtt tctgccctga    2989
tgtcccttgg gtctccatcc tactgcctgg cttttcttggc cctcatttct cagcttctgc    3049
atttccttcc ctgctcctaa caaatgaaga agcaggctgc agcctgcatt gtggaagatc    3109
tccagcctcc ttgtagggga taaggggatg tgtagcatct gtgtggattt tcacggacaa    3169
gttccagtag gtgggacagt gatgccgtca aggcttagtt atgatcatgt gtggtgataa    3229
agaccatcca ccatcaccct ttccccttt ggttttgaag gccttgccct aagctacctg    3289
agggtttagg aggtctgaac acacacagtg gagaggttaa tctaggttgg gaaactgagt    3349
aaaagtccag agcaggaatg agcctgctgt ggcgtgggtt tggaaaggct cacaggaaag    3409
aacctgcagg atcaggggtg ggagggggagg cccctgaggt gctctccagg gaagaggggc    3469
tggggtttaa atagcatgct tggaggaaga ttttccttca atttttccta agtccttgaa    3529
ttcaccagta gattttgta aacaaaatgt aagtcgatgt tttctctcaa ttatcctagg    3589 agtgacctt atatgtgtgg aagattaatg gtatatgctc cttatgtcac tgtttttgag    3649
taaaatccat ttcctttctc tgtttcagcc tatgacaaaa ttgatgttta caggcctgct    3709
ttttgcttat aattgacaac atgtgcaaaa ataccaaatt tgtgtcctgt gcagtatgaa    3769
gaattcagtg aatattcatt aatgtattag cttgttttgc tctctgttca tatatggctc    3829
tattcttaga aatataattt gaatgtgatc tttcaatagt ctgaatattt tacaaattat    3889
agctatgtct tgtgaaaata acctcaaaaa gaaaaatacg actctgttgt cttacttgat    3949
atttcttgcc ctagtaatgt acttgacatt tatgttccta agcagtgtaa gtaccagtag    4009
aatttctctg tcaaactcaa tgatcattta gtactttgt cttctcccat gtgcttgaag    4069
gaaaaataaa gtgtcactac cgtatttctt gttttcatca aaaataaaa ataatttaaa    4129 aaacaaaaaa aaaaaaaaa                                                  4148
```

<210> SEQ ID NO 55
<211> LENGTH: 414
<212> TYPE: PRT
<213> ORGANISM: Homo sapiens

<400> SEQUENCE: 55

```
Met Ser Gly Leu Asp Gly Gly Asn Lys Leu Pro Leu Ala Gln Thr Gly
  1               5                  10                  15

Gly Leu Ala Ala Pro Asp His Ala Ser Gly Asp Pro Asp Leu Asp Gln
             20                  25                  30

Cys Gln Gly Leu Arg Glu Glu Thr Glu Ala Thr Gln Val Met Ala Asn
         35                  40                  45

Thr Gly Gly Gly Ser Leu Glu Thr Val Ala Glu Gly Gly Ala Ser Gln
     50                  55                  60

Asp Pro Val Asp Cys Gly Pro Ala Leu Arg Val Pro Val Ala Gly Ser
 65                  70                  75                  80

Arg Gly Gly Ala Ala Thr Lys Ala Gly Gln Glu Asp Ala Pro Pro Ser
```

-continued

```
                 85                  90                  95
Thr Lys Gly Leu Glu Ala Ala Ser Ala Glu Ala Ala Asp Ser Ser
            100                 105                 110
Gln Lys Asn Gly Cys Gln Leu Gly Glu Pro Arg Gly Pro Ala Gly Gln
        115                 120                 125
Lys Ala Leu Glu Ala Cys Gly Ala Gly Leu Gly Ser Gln Met Ile
    130                 135                 140
Pro Gly Lys Lys Ala Lys Glu Val Thr Thr Lys Lys Arg Ala Ile Ser
145                 150                 155                 160
Ala Ala Val Glu Lys Glu Gly Glu Ala Gly Ala Met Glu Glu Lys
                165                 170                 175
Lys Val Val Gln Lys Glu Lys Lys Val Ala Gly Gly Val Lys Glu Glu
            180                 185                 190
Thr Arg Pro Arg Ala Pro Lys Ile Asn Asn Cys Met Asp Ser Leu Glu
        195                 200                 205
Ala Ile Asp Gln Glu Leu Ser Asn Val Asn Ala Gln Ala Asp Arg Ala
    210                 215                 220
Phe Leu Gln Leu Glu Arg Lys Phe Gly Arg Met Arg Arg Leu His Met
225                 230                 235                 240
Gln Arg Arg Ser Phe Ile Ile Gln Asn Ile Pro Gly Phe Trp Val Thr
                245                 250                 255
Ala Phe Arg Asn His Pro Gln Leu Ser Pro Met Ile Ser Gly Gln Asp
            260                 265                 270
Glu Asp Met Leu Arg Tyr Met Ile Asn Leu Glu Val Glu Glu Leu Lys
        275                 280                 285
His Pro Arg Ala Gly Cys Lys Phe Lys Phe Ile Phe Gln Gly Asn Pro
    290                 295                 300
Tyr Phe Arg Asn Glu Gly Leu Val Lys Glu Tyr Glu Arg Arg Ser Ser
305                 310                 315                 320
Gly Arg Val Val Ser Leu Ser Thr Pro Ile Arg Trp His Arg Gly Gln
                325                 330                 335
Asp Pro Gln Ala His Ile His Arg Asn Arg Glu Gly Asn Thr Ile Pro
            340                 345                 350
Ser Phe Phe Asn Trp Phe Ser Asp His Ser Leu Leu Glu Phe Asp Arg
        355                 360                 365
Ile Ala Glu Ile Ile Lys Gly Glu Leu Trp Pro Asn Pro Leu Gln Tyr
    370                 375                 380
Tyr Leu Met Gly Glu Gly Pro Arg Arg Gly Ile Arg Gly Pro Pro Arg
385                 390                 395                 400
Gln Pro Val Glu Ser Ala Arg Ser Phe Arg Phe Gln Ser Gly
                405                 410
```

<210> SEQ ID NO 56
<211> LENGTH: 2643
<212> TYPE: DNA
<213> ORGANISM: Rattus sp.
<220> FEATURE:
<221> NAME/KEY: CDS
<222> LOCATION: (1)..(801)

<400> SEQUENCE: 56

```
ctg aaa ggg gcg agg ccc agg gtg gtg aac tcc acc tgc agt gac ttc      48
Leu Lys Gly Ala Arg Pro Arg Val Val Asn Ser Thr Cys Ser Asp Phe
  1               5                  10                  15 aac cat ggc tca gct ctg cac atc gct gcc tcg aat ctg tgc ctg ggc      96
Asn His Gly Ser Ala Leu His Ile Ala Ala Ser Asn Leu Cys Leu Gly
```

|  |  |  |  |  |  |  |  |  |  |  |  |  |  |  |
|---|---|---|---|---|---|---|---|---|---|---|---|---|---|---|
|  |  |  | 20 |  |  |  | 25 |  |  |  | 30 |  |  |  |
| gcc | gcc | aaa | tgt | tta | ctg | gag | cat | ggt | gcc | aac | cca | gcg | ctg | agg | aat | 144 |
| Ala | Ala | Lys | Cys | Leu | Leu | Glu | His | Gly | Ala | Asn | Pro | Ala | Leu | Arg | Asn |
|  |  | 35 |  |  |  |  | 40 |  |  |  |  | 45 |  |  |  |

| cga | aaa | gga | cag | gta | cca | gcg | gaa | gtg | gtc | cca | gac | ccc | atg | gac | atg | 192 |
| Arg | Lys | Gly | Gln | Val | Pro | Ala | Glu | Val | Val | Pro | Asp | Pro | Met | Asp | Met |
| 50 |  |  |  |  | 55 |  |  |  |  | 60 |  |  |  |  |  |

| tcc | ctt | gac | aag | gca | gag | gca | gcc | ctg | gtg | gcc | aag | gaa | ttg | cgg | acg | 240 |
| Ser | Leu | Asp | Lys | Ala | Glu | Ala | Ala | Leu | Val | Ala | Lys | Glu | Leu | Arg | Thr |
| 65 |  |  |  |  | 70 |  |  |  |  | 75 |  |  |  |  | 80 |

| ctg | cta | gaa | gag | gct | gtg | cca | ctg | tcc | tgc | acc | ctt | cct | aaa | gtc | aca | 288 |
| Leu | Leu | Glu | Glu | Ala | Val | Pro | Leu | Ser | Cys | Thr | Leu | Pro | Lys | Val | Thr |
|  |  |  |  | 85 |  |  |  |  | 90 |  |  |  |  | 95 |  |

| cta | ccc | aac | tat | gac | aac | gtc | cca | ggc | aat | ctc | atg | ctc | agc | gcg | ctg | 336 |
| Leu | Pro | Asn | Tyr | Asp | Asn | Val | Pro | Gly | Asn | Leu | Met | Leu | Ser | Ala | Leu |
|  |  |  |  | 100 |  |  |  |  | 105 |  |  |  |  | 110 |  |

| ggc | ctg | cgt | cta | gga | gac | cga | gtg | ctc | ctc | gat | ggc | cag | aag | acg | ggc | 384 |
| Gly | Leu | Arg | Leu | Gly | Asp | Arg | Val | Leu | Leu | Asp | Gly | Gln | Lys | Thr | Gly |
|  |  |  | 115 |  |  |  |  | 120 |  |  |  |  | 125 |  |  |

| acg | ctg | agg | ttc | tgc | ggg | acc | acc | gag | ttc | gcc | agt | ggc | cag | tgg | gtg | 432 |
| Thr | Leu | Arg | Phe | Cys | Gly | Thr | Thr | Glu | Phe | Ala | Ser | Gly | Gln | Trp | Val |
| 130 |  |  |  |  | 135 |  |  |  |  | 140 |  |  |  |  |  |

| ggc | gtg | gag | cta | gat | gaa | ccg | gaa | ggc | aag | aac | gac | ggc | agc | gtt | ggg | 480 |
| Gly | Val | Glu | Leu | Asp | Glu | Pro | Glu | Gly | Lys | Asn | Asp | Gly | Ser | Val | Gly |
| 145 |  |  |  |  | 150 |  |  |  |  | 155 |  |  |  |  | 160 |

| ggt | gtc | cgg | tac | ttc | atc | tgc | cct | ccc | aag | cag | ggt | ctc | ttt | gca | tct | 528 |
| Gly | Val | Arg | Tyr | Phe | Ile | Cys | Pro | Pro | Lys | Gln | Gly | Leu | Phe | Ala | Ser |
|  |  |  | 165 |  |  |  |  | 170 |  |  |  |  | 175 |  |  |

| gtg | tcc | aag | gtc | tcc | aag | gca | gtg | gat | gca | ccc | ccc | tca | tct | gtt | acc | 576 |
| Val | Ser | Lys | Val | Ser | Lys | Ala | Val | Asp | Ala | Pro | Pro | Ser | Ser | Val | Thr |
|  |  | 180 |  |  |  |  | 185 |  |  |  |  | 190 |  |  |  |

| tcc | acg | ccc | cgc | act | ccc | cgg | atg | gac | ttc | tcc | cgt | gta | acg | ggc | aaa | 624 |
| Ser | Thr | Pro | Arg | Thr | Pro | Arg | Met | Asp | Phe | Ser | Arg | Val | Thr | Gly | Lys |
|  |  | 195 |  |  |  |  | 200 |  |  |  |  | 205 |  |  |  |

| ggc | cgg | agg | gaa | cac | aaa | ggg | aag | aag | aag | tcc | cca | tct | tcc | cca | tct | 672 |
| Gly | Arg | Arg | Glu | His | Lys | Gly | Lys | Lys | Lys | Ser | Pro | Ser | Ser | Pro | Ser |
|  |  | 210 |  |  |  |  | 215 |  |  |  |  | 220 |  |  |  |

| ctg | ggc | agc | ctg | cag | cag | cgt | gaa | ggg | gcc | aaa | gct | gaa | gtt | gga | gac | 720 |
| Leu | Gly | Ser | Leu | Gln | Gln | Arg | Glu | Gly | Ala | Lys | Ala | Glu | Val | Gly | Asp |
| 225 |  |  |  |  | 230 |  |  |  |  | 235 |  |  |  |  | 240 |

| caa | gtc | ctt | gtg | gca | ggc | cag | aac | agg | gat | tgt | gcg | ttt | cta | tgg | gaa | 768 |
| Gln | Val | Leu | Val | Ala | Gly | Gln | Asn | Arg | Asp | Cys | Ala | Phe | Leu | Trp | Glu |
|  |  |  |  | 245 |  |  |  |  | 250 |  |  |  |  | 255 |  |

| gac | aga | ctt | tgc | tcc | agg | tta | ctg | gta | tgg | cat | tgaactggac | cagcccacgg | 821 |
| Asp | Arg | Leu | Cys | Ser | Arg | Leu | Leu | Val | Trp | His |  |  |  |
|  |  |  | 260 |  |  |  |  | 265 |  |  |  |  |  |

| gcaagcatga | cggctctgtg | ttcggtgtcc | ggtactttac | ctgtgccccg | aggcacgggg | 881 |
| tctttgcacc | agcatctcgt | atccagagga | ttggtggatc | cactgatccc | cctggagaca | 941 |
| gtgttggagc | aaaaaaagtg | catcaagtga | caatgacaca | gcccaaacgc | accttcacaa | 1001 |
| cagtccggac | cccaaaggac | attgcatcag | agaactctat | ctccaggtta | ctcttctgct | 1061 |
| gctggtttcc | ttggatgctg | agggcggaga | tgcagtctta | gagacctgga | tacctgacac | 1121 |
| agagacagag | tccctctag | catctcctga | cacaaggaga | cccagtcac | cctaagatag | 1181 |
| agattcccag | tgacacctcc | agaatagaaa | ccccgttagc | cagccctcga | ttactgaggt | 1241 |
| cccattatta | acagatctcc | catgacgact | cccccaaata | cagacctcat | gttaccccaa | 1301 |
| aagagattcc | ctgagtagca | ccttcaggct | agtccctgtc | ccctacccct | cagagcagat | 1361 |

-continued

```
ttcccccaat aaacattttc cacatcaccc aagggatgct gaccctctcc acgacaggac    1421
gttcttgagt taccagtgga ttagagtccc atgaatgaag accccccca ccccggttct     1481 ccttaagcat aggtcatacc tccagaatag ccagccacat cactatcccc atgtaacatc    1541
agtctcctca aaatggcgtg aggtcactag aaagaccttA tactctcctc tccttctcag    1601
agatgccctc cattcactta agtccctgtt ctcaccctg aacaagacac ctaattaacc     1661
ggcccactca cctcaattac aaacaccaaa atcgtcctgg aagcatgaat tacaggacag    1721
caagtcttcc tgccctctgc acccttgaga accccccagt gccttgtatg aagcccaccc    1781
cacatggccc acagtccctg tgctggccaa ggctcccaga aaattctcta tttttaaag     1841 taataacttc ccccctttg gggggatccc caaatttgga gaccccattc tagaacactg     1901
gggagttcaa attccagaga gaatatatat tatatataat ccccaattcc ccatgcttcc    1961
aagccctaca atctctagaa gaccccaaat ttctaattcc caggacttcc cctacccaag    2021
tcacagaatc ttcaaatccc cagggaatcc caaacttaag ataccaatcc caaaccctca    2081
ggaaatcccc caacacaagg tccttaggac cgggaggaag gaacctgttg ccaggagaac    2141
atcccaggct ctcagggcat ctcaaacctg actcccaggc accaggagac cccaaacaga    2201
aagtcccatc tttggaacaa ggataggact ctaataccct tagtccatgg atctttaatt    2261
tcccaacctc caaactccat gggccccacc ctcaaggaa ccccaagat ccaaatctct      2321 gataactaat atgtgcaggg ccccagggct ctaacaggac cccaaatcat ggagtcccta    2381
cttcaatcta ccttctggtc acaggtccaa gacactaaat ctgagtcatt ggccccaaag    2441
gacttcacag cacctgggcc agactaacag cctgagggag aacctgaggg ccccgtgggt    2501
ccagagcaga cctggggccc tgaccaccaa ggacagctca cgactgcccc ttcactgcat    2561
gtccctaaac tcagcatgac tcctgtcctc ttcaataaag acgtttctat ggcaaaaaaa    2621
aaaaaaaaaa aaaaaaaaaa aa                                            2643
```

<210> SEQ ID NO 57
<211> LENGTH: 267
<212> TYPE: PRT
<213> ORGANISM: Rattus sp.

<400> SEQUENCE: 57

```
Leu Lys Gly Ala Arg Pro Arg Val Val Asn Ser Thr Cys Ser Asp Phe
  1               5                  10                  15

Asn His Gly Ser Ala Leu His Ile Ala Ala Ser Asn Leu Cys Leu Gly
             20                  25                  30

Ala Ala Lys Cys Leu Leu Glu His Gly Ala Asn Pro Ala Leu Arg Asn
         35                  40                  45

Arg Lys Gly Gln Val Pro Ala Glu Val Val Pro Asp Pro Met Asp Met
     50                  55                  60

Ser Leu Asp Lys Ala Glu Ala Ala Leu Val Ala Lys Glu Leu Arg Thr
 65                  70                  75                  80

Leu Leu Glu Glu Ala Val Pro Leu Ser Cys Thr Leu Pro Lys Val Thr
                 85                  90                  95

Leu Pro Asn Tyr Asp Asn Val Pro Gly Asn Leu Met Leu Ser Ala Leu
            100                 105                 110

Gly Leu Arg Leu Gly Asp Arg Val Leu Leu Asp Gly Gln Lys Thr Gly
        115                 120                 125

Thr Leu Arg Phe Cys Gly Thr Thr Glu Phe Ala Ser Gly Gln Trp Val
    130                 135                 140
```

```
Gly Val Glu Leu Asp Glu Pro Glu Gly Lys Asn Asp Gly Ser Val Gly
145                 150                 155                 160

Gly Val Arg Tyr Phe Ile Cys Pro Pro Lys Gln Gly Leu Phe Ala Ser
            165                 170                 175

Val Ser Lys Val Ser Lys Ala Val Asp Ala Pro Pro Ser Ser Val Thr
        180                 185                 190

Ser Thr Pro Arg Thr Pro Arg Met Asp Phe Ser Arg Val Thr Gly Lys
    195                 200                 205

Gly Arg Arg Glu His Lys Gly Lys Lys Ser Pro Ser Ser Pro Ser
210                 215                 220

Leu Gly Ser Leu Gln Gln Arg Glu Gly Ala Lys Ala Glu Val Gly Asp
225                 230                 235                 240

Gln Val Leu Val Ala Gly Gln Asn Arg Asp Cys Ala Phe Leu Trp Glu
                245                 250                 255

Asp Arg Leu Cys Ser Arg Leu Leu Val Trp His
            260                 265

<210> SEQ ID NO 58
<211> LENGTH: 2929
<212> TYPE: DNA
<213> ORGANISM: Rattus sp.
<220> FEATURE:
<221> NAME/KEY: CDS
<222> LOCATION: (1)..(810)

<400> SEQUENCE: 58 gct gac tct acc tct aga tgg gct gag gcc ctc aga gaa atc tct ggt        48
Ala Asp Ser Thr Ser Arg Trp Ala Glu Ala Leu Arg Glu Ile Ser Gly
 1               5                  10                  15 cgc tta gct gaa atg cct gca gat agt gga tac cct gca tac ctt ggt        96
Arg Leu Ala Glu Met Pro Ala Asp Ser Gly Tyr Pro Ala Tyr Leu Gly
             20                  25                  30 gcc cga ctg gct tct ttc tat gag cga gca ggc aga gtg aaa tgt ctt       144
Ala Arg Leu Ala Ser Phe Tyr Glu Arg Ala Gly Arg Val Lys Cys Leu
         35                  40                  45 gga aac cct gag aga gaa ggg agt gtc agc att gta gga gca gtt tct       192
Gly Asn Pro Glu Arg Glu Gly Ser Val Ser Ile Val Gly Ala Val Ser
     50                  55                  60 cca cct ggt ggt gat ttt tct gat cca gtc aca tct gct act ctg ggt       240
Pro Pro Gly Gly Asp Phe Ser Asp Pro Val Thr Ser Ala Thr Leu Gly
 65                  70                  75                  80 att gtt cag gtg ttc tgg ggc ttg gat aag aag cta gct cag cgc aag       288
Ile Val Gln Val Phe Trp Gly Leu Asp Lys Lys Leu Ala Gln Arg Lys
                 85                  90                  95 cac ttc ccg tcc gtc aac tgg ctc att agc tac agc aag tac atg cgc       336
His Phe Pro Ser Val Asn Trp Leu Ile Ser Tyr Ser Lys Tyr Met Arg
            100                 105                 110 gcc ctg gac gag tac tat gac aaa cac ttc aca gag ttc gtg cct ctg       384
Ala Leu Asp Glu Tyr Tyr Asp Lys His Phe Thr Glu Phe Val Pro Leu
        115                 120                 125 agg acc aaa gct aag gag att ctg cag gaa gag gag gat ctg gcg gaa       432
Arg Thr Lys Ala Lys Glu Ile Leu Gln Glu Glu Glu Asp Leu Ala Glu
    130                 135                 140 atc gtg cag ctc gtg gga aag gcg tct tta gca gag aca gat aaa atc       480
Ile Val Gln Leu Val Gly Lys Ala Ser Leu Ala Glu Thr Asp Lys Ile
145                 150                 155                 160 acc ctg gag gta gca aaa ctt atc aaa gat gac ttc cta caa caa aat       528
Thr Leu Glu Val Ala Lys Leu Ile Lys Asp Asp Phe Leu Gln Gln Asn
                165                 170                 175
```

```
ggg tac act cct tat gac agg ttc tgt cca ttc tat aag acg gtg ggg      576
Gly Tyr Thr Pro Tyr Asp Arg Phe Cys Pro Phe Tyr Lys Thr Val Gly
        180                 185                 190 atg ctg tcc aac atg att tca ttc tat gat atg gcc cgc cgg gct gtg      624
Met Leu Ser Asn Met Ile Ser Phe Tyr Asp Met Ala Arg Arg Ala Val
            195                 200                 205 gag acc acc gcc cag agt gac aat aag atc aca tgg tcc att atc cgt      672
Glu Thr Thr Ala Gln Ser Asp Asn Lys Ile Thr Trp Ser Ile Ile Arg
    210                 215                 220 gag cac atg ggg gag att ctc tat aaa ctt tcc tcc atg aaa ttc aag      720
Glu His Met Gly Glu Ile Leu Tyr Lys Leu Ser Ser Met Lys Phe Lys
225                 230                 235                 240 gat cca gtg aag gat ggc gag gca aag atc aag gcc gac tac gca cag      768
Asp Pro Val Lys Asp Gly Glu Ala Lys Ile Lys Ala Asp Tyr Ala Gln
                245                 250                 255 ctt ctt gaa gat atg cag aac gca ttc cgt agc ctg gaa gat             810
Leu Leu Glu Asp Met Gln Asn Ala Phe Arg Ser Leu Glu Asp
            260                 265                 270 tagaactgtg acttctctcc tcctcttccg cagctcatat gtgtatattt tcctgaattt    870
ctcatctcca acctttgct tccatattgt gcagctttga actagtgcc tcgtgcgttc      930 tcgttcattt tgctgtttct ttggtaggtc ttataaaaca cacattcctg tgctccgctg    990
tctgaaggag ctcctgacct ttgtctgaag tggtgaatga agtgcatatg atacacagtg   1050
taacatacac attgtaacat atacgttctg taaacttgta tgtaaggtga ctacccttc    1110 cctcctctcc agtaaactgt aaacaggact actgcatgtg ctctatttgg gatggaaggc   1170
cagatctcca taccgtggac aggtacataa ggaaactaga ccacttgcaa cttagtgttt   1230
gttgagtaac cattttgcag gaagtatttc catttaaaaa acaaaagatt aatgttccaa    1290
ttatttgtag cttccccagt atcaatcagg actgtttgtg gcgcacttgg gaactatttt    1350
gttttcctaa cagacgtttg caaggctgaa cgtaatagat aaatcagttc cctctgaaag   1410
tgtgaaagta aaagagagc taggtggtca gacttaaatt gacatcgtct tgtttaagca     1470
tatttatttt cactgagaga tttaatatca aggactttta tatctcaat tactaggaaa    1530 tctttttttta agtacaattt aaaaatcatt gaaaatgtga tccacatcat agccattttc   1590 cttatatta gtcagatgag ctcagagtgg ggagggtgtg ggttagaata ccacaaggac     1650
acgcagcagt gcctgcaggc agtgtggccg ggggcagag cggcattgtt ttcacgaggt    1710
acgtgtgtgg cgtgtgtgtt tgcttgttga cactctgaaa acagcaagct taccagttcc   1770
aggaaatatt ttgttttctt tcactggctc agaaagctcc tcaaagtacc tggtccctga   1830
agcttcctat ctgttaatag agacgagaga ggttcttaaa tttaactggt gacaaaacaa    1890
aaagaaaaaa aagatcgatt tttgtcttgc tgttttggtg tgtttaaata ataattccat   1950
atttgcataa cgaggctcgc ttctgagagc ttggagatcg tgctccctct tcactctccg   2010
gggtgataat gctggcgcca tgctacctct tcaggagggg aaggggattg aacatggcta   2070
acactctcaa gtacacaagc gtaacgacaa agtatttatt ttaagccttg gtatgttgtt   2130
taaattatta ggtggtgcat ttcttatggt cttttgggta gacatagtat acacttcaga   2190
tgtaatgtgt aaatccttgc tagtgcatgt ctacacgata gactgctatt caagaaggat   2250
attcttccac ataacaattt aaaaactatt aaatcagata tggattatgc aatgacttgt   2310
tgagaggtgg attaacggtg ctgcttaatc agtttgcttc caatatggct tcgtatccag   2370
aagccctgac tagtggagat gagaaagatt tcaaaacctg tctgcctaca cctaccagca   2430
```

-continued

```
acctaggctt gtgatcagaa tgaatgatcc caagaaacta cttgaccaag tgtgttttgt    2490
tgtcctggat ttgagatgtg cgttcttcct ccctctgaga ctgttgatgt atgagtgtga    2550
agaagttaca gaaacaacgc tcagattttc acggtaactt tccctctgcc cacactgtag    2610
agtttcagat tgttcactga tagtgcttct ttcgtaagga tgtgttaaaa tatagcagtc    2670 ttttaaaag attatgcagt tctctattta ttgtgctgtg cctggtccta agtgcagccg     2730
gttaaacaag tttcatatgt attttttccag tgttaaatct catacctatg cccttttggaa  2790 agctccatcc tgaacaatga atagaagagg ctatataaat tgcctcctta tccttaagat    2850
ttcactatct ttatgttaag agtaatgtat aattattaaa atctatgaaa aataaaaagt   2910
ggatttaaat taagagatc                                                 2929
```

<210> SEQ ID NO 59
<211> LENGTH: 270
<212> TYPE: PRT
<213> ORGANISM: Rattus sp.

<400> SEQUENCE: 59

```
Ala Asp Ser Thr Ser Arg Trp Ala Glu Ala Leu Arg Glu Ile Ser Gly
  1               5                  10                  15

Arg Leu Ala Glu Met Pro Ala Asp Ser Gly Tyr Pro Ala Tyr Leu Gly
                 20                  25                  30

Ala Arg Leu Ala Ser Phe Tyr Glu Arg Ala Gly Arg Val Lys Cys Leu
             35                  40                  45

Gly Asn Pro Glu Arg Glu Gly Ser Val Ser Ile Val Gly Ala Val Ser
         50                  55                  60

Pro Pro Gly Gly Asp Phe Ser Asp Pro Val Thr Ser Ala Thr Leu Gly
 65                  70                  75                  80

Ile Val Gln Val Phe Trp Gly Leu Asp Lys Lys Leu Ala Gln Arg Lys
                 85                  90                  95

His Phe Pro Ser Val Asn Trp Leu Ile Ser Tyr Ser Lys Tyr Met Arg
            100                 105                 110

Ala Leu Asp Glu Tyr Tyr Asp Lys His Phe Thr Glu Phe Val Pro Leu
        115                 120                 125

Arg Thr Lys Ala Lys Glu Ile Leu Gln Glu Glu Asp Leu Ala Glu
    130                 135                 140

Ile Val Gln Leu Val Gly Lys Ala Ser Leu Ala Glu Thr Asp Lys Ile
145                 150                 155                 160

Thr Leu Glu Val Ala Lys Leu Ile Lys Asp Asp Phe Leu Gln Gln Asn
                165                 170                 175

Gly Tyr Thr Pro Tyr Asp Arg Phe Cys Pro Phe Tyr Lys Thr Val Gly
            180                 185                 190

Met Leu Ser Asn Met Ile Ser Phe Tyr Asp Met Ala Arg Arg Ala Val
        195                 200                 205

Glu Thr Thr Ala Gln Ser Asp Asn Lys Ile Thr Trp Ser Ile Ile Arg
    210                 215                 220

Glu His Met Gly Glu Ile Leu Tyr Lys Leu Ser Ser Met Lys Phe Lys
225                 230                 235                 240

Asp Pro Val Lys Asp Gly Glu Ala Lys Ile Lys Ala Asp Tyr Ala Gln
                245                 250                 255

Leu Leu Glu Asp Met Gln Asn Ala Phe Arg Ser Leu Glu Asp
            260                 265                 270
```

<210> SEQ ID NO 60

<211> LENGTH: 1489
<212> TYPE: DNA
<213> ORGANISM: Rattus sp.
<220> FEATURE:
<221> NAME/KEY: CDS
<222> LOCATION: (1)..(1053)

<400> SEQUENCE: 60

| | | | | | | | | | | | | | | | | |
|---|---|---|---|---|---|---|---|---|---|---|---|---|---|---|---|---|
| gca | cgg | ctc | ccg | gcc | ccg | gag | cat | gcg | cga | cag | cag | ccc | ctc | ctc | tcc | 48 |
| Ala | Arg | Leu | Pro | Ala | Pro | Glu | His | Ala | Arg | Gln | Gln | Pro | Leu | Leu | Ser | |
| 1 | | | | 5 | | | | | 10 | | | | | 15 | | |
| ggc | cct | gag | ccc | gga | tcg | tcc | gcc | cgg | gtt | cca | gtt | ccc | ggc | gtg | gcc | 96 |
| Gly | Pro | Glu | Pro | Gly | Ser | Ser | Ala | Arg | Val | Pro | Val | Pro | Gly | Val | Ala | |
| | | 20 | | | | | 25 | | | | | 30 | | | | |
| agt | agg | cgg | cag | ccg | cga | ggc | ggc | aag | cca | ccc | agc | ggg | gac | ggc | ctg | 144 |
| Ser | Arg | Arg | Gln | Pro | Arg | Gly | Gly | Lys | Pro | Pro | Ser | Gly | Asp | Gly | Leu | |
| | | | 35 | | | | | 40 | | | | | 45 | | | |
| gag | tcg | ggc | ccc | tct | cca | cgc | ccc | ctt | ctc | cac | gcg | cgc | ggg | gag | gca | 192 |
| Glu | Ser | Gly | Pro | Ser | Pro | Arg | Pro | Leu | Leu | His | Ala | Arg | Gly | Glu | Ala | |
| | 50 | | | | | 55 | | | | | 60 | | | | | |
| ggg | ctc | cac | cgc | cag | tct | gga | agg | gtt | cca | cat | aca | gga | acg | gcc | tac | 240 |
| Gly | Leu | His | Arg | Gln | Ser | Gly | Arg | Val | Pro | His | Thr | Gly | Thr | Ala | Tyr | |
| 65 | | | | | 70 | | | | | 75 | | | | | 80 | |
| ttc | gca | gat | gag | ccc | acc | gag | gct | cag | gct | ccg | ggc | gga | ttc | tgc | gtg | 288 |
| Phe | Ala | Asp | Glu | Pro | Thr | Glu | Ala | Gln | Ala | Pro | Gly | Gly | Phe | Cys | Val | |
| | | | | 85 | | | | | 90 | | | | | 95 | | |
| tca | ccc | tcg | ctc | ctt | ggg | gtc | cgc | tgg | ccg | gcc | tgt | gcc | acc | cgg | acg | 336 |
| Ser | Pro | Ser | Leu | Leu | Gly | Val | Arg | Trp | Pro | Ala | Cys | Ala | Thr | Arg | Thr | |
| | | | 100 | | | | | 105 | | | | | 110 | | | |
| ccc | ggc | tca | ctg | cct | ctg | tct | ccc | cca | tca | gcg | cag | ccc | cgg | acg | cta | 384 |
| Pro | Gly | Ser | Leu | Pro | Leu | Ser | Pro | Pro | Ser | Ala | Gln | Pro | Arg | Thr | Leu | |
| | | 115 | | | | | 120 | | | | | 125 | | | | |
| tgg | ccc | acc | cct | cca | gct | ggc | ccc | tcg | agt | agg | atg | gta | gca | cgt | aac | 432 |
| Trp | Pro | Thr | Pro | Pro | Ala | Gly | Pro | Ser | Ser | Arg | Met | Val | Ala | Arg | Asn | |
| | 130 | | | | | 135 | | | | | 140 | | | | | |
| cag | gtg | gca | gcc | gac | aat | gcg | atc | tcc | ccg | gca | tca | gag | ccc | cga | cgg | 480 |
| Gln | Val | Ala | Ala | Asp | Asn | Ala | Ile | Ser | Pro | Ala | Ser | Glu | Pro | Arg | Arg | |
| 145 | | | | | 150 | | | | | 155 | | | | | 160 | |
| cgg | cca | gag | cca | tcc | tcg | tcc | tcg | tct | tcg | tcc | tcg | ccg | gcg | gcc | ccg | 528 |
| Arg | Pro | Glu | Pro | Ser | Ser | Ser | Ser | Ser | Ser | Ser | Ser | Pro | Ala | Ala | Pro | |
| | | | | 165 | | | | | 170 | | | | | 175 | | |
| gcg | cgt | ccc | cgg | ccc | tgc | ccg | gtg | gtc | ccg | gcc | ccg | gct | ccg | ggc | gac | 576 |
| Ala | Arg | Pro | Arg | Pro | Cys | Pro | Val | Val | Pro | Ala | Pro | Ala | Pro | Gly | Asp | |
| | | | 180 | | | | | 185 | | | | | 190 | | | |
| act | cac | ttc | cgc | acc | ttc | cgc | tcc | cac | tct | gat | tac | cgg | cgc | atc | acg | 624 |
| Thr | His | Phe | Arg | Thr | Phe | Arg | Ser | His | Ser | Asp | Tyr | Arg | Arg | Ile | Thr | |
| | | 195 | | | | | 200 | | | | | 205 | | | | |
| cgg | acc | agc | gct | ctc | ctg | gac | gcc | tgc | ggc | ttc | tac | tgg | gga | ccc | ctg | 672 |
| Arg | Thr | Ser | Ala | Leu | Leu | Asp | Ala | Cys | Gly | Phe | Tyr | Trp | Gly | Pro | Leu | |
| | 210 | | | | | 215 | | | | | 220 | | | | | |
| agc | gtg | cat | ggg | gcg | cac | gaa | cgg | ctg | cgt | gcc | gag | ccc | gtg | ggc | acc | 720 |
| Ser | Val | His | Gly | Ala | His | Glu | Arg | Leu | Arg | Ala | Glu | Pro | Val | Gly | Thr | |
| 225 | | | | | 230 | | | | | 235 | | | | | 240 | |
| ttc | ttg | gtg | cgc | gac | agt | cgc | cag | cgg | aac | tgc | ttc | ttc | gcg | ctc | agc | 768 |
| Phe | Leu | Val | Arg | Asp | Ser | Arg | Gln | Arg | Asn | Cys | Phe | Phe | Ala | Leu | Ser | |
| | | | | 245 | | | | | 250 | | | | | 255 | | |
| gtg | aag | atg | gct | tcg | ggc | ccc | acg | agc | att | cgt | gtg | cac | ttc | cag | gcc | 816 |
| Val | Lys | Met | Ala | Ser | Gly | Pro | Thr | Ser | Ile | Arg | Val | His | Phe | Gln | Ala | |
| | | | 260 | | | | | 265 | | | | | 270 | | | |
| ggc | cgc | ttc | cac | ctg | gac | ggc | agc | cgc | gag | acc | ttc | gac | tgc | ctc | ttc | 864 |
| Gly | Arg | Phe | His | Leu | Asp | Gly | Ser | Arg | Glu | Thr | Phe | Asp | Cys | Leu | Phe | |

-continued

```
                    275                 280                 285
gag ctg ctg gag cac tac gtg gcg gcg ccg cgc cgc atg ttg ggg gcc    912
Glu Leu Leu Glu His Tyr Val Ala Ala Pro Arg Arg Met Leu Gly Ala
    290                 295                 300 cca ctg cgc cag cgc cgc gtg cgg ccg ctg cag gag ctg tgt cgc cag    960
Pro Leu Arg Gln Arg Arg Val Arg Pro Leu Gln Glu Leu Cys Arg Gln
305                 310                 315                 320 cgc atc gtg gcc gcc gtg ggt cgc gag aac ctg gca cgc atc cct ctt   1008
Arg Ile Val Ala Ala Val Gly Arg Glu Asn Leu Ala Arg Ile Pro Leu
                325                 330                 335 aac ccg gta ctc cgt gac tac ctg agt tcc ttc ccc ttc cag atc        1053
Asn Pro Val Leu Arg Asp Tyr Leu Ser Ser Phe Pro Phe Gln Ile
            340                 345                 350 tgaccggctg ccgccgtgcc cgcagcatta agtgggagcg ccttattatt tcttattatt  1113
aattattatt attttctgg aaccacgtgg gagccctccc cgcctaggtc ggagggagtg   1173
ggtgtggagg gtgagatgcc tcccacttct ggctggagac cttatcccgc ctctcggggg  1233
gcctcccctc ctggtgctcc ctcccggtcc cctggttgt agcagcttgt gtctggggcc   1293
aggacctgaa ctccacgcct acctctccat gtttacatgt tcccagtatc tttgcacaaa  1353
ccaggggtgg gggagggtct ctggcttcat tttttctgctg tgcagaatat tctatttat  1413
atttttacat ccagtttaga taataaactt tattatgaaa gttttttttt taaagaaaaa  1473
aaaaaaaaaa aaaaaa                                                  1489
```

<210> SEQ ID NO 61
<211> LENGTH: 351
<212> TYPE: PRT
<213> ORGANISM: Rattus sp.

<400> SEQUENCE: 61

```
Ala Arg Leu Pro Ala Pro Glu His Ala Arg Gln Gln Pro Leu Leu Ser
1               5                   10                  15

Gly Pro Glu Pro Gly Ser Ser Ala Arg Val Pro Val Pro Gly Val Ala
            20                  25                  30

Ser Arg Arg Gln Pro Arg Gly Gly Lys Pro Pro Ser Gly Asp Gly Leu
        35                  40                  45

Glu Ser Gly Pro Ser Pro Arg Pro Leu Leu His Ala Arg Gly Glu Ala
    50                  55                  60

Gly Leu His Arg Gln Ser Gly Arg Val Pro His Thr Gly Thr Ala Tyr
65                  70                  75                  80

Phe Ala Asp Glu Pro Thr Glu Ala Gln Ala Pro Gly Gly Phe Cys Val
                85                  90                  95

Ser Pro Ser Leu Leu Gly Val Arg Trp Pro Ala Cys Ala Thr Arg Thr
            100                 105                 110

Pro Gly Ser Leu Pro Leu Ser Pro Pro Ser Ala Gln Pro Arg Thr Leu
        115                 120                 125

Trp Pro Thr Pro Pro Ala Gly Pro Ser Ser Arg Met Val Ala Arg Asn
    130                 135                 140

Gln Val Ala Ala Asp Asn Ala Ile Ser Pro Ala Ser Glu Pro Arg Arg
145                 150                 155                 160

Arg Pro Glu Pro Ser Ser Ser Ser Ser Ser Pro Ala Ala Pro
                165                 170                 175

Ala Arg Pro Arg Pro Cys Pro Val Val Pro Ala Pro Ala Pro Gly Asp
            180                 185                 190

Thr His Phe Arg Thr Phe Arg Ser His Ser Asp Tyr Arg Arg Ile Thr
```

-continued

```
                  195                 200                 205
Arg Thr Ser Ala Leu Leu Asp Ala Cys Gly Phe Tyr Trp Gly Pro Leu
    210                 215                 220

Ser Val His Gly Ala His Glu Arg Leu Arg Ala Glu Pro Val Gly Thr
225                 230                 235                 240

Phe Leu Val Arg Asp Ser Arg Gln Arg Asn Cys Phe Phe Ala Leu Ser
                245                 250                 255

Val Lys Met Ala Ser Gly Pro Thr Ser Ile Arg Val His Phe Gln Ala
            260                 265                 270

Gly Arg Phe His Leu Asp Gly Ser Arg Glu Thr Phe Asp Cys Leu Phe
        275                 280                 285

Glu Leu Leu Glu His Tyr Val Ala Ala Pro Arg Arg Met Leu Gly Ala
    290                 295                 300

Pro Leu Arg Gln Arg Arg Val Arg Pro Leu Gln Glu Leu Cys Arg Gln
305                 310                 315                 320

Arg Ile Val Ala Ala Val Gly Arg Glu Asn Leu Ala Arg Ile Pro Leu
                325                 330                 335

Asn Pro Val Leu Arg Asp Tyr Leu Ser Ser Phe Pro Phe Gln Ile
            340                 345                 350

<210> SEQ ID NO 62
<211> LENGTH: 1194
<212> TYPE: DNA
<213> ORGANISM: Rattus sp.
<220> FEATURE:
<221> NAME/KEY: CDS
<222> LOCATION: (130)..(765)

<400> SEQUENCE: 62
ggcacggctc ccggccccgg agcatgcgcg acagcagccc cggaaccccc agccgcggcg      60
ccccgcgtcc cgccgccagc gcagcccggg acgctatggc ccaccccctcc agctggcccc     120 tcgagtagg atg gta gca cgt aac cag gtg gca gcc gac aat gcg atc tcc     171
            Met Val Ala Arg Asn Gln Val Ala Ala Asp Asn Ala Ile Ser
              1               5                  10 ccg gca tca gag ccc cga cgg cgg cca gag cca tcg tcg tcg tcg tct     219
Pro Ala Ser Glu Pro Arg Arg Arg Pro Glu Pro Ser Ser Ser Ser Ser
 15                  20                  25                  30 tcg tcc tcg ccg gcg gcc ccg gcg cgt ccc cgg ccc tgc ccg gtg gtc     267
Ser Ser Ser Pro Ala Ala Pro Ala Arg Pro Arg Pro Cys Pro Val Val
                 35                  40                  45 ccg gcc ccg gct ccg ggc gac act cac ttc cgc acc ttc cgc tcc cac     315
Pro Ala Pro Ala Pro Gly Asp Thr His Phe Arg Thr Phe Arg Ser His
             50                  55                  60 tct gat tac cgg cgc atc acg cgg acc agc gct ctc ctg gac gcc tgc     363
Ser Asp Tyr Arg Arg Ile Thr Arg Thr Ser Ala Leu Leu Asp Ala Cys
         65                  70                  75 ggc ttc tac tgg gga ccc ctg agc gtg cat ggg gcg cac gaa cgg ctg     411
Gly Phe Tyr Trp Gly Pro Leu Ser Val His Gly Ala His Glu Arg Leu
     80                  85                  90 cgt gcc gag ccc gtg ggc acc ttc ttg gtg cgc gac agt cgc cag cgg     459
Arg Ala Glu Pro Val Gly Thr Phe Leu Val Arg Asp Ser Arg Gln Arg
 95                 100                 105                 110 aac tgc ttc ttc gcg ctc agc gtg aag atg gct tcg ggc ccc acg agc     507
Asn Cys Phe Phe Ala Leu Ser Val Lys Met Ala Ser Gly Pro Thr Ser
                115                 120                 125 att cgt gtg cac ttc cag gcc ggc cgc ttc cac ctg gac ggc agc cgc     555
Ile Arg Val His Phe Gln Ala Gly Arg Phe His Leu Asp Gly Ser Arg
            130                 135                 140
```

-continued

```
gag acc ttc gac tgc ctc ttc gag ctg ctg gag cac tac gtg gcg gcg    603
Glu Thr Phe Asp Cys Leu Phe Glu Leu Leu Glu His Tyr Val Ala Ala
        145                 150                 155 ccg cgc cgc atg ttg ggg gcc cca ctg cgc cag cgc gtg cgg ccg        651
Pro Arg Arg Met Leu Gly Ala Pro Leu Arg Gln Arg Val Arg Pro
    160                 165                 170 ctg cag gag ctg tgt cgc cag cgc atc gtg gcc gcc gtg ggt cgc gag    699
Leu Gln Glu Leu Cys Arg Gln Arg Ile Val Ala Ala Val Gly Arg Glu
175                 180                 185                 190 aac ctg gca cgc atc cct ctt aac ccg gta ctc cgt gac tac ctg agt    747
Asn Leu Ala Arg Ile Pro Leu Asn Pro Val Leu Arg Asp Tyr Leu Ser
                195                 200                 205 tcc ttc ccc ttc cag atc tgaccggctg ccgccgtgcc cgcagcatta           795
Ser Phe Pro Phe Gln Ile
                210 agtgggagcg ccttattatt tcttattatt aattattatt attttttctgg aaccacgtgg  855 gagccctccc cgcctaggtc ggagggagtg ggtgtggagg gtgagatgcc tcccacttct    915 ggctggagac cttatcccgc ctctcggggg gcctcccctc ctggtgctcc ctcccggtcc    975 ccctggttgt agcagcttgt gtctggggcc aggacctgaa ctccacgcct acctctccat   1035 gtttacatgt tcccagtatc tttgcacaaa ccaggggtgg gggagggtct ctggcttcat   1095 ttttctgctg tgcagaatat tctattttat attttttacat ccagtttaga taataaactt  1155 tattatgaaa gttttttttt taaaaaaaaa aaaaaaaaa                          1194
```

<210> SEQ ID NO 63
<211> LENGTH: 212
<212> TYPE: PRT
<213> ORGANISM: Rattus sp.

<400> SEQUENCE: 63

```
Met Val Ala Arg Asn Gln Val Ala Ala Asp Asn Ala Ile Ser Pro Ala
1               5                   10                  15

Ser Glu Pro Arg Arg Pro Glu Pro Ser Ser Ser Ser Ser Ser Ser Ser
            20                  25                  30

Ser Pro Ala Ala Pro Ala Arg Pro Arg Pro Cys Pro Val Val Pro Ala
        35                  40                  45

Pro Ala Pro Gly Asp Thr His Phe Arg Thr Phe Arg Ser His Ser Asp
    50                  55                  60

Tyr Arg Arg Ile Thr Arg Thr Ser Ala Leu Leu Asp Ala Cys Gly Phe
65                  70                  75                  80

Tyr Trp Gly Pro Leu Ser Val His Gly Ala His Glu Arg Leu Arg Ala
                85                  90                  95

Glu Pro Val Gly Thr Phe Leu Val Arg Asp Ser Arg Gln Arg Asn Cys
            100                 105                 110

Phe Phe Ala Leu Ser Val Lys Met Ala Ser Gly Pro Thr Ser Ile Arg
        115                 120                 125

Val His Phe Gln Ala Gly Arg Phe His Leu Asp Gly Ser Arg Glu Thr
    130                 135                 140

Phe Asp Cys Leu Phe Glu Leu Leu Glu His Tyr Val Ala Ala Pro Arg
145                 150                 155                 160

Arg Met Leu Gly Ala Pro Leu Arg Gln Arg Val Arg Pro Leu Gln
                165                 170                 175

Glu Leu Cys Arg Gln Arg Ile Val Ala Ala Val Gly Arg Glu Asn Leu
            180                 185                 190
```

```
Ala Arg Ile Pro Leu Asn Pro Val Leu Arg Asp Tyr Leu Ser Ser Phe
        195                 200                 205

Pro Phe Gln Ile
    210

<210> SEQ ID NO 64
<211> LENGTH: 600
<212> TYPE: DNA
<213> ORGANISM: Rattus sp.
<220> FEATURE:
<221> NAME/KEY: CDS
<222> LOCATION: (52)..(336)

<400> SEQUENCE: 64
cttccaaaga ctgcagcgcc tcagggccca ggtttcaaca gattcttcaa a atg cca      57
                                                         Met Pro
                                                           1 tcc caa atg gag cat gcc atg gaa acc atg atg ctt aca ttt cac agg     105
Ser Gln Met Glu His Ala Met Glu Thr Met Met Leu Thr Phe His Arg
        5                  10                  15 ttt gca ggg gaa aaa aac tac ttg aca aag gag gac ctg aga gtg ctc     153
Phe Ala Gly Glu Lys Asn Tyr Leu Thr Lys Glu Asp Leu Arg Val Leu
 20                  25                  30 atg gaa agg gag ttc cct ggg ttt ttg gaa aat caa aag gac cct ctg     201
Met Glu Arg Glu Phe Pro Gly Phe Leu Glu Asn Gln Lys Asp Pro Leu
 35                  40                  45                  50 gct gtg gac aaa ata atg aaa gac ctg gac cag tgc cga gat gga aaa     249
Ala Val Asp Lys Ile Met Lys Asp Leu Asp Gln Cys Arg Asp Gly Lys
                 55                  60                  65 gtg ggc ttc cag agc ttt cta tca cta gtg gcg ggg ctc atc att gca     297
Val Gly Phe Gln Ser Phe Leu Ser Leu Val Ala Gly Leu Ile Ile Ala
             70                  75                  80 tgc aat gac tat ttt gta gta cac atg aag cag aag aag taggccaact     346
Cys Asn Asp Tyr Phe Val Val His Met Lys Gln Lys Lys
         85                  90                  95 ggagccctgg tacccacacc ttgatgcgtc ctctcccatg gggtcaactg aggaatctgc    406
cccactgctt cctgtgagca gatcaggacc cttaggaaat gtgcaaataa catccaactc    466
caattcgaca agcagagaaa gaaaagttaa tccaatgaca gaggagcttt cgagttttat    526
attgtttgca tccggttgcc ctcaataaag aaagtctttt tttttaagtt ccgaaaaaaa    586
aaaaaaaaaa aaaa                                                     600

<210> SEQ ID NO 65
<211> LENGTH: 95
<212> TYPE: PRT
<213> ORGANISM: Rattus sp.

<400> SEQUENCE: 65

Met Pro Ser Gln Met Glu His Ala Met Glu Thr Met Met Leu Thr Phe
 1               5                  10                  15

His Arg Phe Ala Gly Glu Lys Asn Tyr Leu Thr Lys Glu Asp Leu Arg
             20                  25                  30

Val Leu Met Glu Arg Glu Phe Pro Gly Phe Leu Glu Asn Gln Lys Asp
         35                  40                  45

Pro Leu Ala Val Asp Lys Ile Met Lys Asp Leu Asp Gln Cys Arg Asp
     50                  55                  60

Gly Lys Val Gly Phe Gln Ser Phe Leu Ser Leu Val Ala Gly Leu Ile
 65                  70                  75                  80

Ile Ala Cys Asn Asp Tyr Phe Val Val His Met Lys Gln Lys Lys
             85                  90                  95
```

<210> SEQ ID NO 66
<211> LENGTH: 639
<212> TYPE: DNA
<213> ORGANISM: Rattus sp.
<220> FEATURE:
<221> NAME/KEY: CDS
<222> LOCATION: (1)..(636)

<400> SEQUENCE: 66

```
atg gcg tac gcc tat ctc ttc aag tac atc atc atc ggc gac aca ggt      48
Met Ala Tyr Ala Tyr Leu Phe Lys Tyr Ile Ile Ile Gly Asp Thr Gly
 1               5                  10                  15 gtt ggt aaa tcg tgc tta ttg cta cag ttt aca gac aag agg ttt cag      96
Val Gly Lys Ser Cys Leu Leu Leu Gln Phe Thr Asp Lys Arg Phe Gln
             20                  25                  30 ccg gtg cat gac ctc aca att ggt gta gag ttt ggt gct cga atg ata     144
Pro Val His Asp Leu Thr Ile Gly Val Glu Phe Gly Ala Arg Met Ile
         35                  40                  45 acc att gat ggg aaa cag ata aaa ctc cag atc tgg gat aca gca ggg     192
Thr Ile Asp Gly Lys Gln Ile Lys Leu Gln Ile Trp Asp Thr Ala Gly
     50                  55                  60 cag gag tcc ttt cgt tct atc aca agg tca tat tac aga ggt gca gcg     240
Gln Glu Ser Phe Arg Ser Ile Thr Arg Ser Tyr Tyr Arg Gly Ala Ala
 65                  70                  75                  80 ggg gct tta cta gtg tat gat att aca agg aga gac acg ttc aac cac     288
Gly Ala Leu Leu Val Tyr Asp Ile Thr Arg Arg Asp Thr Phe Asn His
                 85                  90                  95 ttg aca acc tgg tta gaa gac gcc cgt cag cat tcc aat tcc aac atg     336
Leu Thr Thr Trp Leu Glu Asp Ala Arg Gln His Ser Asn Ser Asn Met
            100                 105                 110 gtc atc atg ctt att gga aat aaa agt gac tta gaa tct agg aga gaa     384
Val Ile Met Leu Ile Gly Asn Lys Ser Asp Leu Glu Ser Arg Arg Glu
        115                 120                 125 gtg aaa aag gaa gaa ggt gaa gct ttt gca cga gag cat gga ctt atc     432
Val Lys Lys Glu Glu Gly Glu Ala Phe Ala Arg Glu His Gly Leu Ile
    130                 135                 140 ttc atg gaa act tct gcc aag act gct tct aat gta gag gag gca ttt     480
Phe Met Glu Thr Ser Ala Lys Thr Ala Ser Asn Val Glu Glu Ala Phe
145                 150                 155                 160 att aac aca gca aaa gaa att tat gaa aaa atc caa gaa ggg gtc ttt     528
Ile Asn Thr Ala Lys Glu Ile Tyr Glu Lys Ile Gln Glu Gly Val Phe
                165                 170                 175 gac att aat aat gag gca aac ggc atc aaa att ggc cct cag cat gct     576
Asp Ile Asn Asn Glu Ala Asn Gly Ile Lys Ile Gly Pro Gln His Ala
            180                 185                 190 gct acc aat gca tct cac gga ggc aac caa gga ggg cag cag gca ggg     624
Ala Thr Asn Ala Ser His Gly Gly Asn Gln Gly Gly Gln Gln Ala Gly
        195                 200                 205 gga ggc tgc tgc tga                                                 639
Gly Gly Cys Cys
    210
```

<210> SEQ ID NO 67
<211> LENGTH: 212
<212> TYPE: PRT
<213> ORGANISM: Rattus sp.

<400> SEQUENCE: 67

```
Met Ala Tyr Ala Tyr Leu Phe Lys Tyr Ile Ile Ile Gly Asp Thr Gly
 1               5                  10                  15
```

-continued

```
Val Gly Lys Ser Cys Leu Leu Leu Gln Phe Thr Asp Lys Arg Phe Gln
             20                  25                  30

Pro Val His Asp Leu Thr Ile Gly Val Glu Phe Gly Ala Arg Met Ile
         35                  40                  45

Thr Ile Asp Gly Lys Gln Ile Lys Leu Gln Ile Trp Asp Thr Ala Gly
     50                  55                  60

Gln Glu Ser Phe Arg Ser Ile Thr Arg Ser Tyr Tyr Arg Gly Ala Ala
 65                  70                  75                  80

Gly Ala Leu Leu Val Tyr Asp Ile Thr Arg Arg Asp Thr Phe Asn His
                 85                  90                  95

Leu Thr Thr Trp Leu Glu Asp Ala Arg Gln His Ser Asn Ser Asn Met
            100                 105                 110

Val Ile Met Leu Ile Gly Asn Lys Ser Asp Leu Glu Ser Arg Arg Glu
        115                 120                 125

Val Lys Lys Glu Glu Gly Glu Ala Phe Ala Arg Glu His Gly Leu Ile
    130                 135                 140

Phe Met Glu Thr Ser Ala Lys Thr Ala Ser Asn Val Glu Glu Ala Phe
145                 150                 155                 160

Ile Asn Thr Ala Lys Glu Ile Tyr Glu Lys Ile Gln Glu Gly Val Phe
                165                 170                 175

Asp Ile Asn Asn Glu Ala Asn Gly Ile Lys Ile Gly Pro Gln His Ala
            180                 185                 190

Ala Thr Asn Ala Ser His Gly Gly Asn Gln Gly Gly Gln Gln Ala Gly
        195                 200                 205

Gly Gly Cys Cys
    210

<210> SEQ ID NO 68
<211> LENGTH: 816
<212> TYPE: DNA
<213> ORGANISM: Rattus sp.
<220> FEATURE:
<221> NAME/KEY: CDS
<222> LOCATION: (1)..(813)

<400> SEQUENCE: 68 atg gtg ctg ctc aag gaa tat cgg gtc atc ctg cct gtg tct gta gat     48
Met Val Leu Leu Lys Glu Tyr Arg Val Ile Leu Pro Val Ser Val Asp
  1               5                  10                  15 gag tat caa gtg ggg cag ctg tac tct gtg gct gaa gcc agt aaa aat     96
Glu Tyr Gln Val Gly Gln Leu Tyr Ser Val Ala Glu Ala Ser Lys Asn
             20                  25                  30 gaa act ggt ggt ggg gaa ggt gtg gag gtc ctg gtg aac gag ccc tac    144
Glu Thr Gly Gly Gly Glu Gly Val Glu Val Leu Val Asn Glu Pro Tyr
         35                  40                  45 gag aag gat gat ggc gag aaa ggc cag tac aca cac aag atc tac cac    192
Glu Lys Asp Asp Gly Glu Lys Gly Gln Tyr Thr His Lys Ile Tyr His
     50                  55                  60 tta cag agc aaa gtt ccc acg ttt gtt cga atg ctg gcc cca gaa ggc    240
Leu Gln Ser Lys Val Pro Thr Phe Val Arg Met Leu Ala Pro Glu Gly
 65                  70                  75                  80 gcc ctg aat ata cat gag aaa gcc tgg aat gcc tac cct tac tgc aga    288
Ala Leu Asn Ile His Glu Lys Ala Trp Asn Ala Tyr Pro Tyr Cys Arg
                 85                  90                  95 acc gtt att aca aat gag tac atg aag gaa gac ttt ctc att aaa att    336
Thr Val Ile Thr Asn Glu Tyr Met Lys Glu Asp Phe Leu Ile Lys Ile
            100                 105                 110
```

| | | |
|---|---|---|
| gaa acc tgg cac aag cca gac ctt ggc acc cag gag aat gtg cat aaa<br>Glu Thr Trp His Lys Pro Asp Leu Gly Thr Gln Glu Asn Val His Lys<br>              115                    120                    125 | | 384 |
| ctg gag cct gag gca tgg aaa cat gtg gaa gct ata tat ata gac atc<br>Leu Glu Pro Glu Ala Trp Lys His Val Glu Ala Ile Tyr Ile Asp Ile<br>130                    135                    140 | | 432 |
| gct gat cga agc caa gta ctt agc aag gat tac aag gca gag gaa gac<br>Ala Asp Arg Ser Gln Val Leu Ser Lys Asp Tyr Lys Ala Glu Glu Asp<br>145                    150                    155                    160 | | 480 |
| cca gca aaa ttt aaa tct atc aaa aca gga cga gga cca ttg ggc ccg<br>Pro Ala Lys Phe Lys Ser Ile Lys Thr Gly Arg Gly Pro Leu Gly Pro<br>              165                    170                    175 | | 528 |
| aat tgg aag caa gaa ctt gtc aat cag aag gac tgc cca tat atg tgt<br>Asn Trp Lys Gln Glu Leu Val Asn Gln Lys Asp Cys Pro Tyr Met Cys<br>                  180                    185                    190 | | 576 |
| gca tac aaa ctg gtt act gtc aag ttc aag tgg tgg ggc ttg cag aac<br>Ala Tyr Lys Leu Val Thr Val Lys Phe Lys Trp Trp Gly Leu Gln Asn<br>              195                    200                    205 | | 624 |
| aaa gtg gaa aac ttt ata cat aag caa gag aag cgt ctg ttt aca aac<br>Lys Val Glu Asn Phe Ile His Lys Gln Glu Lys Arg Leu Phe Thr Asn<br>210                    215                    220 | | 672 |
| ttt cac agg cag ctg ttc tgt tgg ctt gat aaa tgg gtt gat ctg act<br>Phe His Arg Gln Leu Phe Cys Trp Leu Asp Lys Trp Val Asp Leu Thr<br>225                    230                    235                    240 | | 720 |
| atg gat gac att cgg agg atg gaa gaa gag acg aag aga cag ctg gat<br>Met Asp Asp Ile Arg Arg Met Glu Glu Glu Thr Lys Arg Gln Leu Asp<br>                      245                    250                    255 | | 768 |
| gag atg aga caa aag gac ccc gtg aaa gga atg aca gca gat gac tag<br>Glu Met Arg Gln Lys Asp Pro Val Lys Gly Met Thr Ala Asp Asp<br>260                    265                    270 | | 816 |

<210> SEQ ID NO 69
<211> LENGTH: 2263
<212> TYPE: DNA
<213> ORGANISM: Simian sp.

<400> SEQUENCE: 69

| | |
|---|---|
| cgctctcctc ctcccctttc tctagcagta gccttcttaa tgtagtttaa tggctttaca | 60 |
| aagaaagcca ggcagaggag cacttctcag tggctgtggt cggaccatga cctagctgac | 120 |
| catgaacttg gaagggcttg aaatgatagc agttctgatc gtcattgtgc tttttgttaa | 180 |
| attattggaa cagtttggc tgattgaagc aggtttagaa gacagcgtgg aagatgaact | 240 |
| ggagatggcc actgtcaggc atcggcctga ggcccttgag cttctggaag cccagagcaa | 300 |
| atttaccaag aaagagcttc agatccttta cagaggattt aagaacgaat gccccagtgg | 360 |
| tgttgttaat gaagaaacct tcaaagagat ttactcgcag ttctttccac agggagactc | 420 |
| tacaacatat gcacattttc tgttcaatgc gtttgatacg gaccacaatg gagctgtgag | 480 |
| tttcgaggat ttcatcaaag gtctttccat tttgctccgg gggacagtac aagaaaaact | 540 |
| caattgggca tttaatctgt atgatataaa taagatggc tacatcacta agaggaaat | 600 |
| gcttgatata atgaaagcaa tatacgacat gatgggtaaa tgtacatatc ctgtcctcaa | 660 |
| agaagatgca cccagacaac acgtcgaaac atttttcag aaaatggaca aaaataaaga | 720 |
| tggggttgtt accatagatg agttcattga aagctgccaa aaagatgaaa acataatgcg | 780 |
| ctccatgcag ctctttgaaa atgtgattta acttgtcaac tagatcctga atccaacaga | 840 |
| caaatgtgaa ctattctacc cccttaaag tcggagctac cacttttagc atagattgct | 900 |
| cagcttgaca ctgaagcata ttatgcaaac aagctttgtt ttaatataaa gcaatcccca | 960 |

```
aaagatttga gtttctcagt tataaatttg catcctttcc ataatgccac tgagttcatg    1020
ggatgttcta actcatttca tactctgtga atattcaaaa gtaatagaat ctggcatata    1080
gttttattga ttccttagcc atgggattat tgaggctttc acatatcagt gattttaaaa    1140
taccagtgtt ttttgctact catttgtatg tattcagtcc taggattttg aatggttttc    1200
taatatactg acatctgcat ttaatttcca gaaattaaat taattttcat gtctgaatgc    1260
tgtaattcca tttatatact ttaagtaaac aaataagatt actacaatta aacacatagt    1320
tccagtttct atggccttca cttcccacct tctattagaa attaatttta tctggtattt    1380
ttaaacattt aaaaatttat catcagatat cagcatatgc ctaattatgc ctaatgaaac    1440
ttaataagca tttaattttc catcatacat tatagtcaag gcctatatac tatatataat    1500
tttggatttg tttaatctta caggctgttt tccattgtat catcaagtgg aagttcaaga    1560
cggcatcaaa caaacaagg atgtttacag acatatgcaa agggtcagga tatctatcct    1620
ccagtatatg ttaatgctta ataacaagta atcctaacag cattaaaggc caaatctgtc    1680
ctctttcccc tgacttcctt acagcatgtt tatattacaa gccattcagg gacaaagaaa    1740
ccttgactac cccactgtct actaggaaca aacaaacagc aagcaaaatt cactttgaaa    1800
gcaccagtgg ttccattaca ttgacaacta ctaccaagat tcagtagaaa ataagtgctc    1860
aacaactaat ccagattaca atatgattta gtgcatcata aaattccaac aattcagatt    1920 attttaatc acctcagcca caactgtaaa gttgccacat tactaaagac acacacatcg    1980
tccctgtttt gtagaaatat cacaaagacc aagaggctac agaaggagga aatttgcaac    2040
tgtctttgca acaataaatc aggtatctat tctggtgtag agataggatg ttgaaagctg    2100
ccctgctatc accagtgtag aaattaagag tagtacaata catgtacact gaaatttgcc    2160
atcgcgtgtt tgtgtaaact caatgtgcac attttgtatt tcaaaagaa aaaataaaag    2220 caaaataaaa tgtttataac tctaaaaaaa aaaaaaaaa aaa                       2263
```

<210> SEQ ID NO 70
<211> LENGTH: 229
<212> TYPE: PRT
<213> ORGANISM: Simian sp.

<400> SEQUENCE: 70

```
Met Asn Leu Glu Gly Leu Glu Met Ile Ala Val Leu Ile Val Ile Val
  1               5                  10                  15

Leu Phe Val Lys Leu Leu Glu Gln Phe Gly Leu Ile Glu Ala Gly Leu
                 20                  25                  30

Glu Asp Ser Val Glu Asp Glu Leu Glu Met Ala Thr Val Arg His Arg
             35                  40                  45

Pro Glu Ala Leu Glu Leu Leu Glu Ala Gln Ser Lys Phe Thr Lys Lys
         50                  55                  60

Glu Leu Gln Ile Leu Tyr Arg Gly Phe Lys Asn Glu Cys Pro Ser Gly
 65                  70                  75                  80

Val Val Asn Glu Glu Thr Phe Lys Glu Ile Tyr Ser Gln Phe Phe Pro
                 85                  90                  95

Gln Gly Asp Ser Thr Thr Tyr Ala His Phe Leu Phe Asn Ala Phe Asp
            100                 105                 110

Thr Asp His Asn Gly Ala Val Ser Phe Glu Asp Phe Ile Lys Gly Leu
        115                 120                 125

Ser Ile Leu Leu Arg Gly Thr Val Gln Glu Lys Leu Asn Trp Ala Phe
    130                 135                 140
```

Asn Leu Tyr Asp Ile Asn Lys Asp Gly Tyr Ile Thr Lys Glu Glu Met
145                 150                 155                 160

Leu Asp Ile Met Lys Ala Ile Tyr Asp Met Met Gly Lys Cys Thr Tyr
            165                 170                 175

Pro Val Leu Lys Glu Asp Ala Pro Arg Gln His Val Glu Thr Phe Phe
            180                 185                 190

Gln Lys Met Asp Lys Asn Lys Asp Gly Val Val Thr Ile Asp Glu Phe
            195                 200                 205

Ile Glu Ser Cys Gln Lys Asp Glu Asn Ile Met Arg Ser Met Gln Leu
            210                 215                 220

Phe Glu Asn Val Ile
225

<210> SEQ ID NO 71
<211> LENGTH: 2259
<212> TYPE: DNA
<213> ORGANISM: Simian sp.

<400> SEQUENCE: 71

| | |
|---|---:|
| gtcgacagac gcccctggcc ggtggactcc tgagtcttac tcctgcaccc tgcgtcccca | 60 |
| gacatgaatg tgaggagagt ggaaagcatt tcggctcagc tggaggaggc cagctccaca | 120 |
| ggcggtttcc tgtatgctca gaacagcacc aagcgcagca ttaaagagcg gctcatgaag | 180 |
| ctcttgccct gctcagctgc caaaacatcg tctcctgcta ttcaaaacag cgtggaagat | 240 |
| gaactggaga tggccactgt caggcatcgg cctgaggccc ttgagcttct ggaagcccag | 300 |
| agcaaattta ccaagaaaga gcttcagatc ctttacagag gatttaagaa cgaatgcccc | 360 |
| agtggtgttg ttaatgaaga aaccttcaaa gagatttact cgcagttctt tccacaggga | 420 |
| gactctacaa catatgcaca ttttctgttc aatgcgtttg atacggacca caatggagct | 480 |
| gtgagtttcg aggatttcat caaaggtctt tccatttttgc tccgggggac agtacaagaa | 540 |
| aaactcaatt gggcatttaa tctgtatgat ataaataaag atggctacat cactaaagag | 600 |
| gaaatgcttg atataatgaa agcaatatac gacatgatgg gtaaatgtac atatcctgtc | 660 |
| ctcaaagaag atgcacccag acaacacgtc gaaacatttt ttcagaaaat ggacaaaaat | 720 |
| aaagatgggg ttgttaccat agatgagttc attgaaagct gccaaaaaga tgaaaacata | 780 |
| atgcgctcca tgcagctctt tgaaaatgtg atttaacttg tcaactagat cctgaatcca | 840 |
| acagacaaat gtgaactatt ctaccaccct taaagtcgga gctaccactt ttagcataga | 900 |
| ttgctcagct tgacactgaa gcatattatg caaacaagct ttgttttaat ataaagcaat | 960 |
| ccccaaaaga tttgagtttc tcagttataa atttgcatcc tttccataat gccactgagt | 1020 |
| tcatgggatg ttctgactca tttcatactc tgtgaatatt caaaagtaat agaatctggc | 1080 |
| atatagtttt attgattcct tagccatggg attattgagg ctttcacata tcagtgattt | 1140 |
| taaaatacca gtgttttttg ctactcattt gtatgtattc agtcctagga ttttgaatgg | 1200 |
| ttttctaata tactgacatc tgcatttaat ttccagaaat taaattaatt ttcatgtctg | 1260 |
| aatgctgtaa ttccatttat atactttaag taaacaaata agattactac aattaaacac | 1320 |
| atagttccag tttctatggc cttcacttcc caccttctat tagaaattaa ttttatctgg | 1380 |
| tatttttaaa catttaaaaa tttatcatca gatatcagca tatgcctaat tatgcctaat | 1440 |
| gaaacttaat aagcatttaa ttttccatca tacattatag tcaaggccta tatactatat | 1500 |
| ataatttttgg atttgtttaa tcttacaggc tgttttccat tgtatcatca agtggaagtt | 1560 |

-continued

```
caagacggca tcaaacaaaa caaggatgtt tacagacata tgcaaagggt caggatatct    1620
atcctccagt atatgttaat gcttaataac aagtaatcct aacagcatta aaggccaaat    1680
ctgtcctctt tcccctgact tccttacagc atgtttatat tacaagccat tcagggacaa    1740
agaaaccttg actacccccac tgtctactag gaacaaacaa acagcaagca aaattcactt    1800
tgaaagcacc agtggttcca ttacattgac aactactacc aagattcagt agaaaataag    1860
tgctcaacaa ctaatccaga ttacaatatg atttagtgca tcataaaatt ccaacaattc    1920
agattatttt taatcacctc agccacaact gtaaagttgc cacattacta aagacacaca    1980
catcgtccct gttttgtaga aatatcacaa agaccaagag gctacagaag gaggaaatt    2040 gcaactgtct ttgcaacaat aaatcaggta tctattctgg tgtagagata ggatgttgaa    2100
agctgccctg ctatcaccag tgtagaaatt aagagtagta caatacatgt acactgaaat    2160
ttgccatcgc gtgtttgtgt aaactcaatg tgcacatttt gtatttcaaa agaaaaaat    2220 aaaagcaaaa taaatgttta aaaaaaaaaa aaaaaaaa                           2259
```

<210> SEQ ID NO 72
<211> LENGTH: 250
<212> TYPE: PRT
<213> ORGANISM: Simian sp.

<400> SEQUENCE: 72

```
Met Asn Val Arg Arg Val Glu Ser Ile Ser Ala Gln Leu Glu Glu Ala
  1               5                  10                  15

Ser Ser Thr Gly Gly Phe Leu Tyr Ala Gln Asn Ser Thr Lys Arg Ser
             20                  25                  30

Ile Lys Glu Arg Leu Met Lys Leu Leu Pro Cys Ser Ala Ala Lys Thr
         35                  40                  45

Ser Ser Pro Ala Ile Gln Asn Ser Val Glu Asp Glu Leu Glu Met Ala
     50                  55                  60

Thr Val Arg His Arg Pro Glu Ala Leu Glu Leu Glu Ala Gln Ser
 65                  70                  75                  80

Lys Phe Thr Lys Lys Glu Leu Gln Ile Leu Tyr Arg Gly Phe Lys Asn
                 85                  90                  95

Glu Cys Pro Ser Gly Val Val Asn Glu Glu Thr Phe Lys Glu Ile Tyr
            100                 105                 110

Ser Gln Phe Phe Pro Gln Gly Asp Ser Thr Thr Tyr Ala His Phe Leu
        115                 120                 125

Phe Asn Ala Phe Asp Thr Asp His Asn Gly Ala Val Ser Phe Glu Asp
    130                 135                 140

Phe Ile Lys Gly Leu Ser Ile Leu Leu Arg Gly Thr Val Gln Glu Lys
145                 150                 155                 160

Leu Asn Trp Ala Phe Asn Leu Tyr Asp Ile Asn Lys Asp Gly Tyr Ile
                165                 170                 175

Thr Lys Glu Glu Met Leu Asp Ile Met Lys Ala Ile Tyr Asp Met Met
            180                 185                 190

Gly Lys Cys Thr Tyr Pro Val Leu Lys Glu Asp Ala Pro Arg Gln His
        195                 200                 205

Val Glu Thr Phe Phe Gln Lys Met Asp Lys Asn Lys Asp Gly Val Val
    210                 215                 220

Thr Ile Asp Glu Phe Ile Glu Ser Cys Gln Lys Asp Glu Asn Ile Met
225                 230                 235                 240

Arg Ser Met Gln Leu Phe Glu Asn Val Ile
                245                 250
```

<210> SEQ ID NO 73
<211> LENGTH: 10
<212> TYPE: PRT
<213> ORGANISM: Simian sp.

<400> SEQUENCE: 73

Ser Asn Ala Lys Ala Val Glu Thr Asp Val
1               5                   10

<210> SEQ ID NO 74
<211> LENGTH: 17803
<212> TYPE: DNA
<213> ORGANISM: Homo sapiens

<400> SEQUENCE: 74

```
gcgctcacct gctgcctagt gttccctctc ctgctccagg acctccgggt agacctcaga      60
ccccgggccc attcccagac tcagcctcag cccggacttc cccagccccg acagcacagt     120
aggccgccag ggggcgccgt gtgagcgccc tatcccggcc accggcgcc ccctcccacg     180
gcccgggcgg gagcggggcg ccgggggcca tgcggggcca gggccgcaag gagagtttgt     240
ccgattcccg agacctggac ggctcctacg accagctcac gggtgagtca gtgacgtggg     300
ggtcgcggga gggagggtgg attccattcc tccagacccct tccgcctctc cgaccccggc     360
ctggcccgca cccacactct gccccattcc caggcactct tatggccggt ctgggcggca     420
ggacactggg ggttcaaagc cttgggtccc gcaggggttg gggaggaaca gaagaggcag     480
gtgtggagag gcagcaggtg tgggcgtatg tgacacaggg ctgagagggt gtctggagtg     540
ggaggtgtta cgtgcgtgag cacctgtcat tctgtgtgtg tgtgtgtgtg tgcgcgcgca     600
cctcccacag ctggttgcca tgtgccctgg gcttggtgac agctagggtg agtgtgattg     660
tatgtggcag tgcaattgta tggtctcgtc agatgtttga gtttgcgtag gaccctggtt     720
gtactgatga agttgttttg accatgtgtc tctatgtgca acgatgtgtt gtgagtgtgt     780
aattctgtat gaagtggtgt gtaactacca gaatgtgtca gggctctact ttagggtggc     840
ttgtctcttt gtaagccttc atgaccataa gccctctggg caagaatttg ttaaagtagg     900
ttgtgttgtg ttttgtggtt gtgagattag tgttcagtgc tagttgtgta cttttcatgtg     960
gtgatgtctg cagcggggct ctgtgagtgt ctatgacgtg tctcatccct gctgcctctc    1020
tggcttcctg gtacagatag gggtctttag tacaccccac tccttcacca atttttccac    1080
aaatagccca ggtggaccca aggagggact ttagtgttca gctgcccagt ctggttttcca   1140
agagacctta tggctccagc acctggcccc tgtaggagg ctttagttag tgctgggtca     1200
gccctctctc cccacaccaa atcatgtact gagattattc ttacaactga atccttcaac    1260
ccccaacaaa cctttcagaa cttcactcaa accccaggaa aacacatcct cttccttccc    1320
ctccagagac agagctagaa gctctaggcc tgggaagtgc catgtggtgt cctgcatgtc    1380
caccaaacca cttggctgcc cgggcatcct ctctttccca catggggagg tatgtgaggc    1440
cagtacatct gtgcatgtgc atgttcctgg gtttggtagg aagagccatg tgtttgtgta    1500
ggtgactgtg tcaccctggg tacatttcca tgtatgtgtt tgtgtctctc attgtgcagc    1560
ctgctctaga aagccagcag agtgggagga gggaggctgt ctccctgagg ccaaaacaaa    1620
gctggggagg tggagggagg ccatgatcct tgtccttcct gagggagtg agattgagac     1680
ctgggaaggg ggagggagact aggatgaggt gccttgagca tgtgtcttcc cccatccccc    1740
atcactgtcc ctagggaggc cctagtcagg atcaggggag ccactcaggc tggccccaga    1800
```

```
tgagagacca tgccagatgt gcctcagagc tggatggaat ccaaaggacc cactgtccag      1860
ctcttccatg aattctgttc ccatcaccag cttaggattc ttgagagtag taagggccta      1920
ggggccttca atagtatcac attagtcagt gtttgcttcc agctttaatg ggttctcacc      1980
cttagtgaaa ccatcccttc cccacttggc tatttgaatg agattgggtg ggggaagcat      2040
ttgtatttgg agatgccctg ccccagttca gtcaggaatg gaagtgtacc agctatgtga      2100
cttttgttct cttggcctca cctttctcat ctgtaaaagg gaatgttact tcctgcctgc      2160
ctgcctacct cccaaggaaa atggaaaggt caaatgttga caagtatcaa gaattgtggt      2220
ccgggtctac agcagcctag ctgtagatag ctccacacac gacttggaaa gtagaaatag      2280
gactaccagg agctctcctc tcgaagggcg gcttatttta tagcgggaga caaatcgggt      2340
tgggacgcca gtgtcaacga agactcccgg gcgggcgggc ggcgctgagc tctgagcgct      2400
gagagatgcc taagctgaag catgaagggg agtcgttgtc cgcggtgctg aagcgcgcgc      2460
caggcttcgc ctcccctccc ctgcagttgg gattcctggg atcggattta gggtagtctg      2520
cagctcccgt cttcccggcc catcaggctt gcagggaagc agctggaaag ttacacctca      2580
gggcatcctg ggtacctccg aacattttac ttccccactc ccaccccaag ctcaaaaggg      2640
agctgggaga gactctttag gaaaacaaaa caaaacaaaa aacagtccga gccccgcccg      2700 gaccctgtc taatccctca ggtcttccca gcccggcggg gccgctgggc agtgcggttc      2760
cgaggggaaa ggccgcgttt agcagcggcc ctgtctgagc ggaagagaga aaggccaaga      2820
gaagatgcgg agagggttgg agcctggctg gctagccctg agctcggtcc cccgactggg      2880
atctcagtgg agtccctccg gccctgagta ttgttgccgg ggcggggcg ccccgtgtg      2940 gctgcgagga gccatgcgca cggagctgct ttgcggtggg gatagtcgcc gtcaagtgga      3000
caagatttgc ccagagttag gaggtcattc tcaccactta aatgtagggt tttcaaccaa      3060
tcatgcggga tcccagtcga aagagcggga ctatatctct cccgtaggct ttcccaggaa      3120
ttttaaggcg ttagagagtc ctggaagtgt ttacttgggg tctaacctga tagagatgag      3180
tccggagtcc aggaaagggg cgcagcggga ccgaagtggg ggggggtgc gggggggct      3240 cttctcgaag cattcggctg tagccagcgt atggtggtag tctgtgaacc tgccgcaccg      3300
agacaaacac aaatagaaac agttatgaga gcaaggaatt tggagccagg agacagaagg      3360
cagtggggca caactctgct gcctcttctt tgccacccca atacactggc ctctttctcc      3420
ttcctcctgg cttttcttcca ttggcccagg aagtgtgggg agttgccatg acaactctgt      3480
cctcttaccc cttcggctct ttatgccaaa atggtggggg cggggtgcag ggtgcgggga      3540
ggagtgcgac aggcggagaa aggggggctg aaaggggggca ataaaagata cggttcattc      3600
cccatccagc tctttctca aaacccacat gtgcctgcct ggcctccccg ccagaaccca      3660
gaaaaatgct ccctgagaag gctgagtccg cgccgcccct cccgccaccc ccccccccc      3720 gtccaggaac tttgggggcg gctgcttcac atgatggggc cagggtgagc tcctctcgtg      3780
cggccaggag aacatgggaa ggctccaggg tttcgatcct atgcctgccg ggccggccct      3840
cccgcgccgc ccacgcgggc ctacccgggt gagggcggag accggaccgc cccggggcct      3900
gggggtggag cttagacgcc gagctcgccg ccaaaccatg aaccgatgcc cccgcaggtg      3960
ccggagcccg ctggggcagg cagcgcgatc cctctaccag ctggtgactg ggtcgctgtc      4020
cccaggtatg atgaggaagg gaagggaggg gcaggatcct tcaaaaagtg agcgaagtgg      4080
gttaggagct ccgcagaggt agggagggaa gggcccctca aatagatgga gggagcaaca      4140
```

```
tccctccaag gaaagggctt ccaagacgag atcctggaca gaagcggagc aggggatggg      4200
cctccttact gagcaggagg aagacagcgc tcttcaaaga ggaaaggaga ggggcatcaa      4260
ggtccctcac aatggtggag ggggcgggc ttctcaccga aggcagagga ggggccctta      4320
actgaggggc agggcgcctc ccagggatga aggaggagg cctgcagcag agcagggaaa      4380
aagttcagtc ctttcctgca tttcttggct gaagggtct taagatgaag ggttcagtgt      4440
ccagaaggaa aaaccctga gatgggccta gaccaacatg aactcagcta gcaagttcat      4500
acatgacatg ggactgatag acttgtgtgg cttaaggatt gtatgtctct gttttctctc      4560
tctctgggag tgtgtattaa tgggattgtg cattactaag ttgtgcatca ctgggctatg      4620 tatgctgag tctgtgtctc cctggggttg tgatcactgg gattctgtga cactgagact      4680
gtgtgtacct ggagttctgt actttaggac tgggttgagg gttcctgagc ctctaagttg      4740
gttgtgtagc cttcgtgagg ttgtaccttg gtgtgaaatt tgtggagtgt atgaggtgtg      4800
gattgttgag tatcccacgg cactgctgag gtgtatgcac atctccactt gcatttcctt      4860
atgactgctt gggcagggcc catagaacgc aacgtctcct ctgtacctga cctcaaacag      4920
accaaaacaa cctggtcctg tggcattctg agatctgtca ttttctggct ctctccatgg      4980
gtatccactt gagcccctgg agtatagata gggcctgtgg cctctccttg ccatctgtcc      5040
cccaaaagga gggtagatgg atggtcctga gccagaacca tacctggaaa tcttctgggg      5100
agcatacaac ctccaagccc cctgcttggg cctgtctcca gtgacagatg gctggagcca      5160
ggcagggcca gctctcagtc attgcaggca tgacttccag gacccaaaat agccccaacg      5220
tctagggagg tcattaatca ctcgatgcag ctggggctg cagtgtcttt ggcctagctg      5280
ggaatggtgt gggtctgggg gactgagaga agggctttga ggtcttcact ggctgggtta      5340
acagtggcgg tgggggtgg gacaaagcta aactgggaa ggtgggacag ttgcatagag      5400
tgggttcccc cacaaggcag tgttactcac atttgaactg ggggagataa ataaataaat      5460
gataggaata tctctgtggt aagatttgag ggatctgggg aaggcccacc tcatgcctcg      5520
agatggtttt cccttgagtt cccactctgc caaattgctt ccacagagat tttactttga      5580
gtgaagagct aaattcgtgg cacagggatg cttggggagg atggatctgg caagtttctc      5640
actgaacccg aggacttgag aagtctctga gtggggagaa gggacagcct ggaaaaataa      5700
ctcatccttt cactcctgac agactctgcc acaggatgcc tggctgattt aggaccatga      5760
gtcctggcaa ggctgggtca aggtctctga gagttgagag tgggagttag gaaaaggagg      5820
ggccagggcc agggccaggt ccagggcaac tggctgcaag ttatcagtag cagggagcaa      5880 gaagggctg ttgtggggcc cctttccatt caaatagtct ggcttggcat tcaaggtttc      5940
atggaatttg acccttttg attttattac ccatagctcc cttacctaaa ctaagctgta      6000
ggccctagga ttccttgaca ccccgcacat attggagaga ctgcctgagg gagctgacag      6060
atcactgact ctggttaaac aactcattat tattatcatt attattatta ttgagacaga      6120
gttttgctct ttcagtcaga ctggagtgaa gtagcgtgat ctcagttcac tgcaacctcc      6180
gcctcccagg ttcaagcaat tctgccttag cctcctgagt agctgggatt acaggcaagc      6240
accatcacgc ctggctaatt tttgtatttt tagtagagac ggggtttcac catgtgagtc      6300
aggctggtct tgaactcctg accttgtgat ccacccgcct cggcctccca aagtgctggg      6360
attataggcg tgagccactg cacccagcca aactcattct taattagcat gtcagctgtt      6420
atcttggaaa aaaatcact cttttttccc aagataagca gggagcttat cttggcgggg      6480
agcttcaatt ccttcatctg caaaatgggt atactatcac tcactctgac catgtcagct      6540
```

```
gtaaaaacag gaataataga tcctacctct caggtttatt atgaggacta agtgagatac    6600
tacatgtaaa gtatccagga cacaaaatgt gctggataaa tattatcttt gtttatttgt    6660
ttattttgag atggggtctc actttgtcat ctaggctgaa gtacagtggc acaatcatgg    6720
ctcattgcag cctcaaactc cccaccttag cctcccaggt agctgggact ataggtgtgt    6780
gccaccacgc caggctaatt attattattt ttttttgag acagagtctc gctctgttgc    6840
tcaggctgga gtgcagtggc gtgatctcgg ctcactgcaa cctccacctc ctgggttcaa    6900
gcacttctcc tgcctcagcc tcccaagtag ctgggattac aggtgtgtgc caccacgccc    6960
ggctaatttt tgtattttta gtagagacag ggtttcacca ttttggccag gctggtctca    7020
aactcctgac ctcgtgatcc acctgcctcg acctcccaga gtgctgggat tacaggcatg    7080
agccaccttg cccagcccag gctaattttt tgtagagaca gagtttcgcc atgttgccca    7140
ggctggtctg ggactcctga tccaaccttt agggattggc aagcaatccc taaatagact    7200
ttttcctagg ggaaaggagt ggaacagacc aagcctattt gaggccagac gcggtggcac    7260
acgcctggaa ttccagcact ttgggatgcc gacgggggca gatcacttca ggccaggagt    7320
tcgagaccag cctggccagc atgacaaaac cctatttaaa aatataaaaa tcagctgggc    7380
gtggtggtgc acgcctgtaa tcccagctat tcggtggctg aggcacgaga atcgctagcg    7440
ccaccgcact ttagcctggg tgatagaacg agactctgtc tcaaaaaaaa aaaaaaaaaa    7500
aaagagaaaa aaaagcctgt gtgaagcgtc atcttcccac ctcttccctg gatggggcag    7560
gtcggggaga aggaaggtgt atggtactgt gtgaggttgg acgcgtgccc cccggtggtg    7620
gctgtataga actgcagatc agccaacctc gactggggcc ttagggactg gcccccaccc    7680
cacaaattgg gctgagacac agtcatccca gagctggaca agagggaggg ctccttctgg    7740
ggccaatccc cctaaattgg gcctcctggc tgggccagct ttctaagaag ggagccagtg    7800
tagtgtggtg gtttagagtg aaggctgagt cagactgggt taaaattgaa gctctgatct    7860
tgaagatttg cttaacttct ctttgactta gtttcaccac ctgtaatatg aggataatag    7920
tatgccttca taggcttatt gtgaaaattc ggtgttacaa cacctgtaag cacatagtgc    7980
attatctagt acatagtgaa tgctcagtca ccgttagcca gcagcggtag taatggtgtt    8040
actaacccag aggccctagt cttgtggctc attggctctg taggcctctc ccacccctt    8100 tacacacaca aacaccccac caagaagaag cagggaagag gagggaggga ctccggggat    8160
gctggctggg aggggtggct cccttagaag gttcagattt ccctcctaca gcagctgggc    8220
ttctccatca gctcaataac agttcctaag gagcaggcag ggctttagca tctcccggat    8280
gaggtcccag ccacatacgg agccagcaca gtcccccctc ctctcccaag aagcttgggt    8340
ttcttgaccc caaaggcagc tgcagtaagt cccctcccca gagggtcctg atggggttaa    8400
gtggcctttt tctgcctagg ctactactgt atcttatccc cctcccttg ggcctcagtt    8460 tcactgcctg tggcctgtgg gaagagagtg cttccctcct cacagtctcc atggcaacca    8520
aatcgatatt ggtgatatcc tcctagcagg agaggtcact gccttctccg ccattattct    8580
catacaattc catgccaata caatgacaaa acagtagacc caccctccaa attatacaac    8640
acatccatac ctaacaaact tcagacccac atcctacaac cctactaaaa cacaggaacc    8700
tcactcccca tgcacactca caaatacttc aacacactcc tacacatgca gaccatagac    8760
acccagctca catacccata tacgcaagag tcaaaatgca taaccatacg ccaaacacac    8820
acctctgtga caggtgcaca gtcacgtgta agcacacaaa gacacacata agaggagaca    8880
```

```
tatgcactgc catactgaca aacacaggaa tatacacaca ggaaaacacc tggccaccac    8940
aacatattct gacccatgca tctgattact tatacatgtg cagatggtgg tttctcatgc    9000
acatacaccc tgcccttccc tgccttctcc ctaagctcag ctcctccctc tgccccttcc    9060
ctttggcaca gagtagccac aggatgtcta ggggaagcac ttctcaggga cagaggcggg    9120
tcactgctcc ctccctctgg cccatatctt ggccaaaagt tcccaaggag gtgccagtcc    9180
aaaggctgag gtggccctgc gaagaggaag aggcggcggc tgtggttggg aggcttgtgg    9240
ggcagaggcg gggtgatggg ggagaggaag gagatcctgg gagggagagt gggagggagg    9300
ctgcaggcag tcctactcag gctggggagt ctgaggggga ggtggtgtga ggcggtgaac    9360
cggcgtatct gaacctgggc cctgtagggg ccatgcccca gcccaccat gaacctggaa     9420 gggctggaga tggttgctgt gctcgtggtc ctcgctctgt tgtcaaggt cctggagcag     9480 tttggcctct ttgagcctgt ctccttggaa ggtaatccag gtgtcctggc atgtctgagc    9540
tgctggctgg tggggcagct gccccacagc actaggagg gtgtttgtct gtcttcatga     9600
ctggggcagg gatgagcagg tgagtgatgg cacaggatc tgggaggtga gtaggggtgc     9660
ttgggggata caacatctgg gaggggtgaa gaggaggcct caaggagtag atatggaggg    9720
aggagggaat ctggggggacc aaggtgtcag gaggtgatga ggggtgcagt gtgggaggac   9780
tggggtgtgg agatgaggag gtgagggggat tctgggcgat accaggaggg gtctggagat  9840
agggaaggag tgtctagagt agaggaggga ggttctaggg atcctgagat aacaacggat    9900
ttctgggggg tccttttgg agtcagggc ccaccacggt gcctgtgcat cctctccaca     9960
cctccatctg tgcagtgtag cttatggggt gtgtgggcat agtgtgtgag agacacaggg    10020
tgtgactttg tgttcctgta tgtgagagag tacaaagtgt gtaactgtga gcctgtgtat   10080
gggacaggga tatgactgta tgtgtgagag tgacagggca tgtggctttg tgagaaggtg   10140
gatgtggcca ggcctgagtg gcacagtatg tggctgagcc tctgggtatc aggttgtgca   10200
tgtggctgtt tccagaattt cctgaggata taccagctcc atacccaagg cttgggagga   10260
ggtgggttct ggagggaaga gtgtgaacat tgtgaaggag acatttatag cccagctatg   10320
attggggatg aggagtggat cagatcaggg accctgcttc ccaagtcccc ttgcctctcc   10380
aagctcctat caggatccaa gtgcagagtg atctccaggg cctagacatt gggagtggaa   10440
aatcaactcc cctcccagc ccaccccaaa gtcagtaggg agagtaatat tggggtggag    10500
tggggagcac ttctgcctcc cccttgggag ttttgacctc tccctcctct tcacggctag   10560
aactgtgtaa ctccgtagca tggctgttcc ccagtaccac cagggacagg aagacagact   10620
agaaccatga tggaggactg cagggtagat acctggaaga actggaaaaa tatgaaggaa   10680
actgggaaca agaggaaggt gcatgaattg cctgctctag ggttcagtaa gagcagaaaa   10740
ctcctagctc accctccatc ctctgctgca tttattgggg tggagtgggg aacagggagt   10800
tggacctaga taaactggga cagctgggct gagcttgttc tcattcaatc tggaaaaggt   10860
gaagttgatt gagctctaac ttgccattcc ttttagatgg gaaggggga agagagggca    10920 tctgaaaatc ccaggagtct tgggctgaag gcagccattc tgttctcacc tttagaggag   10980
acagaggctt agaagcaggt agggggctgg ggtggggggc aggagagcca ccccgagtc    11040 gggcaactac accattggag gccccaggcg caatccagct ttgggaaact agagtccagg   11100
ctaatggagc cctgggccag aggccaggaa tgccatcgat ccccctgcct ggcccactgc   11160
ctccctccca cctctccatg gctcctgggg tgggagggag gtaaggatgt gttgaaggag   11220
aggaggtggt tactcaccca gtcacctcct gagaacaggg cctgatctgg agggtgaagc   11280
```

```
ctggattggg agggtggggt atatggaggg ggagtaacct ttaactaaag gaagttggac    11340
ccctccagga atggactgag gccaacttta gtcactgtgt cagatccagt gggatctgat    11400
ccaggaatct ggatgcagtg cagctgggag acacagacac acacacacac acacacacac    11460
acacacacac acacacacac agtaacactg agggtcctct gggggtgcaa ttagagctgt    11520
agagcatgtg cagaaataag ggagaagagg ggaaggggag ccatgatcag tgggccatgg    11580
atagccccac aatacaccag aatactcgcc tccaagatct cttattgcca caaagtttac    11640
tattatttca ccctcaaaga gcaagccata ctggaagaga ctgtgaaggg gccacagttt    11700
agggtagatg agttagctga tgaggaaccc tgcccttttgg cagaaagatt ctgggcacct    11760
tggaatgagg aggggttaca ggaaagaaaa gtgggtgtac ccaggaaaaa tgaagcctct    11820
gtgggtgagg tattgaggta cagccttaga tatctgggtg ccatggggac ccaggtcaca    11880
gtatgatatg gatatgtgtc atgacaacct tgatatgtct cataatgtta taaggtcaca    11940
atgtcatagt gttctttgta gactcacatg tcatgatgtc ccagaggcat tgtgtgttct    12000
tgtgtggttt gatcatgctg tgtgtgagat ggcctatatg ggtctccatg tgtatgcatc    12060
ctgttttact taggtcacat ttgtatatgt ttgtgttaag gagttagcag gtcattgtgt    12120
gtgtgtgtgt gagcatgcat attacgccat caggtgtgag ttactggata tcaagctgtc    12180
actggcaccc atcactgtga tgtattgttc tacatgtcac tatacacgcc tgtcactgta    12240
ggtgtgtgta tgagagaggt gttcttaccc aggcaatcct tgggttggac atcatcctga    12300
gaggtccagc catggcactt gagccaaggg tactaggtca gcaaagacac tgaggccact    12360
gccacctcat ccttgccgcc tcgctgtcac cggccacgtc ccattaaacc aagtgcctga    12420
gcctcacctc tatggactca ctgggctccc ctaacccgat tccaaccacc cttgccattc    12480
ctttcctccc cttaattcct cccccagccc ggtccccaga tggggttgat tgtgactgg    12540
cggggagggg acagggaaca gagggacaat gggagttaat gtgccttcct ggggtcttct    12600
ctcttcccag gccaccctcc agggcccact aaaaaagcgc tgaagcagcg attcctcaag    12660
ctgctgccgt gctgcgggcc caagccctg ccctcagtca gtgaaagcaa gtgcctctca    12720
tgtgcttccg ggggcgggc tcgatgtgtg cgtgcgtgtc tgtgcatgag tgtgtgcgcg    12780
tgtgccccag gcctgcgagt gtgcgcatgc tccaggcctg catgtgtggg ggggcgtgcc    12840
ccaggcctgc gtgtgtgggg gtggggcctg ccccaggcct gtgcgtgtgt atgtgtgtgc    12900
atgtgcgcgc gagcgtgccc caggccgcg tgtgtgtg ggggggcgtg ccctacccct    12960
gcatgtgtgt ggagggcgtg ccccaggccc gcgcgcgtgt gtgtgtgtat ggggaggcgt    13020
gccgcacgcc tgcgtgtggg ggaggggcgt gccccaggcc tgcgtgcgtg tgtgtgtgtg    13080
tgtgtgtgtg tgtgtgggcg tgaccagcgt ggcgagggcg ggtgctggca aggctggagc    13140
ataaggggc gtggctactg tgtgcgtgtg cggctgaagc cagcgtgtgt gggcgtggtc    13200
agttgggagc gggtgtgtgt caccgctccc gcaaaactgt gggacccgag agtgtgggtg    13260
tgaccattgt gaccaggctg aggcctgagc ctgtgtagct gtggcggcct gtgtagacca    13320
ggcggccgtg agggtctgta tgtggcttag ctgggttagt gtcttcaact ccgtgcggcc    13380
gcccccttcc ccaccgtgtt ttggacccct gatgtgtgtt gcctatgccc cgacaggatg    13440
gtgacaggtg tagaggatgg cgcctgccct cctccagacg ccagggtatt tgggttttct    13500
gtgccagcct ggtcccctgc tgagtgatct ccagttgagt gacctcgctt tgtctctagg    13560
tctccatttc ctcagttggg ccttgcccac ctcataggat catactgcat tttgcaaacc    13620
```

```
ataaaggccc gctttgtagt tatttgagca tgctgttgtg ttggacttag atgggtccca    13680 cacggggtg gattcggaaa aggacaggcg tgagtcccgc aagcttgtgt gcatgggtc     13740 cgtttcgtgt gtgtctgtgc tggttgggtg tgcctttgca cgggctgggt tgtgaggttt    13800
gctctgagtg tgaggggcca ggtgtgtgtc tgcagttggc cgggtcttcc gctttctcgg    13860
tgacagttcg ctcccttcag cattagccgc cccagcctcc ctccgccccc acagaccccg    13920
cctgctggac ccaggtgact tacgctcctg gtggggcgg ggcggggcag ggcggctttg     13980
ccatcttggg gtgggggca cttgcctggg ggctggacgt tggggcggg gcaggattga      14040 gatgggccg gggtggggt ctggatggag gttggctgag ctgggcgggg catggctcag      14100
gcatggctgg gatagatggg gctgggcggg gcgaggggag gggctgggtg gacgagggg     14160 agggtttggg cggggcaagg ctgggctgg gcggatctga gttggtcccc gaaggcccgg     14220
agctctgacc ctcagacgcc ccctcttgaa ctggcttttc ccactcctcc ctttctaaaa    14280
cgaagatgcg gctgggggcc ttcccctcca acgaggatc gagggccgcg gggcgagcac     14340
tgagtcggat ccctggctct ggggccaggc caggccttgg cccgctgata gacctcgaag    14400
atggccatca tcttttctcc ttacctcagt gtccttggct cggggcccag ggaactggca    14460
gcctggtctc cggcatcgga tgggaccggg gggcggggag ggggtgaatg gggcagtgat   14520
ttgaagaggg gtcgcggagg ctgggcctga ggcgcggctg tcctcaccgc tcccgcagac    14580
agcgtggacg atgaatttga attgtccacc gtgtgtcacc ggcctgaggg tctggagcag    14640
ctgcaggagc aaaccaaatt cacgcgcaag gagttgcagg tcctgtaccg gggcttcaag    14700
aacgtgagtg caaggcgagg ccaaactcag cgagggtggg acaggaggac ccaagccggt    14760
ccacagcttc ccagaaagca tggcttggat gcttgaggtg tgggcggaag ggaggcaagg    14820
ccctgagact gaacttctag ctggaggttc tggggcgggg ccagaacgga agtggcgcct    14880
gtagactgtc agtttcgttc catgtttttt atttgtgcac tgggaaagaa gtcttccctc    14940
ccatcacatg agccacgtgg tgagtcctct ggaggcttga agattatccc cctccctggg    15000
agtcttgggc catggagggt gggggcggtg aacggaaggg gattttgtct ctgccctcag    15060
cctggtgccc tctccttcca ggaatgtccc agcggaattg tcaatgagga gaacttcaag    15120
cagatttact cccagttctt tcctcaagga ggtgagggga caaggcccaa ggggaagcag    15180
ttgtccttct ctaggctgag ggaggaggg attctggagg agctgggaat gccaaggtga    15240 tgggggtat gggagctcc ttagaggag gaagtcctct cctgtgtgga agccaacttc      15300
tccacactca ccctgcagac tccagcacct atgccacttt tctcttcaat gcctttgaca    15360
ccaaccatga tggctcggtc agttttgagg tgagctgggc gaggtgggcc agggaagcct    15420
gtttcctgga gttcagggcc aggatctcca ggccaaaccc agagaaggag ttgggtgaag    15480
agtacccgag gacacagctc cctcctgcct ccttcccagg actttgtggc tggtttgtcc    15540
gtgattcttc ggggaactgt agatgacagg cttaattggg ccttcaacct gtatgacctt    15600
aacaaggacg gctgcatcac caaggaggtg cagggcaact gaagggctgg gggtctgtgg    15660
cggtgatggg ggtggcgtgc agagggtgat gggaggaaa tatgacccac atatgcccac    15720
aagcaaggga tcaagggagg ctggaggctc tgaggaagga tcctcttctc tcttggccta    15780
acaggaaatg cttgacatca tgaagtccat ctatgcatg atgggcaagt acacgtaccc     15840
tgcactccgg gaggaggccc caagggaaca cgtggagagc ttcttccagg tacttgggag    15900
tgggtaggct ggagggccct ggagtgaagg gaagaaggcc aagaaccagc agggaactca    15960
cctgacttct gtctgcctct ctcttgccat ccctcctgtt ctccctgcct gaccaccttc    16020
```

```
ttgcagaaga tggacagaaa caaggatggt gtggtgacca ttgaggaatt cattgagtct    16080
tgtcaaaagg tacagctccc tgccctctac attaccctga cctggactca ggcctgattt    16140
agtaatgcag ggaaaagctt ctttgggaag aataccacct tcccacctca cccccatatt    16200
tcaatcctat tcctttgtgg gaggcttacc ccttccctac ctcaggtctc tctgggcatc    16260
tccttcctct gtgcttttga atgtccccgt ctgtgactca gtgtccctct cactgtctct    16320
gataagctcc ttctctttct ctctcttcaa tctgcctcgc tcacatcatg ccacaggat    16380 gagaacatca tgaggtccat gcagctcttt gacaatgtca tctagccccc aggagagggg    16440
gtcagtgttt cctgggggga ccatgctcta accctagtcc aggcggacct caccccttctc   16500 ttcccaggtc tatcctcatc ctacgcctcc ctgggggctg gagggatcca agagcttggg    16560
gattcagtag tccagatctc tggagctgaa ggggccagag agtgggcaga gtgcatctcg    16620
gggggtgttc ccaactccca ccagctctca ccccccttcct gcctgacacc cagtgttgag    16680
agtgcccctc ctgtaggaat tgagcggttc cccacctcct acccctactc tagaaacaca    16740
ctagacagat gtctcctgct atggtgcttc ccccatccct gacctcataa acatttcccc    16800
taagactccc ctctcagaga gaatgctcca ttcttggcac tggctggctt ctcagaccag    16860
ccattgagag ccctgtggga gggggacaag aatgtatagg gagaaatctt gggcctgagt    16920
caatggatag gtcctaggag gtggctgggg ttgagaatag aagggcctgg acagattatg    16980
attgctcagg cataccaggt tatagctcca agttccacag gtctgctacc acaggccatc    17040
aaaatataag tttccaggct ttgcagaaga ccttgtctcc ttagaaatgc cccagaaatt    17100
ttccacaccc tcctcggtat ccatggagag cctggggcca gatatctggc tcatctctgg    17160
cattgcttcc tctccttcct tcctgcatgt gttggtggtg gttgtggtgg gggaatgtgg    17220
atgggggatg tcctggctga tgcctgccaa aatttcatcc caccctcctt gcttatcgtc    17280
cctgttttga gggctatgac ttgagttttt gtttcccatg ttctctatag acttgggacc    17340
ttcctgaact tggggcctat cactccccac agtggatgcc ttagaaggga gagggaagga    17400
gggaggcagg catagcatct gaacccagtg tgggggcatt cactagaatc ttcaatcaac    17460
ctgggctctc cccaccccac cccagataac ctcctcagtt ccctagggtc tcttcttgct    17520
tgactcaatc tacccagaga tgccccttag cacacctaga gggcagggac cataggaccc    17580
aggttccaac cccattgtca gcaccccagc catgcggcca cccttagca cctgctcg      17640 tcccatttag cttaccctcc cagttggcca gaatctgagg ggagagcccc cagagagccc    17700
ccttccccat cagaagactg ttgactgctt tgcattttgg gctcttctat atattttgta    17760
aagtaagaaa ataccagat ctaataaaac acaatggcta tgc                       17803
```

```
<210> SEQ ID NO 75
<211> LENGTH: 1285
<212> TYPE: DNA
<213> ORGANISM: Rattus sp.
<220> FEATURE:
<221> NAME/KEY: CDS
<222> LOCATION: (1)..(813)

<400> SEQUENCE: 75
```

```
atg cgg ggc caa ggc aga aag gag agt ttg tcc gaa tcc cga gat ctg     48
Met Arg Gly Gln Gly Arg Lys Glu Ser Leu Ser Glu Ser Arg Asp Leu
 1               5                  10                  15 gac ggc tcc tat gac cag ctt acg ggc cac cct cca ggg ccc agt aaa     96
Asp Gly Ser Tyr Asp Gln Leu Thr Gly His Pro Pro Gly Pro Ser Lys
             20                  25                  30
```

```
aaa gcc ctg aag cag cgt ttc ctc aag ctg ctg ccg tgc tgc ggg ccc      144
Lys Ala Leu Lys Gln Arg Phe Leu Lys Leu Leu Pro Cys Cys Gly Pro
         35                  40                  45 caa gcc ctg ccc tca gtc agt gaa aca tta gct gcc cca gcc tcc ctc      192
Gln Ala Leu Pro Ser Val Ser Glu Thr Leu Ala Ala Pro Ala Ser Leu
 50                  55                  60 cgc ccc cac aga ccc cgc ccg ctg gac cca gac agc gta gag gat gag      240
Arg Pro His Arg Pro Arg Pro Leu Asp Pro Asp Ser Val Glu Asp Glu
 65                  70                  75                  80 ttt gaa tta tcc acg gtg tgt cac cga cct gag ggc ctg gaa caa ctc      288
Phe Glu Leu Ser Thr Val Cys His Arg Pro Glu Gly Leu Glu Gln Leu
                 85                  90                  95 cag gaa cag acc aag ttc aca cgc aga gag ctg cag gtc ctg tac cga      336
Gln Glu Gln Thr Lys Phe Thr Arg Arg Glu Leu Gln Val Leu Tyr Arg
            100                 105                 110 ggc ttc aag aac gaa tgc ccc agt ggg att gtc aac gag gag aac ttc      384
Gly Phe Lys Asn Glu Cys Pro Ser Gly Ile Val Asn Glu Glu Asn Phe
        115                 120                 125 aag cag att tat tct cag ttc ttt ccc caa gga gac tcc agc aac tat      432
Lys Gln Ile Tyr Ser Gln Phe Phe Pro Gln Gly Asp Ser Ser Asn Tyr
    130                 135                 140 gct act ttt ctc ttc aat gcc ttt gac acc aac cac gat ggc tct gtc      480
Ala Thr Phe Leu Phe Asn Ala Phe Asp Thr Asn His Asp Gly Ser Val
145                 150                 155                 160 agt ttt gag gac ttt gtg gct ggt ttg tcg gtg att ctt cgg ggg acc      528
Ser Phe Glu Asp Phe Val Ala Gly Leu Ser Val Ile Leu Arg Gly Thr
                165                 170                 175 ata gat gat aga ctg agc tgg gct ttc aac tta tat gac ctc aac aag      576
Ile Asp Asp Arg Leu Ser Trp Ala Phe Asn Leu Tyr Asp Leu Asn Lys
            180                 185                 190 gac ggc tgt atc aca aag gag gaa atg ctt gac att atg aag tcc atc      624
Asp Gly Cys Ile Thr Lys Glu Glu Met Leu Asp Ile Met Lys Ser Ile
        195                 200                 205 tat gac atg atg ggc aag tac aca tac cct gcc ctc cgg gag gag gcc      672
Tyr Asp Met Met Gly Lys Tyr Thr Tyr Pro Ala Leu Arg Glu Glu Ala
    210                 215                 220 cca aga gaa cac gtg gag agc ttc ttc cag aag atg gac agg aac aag      720
Pro Arg Glu His Val Glu Ser Phe Phe Gln Lys Met Asp Arg Asn Lys
225                 230                 235                 240 gac ggc gtg gtg acc atc gag gaa ttc atc gag tct tgt caa cag gac      768
Asp Gly Val Val Thr Ile Glu Glu Phe Ile Glu Ser Cys Gln Gln Asp
                245                 250                 255 gag aac atc atg agg tcc atg cag ctc ttt gat aat gtc atc tag          813
Glu Asn Ile Met Arg Ser Met Gln Leu Phe Asp Asn Val Ile
            260                 265                 270 ctccccaggg agaggggtta gtgtgtccta gggtgaccag gctgtagtcc tagtccagac     873
gaacctaacc ctctctctcc aggcctgtcc tcatcttacc tgtaccctgg gggctgtagg     933
gattcaatat cctggggctt cagtagtcca gatccctgag ctaagtcaca aaagtaggca     993
agagtaggca agctaaatct ggggcttcc caacccccga cagctctcac cccttctcaa     1053
ctgataccta gtgctgagga caccccctggt gtagggacca agtggttctc caccttctag   1113
tcccactcta gaaaccacat tagacagaag gtctcctgct atggtgcttt ccccatccct    1173
aatctcttag attttcctca agactccctt ctcagagaac acgctctgtc catgtcccca   1233
gctggggaca tggacagagc gtgttctcta gttctagatc gcgagcggcc gc            1285

<210> SEQ ID NO 76
```

<211> LENGTH: 270
<212> TYPE: PRT
<213> ORGANISM: Rattus sp.

<400> SEQUENCE: 76

Met Arg Gly Gln Gly Arg Lys Glu Ser Leu Ser Glu Ser Arg Asp Leu
1               5                   10                  15

Asp Gly Ser Tyr Asp Gln Leu Thr Gly His Pro Pro Gly Pro Ser Lys
            20                  25                  30

Lys Ala Leu Lys Gln Arg Phe Leu Lys Leu Leu Pro Cys Cys Gly Pro
        35                  40                  45

Gln Ala Leu Pro Ser Val Ser Glu Thr Leu Ala Ala Pro Ala Ser Leu
    50                  55                  60

Arg Pro His Arg Pro Arg Pro Leu Asp Pro Asp Ser Val Glu Asp Glu
65                  70                  75                  80

Phe Glu Leu Ser Thr Val Cys His Arg Pro Glu Gly Leu Glu Gln Leu
                85                  90                  95

Gln Glu Gln Thr Lys Phe Thr Arg Arg Glu Leu Gln Val Leu Tyr Arg
            100                 105                 110

Gly Phe Lys Asn Glu Cys Pro Ser Gly Ile Val Asn Glu Glu Asn Phe
        115                 120                 125

Lys Gln Ile Tyr Ser Gln Phe Phe Pro Gln Gly Asp Ser Ser Asn Tyr
    130                 135                 140

Ala Thr Phe Leu Phe Asn Ala Phe Asp Thr Asn His Asp Gly Ser Val
145                 150                 155                 160

Ser Phe Glu Asp Phe Val Ala Gly Leu Ser Val Ile Leu Arg Gly Thr
                165                 170                 175

Ile Asp Asp Arg Leu Ser Trp Ala Phe Asn Leu Tyr Asp Leu Asn Lys
            180                 185                 190

Asp Gly Cys Ile Thr Lys Glu Glu Met Leu Asp Ile Met Lys Ser Ile
        195                 200                 205

Tyr Asp Met Met Gly Lys Tyr Thr Tyr Pro Ala Leu Arg Glu Glu Ala
    210                 215                 220

Pro Arg Glu His Val Glu Ser Phe Phe Gln Lys Met Asp Arg Asn Lys
225                 230                 235                 240

Asp Gly Val Val Thr Ile Glu Glu Phe Ile Glu Ser Cys Gln Gln Asp
                245                 250                 255

Glu Asn Ile Met Arg Ser Met Gln Leu Phe Asp Asn Val Ile
            260                 265                 270

<210> SEQ ID NO 77
<211> LENGTH: 2076
<212> TYPE: DNA
<213> ORGANISM: Homo sapiens
<220> FEATURE:
<221> NAME/KEY: CDS
<222> LOCATION: (1)..(678)

<400> SEQUENCE: 77 atg aac cga tgc ccc cgc agg tgc cgg agc ccg ctg ggg cag gca gcg      48
Met Asn Arg Cys Pro Arg Arg Cys Arg Ser Pro Leu Gly Gln Ala Ala
1               5                   10                  15 cga tcc ctc tac cag ctg gtg act ggg tcg ctg tcc cca gac agc gtg      96
Arg Ser Leu Tyr Gln Leu Val Thr Gly Ser Leu Ser Pro Asp Ser Val
            20                  25                  30 gac gat gaa ttt gaa ttg tcc acc gtg tgt cac cgg cct gag ggt ctg     144
Asp Asp Glu Phe Glu Leu Ser Thr Val Cys His Arg Pro Glu Gly Leu
        35                  40                  45

```
gag cag ctg cag gag caa acc aaa ttc acg cgc aag gag ttg cag gtc    192
Glu Gln Leu Gln Glu Gln Thr Lys Phe Thr Arg Lys Glu Leu Gln Val
         50                  55                  60 ctg tac cgg ggc ttc aag aac gaa tgt ccc agc gga att gtc aat gag    240
Leu Tyr Arg Gly Phe Lys Asn Glu Cys Pro Ser Gly Ile Val Asn Glu
 65                  70                  75                  80 gag aac ttc aag cag att tac tcc cag ttc ttt cct caa gga gac tcc    288
Glu Asn Phe Lys Gln Ile Tyr Ser Gln Phe Phe Pro Gln Gly Asp Ser
                 85                  90                  95 agc acc tat gcc act ttt ctc ttc aat gcc ttt gac acc aac cat gat    336
Ser Thr Tyr Ala Thr Phe Leu Phe Asn Ala Phe Asp Thr Asn His Asp
            100                 105                 110 ggc tcg gtc agt ttt gag gac ttt gtg gct ggt ttg tcc gtg att ctt    384
Gly Ser Val Ser Phe Glu Asp Phe Val Ala Gly Leu Ser Val Ile Leu
        115                 120                 125 cgg gga act gta gat gac agg ctt aat tgg gcc ttc aac ctg tat gac    432
Arg Gly Thr Val Asp Asp Arg Leu Asn Trp Ala Phe Asn Leu Tyr Asp
130                 135                 140 ctt aac aag gac ggc tgc atc acc aag gag gaa atg ctt gac atc atg    480
Leu Asn Lys Asp Gly Cys Ile Thr Lys Glu Glu Met Leu Asp Ile Met
145                 150                 155                 160 aag tcc atc tat gac atg atg ggc aag tac acg tac cct gca ctc cgg    528
Lys Ser Ile Tyr Asp Met Met Gly Lys Tyr Thr Tyr Pro Ala Leu Arg
                165                 170                 175 gag gag gcc cca agg gaa cac gtg gag agc ttc ttc cag aag atg gac    576
Glu Glu Ala Pro Arg Glu His Val Glu Ser Phe Phe Gln Lys Met Asp
            180                 185                 190 aga aac aag gat ggt gtg gtg acc att gag gaa ttc att gag tct tgt    624
Arg Asn Lys Asp Gly Val Val Thr Ile Glu Glu Phe Ile Glu Ser Cys
        195                 200                 205 caa aag gat gag aac atc atg agg tcc atg cag ctc ttt gac aat gtc    672
Gln Lys Asp Glu Asn Ile Met Arg Ser Met Gln Leu Phe Asp Asn Val
210                 215                 220 atc tag cccccaggag aggggtcag tgtttcctgg ggggaccatg ctctaaccct      728
Ile
225 agtccaggcg gacctcaccc ttctcttccc aggtctatcc tcatcctacg cctccctggg   788 ggctggaggg atccaagagc ttggggattc agtagtccag atctctggag ctgaaggggc   848 cagagagtgg gcagagtgca tctcgggggg tgttcccaac tcccaccagc tctcaccccc   908 ttcctgcctg acaccagtg ttgagagtgc ccctcctgta ggaattgagc ggttccccac    968 ctcctacccc tactctagaa acacactaga cagatgtctc ctgctatggt gcttccccca  1028 tccctgacct cataaacatt tcccctaaga ctcccctctc agagagaatg ctccattctt  1088 ggcactggct ggcttctcag accagccatt gagagccctg tgggagggggg acaagaatgt  1148 atagggagaa atcttgggcc tgagtcaatg gataggtcct aggaggtggc tggggttgag  1208 aatagaaggg cctggacaga ttatgattgc tcaggcatac caggttatag ctccaagttc  1268 cacaggtctg ctaccacagg ccatcaaaat ataagttttcc aggctttgca gaagaccttg  1328 tctccttaga aatgccccag aaattttcca caccctcctc ggtatccatg gagagcctgg  1388 ggccagatat ctggctcatc tctggcattg cttcctctcc ttccttcctg catgtgttgg  1448 tggtggttgt ggtgggggaa tgtggatggg ggatgtcctg gctgatgcct gccaaaattt  1508 catcccaccc tccttgctta tcgtccctgt tttgagggct atgacttgag ttttttgtttc  1568 ccatgttctc tatagacttg ggaccttcct gaacttgggg cctatcactc cccacagtgg  1628
```

```
atgccttaaa agggagaggg aaggagggag gcaggcatag catctgaacc cagtgtgggg    1688
gcattcacta gaatcttcaa tcaacctggg ctctccccac cccacccag ataacctcct     1748 cagttcccta gggtctcttc ttgcttgact caatctaccc agagatgccc cttagcacac    1808
ctagagggca gggaccatag gacccaggtt ccaaccccat tgtcagcacc ccagccatgc    1868
ggccacccct tagcacacct gctcgtccca tttagcttac cctcccagtt ggccagaatc    1928
tgaggggaga gccccagag agccccttc cccatcagaa gactgttgac tgctttgcat      1988
tttgggctct tctatatatt ttgtaaagta agaaatatac cagatctaat aaaacacaat    2048
ggctatgcac agaaaaaaaa aaaaaaaa                                      2076
```

<210> SEQ ID NO 78
<211> LENGTH: 225
<212> TYPE: PRT
<213> ORGANISM: Homo sapiens

<400> SEQUENCE: 78

```
Met Asn Arg Cys Pro Arg Arg Cys Arg Ser Pro Leu Gly Gln Ala Ala
 1               5                  10                  15

Arg Ser Leu Tyr Gln Leu Val Thr Gly Ser Leu Ser Pro Asp Ser Val
            20                  25                  30

Asp Asp Glu Phe Glu Leu Ser Thr Val Cys His Arg Pro Glu Gly Leu
        35                  40                  45

Glu Gln Leu Gln Glu Gln Thr Lys Phe Thr Arg Lys Glu Leu Gln Val
    50                  55                  60

Leu Tyr Arg Gly Phe Lys Asn Glu Cys Pro Ser Gly Ile Val Asn Glu
65                  70                  75                  80

Glu Asn Phe Lys Gln Ile Tyr Ser Gln Phe Phe Pro Gln Gly Asp Ser
                85                  90                  95

Ser Thr Tyr Ala Thr Phe Leu Phe Asn Ala Phe Asp Thr Asn His Asp
           100                 105                 110

Gly Ser Val Ser Phe Glu Asp Phe Val Ala Gly Leu Ser Val Ile Leu
       115                 120                 125

Arg Gly Thr Val Asp Asp Arg Leu Asn Trp Ala Phe Asn Leu Tyr Asp
   130                 135                 140

Leu Asn Lys Asp Gly Cys Ile Thr Lys Glu Glu Met Leu Asp Ile Met
145                 150                 155                 160

Lys Ser Ile Tyr Asp Met Met Gly Lys Tyr Thr Tyr Pro Ala Leu Arg
                165                 170                 175

Glu Glu Ala Pro Arg Glu His Val Glu Ser Phe Phe Gln Lys Met Asp
           180                 185                 190

Arg Asn Lys Asp Gly Val Val Thr Ile Glu Glu Phe Ile Glu Ser Cys
       195                 200                 205

Gln Lys Asp Glu Asn Ile Met Arg Ser Met Gln Leu Phe Asp Asn Val
   210                 215                 220

Ile
225
```

<210> SEQ ID NO 79
<211> LENGTH: 1477
<212> TYPE: DNA
<213> ORGANISM: Homo sapiens

<400> SEQUENCE: 79

```
ctgagtccct gcatgtgcgg ggctgaagaa ggaagccaga agcctcctag cctcgcctcc     60
```

| | |
|---|---:|
| acgtttgctg aataccaagc tgcaggcgag ctgccgggcg cttttctctc ctccaattca | 120 |
| gagtagacaa accacgggga tttctttcca gggtaggggga ggggccgggc ccggggtccc | 180 |
| aactcgcact caagtcttcg ctgccatggg ggccgtcatg ggcaccttct catctctgca | 240 |
| aaccaaacaa aggcgaccct cgaaagacat cgcctggtgg tattaccagt atcagagaga | 300 |
| taagattgaa gatgagctgg agatgaccat ggtttgccat cggcccgagg gactggagca | 360 |
| gctcgaggcc cagaccaact tcaccaagag ggagctgcag gtcctttatc gaggcttcaa | 420 |
| aaatgagtgc cccagtggtg tggtcaacga agacacattc aagcagatct atgctcagtt | 480 |
| tttccctcat ggagatgcca gcacgtatgc ccattacctc ttcaatgcct tcgacaccac | 540 |
| tcagacaggc tccgtgaagt tcgaggactt tgtaaccgct ctgtcgattt tattgagagg | 600 |
| aactgtccac gagaaactaa ggtggacatt taatttgtat gacatcaaca aggacgggata | 660 |
| cataaacaaa gaggagatga tggacattgt caaagccatc tatgacatga tggggaaata | 720 |
| cacatatcct gtgctcaaag aggacactcc aaggcagcat gtggacgtct tcttccagaa | 780 |
| aatggacaaa aataaagatg gcatcgtaac tttagatgaa tttcttgaat catgtcagga | 840 |
| ggacgacaac atcatgaggt ctctccagct gtttttcaaaat gtcatgtaac tggtgacact | 900 |
| cagccattca gctctcagag acattgtact aaacaaccac cttaacaccc tgatctgccc | 960 |
| ttgttctgat tttacacacc aactcttggg acagaaacac cttttacact ttggaagaat | 1020 |
| tctctgctga agactttctt atggaaccca gcatcatgtg gctcagtctc tgattgccaa | 1080 |
| ctcttcctct ttcttcttct tgagagagac aagatgaaat ttgagtttgt tttggaagca | 1140 |
| tgctcatctc ctcacactgc tgccctatgg aaggtccctc tgcttaagct taaacagtag | 1200 |
| tgcacaaaat atgctgctta cgtgccccca gcccactgcc tccaagtcag gcagaccttg | 1260 |
| gtgaatctgg aagcaagagg acctgagcca gatgcacacc atctctgatg gcctcccaaa | 1320 |
| ccaatgtgcc tgtttctctt cctttggtgg gaagaatgag agttatccag aacaattagg | 1380 |
| atctgtcatg accagattgg gagagccagc acctaacata tgtgggatag gactgaatta | 1440 |
| ttaagcatga cattgtctga tgacccaaac tgccccg | 1477 |

<210> SEQ ID NO 80
<211> LENGTH: 1639
<212> TYPE: DNA
<213> ORGANISM: Homo sapiens
<220> FEATURE:
<221> NAME/KEY: CDS
<222> LOCATION: (353)..(1051)

<400> SEQUENCE: 80

| | |
|---|---:|
| cacacgtttt ctctgagctg ccgagagaat atgccatgag atgttgccag tgatggttac | 60 |
| actcagctag cagaagatta gggactggtt aaaccttttgg agaaattgcc ttgggaaaag | 120 |
| aggaaataaa agcaaatatt actatgaaac atagagatta ccaggtagga ggaggagaga | 180 |
| ggtggaggga ggggtaggag tggaaggaag ggagggaggc agaaagagga aggcagactg | 240 |
| gtggaaaata aaccgtgcac tttagaacag caggaaggga ggcttggaag cctggttttc | 300 |
| tggctttgaa tgaccgccta gcgcttgccg gtgcgccagg gatgctgtga gg atg tgg | 358 |
|  Met Trp | |
|  1 | |
| gca gag ggc gag tcc gaa ggg ctc cag aca ctg gga ata gtg gtg gtc<br>Ala Glu Gly Glu Ser Glu Gly Leu Gln Thr Leu Gly Ile Val Val Val<br> 5                       10                    15 | 406 |
| gtg tgc tcc tcc ctg aaa ctt ttg cac tac ctc gga ctg att gac ttg<br>Val Cys Ser Ser Leu Lys Leu Leu His Tyr Leu Gly Leu Ile Asp Leu | 454 |

-continued

```
              20                  25                  30
tca gac gat aag att gaa gat gag ctg gag atg acc atg gtt tgc cat     502
Ser Asp Asp Lys Ile Glu Asp Glu Leu Glu Met Thr Met Val Cys His
 35                  40                  45                  50 cgg ccc gag gga ctg gag cag ctc gag gcc cag acc aac ttc acc aag     550
Arg Pro Glu Gly Leu Glu Gln Leu Glu Ala Gln Thr Asn Phe Thr Lys
                     55                  60                  65 agg gag ctg cag gtc ctt tat cga ggc ttc aaa aat gag tgc ccc agt     598
Arg Glu Leu Gln Val Leu Tyr Arg Gly Phe Lys Asn Glu Cys Pro Ser
                 70                  75                  80 ggt gtg gtc aac gaa gac aca ttc aag cag atc tat gct cag ttt ttc     646
Gly Val Val Asn Glu Asp Thr Phe Lys Gln Ile Tyr Ala Gln Phe Phe
             85                  90                  95 cct cat gga gat gcc agc acg tat gcc cat tac ctc ttc aat gcc ttc     694
Pro His Gly Asp Ala Ser Thr Tyr Ala His Tyr Leu Phe Asn Ala Phe
         100                 105                 110 gac acc act cag aca ggc tcc gtg aag ttc gag gac ttt gta acc gct     742
Asp Thr Thr Gln Thr Gly Ser Val Lys Phe Glu Asp Phe Val Thr Ala
115                 120                 125                 130 ctg tcg att tta ttg aga gga act gtc cac gag aaa cta agg tgg aca     790
Leu Ser Ile Leu Leu Arg Gly Thr Val His Glu Lys Leu Arg Trp Thr
                 135                 140                 145 ttt aat ttg tat gac atc aac aag gac gga tac ata aac aaa gag gag     838
Phe Asn Leu Tyr Asp Ile Asn Lys Asp Gly Tyr Ile Asn Lys Glu Glu
             150                 155                 160 atg atg gac att gtc aaa gcc atc tat gac atg atg ggg aaa tac aca     886
Met Met Asp Ile Val Lys Ala Ile Tyr Asp Met Met Gly Lys Tyr Thr
         165                 170                 175 tat cct gtg ctc aaa gag gac act cca agg cag cat gtg gac gtc ttc     934
Tyr Pro Val Leu Lys Glu Asp Thr Pro Arg Gln His Val Asp Val Phe
     180                 185                 190 ttc cag aaa atg gac aaa aat aaa gat ggc atc gta act tta gat gaa     982
Phe Gln Lys Met Asp Lys Asn Lys Asp Gly Ile Val Thr Leu Asp Glu
195                 200                 205                 210 ttt ctt gaa tca tgt cag gag gac gac aac atc atg agg tct ctc cag    1030
Phe Leu Glu Ser Cys Gln Glu Asp Asp Asn Ile Met Arg Ser Leu Gln
                 215                 220                 225 ctg ttt caa aat gtc atg taa ctggtgacac tcagccattc agctctcaga       1081
Leu Phe Gln Asn Val Met
             230 gacattgtac taaacaacca ccttaacacc ctgatctgcc cttgttctga ttttacacac  1141 caactcttgg gacagaaaca cctttacac tttggaagaa ttctctgctg aagactttct   1201 tatggaaccc agcatcatgt ggctcagtct ctgattgcca actcttcctc tttcttcttc  1261 ttgagagaga caagatgaaa tttgagtttg ttttggaagc atgctcatct cctcacactg  1321 ctgccctatg aaggtccct ctgcttaagc ttaaacagta gtgcacaaaa tatgctgctt   1381 acgtgccccc agcccactgc ctccaagtca ggcagacctt ggtgaatctg aagcaagag   1441 gacctgagcc agatgcacac catctctgat ggcctcccaa accaatgtgc ctgtttctct  1501 tcctttggtg ggaagaatga gagttatcca gaacaattag gatctgtcat gaccagattg  1561 ggagagccag cacctaacat atgtgggata ggactgaatt attaagcatg acattgtctg  1621 atgacccaaa ctgccccg                                                1639
```

<210> SEQ ID NO 81
<211> LENGTH: 232
<212> TYPE: PRT
<213> ORGANISM: Homo sapiens

<400> SEQUENCE: 81

Met Trp Ala Glu Gly Glu Ser Glu Gly Leu Gln Thr Leu Gly Ile Val
1               5                   10                  15

Val Val Val Cys Ser Ser Leu Lys Leu Leu His Tyr Leu Gly Leu Ile
            20                  25                  30

Asp Leu Ser Asp Asp Lys Ile Glu Asp Glu Leu Glu Met Thr Met Val
        35                  40                  45

Cys His Arg Pro Glu Gly Leu Glu Gln Leu Glu Ala Gln Thr Asn Phe
    50                  55                  60

Thr Lys Arg Glu Leu Gln Val Leu Tyr Arg Gly Phe Lys Asn Glu Cys
65                  70                  75                  80

Pro Ser Gly Val Val Asn Glu Asp Thr Phe Lys Gln Ile Tyr Ala Gln
                85                  90                  95

Phe Phe Pro His Gly Asp Ala Ser Thr Tyr Ala His Tyr Leu Phe Asn
            100                 105                 110

Ala Phe Asp Thr Thr Gln Thr Gly Ser Val Lys Phe Glu Asp Phe Val
        115                 120                 125

Thr Ala Leu Ser Ile Leu Leu Arg Gly Thr Val His Glu Lys Leu Arg
    130                 135                 140

Trp Thr Phe Asn Leu Tyr Asp Ile Asn Lys Asp Gly Tyr Ile Asn Lys
145                 150                 155                 160

Glu Glu Met Met Asp Ile Val Lys Ala Ile Tyr Asp Met Met Gly Lys
                165                 170                 175

Tyr Thr Tyr Pro Val Leu Lys Glu Asp Thr Pro Arg Gln His Val Asp
            180                 185                 190

Val Phe Phe Gln Lys Met Asp Lys Asn Lys Asp Gly Ile Val Thr Leu
        195                 200                 205

Asp Glu Phe Leu Glu Ser Cys Gln Glu Asp Asp Asn Ile Met Arg Ser
    210                 215                 220

Leu Gln Leu Phe Gln Asn Val Met
225                 230

<210> SEQ ID NO 82
<211> LENGTH: 2835
<212> TYPE: DNA
<213> ORGANISM: Homo sapiens
<220> FEATURE:
<221> NAME/KEY: CDS
<222> LOCATION: (16)..(783)

<400> SEQUENCE: 82
tctagagccg ccacc atg cag ccg gct aag gaa gtg aca aag gcg tcg gac       51
              Met Gln Pro Ala Lys Glu Val Thr Lys Ala Ser Asp
                1               5                   10 ggc agc ctc ctg ggg gac ctg ggg cac aca cca ctt agc aag aag gag       99
Gly Ser Leu Leu Gly Asp Leu Gly His Thr Pro Leu Ser Lys Lys Glu
        15                  20                  25 ggt atc aag tgg cag agg ccg agg ctc agc cgc cag gct ttg atg aga      147
Gly Ile Lys Trp Gln Arg Pro Arg Leu Ser Arg Gln Ala Leu Met Arg
    30                  35                  40 tgc tgc ctg gtc aag tgg atc ctg tcc agc aca gcc cca cag ggc tca      195
Cys Cys Leu Val Lys Trp Ile Leu Ser Ser Thr Ala Pro Gln Gly Ser
45                  50                  55                  60 gat agc agc gac agt gag ctg gag ctg tcc acg gtg cgc cac cag cca      243
Asp Ser Ser Asp Ser Glu Leu Glu Leu Ser Thr Val Arg His Gln Pro
                65                  70                  75

```
gag ggg ctg gac cag ctg cag gcc cag acc aag ttc acc aag aag gag    291
Glu Gly Leu Asp Gln Leu Gln Ala Gln Thr Lys Phe Thr Lys Lys Glu
            80                  85                  90 ctg cag tct ctc tac agg ggc ttt aag aat gag tgt ccc acg ggc ctg    339
Leu Gln Ser Leu Tyr Arg Gly Phe Lys Asn Glu Cys Pro Thr Gly Leu
        95                 100                 105 gtg gac gaa gac acc ttc aaa ctc att tac gcg cag ttc ttc cct cag    387
Val Asp Glu Asp Thr Phe Lys Leu Ile Tyr Ala Gln Phe Phe Pro Gln
110                 115                 120 gga gat gcc acc acc tat gca cac ttc ctc ttc aac gcc ttt gat gcg    435
Gly Asp Ala Thr Thr Tyr Ala His Phe Leu Phe Asn Ala Phe Asp Ala
125                 130                 135                 140 gac ggg aac ggg gcc atc cac ttt gag gac ttt gtg gtt ggc ctc tcc    483
Asp Gly Asn Gly Ala Ile His Phe Glu Asp Phe Val Val Gly Leu Ser
                145                 150                 155 atc ctg ctg cgg ggc aca gtc cac gag aag ctc aag tgg gcc ttt aat    531
Ile Leu Leu Arg Gly Thr Val His Glu Lys Leu Lys Trp Ala Phe Asn
                160                 165                 170 ctc tac gac att aac aag gat ggc tac atc acc aaa gag gag atg ctg    579
Leu Tyr Asp Ile Asn Lys Asp Gly Tyr Ile Thr Lys Glu Glu Met Leu
            175                 180                 185 gcc atc atg aag tcc atc tat gac atg atg ggc cgc cac acc tac ccc    627
Ala Ile Met Lys Ser Ile Tyr Asp Met Met Gly Arg His Thr Tyr Pro
        190                 195                 200 atc ctg cgg gag gac gcg ccg gcg gag cac gtg gag agg ttc ttc gag    675
Ile Leu Arg Glu Asp Ala Pro Ala Glu His Val Glu Arg Phe Phe Glu
205                 210                 215                 220 aaa atg gac cgg aac cag gat ggg gta gtg acc att gaa gag ttc ctg    723
Lys Met Asp Arg Asn Gln Asp Gly Val Val Thr Ile Glu Glu Phe Leu
                225                 230                 235 gag gcc tgt cag aag gat gag aac atc atg agc tcc atg cag ctg ttt    771
Glu Ala Cys Gln Lys Asp Glu Asn Ile Met Ser Ser Met Gln Leu Phe
            240                 245                 250 gag aat gtc atc taggacacgt ccaaaggagt gcatggccac agccacctcc        823
Glu Asn Val Ile
            255 acccccaaga aacctccatc ctgccaggag cagcctccaa gaaactttta aaaaatagat    883 ttgcaaaaag tgaacagatt gctacacaca cacacacaca cacacacaca cacacacaca    943 cacagccatt catctgggct ggcagagggg acagagttca gggaggggct gagtctggct   1003 aggggccgag tccaggagcc ccagccagcc cttcccaggc cagcgaggcg aggctgcctc   1063 tgggtgagtg gctgacagag caggtctgca ggccaccagc tgctggatgt caccaagaag   1123 gggctcgagt gcccctgcag gggagggtcc aatctccggt gtgagcccac ctcgtcccgt   1183 tctccattct gctttcttgc cacacagtgg gccggcccca ggctcccctg gtctcctccc   1243 cgtagccact ctctgcccac tacctatgct tctagaaagc ccctcacctc aggaccccag   1303 agggaccagc tgggggggcag gggggagagg gggtaatgaa ggccaagcct gcagctttct   1363 ggaaattctt ccctgggggt cccaggatcc cctgctactc cactgacctg aagagctgg    1423 gtaccaggcc acccactgtg gggcaagcct gagtggtgag gggccactgg gccccattct   1483 ccctccatgg caggaaggcg gggatttcag agtttaggga ttgggtcgtg gtggagaatc   1543 tgagggcact ctctgccagc tccacagggt gggatgagcc tctccttgcc ccagtcctgg   1603 ttcagtggga atgcagtggg tgggctgta cacaccctcc agcacagact gttccctcca    1663 aggtcctctt aggtcccggg aggaacgtgg ttcagagact ggcagccagg gagcccgggg   1723 cagagctcag aggagtctgg aaggggcgt gtccctcctc ttcctgtagt gcccctccca    1783
```

-continued

```
tggcccagca gcttggctga gcccctctc ctgaagcagt gtcgccgtcc ctctgccttg    1843
cacaaaaagc acaagcattc cttagcagct caggcgcagc cctagtggga gcccagcaca    1903
ctgcttctcg gaggccaggc cctcctgctg gctgaggctt gggcccagta gccccaatat    1963
ggtggccctg gggaagaggc cttggggtc tgctctgtgc ctgggatcag tggggcccca    2023
aagcccagcc cggctgacca acattcaaaa gcacaaaccc tggggactct gcttggctgt    2083
cccctccatc tggggatgga gaatgccagc ccaaagctgg agccaatggt gagggctgag    2143
agggctgtgg ctgggtggtc agcagaaacc cccaggagga gagagatgct gctcccgcct    2203
gattggggcc tcacccagaa ggaacccggt cccaggccgc atggcccctc caggaacatt    2263
cccacataat acattccatc acagccagcc cagctccact cagggctggc ccggggagtc    2323
cccgtgtgcc ccaagaggct agcccagggg tgagcagggc cctcagagga aaggcagtat    2383
ggcggaggcc atggggggcc ctcggcattc acacacagcc tggcctcccc tgcggagctg    2443
catggacgcc tggctccagg ctccaggctg actgggggcc tctgcctcca ggagggcatc    2503
agctttccct ggctcaggga tcttctccct cccctcaccc gctgcccagc ctcccagct    2563 ggtgtcactc tgcctctaag gccaaggcct caggagagca tcaccaccac accctgccg    2623 gccttggcct tggggccaga ctggctgcac agcccaacca ggaggggtct gcctcccacg    2683
ctgggacaca gaccggccgc atgtctgcat ggcagaagcg tctcccttgg ccacggcctg    2743
ggagggtggt tcctgttctc agcatccact aatattcagt cctgtatatt ttaataaaat    2803
aaacttgaca aggaaaaaaa aaaaaaaaaa aa                                  2835
```

<210> SEQ ID NO 83
<211> LENGTH: 256
<212> TYPE: PRT
<213> ORGANISM: Homo sapiens

<400> SEQUENCE: 83

```
Met Gln Pro Ala Lys Glu Val Thr Lys Ala Ser Asp Gly Ser Leu Leu
  1               5                  10                  15

Gly Asp Leu Gly His Thr Pro Leu Ser Lys Lys Glu Gly Ile Lys Trp
             20                  25                  30

Gln Arg Pro Arg Leu Ser Arg Gln Ala Leu Met Arg Cys Cys Leu Val
         35                  40                  45

Lys Trp Ile Leu Ser Ser Thr Ala Pro Gln Gly Ser Asp Ser Ser Asp
     50                  55                  60

Ser Glu Leu Glu Leu Ser Thr Val Arg His Gln Pro Glu Gly Leu Asp
 65                  70                  75                  80

Gln Leu Gln Ala Gln Thr Lys Phe Thr Lys Lys Glu Leu Gln Ser Leu
                 85                  90                  95

Tyr Arg Gly Phe Lys Asn Glu Cys Pro Thr Gly Leu Val Asp Glu Asp
            100                 105                 110

Thr Phe Lys Leu Ile Tyr Ala Gln Phe Phe Pro Gln Gly Asp Ala Thr
        115                 120                 125

Thr Tyr Ala His Phe Leu Phe Asn Ala Phe Asp Ala Asp Gly Asn Gly
    130                 135                 140

Ala Ile His Phe Glu Asp Phe Val Val Gly Leu Ser Ile Leu Leu Arg
145                 150                 155                 160

Gly Thr Val His Glu Lys Leu Lys Trp Ala Phe Asn Leu Tyr Asp Ile
                165                 170                 175

Asn Lys Asp Gly Tyr Ile Thr Lys Glu Glu Met Leu Ala Ile Met Lys
```

```
                    180                 185                 190
Ser Ile Tyr Asp Met Met Gly Arg His Thr Tyr Pro Ile Leu Arg Glu
            195                 200                 205

Asp Ala Pro Ala Glu His Val Glu Arg Phe Phe Glu Lys Met Asp Arg
        210                 215                 220

Asn Gln Asp Gly Val Val Thr Ile Glu Glu Phe Leu Glu Ala Cys Gln
225                 230                 235                 240

Lys Asp Glu Asn Ile Met Ser Ser Met Gln Leu Phe Glu Asn Val Ile
                245                 250                 255

<210> SEQ ID NO 84
<211> LENGTH: 2414
<212> TYPE: DNA
<213> ORGANISM: Rattus sp.
<220> FEATURE:
<221> NAME/KEY: CDS
<222> LOCATION: (1)..(579)

<400> SEQUENCE: 84 agt gaa ctg gag ttg tcc acg gtg cgc cat cag cca gag ggc ttg gac      48
Ser Glu Leu Glu Leu Ser Thr Val Arg His Gln Pro Glu Gly Leu Asp
1               5                   10                  15 cag cta cag gcc caa acc aag ttc acc aag aag gag ctg cag tcc ctg      96
Gln Leu Gln Ala Gln Thr Lys Phe Thr Lys Lys Glu Leu Gln Ser Leu
            20                  25                  30 tac cga ggc ttc aag aac gaa tgt ccc acg ggc ctg gtc gat gaa gat     144
Tyr Arg Gly Phe Lys Asn Glu Cys Pro Thr Gly Leu Val Asp Glu Asp
        35                  40                  45 acc ttc aaa ctc att tat tcc cag ttc ttc ccc cag gga gat gcc acc     192
Thr Phe Lys Leu Ile Tyr Ser Gln Phe Phe Pro Gln Gly Asp Ala Thr
    50                  55                  60 acc tat gca cac ttc ctc ttc aat gcc ttc gat gct gat ggg aac ggg     240
Thr Tyr Ala His Phe Leu Phe Asn Ala Phe Asp Ala Asp Gly Asn Gly
65                  70                  75                  80 gcc atc cac ttt gag gac ttt gtg gtt ggg ctc tcc atc ctg ctt cga     288
Ala Ile His Phe Glu Asp Phe Val Val Gly Leu Ser Ile Leu Leu Arg
                85                  90                  95 ggg acc gtc cat gag aag ctc aag tgg gcc ttc aat ctc tac gac atc     336
Gly Thr Val His Glu Lys Leu Lys Trp Ala Phe Asn Leu Tyr Asp Ile
            100                 105                 110 aac aag gac ggt tac atc acc aaa gag gag atg ctg gcc atc atg aag     384
Asn Lys Asp Gly Tyr Ile Thr Lys Glu Glu Met Leu Ala Ile Met Lys
        115                 120                 125 tcc atc tac gac atg atg ggc cgc cac acc tac cct atc ctg cgg gag     432
Ser Ile Tyr Asp Met Met Gly Arg His Thr Tyr Pro Ile Leu Arg Glu
    130                 135                 140 gac gca cct ctg gag cat gtg gag agg ttc ttc cag aaa atg gac agg     480
Asp Ala Pro Leu Glu His Val Glu Arg Phe Phe Gln Lys Met Asp Arg
145                 150                 155                 160 aac cag gat gga gta gtg act att gat gaa ttt ctg gag act tgt cag     528
Asn Gln Asp Gly Val Val Thr Ile Asp Glu Phe Leu Glu Thr Cys Gln
                165                 170                 175 aag gac gag aac atc atg agc tcc atg cag ctg ttt gag aac gtc atc     576
Lys Asp Glu Asn Ile Met Ser Ser Met Gln Leu Phe Glu Asn Val Ile
            180                 185                 190 tag gacatgtagg aggggacccct gggtggccat ggttctcaa cccagagaag            629 cctcaatcct gacaggagaa gcctctatga gaaacatttt tctaatatat ttgcaaaaag    689
tgagcagttt acttccaaga cacagacaca gtcacacaca cacacacaca cacacacaca    749
```

-continued

| | |
|---|---|
| cacacacaca cacacacaca cacacacggt tcctctaact tggtaattga agtggcagcc | 809 |
| tggaggcacc cccagctatt cccaggtcct ctgggatggc cagcccaggc tagatgttac | 869 |
| gcacaaggag ctcagagccc aagagggcca gttaaacaaa gataaggtcc ctgtgtcttt | 929 |
| tctaccactt gggggatcaa actactccct gcccatggac ccatgctcct agggagctcc | 989 |
| cagaaacttc tcaggggcca ggaggggaga ggtctggtag ggagaagtgg tgttggaagc | 1049 |
| tgagtctgca gccttatgct aatgcttacc tgggaccctg gaacccagc atcaggatag | 1109 |
| ctagtggggg tgaacttagt gagggccac tgggttatgc tctcctttaa gagtagggaa | 1169 |
| ggattgaggg ttttggggaa accaagagaa caatttgtcc ataccatcgg atgaagactg | 1229 |
| ctggccaatg ggaatgtgac tggtggagat ctcccaactt ccagcaccag gctggccttt | 1289 |
| ccagggtccc ctttggtctt tcgggagat cacccggctc agggactgat aaccaggag | 1349 |
| ctagactgaa atgggagagg tctggtaggg ggcatccccc tctttctccc tggccacttg | 1409 |
| ccacccagtt cctaacatg gcaaatcggc cagccacacc tctgcagctg tccttgaaca | 1469 |
| ggttcatccc aacccagaca aaagcacaa acatcctagc agctcaggcc atgcccaccg | 1529 |
| ggggaggcag gggggccctg ggtgggatgg ggggttgggt ccatgcagcc ctgatccagt | 1589 |
| gttcggggaa gatgctcaga aatccatcct gtacctcgga gccttgggat ctcacagacc | 1649 |
| tttcccagcc tagctcgcca acattctaaa gcacaaacct gtggactctg cttgcctggg | 1709 |
| ctgcaccccg gggatcggtg tctgtgttag ccctaagctg gagctagccc tgagggctgg | 1769 |
| ggacttgtga ccaggcagca ggtcaacaga gcctcaggaa gagagagagc tgttcctgcc | 1829 |
| tccccagaag ggacagtgac ccaggcagca tcttcctgga ggaacaatcc cacgaaagta | 1889 |
| cattccatca cctgcagccc ggtctctgct caggcttgct ctgagagtcc atgcgtgttc | 1949 |
| cccagaaggc cagccccagg ttaagggagg tccttagagg aagaacgggg tgacagtgcc | 2009 |
| cctacacaca ggtgggcccc cctctcaggg ctgcactgac cccatctcca tcctgactgg | 2069 |
| ggcctccctt gaccctgtca acagaccatc agctctccct ggctcaggga cctcccctac | 2129 |
| cccagcctgg ctctccccat tgaggttcct atcctgtgag aagccaaggc cacgggaaaa | 2189 |
| ggctatcact cgaaacctac tgcgcccctt agcctctggc tgcacgccca acctggaggg | 2249 |
| gtctgtcccc ttggcaggga cccagacggg ccgcatgtct gcatggcaga agcgtctccc | 2309 |
| ttgggtgcag cctggaaggg tggttcctgt ctcggcgccc accaatattc agtcctatat | 2369 |
| attttaataa agaaacttg acaaggaaa aaaaaaaaa aaaaa | 2414 |

<210> SEQ ID NO 85
<211> LENGTH: 192
<212> TYPE: PRT
<213> ORGANISM: Rattus sp.

<400> SEQUENCE: 85

Ser Glu Leu Glu Leu Ser Thr Val Arg His Gln Pro Glu Gly Leu Asp
 1               5                  10                  15

Gln Leu Gln Ala Gln Thr Lys Phe Thr Lys Lys Glu Leu Gln Ser Leu
                20                  25                  30

Tyr Arg Gly Phe Lys Asn Glu Cys Pro Thr Gly Leu Val Asp Glu Asp
            35                  40                  45

Thr Phe Lys Leu Ile Tyr Ser Gln Phe Phe Pro Gln Gly Asp Ala Thr
        50                  55                  60

Thr Tyr Ala His Phe Leu Phe Asn Ala Phe Asp Ala Asp Gly Asn Gly
65                  70                  75                  80

```
Ala Ile His Phe Glu Asp Phe Val Val Gly Leu Ser Ile Leu Leu Arg
                 85                  90                  95

Gly Thr Val His Glu Lys Leu Lys Trp Ala Phe Asn Leu Tyr Asp Ile
            100                 105                 110

Asn Lys Asp Gly Tyr Ile Thr Lys Glu Glu Met Leu Ala Ile Met Lys
        115                 120                 125

Ser Ile Tyr Asp Met Met Gly Arg His Thr Tyr Pro Ile Leu Arg Glu
    130                 135                 140

Asp Ala Pro Leu Glu His Val Glu Arg Phe Phe Gln Lys Met Asp Arg
145                 150                 155                 160

Asn Gln Asp Gly Val Val Thr Ile Asp Glu Phe Leu Glu Thr Cys Gln
                165                 170                 175

Lys Asp Glu Asn Ile Met Ser Ser Met Gln Leu Phe Glu Asn Val Ile
            180                 185                 190

<210> SEQ ID NO 86
<211> LENGTH: 1005
<212> TYPE: DNA
<213> ORGANISM: Macaca sp.
<220> FEATURE:
<221> NAME/KEY: CDS
<222> LOCATION: (2)..(385)

<400> SEQUENCE: 86 a tat gca cat ttt ctg ttc aat gcg ttt gat acg gac cac aat gga gct      49
  Tyr Ala His Phe Leu Phe Asn Ala Phe Asp Thr Asp His Asn Gly Ala
    1               5                  10                  15 gtg agt ttc gag gat ttc atc aaa ggt ctt tcc att ttg ctc cgg ggg        97
Val Ser Phe Glu Asp Phe Ile Lys Gly Leu Ser Ile Leu Leu Arg Gly
                20                  25                  30 aca gta caa gaa aaa ctc aat tgg gca ttt aat ctg tat gat ata aat       145
Thr Val Gln Glu Lys Leu Asn Trp Ala Phe Asn Leu Tyr Asp Ile Asn
            35                  40                  45 aaa gat ggc tac atc act aaa gag gaa atg ctt gat ata atg aaa gca       193
Lys Asp Gly Tyr Ile Thr Lys Glu Glu Met Leu Asp Ile Met Lys Ala
        50                  55                  60 ata tac gac atg atg ggt aaa tgt aca tat cct gtc ctc aaa gaa gat       241
Ile Tyr Asp Met Met Gly Lys Cys Thr Tyr Pro Val Leu Lys Glu Asp
65                  70                  75                  80 gca ccc aga caa cac gtc gaa aca ttt ttt cag gct gtt ttc cat tgt       289
Ala Pro Arg Gln His Val Glu Thr Phe Phe Gln Ala Val Phe His Cys
                85                  90                  95 atc atc aag tgg aag ttc aag acg gca tca aac aaa aca agg atg ttt       337
Ile Ile Lys Trp Lys Phe Lys Thr Ala Ser Asn Lys Thr Arg Met Phe
            100                 105                 110 aca gac ata tgc aaa ggg tca gga tat cta tcc tcc agt ata tgt taa       385
Thr Asp Ile Cys Lys Gly Ser Gly Tyr Leu Ser Ser Ser Ile Cys
        115                 120                 125 tgcttaataa caagtaatcc taacagcatt aaaggccaaa tctgtcctct ttcccctgac     445
ttccttacag catgtttata ttacaagcca ttcagggaca agaaaccttt gactacccca    505
ctgtctacta ggaacaaaca aacagcaagc aaaattcact ttgaaagcac cagtggttcc    565
attacattga caactactac caagattcag tagaaaataa gtgctcaaca actaatccag    625
attacaatat gatttagtgc atcataaaat tccaacaatt cagattattt ttaatcatct    685
cagccacaac tgtaaagttg ccacattact aaagacacac acatcgtccc tgttttgtag    745
aaatatcaca aagaccaaga ggctacagaa ggaggaaatt tgcaactgtc tttgcaacaa    805
taaatcaggt atctattctg gtgtagagat aggatgttga aagctgccct gctatcacca    865
```

```
gtgtagaaat taagagtagt acaatacatg tacactgaaa tttgccatcg cgtgtttgtg      925
taaactcaat gtgcacattt tgtatttcaa aagaaaaaa taaaagcaaa ataaaatgtt       985
aaaaaaaaaa aaaaaaaaaa                                                 1005

<210> SEQ ID NO 87
<211> LENGTH: 127
<212> TYPE: PRT
<213> ORGANISM: Macaca sp.

<400> SEQUENCE: 87

Tyr Ala His Phe Leu Phe Asn Ala Phe Asp Thr Asp His Asn Gly Ala
 1               5                  10                  15

Val Ser Phe Glu Asp Phe Ile Lys Gly Leu Ser Ile Leu Leu Arg Gly
            20                  25                  30

Thr Val Gln Glu Lys Leu Asn Trp Ala Phe Asn Leu Tyr Asp Ile Asn
        35                  40                  45

Lys Asp Gly Tyr Ile Thr Lys Glu Glu Met Leu Asp Ile Met Lys Ala
    50                  55                  60

Ile Tyr Asp Met Met Gly Lys Cys Thr Tyr Pro Val Leu Lys Glu Asp
65                  70                  75                  80

Ala Pro Arg Gln His Val Glu Thr Phe Phe Gln Ala Val His Cys
                85                  90                  95

Ile Ile Lys Trp Lys Phe Lys Thr Ala Ser Asn Lys Thr Arg Met Phe
            100                 105                 110

Thr Asp Ile Cys Lys Gly Ser Gly Tyr Leu Ser Ser Ser Ile Cys
        115                 120                 125

<210> SEQ ID NO 88
<211> LENGTH: 2181
<212> TYPE: DNA
<213> ORGANISM: Homo sapiens
<220> FEATURE:
<221> NAME/KEY: CDS
<222> LOCATION: (56)..(742)

<400> SEQUENCE: 88
gccagggtga ggagcgcttc tcagtggctg tggctggacc atgacctagc tgacc atg     58
                                                             Met
                                                              1 aac ttg gag ggg ctt gaa atg ata gca gtt ctg atc gtc att gtg ctt    106
Asn Leu Glu Gly Leu Glu Met Ile Ala Val Leu Ile Val Ile Val Leu
         5                  10                  15 ttt gtt aaa tta ttg gaa cag ttt ggg ctg att gaa gca ggt tta gaa    154
Phe Val Lys Leu Leu Glu Gln Phe Gly Leu Ile Glu Ala Gly Leu Glu
        20                  25                  30 gac agc gtg gaa gat gag ctg gag atg gct act gtc agg cat cgg cct    202
Asp Ser Val Glu Asp Glu Leu Glu Met Ala Thr Val Arg His Arg Pro
    35                  40                  45 gaa gcc ctg gag ctg ctg gag gcc cag agc aaa ttc acc aag aaa gag    250
Glu Ala Leu Glu Leu Leu Glu Ala Gln Ser Lys Phe Thr Lys Lys Glu
50                  55                  60                  65 ctt cag att ctt tac aga gga ttt aag aat gaa tgc ccc agt ggt gtt    298
Leu Gln Ile Leu Tyr Arg Gly Phe Lys Asn Glu Cys Pro Ser Gly Val
                70                  75                  80 gtt aat gaa gaa act ttc aag gag att tac tca cag ttc ttt cca cag    346
Val Asn Glu Glu Thr Phe Lys Glu Ile Tyr Ser Gln Phe Phe Pro Gln
            85                  90                  95 gga gac tcc acc aca tat gca cat ttt ctc ttc aat gca ttc gac acg    394
```

-continued

| | | |
|---|---|---|
| Gly Asp Ser Thr Thr Tyr Ala His Phe Leu Phe Asn Ala Phe Asp Thr<br>        100                            105                        110 | | |
| gac cac aat gga gct gtg agc ttt gag gat ttc atc aaa ggt ctt tcc<br>Asp His Asn Gly Ala Val Ser Phe Glu Asp Phe Ile Lys Gly Leu Ser<br>115                         120                         125 | | 442 |
| att ttg ctt cga ggg aca gta caa gaa aaa ctc aac tgg gca ttt aat<br>Ile Leu Leu Arg Gly Thr Val Gln Glu Lys Leu Asn Trp Ala Phe Asn<br>130                      135                       140                  145 | | 490 |
| ttg tat gac ata aac aaa gat ggc tac atc act aaa gaa gaa atg ctg<br>Leu Tyr Asp Ile Asn Lys Asp Gly Tyr Ile Thr Lys Glu Glu Met Leu<br>                150                      155                       160 | | 538 |
| gac ata atg aaa gca atc tac gac atg atg ggg aaa tgc aca tac ccg<br>Asp Ile Met Lys Ala Ile Tyr Asp Met Met Gly Lys Cys Thr Tyr Pro<br>165                      170                       175 | | 586 |
| gtc ctc aag gaa gat gct ccc cga cag cat gtg gag acg ttc ttc cag<br>Val Leu Lys Glu Asp Ala Pro Arg Gln His Val Glu Thr Phe Phe Gln<br>            180                      185                      190 | | 634 |
| aag atg gac aaa aat aaa gat ggt gtc gtt acc ata gat gag ttc att<br>Lys Met Asp Lys Asn Lys Asp Gly Val Val Thr Ile Asp Glu Phe Ile<br>195                      200                       205 | | 682 |
| gaa agt tgc caa aaa gat gaa aac ata atg cgc tcc atg cag ctc ttt<br>Glu Ser Cys Gln Lys Asp Glu Asn Ile Met Arg Ser Met Gln Leu Phe<br>210                      215                      220                  225 | | 730 |
| gaa aat gtg atc tagaatgtca gcacctcctc gaccgaagag gcaaatgtga<br>Glu Asn Val Ile | | 782 |
| acgactacac acaagttgaa gcccccactt gtagcataga tagctcagct ttacactgag | | 842 |
| gcagattatg caaacagctt tgttttaata aaaagcaacc caccaccacc accaaaatta | | 902 |
| agttttccag ttacaaatct gcatccatgt caccggggtc atgaaatgtg ctaacttatt | | 962 |
| tcatactcaa aaggcacaga atctggaata gctttgatcc ttagccacgt tattattgag | | 1022 |
| gttttttacag ttcagtgatt ttaaaacacc agtgggtttt cctacttgtt tgtatgtatt | | 1082 |
| cagccctggg ttttaaatgg ttttctaaaa tacttacatc tgcatttaac ttccagaaag | | 1142 |
| tcaatgaact ttcattaaat tcgactcatg taacactgaa aaatgaaaca agattacta | | 1202 |
| caatttaaat agaccaaaaa cacagtccca atttctatgg cttctccacc tgctgttaaa | | 1262 |
| gatattaatg tatttggcat ttttttaaaa ggacacttaa aaaattagtt tattatcaga | | 1322 |
| tgttagcata tacctaataa aattatttta gtatttgtta attttccata ctcaagccaa | | 1382 |
| ggctctatat aatccatgaa actttggacc tgttcaatct tacatgtaga ctgttttgta | | 1442 |
| ttgtgttatg aagtagaaat tcaaagtgtc aaacaaacca aggatgttta cagacttgcc | | 1502 |
| aagggtccgg atgtctgtcc tgcaatgcct agtgacgctt attaacaagt aaccctaaca | | 1562 |
| gcagtaaagg gcagttcttg ccaccctcca agcccttaa tgttttcaca gcatgtttat | | 1622 |
| catacataag ccattcagga acagagaatc cttgacgccc caaagcctac taggaataat | | 1682 |
| gatcaagtaa catactcttt gagaacaccc gtgattctat agtattggaa attatacaca | | 1742 |
| agaatgtata gaaatgact gcaaacactg acggttcatc tgaaatgcat tatgatttag | | 1802 |
| cacatcatat agctcaaagg attcatagtc ctttcagtgg tcttaagcca aaactgtaga | | 1862 |
| gttgccacaa cagtactata gagatacaca tcttccctgt tgcgcagaaa tacaagaacc | | 1922 |
| aagaggatac aggaggagaa aatttacgac tgtctgcaac aataaatcag gtatctattc | | 1982 |
| tggtgtagag ataggatgtt gaaagctgcc ctgctatcac cagtgtagga attaagagta | | 2042 |
| gtacagtaca tgtacagaaa tctgccatcg cgtgtttgtg taaactcaat gtgcacattt | | 2102 |
| tgtatctcaa aacggaaaaa taaaagcaaa ataaagtgtt tattactcta aaaaaaaaaa | | 2162 | aaaaaaaaaa aaaaaaaa                                              2181

<210> SEQ ID NO 89
<211> LENGTH: 229
<212> TYPE: PRT
<213> ORGANISM: Mus musculus

<400> SEQUENCE: 89

Met Asn Leu Glu Gly Leu Glu Met Ile Ala Val Leu Ile Val Ile Val
1               5                   10                  15

Leu Phe Val Lys Leu Leu Glu Gln Phe Gly Leu Ile Glu Ala Gly Leu
            20                  25                  30

Glu Asp Ser Val Glu Asp Glu Leu Glu Met Ala Thr Val Arg His Arg
        35                  40                  45

Pro Glu Ala Leu Glu Leu Leu Glu Ala Gln Ser Lys Phe Thr Lys Lys
    50                  55                  60

Glu Leu Gln Ile Leu Tyr Arg Gly Phe Lys Asn Glu Cys Pro Ser Gly
65                  70                  75                  80

Val Val Asn Glu Glu Thr Phe Lys Glu Ile Tyr Ser Gln Phe Phe Pro
                85                  90                  95

Gln Gly Asp Ser Thr Thr Tyr Ala His Phe Leu Phe Asn Ala Phe Asp
            100                 105                 110

Thr Asp His Asn Gly Ala Val Ser Phe Glu Asp Phe Ile Lys Gly Leu
        115                 120                 125

Ser Ile Leu Leu Arg Gly Thr Val Gln Glu Lys Leu Asn Trp Ala Phe
    130                 135                 140

Asn Leu Tyr Asp Ile Asn Lys Asp Gly Tyr Ile Thr Lys Glu Glu Met
145                 150                 155                 160

Leu Asp Ile Met Lys Ala Ile Tyr Asp Met Met Gly Lys Cys Thr Tyr
                165                 170                 175

Pro Val Leu Lys Glu Asp Ala Pro Arg Gln His Val Glu Thr Phe Phe
            180                 185                 190

Gln Lys Met Asp Lys Asn Lys Asp Gly Val Val Thr Ile Asp Glu Phe
        195                 200                 205

Ile Glu Ser Cys Gln Lys Asp Glu Asn Ile Met Arg Ser Met Gln Leu
    210                 215                 220

Phe Glu Asn Val Ile
225

<210> SEQ ID NO 90
<211> LENGTH: 2022
<212> TYPE: DNA
<213> ORGANISM: Rattus sp.
<220> FEATURE:
<221> NAME/KEY: CDS
<222> LOCATION: (1)..(597)

<400> SEQUENCE: 90 tta gaa gac agt gtg gaa gat gaa ctg gag atg gcc act gtc agg cac         48
Leu Glu Asp Ser Val Glu Asp Glu Leu Glu Met Ala Thr Val Arg His
1               5                   10                  15 cgg cct gaa gcc ctg gag ctg ctg gag gcc cag agc aaa ttc acc aag         96
Arg Pro Glu Ala Leu Glu Leu Leu Glu Ala Gln Ser Lys Phe Thr Lys
            20                  25                  30 aaa gag ctt cag atc ctt tac aga gga ttt aag aat gaa tgc ccc agt        144
Lys Glu Leu Gln Ile Leu Tyr Arg Gly Phe Lys Asn Glu Cys Pro Ser
        35                  40                  45

-continued

```
ggt gtt gtt aat gaa gaa acc ttc aag gag att tac tcg cag ttc ttc      192
Gly Val Val Asn Glu Glu Thr Phe Lys Glu Ile Tyr Ser Gln Phe Phe
 50                  55                  60 cca cag gga gac tcc acc aca tat gca cat ttt ctc ttc aat gca ttc      240
Pro Gln Gly Asp Ser Thr Thr Tyr Ala His Phe Leu Phe Asn Ala Phe
 65                  70                  75                  80 gac acg gac cac aat gga gct gtg agc ttt gag gat ttc atc aaa ggt      288
Asp Thr Asp His Asn Gly Ala Val Ser Phe Glu Asp Phe Ile Lys Gly
                 85                  90                  95 ctt tcc att ttg ctt cga ggg aca gta caa gaa aaa ctg aac tgg gca      336
Leu Ser Ile Leu Leu Arg Gly Thr Val Gln Glu Lys Leu Asn Trp Ala
            100                 105                 110 ttt aat ttg tat gac ata aac aaa gat ggc tac atc act aaa gag gaa      384
Phe Asn Leu Tyr Asp Ile Asn Lys Asp Gly Tyr Ile Thr Lys Glu Glu
        115                 120                 125 atg ctg gac ata atg aaa gca att tac gac atg atg ggg aaa tgc aca      432
Met Leu Asp Ile Met Lys Ala Ile Tyr Asp Met Met Gly Lys Cys Thr
130                 135                 140 tac cct gtc ctc aag gaa gat gct ccc cga cag cac gtg gag aca ttt      480
Tyr Pro Val Leu Lys Glu Asp Ala Pro Arg Gln His Val Glu Thr Phe
145                 150                 155                 160 ttc cag aag atg gac aag aat aaa gat ggt gtc gtt acc ata gac gag      528
Phe Gln Lys Met Asp Lys Asn Lys Asp Gly Val Val Thr Ile Asp Glu
                165                 170                 175 ttc att gaa agt tgc caa aaa gat gaa aac ata atg cgc tcc atg cag      576
Phe Ile Glu Ser Cys Gln Lys Asp Glu Asn Ile Met Arg Ser Met Gln
            180                 185                 190 ctc ttt gaa aat gtg atc tag actgtcggtg ccttgaccgg aggcaaatgt        627
Leu Phe Glu Asn Val Ile
            195 ggacgactac acacgagttg aagccaccat ttctagcata gattgctcag ctttacactg     687 aggcatatta tgcaaacagc tttgttttaa tataaagacc cccgcgccca aatttaagtt     747 ttccagttac aaatccgcat ccacgtcact ggggtcccga aatgtgctca cttatttcat     807 actctgagaa cactcaaaag gcacagaatc tggaacagct ttgatcctca gccacgtgtt     867 acgggggctt ttacagatga gtgattttaa acaccagtg gttttccta cttgtttgta      927 ttcagccctg gattttaagt ggttttctaa aatatttaca tctgcattta acttccagaa     987 agccaatgac cttttcattt aactcaattc atgtaatact gaaaaaagga acaaagatta    1047 ttacaattaa aaaagaccaa aaacacagtc ccgatttcta tagcttctcc acctgctgtt    1107 aaagacagtc atgtatttgg cttttttttt tttttaaaa agaacactta aaaaattagt    1167 ttattatcag atgttagcat atacctaata aaattatttt agtatttgtt aattttccat    1227 attcaagcca aggctctata taatccatgt aactttggac ctgttcaatc ttacatgtag    1287 actgttttgt attgtgttct gaagtagaag ttcaaagtgt caaacaaacc aaggatgttt    1347 acagacttgc aaagggtcca gatgtctgtc ctgcaatgcc tagtgacgct tattaaccag    1407 taacctgaag agcagtaact ggcaattcta gccaccaccc ctccccaagc cccttcatgt    1467 tctcacagca tgtttatcac acacaagcca ttcagggaca gagaatcctt gactgcccca    1527 aagcctacta ggaataaaga tcaagcaaaa tcttctttga aaacaccagt gattctatca    1587 tattggaaat atacataaga gtgtatagaa acgaatgta gacattggac agttcatccg    1647 aattgcatta tgatttagca catcatgtag ttcaaaggat tcacattcct ttccgtgatc    1707 ttaagccaaa actgtagaat tgccacaaca gtactagata tacacacatt ccctgtttcg    1767 tggaaatcca agaaccaaga ggatacggga agagaaaatt tgcgactgtc tgcaacaata    1827
```

```
aatcaggtat ctattctggt gtagagatag gatgttgaga gccgccctgc tatcaccagt    1887
gtaggaatta agagtagtac agtacatgta cagaaatctg ccatcgcgtg tttgtgtaaa    1947
ctcaatgtgc acattttgta tctcaaaaag gaaaaataaa gcaaaataaa gtgttaaaaa    2007
aaaaaaaaaa aaaaa                                                     2022

<210> SEQ ID NO 91
<211> LENGTH: 198
<212> TYPE: PRT
<213> ORGANISM: Rattus sp.

<400> SEQUENCE: 91

Leu Glu Asp Ser Val Glu Asp Glu Leu Glu Met Ala Thr Val Arg His
 1               5                  10                  15

Arg Pro Glu Ala Leu Glu Leu Leu Glu Ala Gln Ser Lys Phe Thr Lys
                20                  25                  30

Lys Glu Leu Gln Ile Leu Tyr Arg Gly Phe Lys Asn Glu Cys Pro Ser
            35                  40                  45

Gly Val Val Asn Glu Glu Thr Phe Lys Glu Ile Tyr Ser Gln Phe Phe
        50                  55                  60

Pro Gln Gly Asp Ser Thr Thr Tyr Ala His Phe Leu Phe Asn Ala Phe
 65                  70                  75                  80

Asp Thr Asp His Asn Gly Ala Val Ser Phe Glu Asp Phe Ile Lys Gly
                 85                  90                  95

Leu Ser Ile Leu Leu Arg Gly Thr Val Gln Glu Lys Leu Asn Trp Ala
            100                 105                 110

Phe Asn Leu Tyr Asp Ile Asn Lys Asp Gly Tyr Ile Thr Lys Glu Glu
        115                 120                 125

Met Leu Asp Ile Met Lys Ala Ile Tyr Asp Met Met Gly Lys Cys Thr
    130                 135                 140

Tyr Pro Val Leu Lys Glu Asp Ala Pro Arg Gln His Val Glu Thr Phe
145                 150                 155                 160

Phe Gln Lys Met Asp Lys Asn Lys Asp Gly Val Val Thr Ile Asp Glu
                165                 170                 175

Phe Ile Glu Ser Cys Gln Lys Asp Glu Asn Ile Met Arg Ser Met Gln
            180                 185                 190

Leu Phe Glu Asn Val Ile
        195

<210> SEQ ID NO 92
<211> LENGTH: 2366
<212> TYPE: DNA
<213> ORGANISM: Homo sapiens
<220> FEATURE:
<221> NAME/KEY: CDS
<222> LOCATION: (319)..(885)

<400> SEQUENCE: 92
gagaggtccg tgcgctgtgg tagcaggggg gaagcccgc cagccaaatg ccaggatcag      60
catgagaagc tggactttag cccaggtctg tcctcacccc gggggccgc cggctttgca     120 gggtgcatct gccaggagct gctcactttt tccccttgca agtctttgtt ccaagcctga    180
cgttgctacg attctgtaat taactccctc cactccaaag gggtctggag ctgggatgc     240 tctgccagct cagaggatgt tgactctgga gtgggagtcc gaaggactgc aaacaacagc    300
gtggaagatg aactggag atg gcc acc gtc agg cat cgg ccc gaa gcc ctt      351
                    Met Ala Thr Val Arg His Arg Pro Glu Ala Leu
```

-continued

|  | 1 |  |  |  | 5 |  |  |  |  | 10 |  |  |  |  |
|---|---|---|---|---|---|---|---|---|---|---|---|---|---|---|
| gag | ctt | ctg | gaa | gcc | cag | agc | aaa | ttt | acc | aag | aaa | gag | ctt | cag | atc | 399 |
| Glu | Leu | Leu | Glu | Ala | Gln | Ser | Lys | Phe | Thr | Lys | Lys | Glu | Leu | Gln | Ile |
|  |  |  |  | 15 |  |  |  |  | 20 |  |  |  |  | 25 |  |

```
gag ctt ctg gaa gcc cag agc aaa ttt acc aag aaa gag ctt cag atc      399
Glu Leu Leu Glu Ala Gln Ser Lys Phe Thr Lys Lys Glu Leu Gln Ile
             15                  20                  25 ctt tac aga gga ttt aag aac gaa tgc ccc agt ggt gtt gtt aat gaa      447
Leu Tyr Arg Gly Phe Lys Asn Glu Cys Pro Ser Gly Val Val Asn Glu
         30                  35                  40 gaa acc ttc aaa gag att tac tcg cag ttc ttt cca cag gga gac tct      495
Glu Thr Phe Lys Glu Ile Tyr Ser Gln Phe Phe Pro Gln Gly Asp Ser
     45                  50                  55 aca aca tat gca cat ttt ctg ttc aat gca ttt gat aca gac cac aat      543
Thr Thr Tyr Ala His Phe Leu Phe Asn Ala Phe Asp Thr Asp His Asn
 60                  65                  70                  75 gga gct gtg agt ttc gag gat ttc atc aaa ggt ctt tcc att ttg ctc      591
Gly Ala Val Ser Phe Glu Asp Phe Ile Lys Gly Leu Ser Ile Leu Leu
                     80                  85                  90 cgg ggg aca gta caa gaa aaa ctc aat tgg gca ttt aat ctg tat gac      639
Arg Gly Thr Val Gln Glu Lys Leu Asn Trp Ala Phe Asn Leu Tyr Asp
                 95                 100                 105 ata aat aaa gat ggc tac atc act aaa gag gaa atg ctt gat ata atg      687
Ile Asn Lys Asp Gly Tyr Ile Thr Lys Glu Glu Met Leu Asp Ile Met
            110                 115                 120 aaa gca ata tac gat atg atg ggt aaa tgt aca tat cct gtc ctc aaa      735
Lys Ala Ile Tyr Asp Met Met Gly Lys Cys Thr Tyr Pro Val Leu Lys
        125                 130                 135 gaa gat gct ccc aga caa cac gtt gaa aca ttt ttt cag aaa atg gac      783
Glu Asp Ala Pro Arg Gln His Val Glu Thr Phe Phe Gln Lys Met Asp
140                 145                 150                 155 aaa aat aaa gat ggg gtt gtt acc ata gat gag ttc att gaa agc tgc      831
Lys Asn Lys Asp Gly Val Val Thr Ile Asp Glu Phe Ile Glu Ser Cys
                    160                 165                 170 caa aaa gat gaa aac ata atg cgc tcc atg cag ctc ttt gaa aat gtg      879
Gln Lys Asp Glu Asn Ile Met Arg Ser Met Gln Leu Phe Glu Asn Val
                175                 180                 185 att taa cttgtcaaat agatcctgaa tccaacagac aaatgtgaac tattctacca      935
Ile cccttaaagt tggagctacc acttttagca tagattgctc agcttgacac tgaagcatat      995
tatgcaaaca agctttgttt taatataaag caatccccaa aagatttgag ctttcagtta     1055
taaatttgca tcctttcat aatgccactg agttcagggg atggtctaac tcatttcata     1115
ctctgtgaat attcaaaagt aatagaatct ggcatatagt tttattggtt ccttagccat     1175
gggattattg aggctttcac atatcagtga ttttaaaata tcagtgtttt ttgctactca     1235
tttgtatgta ttcagtccta ggattttgaa tggttttcta atatagtgac atctgcattt     1295
aatttccaga aattaaatta attttcatgt ttgaatgctg taattccatt taaattccat     1355
ttatatactt taaggaaaca agattacaac aattaaaaaa acacatagtt ccagtttcta     1415
tggccttccc accttctgtt agaaattagt tttatctggc atttttaaac atttaaaaat     1475
tattaaacat ttaaaaatta gtttattatc agatatcagc atatgcctaa taaaacttat     1535
tttaataagc atttaatttt ccatagtatg ttacagccaa ggcctatata ataatttttgg     1595 atttgttcaa tctttcttac aggctgtttt ctattgtatc aatcattagt atcaatcatt     1655
aagtggaagt tgaagaaggc atcaaacaaa acaaggatgt ttacagacat atgcaaaggg     1715
tcaggatatc tatcctccag tatatagtaa tgcttaataa caagtaatcc taacagcatt     1775
aaaggccaaa tctgtcctct ttcccctgac ttccttacag catgtttatt tatattacaa     1835
```

```
gccattcagg gacaaagaaa gaaaccttga ctaccccact gtctactaag aacaaacagc    1895
aagcaaaatt agcaagcaaa attcactttg aaagcaccag tggttccatt acattgacaa    1955
ctactaccaa gatttagtag aaaataagtg ctcaacaact aatccagatt acagtatgat    2015
ttagctcatc ataattcaga ttatttttaa tcatcttagc caaaactgta aagttgccac    2075
attactaaag ccacacacat cgtccctgtt ttgtagaaat atcacaaaga ccaagaggct    2135
acagaaggag gaaatttgca actgtctttg caacaataaa tcaggtatct attctggtgt    2195
agagatagga tgttgaaagc tgccctgcta tcaccagtgt agaaattaag agtagtacaa    2255
tacatgtaca ctgaaatttg ccatcacgtg tttgtgtaaa ctcaatgtgc acattttgta    2315
tttcaaaaag aaaaaataaa agcaaaataa aatgttaaaa aaaaaaaaa a              2366

<210> SEQ ID NO 93
<211> LENGTH: 188
<212> TYPE: PRT
<213> ORGANISM: Homo sapiens

<400> SEQUENCE: 93

Met Ala Thr Val Arg His Arg Pro Glu Ala Leu Glu Leu Leu Glu Ala
  1               5                  10                  15

Gln Ser Lys Phe Thr Lys Lys Glu Leu Gln Ile Leu Tyr Arg Gly Phe
             20                  25                  30

Lys Asn Glu Cys Pro Ser Gly Val Val Asn Glu Glu Thr Phe Lys Glu
         35                  40                  45

Ile Tyr Ser Gln Phe Phe Pro Gln Gly Asp Ser Thr Thr Tyr Ala His
     50                  55                  60

Phe Leu Phe Asn Ala Phe Asp Thr Asp His Asn Gly Ala Val Ser Phe
 65                  70                  75                  80

Glu Asp Phe Ile Lys Gly Leu Ser Ile Leu Leu Arg Gly Thr Val Gln
                 85                  90                  95

Glu Lys Leu Asn Trp Ala Phe Asn Leu Tyr Asp Ile Asn Lys Asp Gly
            100                 105                 110

Tyr Ile Thr Lys Glu Glu Met Leu Asp Ile Met Lys Ala Ile Tyr Asp
        115                 120                 125

Met Met Gly Lys Cys Thr Tyr Pro Val Leu Lys Glu Asp Ala Pro Arg
    130                 135                 140

Gln His Val Glu Thr Phe Phe Gln Lys Met Asp Lys Asn Lys Asp Gly
145                 150                 155                 160

Val Val Thr Ile Asp Glu Phe Ile Glu Ser Cys Gln Lys Asp Glu Asn
                165                 170                 175

Ile Met Arg Ser Met Gln Leu Phe Glu Asn Val Ile
            180                 185

<210> SEQ ID NO 94
<211> LENGTH: 2431
<212> TYPE: DNA
<213> ORGANISM: Homo sapiens
<220> FEATURE:
<221> NAME/KEY: CDS
<222> LOCATION: (248)..(949)

<400> SEQUENCE: 94
gtgcgctgtg gtagcagggg ggaagccccg ccagccaaat gccaggatca gcatgagaag     60
ctggacttta gcccaggtct gtcctcaccc cggggggccg ccggctttgc agggtgcatc    120
tgccaggagc tgctcacttt ttcccccttgc aagtctttgt tccaagcctg acgttgctac    180
```

-continued

```
gattctgtaa ttaactccct ccactccaaa ggggtctgga ggctgggatg ctctgccagc      240 tcagagg atg ttg act ctg gag tgg gag tcc gaa gga ctg caa aca gtg       289
        Met Leu Thr Leu Glu Trp Glu Ser Glu Gly Leu Gln Thr Val
        1               5                   10 ggt att gtt gtg att ata tgt gca tct ctg aag ctt ctt cat ttg ctg       337
Gly Ile Val Val Ile Ile Cys Ala Ser Leu Lys Leu Leu His Leu Leu
15                  20                  25                  30 gga ctg att gat ttt tcg gaa gac agc gtg gaa gat gaa ctg gag atg       385
Gly Leu Ile Asp Phe Ser Glu Asp Ser Val Glu Asp Glu Leu Glu Met
                35                  40                  45 gcc acc gtc agg cat cgg cct gaa gcc ctt gag ctt ctg gaa gcc cag       433
Ala Thr Val Arg His Arg Pro Glu Ala Leu Glu Leu Leu Glu Ala Gln
                50                  55                  60 agc aaa ttt acc aag aaa gag ctt cag atc ctt tac aga gga ttt aag       481
Ser Lys Phe Thr Lys Lys Glu Leu Gln Ile Leu Tyr Arg Gly Phe Lys
        65                  70                  75 aat gaa tgc ccc agt ggt gtt gtt aat gaa gaa acc ttc aaa gag att       529
Asn Glu Cys Pro Ser Gly Val Val Asn Glu Glu Thr Phe Lys Glu Ile
80                  85                  90 tac tcg cag ttc ttt cca cag gga gac tct aca aca tat gca cat ttt       577
Tyr Ser Gln Phe Phe Pro Gln Gly Asp Ser Thr Thr Tyr Ala His Phe
95                  100                 105                 110 ctg ttc aat gca ttt gat aca gac cac aat gga gct gtg agt ttc gag       625
Leu Phe Asn Ala Phe Asp Thr Asp His Asn Gly Ala Val Ser Phe Glu
                115                 120                 125 gat ttc atc aaa ggt ctt tcc att ttg ctc cgg ggg aca gta caa gaa       673
Asp Phe Ile Lys Gly Leu Ser Ile Leu Leu Arg Gly Thr Val Gln Glu
                130                 135                 140 aaa ctc aat tgg gca ttt aat ctg tat gac ata aat aaa gat ggc tac       721
Lys Leu Asn Trp Ala Phe Asn Leu Tyr Asp Ile Asn Lys Asp Gly Tyr
                145                 150                 155 atc act aaa gag gaa atg ctt gat ata atg aaa gca ata tac gat atg       769
Ile Thr Lys Glu Glu Met Leu Asp Ile Met Lys Ala Ile Tyr Asp Met
160                 165                 170 atg ggt aaa tgt aca tat cct gtc ctc aaa gaa gat gct ccc aga caa       817
Met Gly Lys Cys Thr Tyr Pro Val Leu Lys Glu Asp Ala Pro Arg Gln
175                 180                 185                 190 cac gtt gaa aca ttt ttt cag aaa atg gac aaa aat aaa gat ggg gtt       865
His Val Glu Thr Phe Phe Gln Lys Met Asp Lys Asn Lys Asp Gly Val
                195                 200                 205 gtt acc ata gat gag ttc att gaa agc tgc caa aaa gat gaa aac ata       913
Val Thr Ile Asp Glu Phe Ile Glu Ser Cys Gln Lys Asp Glu Asn Ile
                210                 215                 220 atg cgc tcc atg cag ctc ttt gaa aat gtg att taa cttgtcaaat            959
Met Arg Ser Met Gln Leu Phe Glu Asn Val Ile
                225                 230 agatcctgaa tccaacagac aaatgtgaac tattctacca cccttaaagt tggagctacc    1019
acttttagca tagattgctc agcttgacac tgaagcatat tatgcaaaca agctttgttt    1079
taatataaag caatccccaa aagatttgag ctttcagtta taaatttgca tccttttcat    1139
aatgccactg agttcagggg atggtctaac tcatttcata ctctgtgaat attcaaaagt    1199
aatagaatct ggcatatagt tttattggtt ccttagccat gggattattg aggctttcac    1259
atatcagtga ttttaaaata tcagtgtttt ttgctactca tttgtatgta ttcagtccta    1319
ggattttgaa tggttttcta atatagtgac atctgcattt aatttccaga aattaaatta    1379 atttttcatgt tgaatgctg taattccatt taaattccat ttatatactt taaggaaaca    1439
agattacaac aattaaaaaa acacatagtt ccagtttcta tggccttccc accttctgtt    1499
```

-continued

```
agaaattagt tttatctggc attttttaaac atttaaaaat tattaaacat ttaaaaatta   1559
gtttattatc agatatcagc atatgcctaa taaaacttat tttaataagc atttaatttt   1619
ccataatatg ttacagccaa ggcctatata ataattttgg atttgttcaa tctttcttac   1679
aggctgtttt ctattgtatc aatcattagt atcaatcatt aagtggaagt tgaagaaggc   1739
atcaaacaaa acaaggatgt ttacagacat atgcaaaggg tcaggatatc tatcctccag   1799
tatatagtaa tgcttaataa caagtaatcc taacagcatt aaaggccaaa tctgtcctct   1859
ttcccctgac ttccttacag catgtttatt tatattacaa gccattcagg gacaaagaaa   1919
gaaaccttga ctaccccact gtctactaag aacaaacagc aagcaaaatt agcaagcaaa   1979
attcactttg aaagcaccag tggttccatt acattgacaa ctactaccaa gatttagtag   2039
aaaataagtg ctcaacaact aatccagatt acagtatgat ttagctcatc ataattcaga   2099 ttattttttaa tcatcttagc caaaactgta aagttgccac attactaaag ccacacacat   2159
cgtccctgtt ttgtagaaat atcacaaaga ccaagaggct acagaaggag gaaatttgca   2219
actgtctttg caacaataaa tcaggtatct attctggtgt agagatagga tgttgaaagc   2279
tgccctgcta tcaccagtgt agaaattaag agtagtacaa tacatgtaca ctgaaatttg   2339
ccatcacgtg tttgtgtaaa ctcaatgtgc acattttgta tttcaaaaag aaaaaataaa   2399
agcaaaataa aatgttaaaa aaaaaaaaaa aa                                  2431
```

<210> SEQ ID NO 95
<211> LENGTH: 233
<212> TYPE: PRT
<213> ORGANISM: Homo sapiens

<400> SEQUENCE: 95

```
Met Leu Thr Leu Glu Trp Glu Ser Glu Gly Leu Gln Thr Val Gly Ile
  1               5                  10                  15

Val Val Ile Ile Cys Ala Ser Leu Lys Leu Leu His Leu Leu Gly Leu
                 20                  25                  30

Ile Asp Phe Ser Glu Asp Ser Val Glu Asp Glu Leu Glu Met Ala Thr
             35                  40                  45

Val Arg His Arg Pro Glu Ala Leu Glu Leu Leu Glu Ala Gln Ser Lys
         50                  55                  60

Phe Thr Lys Lys Glu Leu Gln Ile Leu Tyr Arg Gly Phe Lys Asn Glu
 65                  70                  75                  80

Cys Pro Ser Gly Val Val Asn Glu Glu Thr Phe Lys Glu Ile Tyr Ser
                 85                  90                  95

Gln Phe Phe Pro Gln Gly Asp Ser Thr Thr Tyr Ala His Phe Leu Phe
            100                 105                 110

Asn Ala Phe Asp Thr Asp His Asn Gly Ala Val Ser Phe Glu Asp Phe
        115                 120                 125

Ile Lys Gly Leu Ser Ile Leu Leu Arg Gly Thr Val Gln Glu Lys Leu
    130                 135                 140

Asn Trp Ala Phe Asn Leu Tyr Asp Ile Asn Lys Asp Gly Tyr Ile Thr
145                 150                 155                 160

Lys Glu Glu Met Leu Asp Ile Met Lys Ala Ile Tyr Asp Met Met Gly
                165                 170                 175

Lys Cys Thr Tyr Pro Val Leu Lys Glu Asp Ala Pro Arg Gln His Val
            180                 185                 190

Glu Thr Phe Phe Gln Lys Met Asp Lys Asn Lys Asp Gly Val Val Thr
        195                 200                 205
```

```
Ile Asp Glu Phe Ile Glu Ser Cys Gln Lys Asp Glu Asn Ile Met Arg
    210                 215                 220

Ser Met Gln Leu Phe Glu Asn Val Ile
225                 230
```

<210> SEQ ID NO 96
<211> LENGTH: 2261
<212> TYPE: DNA
<213> ORGANISM: Mus musculus
<220> FEATURE:
<221> NAME/KEY: CDS
<222> LOCATION: (90)..(776)

<400> SEQUENCE: 96

```
ccttcttaag gaggtttaag gccttccaaa gaaagccagg cagagaggca cttctcagtg        60
gctgtggtcg gaccatgacc tagctgacc atg aac ttg gaa ggg ctt gaa atg        113
                                Met Asn Leu Glu Gly Leu Glu Met
                                  1               5 ata gca gtt ctg atc gtc att gtg ctt ttt gtt aaa tta ttg gaa cag        161
Ile Ala Val Leu Ile Val Ile Val Leu Phe Val Lys Leu Leu Glu Gln
         10                  15                  20 ttt ggg ctg att gaa gca ggt tta gaa gac agc gtg gaa gat gaa ctg        209
Phe Gly Leu Ile Glu Ala Gly Leu Glu Asp Ser Val Glu Asp Glu Leu
 25                  30                  35                  40 gag atg gcc acc gtc agg cat cgg cct gaa gcc ctt gag ctt ctg gaa        257
Glu Met Ala Thr Val Arg His Arg Pro Glu Ala Leu Glu Leu Leu Glu
                 45                  50                  55 gcc cag agc aaa ttt acc aag aaa gag ctt cag atc ctt tac aga gga        305
Ala Gln Ser Lys Phe Thr Lys Lys Glu Leu Gln Ile Leu Tyr Arg Gly
             60                  65                  70 ttt aag aat gaa tgc ccc agt ggt gtt gtt aat gaa gaa acc ttc aaa        353
Phe Lys Asn Glu Cys Pro Ser Gly Val Val Asn Glu Glu Thr Phe Lys
         75                  80                  85 gag att tac tcg cag ttc ttt cca cag gga gac tct aca aca tat gca        401
Glu Ile Tyr Ser Gln Phe Phe Pro Gln Gly Asp Ser Thr Thr Tyr Ala
     90                  95                 100 cat ttt ctg ttc aat gca ttt gat aca gac cac aat gga gct gtg agt        449
His Phe Leu Phe Asn Ala Phe Asp Thr Asp His Asn Gly Ala Val Ser
105                 110                 115                 120 ttc gag gat ttc atc aaa ggt ctt tcc att ttg ctc cgg ggg aca gta        497
Phe Glu Asp Phe Ile Lys Gly Leu Ser Ile Leu Leu Arg Gly Thr Val
                125                 130                 135 caa gaa aaa ctc aat tgg gca ttt aat ctg tat gac ata aat aaa gat        545
Gln Glu Lys Leu Asn Trp Ala Phe Asn Leu Tyr Asp Ile Asn Lys Asp
            140                 145                 150 ggc tac atc act aaa gag gaa atg ctt gat ata atg aaa gca ata tac        593
Gly Tyr Ile Thr Lys Glu Glu Met Leu Asp Ile Met Lys Ala Ile Tyr
        155                 160                 165 gat atg atg ggt aaa tgt aca tat cct gtc ctc aaa gaa gat gct ccc        641
Asp Met Met Gly Lys Cys Thr Tyr Pro Val Leu Lys Glu Asp Ala Pro
    170                 175                 180 aga caa cac gtt gaa aca ttt ttt cag aaa atg gac aaa aat aaa gat        689
Arg Gln His Val Glu Thr Phe Phe Gln Lys Met Asp Lys Asn Lys Asp
185                 190                 195                 200 ggg gtt gtt acc ata gat gag ttc att gaa agc tgc caa aaa gat gaa        737
Gly Val Val Thr Ile Asp Glu Phe Ile Glu Ser Cys Gln Lys Asp Glu
                205                 210                 215 aac ata atg cgc tcc atg cag ctc ttt gaa aat gtg att taacttgtca        786
Asn Ile Met Arg Ser Met Gln Leu Phe Glu Asn Val Ile
            220                 225
```

```
aatagatcct gaatccaaca gacaaatgtg aactattcta ccacccttaa agttggagct    846
accacttta gcatagattg ctcagcttga cactgaagca tattatgcaa acaagctttg    906
ttttaatata aagcaatccc caaaagattt gagctttcag ttataaattt gcatccttt    966
cataatgcca ctgagttcag gggatggtct aactcatttc atactctgtg aatattcaaa   1026
agtaatagaa tctggcatat agttttattg gttccttagc catgggatta ttgaggcttt   1086
cacatatcag tgattttaaa atatcagtgt ttttgctac tcatttgtat gtattcagtc    1146
ctaggatttt gaatggtttt ctaatatagt gacatctgca tttaatttcc agaaattaaa   1206
ttaatttca tgtttgaatg ctgtaattcc atttaaattc catttatata ctttaaggaa    1266
acaagattac aacaattaaa aaacacata gttccagttt ctatggcctt cccaccttct    1326
gttagaaatt agttttatct ggcatttta aacatttaaa aattattaaa catttaaaaa    1386
ttagtttatt atcagatatc agcatatgcc taataaaact tattttaata agcatttaat   1446
tttccataat atgttacagc caaggcctat ataataattt tggatttgtt caatctttct   1506
tacaggctgt tttctattgt atcaatcatt agtatcaatc attaagtgga agttgaagaa   1566
ggcatcaaac aaaacaagga tgtttacaga catatgcaaa gggtcaggat atctatcctc   1626
cagtatatag taatgcttaa taacaagtaa tcctaacagc attaaaggcc aaatctgtcc   1686
tcttcccct gacttcctta cagcatgttt atttatatta caagccattc agggacaaag    1746
aaagaaacct tgactacccc actgtctact aagaacaaac agcaagcaaa attagcaagc   1806
aaaattcact ttgaaagcac cagtggttcc attacattga caactactac caagatttag   1866
tagaaaataa gtgctcaaca actaatccag attacagtat gatttagctc atcataattc   1926
agattatttt taatcatctt agccaaaact gtaaagttgc cacattacta aagccacaca   1986
catcgtccct gttttgtaga aatatcacaa agaccaagag gctacagaag gaggaaattt   2046
gcaactgtct ttgcaacaat aaatcaggta tctattctgg tgtagagata ggatgttgaa   2106
agctgccctg ctatcaccag tgtagaaatt aagagtagta caatacatgt acactgaaat   2166
ttgccatcac gtgtttgtgt aaactcaatg tgcacatttt gtatttcaaa agaaaaaat   2226
aaaagcaaaa taaatgtta aaaaaaaaaa aaaaa                              2261
```

<210> SEQ ID NO 97
<211> LENGTH: 229
<212> TYPE: PRT
<213> ORGANISM: Homo sapiens

<400> SEQUENCE: 97

```
Met Asn Leu Glu Gly Leu Glu Met Ile Ala Val Leu Ile Val Ile
  1               5                  10                  15

Leu Phe Val Lys Leu Leu Glu Gln Phe Gly Leu Ile Glu Ala Gly Leu
                 20                  25                  30

Glu Asp Ser Val Glu Asp Glu Leu Glu Met Ala Thr Val Arg His Arg
             35                  40                  45

Pro Glu Ala Leu Glu Leu Leu Glu Ala Gln Ser Lys Phe Thr Lys Lys
         50                  55                  60

Glu Leu Gln Ile Leu Tyr Arg Gly Phe Lys Asn Glu Cys Pro Ser Gly
     65                  70                  75                  80

Val Val Asn Glu Glu Thr Phe Lys Glu Ile Tyr Ser Gln Phe Phe Pro
                 85                  90                  95

Gln Gly Asp Ser Thr Thr Tyr Ala His Phe Leu Phe Asn Ala Phe Asp
                100                 105                 110
```

```
Thr Asp His Asn Gly Ala Val Ser Phe Glu Asp Phe Ile Lys Gly Leu
        115                 120                 125

Ser Ile Leu Leu Arg Gly Thr Val Gln Glu Lys Leu Asn Trp Ala Phe
    130                 135                 140

Asn Leu Tyr Asp Ile Asn Lys Asp Gly Tyr Ile Thr Lys Glu Glu Met
145                 150                 155                 160

Leu Asp Ile Met Lys Ala Ile Tyr Asp Met Met Gly Lys Cys Thr Tyr
                165                 170                 175

Pro Val Leu Lys Glu Asp Ala Pro Arg Gln His Val Glu Thr Phe Phe
            180                 185                 190

Gln Lys Met Asp Lys Asn Lys Asp Gly Val Val Thr Ile Asp Glu Phe
        195                 200                 205

Ile Glu Ser Cys Gln Lys Asp Glu Asn Ile Met Arg Ser Met Gln Leu
    210                 215                 220

Phe Glu Asn Val Ile
225
```

<210> SEQ ID NO 98
<211> LENGTH: 2299
<212> TYPE: DNA
<213> ORGANISM: Homo sapiens
<220> FEATURE:
<221> NAME/KEY: CDS
<222> LOCATION: (65)..(817)
<221> NAME/KEY: misc_feature
<222> LOCATION: (13)..(13)
<223> OTHER INFORMATION: n = any nucleotide

<400> SEQUENCE: 98

```
gtggacagac gcnccctggc ggtggacttc tcgagtctcg cttctgcacc ctgcgtcccc    60 agac atg aat gtg agg agg gtg gag agc att tcg gct cag ctg gag gag   109
     Met Asn Val Arg Arg Val Glu Ser Ile Ser Ala Gln Leu Glu Glu
     1               5                   10                  15 gcc agc tct aca ggc ggt ttc ctg tac gct cag aac agc acc aag cgc   157
Ala Ser Ser Thr Gly Gly Phe Leu Tyr Ala Gln Asn Ser Thr Lys Arg
                20                  25                  30 agc att aaa gag cgg ctc atg aag ctc ttg ccc tgc tca gct gcc aaa   205
Ser Ile Lys Glu Arg Leu Met Lys Leu Leu Pro Cys Ser Ala Ala Lys
            35                  40                  45 acg tcg tct cct gct att caa aac agc gtg gaa gat gaa ctg gag atg   253
Thr Ser Ser Pro Ala Ile Gln Asn Ser Val Glu Asp Glu Leu Glu Met
        50                  55                  60 gcc acc gtc agg cat cgg cct gaa gcc ctt gag ctt ctg gaa gcc cag   301
Ala Thr Val Arg His Arg Pro Glu Ala Leu Glu Leu Leu Glu Ala Gln
    65                  70                  75 agc aaa ttt acc aag aaa gag ctt cag atc ctt tac aga gga ttt aag   349
Ser Lys Phe Thr Lys Lys Glu Leu Gln Ile Leu Tyr Arg Gly Phe Lys
80                  85                  90                  95 aat gaa tgc ccc agt ggt gtt gtt aat gaa gaa acc ttc aaa gag att   397
Asn Glu Cys Pro Ser Gly Val Val Asn Glu Glu Thr Phe Lys Glu Ile
                100                 105                 110 tac tcg cag ttc ttt cca cag gga gac tct aca aca tat gca cat ttt   445
Tyr Ser Gln Phe Phe Pro Gln Gly Asp Ser Thr Thr Tyr Ala His Phe
            115                 120                 125 ctg ttc aat gca ttt gat aca gac cac aat gga gct gtg agt ttc gag   493
Leu Phe Asn Ala Phe Asp Thr Asp His Asn Gly Ala Val Ser Phe Glu
        130                 135                 140 gat ttc atc aaa ggt ctt tcc att ttg ctc cgg ggg aca gta caa gaa   541
Asp Phe Ile Lys Gly Leu Ser Ile Leu Leu Arg Gly Thr Val Gln Glu
    145                 150                 155
```

```
                145                 150                 155
aaa ctc aat tgg gca ttt aat ctg tat gac ata aat aaa gat ggc tac     589
Lys Leu Asn Trp Ala Phe Asn Leu Tyr Asp Ile Asn Lys Asp Gly Tyr
160                 165                 170                 175 atc act aaa gag gaa atg ctt gat ata atg aaa gca ata tac gat atg     637
Ile Thr Lys Glu Glu Met Leu Asp Ile Met Lys Ala Ile Tyr Asp Met
                180                 185                 190 atg ggt aaa tgt aca tat cct gtc ctc aaa gaa gat gct ccc aga caa     685
Met Gly Lys Cys Thr Tyr Pro Val Leu Lys Glu Asp Ala Pro Arg Gln
            195                 200                 205 cac gtt gaa aca ttt ttt cag aaa atg gac aaa aat aaa gat ggg gtt     733
His Val Glu Thr Phe Phe Gln Lys Met Asp Lys Asn Lys Asp Gly Val
        210                 215                 220 gtt acc ata gat gag ttc att gaa agc tgc caa aaa gat gaa aac ata     781
Val Thr Ile Asp Glu Phe Ile Glu Ser Cys Gln Lys Asp Glu Asn Ile
    225                 230                 235 atg cgc tcc atg cag ctc ttt gaa aat gtg att taa cttgtcaaat          827
Met Arg Ser Met Gln Leu Phe Glu Asn Val Ile
240                 245                 250 agatcctgaa tccaacagac aaatgtgaac tattctacca cccttaaagt tggagctacc    887
acttttagca tagattgctc agcttgacac tgaagcatat tatgcaaaca agctttgttt    947
taatataaag caatccccaa aagatttgag ctttcagtta taaatttgca tccttttcat   1007
aatgccactg agttcagggg atggtctaac tcatttcata ctctgtgaat attcaaaagt   1067
aatagaatct ggcatatagt tttattggtt ccttagccat gggattattg aggctttcac   1127
atatcagtga ttttaaaata tcagtgtttt ttgctactca tttgtatgta ttcagtccta   1187
ggattttgaa tggttttcta atatagtgac atctgcattt aatttccaga aattaaatta   1247
attttcatgt ttgaatgctg taattccatt taaattccat ttatatactt taaggaaaca   1307
agattacaac aattaaaaaa acacatagtt ccagtttcta tggccttccc accttctgtt   1367
agaaattagt tttatctggc attttaaac atttaaaaat tattaaacat ttaaaaatta    1427
gtttattatc agatatcagc atatgcctaa taaaacttat tttaataagc atttaatttt   1487
ccataatatg ttacagccaa ggcctatata ataattttgg atttgttcaa tctttcttac   1547
aggctgtttt ctattgtatc aatcattagt atcaatcatt aagtggaagt tgaagaaggc   1607
atcaaacaaa acaaggatgt ttacagacat atgcaaaggg tcaggatatc tatcctccag   1667
tatatagtaa tgcttaataa caagtaatcc taacagcatt aaaggccaaa tctgtcctct   1727
ttcccctgac ttccttacag catgtttatt tatattacaa gccattcagg gacaaagaaa   1787
gaaaccttga ctaccccact gtctactaag aacaaacagc aagcaaaatt agcaagcaaa   1847
attcactttg aaagcaccag tggttccatt acattgacaa ctactaccaa gatttagtag   1907
aaaataagtg ctcaacaact aatccagatt acagtatgat ttagctcatc ataattcaga   1967
ttatttttaa tcatcttagc caaaactgta agttgccac attactaaag ccacacacat    2027
cgtccctgtt ttgtagaaat atcacaaaga ccaagaggct acagaaggag gaaatttgca   2087
actgtctttg caacaataaa tcaggtatct attctggtgt agagatagga tgttgaaagc   2147
tgccctgcta tcaccagtgt agaaattaag agtagtacaa tacatgtaca ctgaaatttg   2207
ccatcacgtg tttgtgtaaa ctcaatgtgc acattttgta tttcaaaaag aaaaaataaa   2267
agcaaaataa aatgttaaaa aaaaaaaaaa aa                                 2299

<210> SEQ ID NO 99
<211> LENGTH: 250
```

```
<212> TYPE: PRT
<213> ORGANISM: Homo sapiens

<400> SEQUENCE: 99

Met Asn Val Arg Arg Val Glu Ser Ile Ser Ala Gln Leu Glu Ala
 1               5                  10                  15

Ser Ser Thr Gly Gly Phe Leu Tyr Ala Gln Asn Ser Thr Lys Arg Ser
             20                  25                  30

Ile Lys Glu Arg Leu Met Lys Leu Leu Pro Cys Ser Ala Ala Lys Thr
         35                  40                  45

Ser Ser Pro Ala Ile Gln Asn Ser Val Glu Asp Glu Leu Glu Met Ala
 50                  55                  60

Thr Val Arg His Arg Pro Glu Ala Leu Glu Leu Leu Glu Ala Gln Ser
 65                  70                  75                  80

Lys Phe Thr Lys Lys Glu Leu Gln Ile Leu Tyr Arg Gly Phe Lys Asn
                 85                  90                  95

Glu Cys Pro Ser Gly Val Val Asn Glu Glu Thr Phe Lys Glu Ile Tyr
             100                 105                 110

Ser Gln Phe Phe Pro Gln Gly Asp Ser Thr Thr Tyr Ala His Phe Leu
         115                 120                 125

Phe Asn Ala Phe Asp Thr Asp His Asn Gly Ala Val Ser Phe Glu Asp
130                 135                 140

Phe Ile Lys Gly Leu Ser Ile Leu Leu Arg Gly Thr Val Gln Glu Lys
145                 150                 155                 160

Leu Asn Trp Ala Phe Asn Leu Tyr Asp Ile Asn Lys Asp Gly Tyr Ile
                165                 170                 175

Thr Lys Glu Glu Met Leu Asp Ile Met Lys Ala Ile Tyr Asp Met Met
            180                 185                 190

Gly Lys Cys Thr Tyr Pro Val Leu Lys Glu Asp Ala Pro Arg Gln His
        195                 200                 205

Val Glu Thr Phe Phe Gln Lys Met Asp Lys Asn Lys Asp Gly Val Val
210                 215                 220

Thr Ile Asp Glu Phe Ile Glu Ser Cys Gln Lys Asp Glu Asn Ile Met
225                 230                 235                 240

Arg Ser Met Gln Leu Phe Glu Asn Val Ile
                245                 250

<210> SEQ ID NO 100
<211> LENGTH: 2246
<212> TYPE: DNA
<213> ORGANISM: Rattus sp.
<220> FEATURE:
<221> NAME/KEY: CDS
<222> LOCATION: (3)..(821)

<400> SEQUENCE: 100 cc cct cgc cag acg ccc ctg ggt caa gtg gac tct aag agt gtc gct      47
   Pro Arg Gln Thr Pro Leu Gly Gln Val Asp Ser Lys Ser Val Ala
    1               5                  10                  15 cca gca tct atc atc cct aaa gat gaa cgt gag aag ggt gga aag cat     95
Pro Ala Ser Ile Ile Pro Lys Asp Glu Arg Glu Lys Gly Gly Lys His
             20                  25                  30 ctc ggc tca gct gga gga ggc gag ctc cac agg cgg ttt cct cta cct    143
Leu Gly Ser Ala Gly Gly Gly Glu Leu His Arg Arg Phe Pro Leu Pro
         35                  40                  45 cag aac aac acc aag cgc agc att aaa gag cgg ctc atg aag ctc ttg    191
Gln Asn Asn Thr Lys Arg Ser Ile Lys Glu Arg Leu Met Lys Leu Leu
 50                  55                  60
```

```
ccc tgc tca gct gcc aaa acg tcg tct cct gct ata caa aac agt gtg    239
Pro Cys Ser Ala Ala Lys Thr Ser Ser Pro Ala Ile Gln Asn Ser Val
 65                  70                  75 gaa gat gaa ctg gag atg gcc act gtc agg cac cgg cct gaa gcc ctg    287
Glu Asp Glu Leu Glu Met Ala Thr Val Arg His Arg Pro Glu Ala Leu
 80                  85                  90                  95 gag ctg ctg gag gcc cag agc aaa ttc acc aag aaa gag ctt cag atc    335
Glu Leu Leu Glu Ala Gln Ser Lys Phe Thr Lys Lys Glu Leu Gln Ile
                    100                 105                 110 ctt tac aga gga ttt aag aat gaa tgc ccc agt ggt gtt gtt aat gaa    383
Leu Tyr Arg Gly Phe Lys Asn Glu Cys Pro Ser Gly Val Val Asn Glu
                115                 120                 125 gaa acc ttc aag gag att tac tcg cag ttc ttc cca cag gga gac tcc    431
Glu Thr Phe Lys Glu Ile Tyr Ser Gln Phe Phe Pro Gln Gly Asp Ser
130                 135                 140 acc aca tat gca cat ttt ctc ttc aat gca ttc gac acg gac cac aat    479
Thr Thr Tyr Ala His Phe Leu Phe Asn Ala Phe Asp Thr Asp His Asn
        145                 150                 155 gga gct gtg agc ttt gag gat ttc atc aaa ggt ctt tcc att ttg ctt    527
Gly Ala Val Ser Phe Glu Asp Phe Ile Lys Gly Leu Ser Ile Leu Leu
160                 165                 170                 175 cga ggg aca gta caa gaa aaa ctg aac tgg gca ttt aat ttg tat gac    575
Arg Gly Thr Val Gln Glu Lys Leu Asn Trp Ala Phe Asn Leu Tyr Asp
                180                 185                 190 ata aac aaa gat ggc tac atc act aaa gag gaa atg ctg gac ata atg    623
Ile Asn Lys Asp Gly Tyr Ile Thr Lys Glu Glu Met Leu Asp Ile Met
                195                 200                 205 aaa gca att tac gac atg atg ggg aaa tgc aca tac cct gtc ctc aag    671
Lys Ala Ile Tyr Asp Met Met Gly Lys Cys Thr Tyr Pro Val Leu Lys
        210                 215                 220 gaa gat gct ccc cga cag cac gtg gag aca ttt ttc cag aag atg gac    719
Glu Asp Ala Pro Arg Gln His Val Glu Thr Phe Phe Gln Lys Met Asp
225                 230                 235 aag aat aaa gat ggt gtc gtt acc ata gac gag ttc att gaa agt tgc    767
Lys Asn Lys Asp Gly Val Val Thr Ile Asp Glu Phe Ile Glu Ser Cys
240                 245                 250                 255 caa aaa gat gaa aac ata atg cgc tcc atg cag ctc ttt gaa aat gtg    815
Gln Lys Asp Glu Asn Ile Met Arg Ser Met Gln Leu Phe Glu Asn Val
                260                 265                 270 atc tag actgtcggtg ccttgaccgg aggcaaatgt ggacgactac acacgagttg    871
Ile aagccaccat ttctagcata gattgctcag ctttacactg aggcatatta tgcaaacagc    931
tttgttttaa tataaagacc cccgcgccca aatttaagtt ttccagttac aaatccgcat    991
ccacgtcact ggggtcccga aatgtgctca cttatttcat actctgagaa cactcaaaag   1051
gcacagaatc tggaacagct tgatcctca gccacgtgtt acgggggctt ttacagatga   1111
gtgattttaa acaccagtg gttttccta cttgtttgta ttcagccctg gattttaagt    1171
ggttttctaa aatatttaca tctgcattta acttccagaa agccaatgac ctttttcattt   1231 aactcaattc atgtaatact gaaaaaagga acaaagatta ttacaattaa aaaagaccaa   1291
aaacacagtc ccgatttcta tagcttctcc acctgctgtt aaagacagtc atgtatttgg   1351
cttttttttt tttttaaaa agaacactta aaaaattagt ttattatcag atgttagcat   1411
atacctaata aaattatttt agtatttgtt aattttccat attcaagcca aggctctata   1471
taatccatgt aactttggac ctgttcaatc ttacatgtag actgttttgt attgtgttct   1531
gaagtagaag ttcaaagtgt caaacaaacc aaggatgttt acagacttgc aaagggtcca   1591
```

-continued

```
gatgtctgtc ctgcaatgcc tagtgacgct tattaaccag taacctgaag agcagtaact   1651
ggcaattcta gccaccaccc ctccccaagc cccttcatgt tctcacagca tgtttatcac   1711
acacaagcca ttcagggaca gagaatcctt gactgcccca agcctacta ggaataaaga    1771 tcaagcaaaa tcttctttga aaacaccagt gattctatca tattggaaat atacataaga   1831
gtgtatagaa aacgaatgta gacattggac agttcatccg aattgcatta tgatttagca   1891
catcatgtag ttcaaaggat tcacattcct ttccgtgatc ttaagccaaa actgtagaat   1951
tgccacaaca gtactagata tacacacatt ccctgtttcg tggaaatcca agaaccaaga   2011
ggatacggga agagaaaatt tgcgactgtc tgcaacaata aatcaggtat ctattctggt   2071
gtagagatag gatgttgaga gccgccctgc tatcaccagt gtaggaatta agagtagtac   2131
agtacatgta cagaaatctg ccatcgcgtg tttgtgtaaa ctcaatgtgc acattttgta   2191
tctcaaaaag gaaaataaa gcaaataaa gtgttaaaaa aaaaaaaaaa aaaaa          2246
```

<210> SEQ ID NO 101
<211> LENGTH: 272
<212> TYPE: PRT
<213> ORGANISM: Rattus sp.

<400> SEQUENCE: 101

```
Pro Arg Gln Thr Pro Leu Gly Gln Val Asp Ser Lys Ser Val Ala Pro
 1               5                   10                  15

Ala Ser Ile Ile Pro Lys Asp Glu Arg Glu Lys Gly Gly Lys His Leu
                20                  25                  30

Gly Ser Ala Gly Gly Gly Glu Leu His Arg Arg Phe Pro Leu Pro Gln
            35                  40                  45

Asn Asn Thr Lys Arg Ser Ile Lys Glu Arg Leu Met Lys Leu Leu Pro
        50                  55                  60

Cys Ser Ala Ala Lys Thr Ser Pro Ala Ile Gln Asn Ser Val Glu
 65                  70                  75                  80

Asp Glu Leu Glu Met Ala Thr Val Arg His Arg Pro Glu Ala Leu Glu
                85                  90                  95

Leu Leu Glu Ala Gln Ser Lys Phe Thr Lys Lys Glu Leu Gln Ile Leu
            100                 105                 110

Tyr Arg Gly Phe Lys Asn Glu Cys Pro Ser Gly Val Val Asn Glu Glu
        115                 120                 125

Thr Phe Lys Glu Ile Tyr Ser Gln Phe Phe Pro Gln Gly Asp Ser Thr
    130                 135                 140

Thr Tyr Ala His Phe Leu Phe Asn Ala Phe Asp Thr Asp His Asn Gly
145                 150                 155                 160

Ala Val Ser Phe Glu Asp Phe Ile Lys Gly Leu Ser Ile Leu Leu Arg
                165                 170                 175

Gly Thr Val Gln Glu Lys Leu Asn Trp Ala Phe Asn Leu Tyr Asp Ile
            180                 185                 190

Asn Lys Asp Gly Tyr Ile Thr Lys Glu Glu Met Leu Asp Ile Met Lys
        195                 200                 205

Ala Ile Tyr Asp Met Met Gly Lys Cys Thr Tyr Pro Val Leu Lys Glu
    210                 215                 220

Asp Ala Pro Arg Gln His Val Glu Thr Phe Phe Gln Lys Met Asp Lys
225                 230                 235                 240

Asn Lys Asp Gly Val Val Thr Ile Asp Glu Phe Ile Glu Ser Cys Gln
                245                 250                 255
```

```
Lys Asp Glu Asn Ile Met Arg Ser Met Gln Leu Phe Glu Asn Val Ile
            260                 265                 270

<210> SEQ ID NO 102
<211> LENGTH: 1856
<212> TYPE: DNA
<213> ORGANISM: Rattus sp.
<220> FEATURE:
<221> NAME/KEY: CDS
<222> LOCATION: (339)..(1037)

<400> SEQUENCE: 102
ggcacacaac ccctggattc ttcggagaat atgccgtgag gtgttgccaa ttattagttc        60
tcttggctag cagatgttta gggactggtt aagcctttgg agaaattacc ttaggaaaac       120
ggggaaataa aagcaaagat taccatgaat tgcaagatta cctagcaatt gcaaggtagg       180
aggagagagg tggagggcgg agtagacagg agggagggag aaagtgagag gaagctaggc       240
tggtggaaat aaccctgcac ttggaacagc ggcaaagaag cgcgattttc cagctttaaa       300
tgcctgcccg cgttctgctt gcctacccgg gaacggag atg ttg acc cag ggc gag       356
                                         Met Leu Thr Gln Gly Glu
                                           1               5 tct gaa ggg ctc cag acc ttg gga ata gta gtg gtc ctg tgt tcc tct       404
Ser Glu Gly Leu Gln Thr Leu Gly Ile Val Val Val Leu Cys Ser Ser
             10                  15                  20 ctg aaa cta ctg cac tac ctc ggg ctg att gac ttg tcg gat gac aag       452
Leu Lys Leu Leu His Tyr Leu Gly Leu Ile Asp Leu Ser Asp Asp Lys
         25                  30                  35 atc gag gat gat ctg gag atg acc atg gtt tgc cat cgg cct gag gga       500
Ile Glu Asp Asp Leu Glu Met Thr Met Val Cys His Arg Pro Glu Gly
     40                  45                  50 ctg gag cag ctt gag gca cag acg aac ttc acc aag aga gaa ctg caa       548
Leu Glu Gln Leu Glu Ala Gln Thr Asn Phe Thr Lys Arg Glu Leu Gln
 55                  60                  65                  70 gtc ctt tac cgg gga ttc aaa aac gag tgc ccc agt ggt gtg gtt aac       596
Val Leu Tyr Arg Gly Phe Lys Asn Glu Cys Pro Ser Gly Val Val Asn
                 75                  80                  85 gaa gag aca ttc aag cag atc tac gct cag ttt ttc cct cat gga gat       644
Glu Glu Thr Phe Lys Gln Ile Tyr Ala Gln Phe Phe Pro His Gly Asp
             90                  95                 100 gcc agc aca tac gca cat tac ctc ttc aat gcc ttc gac acc acc cag       692
Ala Ser Thr Tyr Ala His Tyr Leu Phe Asn Ala Phe Asp Thr Thr Gln
        105                 110                 115 aca ggc tct gta aag ttc gag gac ttt gtg act gct ctg tcg att tta       740
Thr Gly Ser Val Lys Phe Glu Asp Phe Val Thr Ala Leu Ser Ile Leu
    120                 125                 130 ctg aga gga acg gtc cat gaa aaa ctg agg tgg acg ttt aat ttg tac       788
Leu Arg Gly Thr Val His Glu Lys Leu Arg Trp Thr Phe Asn Leu Tyr
135                 140                 145                 150 gac atc aat aaa gac ggc tac ata aac aaa gag gag atg atg gac ata       836
Asp Ile Asn Lys Asp Gly Tyr Ile Asn Lys Glu Glu Met Met Asp Ile
                155                 160                 165 gtg aaa gcc atc tat gac atg atg ggg aaa tac acc tat cct gtg ctc       884
Val Lys Ala Ile Tyr Asp Met Met Gly Lys Tyr Thr Tyr Pro Val Leu
            170                 175                 180 aaa gag gac act ccc agg cag cac gtg gac gtc ttc ttc cag aaa atg       932
Lys Glu Asp Thr Pro Arg Gln His Val Asp Val Phe Phe Gln Lys Met
        185                 190                 195 gat aaa aat aaa gat ggc att gta acg tta gac gaa ttt ctc gag tcc       980
Asp Lys Asn Lys Asp Gly Ile Val Thr Leu Asp Glu Phe Leu Glu Ser
    200                 205                 210
```

-continued

```
tgt cag gag gat gac aac atc atg agg tct cta cag ctg ttc caa aat    1028
Cys Gln Glu Asp Asp Asn Ile Met Arg Ser Leu Gln Leu Phe Gln Asn
215                 220                 225                 230 gtc atg taa ctgaggacac tggccatcct gctctcagag acactgacaa             1077
Val Met acacctcaat gccctgatct gcccttgttc cagttttaca catcaactct cgggacagaa   1137
ataccttta cactttggaa gaattctctg ctgaagactt tctacaaaac ctggcaccga    1197
gtggctcagt ctctgattgc caactcttcc tccctcctcc tcttgagagg gacgagctga   1257
aatccgaagt ttgttttgga agcatgccca tctctccatg ctgctgctgc cctgtggaag   1317
gcccctctgc ttgagcttaa acagtagtgc acagttttct gcgtatacag atccccaact   1377
cactgcctct aagtcaggca gaccctgatc aatctgaacc aaatgtgcac catcctccga   1437
tggcctccca agccaatgtg cctgcttctc ttcctctggt gggaagaaag aacgctctac   1497
agagcactta gagcttacca tgaaaatact gggagaggca gcacctaaca catgtagaat   1557
aggactgaat tattaagcat ggtggtatca gatgatgcaa acagcccatg tcatttttt    1617
ttccagaggt agggactaat aattctccca cactagcacc tacgatcata gaacaagtct   1677
tttaacacat ccaggaggga aaccgctgcc cagtggtcta tcccttctct ccatcccctg   1737
ctcaagccca gcactgcatg tctctcccgg aaggtccaga atgcctgtga aatgctgtaa   1797
ctttttatacc ctgttataat caataaacag aactatttcg tacaaaaaaa aaaaaaaaa   1856
```

<210> SEQ ID NO 103
<211> LENGTH: 232
<212> TYPE: PRT
<213> ORGANISM: Rattus sp.

<400> SEQUENCE: 103

```
Met Leu Thr Gln Gly Glu Ser Glu Gly Leu Gln Thr Leu Gly Ile Val
  1               5                  10                  15

Val Val Leu Cys Ser Ser Leu Lys Leu Leu His Tyr Leu Gly Leu Ile
                 20                  25                  30

Asp Leu Ser Asp Asp Lys Ile Glu Asp Leu Glu Met Thr Met Val
             35                  40                  45

Cys His Arg Pro Glu Gly Leu Glu Gln Leu Glu Ala Gln Thr Asn Phe
         50                  55                  60

Thr Lys Arg Glu Leu Gln Val Leu Tyr Arg Gly Phe Lys Asn Glu Cys
 65                  70                  75                  80

Pro Ser Gly Val Val Asn Glu Glu Thr Phe Lys Gln Ile Tyr Ala Gln
                 85                  90                  95

Phe Phe Pro His Gly Asp Ala Ser Thr Tyr Ala His Tyr Leu Phe Asn
            100                 105                 110

Ala Phe Asp Thr Thr Gln Thr Gly Ser Val Lys Phe Glu Asp Phe Val
        115                 120                 125

Thr Ala Leu Ser Ile Leu Leu Arg Gly Thr Val His Glu Lys Leu Arg
130                 135                 140

Trp Thr Phe Asn Leu Tyr Asp Ile Asn Lys Asp Gly Tyr Ile Asn Lys
145                 150                 155                 160

Glu Glu Met Met Asp Ile Val Lys Ala Ile Tyr Asp Met Met Gly Lys
                165                 170                 175

Tyr Thr Tyr Pro Val Leu Lys Glu Asp Thr Pro Arg Gln His Val Asp
            180                 185                 190

Val Phe Phe Gln Lys Met Asp Lys Asn Lys Asp Gly Ile Val Thr Leu
```

```
                195                 200                 205
Asp Glu Phe Leu Glu Ser Cys Gln Glu Asp Asp Asn Ile Met Arg Ser
    210                 215                 220

Leu Gln Leu Phe Gln Asn Val Met
225                 230
```

<210> SEQ ID NO 104
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 104
ggtaccttct cgtccctgca gaccaaacaa ag                          32

<210> SEQ ID NO 105
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 105
cggtaaagga cttgcagttc tctc                                   24

<210> SEQ ID NO 106
<211> LENGTH: 19
<212> TYPE: DNA
<213> ORGANISM: Homo sapiens

<400> SEQUENCE: 106
ggcaaagaag cgcgatttt                                         19

<210> SEQ ID NO 107
<211> LENGTH: 17
<212> TYPE: DNA
<213> ORGANISM: Homo sapiens

<400> SEQUENCE: 107
tcccgggtag gcaagca                                           17

<210> SEQ ID NO 108
<211> LENGTH: 22
<212> TYPE: DNA
<213> ORGANISM: Homo sapiens

<400> SEQUENCE: 108
cctgctcaag cccagcactg ca                                     22

<210> SEQ ID NO 109
<211> LENGTH: 227
<212> TYPE: PRT
<213> ORGANISM: Homo sapiens

<400> SEQUENCE: 109

```
Met Gly Ala Val Met Gly Thr Phe Ser Ser Leu Gln Thr Lys Gln Arg
1               5                   10                  15

Arg Pro Ser Lys Asp Ile Ala Trp Trp Tyr Tyr Gln Tyr Gln Arg Asp
                20                  25                  30

Lys Ile Glu Asp Glu Leu Glu Met Thr Met Val Cys His Arg Pro Glu
        35                  40                  45
```

-continued

```
Gly Leu Glu Gln Leu Glu Ala Gln Thr Asn Phe Thr Lys Arg Glu Leu
     50                  55                  60
Gln Val Leu Tyr Arg Gly Phe Lys Asn Glu Cys Pro Ser Gly Val Val
 65              70                  75                      80
Asn Glu Asp Thr Phe Lys Gln Ile Tyr Ala Gln Phe Phe Pro His Gly
                 85                  90                  95
Asp Ala Ser Thr Tyr Ala His Tyr Leu Phe Asn Ala Phe Asp Thr Thr
                100                 105                 110
Gln Thr Gly Ser Val Lys Phe Glu Asp Phe Val Thr Ala Leu Ser Ile
            115                 120                 125
Leu Leu Arg Gly Thr Val His Glu Lys Leu Arg Trp Thr Phe Asn Leu
    130                 135                 140
Tyr Asp Ile Asn Lys Asp Gly Tyr Ile Asn Lys Glu Glu Met Met Asp
145                 150                 155                 160
Ile Val Lys Ala Ile Tyr Asp Met Met Gly Lys Tyr Thr Tyr Pro Val
                165                 170                 175
Leu Lys Glu Asp Thr Pro Arg Gln His Val Asp Val Phe Phe Gln Lys
            180                 185                 190
Met Asp Lys Asn Lys Asp Gly Ile Val Thr Leu Asp Glu Phe Leu Glu
        195                 200                 205
Ser Cys Gln Glu Asp Asp Asn Ile Met Arg Ser Leu Gln Leu Phe Gln
    210                 215                 220
Asn Val Met
225
```

NUCLEIC ACIDS ENCODING POTASSIUM CHANNEL INTERACTORS

CROSS-REFERENCE TO RELATED APPLICATIONS

This is a continuation-in-part of U.S. application Ser. No. 09/670,756, filed Sep. 27, 2000, now U.S. Pat. No. 7,078,483, which is a continuation-in-part of U.S. application Ser. No. 09/400,492, filed Sep. 21, 1999, now U.S. Pat. No. 7,115,381, which is a continuation-in-part of U.S. application Ser. No. 09/399,913, filed Sep. 21, 1999, now U.S. Pat. No. 6,361,971, which is a continuation-in-part of each of (1) U.S. application Ser. No. 09/350,874, filed Jul. 9, 1999, now abandoned, and (2) U.S. application Ser. No. 09/350,614, filed Jul. 9, 1999, now U.S. Pat. No. 6,698,581, each of which are continuations-in-part of U.S. application Ser. No. 09/298,731, filed Apr. 23, 1999, Now U.S. Pat. No. 6,369,197, which claims benefit under 35 U.S.C. §119(e) to U.S. Provisional Application Nos. 60/109,333, filed Nov. 20, 1998, 60/110,033, filed Nov. 25, 1998 and 60/110,277, filed Nov. 30, 1998. The entire contents of each of the above-listed patent applications are incorporated by reference herein.

BACKGROUND OF THE INVENTION

Mammalian cell membranes are important to the structural integrity and activity of many cells and tissues. Of particular interest in membrane physiology is the study of trans-membrane ion channels which act to directly control a variety of pharmacological, physiological, and cellular processes. Numerous ion channels have been identified including calcium, sodium, and potassium channels, each of which have been investigated to determine their roles in vertebrate and insect cells.

Because of their involvement in maintaining normal cellular homeostasis, much attention has been given to potassium channels. A number of these potassium channels open in response to changes in the cell membrane potential. Many voltage-gated potassium channels have been identified and characterized by their electrophysiological and pharmacological properties. Potassium currents are more diverse than sodium or calcium currents and are further involved in determining the response of a cell to external stimuli. The diversity of potassium channels and their important physiological role highlights their potential as targets for developing therapeutic agents for various diseases.

One of the best characterized classes of potassium channels are the voltage-gated potassium channels. The prototypical member of this class is the protein encoded by the Shaker gene in *Drosophila melanogaster*. Proteins of the Shal or Kv4 family are a type of voltage-gated potassium channels that underlies many of the native A type currents that have been recorded from different primary cells. Kv4 channels have a major role in the repolarization of cardiac action potentials. In neurons, Kv4 channels and the A currents they may comprise play an important role in modulation of firing rate, action potential initiation and in controlling dendritic responses to synaptic inputs.

The fundamental function of a neuron is to receive, conduct, and transmit signals. Despite the varied purpose of the signals carried by different classes of neurons, the form of the signal is always the same and consists of changes in the electrical potential across the plasma membrane of the neuron. The plasma membrane of a neuron contains voltage-gated cation channels, which are responsible for propagating this electrical potential (also referred to as an action potential or nerve impulse) across and along the plasma membrane.

The Kv family of channels includes, among others: (1) the delayed-rectifier potassium channels, which repolarize the membrane after each action potential to prepare the cell to fire again; and (2) the rapidly inactivating (A-type) potassium channels, which are active predominantly at subthreshold voltages and act to reduce the rate at which excitable cells reach firing threshold. In addition to being critical for action potential conduction, Kv channels also control the response to depolarizing, e.g., synaptic, inputs and play a role in neurotransmitter release. As a result of these activities, voltage-gated potassium channels are key regulators of neuronal excitability (Hille B., Ionic Channels of Excitable Membranes, Second Edition, Sunderland, Mass.: Sinauer, (1992)).

There is tremendous structural and functional diversity within the Kv potassium channel superfamily. This diversity is generated both by the existence of multiple genes and by alternative splicing of RNA transcripts produced from the same gene. Nonetheless, the amino acid sequences of the known Kv potassium channels show high similarity. All appear to be comprised of four, pore forming α-subunits and some are known to have four cytoplasmic (β-subunit) polypeptides (Jan L. Y. et al. (1990) *Trends Neurosci* 13:415-419, and Pongs, O. et al. (1995) *Sem Neurosci.* 7:137-146). The known Kv channel (α-subunits fall into four sub-families named for their homology to channels first isolated from *Drosophila*: the Kv1, or Shaker-related subfamily; the Kv2, or Shab-related subfamily; the Kv3, or Shaw-related subfamily; and the Kv4, or Shal-related subfamily.

Kv4.2 and Kv4.3 are examples of Kv channel (α-subunits of the Shal-related subfamily. Kv4.3 has a unique neuroanatomical distribution in that its mRNA is highly expressed in brainstem monoaminergic and forebrain cholinergic neurons, where it is involved in the release of the neurotransmitters dopamine, norepinephrine, serotonin, and acetylcholine.

This channel is also highly expressed in cortical pyramidal cells and in interneurons. (Serdio P. et al. (1996) *J. Neurophys* 75:2174-2179). Interestingly, the Kv4.3 polypeptide is highly expressed in neurons which express the corresponding mRNA. The Kv4.3 polypeptide is expressed in the somatodendritic membranes of these cells, where it is thought to contribute to the rapidly inactivating K+ conductance. Kv4.2 mRNA is widely expressed in brain, and the corresponding polypeptide also appears to be concentrated in somatodendritic membranes where it also contributes to the rapidly inactivating K$^+$ conductance (Sheng et al. (1992) Neuron 9:271-84). These somatodendritic A-type Kv channels, like Kv4.2 and Kv4.3, are likely involved in processes which underlie learning and memory, such as integration of subthreshold synaptic responses and the conductance of back-propagating action potentials (Hoffman D. A. et al. (1997) *Nature* 387:869-875).

Thus, proteins which interact with and modulate the activity of potassium channel proteins e.g., potassium channels having a Kv4.2 or Kv4.3 subunit, provide novel molecular targets to modulate neuronal or cardiac excitability, e.g., action potential conduction, somatodendritic excitability and neurotransmitter release, in cells expressing these channels. In addition, detection of genetic lesions in the gene encoding these proteins could be used to diagnose and treat central nervous system disorders such as epilepsy, spinocerebellar ataxia, anxiety, depression, age-related memory loss, migraine, obesity, Parkinsons disease or Alzheimer's disease; or cardiovascular disorders such as heart failure, hypertension, atrial fibrillation, dilated cardiomyopathy, idiopathic cardiomyopathy, or angina.

SUMMARY OF THE INVENTION

The present invention is based, at least in part, on the discovery of novel nucleic acid molecules which encode gene products that interact with potassium channel proteins or possess substantial homology to the gene products of the invention that interact with potassium channel proteins (paralogs). Potassium channel proteins are, for example, potassium channels having a Kv4.2 or Kv4.3 subunit. The nucleic acid molecules of the invention and their gene products are referred to herein as "Potassium Channel Interacting Proteins", "PCIP", or "KChIP" nucleic acid and protein molecules. The PCIP proteins of the present invention interact with, e.g., bind to a potassium channel protein, modulate the activity of a potassium channel protein, and/or modulate a potassium channel mediated activity in a cell, e.g., a neuronal or cardiac cell. The PCIP molecules of the present invention are useful as modulating agents to regulate a variety of cellular processes, e.g., neuronal or cardiac cell processes. Accordingly, in one aspect, this invention provides isolated nucleic acid molecules encoding PCIP proteins or biologically active portions thereof, as well as nucleic acid fragments suitable as primers or hybridization probes for the detection of PCIP-encoding nucleic acids.

In one embodiment, a PCIP nucleic acid molecule of the invention is at least 50%, 55%, 60%, 65%, 70%, 75%, 80%, 85%, 90%, 95%, 98% or more identical to the nucleotide sequence (e.g., to the entire length of the nucleotide sequence) shown in SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, SEQ ID NO:71, SEQ ID NO:74, SEQ ID NO:75, SEQ ID NO:77, SEQ ID NO:79, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO: 100, or SEQ ID NO:102, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, or a complement thereof.

In another preferred embodiment, the isolated nucleic acid molecule includes the nucleotide sequence shown SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, SEQ ID NO:71, SEQ ID NO:74, SEQ ID NO:75, SEQ ID NO:77, SEQ ID NO:79, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, or SEQ ID NO:102 or a complement thereof. In another preferred embodiment, the nucleic acid molecule includes a fragment of at least 300, 350, 400, 426, 471, or 583 nucleotides of the nucleotide sequence of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, SEQ ID NO:71, SEQ ID NO:74, SEQ ID NO:75, SEQ ID NO:77, SEQ ID NO:79, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO: 1100, or SEQ ID NO:102, or a complement thereof.

In another embodiment, a PCIP nucleic acid molecule includes a nucleotide sequence encoding a protein having an amino acid sequence sufficiently identical to the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, SEQ ID NO:72, SEQ ID NO:76, SEQ ID NO:78, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO: 101, SEQ ID NO:103, or SEQ ID NO:109, or an amino acid sequence encoded by the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994. In a preferred embodiment, a PCIP nucleic acid molecule includes a nucleotide sequence encoding a protein having an amino acid sequence at least 50%, 55%, 60%, 65%, 70%, 75%, 80%, 85%, 90%, 95% or more identical to the amino acid sequence of SEQ ID NO: 2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, SEQ ID NO:72, SEQ ID NO:76, SEQ ID NO:78, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO: 901, SEQ ID NO:103, or SEQ ID NO:109, or the amino acid sequence encoded by the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994.

In another preferred embodiment, an isolated nucleic acid molecule encodes the amino acid sequence of 1v, 9q, p19, W28559, KChIP4a, KChIP4b, 33b07, 1p, and rat 7s protein. In yet another preferred embodiment, the nucleic acid molecule includes a nucleotide sequence encoding a protein having the amino acid sequence of SEQ ID NO: 2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, SEQ ID NO:72, SEQ ID NO:76, SEQ ID NO:78, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, or SEQ ID NO:109, or the amino acid sequence encoded by the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994. In yet another preferred embodiment, the nucleic acid molecule is at least 426, 471, or 583 nucleotides in length and encodes a protein having a PCIP activity (as described herein).

Another embodiment of the invention features nucleic acid molecules, preferably PCIP nucleic acid molecules, which specifically detect PCIP nucleic acid molecules relative to nucleic acid molecules encoding non-PCIP proteins. For example, in one embodiment, such a nucleic acid molecule is at least 426, 400-450, 471, 450-500, 500-550, 583, 550-600, 600-650, 650-700, 700-750, 750-800 or more nucleotides in length and hybridizes under stringent conditions to a nucleic acid molecule comprising the nucleotide sequence shown in SEQ ID NO:1, SEQ ID NO:3 SEQ ID NO:5, SEQ ID NO:7, SEQ ID NO:9, SEQ ID NO: 11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, SEQ ID NO:71, SEQ ID NO:74, SEQ ID NO:75, SEQ ID NO:77, SEQ ID NO:79, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, or SEQ ID NO:102, the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, or a complement thereof. In preferred embodiments, the nucleic acid molecules are at least 15 (e.g., contiguous) nucleotides in length and hybridize under stringent conditions to nucleotides 93-126, 360-462, 732-825, 1028-1054, or 1517-1534 of SEQ ID NO:7. In other preferred embodiments, the nucleic acid molecules comprise nucleotides 93-126, 360-462, 732-825, 1028-1054, or 1517-1534 of SEQ ID NO:7.

In other preferred embodiments, the nucleic acid molecules are at least 15 (e.g., contiguous) nucleotides in length and hybridize under stringent conditions to nucleotides 1-14, 49-116, 137-311, 345-410, 430-482, 503-518, 662-693, 1406-1421, 1441-1457, 1478-1494, or 1882-1959 of SEQ ID NO:13. In other preferred embodiments, the nucleic acid molecules comprise nucleotides 1-14, 49-116, 137-311, 345-410, 430-482, 503-518, 662-693, 1406-1421, 1441-1457, 1478-1494, or 1882-1959 of SEQ ID NO:13.

In preferred embodiments, the nucleic acid molecules are at least 15 (e.g., contiguous) nucleotides in length and hybridize under stringent conditions to nucleotides 932-1527, 1548-1765, 1786-1871, 1908-2091, 2259-2265, or 2630-2654 of SEQ ID NO:35. In other preferred embodiments, the nucleic acid molecules comprise nucleotides 932-1527, 1548-1765, 1786-1871, 1908-2091, 2259-2265, or 2630-2654 of SEQ ID NO:35.

In other preferred embodiments, the nucleic acid molecule encodes a naturally occurring allelic variant of a polypeptide comprising the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, SEQ ID NO:72, SEQ ID NO:76, SEQ ID NO:78, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO: 101, SEQ ID NO:103, or SEQ ID NO:109 or an amino acid sequence encoded by the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, wherein the nucleic acid molecule hybridizes to a nucleic acid molecule comprising SEQ ID NO:1, SEQ ID NO: 3 SEQ ID NO: 5, SEQ ID NO:7, SEQ ID NO:9, SEQ ID NO: 71, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, SEQ ID NO:71, SEQ ID NO:74, SEQ ID NO:75, SEQ ID NO:77, SEQ ID NO:79, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, or SEQ ID NO:102 under stringent conditions.

Another embodiment of the invention provides an isolated nucleic acid molecule which is antisense to a PCIP nucleic acid molecule, e.g., the coding strand of a PCIP nucleic acid molecule.

Another aspect of the invention provides a vector comprising a PCIP nucleic acid molecule. In certain embodiments, the vector is a recombinant expression vector. In another embodiment, the invention provides a host cell containing a vector of the invention. The invention also provides a method for producing a protein, preferably a PCIP protein, by culturing in a suitable medium, a host cell, e.g., a mammalian host cell such as a non-human mammalian cell, of the invention containing a recombinant expression vector, such that the protein is produced.

Another aspect of this invention features isolated or recombinant PCIP proteins and polypeptides. In one embodiment, the isolated protein, preferably a PCIP protein, includes at least one calcium binding domain. In a preferred embodiment, the protein, preferably a PCIP protein, includes at least one calcium binding domain and has an amino acid sequence at least about 50%, 55%, 60%, 65%, 70%, 75%, 80%, 85%, 90%, 95% or more identical to the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, SEQ ID NO:72, SEQ ID NO:76, SEQ ID NO:78, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, or SEQ ID NO:109, or the amino acid sequence encoded by the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994. In another preferred embodiment, the protein, preferably a PCIP protein, includes at least one calcium binding domain and modulates a potassium channel mediated activity. In yet another preferred embodiment, the protein, preferably a PCIP protein, includes at least one calcium binding domain and is encoded by a nucleic acid molecule having a nucleotide sequence which hybridizes under stringent hybridization conditions to a nucleic acid molecule comprising the nucleotide sequence of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, SEQ ID NO:71, SEQ ID NO:74, SEQ ID NO:75, SEQ ID NO:77, SEQ ID NO:79, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, or SEQ ID NO:102.

In another embodiment, the invention features fragments of the proteins having the amino acid sequence of SEQ ID NO:2, SEQ ID NO:4, SEQ ID NO:6, SEQ ID NO:8, SEQ ID NO: 10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, SEQ ID NO:72, SEQ ID NO:76, SEQ ID NO:78, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO: 101, SEQ ID NO:103, or SEQ ID NO:109, wherein the fragment comprises at least 15 amino acids (e.g., contiguous amino acids) of the amino acid sequence of SEQ ID NO:2, SEQ ID NO:4, SEQ ID NO:6, SEQ ID NO:8, SEQ ID NO: 70, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, SEQ ID NO:72, SEQ ID NO:76, SEQ ID NO:78, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, or SEQ ID NO:109, or an amino acid sequence encoded by the DNA insert of the plasmid deposited with the ATCC as Accession Number 98936, 98937, 98938, 98939, 98940, 98941, 98942, 98943, 98944, 98945, 98946, 98947, 98948, 98949, 98950, 98951, 98991, 98993, or 98994. In another embodiment, the protein, preferably a PCIP protein, has the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, SEQ ID NO:72, SEQ ID NO:76, SEQ ID NO:76, SEQ ID NO:78, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, or SEQ ID NO:109.

In another embodiment, the invention features an isolated protein, preferably a PCIP protein, which is encoded by a nucleic acid molecule having a nucleotide sequence at least about 50%, 55%, 60%, 65%, 70%, 75%, 80%, 85%, 90%, 95%, 98% or more identical to a nucleotide sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, SEQ ID NO:71, SEQ ID NO:74, SEQ ID NO:75, SEQ ID NO:77, SEQ ID NO:79, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO: 100, or SEQ ID NO:102, or a complement thereof.

The proteins of the present invention or biologically active portions thereof, can be operatively linked to a non-PCIP polypeptide (e.g., heterologous amino acid sequences) to form fusion proteins. The invention further features antibodies, such as monoclonal or polyclonal antibodies, that specifically bind proteins of the invention, preferably PCIP proteins. In addition, the PCIP proteins or biologically active portions thereof can be incorporated into pharmaceutical compositions, which optionally include pharmaceutically acceptable carriers.

In another aspect, the present invention provides a method for detecting the presence of a PCIP nucleic acid molecule, protein or polypeptide in a biological sample by contacting the biological sample with an agent capable of detecting a PCIP nucleic acid molecule, protein or polypeptide such that the presence of a PCIP nucleic acid molecule, protein or polypeptide is detected in the biological sample.

In another aspect, the present invention provides a method for detecting the presence of PCIP activity in a biological sample by contacting the biological sample with an agent capable of detecting an indicator of PCIP activity such that the presence of PCIP activity is detected in the biological sample.

In another aspect, the invention provides a method for modulating PCIP activity comprising contacting a cell capable of expressing PCIP with an agent that modulates PCIP activity such that PCIP activity in the cell is modulated. In one embodiment, the agent inhibits PCIP activity. In another embodiment, the agent stimulates PCIP activity. In one embodiment, the agent is an antibody that specifically binds to a PCIP protein. In another embodiment, the agent modulates expression of PCIP by modulating transcription of a PCIP gene or translation of a PCIP mRNA. In yet another embodiment, the agent is a nucleic acid molecule having a nucleotide sequence that is antisense to the coding strand of a PCIP mRNA or a PCIP gene.

In one embodiment, the methods of the present invention are used to treat a subject having a disorder characterized by aberrant PCIP protein or nucleic acid expression or activity by administering an agent which is a PCIP modulator to the subject. In one embodiment, the PCIP modulator is a PCIP protein. In another embodiment the PCIP modulator is a PCIP nucleic acid molecule. In yet another embodiment, the PCIP modulator is a peptide, peptidomimetic, or other small molecule. In a preferred embodiment, the disorder characterized by aberrant PCIP protein or nucleic acid expression is a CNS disorder or a cardiovascular disorder.

The present invention also provides a diagnostic assay for identifying the presence or absence of a genetic alteration characterized by at least one of (i) aberrant modification or mutation of a gene encoding a PCIP protein; (ii) mis-regulation of the gene; and (iii) aberrant post-translational modification of a PCIP protein, wherein a wild-type form of the gene encodes a protein with a PCIP activity.

In another aspect the invention provides a method for identifying a compound that binds to or modulates the activity of a PCIP protein, by providing an indicator composition comprising a PCIP protein having PCIP activity, contacting the indicator composition with a test compound, and determining the effect of the test compound on PCIP activity in the indicator composition to identify a compound that modulates the activity of a PCIP protein.

Other features and advantages of the invention will be apparent from the following detailed description and claims.

BRIEF DESCRIPTION OF THE DRAWINGS

FIG. 1 depicts the cDNA sequence and predicted amino acid sequence of human 1v. The nucleotide sequence corresponds to nucleic acids 1 to 1463 of SEQ ID NO:1. The amino acid sequence corresponds to amino acids 1 to 216 of SEQ ID NO:2.

FIG. 2 depicts the cDNA sequence and predicted amino acid sequence of rat 1v. The nucleotide sequence corresponds to nucleic acids 1 to 1856 of SEQ ID NO:3. The amino acid sequence corresponds to amino acids 1 to 245 of SEQ ID NO:4.

FIG. 3 depicts the cDNA sequence and predicted amino acid sequence of mouse 1v. The nucleotide sequence corresponds to nucleic acids 1 to 1907 of SEQ ID NO:5. The amino acid sequence corresponds to amino acids 1 to 216 of SEQ ID NO:6.

FIG. 4 depicts the cDNA sequence and predicted amino acid sequence of rat 1vl. The nucleotide sequence corresponds to nucleic acids 1 to 1534 of SEQ ID NO:7. The amino acid sequence corresponds to amino acids 1 to 227 of SEQ ID NO:8.

FIG. 5 depicts the cDNA sequence and predicted amino acid sequence of mouse 1vl. The nucleotide sequence corresponds to nucleic acids 1 to 1540 of SEQ ID NO:9. The amino acid sequence corresponds to amino acids 1 to 227 of SEQ ID NO:10.

FIG. 6 depicts the cDNA sequence and predicted amino acid sequence of the partial rat 1vn. The nucleotide sequence corresponds to nucleic acids 1 to 955 of SEQ ID NO:11. The amino acid sequence corresponds to amino acids 1 to 203 of SEQ ID NO:12. (The full length rat 1vn sequences are set forth herein in FIG. 63, see below).

FIG. 7 depicts the cDNA sequence and predicted amino acid sequence of human 9ql. The nucleotide sequence corresponds to nucleic acids 1 to 2009 of SEQ ID NO:13. The amino acid sequence corresponds to amino acids 1 to 270 of SEQ ID NO:14.

FIG. 8 depicts the cDNA sequence and predicted amino acid sequence of rat 9ql. The nucleotide sequence corresponds to nucleic acids 1 to 1247 of SEQ ID NO:15. The amino acid sequence corresponds to amino acids 1 to 257 of SEQ ID NO:16.

FIG. 9 depicts the cDNA sequence and predicted amino acid sequence of mouse 9ql. The nucleotide sequence corresponds to nucleic acids 1 to 2343 of SEQ ID NO:17. The amino acid sequence corresponds to amino acids 1 to 270 of SEQ ID NO:18.

FIG. 10 depicts the cDNA sequence and predicted amino acid sequence of human 9qm. The nucleotide sequence corresponds to nucleic acids 1 to 1955 of SEQ ID NO:19. The amino acid sequence corresponds to amino acids 1 to 252 of SEQ ID NO:20.

FIG. 11 depicts the cDNA sequence and predicted amino acid sequence of rat 9qm. The nucleotide sequence corresponds to nucleic acids 1 to 2300 of SEQ ID NO:21. The amino acid sequence corresponds to amino acids 1 to 252 of SEQ ID NO:22.

FIG. 12 depicts the cDNA sequence and predicted amino acid sequence of human 9qs. The nucleotide sequence corresponds to nucleic acids 1 to 1859 of SEQ ID NO:23. The amino acid sequence corresponds to amino acids 1 to 220 of SEQ ID NO:24.

FIG. 13 depicts the cDNA sequence and predicted amino acid sequence of monkey 9qs. The nucleotide sequence corresponds to nucleic acids 1 to 2191 of SEQ ID NO:25. The amino acid sequence corresponds to amino acids 1 to 220 of SEQ ID NO:26.

FIG. 14 depicts the cDNA sequence and predicted amino acid sequence of rat 9qc. The nucleotide sequence corresponds to nucleic acids 1 to 2057 of SEQ ID NO:27. The amino acid sequence corresponds to amino acids 1 to 252 of SEQ ID NO:28.

FIG. 15 depicts the cDNA sequence and predicted amino acid sequence of rat 8t. The nucleotide sequence corresponds to nucleic acids 1 to 1904 of SEQ ID NO:29. The amino acid sequence corresponds to amino acids 1 to 225 of SEQ ID NO:30.

FIG. 16 depicts the cDNA sequence and predicted amino acid sequence of human p19. The nucleotide sequence corresponds to nucleic acids 1 to 619 of SEQ ID NO:31. The amino acid sequence corresponds to amino acids 1 to 200 of SEQ ID NO:32.

FIG. 17 depicts the cDNA sequence and predicted amino acid sequence of rat p19 The nucleotide sequence corresponds to nucleic acids 1 to 442 of SEQ ID NO:33. The amino acid sequence corresponds to amino acids 1 to 109 of SEQ ID NO:34.

FIG. 18 depicts the cDNA sequence and predicted amino acid sequence of mouse p19. The nucleotide sequence corresponds to nucleic acids 1 to 2644 of SEQ ID NO:35. The amino acid sequence corresponds to amino acids 1 to 256 of SEQ ID NO:36.

FIG. 19 depicts the cDNA sequence and predicted amino acid sequence of human W28559. The nucleotide sequence corresponds to nucleic acids 1 to 380 of SEQ ID NO:37. The amino acid sequence corresponds to amino acids 1 to 126 of SEQ ID NO:38.

FIG. 20 depicts the cDNA sequence and predicted amino acid sequence of human P193. The nucleotide sequence corresponds to nucleic acids 1 to 2176 of SEQ ID NO:39. The amino acid sequence corresponds to amino acids 1 to 41 of SEQ ID NO:40.

FIG. 22 depicts the genomic DNA sequence of human 9q. FIG. 22A depicts exon 1 and its flanking intron sequences (SEQ ID NO:46). FIG. 22B depicts exons 2-11 and the flanking intron sequences (SEQ ID NO:47).

FIG. 23 depicts the cDNA sequence and predicted amino acid sequence of monkey KChIP4a. The nucleotide sequence corresponds to nucleic acids 1 to 2413 of SEQ ID NO:48. The amino acid sequence corresponds to amino acids 1 to 233 of SEQ ID NO:49.

FIG. 24 depicts the cDNA sequence and predicted amino acid sequence of monkey KChIP4b. The nucleotide sequence corresponds to nucleic acids 1 to 1591 of SEQ ID NO:50. The amino acid sequence corresponds to amino acids 1 to 233 of SEQ ID NO:51.

FIG. 25 depicts an alignment of KChIP4a, KChIP4b, 9ql, 1v, p19, and related human paralog (hsncspara) W28559. Amino acids identical to the consensus are shaded in black, conserved amino acids are shaded in gray.

FIG. 26 depicts the cDNA sequence and predicted amino acid sequence of rat 33b07. The nucleotide sequence corresponds to nucleic acids 1 to 2051 of SEQ ID NO:52. The amino acid sequence corresponds to amino acids 1 to 407 of SEQ ID NO:53.

FIG. 27 depicts the cDNA sequence and predicted amino acid sequence of human 33b07. The nucleotide sequence corresponds to nucleic acids 1 to 4148 of SEQ ID NO:54. The amino acid sequence corresponds to amino acids 1 to 414 of SEQ ID NO:55.

FIG. 28 depicts the cDNA sequence and predicted amino acid sequence of rat 1p. The nucleotide sequence corresponds to nucleic acids 1 to 2643 of SEQ ID NO:56. The amino acid sequence corresponds to amino acids 1 to 267 of SEQ ID NO:57.

FIG. 29 depicts the cDNA sequence and predicted amino acid sequence of rat 7s. The nucleotide sequence corresponds to nucleic acids 1 to 2929 of SEQ ID NO:58. The amino acid sequence corresponds to amino acids 1 to 270 of SEQ ID NO:59.

FIG. 30 depicts the cDNA sequence and predicted amino acid sequence of rat 29x. The nucleotide sequence corresponds to nucleic acids 1 to 1489 of SEQ ID NO:60. The amino acid sequence corresponds to amino acids 1 to 351 of SEQ ID NO:61.

FIG. 31 depicts the cDNA sequence of rat 25r. The nucleotide sequence corresponds to nucleic acids 1 to 1194 of SEQ ID NO:62.

FIG. 32 depicts the cDNA sequence and predicted amino acid sequence of rat 5p. The nucleotide sequence corresponds to nucleic acids 1 to 600 of SEQ ID NO:63. The amino acid sequence corresponds to amino acids 1 to 95 of SEQ ID NO:64.

FIG. 33 depicts the cDNA sequence and predicted amino acid sequence of rat 7q. The nucleotide sequence corresponds to nucleic acids 1 to 639 of SEQ ID NO:65. The amino acid sequence corresponds to amino acids 1 to 212 of SEQ ID NO:66.

FIG. 34 depicts the cDNA sequence and predicted amino acid sequence of rat 19r. The nucleotide sequence corresponds to nucleic acids 1 to 816 of SEQ ID NO:67. The amino acid sequence corresponds to amino acids 1 to 271 of SEQ ID NO:68.

FIG. 35 depicts the cDNA sequence and predicted amino acid sequence of monkey KChIP4c. The nucleotide sequence corresponds to nucleic acids 1 to 2263 of SEQ ID NO:69. The amino acid sequence corresponds to amino acids 1 to 229 of SEQ ID NO:70.

FIG. 36 depicts the cDNA sequence and predicted amino acid sequence of monkey KChIP4d. The nucleotide sequence corresponds to nucleic acids 1 to 2259 of SEQ ID NO:71. The amino acid sequence corresponds to amino acids 1 to 250 of SEQ ID NO:72.

FIG. 37 depicts an alignment of KChIP4a, KChIP4b, KChIP4c, and KChIP4d.

FIG. 38 further depicts a table showing the amplitude and kinetic effects of KChIP2 (9ql) on Kv4.2. KChIP2 expression alters the peak current amplitude, inactivation and recovery from inactivation time constants, and activation $V_{1/2}$.

FIG. 39 further depicts a table showing the amplitude and kinetic effects of KChIP3 (p19) on Kv4.2. KChIP3 causes alterations in peak current and inactivation and recovery from inactivation time constants.

FIG. 40 depicts results from electrophysiological experiments demonstrating that coexpression of KChIP1 dramatically alters the current density and kinetics of Kv4.2 channels expressed in CHO cells.

FIG. 41 depicts an alignment of human KChIP family members with closely related members of the recoverin family of Ca 2+ sensing proteins. (HIP: human hippocalcin; NCS1:rat neuronal calcium sensor 1). The alignment was performed using the MegAlign program for Macintosh (version 4.00 from DNASTAR) using the Clustal method with the PAM250 residue weight table and default parameters, and shaded using BOXSHADES. Residues identical to the consensus are shaded black, conservative substitutions are shaded grey. X, Y, Z and −X, −Y, −Z denote the positions of residues which are responsible for binding to the calcium ion in the EF hand.

FIG. 44 depicts the cDNA sequence and predicted amino acid sequence of human 1vl (KChIP1l). The nucleotide sequence corresponds to nucleic acids 1 to 1477 of SEQ ID NO:79. The alternation of upper and lower case letters indicates the individual exons. The KChIP1l (KChIP1long) specific exon is the second exon in the indicated sequence. The amino acid sequence corresponds to amino acids 1 to 227 of SEQ ID NO:109.

FIG. 45 depicts the cDNA sequence and predicted amino acid sequence of an N-terminal splice variant of human KChIP1N. The nucleotide sequence corresponds to nucleic acids 1 to 1639 of SEQ ID NO:80. The amino acid sequence corresponds to amino acids 1 to 232 of SEQ ID NO:81.

FIG. 46 depicts an alignment of the N-terminal domains of the rat and human KChIP1N, indicating that this N-terminal domain is conserved between the two sequences.

FIG. 47 depicts the genomic DNA sequence of human KChIP2 (including KChIP2 l, m, s, and N). The nucleotide sequence corresponds to nucleic acids 1 to 17,803 of SEQ ID NO:74. Upper case letters indicate the exons and lower case letters indicate the introns.

FIG. 48 depicts the cDNA sequence and predicted amino acid sequence of the rat KChIP2L. The nucleotide sequence corresponds to nucleic acids 1 to 1285 of SEQ ID NO:75. The amino acid sequence corresponds to amino acids 1 to 270 of SEQ ID NO:76.

FIG. 49 depicts the cDNA sequence and predicted amino acid sequence of the human 8t (KChIP2N). The nucleotide sequence corresponds to nucleic acids 1 to 2076 of SEQ ID NO:77. The amino acid sequence corresponds to amino acids 1 to 225 of SEQ ID NO:78.

FIG. 51 depicts the cDNA sequence and predicted amino acid sequence of the full length human KChIP3. The nucleotide sequence corresponds to nucleic acids 1 to 2835 of SEQ ID NO:82. The amino acid sequence corresponds to amino acids 1 to 256 of SEQ ID NO:83. The alternation of upper and lower case letters indicates the individual exons.

FIG. 52 depicts the cDNA sequence and predicted amino acid sequence of the rat KChIP3. The nucleotide sequence corresponds to nucleic acids 1 to 2414 of SEQ ID NO:84. The amino acid sequence corresponds to amino acids 1 to 178 of SEQ ID NO:85. Upper case letters indicate the coding region and lower case letters indicate the 3' UTR.

FIG. 53 depicts the cDNA sequence and predicted amino acid sequence of the monkey KChIP4XC (KChIP4b). The nucleotide sequence corresponds to nucleic acids 1 to 1005 of SEQ ID NO:86. The amino acid sequence corresponds to amino acids 1 to 127 of SEQ ID NO:87.

FIG. 54 depicts the cDNA sequence and predicted amino acid sequence of the mouse KChIP4N2 (KChIP4c). The nucleotide sequence corresponds to nucleic acids 1 to 2181 of SEQ ID NO:88. The amino acid sequence corresponds to amino acids 1 to 229 of SEQ ID NO:89.

FIG. 55 depicts the cDNA sequence and predicted amino acid sequence of the rat KChIP4. The nucleotide sequence corresponds to nucleic acids 1 to 2022 of SEQ ID NO:90. The amino acid sequence corresponds to amino acids 1 to 198 of SEQ ID NO:91.

FIG. 56 depicts the cDNA sequence and predicted amino acid sequence of the human KChIP4aS (KChIP4N1S) a shorter splice variant of KChIP4N1. The nucleotide sequence corresponds to nucleic acids 1 to 2366 of SEQ ID NO:92. The amino acid sequence corresponds to amino acids 1 to 188 of SEQ ID NO:93.

FIG. 57 depicts the cDNA sequence and predicted amino acid sequence of the human KChIP4a (KChIP4N1). The nucleotide sequence corresponds to nucleic acids 1 to 2431 of SEQ ID NO:94. The amino acid sequence corresponds to amino acids 1 to 233 of SEQ ID NO:95.

FIG. 58 depicts the cDNA sequence and predicted amino acid sequence of the human KChIP4c (KChIPN2). The nucleotide sequence corresponds to nucleic acids 1 to 2261 of SEQ ID NO:96. The amino acid sequence corresponds to amino acids 1 to 229 of SEQ ID NO:97.

FIG. 59 depicts the cDNA sequence and predicted amino acid sequence of the human KChIP4d (KChIP4N3). The nucleotide sequence corresponds to nucleic acids 1 to 2299 of SEQ ID NO:98. The amino acid sequence corresponds to amino acids 1 to 250 of SEQ ID NO:99.

FIG. 60 depicts the cDNA sequence and predicted amino acid sequence of the rat KChIP4N1x, a splice variant of KChIP4N1. The nucleotide sequence corresponds to nucleic acids 1 to 2246 of SEQ ID NO:100. The amino acid sequence corresponds to amino acids 1 to 272 of SEQ ID NO:101.

FIG. 62 depicts protein alignments indicating that the N-terminal domains of human KChIP1N and monkey KChIP4N2 are homologous and that the N-terminal domains of human/rat KChIP1 and monkey KChIP4N2 are divergent.

FIG. 63 depicts the cDNA sequence and predicted amino acid sequence of the rat KChIP1N (1vn). The nucleotide sequence corresponds to nucleic acids 1 to 1856 of SEQ ID NO:102. The amino acid sequence corresponds to amino acids 1 to 232 of SEQ ID NO:103.

DETAILED DESCRIPTION OF THE INVENTION

Figure 21:
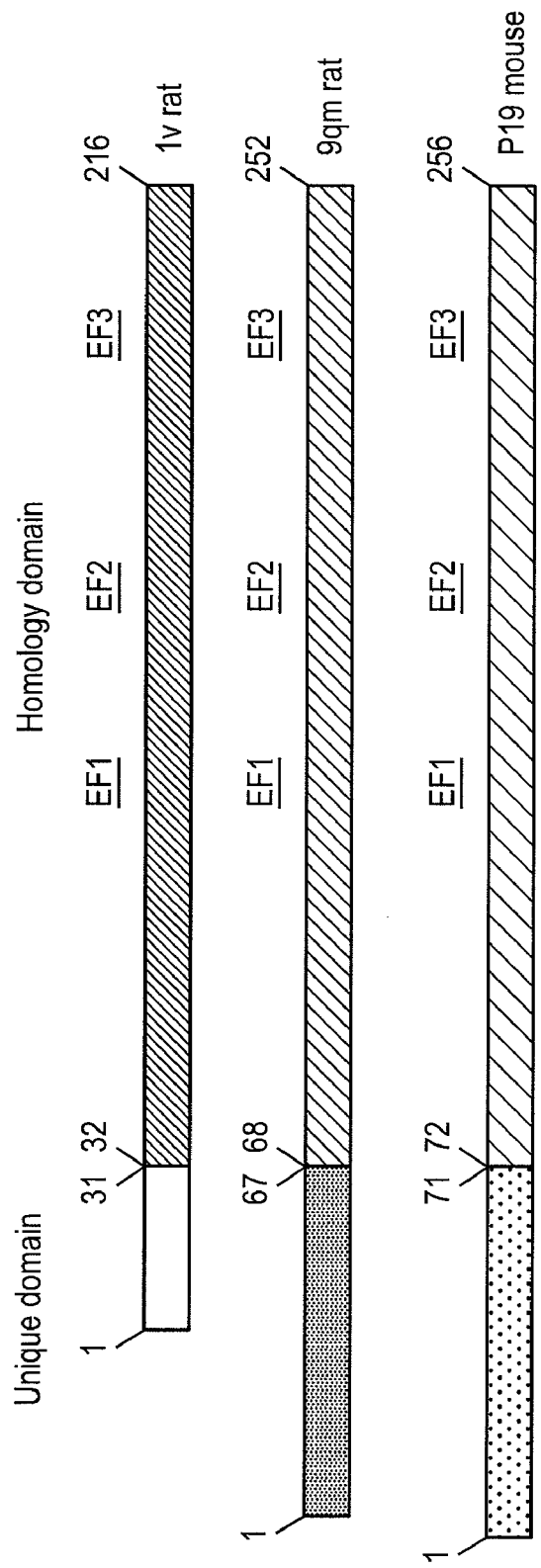
FIG. 21 depicts a schematic representation of the rat 1v, the rat 9qm, and the mouse P19 proteins, aligned to indicate the conserved domains among these proteins.
Figure 38:
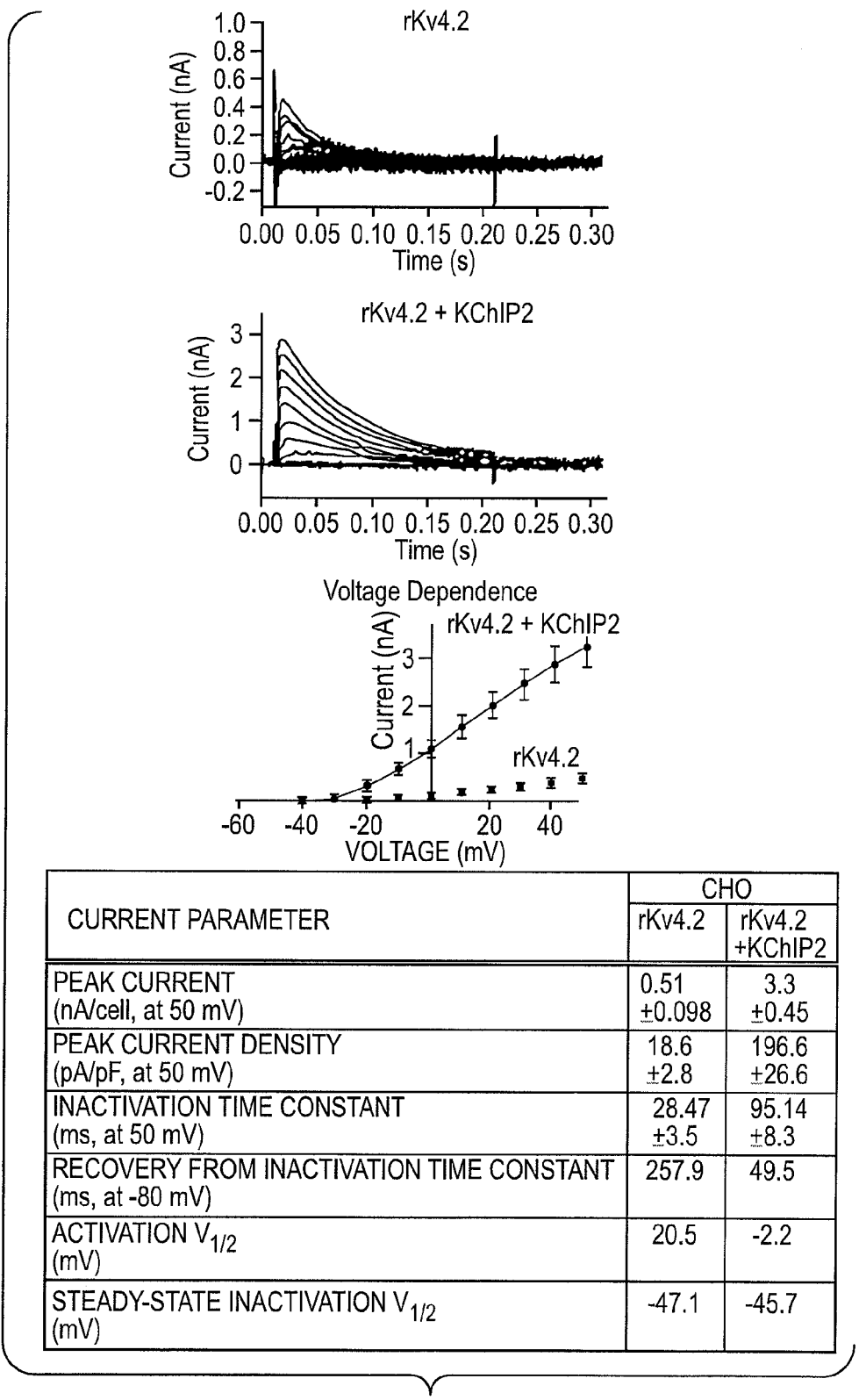
FIG. 38 depicts a graph showing the current traces from CHO cells which express Kv4.2 with or without KChIP2 (9ql). Cells are voltage clamped at −80 mV and stepped from −60 mV to +50 mV for 200 ms. Peak current amplitudes at the various test voltages are shown in the right panel.
Figure 39:
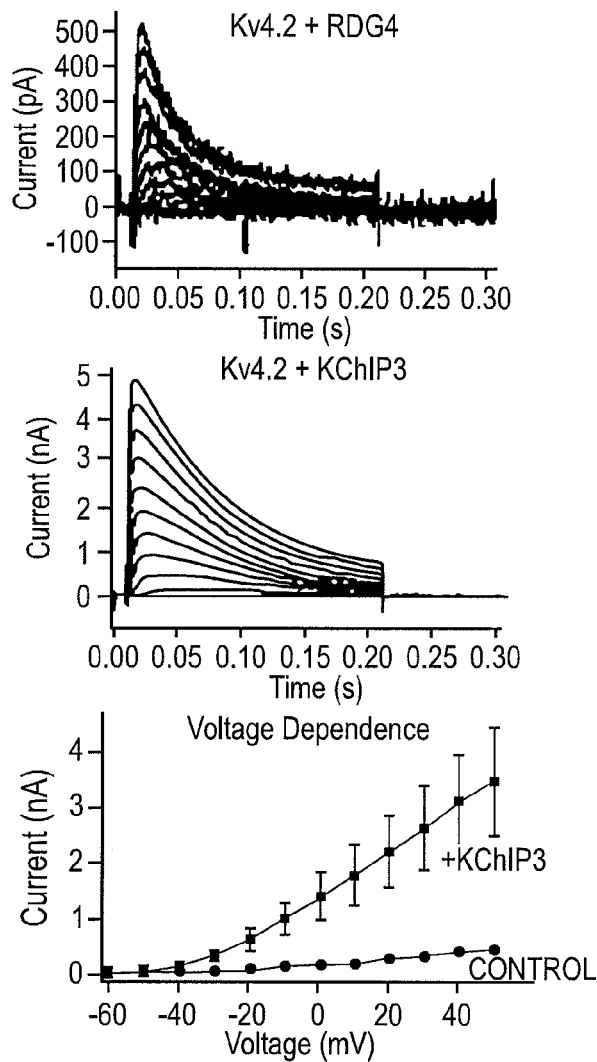
FIG. 39 depicts a graph showing the current traces from CHO cells which express Kv4.2 with or without KChIP3 (p19). Cells are voltage clamped at −80 mV and stepped from −60 mV to +50 mV for 200 ms. Peak current amplitudes at the various test voltages are shown in the right panel.
Figure 40A:
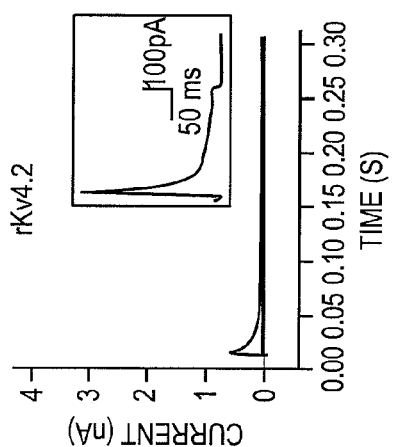
FIG. 40A depicts current traces from a Kv4.2 transfected CHO cell. Current was evoked by depolarizing the cell sequentially from a holding potential of −80 mV to test potentials from −60 to 50 mV. Current traces are leak subtracted using a p/5 protocol. The current axis is shown at the same magnification as in (b) to emphasize the change in current amplitudes. Inset-Single current trace at 50 mV at an expanded current axis to show the kinetics of current activation and inactivation.
Figure 40B:
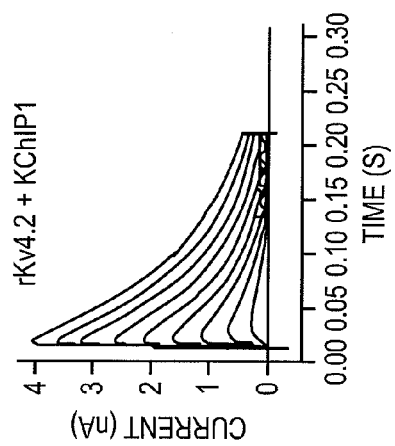
FIG. 40B depicts current traces as in (a), but from a cell transfected with equal amounts of DNA for Kv4.2 and KChIP1.
Figure 40C:
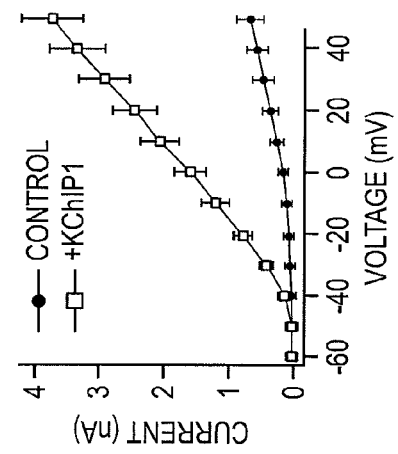
FIG. 40C depicts peak current amplitude at all voltages from cells transfected with Kv4.2 alone (n=11) or cotransfected with KChIP1 (n=9).
Figure 40D:
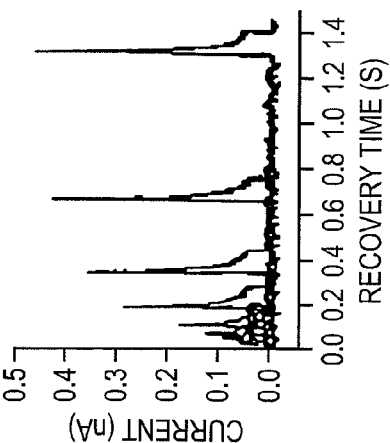
FIGS. 40D and 40E depict recovery from inactivation using a two pulse protocol. Kv4.2 alone (D) or coexpressed with KChIP1 (E) is driven into the inactivated state using a first pulse to 50 mV, then a second pulse to 50 mV is applied at varying times after the first pulse. Holding potential is −80 mV before and after all pulses.
Figure 40E:
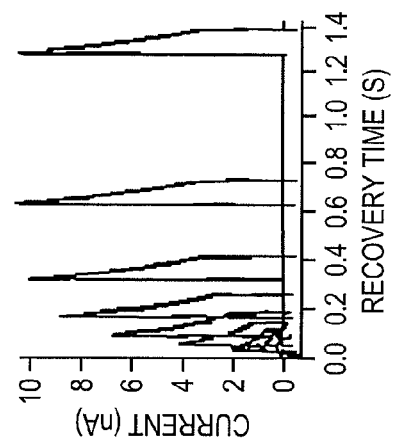
Figure 40F:
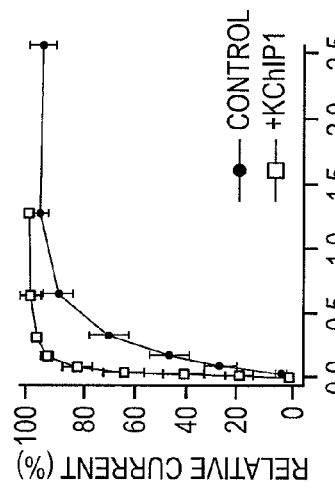
FIG. 40F depicts a summary of the percentage the peak current recovers between pulses for Kv4.2 (n=8) and Kv4.2 plus KChIP1 (n=5) transfected cells. The time constant of recovery from inactivation is fit to a single exponential.

The present invention is based, at least in part, on the discovery of novel nucleic acid molecules which encode gene products that interact with potassium channel proteins or possess substantial homology to the gene products of the invention that interact with potassium channel proteins (paralogs). Potassium channel proteins are, for example, potassium channels having a Kv4.2 or Kv4.3 subunit. The nucleic acid molecules of the invention and their gene products are referred to herein as "Potassium Channel Interacting Proteins", "PCIP", or "KChIP" nucleic acid and protein molecules. Preferably, the PCIP proteins of the present invention interact with, e.g., bind to a potassium channel protein, modulate the activity of a potassium channel protein, and/or modulate a potassium channel mediated activity in a cell, e.g., a neuronal or cardiac cell.

As used herein, the term "PCIP family" when referring to the protein and nucleic acid molecules of the invention is intended to mean two or more proteins or nucleic acid molecules having a PCIP activity as defined herein. Such PCIP family members can be naturally or non-naturally occurring and can be from either the same or different species. For example, a PCIP family can contain a first protein of human origin, as well as other, distinct proteins of human origin or alternatively, can contain homologues of non-human origin.

As used interchangeably herein, a "PCIP activity", "biological activity of PCIP" or "functional activity of PCIP", refers to an activity exerted by a PCIP protein, polypeptide or nucleic acid molecule on a PCIP responsive cell or on a PCIP protein substrate, as determined in vivo, or in vitro, according to standard techniques. In one embodiment, a PCIP activity is a direct activity, such as an association with a PCIP-target molecule. As used herein, a "target molecule" or "binding partner" is a molecule with which a PCIP protein binds or interacts in nature, such that PCIP-mediated function is achieved. A PCIP target molecule can be a non-PCIP molecule or a PCIP protein or polypeptide of the present invention. In an exemplary embodiment, a PCIP target molecule is a PCIP ligand. Alternatively, a PCIP activity is an indirect activity, such as a cellular signaling activity mediated by interaction of the PCIP protein with a PCIP ligand. The biological activities of PCIP are described herein.

For example, the PCIP proteins of the present invention can have one or more of the following activities: (1) they can interact with (e.g., bind to) a potassium channel protein or portion thereof; (2) they can regulate the phosphorylation state of a potassium channel protein or portion thereof; (3) they can associate with (e.g., bind) calcium and can, for example, act as calcium dependent kinases, e.g., phosphorylate a potassium channel or a G-protein coupled receptor in a calcium-dependent manner; (4) they can associate with (e.g., bind) calcium and can, for example, act in a calcium-dependent manner in cellular processes, e.g., act as calcium dependent transcription factors; (5) they can modulate a potassium channel mediated activity in a cell (e.g., a neuronal cell such as a sensory neuron cell or a motor neuron cell, or a cardiac cell) to, for example, beneficially affect the cell; (6) they can modulate chromatin formation in a cell, e.g., a neuronal or cardiac cell; (7) they can modulate vesicular traffic and protein transport in a cell, e.g., a neuronal or cardiac cell; (8) they can modulate cytokine signaling in a cell, e.g., a neuronal or cardiac cell; (9) they can regulate the association of a potassium channel protein or portion thereof with the cellular cytoskeleton; (10) they can modulate cellular proliferation; (11) they can modulate the release of neurotransmitters; (12) they can modulate membrane excitability; (13) they can influence the resting potential of membranes; (14) they can modulate wave forms and frequencies of action potentials; and (15) they can modulate thresholds of excitation.

As used herein, a "potassium channel" includes a protein or polypeptide that is involved in receiving, conducting, and transmitting signals in an excitable cell. Potassium channels are typically expressed in electrically excitable cells, e.g., neurons, cardiac, skeletal and smooth muscle, renal, endocrine, and egg cells, and can form heteromultimeric structures, e.g., composed of pore-forming and cytoplasmic subunits. Examples of potassium channels include: (1) the voltage-gated potassium channels, (2) the ligand-gated potassium channels, and (3) the mechanically-gated potassium channels. For a detailed description of potassium channels, see Kandel E. R. et al., Principles of Neural Science, second edition, (Elsevier Science Publishing Co., Inc., N.Y. (1985)), the contents of which are incorporated herein by reference. The PCIP proteins of the present invention have been shown to interact with, for example, potassium channels having a Kv4.3 subunit or a Kv4.2 subunit.

As used herein, a "potassium channel mediated activity" includes an activity which involves a potassium channel, e.g., a potassium channel in a neuronal cell or a cardiac cell, associated with receiving, conducting, and transmitting signals in, for example, the nervous system or in the heart. Potassium channel mediated activities include release of neurotransmitters, e.g., dopamine or norepinephrine, from cells, e.g., neuronal or cardiac cells; modulation of resting potential of membranes, wave forms and frequencies of action potentials, and thresholds of excitation; and modulation of processes such as integration of sub-threshold synaptic responses and the conductance of back-propagating action potentials in, for example, neuronal cells or cardiac cells.

As the PCIP proteins of the present invention modulate potassium channel mediated activities, they may be useful as novel diagnostic and therapeutic agents for potassium channel associated disorders and/or nervous system related disorders. Moreover, the PCIP proteins of the present invention modulate Kv4 potassium channels, e.g., potassium channels having a Kv4.2 or Kv43 subunit, which underlie the voltage-gated K+ current known as $I_{to}$ (transient outward current) in the mammalian heart (Kaab S. et al. (1998) *Circulation* 98(14):1383-93; Dixon J. E. et al. (1996) *Circulation Research* 79(4):659-68; Nerbonne J M (1998) *Journal of Neurobiology* 37(1):37-59; Barry D. M. et al. (1998) *Circulation Research* 83(5):560-7; Barry D. M. et al. (1996) *Annual Review of Physiology* 58:363-94. This current underlies the rapid repolarization of cardiac myocytes during an action potential. It also participates in the inter-beat interval by controlling the rate at which cardiac myocytes reach the threshold for firing a subsequent action potential.

This current is also known to be down regulated in patients with cardiac hypertrophy, resulting in prolongation of the cardiac action potential. In these patients, action potential prolongation is thought to produce changes in calcium load and calcium handling within the myocardium, which contributes to the progression of cardiac disease from hypertrophy to heart failure (Wickenden et al. (1998) *Cardiovascular Research* 37:312). Interestingly, several PCIPs of the present invention (e.g., 9ql, 9qm, 9qs, shown in SEQ ID NOs:13, 15, 17, 19, 21, 23, and 25) bind to and modulate potassium channels containing a Kv4.2 or Kv4.3 subunit and contain calcium binding EF-hand domains. Because of mutations in these PCIP genes, defects in the expression of these calcium-binding PCIP proteins themselves, or defects in the interaction between these PCIPs and Kv4.2 or Kv4.3 channels, might be expected to lead to decreases in KV4.3 or Kv4.3 ($I_m$) currents in the myocardium, therapeutic agents that alter PCIP expression or modulate the interaction between these PCIPs and Kv4.2 or Kv4.3 may be extremely valuable agents to slow or prevent the progression of disease from hypertrophy to heart failure.

As used herein, a "potassium channel associated disorder" includes a disorder, disease or condition which is characterized by a misregulation of a potassium channel mediated activity. Potassium channel associated disorders can detrimentally affect conveyance of sensory impulses from the periphery to the brain and/or conductance of motor impulses from the brain to the periphery; integration of reflexes; interpretation of sensory impulses; and emotional, intellectual (e.g., learning and memory), or motor processes. Potassium channel associated disorders can further detrimentally affect electrical impulses that stimulate the cardiac muscle fibers to contract. Examples of potassium channel associated disorders include nervous system related disorders, as well as cardiovascular disorders.

As used herein, a "nervous system related disorder" includes a disorder, disease or condition which affects the nervous system. Examples of potassium channel associated disorders and nervous system related disorders include cognitive disorders, e.g., memory and learning disorders, such as amnesia, apraxia, agnosia, amnestic dysnomia, amnestic spatial disorientation, Kluver-Bucy syndrome, Alzheimer's related memory loss (Eglen R. M. (1996) *Pharmacol. and Toxicol.* 78(2):59-68; Perry E. K. (1995) *Brain and Cognition* 28(3):240-58) and learning disability; disorders affecting consciousness, e.g., visual hallucinations, perceptual disturbances, or delerium associated with Lewy body dementia; schitzo-effective disorders (Dean B. (1996) *Mol. Psychiatry* 1(1):54-8), schizophrenia with mood swings (Bymaster F. P. (1997) *J. Clin. Psychiatry* 58 (suppl. 10):28-36; Yeomans J. S. (1995) *Neuropharmacol.* 12(1):3-16; Reimann D. (1994) *J. Psychiatric Res.* 28(3):195-210), depressive illness (primary or secondary); affective disorders (Janowsky D. S. (1994) *Am. J. Med. Genetics* 54(4):335-44); sleep disorders (Kimura F. (1997) *J. Neurophysiol.* 77(2):709-16), e.g., REM sleep abnormalities in patients suffering from, for example, depression (Riemann D. (1994) *J. Psychosomatic Res.* 38 Suppl. 1: 15-25; Bourgin P. (1995) *Neuroreport* 6(3): 532-6), paradoxical sleep abnormalities (Sakai K. (1997) *Eur. J. Neuroscience* 9(3):415-23), sleep-wakefulness, and body temperature or respiratory depression abnormalities during sleep (Shuman S. L. (1995) *Am. J. Physiol.* 269(2 Pt 2):R308-17; Mallick B. N. (1997) *Brain Res.* 750(1-2):311-7). Other examples of nervous system related disorders include disorders affecting pain generation mechanisms, e.g., pain related to irritable bowel syndrome (Mitch C. H. (1997) *J. Med. Chem.* 40(4): 538-46; Shannon H. E. (1997) *J. Pharmac. and Exp. Therapeutics* 281(2):884-94; Bouaziz H. (1995) *Anesthesia and Analgesia* 80(6):1140-4; or Guimaraes A. P. (1994) *Brain Res.* 647(2):220-30) or chest pain; movement disorders (Monassi C. R. (1997) *Physiol. and Behav.* 62(1):53-9), e.g., Parkinson's disease related movement disorders (Finn M. (1997) *Pharmacol. Biochem. & Behavior* 57(1-2):243-9; Mayorga A. J. (1997) *Pharmacol. Biochem. & Behavior* 56(2):273-9); eating disorders, e.g., insulin hypersecretion related obesity (Maccario M. (1997) *J. Endocrinol. Invest.* 20(1):8-12; Premawardhana L. D. (1994) *Clin. Endocrinol.* 40(5): 617-21); drinking disorders, e.g., diabetic polydipsia (Murzi E. (1997) *Brain Res.* 752(1-2):184-8; Yang X. (1994) *Pharmacol. Biochem. & Behavior* 49(1):1-6); neurodegenerative disorders, e.g., Alzheimer's disease, dementias related to Alzheimer's disease (such as Pick's disease), Parkinson's and other Lewy diffuse body diseases, multiple sclerosis, amyotrophic lateral sclerosis, progressive supranuclear palsy, epilepsy, spinocerebellar ataxia, epileptic syndromes, and Jakob-Creutzfieldt disease; psychiatric disorders, e.g., depression, schizophrenic disorders, Korsakoff's psychosis, mania, anxiety disorders, bipolar affective disorders, or phobic disorders; neurological disorders, e.g., migraine; spinal cord injury; stroke; and head trauma.

As used herein, "epilepsy" includes a common neurological disorder caused by disturbances in the normal electrical functions of the brain. In normal brain function millions of tiny electrical charges pass from nerve cells in the brain to all parts of the body. In patients with epilepsy, this normal pattern is interrupted by sudden and unusually intense bursts of electrical energy, which may briefly affect a person's consciousness, bodily movements, or sensations. These physical changes are called epileptic seizures. There are two categories of seizures: partial seizures, which occur in one area of the brain, and generalized seizures, which affect nerve cells throughout the brain. Epilepsy may result from a brain injury before, during, or after birth; head trauma; poor nutrition; some infectious diseases; brain tumors; and some poisons. However, in many cases the cause is unknown. Attacks of epilepsy may be preceded by a feeling of unease or sensory discomfort called an aura, which indicates the beginning of the seizure. Signs of an impending epileptic seizure, which vary among patients, may include visual phenomena such as flickering lights or "sunbursts." Recently, a genetic linkage for epilepsy has been found on chromosome 10q, near marker D10S192: 10q22-q24 (Ottman et al. (1995) *Nature Genetics* 10:56-60). The many forms of epilepsy include: grand mal, Jacksonian, myoclonic progressive familial, petit mal, Lennox-Gastaut syndrome, febrile seizures, psycho-motor, and temporal lobe. The observations described herein are particularly useful in developing treatments for partial epilepsy.

As used herein, "ataxia" includes a common neurological disorder caused by disturbances in the normal electrical functions of the brain. Spinocerebellar ataxia type 1 (SCA1) is an autosomal dominant disorder which is genetically linked to the short arm of chromosome 6 based on linkage to the human major histocompatibility complex (HLA). See, for example, H. Yakura et al. (1974) *N. Engl. J. Med.,* 291, 154-155; and J. F. Jackson et al. (1977) *N. Engl. J. Med* 296, 1138-1141. SCA1 has been shown to be tightly linked to the marker D6S89 on the short arm of chromosome 6, telomeric to HLA. See, for example, L. P. W. Ranum et al., *Am. J. Hum. Genet.,* 49, 31-41 (1991); and H. Y. Zoghbi et al., *Am. J. Hum. Genet.,* 49, 23-30 (1991). The observations described herein are particularly useful in developing treatments for infantile onset spinocerebellar ataxia (IOSCA).

As used herein, a "cardiovascular disorder" includes a disorder affecting the cardiovascular system, e.g., the heart. Examples of cardiovascular disorders include arteriosclerosis, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, atrial fibrilation, long-QT syndrome, congestive heart failure, sinus node disfunction, angina, heart failure, hypertension, atrial fibrillation, atrial flutter, dilated cardiomyopathy, idiopathic cardiomyopathy, myocardial infarction, coronary artery disease, coronary artery spasm, or arrhythmia. In a preferred embodiment, the cardiovascular disorder is associated with an abnormal $I_{to}$ current.

Some members of a PCIP family may also have common structural characteristics, such as a common structural domain or motif or a sufficient amino acid or nucleotide sequence homology as defined herein. Such PCIP family members can be naturally or non-naturally occurring and can be from either the same or different species. For example, a PCIP family can contain a first protein of human origin, as well as other, distinct proteins of human origin or alternatively, can contain homologues of non-human origin.

For example, members of a PCIP family which have common structural characteristics, may comprise at least one "calcium binding domain". As used herein, the term "calcium binding domain" includes an amino acid domain, e.g., an EF hand (Baimbridge K. G. et al. (1992) *TINS* 15(8): 303-308), which is involved in calcium binding. Preferably, a calcium binding domain has a sequence, which is substantially identical to the consensus sequence:

EO••OO••O<u>D</u>KDGD<u>G</u>•<u>O</u>•••EF••O<u>O</u>. (SEQ ID NO:43).

O can be I, L, V or M, and "•" indicates a position with no strongly preferred residue. Each residue listed is present in more than 25% of sequences, and those underlined are present in more than 80% of sequences. Amino acid residues 126-154 and 174-202 of the human 1v protein, amino acid residues 126-154 and 174-202 of the rat 1v protein, amino acid residues 137-165 and 185-213 of the rat 1vl protein, amino acid residues 142-170 of the rat 1vn protein, amino acid residues 126-154 and 174-202 of the mouse 1v protein, amino acid residues 137-165 and 185-213 of the mouse 1vl protein, amino acid residues 144-172, 180-208, and 228-256 of the human 9ql protein, amino acid residues 126-154, 162-190, and 210-238 of the human 9qm protein, amino acid residues 94-122, 130-158, and 178-206 of the human 9qs protein, amino acid residues 126-154, 162-190, and 210-238 of the rat 9qm protein, amino acid residues 131-159, 167-195, and 215-243 of the rat 9ql protein, amino acid residues 126-154, 162-190, and 210-238 of the rat 9qc protein, amino acid residues 99-127, 135-163, and 183-211 of the rat 8t protein, amino acid residues 144-172, 180-208, and 228-256 of the mouse 9ql protein, amino acid residues 94-122, 130-158, and 178-206 of the monkey 9qs protein, amino acid residues 94-122, 130-158, and 178-206 of the human p19 protein, amino acid residues 19-47 and 67-95 of the rat p19 protein, and amino acid residues 130-158, 166-194, and 214-242 of the mouse p19 protein comprise calcium binding domains (EF hands) (see FIG. 21). Amino acid residues 116-127 and 152-163 of the monkey KChIP4a and KChIP4b proteins comprise calcium binding domains.

In another embodiment, the isolated PCIP proteins of the present invention are identified based on the presence of at least one conserved carboxyl-terminal domain which includes an amino acid sequence of about 100-200 amino acid residues in length, preferably 150-200 amino acid residues in length, and more preferably 185 amino acid residues in length, and which includes three EF hands. PCIP proteins of the present invention preferably contain a carboxyl-terminal domain which is at least about 70%, 71%, 74%, 75%, 76%, 80%, or more identical to the carboxyl terminal 185 amino acid residues of rat 1v, rat 9q, or mouse p19 (see FIGS. 21, 25, and 41).

Members of the PCIP family which also have common structural characteristics are listed in Table I. Other members of the PCIP family, e.g., members of the PCIP family which do not have common structural characteristics, are listed in Table II and are described below. The present invention provides a full length human and a partial length rat 33b07 clone and the proteins encoded by these cDNAs. The present invention further provides partial length rat 1p clone and the protein encoded by this cDNA. In addition, the present invention provides a partial length rat 7s clone and the protein encoded by this cDNA.

The present invention further provides PCIP family members which represent previously identified cDNAs (29x, 25r, 5p, 7q, and 19r). These previously identified cDNAs are identified herein as PCIP family members, i.e., as molecules which have a PCIP activity, as described herein. Accordingly, the present invention provides methods for using these previously identified cDNAs, e.g., methods for using these cDNAs in the screening assays, the diagnostic assays, the prognostic assays, and the methods of treatment described herein.

The PCIP molecules of the present invention were initially identified based on their ability, as determined using yeast two-hybrid assays (described in detail in Example 1), to interact with the amino-terminal 180 amino acids of rat Kv4.3 subunit. Further binding studies with other potassium subunits were performed to demonstrate specificity of the PCIP for Kv4.3 and Kv4.2. In situ localization, immuno-histochemical methods, co-immunoprecipitation and patch clamping methods were then used to clearly demonstrate that the PCIPs of the present invention interact with and modulate the activity of potassium channels, particularly those comprising a 4.3 or 4.2 subunit.

Several novel human, mouse, monkey, and rat PCIP family members have been identified, referred to herein as 1v, 9q, p19, W28559, KChIP4, 33b07, 1p, and rat 7s proteins and nucleic acid molecules. The human, rat, and mouse cDNAs encoding the 1v polypeptide are represented by SEQ ID NOs: 1, 3, and 5, and shown in FIGS. 1, 2, and 3, respectively. In the brain, 1v mRNA is highly expressed in neocortical and hippocampal interneurons, in the thalamic reticular nucleus and medial habenula, in basal forebrain and striatal cholinergic neurons, in the superior colliculus, and in cerebellar granule cells. The 1v polypeptide is highly expressed in the somata, dendrites, axons and axon terminals of cells that express 1v mRNA. Splice variants of the 1v gene have been identified in rat and mouse and are represented by SEQ ID NOs: 7, 9, and 11 and shown in FIGS. 4, 5, and 6, respectively. 1v polypeptide interacts with potassium channels comprising Kv4.3 or kv4.2 subunits, but not with Kv1.1 subunits. As determined by Northern blot, the 1v transcripts (mRNA) are expressed predominantly in the brain The 8t cDNA (SEQ ID NO: 29) encodes a polypeptide having a molecular weight of approximately 26 kD corresponding to SEQ ID NO:30 (see FIG. 15). The 8t polypeptide interacts with potassium channel comprising Kv4.3 or Kv4.2 subunits, but not with Kv1.1 subunits. As determined by Northern blot and in situ data, the 8t mRNA is expressed predominantly in the heart and the brain. The 8t cDNA is a splice variant of 9q.

Human, rat, monkey, and mouse 9q cDNA were also isolated. Splice variants include human 9ql (SEQ ID NO:13; FIG. 7) rat 9ql (SEQ ID NO:15; FIG. 8), mouse 9ql (SEQ ID NO:17; FIG. 9), human 9qm (SEQ ID NO:19; FIG. 10), rat 9qm (SEQ ID NO:21; FIG. 11), human 9qs (SEQ ID NO:23; FIG. 12), monkey 9qs (SEQ ID NO:25; FIG. 13), and rat 9qc (SEQ ID NO:27; FIG. 14). The genomic DNA sequence of 9q has also be determined. Exon 1 and its flanking intron sequences (SEQ ID NO:46) are shown in FIG. 22A. Exons 2-11 and the flanking intron sequences (SEQ ID NO:47) are shown in FIG. 22B. 9q polypeptides interact with potassium channels comprising Kv4.3 or Kv4.2 subunits, but not with Kv1.1 subunits. As determined by Northern blot and in situ data, the 9q proteins are expressed predominantly in the heart and the brain. In the brain, 9q mRNA is highly expressed in the neostriatum, hippocampal formation, neocortical pyramidal cells and interneurons, and in the thalamus, superior colliculus, and cerebellum.

Human, rat, and mouse P19 cDNA was also isolated. Human P19 is shown in SEQ ID NO:31 and FIG. 16; and in SEQ ID NO:39 and FIG. 20 (the 3' sequence). Rat P19 is shown in SEQ ID NO:33 and FIG. 17, and mouse P19 is shown in SEQ ID NO:35 and FIG. 18. P19 polypeptides interact with potassium channels comprising Kv4.3 or Kv4.2 subunits, but not with Kv1.1 subunits. As determined by Northern blot analysis, the P19 transcripts (mRNA) are expressed predominantly in the brain.

A partial human paralog of the PCIP molecules was also identified. This paralog is referred to herein as W28559 and is shown in SEQ ID NO:37 and FIG. 19.

Monkey KChIP4a and its splice variants KChIP4b, KChIP4c, and KChIP4d were also identified. Monkey KChIP4a is shown in SEQ ID NO:48 and FIG. 23. Monkey KChIP4b is shown in SEQ ID NO:50 and FIG. 24. Monkey KChIP4c is shown in SEQ ID NO:69 and FIG. 35. Monkey KChIP4d is shown in SEQ ID NO:71 and FIG. 36.

The nucleotide sequence of the full length rat 33b07 cDNA and the predicted amino acid sequence of the rat 33b07 polypeptide are shown in FIG. 26 and in SEQ ID NOs:52 and 53, respectively. The rat 33b07 cDNA encodes a protein having a molecular weight of approximately 44.7 kD and which is 407 amino acid residues in length. Rat 33b07 binds rKv4.3N and rKv4.2N with slight preference for rKv4.2N in yeast 2-hybrid assays.

The nucleotide sequence of the full length human 33b07 cDNA and the predicted amino acid sequence of the human 33b07 polypeptide are shown in FIG. 27 and in SEQ ID NOs:54 and 55, respectively.

The nucleotide sequence of the partial length rat 1p cDNA and the predicted amino acid sequence of the rat 1p polypeptide are shown in FIG. 28 and in SEQ ID NOs:56 and 57, respectively. The rat 1p cDNA encodes a protein having a molecular weight of approximately 28.6 kD and which is 267 amino acid residues in length. Rat 1p binds rKv4.3N and rKv4.2N with slight preference for rKv4.3N in yeast two-hybrid assays.

The nucleotide sequence of the partial length rat 7s cDNA and the predicted amino acid sequence of the rat 7s polypeptide are shown in FIG. 29 and in SEQ ID NOs:58 and 59, respectively. The rat 7s cDNA encodes a protein having a molecular weight of approximately 28.6 kD and which is 270 amino acid residues in length. Rat 7s binds rKv4.3N and rKv4.2N with preference for rKv4.3N in yeast two-hybrid assays.

The sequences of the present invention are summarized below, in Tables I and II.

TABLE I

Novel Polynucleotides and Polypeptides of the Present Invention (full length except where noted)

| PCIP | Nucleic Acid Molecule Form | Source | SEQ ID NO: DNA | SEQ ID NO: PROTEIN | ATCC |
|---|---|---|---|---|---|
| 1v or KChIP1 | 1v | human (225-875)* | 1 | 2 | 98994 |
| | KChIP1N (1vN) N-terminal splice variant | human (353-461) | 80 | 81 | |
| | 1v | rat (210-860) | 3 | 4 | 98946 |
| | 1v | mouse (477-1127) | 5 | 6 | 98945 |
| | 1vl | human | 79 | 109 | |
| | 1vl | rat (31-714) | 7 | 8 | 98942 |
| | 1vl | Mouse (77-760) | 9 | 10 | 98943 |
| | 1vn | rat (345-955) (339-1037) | 11 (partial) 102 (full) | 12 (partial) 103 (full) | 98944 |
| 9q or KChIP2 | Genomic DNA sequence | human | 74 | | |
| | Genomic DNA sequence (Exon 1 and flanking intron sequences) | human | 46 | | |
| | Genomic DNA sequence (Exons 2-11 and flanking intron sequences) | human | 47 | | |
| | 9ql | human (207-1019) | 13 | 14 | 98993 98991 |
| | 9ql | rat (2-775) (1-813) | 15 (partial) 75 (full length) | 16 (partial) 76 (full length) | 98948 |
| | 9ql | mouse (181-993) | 17 | 18 | 98937 |
| | 9qm | human (207-965) | 19 | 20 | 98993 98991 |
| | 9qm | rat (214-972) | 21 | 22 | 98941 |
| | 9qs | human (207-869) | 23 | 24 | 98951 |
| | 9qs | monkey (133-795) | 25 | 26 | 98950 |
| | 9qc | rat (208-966) | 27 | 28 | 98947 |
| | 8t | Human (1-678) | 77 (partial) | 78 (partial) | |
| | | rat (1-678) | 29 (partial) | 30 (partial) | 98939 |
| p19 or KChIP3 | KChIP3 (full length) | Human (16-786) | 82 | 83 | |
| | p19 | human (1-771) | 31 | 32 | PTA-316 |
| | p19 | rat (1-330) (1-579) | 33 (partial) 84 (partial) | 34 (partial) 85 (partial) | 98936 |
| | p19 | mouse (49-819) | 35 | 36 | 98940 |

TABLE I-continued

Novel Polynucleotides and Polypeptides of the Present Invention (full length except where noted)

| PCIP | Nucleic Acid Molecule Form | Source | SEQ ID NO: DNA | SEQ ID NO: PROTEIN | ATCC |
|---|---|---|---|---|---|
| | p193 (partial) | Human (2-127) | 39 | 40 | 98949 |
| W28559 | W28559 (partial) | human (1-339) | 37 | 38 | |
| KChIP4 | KChIP4a (KChIP4N1) | human (248-949) | 94 | 95 | |
| | KChIP4aS (KChIP4N1S) shorter splice variant of KChIP4N1 | human (319-885) | 92 | 93 | |
| | KChIP4c (KChIP4N2) | Human (90-779) | 96 | 97 | |
| | KChIP4d (KChIP4N3) | Human (65-817) | 98 | 99 | |
| | KChIP4a (KChIP4N1) | Monkey (265-966) | 48 | 49 | |
| | KChIP4b C-terminal splice variant | Monkey (265-966) | 50 (partial) | 51 (partial) | |
| | KChIP4b (KChIP4XC) | Monkey (1-385) | 86 (partial) | 87 (partial) | |
| | KChIP4c (KChIP4N2) splice variant | Monkey (122-811) | 69 | 70 | |
| | KChIP4d (KChIP4N3) splice variant | Monkey (64-816) | 71 | 72 | |
| | KChIP4c (KChIP4N2) | Mouse (56-745) | 88 | 89 | |
| | KChIP4 | Rat (1-597) | 90 (partial) | 91 (partial) | |
| | KChIP4aX (KChIP4N1x) splice variant of KChIP4N1 | Rat (1-821) | 100 (partial) | 101 (partial) | |

*The coordinates of the coding sequence are shown in parenthesis. The first column indicates the PCIPs which were identified and column 2 indicates the various nucleic acid forms identified for each PCIP.

TABLE II

Polynucleotides and Polypeptides of the Present Invention (full length except where noted)

| PCIP | Nucleic Acid Molecule Form | Source | SEQ ID NO: DNA | SEQ ID NO: PROTEIN | ATCC |
|---|---|---|---|---|---|
| 33b07 Novel | 33b07 | Human (88-1332) | 52 | 53 | PTA-316 |
| | 33b07 | Rat (85-1308) | 54 | 55 | |
| 1p Novel | 1p (partial) | Rat (1-804) | 56 | 57 | |
| 7s Novel | 7s (partial) | Rat (1-813) | 58 | 59 | |
| 29x | 29x | Rat (433-1071) | 60 | 61 | |
| | 25r splice variant of 29x | Rat (130-768) | 62 | | |
| 5p | 5p | Rat (52-339) | 63 | 64 | |
| 7q | 7q | Rat (1-639) | 65 | 66 | |
| 19r | 19r | Rat (1-816) | 67 | 68 | |

*The coordinates of the coding sequence are shown in parenthesis. The first column indicates the four families of PCIPs which were identified and column 2 indicates the various nucleic acid forms identified for each family. Novel molecules are also indicated.

Plasmids containing the nucleotide sequences encoding human, rat and monkey PCIPs were deposited with American Type Culture Collection (ATCC), 10801 University Boulevard, Manassas, Va. 20110-2209, on Nov. 17, 1998, and assigned the Accession Numbers described above. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. § 112.

Clones containing cDNA molecules encoding human p19 (clone EphP19) and human 33b07 (clone Eph33b07) were deposited with American Type Culture Collection (Manassas, Va.) on Jul. 8, 1998 as Accession Number PTA-316, as part of a composite deposit representing a mixture of two strains, each carrying one recombinant plasmid harboring a particular cDNA clone. (The ATCC strain designation for the mixture of hP19 and h33b07 is EphP19h33b07mix).

To distinguish the strains and isolate a strain harboring a particular cDNA clone, an aliquot of the mixture can be streaked out to single colonies on LB plates supplemented with 100 ug/ml ampicillin, single colonies grown, and then plasmid DNA extracted using a standard minipreparation procedure. Next, a sample of the DNA minipreparation can be digested with NotI and the resultant products resolved on a 0.8% agarose gel using standard DNA electrophoresis conditions. The digest gives the following band patterns: EphP9: 7 kb 9 (single band), Eph33b07: 5.8 kb (single band).

Various aspects of the invention are described in further detail in the following subsections:

I. Isolated Nucleic Acid Molecules

One aspect of the invention pertains to isolated nucleic acid molecules that encode PCIP proteins or biologically active portions thereof, as well as nucleic acid fragments sufficient for use as hybridization probes to identify PCIP-encoding nucleic acid molecules (e.g., PCIP mRNA) and fragments for use as PCR primers for the amplification or mutation of PCIP nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated PCIP nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52. SEQ ID NO:54, SEQ ID NO:56, SEQ ID NO:58, SEQ ID NO:69, SEQ ID NO:71, SEQ ID NO:74, SEQ ID NO:75, SEQ ID NO:77, SEQ ID NO:79, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, or SEQ ID NO:102, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, or a portion thereof, can be isolated using standard molecular biology techniques and the sequence information provided herein. Using all or portion of the nucleic acid sequence of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, SEQ ID NO:71, SEQ ID NO:74, SEQ ID NO:75, SEQ ID NO:77, SEQ ID NO:79, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, or SEQ ID NO:102, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, as a hybridization probe, PCIP nucleic acid molecules can be isolated using standard hybridization and cloning techniques (e.g., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989).

Moreover, a nucleic acid molecule encompassing all or a portion of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, SEQ ID NO:71, SEQ ID NO:74, SEQ ID NO:75, SEQ ID NO:77, SEQ ID NO:79, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, or SEQ ID NO:102, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994 can be isolated by the polymerase chain reaction (PCR) using synthetic oligonucleotide primers designed based upon the sequence of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, SEQ ID NO:71, SEQ ID NO:74, SEQ ID NO:75, SEQ ID NO:77, SEQ ID NO:79, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, or SEQ ID NO:102, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to PCIP nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27. SEQ ID NO:29, SEQ ID NO: 31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, SEQ ID NO:71, SEQ ID NO:74, SEQ ID NO:75, SEQ ID NO:77, SEQ ID NO:79, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, or SEQ ID NO:102, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, or a portion of any of these nucleotide sequences.

In another preferred embodiment, an isolated nucleic acid molecule of the invention comprises a nucleic acid molecule which is a complement of the nucleotide sequence shown in SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, SEQ ID NO:71, SEQ ID NO:74, SEQ ID NO:75, SEQ ID NO:77, SEQ ID NO:79, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, or SEQ ID NO:102, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, or a portion of any of these nucleotide sequences. A nucleic acid molecule which is complementary to the nucleotide sequence shown in SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, SEQ ID NO:71, SEQ ID NO:74, SEQ ID NO:75, SEQ ID NO:77, SEQ ID NO:79, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO: 1000, or SEQ ID NO:102, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, is one which is sufficiently complementary to the nucleotide sequence shown in SEQ ID NO:1, SEQ ID NO:3, SEQ ID NO:4, SEQ ID NO:6, SEQ ID NO:7, SEQ ID NO:9, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, such that it can hybridize to the nucleotide sequence shown in SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, SEQ ID NO:71, SEQ ID NO:74, SEQ ID NO:75, SEQ ID NO:77, SEQ ID NO:79, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, or SEQ ID NO:102, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, thereby forming a stable duplex.

In still another preferred embodiment, an isolated nucleic acid molecule of the present invention comprises a nucleotide sequence which is at least about 50%, 55%, 60%, 65%, 70%, 75%, 80%, 85%, 90%, 95%, 98% or more identical to the entire length of the nucleotide sequence shown in SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, SEQ ID NO:71, SEQ ID NO:74, SEQ ID NO:75, SEQ ID NO:77, SEQ ID NO:79, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, or SEQ ID NO: 102, or the entire length of the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, or a portion of any of these nucleotide sequences.

Moreover, the nucleic acid molecule of the invention can comprise only a portion of the nucleic acid sequence of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, SEQ ID NO:71, SEQ ID NO:74, SEQ ID NO:75, SEQ ID NO:77, SEQ ID NO:79, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, or SEQ ID NO:102, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, for example a fragment which can be used as a probe or primer or a fragment encoding a biologically active portion of a PCIP protein. The nucleotide sequence determined from the cloning of the PCIP gene allows for the generation of probes and primers designed for use in identifying and/or cloning other PCIP family members, as well as PCIP homologues from other species.

The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, SEQ ID NO:71, SEQ ID NO:74, SEQ ID NO:75, SEQ ID NO:77, SEQ ID NO:79, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO: 900, or SEQ ID NO:102, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, of an anti-sense sequence of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, SEQ ID NO:71, SEQ ID NO:74, SEQ ID NO:75, SEQ ID NO:77, SEQ ID NO:79, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, or SEQ ID NO:102, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, or of a naturally occurring allelic variant or mutant of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, SEQ ID NO:71, SEQ ID NO:74, SEQ ID NO:75, SEQ ID NO:77, SEQ ID NO:79, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, or SEQ ID NO:102, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994. In an exemplary embodiment, a nucleic acid molecule of the present invention comprises a nucleotide sequence which is 350-400, 400-450, 450-500, 500-550, 550-600, 600-650, 650-700, 700-750, 750-800, 800-850, 850-900, 949, 950-1000, or more nucleotides in length and hybridizes under stringent hybridization conditions to a nucleic acid molecule of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, SEQ ID NO:71, SEQ ID NO:74, SEQ ID NO:75, SEQ ID NO:77, SEQ ID NO:79, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, or SEQ ID NO:102, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994.

Probes based on the PCIP nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a PCIP protein, such as by measuring a level of a PCIP-encoding nucleic acid in a sample of cells from a subject e.g., detecting PCIP mRNA levels or determining whether a genomic PCIP gene has been mutated or deleted.

A nucleic acid fragment encoding a "biologically active portion of a PCIP protein" can be prepared by isolating a portion of the nucleotide sequence of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, SEQ ID NO:71, SEQ ID NO:74, SEQ ID NO:75, SEQ ID NO:77, SEQ ID NO:79, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, or SEQ ID NO:102, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, which encodes a polypeptide having a PCIP biological activity (the biological activities of the PCIP proteins are described herein), expressing the encoded portion of the PCIP protein (e.g., by recombinant expression in vitro) and assessing the activity of the encoded portion of the PCIP protein.

The invention further encompasses nucleic acid molecules that differ from the nucleotide sequence shown in SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, SEQ ID NO:71, SEQ ID NO:74, SEQ ID NO:75, SEQ ID NO:77, SEQ ID NO:79, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, or SEQ ID NO:102 or the nucleotide sequence of the DNA insert of the plasmid deposited with 98936, 98937, 98938, 98939, 98940, 98941, 98942, 98943, 98944, 98945, 98946, 98947, 98948, 98949, 98950, 98951, 98991, 98993, or 98994, due to degeneracy of the genetic code and thus encode the same PCIP proteins as those encoded by the nucleotide sequence shown in SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, SEQ ID NO:71, SEQ ID NO:74, SEQ ID NO:75, SEQ ID NO:77, SEQ ID NO:79, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO: 800, or SEQ ID NO:102 or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994. In another embodiment, an isolated nucleic acid molecule of the invention has a nucleotide sequence encoding a protein having an amino acid sequence shown in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, SEQ ID NO:72, SEQ ID NO:76, SEQ ID NO:78, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, or SEQ ID NO:109.

In addition to the PCIP nucleotide sequences shown in SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, SEQ ID NO:71, SEQ ID NO:74, SEQ ID NO:75, SEQ ID NO:77, SEQ ID NO:79, SEQ ID NO:80, SEQ ID NO:82, SEQ ID NO:84, SEQ ID NO:86, SEQ ID NO:88, SEQ ID NO:90, SEQ ID NO:91, SEQ ID NO:94, SEQ ID NO:96, SEQ ID NO:98, SEQ ID NO:100, or SEQ ID NO:102, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, it will be appreciated by those skilled in the art that DNA sequence polymorphisms that lead to changes in the amino acid sequences of the PCIP proteins may exist within a population (e.g., the human population). Such genetic polymorphism in the PCIP genes may exist among individuals within a population due to natural allelic variation. As used herein, the terms "gene" and "recombinant gene" refer to nucleic acid molecules which include an open reading frame encoding a PCIP protein, preferably a mammalian PCIP protein, and can further include non-coding regulatory sequences, and introns.

Allelic variants of human PCIP include both functional and non-functional PCIP proteins. Functional allelic variants are naturally occurring amino acid sequence variants of the human PCIP protein that maintain the ability to bind a PCIP ligand and/or modulate any of the PCIP activities described herein. Functional allelic variants will typically contain only conservative substitution of one or more amino acids of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, SEQ ID NO:72, SEQ ID NO:76, SEQ ID NO:78, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, or SEQ ID NO:109 or substitution, deletion or insertion of non-critical residues in non-critical regions of the protein.

Non-functional allelic variants are naturally occurring amino acid sequence variants of the human PCIP protein that do not have the ability to either bind a PCIP ligand and/or modulate any of the PCIP activities described herein. Non-functional allelic variants will typically contain a non-conservative substitution, a deletion, or insertion or premature truncation of the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, SEQ ID NO:72, SEQ ID NO:76, SEQ ID NO:78, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, or SEQ ID NO:109 or a substitution, insertion or deletion in critical residues or critical regions.

The present invention further provides non-human orthologues of the human PCIP protein. Orthologues of the human PCIP protein are proteins that are isolated from non-human organisms and possess the same PCIP ligand binding and/or modulation of potassium channel mediated activities of the human PCIP protein. Orthologues of the human PCIP protein can readily be identified as comprising an amino acid sequence that is substantially identical to SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, SEQ ID NO:72, SEQ ID NO:76, SEQ ID NO:78, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, or SEQ ID NO:109.

Moreover, nucleic acid molecules encoding other PCIP family members and, thus, which have a nucleotide sequence which differs from the PCIP sequences of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, SEQ ID NO:71, SEQ ID NO:74, SEQ ID NO:75, SEQ ID NO:77, SEQ ID NO:79, SEQ ID NO: 80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, or SEQ ID NO:102, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994 are intended to be within the scope of the invention. For example, another PCIP cDNA can be identified based on the nucleotide sequence of human PCIP. Moreover, nucleic acid molecules encoding PCIP proteins from different species, and thus which have a nucleotide sequence which differs from the PCIP sequences of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, SEQ ID NO:71, SEQ ID NO:74, SEQ ID NO:75, SEQ ID NO:77, SEQ ID NO:79, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, or SEQ ID NO:102 or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994 are intended to be within the scope of the invention. For example, a mouse PCIP cDNA can be identified based on the nucleotide sequence of a human PCIP.

Nucleic acid molecules corresponding to natural allelic variants and homologues of the PCIP cDNAs of the invention can be isolated based on their homology to the PCIP nucleic acids disclosed herein using the cDNAs disclosed herein, or a portion thereof, as a hybridization probe according to standard hybridization techniques under stringent hybridization conditions.

Accordingly, in another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, SEQ ID NO:71, SEQ ID NO:74, SEQ ID NO:75, SEQ ID NO:77, SEQ ID NO:79, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO: 800, or SEQ ID NO:102 or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994. In other embodiment, the nucleic acid is at least 30, 50, 100, 150, 200, 250, 300, 307, 350, 400, 450, 500, 550, 600, 650, 700, 750, 800, 850, 900, 949, or 950 nucleotides in length. As used herein, the term "hybridizes under stringent conditions" is intended to describe conditions for hybridization and washing under which nucleotide sequences at least 60% identical to each other typically remain hybridized to each other. Preferably, the conditions are such that sequences at least about 70%, more preferably at least about 80%, even more preferably at least about 85% or 90% identical to each other typically remain hybridized to each other.

Such stringent conditions are known to those skilled in the art and can be found in *Current Protocols in Molecular Biology*, Ausubel et al., eds., John Wiley & Sons, Inc. (1995), sections 2, 4, and 6. Additional stringent conditions can be found in *Molecular Cloning: A Laboratory Manual*, Sambrook et al., Cold Spring Harbor Press, Cold Spring Harbor, N.Y. (1989), chapters 7, 9, and 11. A preferred, non-limiting example of stringent hybridization conditions includes hybridization in 4× sodium chloride/sodium citrate (SSC), at about 65-70° C. (or alternatively hybridization in 4×SSC plus 50% formamide at about 42-50° C.) followed by one or more washes in 1×SSC, at about 65-70° C. A preferred, non-limiting example of highly stringent hybridization conditions includes hybridization in 1×SSC, at about 65-70° C. (or alternatively hybridization in 1×SSC plus 50% formamide at about 42-50° C.) followed by one or more washes in 0.3× SSC, at about 65-70° C. A preferred, non-limiting example of reduced stringency hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Ranges intermediate to the above-recited values, e.g., at 65-70° C. or at 42-50° C. are also intended to be encompassed by the present invention. SSPE (1×SSPE is 0.15M NaCl, 10 mM $NaH_2PO_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m(° C.)=2(\# \text{ of A+T bases})+4(\# \text{ of G+C bases})$. For hybrids between 18 and 49 base pairs in length, $T_m(° C.)=81.5+16.6(\log_{10}[Na^+])+0.41(\% G+C)-(600/N)$, where N is the number of bases in the hybrid, and [$Na^+$] is the concentration of sodium ions in the hybridization buffer ([$Na^+$] for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25-0.5M $NaH_2PO_4$, 7% SDS at about 65° C., followed by one or more washes at 0.02M $NaH_2PO_4$, 1% SDS at 65° C. (see e.g., Church and Gilbert (1984) *Proc. Natl. Acad. Sci. USA* 81:1991-1995), or alternatively 0.2×SSC, 1% SDS.

Preferably, an isolated nucleic acid molecule of the invention that hybridizes under stringent conditions to the sequence of SEQ ID NO:1 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the PCIP sequences that may exist in the population, the skilled artisan will further appreciate that changes can be introduced by mutation into the nucleotide sequences of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, SEQ ID NO:71, SEQ ID NO:74, SEQ ID NO:75, SEQ ID NO:77, SEQ ID NO:79, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, or SEQ ID NO:102, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, thereby leading to changes in the amino acid sequence of the encoded PCIP proteins, without altering the functional ability of the PCIP proteins. For example, nucleotide substitutions leading to amino acid substitutions at "non-essential" amino acid residues can be made in the sequence of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, SEQ ID NO:71, SEQ ID NO:74, SEQ ID NO:75, SEQ ID NO:77, SEQ ID NO:79, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, or SEQ ID NO:102, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994. A "non-essential" amino acid residue is a residue that can be altered from the wild-type sequence of PCIP (e.g., the sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, SEQ ID NO:72, SEQ ID NO:76, SEQ ID NO:78, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO: 801, SEQ ID NO:103, or SEQ ID NO:109) without altering the biological activity, whereas an "essential" amino acid residue is required for biological activity. For example, amino acid residues that are conserved among the PCIP proteins of the present invention, are predicted to be particularly unamenable to alteration. Furthermore, additional amino acid residues that are conserved between the PCIP proteins of the present invention and other members of the PCIP family of proteins are not likely to be amenable to alteration.

Accordingly, another aspect of the invention pertains to nucleic acid molecules encoding PCIP proteins that contain changes in amino acid residues that are not essential for activity. Such PCIP proteins differ in amino acid sequence from SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57; SEQ ID NO:59, SEQ ID NO:70, SEQ ID NO:72, SEQ ID NO:76, SEQ ID NO:78, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO: 101, SEQ ID NO:103, or SEQ ID NO:109, yet retain biological activity. In one embodiment, the isolated nucleic acid molecule comprises a nucleotide sequence encoding a protein, wherein the protein comprises an amino acid sequence at least about 50%, 55%, 60%, 65%, 70%, 75%, 80%, 85%, 90%, 95% or more identical to SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, SEQ ID NO:72, SEQ ID NO:76, SEQ ID NO:78, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, or SEQ ID NO:109.

An isolated nucleic acid molecule encoding a PCIP protein homologous to the protein of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, SEQ ID NO:72, SEQ ID NO:76, SEQ ID NO:78, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO: 103, or SEQ ID NO:109 can be created by introducing one or more nucleotide substitutions, additions or deletions into the nucleotide sequence of SEQ ID NO: 5, SEQ ID NO:3 SEQ ID NO:5, SEQ ID NO:7, SEQ ID NO:9, SEQ ID NO: 81, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, SEQ ID NO:71, SEQ ID NO:74, SEQ ID NO:75, SEQ ID NO:77, SEQ ID NO:79, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, or SEQ ID NO:102, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, such that one or more amino acid substitutions, additions or deletions are introduced into the encoded protein. Mutations can be introduced into SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, SEQ ID NO:71, SEQ ID NO:74, SEQ ID NO:75, SEQ ID NO:77, SEQ ID NO:79, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, or SEQ ID NO:102, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994 by standard techniques, such as site-directed mutagenesis and PCR-mediated mutagenesis. Preferably, conservative amino acid substitutions are made at one or more predicted nonessential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a PCIP protein is preferably replaced with another amino acid residue from the same side chain family. Alternatively, in another embodiment, mutations can be introduced randomly along all or part of a PCIP coding sequence, such as by saturation mutagenesis, and the resultant mutants can be screened for PCIP biological activity to identify mutants that retain activity. Following mutagenesis of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, SEQ ID NO:71, SEQ ID NO:74, SEQ ID NO:75, SEQ ID NO:77, SEQ ID NO:79, SEQ ID NO:80, SEQ ID NO:82; SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, or SEQ ID NO:102, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, the encoded protein can be expressed recombinantly and the activity of the protein can be determined.

In a preferred embodiment, a mutant PCIP protein can be assayed for the ability to (1) interact with (e.g., bind to) a potassium channel protein or portion thereof; (2) regulate the phosphorylation state of a potassium channel protein or portion thereof; (3) associate with (e.g., bind) calcium and, for example, act as a calcium dependent kinase, e.g., phosphorylate a potassium channel in a calcium-dependent manner; (4) associate with (e.g., bind) calcium and, for example, act as a calcium dependent transcription factor; (5) modulate a potassium channel mediated activity in a cell (e.g., a neuronal or cardiac cell) to, for example, beneficially affect the cell; (6) modulate the release of neurotransmitters; (7) modulate membrane excitability; (8) influence the resting potential of membranes; (9) modulate wave forms and frequencies of action potentials; and (10) modulate thresholds of excitation.

In addition to the nucleic acid molecules encoding PCIP proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire PCIP coding strand, or to only a portion thereof. In one embodiment, an antisense nucleic acid molecule is antisense to a "coding region" of the coding strand of a nucleotide sequence encoding PCIP. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding PCIP. The term "noncoding region" refers to 5' and 3' sequences which flank the coding region that are not translated into amino acids (i.e., also referred to as 5' and 3' untranslated regions).

Given the coding strand sequences encoding PCIP disclosed herein, antisense nucleic acids of the invention can be designed according to the rules of Watson and Crick base pairing. The antisense nucleic acid molecule can be complementary to the entire coding region of PCIP mRNA, but more preferably is an oligonucleotide which is antisense to only a portion of the coding or noncoding region of PCIP mRNA. For example, the antisense oligonucleotide can be complementary to the region surrounding the translation start site of PCIP mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a PCIP protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585-591)) can be used to catalytically cleave PCIP mRNA transcripts to thereby inhibit translation of PCIP mRNA. A ribozyme having specificity for a PCIP-encoding nucleic acid can be designed based upon the nucleotide sequence of a PCIP cDNA disclosed herein (i.e., SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO: 31, SEQ ID NO: 33, SEQ ID NO: 35, SEQ ID NO: 37, SEQ ID NO: 39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, SEQ ID NO:71, SEQ ID NO:74, SEQ ID NO:75, SEQ ID NO:77, SEQ ID NO:79, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, or SEQ ID NO:102, or the nucleotide sequence of the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994). For example, a derivative of a Tetrahymena L-19 IVS RNA can be constructed in which the nucleotide sequence of the active site is complementary to the nucleotide sequence to be cleaved in a PCIP-encoding mRNA. See, e.g., Cech et al. U.S. Pat. No. 4,987,071; and Cech et al. U.S. Pat. No. 5,116,742. Alternatively, PCIP mRNA can be used to select a catalytic RNA having a specific ribonuclease activity from a pool of RNA molecules. See, e.g., Bartel, D. and Szostak, J. W. (1993) *Science* 261:1411-1418.

Alternatively, PCIP gene expression can be inhibited by targeting nucleotide sequences complementary to the regulatory region of the PCIP (e.g., the PCIP promoter and/or enhancers) to form triple helical structures that prevent transcription of the PCIP gene in target cells. See generally, Helene, C. (1991) *Anticancer Drug Des.* 6(6):569-84; Helene, C. et al. (1992) *Ann. N.Y. Acad. Sci.* 660:27-36; and Maher, L. J. (1992) *Bioassays* 14(12):807-15.

In yet another embodiment, the PCIP nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. Proc. Natl. Acad. Sci. 93: 14670-675.

PNAs of PCIP nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of PCIP nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of PCIP can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of PCIP nucleic acid molecules can be generated which may combine the advantageous properties of PNA and DNA. Such chimeras allow DNA recognition enzymes, (e.g., RNAse H and DNA pblymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17): 3357-63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acid Res.* 17: 5973-88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119-11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. US.* 86:6553-6556; Lemaitre et al. (1987) *Proc. Natl. Acad. Sci. USA* 84:648-652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Bio-Techniques* 6:958-976) or intercalating agents. (See, e.g., Zon (1988) *Pharm. Res.* 5:539-549). To this end, the oligonucleotide may be conjugated to another molecule, (e.g., a peptide, hybridization triggered cross-linking agent, transport agent, or hybridization-triggered cleavage agent).

II. Isolated PCIP Proteins and Anti-PCIP Antibodies

One aspect of the invention pertains to isolated PCIP proteins, and biologically active portions thereof, as well as polypeptide fragments suitable for use as immunogens to raise anti-PCIP antibodies. In one embodiment, native PCIP proteins can be isolated from cells or tissue sources by an appropriate purification scheme using standard protein purification techniques. In another embodiment, PCIP proteins are produced by recombinant DNA techniques. Alternative to recombinant expression, a PCIP protein or polypeptide can be synthesized chemically using standard peptide synthesis techniques.

An "isolated" or "purified" protein or biologically active portion thereof is substantially free of cellular material or other contaminating proteins from the cell or tissue source from which the PCIP protein is derived, or substantially free from chemical precursors or other chemicals when chemically synthesized. The language "substantially free of cellular material" includes preparations of PCIP protein in which the protein is separated from cellular components of the cells from which it is isolated or recombinantly produced. In one embodiment, the language "substantially free of cellular material" includes preparations of PCIP protein having less than about 30% (by dry weight) of non-PCIP protein (also referred to herein as a "contaminating protein"), more preferably less than about 20% of non-PCIP protein, still more preferably less than about 10% of non-PCIP protein, and most preferably less than about 5% non-PCIP protein. When the PCIP protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of PCIP protein in which the protein is separated from chemical precursors or other chemicals which are involved in the synthesis of the protein. In one embodiment, the language "substantially free of chemical precursors or other chemicals" includes preparations of PCIP protein having less than about 30% (by dry weight) of chemical precursors or non-PCIP chemicals, more preferably less than about 20% chemical precursors or non-PCIP chemicals, still more preferably less than about 10% chemical precursors or non-PCIP chemicals, and most preferably less than about 5% chemical precursors or non-PCIP chemicals.

As used herein, a "biologically active portion" of a PCIP protein includes a fragment of a PCIP protein which participates in an interaction between a PCIP molecule and a non-PCIP molecule. Biologically active portions of a PCIP protein include peptides comprising amino acid sequences sufficiently identical to or derived from the amino acid sequence of the PCIP protein, e.g., the amino acid sequence shown in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, SEQ ID NO:72, SEQ ID NO:76, SEQ ID NO:78, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, or SEQ ID NO:109, which include less amino acids than the full length PCIP proteins, and exhibit at least one activity of a PCIP protein. Typically, biologically active portions comprise a domain or motif with at least one activity of the PCIP protein, e.g., binding of a potassium channel subunit. A biologically active portion of a PCIP protein can be a polypeptide which is, for example, 10, 25, 50, 100, 200, or more amino acids in length. Biologically active portions of a PCIP protein can be used as targets for developing agents which modulate a potassium channel mediated activity.

In one embodiment, a biologically active portion of a PCIP protein comprises at least one calcium binding domain.

It is to be understood that a preferred biologically active portion of a PCIP protein of the present invention may contain at least one of the above-identified structural domains. A more preferred biologically active portion of a PCIP protein may contain at least two of the above-identified structural domains. Moreover, other biologically active portions, in which other regions of the protein are deleted, can be prepared by recombinant techniques and evaluated for one or more of the functional activities of a native PCIP protein.

In a preferred embodiment, the PCIP protein has an amino acid sequence shown in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, SEQ ID NO:72, SEQ ID NO:76, SEQ ID NO:78, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO: 101, SEQ ID NO:103, or SEQ ID NO:109. In other embodiments, the PCIP protein is substantially homologous to SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, SEQ ID NO:72, SEQ ID NO:76, SEQ ID NO:78, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, or SEQ ID NO:109, and retains the functional activity of the protein of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, SEQ ID NO:72, SEQ ID NO:76, SEQ ID NO:78, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, or SEQ ID NO:109, yet differs in amino acid sequence due to natural allelic variation or mutagenesis, as described in detail in subsection I above. Accordingly, in another embodiment, the PCIP protein is a protein which comprises an amino acid sequence at least about 50%, 55%, 60%, 65%, 70%, 75%, 80%, 85%, 90%, 95%, 98% or more identical to SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, SEQ ID NO:72, SEQ ID NO:76, SEQ ID NO:78, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, or SEQ ID NO:109.

Isolated proteins of the present invention, preferably 1v, 9q, p19, W28559, KChIP4a, KChIP4b, 33b07, 1p, or 7s proteins, have an amino acid sequence sufficiently identical to the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, SEQ ID NO:72, SEQ ID NO:76, SEQ ID NO:78, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, or SEQ ID NO:109 or are encoded by a nucleotide sequence sufficiently identical to SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, SEQ ID NO:71, SEQ ID NO:74, SEQ ID NO:75, SEQ ID NO:77, SEQ ID NO:79, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, or SEQ ID NO:102. As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30%, 40%, or 50% identity, preferably 60% identity, more preferably 70%-80%, and even more preferably 90-95% identity across the amino acid sequences of the domains and contain at least one and preferably two structural domains or motifs, are defined herein as sufficiently identical. Furthermore, amino acid or nucleotide sequences which share at least 30%, 40%, or 50%, preferably 60%, more preferably 70-80%, or 90-95% identity and share a common functional activity are defined herein as sufficiently identical.

Preferred proteins are PCIP proteins having at least one calcium binding domain and, preferably, a PCIP activity. Other preferred proteins are PCIP proteins having at least one calcium binding domain, and are, preferably, encoded by a nucleic acid molecule having a nucleotide sequence which hybridizes under stringent hybridization conditions to a nucleic acid molecule comprising the nucleotide sequence of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, SEQ ID NO:71, SEQ ID NO:74, SEQ ID NO:75, SEQ ID NO:77, SEQ ID NO:79, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, or SEQ ID NO:102.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the PCIP amino acid sequence of SEQ ID NO:2, SEQ ID NO:4, SEQ ID NO:6, SEQ ID NO:8, SEQ ID NO: 10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, SEQ ID NO:72, SEQ ID NO:76, SEQ ID NO:78, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, or SEQ ID NO:109 having 177 amino acid residues, at least 80, preferably at least 100, more preferably at least 120, even more preferably at least 140, and even more preferably at least 150, 160 or 170 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48): 444-453 (1970)) algorithm which has been incorporated into the GAP program in the GCG software package (available at http://www.gcg.com), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0 or 2.0U), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to PCIP nucleic acid molecules of the invention. BLAST protein searches can be performed with the XBLAST program, score=50, wordlength=3 to obtain amino acid sequences homologous to PCIP protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See http://www.ncbi.nlm.nih.gov.

The invention also provides PCIP chimeric or fusion proteins. As used herein, a PCIP "chimeric protein" or "fusion protein" comprises a PCIP polypeptide operatively linked to a non-PCIP polypeptide. An "PCIP polypeptide" refers to a polypeptide having an amino acid sequence corresponding to PCIP, whereas a "non-PCIP polypeptide" refers to a polypeptide having an amino acid sequence corresponding to a protein which is not substantially homologous to the PCIP protein, e.g., a protein which is different from the PCIP protein and which is derived from the same or a different organism. Within a PCIP fusion protein the PCIP polypeptide can correspond to all or a portion of a PCIP protein. In a preferred embodiment, a PCIP fusion protein comprises at least one biologically active portion of a PCIP protein. In another preferred embodiment, a PCIP fusion protein comprises at least two biologically active portions of a PCIP protein. Within the fusion protein, the term "operatively linked" is intended to indicate that the PCIP polypeptide and the non-PCIP polypeptide are fused in-frame to each other. The non-PCIP polypeptide can be fused to the N-terminus or C-terminus of the PCIP polypeptide.

For example, in one embodiment, the fusion protein is a GST-PCIP fusion protein in which the PCIP sequences are fused to the C-terminus of the GST sequences. Such fusion proteins can facilitate the purification of recombinant PCIP.

In another embodiment, the fusion protein is a PCIP protein containing a heterologous signal sequence at its N-terminus. In certain host cells (e.g., mammalian host cells), expression and/or secretion of PCIP can be increased through use of a heterologous signal sequence.

The PCIP fusion proteins of the invention can be incorporated into pharmaceutical compositions and administered to a subject in vivo. The PCIP fusion proteins can be used to affect the bioavailability of a PCIP substrate. Use of PCIP fusion proteins may be useful therapeutically for the treatment of potassium channel associated disorders such as CNS disorders, e.g., neurodegenerative disorders such as Alzheimer's disease, dementias related to Alzheimer's disease (such as Pick's disease), Parkinson's and other Lewy diffuse body diseases, multiple sclerosis, amyotrophic lateral sclerosis, progressive supranuclear palsy, epilepsy, spinocerebellar ataxia, and Jakob-Creutzfieldt disease; psychiatric disorders, e.g., depression, schizophrenic disorders, Korsakoff's psychosis, mania, anxiety disorders, or phobic disorders; learning or memory disorders, e.g., amnesia or age-related memory loss; and neurological disorders; e.g., migraine. Use of PCIP fusion proteins may also be useful therapeutically for the treatment of potassium channel associated disorders such as cardiovascular disorders, e.g., arteriosclerosis, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, atrial fibrilation or congestive heart failure.

Moreover, the PCIP-fusion proteins of the invention can be used as immunogens to produce anti-PCIP antibodies in a subject, to purify PCIP ligands and in screening assays to identify molecules which inhibit the interaction of PCIP with a PCIP substrate.

Preferably, a PCIP chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A PCIP-encoding nucleic acid can be cloned into such an expression vector such that the fusion moiety is linked in-frame to the PCIP protein.

The present invention also pertains to variants of the PCIP proteins which function as either PCIP agonists (mimetics) or as PCIP antagonists. Variants of the PCIP proteins can be generated by mutagenesis, e.g., discrete point mutation or truncation of a PCIP protein. An agonist of the PCIP proteins can retain substantially the same, or a subset, of the biological activities of the naturally occurring form of a PCIP protein. An antagonist of a PCIP protein can inhibit one or more of the activities of the naturally occurring form of the PCIP protein by, for example, competitively modulating a potassium channel mediated activity of a PCIP protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the PCIP protein.

In one embodiment, variants of a PCIP protein which function as either PCIP agonists (mimetics) or as PCIP antagonists can be identified by screening combinatorial libraries of mutants, e.g., truncation mutants, of a PCIP protein for PCIP protein agonist or antagonist activity. In one embodiment, a variegated library of PCIP variants is generated by combinatorial mutagenesis at the nucleic acid level and is encoded by a variegated gene library. A variegated library of PCIP variants can be produced by, for example, enzymatically ligating a mixture of synthetic oligonucleotides into gene sequences such that a degenerate set of potential PCIP sequences is expressible as individual polypeptides, or alternatively, as a set of larger fusion proteins (e.g., for phage display) containing the set of PCIP sequences therein. There are a variety of methods which can be used to produce libraries of potential PCIP variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential PCIP sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a PCIP protein coding sequence can be used to generate a variegated population of PCIP fragments for screening and subsequent selection of variants of a PCIP protein. In one embodiment, a library of coding sequence fragments can be generated by treating a double stranded PCR fragment of a PCIP coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the PCIP protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of PCIP proteins. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recrusive ensemble mutagenesis (REM), a new technique which enhances the frequency of functional mutants in the libraries, can be used in combination with the screening assays to identify PCIP variants (Arkin and Yourvan (1992) *Proc. Natl. Acad. Sci. USA* 89:7811-7815; Delgrave et al. (1993) *Protein Engineering* 6(3):327-331).

In one embodiment, cell based assays can be exploited to analyze a variegated PCIP library. For example, a library of expression vectors can be transfected into a cell line which ordinarily possesses a potassium channel mediated activity. The effect of the PCIP mutant on the potassium channel mediated activity can then be detected, e.g., by any of a number of enzymatic assays or by detecting the release of a neurotransmitter. Plasmid DNA can then be recovered from the cells which score for inhibition, or alternatively, potentiation of the potassium channel mediated activity, and the individual clones further characterized.

An isolated PCIP protein, or a portion or fragment thereof, can be used as an immunogen to generate antibodies that bind PCIP using standard techniques for polyclonal and monoclonal antibody preparation. A full-length PCIP protein can be used or, alternatively, the invention provides antigenic peptide fragments of PCIP for use as immunogens. The antigenic peptide of PCIP comprises at least 8 amino acid residues of the amino acid sequence shown in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:49, SEQ ID NO:51, SEQ ID NO:53, SEQ ID NO:55, SEQ ID NO:57, SEQ ID NO:59, SEQ ID NO:70, SEQ ID NO:72, SEQ ID NO:76, SEQ ID NO:78, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, or SEQ ID NO:109 and encompasses an epitope of PCIP such that an antibody raised against the peptide forms a specific immune complex with PCIP. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of PCIP that are located on the surface of the protein, e.g., hydrophilic regions, as well as regions with high antigenicity.

A PCIP immunogen typically is used to prepare antibodies by immunizing a suitable subject, (e.g., rabbit, goat, mouse or other mammal) with the immunogen. An appropriate immunogenic preparation can contain, for example, recombinantly expressed PCIP protein or a chemically synthesized PCIP polypeptide. The preparation can further include an adjuvant, such as Freund's complete or incomplete adjuvant, or similar immunostimulatory agent. Immunization of a suitable subject with an immunogenic PCIP preparation induces a polyclonal anti-PCIP antibody response.

Accordingly, another aspect of the invention pertains to anti-PCIP antibodies. The term "antibody" as used herein refers to immunoglobulin molecules and immunologically active portions of immunoglobulin molecules, i.e., molecules that contain an antigen binding site which specifically binds (immunoreacts with) an antigen, such as PCIP. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind PCIP. The term "monoclonal antibody" or "monoclonal antibody composition", as used herein, refers to a population of antibody molecules that contain only one species of an antigen binding site capable of immunoreacting with a particular epitope of PCIP. A monoclonal antibody composition thus typically displays a single binding affinity for a particular PCIP protein with which it immunoreacts.

Polyclonal anti-PCIP antibodies can be prepared as described above by immunizing a suitable subject with a PCIP immunogen. The anti-PCIP antibody titer in the immunized subject can be monitored over time by standard techniques, such as with an enzyme linked immunosorbent assay (ELISA) using immobilized PCIP. If desired, the antibody molecules directed against PCIP can be isolated from the mammal (e.g., from the blood) and further purified by well known techniques, such as protein A chromatography to obtain the IgG fraction. At an appropriate time after immunization, e.g. when the anti-PCIP antibody titers are highest, antibody-producing cells can be obtained from the subject and used to prepare monoclonal antibodies by standard techniques, such as the hybridoma technique originally described by Kohler and Milstein (1975) *Nature* 256:495-497) (see also, Brown et al. (1981) *J. Immunol.* 127:539-46; Brown et al. (1980) *J. Biol. Chem.* 255:4980-83; Yeh et al. (1976) *Proc. Natl. Acad. Sci. USA* 76:2927-31; and Yeh et al. (1982) *Int. J. Cancer* 29:269-75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77-96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.,* 54:387-402; M. L. Gefter et al. (1977) *Somatic Cell Genet.* 3:231-36). Briefly, an immortal cell line (typically a myeloma) is fused to lymphocytes (typically splenocytes) from a mammal immunized with a PCIP immunogen as described above, and the culture supernatants of the resulting hybridoma cells are screened to identify a hybridoma producing a monoclonal antibody that binds PCIP.

Any of the many well known protocols used for fusing lymphocytes and immortalized cell lines can be applied for the purpose of generating an anti-PCIP monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind PCIP, e.g., using a standard ELISA assay.

Alternative to preparing monoclonal antibody-secreting hybridomas, a monoclonal anti-PCIP antibody can be identified and isolated by screening a recombinant combinatorial immunoglobulin library (e.g., an antibody phage display library) with PCIP to thereby isolate immunoglobulin library members that bind PCIP. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370-1372; Hay et al. (1992) *Hum. Antibod. Hybridomnas* 3:81-85; Huse et al. (1989) *Science* 246: 1275-1281; Griffiths et al. (1993) *EMBO J* 12:725-734; Hawkins et al. (1992) *J. Mol. Biol.* 226:889-896; Clarkson et al. (1991) *Nature* 352:624-628; Gram et al. (1992) *Proc. Natl. Acad. Sci. USA* 89:3576-3580; Garrad et al. (1991) *Bio/Technology* 9:1373-1377; Hoogenboom et al. (1991) *Nuc. Acid Res.* 19:4133-4137; Barbas et al. (1991) *Proc. Natl. Acad. Sci. USA* 88:7978-7982; and McCafferty et al. *Nature* (1990) 348:552-554.

Additionally, recombinant anti-PCIP antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *BioTechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

An anti-PCIP antibody (e.g., monoclonal antibody) can be used to isolate PCIP by standard techniques, such as affinity chromatography or immunoprecipitation. An anti-PCIP antibody can facilitate the purification of natural PCIP from cells and of recombinantly produced PCIP expressed in host cells. Moreover, an anti-PCIP antibody can be used to detect PCIP protein (e.g., in a cellular lysate or cell supernatant) in order to evaluate the abundance and pattern of expression of the PCIP protein. Anti-PCIP antibodies can be used diagnostically to monitor protein levels in tissue as part of a clinical testing procedure, e.g., to, for example, determine the efficacy of a given treatment regimen. Detection can be facilitate by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, -galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

III. Recombinant Expression Vectors and Host Cells

Another aspect of the invention pertains to vectors, preferably expression vectors, containing a nucleic acid encoding a PCIP protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., PCIP proteins, mutant forms of PCIP proteins, fusion proteins, and the like).

The recombinant expression vectors of the invention can be designed for expression of PCIP proteins in prokaryotic or eukaryotic cells. For example, PCIP proteins can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in PCIP activity assays, (e.g., direct assays or competitive assays described in detail below), or to generate antibodies specific for PCIP proteins, for example. In a preferred embodiment, a PCIP fusion protein expressed in a retroviral expression vector of the present invention can be utilized to infect bone marrow cells which are subsequently transplanted into irradiated recipients. The pathology of the subject recipient is then examined after sufficient time has passed (e.g., six (6) weeks).

Examples of suitable inducible non-fusion *E. coli* expression vectors include pTrc (Amann et al., (1988) *Gene* 69:301-315) and pET 11d (Studier et al., *Gene Expression Technology Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111-2118). Such alteration of nucleic acid sequences of the invention can be carried out by standard DNA synthesis techniques.

In another embodiment, the PCIP expression vector is a yeast expression vector. Examples of vectors for expression in yeast *S. cerivisae* include pYepSec1 (Baldari, et al., (1987) *Embo J.* 6:229-234), pMFa (Kurjan and Herskowitz, (1982) *Cell* 30:933-943), pJRY88 (Schultz et al., (1987) *Gene* 54:113-123), pYES2 (Invitrogen Corporation, San Diego, Calif.), and picZ (InVitrogen Corp, San Diego, Calif.).

Alternatively, PCIP proteins can be expressed in insect cells using baculovirus expression vectors. Baculovirus vectors available for expression of proteins in cultured insect cells (e.g., Sf9 cells) include the pAc series (Smith et al. (1983) *Mol. Cell Biol.* 3:2156-2165) and the pVL series (Lucklow and Summers (1989) *Virology* 170:31-39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to PCIP mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a PCIP protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed, Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a PCIP protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a PCIP protein. Accordingly, the invention further provides methods for producing a PCIP protein using the host cells of the invention. In one embodiment, the method comprises culturing the host cell of invention (into which a recombinant expression vector encoding a PCIP protein has been introduced) in a suitable medium such that a PCIP protein is produced. In another embodiment, the method further comprises isolating a PCIP protein from the medium or the host cell.

The host cells of the invention can also be used to produce non-human transgenic animals. For example, in one embodiment, a host cell of the invention is a fertilized oocyte or an embryonic stem cell into which PCIP-coding sequences have been introduced. Such host cells can then be used to create non-human transgenic animals in which exogenous PCIP sequences have been introduced into their genome or homologous recombinant animals in which endogenous PCIP sequences have been altered. Such animals are useful for studying the function and/or activity of a PCIP and for identifying and/or evaluating modulators of PCIP activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous PCIP gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a PCIP-encoding nucleic acid into the male pronuclei of a fertilized oocyte, e.g., by microinjection, retroviral infection, and allowing the oocyte to develop in a pseudopregnant female foster animal. The PCIP cDNA sequence of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, SEQ ID NO:71, SEQ ID NO:74, SEQ ID NO:75, SEQ ID NO:77, SEQ ID NO:79, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, or SEQ ID NO:102 can be introduced as a transgene into the genome of a non-human animal. Alternatively, a nonhuman homologue of a human PCIP gene, such as a mouse or rat PCIP gene, can be used as a transgene. Alternatively, a PCIP gene homologue, such as another PCIP family member, can be isolated based on hybridization to the PCIP cDNA sequences of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, SEQ ID NO:71, SEQ ID NO:74, SEQ ID NO:75, SEQ ID NO:77, SEQ ID NO:79, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, or SEQ ID NO:102 or the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994 (described further in subsection I above) and used as a transgene. Intronic sequences and polyadenylation signals can also be included in the transgene to increase the efficiency of expression of the transgene. A tissue-specific regulatory sequence(s) can be operably linked to a PCIP transgene to direct expression of a PCIP protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of a PCIP transgene in its genome and/or expression of PCIP mRNA in tissues or cells of the animals. A transgenic founder animal can then be used to breed additional animals carrying the transgene. Moreover, transgenic animals carrying a transgene encoding a PCIP protein can further be bred to other transgenic animals carrying other transgenes.

To create a homologous recombinant animal, a vector is prepared which contains at least a portion of a PCIP gene into which a deletion, addition or substitution has been introduced to thereby alter, e.g., functionally disrupt, the PCIP gene. The PCIP gene can be a human gene (e.g., the cDNA of SEQ ID NO:1), but more preferably, is a non-human homologue of a human PCIP gene (e.g., the cDNA of SEQ ID NO:3 or 5). For example, a mouse PCIP gene can be used to construct a homologous recombination vector suitable for altering an endogenous PCIP gene in the mouse genome. In a preferred embodiment, the vector is designed such that, upon homologous recombination, the endogenous PCIP gene is functionally disrupted (i.e., no longer encodes a functional protein; also referred to as a "knock out" vector). Alternatively, the vector can be designed such that, upon homologous recombination, the endogenous PCIP gene is mutated or otherwise altered but still encodes functional protein (e.g., the upstream regulatory region can be altered to thereby alter the expression of the endogenous PCIP protein). In the homologous recombination vector, the altered portion of the PCIP gene is flanked at its 5' and 3' ends by additional nucleic acid sequence of the PCIP gene to allow for homologous recombination to occur between the exogenous PCIP gene carried by the vector and an endogenous PCIP gene in an embryonic stem cell. The additional flanking PCIP nucleic acid sequence is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced PCIP gene has homologously recombined with the endogenous PCIP gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823-829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al. (1991) *Science* 251:1351-1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810-813 and PCT International Publication Nos. WO 97/07668 and WO 97/07669. In brief, a cell, e.g., a somatic cell, from the transgenic animal can be isolated and induced to exit the growth cycle and enter $G_O$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The PCIP nucleic acid molecules, fragments of PCIP proteins, and anti-PCIP antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a fragment of a PCIP protein or an anti-PCIP antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha.-interferon, beta.-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982). Alternatively, an antibody can be conjugated to a second antibody to Form an antibody heteroconjugate as described by Segal in U.S. Pat. No. 4,676, 980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). As described herein, a PCIP protein of the invention has one or more of the following activities: (1) it interacts with (e.g., binds to) a potassium channel protein or portion thereof; (2) it regulates the phosphorylation state of a potassium channel protein or portion thereof; (3) it associates with (e.g., binds to) calcium and can, for example, act as a calcium dependent kinase, e.g., phosphorylate a potassium channel or a G-protein coupled receptor in a calcium-dependent manner; (4) it associates with (e.g., binds to) calcium and can, for example, act as a calcium dependent transcription factor; (5) it modulates a potassium channel mediated activity in a cell (e.g., a neuronal or cardiac cell) to, for example, beneficially affect the cell; (6) it modulates chromatin formation in a cell, e.g., a neuronal or cardiac cell; (7) it modulates vesicular traffic and protein transport in a cell, e.g., a neuronal or cardiac cell; (8) it modulates cytokine signaling in a cell, e.g., a neuronal or cardiac cell; (9) it regulates the association of a potassium channel protein or portion thereof with the cellular cytoskeleton; (10) it modulates cellular proliferation; (11) it modulates the release of neurotransmitters; (12) it modulates membrane excitability; (13) it influences the resting potential of membranes; (14) it modulates wave forms and frequencies of action potentials; and (15) it modulates thresholds of excitation and, thus, can be used to, for example, (1) modulate the activity of a potassium channel protein or portion thereof; (2) modulate the phosphorylation state of a potassium channel protein or portion thereof; (3) modulate the phosphorylation state of a potassium channel or a G-protein coupled receptor in a calcium-dependent manner; (4) associate with (e.g., bind to) calcium and act as a calcium dependent transcription factor; (5) modulate a potassium channel mediated activity in a cell (e.g., a neuronal or cardiac cell) to, for example, beneficially affect the cell; (6) modulate chromatin formation in a cell, e.g., a neuronal or cardiac cell; (7) modulate vesicular traffic and protein transport in a cell, e.g., a neuronal or cardiac cell; (8) modulate cytokine signaling in a cell, e.g., a neuronal or cardiac cell; (9) regulate the association of a potassium channel protein or portion thereof with the cellular cytoskeleton; (10) modulate cellular proliferation; (11) modulate the release of neurotransmitters; (12) modulate membrane excitability; (13) influence the resting potential of membranes; (14) modulate wave forms and frequencies of action potentials; and (15) modulate thresholds of excitation.

The isolated nucleic acid molecules of the invention can be used, for example, to express PCIP protein (e.g., via a recombinant expression vector in a host cell in gene therapy applications), to detect PCIP mRNA (e.g., in a biological sample) or a genetic alteration in a PCIP gene, and to modulate PCIP activity, as described further below. The PCIP proteins can be used to treat disorders characterized by insufficient or excessive production of a PCIP substrate or production of PCIP inhibitors. In addition, the PCIP proteins can be used to screen for naturally occurring PCIP substrates, to screen for drugs or compounds which modulate PCIP activity, as well as to treat disorders characterized by insufficient or excessive production of PCIP protein or production of PCIP protein forms which have decreased or aberrant activity compared to PCIP wild type protein (e.g., CNS disorders such as neurodegenerative disorders, e.g., Alzheimer's disease, dementias related to Alzheimer's disease (such as Pick's disease), Parkinson's and other Lewy diffuse body diseases, multiple sclerosis, amyotrophic lateral sclerosis, progressive supranuclear palsy, epilepsy, spinocerebellar ataxia, and Jakob-Creutzfieldt disease; psychiatric disorders, e.g., depression, schizophrenic disorders, Korsakoff's psychosis, mania, anxiety disorders, bipolar affective disorders, or phobic disorders; learning or memory disorders, e.g., amnesia or age-related memory loss; neurological disorders, e.g., migraine; pain disorders, e.g., hyperalgesia or pain associated with muscoloskeletal disorders; spinal cord injury; stroke; and head trauma; or cardiovascular disorders such as sinus node disfunction, angina, heart failure, hypertension, atrial fibrillation, atrial flutter, dilated cardiomyopathy, idiopathic cardiomyopathy, myocardial infarction, coronary artery disease, coronary artery spasm, or arrythmia). Moreover, the anti-PCIP antibodies of the invention can be used to detect and isolate PCIP proteins, regulate the bioavailability of PCIP proteins, and modulate PCIP activity.

A. Screening Assays:

The invention provides a method (also referred to herein as a "screening assay") for identifying modulators, i.e., candidate or test compounds or agents (e.g., peptides, peptidomimetics, small molecules or other drugs) which bind to PCIP proteins, have a stimulatory or inhibitory effect on, for example, PCIP expression or PCIP activity, or have a stimulatory or inhibitory effect on, for example, the expression or activity of PCIP substrate.

In one embodiment, the invention provides assays for screening candidate or test compounds which are substrates of a PCIP protein or polypeptide or biologically active portion thereof. In another embodiment, the invention provides assays for screening candidate or test compounds which bind to or modulate the activity of a PCIP protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37; 1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310); (Ladner supra.).

In one embodiment, an assay is a cell-based assay in which a cell which expresses a PCIP protein or biologically active portion thereof is contacted with a test compound and the ability of the test compound to modulate PCIP activity, e.g., binding to a potassium channel or a portion thereof, is determined. Determining the ability of the test compound to modulate PCIP activity can be accomplished by monitoring, for example, the release of a neurotransmitter, e.g., dopamine, form a cell which expresses PCIP such as a neuronal cell, e.g., a substantia nigra neuronal cell, or a cardiac cell. Furthermore, determining the ability of the test compound to modulate PCIP activity can be accomplished by monitoring, for example, the $I_{to}$ current or the release of a neurotransmitter from a cell which expresses PCIP such as a cardiac cell. Currents in cells, e.g., the $I_{to}$ current, can be measured using the patch-clamp technique as described in the Examples section using the techniques described in, for example, Hamill et al. 1981. Pfluegers Arch. 391: 85-100). The cell, for example, can be of mammalian origin. Determining the ability of the test compound to modulate the ability of PCIP to bind to a substrate can be accomplished, for example, by coupling the PCIP substrate with a radioisotope or enzymatic label such that binding of the PCIP substrate to PCIP can be determined by detecting the labeled PCIP substrate in a complex. For example, compounds (e.g., PCIP substrates) can be labeled with $^{125}I$, $^{35}S$, $^{14}C$, or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., PCIP substrate) to interact with PCIP without the labeling of any of the interactants. For example, a microphysiometer can be used to detect the interaction of a compound with PCIP without the labeling of either the compound or the PCIP. McConnell, H. M. et al. (1992) *Science* 257:1906-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and PCIP.

In another embodiment, an assay is a cell-based assay comprising contacting a cell expressing a PCIP target molecule (e.g., a potassium channel or a fragment thereof) with a test compound and determining the ability of the test compound to modulate (e.g. stimulate or inhibit) the activity of the PCIP target molecule. Determining the ability of the test compound to modulate the activity of a PCIP target molecule can be accomplished, for example, by determining the ability of the PCIP protein to bind to or interact with the PCIP target molecule, e.g., a potassium channel or a fragment thereof.

Determining the ability of the PCIP protein or a biologically active fragment thereof, to bind to or interact with a PCIP target molecule can be accomplished by one of the methods described above for determining direct binding. In a preferred embodiment, determining the ability of the PCIP protein to bind to or interact with a PCIP target molecule can be accomplished by determining the activity of the target molecule. For example, the activity of the target molecule can be determined by detecting induction of a cellular second messenger of the target (i.e., intracellular $Ca^{2+}$, diacylglycerol, $IP_3$, and the like), detecting catalytic/enzymatic activity of the target an appropriate substrate, detecting the induction of a reporter gene (comprising a target-responsive regulatory element operatively linked to a nucleic acid encoding a detectable marker, e.g., luciferase), or detecting a target-regulated cellular response such as the release of a neurotransmitter.

In yet another embodiment, an assay of the present invention is a cell-free assay in which a PCIP protein or biologically active portion thereof is contacted with a test compound and the ability of the test compound to bind to the PCIP protein or biologically active portion thereof is determined. Preferred biologically active portions of the PCIP proteins to be used in assays of the present invention include fragments which participate in interactions with non-PCIP molecules, e.g., potassium channels or fragments thereof, or fragments with high surface probability scores. Binding of the test compound to the PCIP protein can be determined either directly or indirectly as described above. In a preferred embodiment, the assay includes contacting the PCIP protein or biologically active portion thereof with a known compound which binds PCIP to form an assay mixture, contacting the assay mixture with a test compound, and determining the ability of the test compound to interact with a PCIP protein, wherein determining the ability of the test compound to interact with a PCIP protein comprises determining the ability of the test compound to preferentially bind to PCIP or biologically active portion thereof as compared to the known compound.

In another embodiment, the assay is a cell-free assay in which a PCIP protein or biologically active portion thereof is contacted with a test compound and the ability of the test compound to modulate (e.g., stimulate or inhibit) the activity of the PCIP protein or biologically active portion thereof is determined. Determining the ability of the test compound to modulate the activity of a PCIP protein can be accomplished, for example, by determining the ability of the PCIP protein to bind to a PCIP target molecule by one of the methods described above for determining direct binding. Determining the ability of the PCIP protein to bind to a PCIP target molecule can also be accomplished using a technology such as real-time Biomolecular Interaction Analysis (BIA). Sjolander, S, and Urbaniczky, C. (1991) *Anal. Chem.* 63:2338-2345 and Szabo et al. (1995) *Curr. Opin. Struct. Biol.* 5:699-705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of a PCIP protein can be accomplished by determining the ability of the PCIP protein to further modulate the activity of a downstream effector of a PCIP target molecule. For example, the activity of the effector molecule on an appropriate target can be determined or the binding of the effector to an appropriate target can be determined as previously described.

In yet another embodiment, the cell-free assay involves contacting a PCIP protein or biologically active portion thereof with a known compound which binds the PCIP protein to form an assay mixture, contacting the assay mixture with a test compound, and determining the ability of the test compound to interact with the PCIP protein, wherein determining the ability of the test compound to interact with the PCIP protein comprises determining the ability of the PCIP protein to preferentially bind to or modulate the activity of a PCIP target molecule.

The cell-free assays of the present invention are amenable to use of both soluble and/or membrane-bound forms of isolated proteins. In the case of cell-free assays in which a membrane-bound form of an isolated protein is used (e.g., a potassium channel) it may be desirable to utilize a solubilizing agent such that the membrane-bound form of the isolated protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either PCIP or its target molecule to facilitate separation of complexed from uncomplexed forms of one or both of the proteins, as well as to accommodate automation of the assay. Binding of a test compound to a PCIP protein, or interaction of a PCIP protein with a target molecule in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows one or both of the proteins to be bound to a matrix. For example, glutathione-S-transferase/PCIP fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or PCIP protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of PCIP binding or activity determined using standard techniques.

Other techniques for immobilizing proteins on matrices can also be used in the screening assays of the invention. For example, either a PCIP protein or a PCIP target molecule can be immobilized utilizing conjugation of biotin and streptavidin. Biotinylated PCIP protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with PCIP protein or target molecules but which do not interfere with binding of the PCIP protein to its target molecule can be derivatized to the wells of the plate, and unbound target or PCIP protein trapped in the wells by antibody conjugation. Methods for detecting such complexes, in addition to those described above for the GST-immobilized complexes, include immunodetection of complexes using antibodies reactive with the PCIP protein or target molecule, as well as enzyme-linked assays which rely on detecting an enzymatic activity associated with the PCIP protein or target molecule.

In a preferred embodiment, candidate or test compounds or agents are tested for their ability to inhibit or stimulate a PCIP molecule's ability to modulate vesicular traffic and protein transport in a cell, e.g., a neuronal or cardiac cell, using the assays described in, for example, Komada M. et al. (1999) *Genes Dev.* 13(11):1475-85, and Roth M. G. et al. (1999) *Chem. Phys. Lipids.* 98(1-2):141-52, the contents of which are incorporated herein by reference.

In another preferred embodiment, candidate or test compounds or agents are tested for their ability to inhibit or stimulate a PCIP molecule's ability to regulate the phosphorylation state of a potassium channel protein or portion thereof, using for example, an in vitro kinase assay. Briefly, a PCIP target molecule, e.g., an immunoprecipitated potassium channel from a cell line expressing such a molecule, can be incubated with the PCIP protein and radioactive ATP, e.g., [$\gamma$-$^{32}$P] ATP, in a buffer containing $MgCl_2$ and $MnCl_2$, e.g., 10 mM $MgCl_2$ and 5 mM $MnCl_2$. Following the incubation, the immunoprecipitated PCIP target molecule, e.g., the potassium channel, can be separated by SDS-polyacrylamide gel electrophoresis under reducing conditions, transferred to a membrane, e.g., a PVDF membrane, and autoradiographed. The appearance of detectable bands on the autoradiograph indicates that the PCIP substrate, e.g., the potassium channel, has been phosphorylated. Phosphoaminoacid analysis of the phosphorylated substrate can also be performed in order to determine which residues on the PCIP substrate are phosphorylated. Briefly, the radiophosphorylated protein band can be excised from the SDS gel and subjected to partial acid hydrolysis. The products can then be separated by one-dimensional electrophoresis and analyzed on, for example, a phosphoimager and compared to ninhydrin-stained phosphoaminoacid standards. Assays such as those described in, for example, Tamaskovic R. et al. (1999) *Biol. Chem.* 380(5): 569-78, the contents of which are incorporated herein by reference, can also be used.

In another preferred embodiment, candidate or test compounds or agents are tested for their ability to inhibit or stimulate a PCIP molecule's ability to associate with (e.g., bind) calcium, using for example, the assays described in Liu L. (1999) *Cell Signal.* 11(5):317-24 and Kawai T. et al. (1999) *Oncogene* 18(23):3471-80, the contents of which are incorporated herein by reference.

In another preferred embodiment, candidate or test compounds or agents are tested for their ability to inhibit or stimulate a PCIP molecule's ability to modulate chromatin formation in a cell, using for example, the assays described in Okuwaki M. et al. (1998) *J. Biol. Chem.* 273(51):34511-8 and Miyaji-Yamaguchi M. (1999) *J. Mol. Biol.* 290(2): 547-557, the contents of which are incorporated herein by reference.

In yet another preferred embodiment, candidate or test compounds or agents are tested for their ability to inhibit or stimulate a PCIP molecule's ability to modulate cellular proliferation, using for example, the assays described in Baker F. L. et al. (1995) *Cell Prolif.* 28(1):1-15, Cheviron N. et al. (1996) *Cell Prolif.* 29(8):437-46, Hu Z. W. et al. (1999) *J. Pharmacol. Exp. Ther.* 290(1):28-37 and Elliott K. et al. (1999) *Oncogene* 18(24):3564-73, the contents of which are incorporated herein by reference.

In a preferred embodiment, candidate or test compounds or agents are tested for their ability to inhibit or stimulate a PCIP molecule's ability to regulate the association of a potassium channel protein or portion thereof with the cellular cytoskeleton, using for example, the assays described in Gonzalez C. et al. (1998) *Cell Mol. Biol.* 44(7): 1117-27 and Chia C. P. et al. (1-998) *Exp. Cell Res.* 244(1):340-8, the contents of which are incorporated herein by reference.

In another preferred embodiment, candidate or test compounds or agents are tested for their ability to inhibit or stimulate a PCIP molecule's ability to modulate membrane excitability, using for example, the assays described in Bar-Sagi D. et al. (1985) *J. Biol. Chem.* 260(8):4740-4 and Barker J. L. et al. (1984) *Neurosci. Lett.* 47(3):313-8, the contents of which are incorporated herein by reference.

In another preferred embodiment, candidate or test compounds or agents are tested for their ability to inhibit or stimulate a PCIP molecule's ability to modulate cytokine signaling in a cell, e.g., a neuronal or cardiac cell, the assays described in Nakashima Y. et al. (1999) *J. Bone Joint Surg. Am.* 81(5):603-15, the contents of which are incorporated herein by reference.

In another embodiment, modulators of PCIP expression are identified in a method wherein a cell is contacted with a candidate compound and the expression of PCIP mRNA or protein in the cell is determined. The level of expression of PCIP mRNA or protein in the presence of the candidate compound is compared to the level of expression of PCIP mRNA or protein in the absence of the candidate compound. The candidate compound can then be identified as a modulator of PCIP expression based on this comparison. For example, when expression of PCIP mRNA or protein is greater (statistically significantly greater) in the presence of the candidate compound than in its absence, the candidate compound is identified as a stimulator of PCIP mRNA or protein expression. Alternatively, when expression of PCIP mRNA or protein is less (statistically significantly less) in the presence of the candidate compound than in its absence, the candidate compound is identified as an inhibitor of PCIP mRNA or protein expression. The level of PCIP mRNA or protein expression in the cells can be determined by methods described herein for detecting PCIP mRNA or protein.

In yet another aspect of the invention, the PCIP proteins can be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO94/10300), to identify other proteins, which bind to or interact with PCIP ("PCIP-binding proteins" or "PCIP-bp") and are involved in PCIP activity (described in more detail in the Examples section below). Such PCIP-binding proteins are also likely to be involved in the propagation of signals by the PCIP proteins or PCIP targets as, for example, downstream elements of a PCIP-mediated signaling pathway. Alternatively, such PCIP-binding proteins are likely to be PCIP inhibitors.

The two-hybrid system is based on the modular nature of most transcription factors, which consist of separable DNA-binding and activation domains. Briefly, the assay utilizes two different DNA constructs. In one construct, the gene that codes for a PCIP protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a PCIP-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the PCIP protein.

This invention further pertains to novel agents identified by the above-described screening assays. Accordingly, it is within the scope of this invention to further use an agent identified as described herein in an appropriate animal model. For example, an agent identified as described herein (e.g., a PCIP modulating agent, an antisense PCIP nucleic acid molecule, a PCIP-specific antibody, or a PCIP-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments, e.g., treatments of a CNS disorder or a cardiovascular disorder, as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the PCIP nucleotide sequences, described herein, can be used to map the location of the PCIP genes on a chromosome. The mapping of the PCIP sequences to chromosomes is an important first step in correlating these sequences with genes associated with disease.

Briefly, PCIP genes can be mapped to chromosomes by preparing PCR primers (preferably 15-25 bp in length) from the PCIP nucleotide sequences. Computer analysis of the PCIP sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the PCIP sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220:919-924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the PCIP nucleotide sequences to design oligonucleotide primers, sublocalization can be achieved with panels of fragments from specific chromosomes. Other mapping strategies which can similarly be used to map a PCIP sequence to its chromosome include in situ hybridization (described in Fan, Y. et al. (1990) *Proc. Natl. Acad. Sci. USA,* 87:6223-27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature,* 325:783-787.

Moreover, differences in the DNA sequences between individuals affected and unaffected with a disease associated with the PCIP gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The PCIP sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the PCIP nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The PCIP nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. Non-coding sequences can comfortably provide positive individual identification with a panel of perhaps 10 to 1,000 primers which each yield a noncoding amplified sequence of 100 bases. If predicted coding sequences are used, a more appropriate number of primers for positive individual identification would be 500-2,000.

If a panel of reagents from PCIP nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of Partial PCIP Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions are particularly appropriate for this use as greater numbers of polymorphisms occur in the noncoding regions, making it easier to differentiate individuals using this technique. Examples of polynucleotide reagents include the PCIP nucleotide sequences or portions thereof, having a length of at least 20 bases, preferably at least 30 bases.

The PCIP nucleotide sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such PCIP probes can be used to identify tissue by species and/or by organ type.

In a similar fashion, these reagents, e.g., PCIP primers or probes can be used to screen tissue culture for contamination (i.e. screen for the presence of a mixture of different types of cells in a culture).

C. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining PCIP protein and/or nucleic acid expression as well as PCIP activity, in the context of a biological sample (e.g., blood, serum, cells, tissue) to thereby determine whether an individual is afflicted with a disease or disorder, or is at risk of developing a disorder, associated with aberrant PCIP expression or activity. The invention also provides for prognostic (or predictive) assays for determining whether an individual is at risk of developing a disorder associated with PCIP protein, nucleic acid expression or activity. For example, mutations in a PCIP gene can be assayed in a biological sample. Such assays can be used for prognostic or predictive purpose to thereby phophylactically treat an individual prior to the onset of a disorder characterized by or associated with PCIP protein, nucleic acid expression or activity.

Another aspect of the invention pertains to monitoring the influence of agents (e.g., drugs, compounds) on the expression or activity of PCIP in clinical trials.

These and other agents are described in further detail in the following sections.

1. Diagnostic Assays

An exemplary method for detecting the presence or absence of PCIP protein or nucleic acid in a biological sample involves obtaining a biological sample from a test subject and contacting the biological sample with a compound or an agent capable of detecting PCIP protein or nucleic acid (e.g., mRNA, genomic DNA) that encodes PCIP protein such that the presence of PCIP protein or nucleic acid is detected in the biological sample. A preferred agent for detecting PCIP mRNA or genomic DNA is a labeled nucleic acid probe capable of hybridizing to PCIP mRNA or genomic DNA. The nucleic acid probe can be, for example, a full-length PCIP nucleic acid, such as the nucleic acid of SEQ ID NO:1, SEQ ID NO:3 SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:46, SEQ ID NO:47, SEQ ID NO:48, SEQ ID NO:50, SEQ ID NO:52, SEQ ID NO:54, SEQ ID NO:56, SEQ ID NO:58, SEQ ID NO:69, SEQ ID NO:71, SEQ ID NO:74, SEQ ID NO:75, SEQ ID NO:77, SEQ ID NO:79, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, or SEQ ID NO:102, or the DNA insert of the plasmid deposited with ATCC as Accession Number 98936, 98937, 98938, 98939, 98940, 98941, 98942, 98943, 98944, 98945, 98946, 98947, 98948, 98949, 98950, 98951, 98991, 98993, or 98994, or a portion thereof, such as an oligonucleotide of at least 15, 30, 50, 100, 250 or 500 nucleotides in length and sufficient to specifically hybridize under stringent conditions to PCIP mRNA or genomic DNA. Other suitable probes for use in the diagnostic assays of the invention are described herein.

A preferred agent for detecting PCIP protein is an antibody capable of binding to PCIP protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect PCIP mRNA, protein, or genomic DNA in a biological sample in vitro as well as in vivo. For example, in vitro techniques for detection of PCIP mRNA include Northern hybridizations and in situ hybridizations. In vitro techniques for detection of PCIP protein include enzyme linked immunosorbent assays (ELISAs), Western blots, immunoprecipitations and immunofluorescence. In vitro techniques for detection of PCIP genomic DNA include Southern hybridizations. Furthermore, in vivo techniques for detection of PCIP protein include introducing into a subject a labeled anti-PCIP antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample or cerebrospinal fluid isolated by conventional means from a subject.

In another embodiment, the methods further involve obtaining a control biological sample from a control subject, contacting the control sample with a compound or agent capable of detecting PCIP protein, mRNA, or genomic DNA, such that the presence of PCIP protein, mRNA or genomic DNA is detected in the biological sample, and comparing the presence of PCIP protein, mRNA or genomic DNA in the control sample with the presence of PCIP protein, mRNA or genomic DNA in the test sample.

The invention also encompasses kits for detecting the presence of PCIP in a biological sample. For example, the kit can comprise a labeled compound or agent capable of detecting PCIP protein or mRNA in a biological sample; means for determining the amount of PCIP in the sample; and means for comparing the amount of PCIP in the sample with a standard. The compound or agent can be packaged in a suitable container. The kit can further comprise instructions for using the kit to detect PCIP protein or nucleic acid.

2. Prognostic Assays

The diagnostic methods described herein can furthermore be utilized to identify subjects having or at risk of developing a disease or disorder associated with aberrant PCIP expression or activity. For example, the assays described herein, such as the preceding diagnostic assays or the following assays, can be utilized to identify a subject having or at risk of developing a disorder associated with a misregulation in PCIP protein activity or nucleic acid expression, such as a neurodegenerative disorder, e.g., Alzheimer's disease, dementias related to Alzheimer's disease (such as Pick's disease), Parkinson's and other Lewy diffuse body diseases, multiple sclerosis, amyotrophic lateral sclerosis, progressive supranuclear palsy, epilepsy, spinocerebellar ataxia, and Jakob-Creutzfieldt disease; a psychiatric disorder, e.g., depression, schizophrenic disorders, Korsakoff's psychosis, mania, anxiety disorders, bipolar affective disorders, or phobic disorders; a learning or memory disorder, e.g., amnesia or age-related memory loss; a neurological disorder, e.g., migraine; a pain disorder, e.g., hyperalgesia or pain associated with muscoloskeletal disorders; spinal cord injury; stroke; and head trauma; or a cardiovascular disorder, e.g., sinus node dysfunction, angina, heart failure, hypertension, atrial fibrillation, atrial flutter, dilated cardiomyopathy, idiopathic cardiomyopathy, myocardial infarction, coronary artery disease, coronary artery spasm, or arrythmia.

Alternatively, the prognostic assays can be utilized to identify a subject having or at risk for developing a disorder associated with a misregulation in PCIP protein activity or nucleic acid expression, such as a potassium channel associated disorder. Thus, the present invention provides a method for identifying a disease or disorder associated with aberrant PCIP expression or activity in which a test sample is obtained from a subject and PCIP protein or nucleic acid (e.g., mRNA or genomic DNA) is detected, wherein the presence of PCIP protein or nucleic acid is diagnostic for a subject having or at risk of developing a disease or disorder associated with aberrant PCIP expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant PCIP expression or activity. For example, such methods can be used to determine whether a subject can be effectively treated with an agent for a CNS disorder or a cardiovascular disorder. Thus, the present invention provides methods for determining whether a subject can be effectively treated with an agent for a disorder associated with aberrant PCIP expression or activity in which a test sample is obtained and PCIP protein or nucleic acid expression or activity is detected (e.g., wherein the abundance of PCIP protein or nucleic acid expression or activity is diagnostic for a subject that can be administered the agent to treat a disorder associated with aberrant PCIP expression or activity).

The methods of the invention can also be used to detect genetic alterations in a PCIP gene, thereby determining if a subject with the altered gene is at risk for a disorder characterized by misregulation in PCIP protein activity or nucleic acid expression, such as a CNS disorder or a cardiovascular disorder. In preferred embodiments, the methods include detecting, in a sample of cells from the subject, the presence or absence of a genetic alteration characterized by at least one of an alteration affecting the integrity of a gene encoding a PCIP-protein, or the mis-expression of the PCIP gene. For example, such genetic alterations can be detected by ascertaining the existence of at least one of 1) a deletion of one or more nucleotides from a PCIP gene; 2) an addition of one or more nucleotides to a PCIP gene; 3) a substitution of one or more nucleotides of a PCIP gene, 4) a chromosomal rearrangement of a PCIP gene; 5) an alteration in the level of a messenger RNA transcript of a PCIP gene, 6) aberrant modification of a PCIP gene, such as of the methylation pattern of the genomic DNA, 7) the presence of a non-wild type splicing pattern of a messenger RNA transcript of a PCIP gene, 8) a non-wild type level of a PCIP-protein, 9) allelic loss of a PCIP gene, and 10) inappropriate post-translational modification of a PCIP-protein. As described herein, there are a large number of assays known in the art which can be used for detecting alterations in a PCIP gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683, 202), such as anchor PCR or RACE PCR, or, alternatively, in a ligation chain reaction (LCR) (see, e.g., Landegran et al. (1988) *Science* 241:1077-1080; and Nakazawa et al. (1994) *Proc. Natl. Acad. Sci. USA* 91:360-364), the latter of which can be particularly useful for detecting point mutations in the PCIP-gene (see Abravaya et al. (1995) *Nucleic Acids Res* 23:675-682). This method can include the steps of collecting a sample of cells from a subject, isolating nucleic acid (e.g., genomic, mRNA or both) from the cells of the sample, contacting the nucleic acid sample with one or more primers which specifically hybridize to a PCIP gene under conditions such that hybridization and amplification of the PCIP-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad. Sci. USA* 87:1874-1878), transcriptional amplification system (Kwoh, D. Y. et al., (1989) *Proc. Natl. Acad. Sci. USA* 86:1173-1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a PCIP gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in PCIP can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244-255; Kozal, M. J. et al. (1996) *Nature Medicine* 2: 753-759). For example, genetic mutations in PCIP can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the PCIP gene and detect mutations by comparing the sequence of the sample PCIP with the corresponding wild-type (control) sequence. Examples of sequencing reactions include those based on techniques developed by Maxam and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127-162; and Griffin et al. (1993) *Appl. Biochem. Biotechnol.* 38:147-159).

Other methods for detecting mutations in the PCIP gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type PCIP sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl Acad Sci USA* 85:4397; Saleeba et al. (1992) *Methods Enzymol.* 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in PCIP cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662). According to an exemplary embodiment, a probe based on a PCIP sequence, e.g., a wild-type PCIP sequence, is hybridized to a cDNA or other DNA product from a test cell(s). The duplex is treated with a DNA mismatch repair enzyme, and the cleavage products, if any, can be detected from electrophoresis protocols or the like. See, for examples U.S. Pat. No. 5,459,039.

In other embodiments, alterations in electrophoretic mobility will be used to identify mutations in PCIP genes. For example, single strand conformation polymorphism (SSCP) may be used to detect differences in electrophoretic mobility between mutant and wild type nucleic acids (Orita et al. (1989) *Proc Natl. Acad. Sci. USA:* 86:2766, see also Cotton (1993) *Mutat. Res.* 285:125-144; and Hayashi (1992) *Genet. Anal. Tech. Appl.* 9:73-79). Single-stranded DNA fragments of sample and control PCIP nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313: 495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl. Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a PCIP gene.

Furthermore, any cell type or tissue in which PCIP is expressed may be utilized in the prognostic assays described herein.

3. Monitoring of Effects During Clinical Trials

Monitoring the influence of agents (e.g., drugs) on the expression or activity of a PCIP protein (e.g., the modulation of membrane excitability or resting potential) can be applied not only in basic drug screening, but also in clinical trials. For example, the effectiveness of an agent determined by a screening assay as described herein to increase PCIP gene expression, protein levels, or upregulate PCIP activity, can be monitored in clinical trials of subjects exhibiting decreased PCIP gene expression, protein levels, or downregulated PCIP activity. Alternatively, the effectiveness of an agent determined by a screening assay to decrease PCIP gene expression, protein levels, or down-regulate PCIP activity, can be monitored in clinical trials of subjects exhibiting increased PCIP gene expression, protein levels, or upregulated PCIP activity. In such clinical trials, the expression or activity of a PCIP gene, and preferably, other genes that have been implicated in, for example, a potassium channel associated disorder can be used as a "read out" or markers of the phenotype of a particular cell.

For example, and not by way of limitation, genes, including PCIP, that are modulated in cells by treatment with an agent (e.g., compound, drug or small molecule) which modulates PCIP activity (e.g., identified in a screening assay as described herein) can be identified. Thus, to study the effect of agents on potassium channel associated disorders, for example, in a clinical trial, cells can be isolated and RNA prepared and analyzed for the levels of expression of PCIP and other genes implicated in the potassium channel associated disorder, respectively. The levels of gene expression (e.g., a gene expression pattern) can be quantified by northern blot analysis or RT-PCR, as described herein, or alternatively by measuring the amount of protein produced, by one of the methods as described herein, or by measuring the levels of activity of PCIP or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a preadministration sample from a subject prior to administration of the agent; (ii) detecting the level of expression of a PCIP protein, mRNA, or genomic DNA in the preadministration sample; (iii) obtaining one or more post-administration samples from the subject; (iv) detecting the level of expression or activity of the PCIP protein, mRNA, or genomic DNA in the post-administration samples; (v) comparing the level of expression or activity of the PCIP protein, mRNA, or genomic DNA in the pre-administration sample with the PCIP protein, mRNA, or genomic DNA in the post administration sample or samples; and (vi) altering the administration of the agent to the subject accordingly. For example, increased administration of the agent may be desirable to increase the expression or activity of PCIP to higher levels than detected, i.e., to increase the effectiveness of the agent. Alternatively, decreased administration of the agent may be desirable to decrease expression or activity of PCIP to lower levels than detected, i.e. to decrease the effectiveness of the agent. According to such an embodiment, PCIP expression or activity may be used as an indicator of the effectiveness of an agent, even in the absence of an observable phenotypic response.

D. Methods of Treatment:

The present invention provides for both prophylactic and therapeutic methods of treating a subject at risk of (or susceptible to) a disorder or having a disorder associated with aberrant PCIP expression or activity. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the PCIP molecules of the present invention or PCIP modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant PCIP expression or activity, by administering to the subject a PCIP or an agent which modulates PCIP expression or at least one PCIP activity. Subjects at risk for a disease which is caused or contributed to by aberrant PCIP expression or activity can be identified by, for example, any or a combination of diagnostic or prognostic assays as described herein. Administration of a prophylactic agent can occur prior to the manifestation of symptoms characteristic of the PCIP aberrancy, such that a disease or disorder is prevented or, alternatively, delayed in its progression. Depending on the type of PCIP aberrancy, for example, a PCIP, PCIP agonist or PCIP antagonist agent can be used for treating the subject. The appropriate agent can be determined based on screening assays described herein.

2. Therapeutic Methods

Another aspect of the invention pertains to methods of modulating PCIP expression or activity for therapeutic purposes. Accordingly, in an exemplary embodiment, the modulatory method of the invention involves contacting a cell with a PCIP or agent that modulates one or more of the activities of PCIP protein activity associated with the cell. An agent that modulates PCIP protein activity can be an agent as described herein, such as a nucleic acid or a protein, a naturally-occurring target molecule of a PCIP protein (e.g., a PCIP substrate), a PCIP antibody, a PCIP agonist or antagonist, a peptidomimetic of a PCIP agonist or antagonist, or other small molecule. In one embodiment, the agent stimulates one or more PCIP activities. Examples of such stimulatory agents include active PCIP protein and a nucleic acid molecule encoding PCIP that has been introduced into the cell. In another embodiment, the agent inhibits one or more PCIP activities. Examples of such inhibitory agents include antisense PCIP nucleic acid molecules, anti-PCIP antibodies, and PCIP inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a PCIP protein or nucleic acid molecule. Examples of such disorders include CNS disorders such as neurodegenerative disorders, e.g., Alzheimer's disease, dementias related to Alzheimer's disease (such as Pick's disease), Parkinson's and other Lewy diffuse body diseases, multiple sclerosis, amyotrophic lateral sclerosis, progressive supranuclear palsy, epilepsy, and Jakob-Creutzfieldt disease; psychiatric disorders, e.g., depression, schizophrenic disorders, Korsakoff's psychosis, mania, anxiety disorders, bipolar affective disorders, or phobic disorders; learning or memory disorders; e.g., amnesia or age-related memory loss; neurological disorders, e.g., migraine; pain disorders, e.g., hyperalgesia or pain associated with muscoloskeletal disorders; spinal cord injury; stroke; and head trauma; or cardiovascular disorders, e.g., arteriosclerosis, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, atrial fibrillation, long-QT syndrome, congestive heart failure, sinus node disfunction, angina, heart failure, hypertension, atrial fibrillation, atrial flutter, dilated cardiomyopathy, idiopathic cardiomyopathy, myocardial infarction, coronary artery disease, coronary artery spasm, or arrhythmia. In one embodiment, the method involves administering an agent (e.g., an agent identified by a screening assay described herein), or combination of agents that modulates (e.g., upregulates or downregulates) PCIP expression or activity. In another embodiment, the method involves administering a PCIP protein or nucleic acid molecule as therapy to compensate for reduced or aberrant PCIP expression or activity.

A preferred embodiment of the present invention involves a method for treatment of a PCIP associated disease or disorder which includes the step of administering a therapeutically effective amount of a PCIP antibody to a subject. As defined herein, a therapeutically effective amount of antibody (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an antibody can include a single treatment or, preferably, can include a series of treatments. In a preferred example, a subject is treated with antibody in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody used for treatment may increase or decrease over the course of a particular treatment. Changes in dosage may result from the results of diagnostic assays as described herein.

Stimulation of PCIP activity is desirable in situations in which PCIP is abnormally downregulated and/or in which increased PCIP activity is likely to have a beneficial effect. For example, stimulation of PCIP activity is desirable in situations in which a PCIP is downregulated and/or in which increased PCIP activity is likely to have a beneficial effect. Likewise, inhibition of PCIP activity is desirable in situations in which PCIP is abnormally upregulated and/or in which decreased PCIP activity is likely to have a beneficial effect.

3. Pharmacogenomics

The PCIP molecules of the present invention, as well as agents, or modulators which have a stimulatory or inhibitory effect on PCIP activity (e.g., PCIP gene expression) as identified by a screening assay described herein can be administered to individuals to treat (prophylactically or therapeutically) potassium channel associated disorders associated with aberrant PCIP activity (e.g, CNS disorders such as neurodegenerative disorders, e.g., Alzheimer's disease, dementias related to Alzheimer's disease (such as Pick's disease), Parkinson's and other Lewy diffuse body diseases, multiple sclerosis, amyotrophic lateral sclerosis, progressive supranuclear palsy, epilepsy, spinocerebellar ataxia, and Jakob-Cretitzfieldt disease; psychiatric disorders, e.g., depression, schizophrenic disorders, Korsakoff's psychosis, mania, anxiety disorders, bipolar affective disorders, or phobic disorders; learning or memory disorders, e.g., amnesia or age-related memory loss; neurological disorders, e.g., migraine; pain disorders, e.g., hyperalgesia or pain associated with muscoloskeletal disorders; spinal cord injury; stroke; and head trauma; or cardiovascular disorders such as arteriosclerosis, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, atrial fibrilation, long-QT syndrome, congestive heart failure, sinus node disfunction, angina, heart failure, hypertension, atrial fibrillation, atrial flutter, dilated cardiomyopathy, idiopathic cardiomyopathy, myocardial infarction, coronary artery disease, coronary artery spasm, or arrhythmia). In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a PCIP molecule or PCIP modulator as well as tailoring the dosage and/or therapeutic regimen of treatment with a PCIP molecule or PCIP modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10-11):983-985 and Linder, M. W. et al. (1997) *Clin. Chem.* 43(2):254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., a PCIP protein of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyl-transferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a PCIP molecule or PCIP modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a PCIP molecule or PCIP modulator, such as a modulator identified by one of the exemplary screening assays described herein.

4. Use of PCIP Molecules as Surrogate Markers

The PCIP molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the PCIP molecules of the invention may be detected, and may be correlated with one or more biological states in vivo. For example, the PCIP molecules of the invention may serve as surrogate markers for one or more disorders or disease states or for conditions leading up to disease states.

As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the causation of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35:258-264; and James (1994) *AIDS Treatment News Archive* 209.

The PCIP molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., a PCIP marker) transcription or expression, the amplified marker may be in a quantity which is more readily detectable than the drug itself. Also, the marker may be more easily detected due to the nature of the marker itself; for example, using the methods described herein, anti-PCIP antibodies may be employed in an immune-based detection system for a PCIP protein marker, or PCIP-specific radiolabeled probes may be used to detect a PCIP mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90:229-238; Schentag (1999) *Am. J. Health-Syst. Pharm.* 56 Suppl. 3:S21-S24; and Nicolau (1999) *Am. J. Health-Syst. Pharm.* 56 Suppl. 3:S16-S20.

The PCIP molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35(12):1650-1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., PCIP protein or RNA) for specific tumor markers in a subject, a drug or course of treatment may be selected that is optimized for the treatment of the specific tumor likely to be present in the subject. Similarly, the presence or absence of a specific sequence mutation in PCIP DNA may correlate PCIP drug response. The use of pharmacogenomic markers therefore permits the application of the most appropriate treatment for each subject without having to administer the therapy.

This invention is further illustrated by the following examples which should not be construed as limiting. The contents of all references, patents and published patent appli-

EXAMPLES

The following materials and methods were used in the Examples.

Strains, Plasmids, Bait cDNAs, and General Microbiological Techniques

Basic yeast strains (HF7c, Y187) bait (pGBT9) and fish (pACT2) plasmids used in this work were purchased from Clontech (Palo Alto, Calif.). cDNAs encoding rat Kv4.3, Kv4.2, and Kv1.1, were provided by Wyeth-Ayerst Research (865 Ridge Rd., Monmouth Junction, N.J. 08852) Standard yeast media including synthetic complete medium lacking L-leucine, L-tryptophan, and L-histidine were prepared and yeast genetic manipulations were performed as described (Sherman (1991) *Meth. Enzymol.* 194:3-21). Yeast transformations were performed using standard protocols (Gietz et al. (1992) *Nucleic Acids Res.* 20:1425; Ito et al (1983) *J. Bacteriol.* 153:163-168). Plasmid DNAs were isolated from yeast strains by a standard method (Hoffman and Winston (1987) *Gene* 57:267-272).

Bait and Yeast Strain Construction

The first 180 amino acids of rKv4.3 (described in Serdio P. et al. (1996) *J. Neurophys* 75:2174-2179) were amplified by PCR and cloned in frame into pGBT9 resulting in plasmid pFWA2, (hereinafter "bait"). This bait was transformed into the two-hybrid screening strain HF7c and tested for expression and self-activation. The bait was validated for expression by Western blotting. The rKv4.3 bait did not self-activate in the presence of 10 mM 3-amino-1,2,3-Triazole (3-AT).

Library Construction

Rat mid brain tissue was provided by Wyeth-Ayerst Research (Monmouth Junction, N.J.). Total cellular RNA was extracted from the tissues using standard techniques (Sambrook, J., Fritsh, E. F., and Maniatis, T. *Molecular Cloning: A Laboratory Manual.* 2nd, ed, Cold Spring Harbor Laboratory, Cold Spring Harbor Laboratory Press, Cold Spring Harbor, N.Y., (1989)). mRNA was prepared using a Poly-A Spin mRNA Isolation Kit from New England Biolabs (Beverly, Mass.). cDNA from the mRNA sample was synthesized using a cDNA Synthesis Kit from Stratagene (La Jolla, Calif.) and ligated into pACT2's EcoRI and XhoI sites, giving rise to a two-hybrid library.

Two-Hybrid Screening

Two-hybrid screens were carried out essentially as described in Bartel, P. et al. (1993) "Using the Two-Hybrid System to Detect Polypeptide-Polypeptide Interactions" in Cellular Interactions in Development: A Practical Approach, Hartley, D. A. ed. Oxford University Press, Oxford, pp. 153-179, with a bait-library pair of rkv4.3 bait-rat mid brain library. A filter disk beta-galactosidase (beta-gal) assay was performed essentially as previously described (Brill et al. (1994) *Mol. Biol. Cell.* 5:297-312). Clones that were positive for both reporter gene activity (His and beta-galactosidase) were scored and fish, plasmids were isolated from yeast, transformed into *E. coli* strain KC8, DNA plasmids were purified and the resulting plasmids were sequenced by conventional methods (Sanger F. et al. (1977) *PNAS,* 74: 5463-67).

Specificity Test

Positive interactor clones were subjected to a binding specificity test where they were exposed to a panel of related and unrelated baits by a mating scheme previously described (Finley R. L. Jr. et al. (1994) *PNAS,* 91(26):12980-12984). Briefly, positive fish plasmids were transformed into Y187 and the panel of baits were transformed into HF7c. Transformed fish and bait cells were streaked out as stripes on selective medium plates, mated on YPAD plates, and tested for reporter gene activity.

Analysis

PCIP nucleotides were analyzed for nucleic acid hits by the BLASTN 1.4.8 MP program (Altschul et al. (1990) Basic Local Alignment Search Tool. *J. Mol. Biol.* 215: 403-410). PCIP proteins were analyzed for polypeptide hits by the BLASTP 1.4.9 MP program.

Electrophysiology Methods

Mammalian In Vitro Studies

HEK 293 and CHO cells were used for recordings 1-3 days after a transient transfection. Whole-cell currents were recorded from cells expressing GFP, identified by their green fluorescence. Electrodes pulled from filamented borosilicate glass (Sutter Instrument Co, Novato, Calif.) had an initial resistance of 3-5 MOhms. After Gigaseal and ruptured whole-cell configuration access, resistance was less than 10 MOhms. Whole-cell bath solutions were made from a 10× Hank's balanced salt solution (GibcoBRL) with the following final concentration (in mM): 138 NaCl, 5.4 KCl, 1.3 $MgCl_2$, 1.3 $CaCl_2$, 5.5 D-Glukos and 10 HEPES, pH 7.4. The intracellular electrode solution consisted of (in mM) 140 KCl, 10 HEPES, 10 EGTA, 0.5 MgCl2, pH 7.3. All chemicals were from Sigma (St. Louis, Mo.) or Fisher Scientific (Houston, Tex.). Membrane currents were recorded using a EPC9 patch-clamp amplifier (HEKA, Germany). Data were analyzed using Matlab (Natick, Ma), and leak subtracted if necessary. All experiments were done at room temperature.

*Xenopus* Oocyte Studies

Frogs underwent no more than two surgeries and surgeries were performed by well established techniques. Frogs were anesthetized with ice. Total cRNA (1-10 ng) was injected into stage IV *Xenopus* oocytes that were harvested the previous day. The *Xenopus* oocytes were incubated in ND96 containing (in mM) 96 NaCl, 2 KCl, 1.8 $CaCl_2$, 1 $MgCl_2$, 5 HEPES, pH 7.6, plus (Gentamycin 50 µg/ml) at 18° C. *Xenopus* oocytes were studied 3-7 days after injection. The two-electrode voltage-clamp recordings were performed in ND96 solution using a TURBO TEC 03 Clamp Amplifier (ALA Scientific Instruments, Westbury, N.Y.). Both electrodes were filled with 3 M KCl and had electrode resistances ranging from 0.2-1 MOhm. The current signals were filtered at 1000 Hz before transferred on a PC (Gateway, Calif.) using the PULSE software (HEKA, Germany).

Example 1

Identification of Rat PCIP cDNAs

The Kv4.3 gene coding sequence (coding for the first 180 amino acids) was amplified by PCR and cloned into pGBT9 creating a GAL4 DNA-binding domain-Kv4.3(1-180) gene fusion (plasmid pFWA2). HF7c was transformed with this construct. The resulting strain grew on synthetic complete medium lacking L-tryptophan but not on synthetic complete medium lacking L-tryptophan and L-histidine in the presence of 10 mM 3-AT demonstrating that the {GAL4 DNA-binding domain}-{vKv4.3(1-180)} gene fusion does not have intrinsic transcriptional activation activity higher than the threshold allowed by 10 mM 3-AT.

In this example, a yeast two-hybrid assay was performed in which a plasmid containing a {GAL4 DNA-binding domain}-{rKv4.3(1-180)} gene fusion was introduced into the yeast two-hybrid screening strain HF7c described above. HF7c was then transformed with the rat mid brain two-hybrid library. Approximately six million transformants were obtained and plated in selection medium. Colonies that grew in the selection medium and expressed the beta-galactosidase reporter gene were further characterized and subjected to retransformation and specificity assays. The retransformation and specificity tests yielded three PCIP clones (rat 1v, 8t, and 9qm) that were able to bind to the Kv4.3 polypeptide.

The full length sequences for the rat 1v gene, and partial sequences for 8t and 9q genes were derived as follows. The partial rat PCIP sequences were used to prepare probes, which were then used to screen, for example, rat mid brain cDNA libraries. Positive clones were identified, amplified and sequenced using standard techniques, to obtain the full length sequence. Additionally, a rapid amplification of the existing rat PCIP cDNA ends (using for example, 5' RACE, by Gibco, BRL) was used to complete the 5' end of the transcript.

Example 2

Identification of Human 1v cDNA

To obtain the human 1v nucleic acid molecule, a cDNA library made from a human hippocampus (Clontech, Palo Alto, Calif.) was screened under low stringency conditions as follows: Prehybridization for 4 hours at 42° C. in Clontech Express Hyb solution, followed by overnight hybridization at 42° C. The probe used was a PCR-generated fragment including nucleotides 49-711 of the rat sequence labeled with $^{32}P$ dCTP. The filters were washed 6 times in 2×SSC/0.1% SDS at 55° C. The same conditions were used for secondary screening of the positive isolates. Clones thus obtained were sequenced using an ABI automated DNA Sequencing system, and compared to the rat sequences shown in SEQ ID NO:3 as well as to known sequences from the GenBank database. The largest clone from the library screen was subsequently subcloned into pBS-KS+ (Stratagene, La Jolla, Calif.) for sequence verification. The 515 base pair clone was determined to represent the human homolog of the 1v gene, encompassing 211 base pairs of 5' UTR and a 304 base pair coding region. To generate the full-length cDNA, 3' RACE was used according to the manufacturers instructions (Clontech Advantage PCR kit).

Example 3

Isolation and Characterization of 1v Splice Variants

The mouse 1v shown in SEQ ID NO:5 and the rat 1vl splice variant shown in SEQ ID NO:7 was isolated using a two-hybrid assay as described in Example 1. The mouse 1vl splice variant shown in SEQ ID NO: 7 was isolated by screening a mouse brain cDNA library, and the rat 1vn splice variant shown in SEQ ID NO:11 was isolated by BLAST searching.

Example 4

Isolation and Identification of 9Q and Other PCIPs

Rat 9ql (SEQ ID NO: 15) was isolated by database mining, rat 9qm (SEQ ID NO: 21) was isolated by a two-hybrid assay, and rat 9qc (SEQ ID NO:27) was identified by database mining. Human 9ql (SEQ ID NO: 13), and human 9qs (SEQ ID NO: 23) were identified as described in Example 2. Mouse 9ql (SEQ ID NO:17), monkey 9qs (SEQ ID NO:25), human p193 (SEQ ID NO:39), rat p19 (SEQ ID NO:33), and mouse p19 (SEQ ID NO:35) were identified by database mining. Rat 8t (SEQ ID NO:29) was identified using a two-hybrid assay. The sequence of W28559 (SEQ ID NO:37) was identified by database mining and sequencing of the identified EST with Genbank Accession Number A1352454. The protein sequence was found to contain a 41 amino acid region with strong homology to 1v, 9ql, and p19 (see alignment in FIG. 25). However, downstream of this homologous region the sequence diverges from that of the PCIP family. This sequence could represent a gene which possesses a 41 amino acid domain with homology to a similar domain found in the PCIP family members.

The human genomic 9q sequence (SEQ ID NOs:46 and 47) was isolated by screening a BAC genomic DNA library (Research Genetics) using primers which were designed based on the sequence of the human 9qm cDNA. Two positive clones were identified (44802 and 721117) and sequenced.

Example 5

Expression of 1V, 8T, AND 9Q mRNA in Rat Tissues

Rat and mouse multiple tissue Northern blots (Clontech) were probed with a [$^{32}P$]-labeled cDNA probe directed at the 5'-untranslated and 5'-coding region of the rat 1v sequence (nucleotides 35-124; SEQ ID NO:3) (this probe is specific for rat 1v and rat 1vl), the 5' coding region of the 8t sequence (nucleotides 1-88; SEQ ID NO:29) (this probe is specific for 8t), or the 5' end of the rat 9qm sequence (nucleotides 1-195; SEQ ID NO:21) (this probe is specific for all 9q isoforms, besides 8t). Blots were hybridize using standard techniques. Northern blots hybridized with the rat 1v probe revealed a single band at 2.3 kb only in the lane containing brain RNA, suggesting that 1v expression is brain specific. Northern blots probed with the rat 8t probe revealed a major band at 2.4 kb. The rat 8t band was most intense in the lane containing heart RNA and there was also a weaker band in the lane containing brain RNA. Northern blots hybridized with the 9q cDNA probe revealed a major band at 2.5 kb and a minor band at over 4 kb with predominant expression in brain and heart. The minor band may represent incompletely spliced or processed 9q mRNA. The results from the northern blots further indicated that p19 is expressed predominantly in the heart.

Example 6

Expression of 1V, 8T, AND 9Q in Brain

Expression of the rat 1v and 8t/9q genes in the brain was examined by in situ hybridization histochemistry (ISHH) using [$^{35}S$]-labeled cRNA probes and a hybridization procedure identical to that described in Rhodes et al. (1996) J.

Neurosci., 16:4846-4860. Templates for preparing the cRNA probes were generated by standard PCR methods. Briefly, oligonucleotide primers were designed to amplify a fragment of 3'- or 5'-untranslated region of the target cDNA and in addition, add the promoter recognition sequences for T7 and T3 polymerase. Thus, to generate a 300 nucleotide probe directed at the 3'-untranslated region of the 1v mRNA, we used the following primers:

5-<u>TAATACGACTCACTATAGGG</u>ACTGGCCATCCTGCT-CTCAG-3 (<u>T7</u>, forward, sense; SEQ ID NO:42)

5-<u>ATTAACCCTCACTAAAGGGA</u>CACTACTGTTTAAG-CTCAAG-3 (<u>T3</u>, reverse, antisense; SEQ ID NO:43). The underlined bases correspond to the T7 and T3 promoter sequences. To generate a probe directed at a 325 bp region of 3'-untranslated sequence shared by the 8t and 9q mRNAs, the following primers were used:

5-<u>TAATACGACTCACTATAGGG</u>CACCTCCCCTCCGG-CTGTTC-3 (<u>T7</u>, forward, sense; SEQ ID NO:44)

5-<u>ATTAACCCTCACTAAAGGGA</u>GAGCAGCAGCATG-GCAGGGT-3 (<u>T3</u>, reverse, antisense; SEQ ID NO:45).

Autoradiograms of rat brain tissue sections processed for ISHH localization of 1v or 8t/9q mRNA expression revealed that 1v mRNA is expressed widely in brain in a pattern consistent with labeling of neurons as opposed to glial or endothelial cells. 1v mRNA is highly expressed in cortical, hippocampal, and striatal interneurons, the reticlar nucleus of the thalamus, the medial habenula, and in cerebellar granule cells. 1v mRNA is expressed at moderate levels in midbrain nuclei including the substantia nigra and superior colliculus, in several other thalamic nuclei, and in the medial septal and diagonal band nuclei of the basal forebrain.

Because the probe used to analyze the expression of 8t and 9q hybridizes to a region of the 3-untranslated region that is identical in the 8t and 9q mRNAs, this probe generates a composite image that reveals that 8t/9q mRNA is expressed widely in brain in a pattern that partly overlaps with that for 1v as described above. However, 8t/9q mRNA is highly expressed in the striatum, hippocampal formation, cerebellar granule cells, and neocortex. 8t/9q mRNA is expressed at moderate levels in the midbrain, thalamus, and brainstem. In may of these areas, 8t./9q mRNA appears to be concentrated in interneurons in addition to principal cells, and in all regions 8t/9q expression appears to be concentrated in neurons as apposed to glial cells.

Single- and double-label immunohistochemistry revealed that the PCIP and Kv4 polypeptides are precisely colocalized in many of the cell types and brain regions where PCIP and Kv4 mRNAs are coexpressed. For example, 9qm colocalized with Kv4.2 in the somata and dendrites of hippocampal granule and pyramidal cells, neurons in the medial habenular nucleus and in cerebellar basket cells, while 1v colocalized with Kv4.3 in layer II neurons of posterior cingulate cortex, hippocampal interneurons, and in a subset of cerebellar granule cells. Immunoprecipitation analyses indicated that 1v and 9qm are coassociated with Kv4 α-subunits in rat brain membranes.

Example 7

Co-Association of PCIPs and Kv4 Channels in COS and CHO Cells

COS1 and CHO cells were transiently transfected with individual PCIPs (KChIP1, KChIP2, KChIP3) alone or together with Kv4.2 or Kv4.3 using the lipofectamine plus procedure essentially as described by the manufacturer (Boehringer Mannheim). Forty-eight hours after the transfection, cells were washed, fixed, and processed for immunofluorescent visualization as described previously (Bekele-Arcuri et al. (1996) Neuropharmacology, 35:851-865). Affinity-purified rabbit polyclonal or mouse monoclonal antibodies to the Kv4 channel or the PCIP protein were used for immunofluorescent detection of the target proteins.

When expressed alone, the PCIPs were diffusely distributed throughout the cytoplasm of COS-1 and CHO cells, as would be expected for cytoplasmic proteins. In contrast, when expressed alone, the Kv4.2 and Kv4.3 polypeptides were concentrated within the perinuclear ER and Golgi compartments, with some immunoreactivity concentrated in the outer margins of the cell. When the PCIPs were coexpressed with Kv4 α-subunits, the characteristic diffuse PCIP distribution changed dramatically, such that the PCIPs precisely colocalized with the Kv4 α-subunits. This redistribution of the PCIPs did not occur when they were coexpressed with the Kv1.4 α-subunit, indicating that altered PCIP localization is not a consequence of overexpression and that these PCIPs associate specifically with Kv4-family α-subunits.

To verify that the PCIP and Kv4 polypeptides are tightly associated and not simply colocalized in co-transfected cells, reciprocal immunoprecipitation analyses were performed using the PCIP and channel-specific antibodies described above. All three PCIP polypeptides coassociated with Kv4 α-subunits in cotransfected cells, as evidenced by the ability of anti-Kv4.2 and anti-Kv4.3 antibodies to immunoprecipitate the KChIP1, KChIP2, and KChIP3 proteins from lysates prepared from cotransfected cells, and by the ability of anti-PCIP antibodies to immunoprecipitate Kv4.2 and Kv4.3 α-subunits from these same lysates. The cells were lysed in buffer containing detergent and protease inhibitors, and prepared for immunoprecipitation reactions essentially as described previously (Nakahira et al. (1996) J. Biol. Chem., 271:7084-7089). Immunoprecipitations were performed as described in Nakahira et al. (1996) J. Biol. Chem., 271:7084-7089 and in Harlow E. and Lane, D., Antibodies: A Laboratory Manual, Cold Spring Harbor Laboratory, c1988. The products resulting from the immunoprecipitation were size fractionated by SDS-PAGE and transferred to nitrocellulose filters using standard procedures.

To confirm that the cytoplasmic N-terminus of Kv4 channels is sufficient for the interaction with the PCIPs KChIP1 or KChIP2 were co-expressed with a Kv4.3 mutant (Kv4.3ΔC) that lacks the entire 219 amino acid cytoplasmic C-terminal tail. In transiently transfected COS-1 cells, the Kv4.3ΔC mutant was extensively trapped within the perinuclear ER and Golgi: little or no staining was observed at the outer margins of the cell. Nonetheless, KChIP1 and KChIP2 precisely colocalized with Kv4.3ΔC in cotransfected cells, and moreover, Kv4.3ΔC was efficiently coimmunoprecipitated by PCIP antibodies, indicating that the interaction of these PCIPs with Kv4 α-subunits does not require the cytoplasmic C-terminus of the channel.

Example 8

Co-Association of PCIPs and Kv4 Channels in Native Tissues

To determine whether PCIPs colocalize and co-associate with Kv4 subunits in native tissues, Kv4- and PCIP-specific antibodies were used for single and double-label immunohistochemical analyses and for reciprocal coimmunoprecipitation analyses of rat brain membranes. Immunohistochemical staining of rat brain sections indicated that KChIP1 and KChIP2 colocalize with Kv4.2 and Kv4.3 in a region and cell type-specific manner. For example, KChIP1 colocalized with Kv4.3 in hippocampal interneurons, cerebellar granule cells, and cerebellar glomeruli, a specialized synaptic arrangement between the dendrites of cerebellar basket and golgi cells and mossy fiber terminals. KChIP2 colocalized with Kv4.3 and Kv4.2 in the dendrites of granule cells in the dentate gyrus, in the apical and basal dendrites of hippocampal and neocortical pyramidal cells, and in several subcortical structures including the striatum and superior colliculus. Co-immunoprecipitation analyses performed using synaptic membranes prepared from whole rat brain revealed that the PCIPs (KChIPs 1, 2, and 3) are tightly associated with Kv4.2 and Kv4.3 in brain K+ channel complexes. Anti-PCIP antibodies immunoprecipitated Kv4.2 and Kv4.3 from brain membranes, and anti-Kv4.2 and Kv4.3 antibodies immunoprecipitated the PCIPs. None of the PCIP polypeptides were immunoprecipitated by anti-Kv2.1 antibodies, indicating that the association of these PCIPs with brain Kv channels may be specific for Kv4 α-subunits. Taken together, these anatomical and biochemical analyses indicate that these PCIPs are integral components of native Kv4 channel complexes.

Example 9

PCIPs are Calcium Binding Proteins

To determine whether KChIPs 1, 2, and 3 bind Ca2+, GST-fusion proteins were generated for each PCIP and the ability of the GST-PCIP proteins, as well as the recombinant PCIP polypeptides enzymatically cleaved from GST, to bind $^{45}$Ca2+ was examined using a filter overlay assay (described in, for example, Kobayashi et al. (1993) Biochem. Biophys. Res. Commun. 189(1):511-7). All three PCIP polypeptides, but not an unrelated GST-fusion protein, display strong $^{45}$Ca2+ binding in this assay. Moreover, all three PCIP polypeptides display a Ca2+-dependent mobility shift on SDS-PAGE, indicating that like the other members of this family, KChIPs 1, 2 and 3 are in fact Ca2+-binding proteins (Kobuyashi et al. (1993) supra; Buxbaum et al. Nef (1996). Neuron-specific calcium sensors (the NCS-1 subfamily). In: Celio M R (ed) Guidebook to the calcium-binding proteins. Oxford University Press, New York, pp 94-98; Buxbaum J. D., et al. (1998) Nature Med. 4(10):1177-81.

Example 10

Electrophysiological Characterization of PCIPs

Because PCIPs, e.g., KChIP1 (1v), KChIP2 (9ql), and KChIP3 (p19), colocalize and coassociate with Kv4 α-subunits in brain, another critical question was to determine whether these PCIPs alter the conductance properties of Kv4 channels. To address this issue, Kv4.2 and Kv4.3 were expressed alone and in combination with individual PCIPs. CHO cells were transiently-transfected with cDNA using the DOTAP lipofection method as described by the manufacturer (Boehringer Mannheim, Inc.). Transfected cells were identified by cotransfecting enhanced GFP along with the genes of interest and subsequently determining if the cells contained green GFP fluorescence. Currents in CHO cells were measured using the patch-clamp technique (Hamill et al. 1981. Pfluegers Arch. 391: 85-100).

Figure 41:
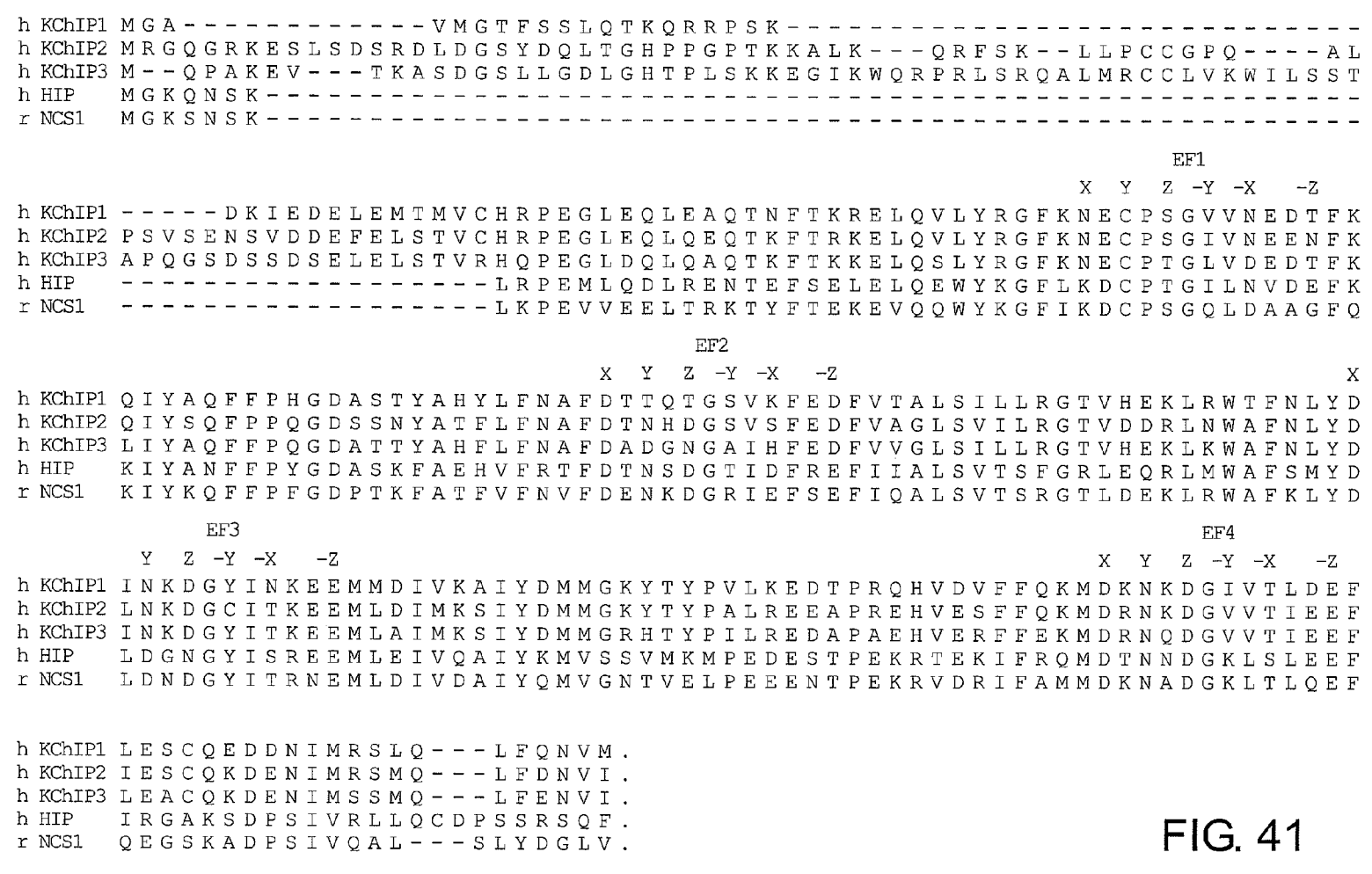

Transient transfection of the rat Kv4.2 α-subunit in CHO cells resulted in expression of a typical A-type K+ conductance. Coexpression of Kv4.2 with KChIP I revealed several dramatic effects of KChIP1 on the channel (FIG. 41 and Table 1). First, the amplitude of the Kv4.2 current increased approximately 7.5 fold in the presence of KChIP1 (amplitude of Kv4.2 alone=0.60+/−0.096 nA/cell; Kv4.2+ KChIP1=4.5+/−0.55 nA/cell). When converted into current density by correcting for cell capacitance, a measure of cell surface membrane area, the Kv4.2 current density increased 12 fold with coexpression of KChIP1 (Kv4.2 alone=25.5+/− 3.2 pA/pF; Kv4.2+KChIP1=306.9+/−57.9 pA/pF), indicating that KChIPs promote and/or stabilize Kv4.2 surface expression. Together with this increase in current density, a dramatic leftward shift in the threshold for activation of Kv4.2 currents was observed in cells expressing Kv4.2 and KChIP1 (activation V1/2 for Kv4.2 alone=20.8+/−7.0 mV, Kv4.2+KChIP1=−12.1+/−1.4 mV). Finally, the kinetics of Kv4.2 inactivation slowed considerably when Kv4.2 was coexpressed with KChIP1 (inactivation time constant of Kv4.2 alone=28.2+/−2.6 ms; Kv4.2+KChIP1=104.1+/−10.4 ms), while channels recovered from inactivation much more rapidly in cells expressing both Kv4.2 and KChIP1 (recovery tau=53.6+/−7.6 ms) versus cells expressing Kv4.2 alone (recovery tau=272.2+/−26.1 ms).

KChIPs1, 2 and 3 have distinct N-termini but share considerable amino acid identity within the C-terminal "core" domain. Despite their distinct N-termini, the effects of KChIP2 and KChIP3 on Kv4.2 current density and kinetics were strikingly similar to those produced by KChIP1 (Table 1). Thus to confirm that the conserved C-terminal core domain, which contains all three EF-hands, is sufficient to modulate Kv4 current density and kinetics, N-terminal truncation mutants of KChIP1 and KChIP2 were prepared. The KChIP1ΔN2-31 and KChIP2ΔN2-67 mutants truncated KChIP1 and KChIP2, respectively, to the C-terminal 185 amino acid core sequence. Coexpression of KChIP1ΔN2-31 or KChIP2ΔN2-67 with Kv4.2 in CHO cells produced changes in Kv4.2 current density and kinetics that were indistinguishable from the effects produced by full-length KChIP1 or KChIP2 (Table 1).

To investigate whether the modulatory effects of these KChIPs are specific for Kv4 channels, KChIP1 was coexpressed with Kv1.4 and Kv2.1 in *Xenopus* oocytes. *Xenopus* oocytes were injected with 1-3 ng/oocyte of cRNA which was prepared using standard in vitro transcription techniques (Sambrook et al. 1989. Molecular Cloning: a laboratory manual, Cold Spring Harbor Press). Currents in *Xenopus* oocytes were measured with a two-electrode voltage clamp. KChIP I did not appear to have any effect on Kv1.4 or Kv2.1 currents (Table 2), indicating that these functional effects may be specific for Kv4 channels. As a final control for the KChIP effects and to verify that the KChIPs' effects on Kv4 currents are independent of expression system, the above kinetic analyses were repeated after expressing Kv4.3 and KChIP mRNAs in *Xenopus* oocytes. The effects KChIP1 on for Kv4.3 in the *Xenopus* oocyte system were strikingly similar to those on Kv4.2 in CHO cells (Table 1).

Since these KChIPs bind Ca2+, another important question is to determine whether the effects of KChIP1 on Kv4.2 currents are Ca2+-dependent. This question was addressed indirectly by introducing point mutations within each of KChIP1's EF-hand domains: one mutant has point mutations in the first two EF hands ($D_{199}$ to A, $G_{104}$ to A, $D_{135}$ to A, and $G_{140}$ to A) and the other one has point muations in all three EF hands ($D_{199}$ to A, $G_{104}$ to A, $D_{135}$ to A, $G_{140}$ to A, $D_{183}$ to A, and $G_{188}$ to A). These mutations substituted alanine for the two most highly conserved amino acids within the EF-hand consensus (FIG. 25; Linse, S, and Forsen, S. (1995) Determinants that govern high-affinity Calcium binding. In Means, S. (Ed.) Advances in second messenger and phosphoprotein research. New York, Ravens Press, 30:89-150). Coexpression of this KChIP1 triple EF-hand mutant with Kv4.2 or Kv4.3 in COS cells indicated that this mutant colocalizes and is efficiently coimmunoprecipitated with Kv4 α-subunits in COS-1 cells. However, these EF-hand point mutations completely eliminated the effects of KChIP1 on Kv4.2 kinetics (Table 1). Taken together, these results indicate that the binding interaction between KChIP1 and Kv4.2 is Ca2+ independent, while modulation of Kv4.2 kinetics by KChIP1 is either Ca2+-dependent or sensitive to structural changes induced by point mutations within the EF-hand domains.

Example 11

Effects of KChIP1 on Surface Expression of KV4-α Subunits in COS-1 Cells

To examine the ability of KChIP1 to enhance the surface expression of Kv4 channels, the ability of KChIP1 to promote the formation of surface co-clusters of Kv4 channels and PSD-95 was monitored. PSD-95 is used to facilitate the visualization of the complex.

To facilitate the interaction between Kv4.3 and PSD-95, a chimeric Kv4.3 subunit (Kv4.3ch) was generated in which the C-terminal 10 amino acids from rKv1.4 (SNAKAVETDV, SEQ ID NO:73) were appended to the C-terminus of Kv4.3. The C-terminal 10 amino acids from rKv1.4 were used because they associate with PSD-95 and confer the ability to associate with PSD-95 to the Kv4.3 protein when fused to the Kv4.3 C-terminus. Expression of Kv4.3ch in COS-1 cells revealed that the Kv4.3ch polypeptide was trapped in the perinuclear cytoplasm, with minimal detectable Kv4.3ch immunoreactivity at the outer margins of the cell. When Kv4.3ch was co-expressed with PSD-95, PSD-95 became trapped in the perinuclear cytoplasm and co-localized with Kv4.3ch. However, when KChIP1 was co-expressed with Kv4.3ch and PSD-95, large plaque-like surface co-clusters of Kv4.3ch, KChIP1 and PSD-95 were observed. Triple-label immunofluorescence confirmed that these surface clusters contain all three polypeptides, and reciprocal co-immunoprecipitation analyses indicated that the three polypeptides are co-associated in these surface clusters. Control experiments indicated that KChIP does not interact with PSD-95 alone, and does not co-localize with Kv1.4 and PSD-95 in surface clusters. Taken together, these data indicate that KChIP1 may promote the transit of the Kv4.3 subunits to the cell surface.

TABLE 1

Functional effect of KChIPs on Kv4 channels

| Current Parameter | rKv4.2 + vector | rKv4.2 + KChIP1 | rKv4.2 + KChIP1 ΔN2-31 | rKv4.2 + KChIP2 |
|---|---|---|---|---|
| Peak Current (nA/cell at 50 MV) | 0.60* ± 0.096 | 4.5* ± 0.055 | 6.0* ± 1.1 | 3.3* ± 0.45 |
| Peak Current Density (pA/pF at 50 mV) | 25.5 ± 3.2 | 306.9* ± 57.9 | 407.2* ± 104.8 | 196.6* ± 26.6 |
| Inactivation time constant (ms, at 50 mV) | 28.2 ± 2.6 | 104.1 ± 10.4 | 129.2 ± 14.2 | 95.1* ± 8.3 |
| Recovery from Inactivation Time constant | 272.2 | 53.6* | 98.1* | 49.5* |

| Current Parameter | rKv4.2 + KChIP2 ΔN2-67 | rKv4.2 + KChIP3 | rKv4.3 | rKv4.3 + KChIP1 |
|---|---|---|---|---|
| Peak Current (nA/cell at 50 MV) | 58* ± 1.1 | 3.5* ± 0.99 | 7.7 μA ± 2.6 | 18.1 μA* ± 3.8 |
| Peak Current Density (pA/pF at 50 mV) | 202.6* ± 27.5 | 161.7* ± 21.8 | — | — |
| Inactivation time constant (ms, at 50 mV) | 109.5* ± 9.6 | 67.2* ± 14.1 | 56.3 ± 6.6 | 135.0 ± 15.1 |
| Recovery from Inactivation Time constant | 36.1* | 126.1* | 327.0 | 34.5* |

*Significantly different from control.

TABLE 2

Functional effects of KChIPs on other Kv channels

| | Xenopus oocytes | | Xenopus oocytes | |
|---|---|---|---|---|
| Current Parameter | HKv1.4 | hKv1.4 + 1v | HKv2.1 | HKv2.1 + 1v |
| Peak Current (μA/cell at 50 MV) | 8.3 ± 2.0 | 6.5 ± 0.64 | 3.7 ± 0.48 | 2.9 ± 0.37 |
| Inactivation time constant (ms, at 50 mV) | 53.2 ± 2.8 | 58.2 ± 6.6 | 1.9 s ± 0.079 | 1.7 s 0.078 |
| Recovery from Inactivation time constant (sec, at −80 mV) | 1.9 | 1.6 | 7.6 | 7.7 |
| Activation $V_{1/2}$ (mV) | −21.0 | −20.9 | 12.0 | 12.4 |
| Steady-state Inactivation $V_{1/2}$ (mV) | −48.1 | −47.5 | −25.3 | −23.9 |

Example 12

Characterization of the PCIP Proteins

In this example, the amino acid sequences of the PCIP proteins were compared to amino acid sequences of known proteins and various motifs were identified.

The 1v polypeptide, the amino acid sequence of which is shown in SEQ ID NO:3 is a novel polypeptide which includes 216 amino acid residues. Domains that are putatively involved in calcium binding (Linse, S, and Forsen, S. (1995) *Advances in Second Messenger and Phosphoprotein Research* 30, Chapter 3, p89-151, edited by Means, A R., Raven Press, Ltd., New York), were identified by sequence alignment (see FIG. 21).

The 8t polypeptide, the amino acid sequence of which is shown in SEQ ID NO:30 is a novel polypeptide which includes 225 amino acid residues. Calcium binding domains that are putatively involved in calcium binding (Linse, S, and Forsen, S. (1995) *Advances in Second Messenger and Phosphoprotein Research* 30, Chapter 3, p89-151, edited by Means, A R., Raven Press, Ltd., New York), were identified by sequence alignment (see FIG. 21).

The 9q polypeptide is a novel polypeptide which includes calcium binding domains that are putatively involved in calcium binding (Linse, S, and Forsen, S. (1995) *Advances in Second Messenger and Phosphoprotein Research* 30, Chapter 3, p89-151, edited by Means, A R., Raven Press, Ltd., New York (see FIG. 21).

The p19 polypeptide is a novel polypeptide which includes calcium binding domains that are putatively involved in calcium binding (Linse, S, and Forsen, S. (1995) *Advances in Second Messenger and Phosphoprotein Research* 30, Chapter 3, p89-151, edited by Means, A R., Raven Press, Ltd., New York (see FIG. 21).

A BLASTN 2.0.7 search (Altschul et al. (1990) *J. Mol. Biol.* 215:403) of the nucleotide sequence of rat 1vl revealed that the rat 1vl is similar to the rat cDNA clone RMUAH89 (Accession Number AA849706). The rat 1vl nucleic acid molecule is 98% identical to the rat cDNA clone RMUAH89 (Accession Number AA849706) over nucleotides 1063 to 1488.

A BLASTN 2.0.7 search (Altschul et al. (1990) *J. Mol. Biol.* 215:403) of the nucleotide sequence of human 9ql revealed that the human 9ql is similar to the human cDNA clone 1309405 (Accession Number AA757119). The human 9ql nucleic acid molecule is 98% identical to the human cDNA clone 1309405 (Accession Number AA757119) over nucleotides 937 to 1405.

A BLASTN 2.0.7 search (Altschul et al. (1990) *J. Mol. Biol.* 215:403) of the nucleotide sequence of mouse P19 revealed that the mouse P19 is similar to the *Mus musculus* cDNA clone MNCb-7005 (Accession Number AU035979). The mouse P19 nucleic acid molecule is 98% identical to the *Mus musculus* cDNA clone MNCb-7005 (Accession Number AU035979) over nucleotides 1 to 583.

Example 13

Expression of Recombinant PCIP Proteins in Bacterial Cells

In this example, PICP is expressed as a recombinant glutathione-S-transferase (GST) fusion polypeptide in *E. coli* and the fusion polypeptide is isolated and characterized. Specifically, PCIP is fused to GST and this fusion polypeptide is expressed in *E. coli*, e.g., strain B121. Expression of the GST-PCIP fusion protein in BI21 is induced with IPTG. The recombinant fusion polypeptide is purified from crude bacterial lysates of the induced BI21 strain by affinity chromatography on glutathione beads. Using polyacrylamide gel electrophoretic analysis of the polypeptide purified from the bacterial lysates, the molecular weight of the resultant fusion polypeptide is determined.

Rat 1v and 9ql were cloned into pGEX-6p-2 (Pharmacia). The resulting recombinant fusion proteins were expressed in *E. coli* cells and purified following art known methods (described in, for example, *Current Protocols in Molecular Biology*, eds. Ausubel et al. John Wiley & Sons: 1992). The identities of the purified proteins were verified by western blot analysis using antibodies raised against peptide epitopes of rat 1v and 9ql.

Example 14

Expression of Recombinant PCIP Proteins in COS Cells

To express the PCIP gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire PCIP protein and an HA tag (Wilson et al. (1984) Cell 37:767) or a FLAG tag fused in-frame to its 3' end of the fragment is cloned into the polylinker region of the vector, thereby placing the expression of the recombinant protein under the control of the CMV promoter.

To construct the plasmid, the PCIP DNA sequence is amplified by PCR using two primers. The 5' primer contains the restriction site of interest followed by approximately twenty nucleotides of the PCIP coding sequence starting from the initiation codon; the 3' end sequence contains complementary sequences to the other restriction site of interest, a translation stop codon, the HA tag or FLAG tag and the last 20 nucleotides of the PCIP coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the PCIP gene is inserted in the correct orientation. The ligation mixture is transformed into *E. coli* cells (strains HB101, DH5a, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the PCIP-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989. The expression of the PCIP polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labelled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the PCIP coding sequence is cloned directly into the polylinker of the pCDNA/Amp vector using the appropriate restriction sites. The resulting plasmid is transfected into COS cells in the manner described above, and the expression of the PCIP polypeptide is detected by radiolabelling and immunoprecipitation using a PCIP specific monoclonal antibody.

Rat 1v was cloned into the mammalian expression vector pRBG4. Transfections into COS cells were performed using LipofectAmine Plus (Gibco BRL) following the manufacturer's instructions. The expressed 1v protein was detected by immunocytochemistry and/or western blot analysis using antibodies raised against 1v in rabbits or mice.

Example 15

Identification and Characterization of Human Full Length P19

The human full length p19 sequence was identified using RACE PCR. The sequence of p19 (also referred to as KChIP3) is shown in FIG. 16. The amino acid sequence of human p19 is 92% identical to the mouse p19 gene (SEQ ID NO:35).

TBLASTN searches using the protein sequence of human p19 revealed that human p19 is homologous to two sequences, Calsenilin (described in (1998) *Nature Medicine* 4: 1177-1181) and DREAM, a Ca2+-dependent regulator of prodynorphin and c-fos transcription (described in Carrion et al. (1999) *Nature* 398: 80-84). Human p19 is 100% identical at the nucleotide level to Calsenilin (but extends 3' to the published sequence) and 99% identical at the nucleotide level to DREAM.

The ability of p19 (as well as other PCIP family members) to co-localize with presenilin and act as transcription factors is determined using art known techniques such as northern blots, in situ hybridization, β-gal assays, DNA mobility assays (described in, for example, Carrion et al. (1999) *Nature* 398:80) and DNA mobility supershift assays, using antibodies specific for KChIPs.

Other assays suitable for evaluating the association of PCIP family members with presenilins is co-immunoprecipitation (described in, for example, Buxbaum et al. (1998) *Nature Medicine* 4:1177).

Example 16

Identification and Characterization of Monkey KChIP4

In this example, the identification and characterization of the genes encoding monkey KChIP4a (jlkbd352e01t1) and alternatively spliced monkey KChIP4b (jlkbb231c04t1), KChIP4c (jlkxa053c02), and KChIP4d (jlkx015b10) is described. TBLASTN searches in proprietary databases with the sequence of the known PCIP family members, lead to the identification of four clones jlkbb231c04t1, jlkbd352e01t1, jlkxa053c02, and jlkx015b10. The four monkey clones were obtained and sequenced.

The sequences of proprietary monkey clones jlkbb231c04t1 and jlkbd352e01t1 were found to correspond to alternately spliced variants of an additional PCIP family member, referred to herein as KChIP4. Clone jlkbb231c14t1 contains a 822 bp deletion relative to jlkbd352e01t1 (presumably due to splicing out of an exon), resulting in the loss of the final EF hand domain. In clone jlkbd352e01t1, the final EF hand domain is preserved, and the C-terminus is highly homologous to that of PCIP family members I v, 9ql, and p19. Overall identity in the homologous C-termini among KChIP4, 1v, 9ql, and p19 ranged from 71%-80% at the amino acid level (alignments were performed using the CLUSTALW).

Monkey KChIP4c and KChIP4d were discovered by BLASTN search using monkey KChIP4a as a query for searching a proprietary database.

The nucleotide sequence of the monkey KChIP4a cDNA and the predicted amino acid sequence of the KChIP4a polypeptide are shown in FIG. 23 and in SEQ ID NOs:48 and 49, respectively.

The nucleotide sequence of the monkey KChIP4b cDNA and the predicted amino acid sequence of the KChIP4b polypeptide are shown in FIG. 24 and in SEQ ID NOs:50 and 51, respectively.

The nucleotide sequence of the monkey KChIP4c cDNA and the predicted amino acid sequence of the KChIP4c polypeptide are shown in FIG. 35 and in SEQ ID NOs:69 and 70, respectively.

The nucleotide sequence of the monkey KChIP4d cDNA and the predicted amino acid sequence of the KChIP4d polypeptide are shown in FIG. 36 and in SEQ ID NOs:71 and 72, respectively.

FIG. 37 depicts an alignment of the protein sequences of KChIP4a, KChIP4b, KChIP4c, and KChIP4d.

Rat KChIP4 is predominantly expressed in the brain, and weakly in the kidney, but not in the heart, brain, spleen, lung, liver, skeletal muscle or testes, as indicated by northern blot experiments in which a northern blot purchased from Clontech was probed with a DNA fragment from the 3'-untranslated region of rat KChIP4.

Example 17

Identification and Characterization of Human and Rat 33b07

In this example, the identification and characterization of the genes encoding rat and human 33b07 is described. Partial rat 33b07 (clone name 9o) was isolated as a positive clone from the yeast two-hybrid screen described above, using rKv4.3N as bait. The full length rat 33b07 clone was identified by mining of proprietary databases.

The nucleotide sequence of the full length rat 33b07 cDNA and the predicted amino acid sequence of the rat 33b07 polypeptide are shown in FIG. 26 and in SEQ ID NOs:52 and 53, respectively. The rat 33b07 cDNA encodes a protein having a molecular weight of approximately 44.7 kD and which is 407 amino acid residues in length.

Rat 33b07 binds rKv4.3N and rKv4.2N with slight preference for rKv4.2N in yeast 2-hybrid assays. In contrast, rat 33b07 does not bind rKv1.1N, indicating that the rat 33b07-Kv4N interaction is specific.

Rat 33b07 is expressed predominantly in the brain as determined by northern blot analysis.

The human 33b07 ortholog (clone 106d5) was also identified by mining of proprietary databases. The nucleotide sequence of the full length human 33b07 cDNA and the predicted amino acid sequence of the human 33b07 polypeptide are shown in FIG. 27 and in SEQ ID NOs:54 and 55, respectively. The human 33b07 cDNA encodes a protein having a molecular weight of approximately 45.1 kD and which is 414 amino acid residues in length.

Human 33b07 is 99% identical to the human KIAA0721 protein (GenBank Accession Number: AB018264) at the amino acid level. However, GenBank Accession Number: AB018264 does not have a functional annotation. Human 33b07 is also homologous to Testes-specific (Y-encoded) proteins (TSP(Y)s), SET, and Nucleosome Assembly Proteins (NAPs). The human 33b07 is 38% identical to human SET protein (GenBank Accession Number Q01105=U51924) over amino acids 204 to 337 and 46% identical over amino acids 334 to 387.

Human SET is also called HLA-DR associated protein II (PHAPII) (Hoppe-Seyler (1994) *Biol. Chem.* 375:113-126) and in some cases is associated with acute undifferentiated leukemia (AUL) as a result of a translocation event resulting in the formation of a SET-CAN fusion gene (Von Lindern M. et al. (1992) *Mol. Cell. Biol.* 12:3346-3355). An alternative spliced form of SET is also called Template Activating Factor-1 alpha (TAF). TAF is found to be associated with myeloid leukemogenesis (Nagata K. et al. (1995) *Proc. Natl. Acad. Sci. U.S.A.* 92 (10), 4279-4283). Human SET is also a potent protein inhibitor of phosphatase 2A (Adachi Y. et al. (1994) *J. Biol. Chem.* 269:2258-2262). NAPs may be involved in modulating chromatin formation and contribute to regulation of cell proliferation (Simon H. U. et al. (1994) *Biochem. J.* 297, 389-397).

Thus, due to its homology to the above identified proteins, 33b07 may function as a protein inhibitor of phosphatase, an oncogene, and/or a chromatin modulator. The homology of 33b07 to SET, a protein phosphatase inhibitor, is of particular interest. Many channels, in particular the Kv4 channels (with which 33b07 is associated), are known to be regulated by phosphorylation by PKC and PKA ((1998) *J. Neuroscience* 18(10): 3521-3528; Am J Physiol 273: H1775-86 (1997)). Thus, 33b07 may modulate Kv4 activity by regulating the phosphorylation status of the potassium channel.

Example 18

Identification and Characterization of Rat 1p

In this example, the identification and characterization of the gene encoding rat 1p is described. Partial rat 1p was isolated as a positive clone from the yeast two-hybrid screen described above, using rKv4.3N as a bait.

The nucleotide sequence of the partial length rat I p cDNA and the predicted amino acid sequence of the rat 1p polypeptide are shown in FIG. 28 and in SEQ ID NOs:56 and 57, respectively. The rat 1p cDNA encodes a protein having a molecular weight of approximately 28.6 kD and which is 267 amino acid residues in length.

Rat 1p binds rKv4.3N and rKv4.2N with slight preference for rKv4.3N in yeast two-hybrid assays. In contrast, 1p does not bind rKv1.1N, indicating that the 1p-Kv4N interaction is specific.

Rat 1p is predominantly expressed in the brain as determined by northern blot analysis.

A BLASTP 1.4 search, using a score of 100 and a word length of 3 (Altschul et al. (1990) *J. Mol. Biol.* 215:403) of the amino acid sequences of rat 1p revealed that rat 1p is similar to the human Restin (GenBank Accession Number P30622; also named cytoplasmic linker protein-170 alpha-2 (CLIP-170), M97501)). The rat 1p protein is 58% identical to the human Restin over amino acid residues 105 to 182, 55% identical to the human, Restin over amino acid residues 115 to 186, 22% identical to the human Restin over amino acid residues 173 to 246, 22% identical to the human Restin over amino acid residues 169 to 218, and 58% identical to the human Restin over amino acid residues 217 to 228.

Restin is also named Reed-Sternberg intermediate filament associated protein. Reed-Sternberg cells are the tumoral cells diagnostic for Hodgkin's disease. It is suggested that Restin overexpression may be a contributing factor in the progression of Hodgkin's disease (Bilbe G. et al. (1992) *EMBO J.* 11: 2103-13) and Restin appears to be an intermediate filament associated protein that links endocytic vesicles to microtubules (Pierre P, et al. (1992) *Cell* 70 (6), 887-900).

The cytoskeleton regulates the activity of potassium channels (see, for example, Honore E, et al. (1992) *EMBO J.* 11:2465-2471 and Levin G, et al. (1996) *J. Biol. Chem.* 271: 29321-29328), as well as the activity of other channels, e.g., $Ca^{++}$ channels (Johnson B. D. et al. (1993) *Neuron* 10:797-804); or $Na^+$ channels (Fukuda J. et al. (1981) *Nature* 294: 82-85).

Accordingly, based on its homology to the Restin protein, the rat I p protein may be associated with the cytoskeleton and may modulate the activity of potassium channels, e.g., Kv4, via its association to the cytoskeleton.

Example 19

Identification and Characterization of Rat 7s

In this example, the identification and characterization of the gene encoding rat 7s is described. Partial rat 7s was isolated as a positive clone from the yeast two-hybrid screen described above, using rKv4.3N as a bait. Rat 7s is the rat ortholog of the human vacuolar H(+)-ATPase catalytic subunit A (Accession Number P38606 and B46091) described in, for example, van Hille B. et al. (1993) *J. Biol. Chem.* 268 (10), 7075-7080.

The nucleotide sequence of the partial length rat 7s cDNA and the predicted amino acid sequence of the rat 7s polypeptide are shown in FIG. 29 and in SEQ ID NOs:58 and 59, respectively. The rat 7s cDNA encodes a protein having a molecular weight of approximately 28.6 kD and which is 270 amino acid residues in length.

Rat 7s binds rKv4.3N and rKv4.2N with preference for rKv4.3N in yeast two-hybrid assays. In contrast, 7s does not bind rKv1.1N, indicating that the 7s-Kv4N interaction is specific.

Rat 7s is expressed at significantly higher levels in the brain and the kidney than in the lung, liver, heart, testes, and skeletal muscle, as determined by northern blot analysis.

Example 20

Identification and Characterization of Rat 29x AND 25r

In this example, the identification and characterization of the gene encoding rat 29x is described. Rat 29x was isolated as a positive clone from the yeast two-hybrid screen described above, using rKv4.3N as a bait. Rat 25r is a splice variant of 29x. They differ in the 5' untranslated region, but are identical in the coding region and at the amino acid level.

The nucleotide sequence of the rat 29x cDNA and the predicted amino acid sequence of the rat 29x polypeptide are shown in FIG. 30 and in SEQ ID NOs:60 and 61, respectively.

The rat 29x cDNA encodes a protein having a molecular weight of approximately 40.4 kD and which is 351 amino acid residues in length.

The nucleotide sequence of the rat 25r cDNA is shown in FIG. 31 and in SEQ ID NO:62. The rat 25r cDNA encodes a protein having a molecular weight of approximately 40.4 kD and which is 351 amino acid residues in length.

Rat 29x is expressed in the spleen, lung, kidney, heart, brain, testes, skeletal muscle and liver, with the highest level of expression being in the spleen and the lowest being in the liver.

Rat 29x binds rKv4.3N and rKv4.2N with slight preference for rKv4.3N in yeast two-hybrid assays. In contrast, 29x does not bind rKv1.1N, indicating that the 29x-Kv4N interaction is specific.

Rat 29x is identical at the amino acid level to rat SOCS-1 (Suppressor Of Cytokine Signaling) described in Starr R. et al. (1997) *Nature* 387: 917-921; to JAB described in Endo T. A. et al. (1997) *Nature* 387: 921-924; and to SSI-1 (STAT-induced STAT inhibitor-1) described in Naka T. et al. (1997) *Nature* 387:924-928. These proteins are characterized in that they have an SH2 domain, bind to and inhibit JAK kinase, and, as a result, regulate cytokine signaling.

As used herein, the term "SH2 domain", also referred to a Src Homology 2 domain, includes a protein domain of about 100 amino acids in length which is involved in binding of phosphotyrosine residues, e.g., phosphotyrosine residues in other proteins. The target site is called an SH2-binding site. The SH2 domain has a conserved 3D structure consisting of two alpha helices and six to seven beta-strands. The core of the SH2 domain is formed by a continuous beta-meander composed of two connected beta-sheets (Kuriyan J. et al. (1997) *Curr. Opin. Struct. Biol.* 3:828-837). SH2 domains function as regulatory modules of intracellular signaling cascades by interacting with high affinity to phosphotyrosine-containing target peptides in a sequence-specific and strictly phosphorylation-dependent manner (Pawson T. (1995) *Nature* 373:573-580). Some proteins contain multiple SH2 domains, which increases their affinity for binding to phosphoproteins or confers the ability to bind to different phosphoproteins. Rat 29x contains an SH2 domain at amino acid residues 219-308 of SEQ ID NO:61.

Tyrosine phosphorylation regulates potassium channel activity (Prevarskaya N. B. et al. (1995) *J. Biol. Chem.* 270: 24292-24299). JAK kinase phosphorylates proteins at tyrosines and is implicated in the regulation of channel activity (Prevarskaya N. B. et al. supra). Accordingly, based on its homology to SOCS-1, JAB, and SSI-1, rat 29x may modulate the activity of potassium channels, e.g., Kv4, by modulating JAK kinase activity.

Example 21

Identification and Characterization of Rat 5p

In this example, the identification and characterization of the gene encoding rat 5p is described. Rat 5p was isolated as a positive clone from the yeast two-hybrid screen described above, using rKv4.3N as a bait.

The nucleotide sequence of the rat 5pc DNA and the predicted amino acid sequence of the rat 5p polypeptide are shown in FIG. 32 and in SEQ ID NOs:63 and 64, respectively. The rat 5p cDNA encodes a protein having a molecular weight of approximately 11.1 kD and which is 95 amino acid residues in length.

Rat 5p binds rKv4.3N and rKv4.2N with similar strength in yeast two-hybrid assays. In contrast, 5p does not bind rKv1.1N, indicating that the 5p-Kv4N interaction is specific.

Rat 5p is expressed in the spleen, lung, skeletal muscle, heart, kidney, brain, liver, and testes, as determined by northern blot analysis.

The rat 5p is identical to rat Calpactin I light chain or P10 (Accession Number P05943). P10 binds and induces the dimerization of annexin II (p36). P10 may function as a regulator of protein phosphorylation in that the p36 monomer is the preferred target of a tyrosine-specific kinase (Masiakowski P. et al. (1998) *Proc. Natl. Acad. Sci. U.S.A.* 85 (4): 1277-1281).

Tyrosine phosphorylation regulates the activity of potassium channels (Prevarskaya N. B. et al. supra). Thus, due to its identity to P10, rat 5p may modulate the activity of potassium channels, e.g., Kv4, by modulating the activity of a tyrosine-specific kinase.

Example 22

Identification and Characterization of Rat 7q

In this example, the identification and characterization of the gene encoding rat 7q is described. Rat 7q was isolated as a positive clone from the yeast two-hybrid screen described above, using rKv4.3N as a bait. Full length rat 7q was obtained by RACE PCR.

The nucleotide sequence of the rat 7q cDNA and the predicted amino acid sequence of the rat 7q polypeptide are shown in FIG. 33 and in SEQ ID NOs:65 and 66, respectively. The rat 7q cDNA encodes a protein having a molecular weight of approximately 23.5 kD and which is 212 amino acid residues in length.

Rat 7q binds rKv4.3N and rKv4.2N with same strength in yeast two-hybrid assays. In contrast, 7q does not bind rKv1.1N, indicating that the 7q-Kv4N interaction is specific.

Rat 7q is expressed in the heart, brain, spleen, lung, liver, skeletal muscle, kidney, and testes, as determined by northern blot analysis.

Rat 7q is identical to RAB2 (rat RAS-related protein, Accession Number P05712) at the amino acid level. RAB2 appears to be involved in vesicular traffic and protein transport (Touchot N. et al. (1987) *Proc. Natl. Acad. Sci. U.S.A.* 84 (23): 8210-8214). Accordingly, based on its homology to RAB2, rat 7q may be involved in potassium channel, e.g., Kv4, trafficking.

Example 23

Identification and Characterization of Rat 19r

In this example, the identification and characterization of the gene encoding rat 19r is described. Partial rat 19r was isolated as a positive clone from the yeast two-hybrid screen described above, using rKv4.3N as a bait. Full length rat 19r was obtained by RACE PCR.

The nucleotide sequence of the rat 19r cDNA and the predicted amino acid sequence of the rat 19r polypeptide are shown in FIG. 34 and in SEQ ID NOs:67 and 68, respectively. The rat 19r cDNA encodes a protein having a molecular weight of approximately 31.9 kD and which is 271 amino acid residues in length.

Rat 19r is expressed in the heart, brain, spleen, lung, liver, skeletal muscle, kidney, and testes, as determined by northern blot analysis.

Rat 19r binds rKv4.3N and rKv4.2N with slight preference for rKv4.3N in yeast two-hybrid assays. In contrast, 19r does not bind rKv1.1N, indicating that the 19r-Kv4N interaction is specific.

Rat 19r is identical to Rat phosphatidylinositol (PTDINS) transfer protein alpha (PTDINSTP, Accession Number M25758 or P16446) described in Dickeson S. K. et al. (1989) *J. Biol. Chem.* 264:16557-16564. PTDINSTP is believed to be involved in phospholipase C-beta (PLC-beta) signaling, phosphatidylinositol transfer protein (PtdIns-TP) synthesis, secrettory vesicle formation, and enhancement of phosphatidylinositol 3-kinase (PtdIns 3-kinase) activity (Cunningham E. et al. (1995) *Curr. Biol.* 5 (7): 775-783; (1995) *Nature* 377 (6549): 544-547; and Panaretou C. et al. (1997) *J. Biol. Chem.* 272 (4): 2477-2485).

Accordingly, based on its homology with PTDINSTP, rat 19r may modulate potassium channel, e.g., Kv4, activity via the PLC-beta signaling pathway and/or the PtdIns 3-kinase signaling pathway. Rat p19r may also be involved in potassium channel, e.g., Kv4, trafficking.

Example 24

Chromosomal Localization of Human 9q

In this example, the human PCIP 9q was chromosomally mapped using a radiation hybrid panel (Panel GB4). h9q mapped to a region of chromosome 10q that had been previously shown to contain a linkage with partial epilepsy, namely D10S192: 10q22-q24 (Ottman et al. (1995) *Nature Genetics* 10:56-60) (see FIG. 43). Based on this observation, the present invention clearly demonstrates that the 9q family of proteins can serve as targets for developing anti-epilepsy drugs and as targets for medical intervention of epilepsy.

Figure 42:
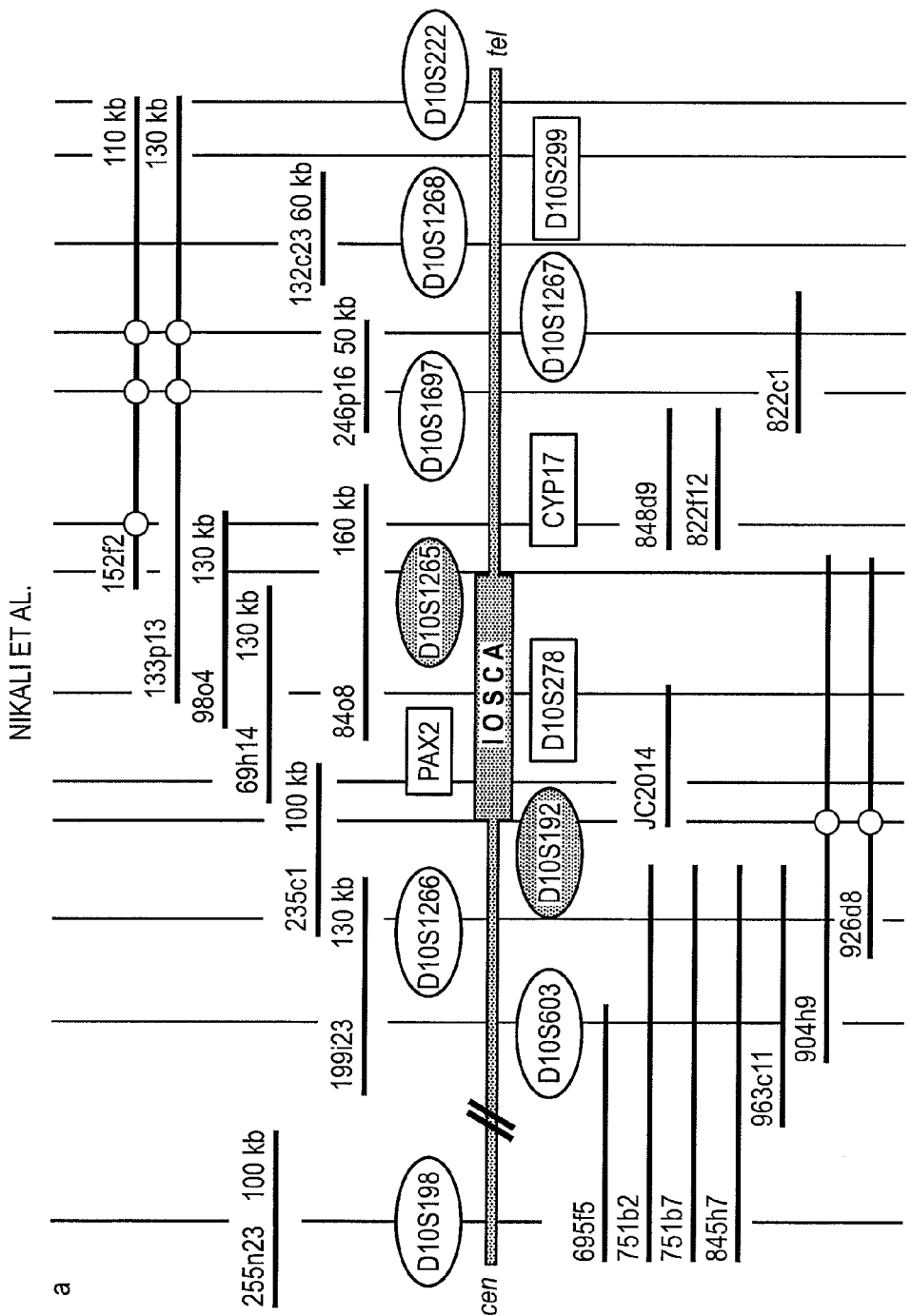
FIG. 42 depicts a physical map of the IOSCA region.
Figure 43:
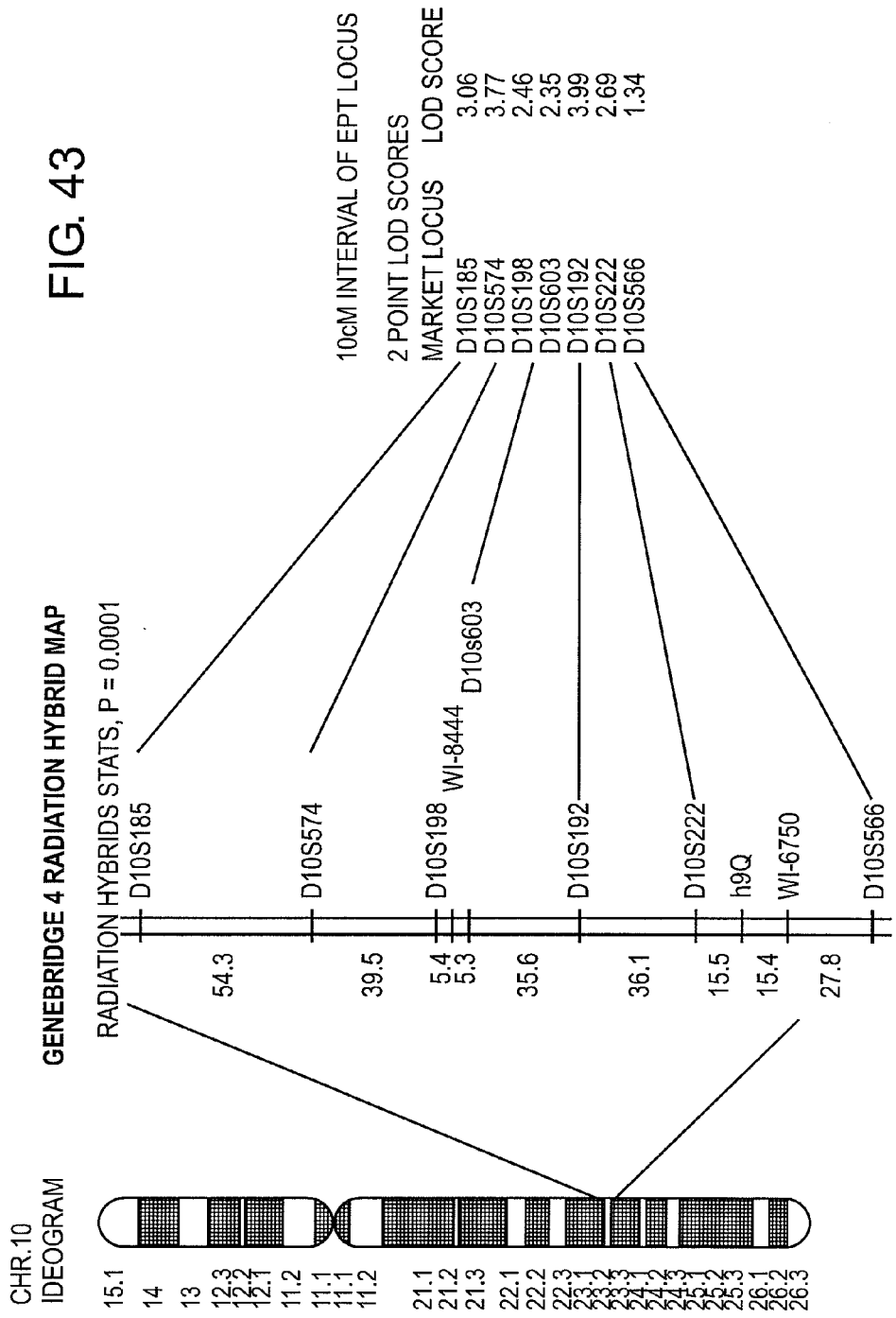
FIG. 43 depicts a linkage map showing the location of h9q and known markers associating with IOSCA and epilepsy.
Figure 50:
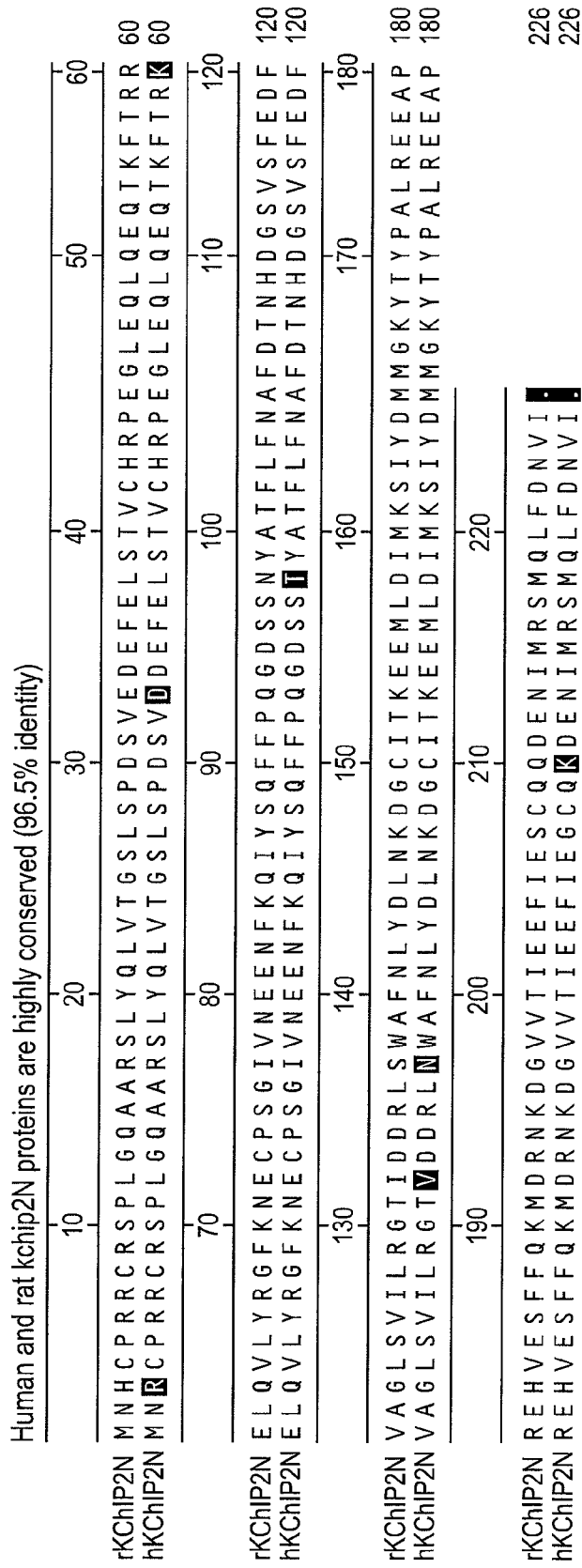
FIG. 50 depicts an alignment of the N-terminal domains of the rat and human KChIP2N (8t) proteins, indicating that these proteins exhibit a 96.5% identity.

Furthermore, h9q mapped to a region of chromosome 10q that had been previously shown to contain a linkage with IOSCA, namely D10S192 and D10S1265: 10q24-Nikali (Genomics 39:185-191 (1997)) (see FIGS. 42 and 43). Based on this observation, the present invention clearly demonstrates that the 9q family of proteins can serve as targets for developing anti-spinocerebellar ataxia drugs and as targets for medical intervention of spinocerebellar ataxia.

Example 25

Arachidonic Acid Modulation of Kv4/KChIP Channels

Kinetic Modulation of Kv4 Current by AA is KChIP-Dependent

Arachidonic Acid (AA) was shown to inhibit recombinant Kv4 current expressed in *Xenopus* oocytes (Villarroel, A. and Schwarz, T. L. (1996) *J. Neuroscience* 16:2522-32). However, the modulation was only observed with peak current amplitude whereas the current kinetic parameters were not affected by the presence of AA. In contrast, recordings of membrane patches from hippocampal neurons showed that in additional to suppression of peak amplitude, AA changed the kinetic parameters of the A-current by Kv4 channels (Keros, S, and McBain, C. J. (1997) *J. Neuroscience* 17: 3476-87). Notably, the inactivation time constant was considerably reduced (note: inactivation time constant is in inversely correlated to rate of inactivation. Therefore, inactivation was sped up [Keros (1997) supra].

In this Example, the hypothesis that KChIPs were the missing auxiliary subunits that accounted for the above kinetic discrepancy was investigated by expressing Kv4 alone or together with KChIPs in both CHO cells and *Xenopus* oocytes, and measuring their inactivation time constants (using art known techniques as described in, for example, An et al. (2000) *Nature* 403:553-6; Keros, S. and McBain, C. J. (1997) *J. Neuroscience* 17: 3476-87; and Villarroel, A. and Schwarz, T. L. (1996) *J. Neuroscience* 16:2522-32).

The kinetic modulation of Kv4 by AA was demonstrated to be KChIP-dependent (Table 3). When Kv4.2 was expressed alone in CHO cells, the inactivation time constant of the resulting current was unchanged in the absence or presence of 10 μM of AA (32±3 vs. 32±2 milliseconds(ms)±standard error mean (SEM)). In contrast, when co-expressed with KChIP1, the inactivation time constant of Kv4.2 current was decreased from 88±8 ms in the absence of AA to 37±3 ms in the presence of 10 μM of AA. Similar results were obtained with KChIP1 (Table 4) and KChIP2 in *Xenopus* oocytes. These results demonstrate that kinetic modulation of Kv4 current by AA is dependent on the presence of KChIP1.

Similar results were also obtained in *Xenopus* oocytes with both KChIP1 and KChIP2 (Table 4). The kinetic change of Kv4/KChIPs in the presence of AA is consistent with that described on neuronal membranes [Keros (1997) supra) supporting the notion that KChIPs are the endogenous subunits of Kv4-underlying current. The foregoing results demonstrate that AA modulation of Kv4 current kinetics is KChIP-dependent It is noted that AA also suppressed peak amplitude of Kv4/KChIP current in both CHO cells and *Xenopus* oocytes (Tables 3 and 4). This indicates that modulation of peak amplitude of Kv4 currents is independent of KChIPs.

TABLE 3

| AA modulation of Kv4 and Kv4/KChIP1 currents in CHO cells. | | | | |
|---|---|---|---|---|
| | Kv4.2 0 μM AA | Kv4.2 10 μM AA | KV4.2/KChIP1 0 μM AA | KV4.2/KChIP1 10 μM AA |
| Inactivation time constant (ms ± SEM) | 32 ± 3 | 32 ± 2 | 88 ± 8 | 37 ± 3 |
| Peak amplitude (pA ± SEM) | 620 ± 80 | 336 ± 82 | 4539 ± 448 | 2827 ± 496 |

The arachidonic acid effects on the A-current were also investigated in a neuronal system (cultured primary cerebellar granule neurons) where both Kv4 and KChIPs are present. TEA (10 mM) was applied to block a small sustained outward component. Inactivation time constants of the A current in the absence and presence of 10 μM arachidonic acid were 44±5 ms and 21±3 ms (mean±SEM), respectively. The corresponding peak amplitude was reduced from 2.0±0.6 nA to 1.2±0.4 nA. These results confirm that arachidonic acid modulates both Kv4 A-current current amplitude and kinetics in native cells.

Figure 64A:
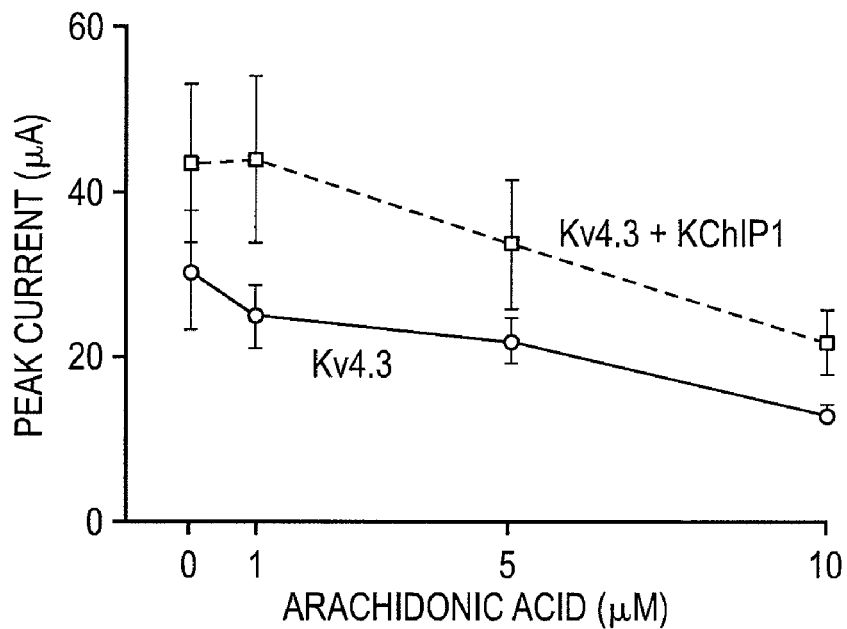
FIG. 64 is a graph depicting the concentration-dependent modulation of Kv4.3 and Kv4.3/KChIP1 currents in *Xenopus* oocytes by arachidonic acid. Depolarizing pulses from a holding potential of −80 mV to +40 mV (duration=500 ms). Arachidonic acid at 1-10 μM inhibited peak amplitudes (A) and decreased inactivation time constants ($\tau_{inact}$) (B) in oocytes injected with Kv4.3 cRNA itself (solid line) and those co-injected with both Kv4.3 and KChIP1 cRNA (dashed line). n=5 oocytes for each data point.
Figure 64B:
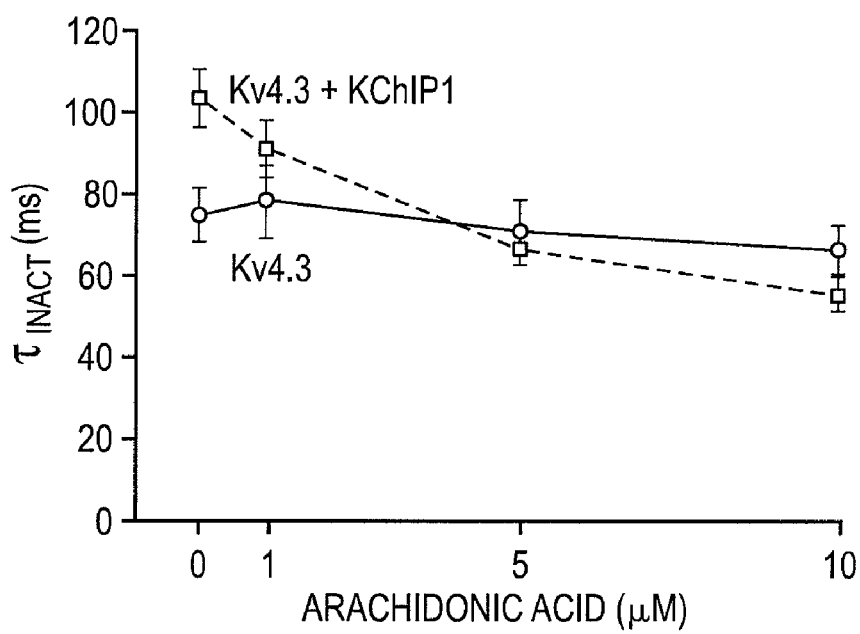

Arachidonic Acid Modulation of Kv4/KChIP Current is Concentration-Dependent and Reversible The effects of different concentrations of arachidonic acid on Kv4/KChIP current was studied in *Xenopus* oocytes. Because the physiological concentrations of arachidonic acid are often under 10 μM (Needleman, et al., 1986 Annu Rev Biochem 55:69-102; Anderson and Welsh, 1990, Proc Natl Acad Sci USA 87:7334-8; Meves, 1994, Prog Neurobiol 43:175-86), arachidonic acid was tested in the 1-10 μM range. The concentration-dependent block of peak amplitude of the Kv4.3 current was independent of the presence of KChIP1 (see FIG. 64A). Further, the slope of amplitude reduction as a function of increasing concentrations was very similar with or without the presence of KChIPs. Peak current block did not appear to saturate up to 10 µM. Villarroel and Schwarz, (1996) *J. Neurosci* 16:2522-32 reported that the $IC_{50}$ of arachidonic acid on Kv4 α subunits was approximately 8 µM in oocytes. The inactivation time constant in the absence of KChIP1 was unchanged at all arachidonic acid concentrations tested. However, in the presence of KChIP1, inactivation time constant decreased in a concentration-dependent manner (see FIG. 64B).

Figure 65A:
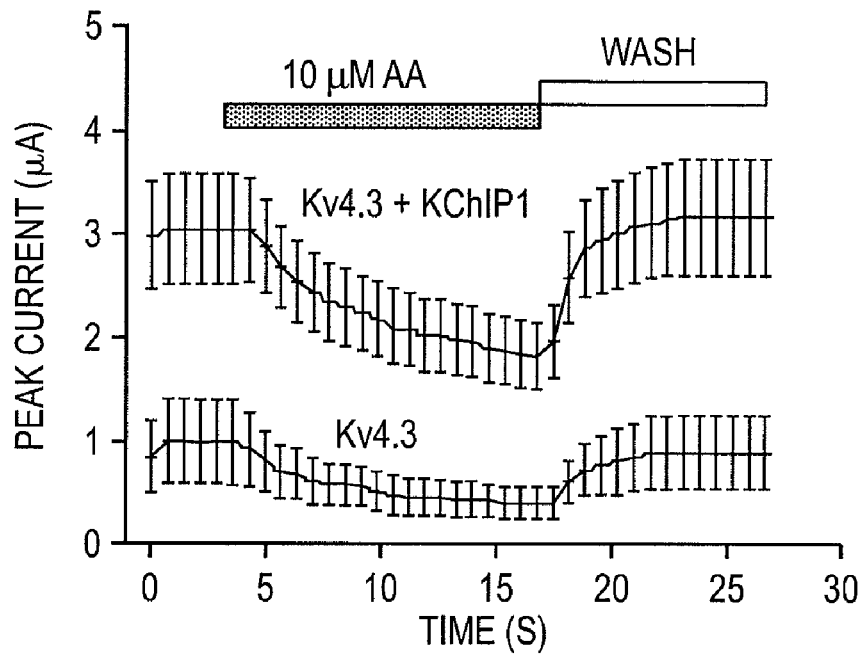
FIG. 65 is a graph depicting the modulation of Kv4.3 and Kv4.3/KChIP1 currents by arachidonic acid is reversible. Currents in *Xenopus* oocytes were evoked every 7 seconds with depolarizing pulses to +40 mV (duration=500 ms) from a holding potential of −80 mV. Effects on peak amplitude (A) and inactivation time constants ($\tau_{inact}$) (B) are shown with shaded bars indicating application of 10 μM arachidonic acid and open bars wash-out with ND96 medium supplemented with 0.5 mg/ml BSA (n=5 for each data point).
Figure 65B:
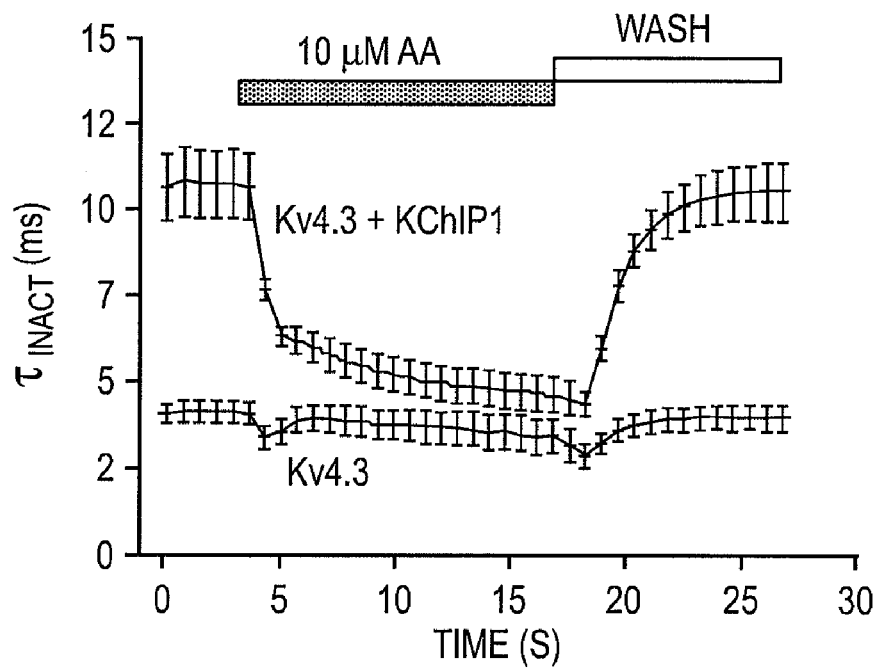

The onset of the KChIP-dependent acceleration of inactivation and the KChIP-independent current block of Kv4.3 by 10 µM arachidonic acid was almost immediate (FIG. 65). At least part of the slight delay (14 seconds) was attributed to the transit of solution from the reservoir to the recording chamber. The amplitude block developed gradually over time (FIG. 65A). The presence of KChIP1 did not substantially alter either the percent decrease or the rate of current block over time, nor did it change the rate of recovery of Kv4.3 current amplitude over time (FIG. 65A). In contrast to the gradual development of amplitude block, the KChIP1-dependent effect on Kv4 kinetics appeared much more rapidly following arachidonic acid perfusion, and tended to plateau quickly (FIG. 65B). When arachidonic acid was washed out, Kv4.3 current amplitude and inactivation time constants fully recovered with similar rates in the presence of KChIP1 (compare FIGS. 65A and 65B). The two small inflections in the Kv4.3 alone plot in panel B were artifacts due to buffer changes.

Modulation of Kv4/KChIP Current by Other Fatty Acids

Figure 66A:
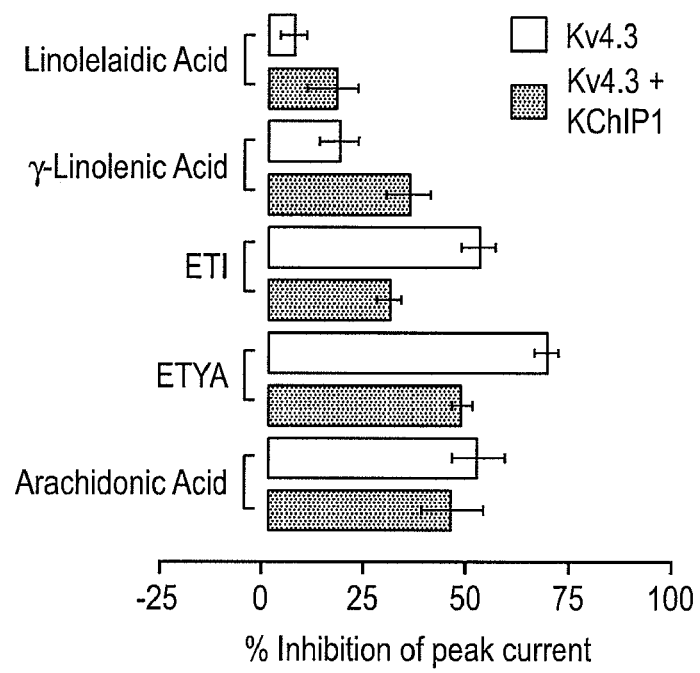
FIG. 66 is a graph depicting the modulation of Kv4.3 and Kv4.3/KChIP1 by fatty acids. (A) Percentage block of Kv4 (open bars) and Kv4.3/KChIP (shaded bars) peak amplitudes by 10 μM linolelaidic acid (n=9, 8, Kv4.3, Kv4.3/KChIP1, respectively), γ-linolenic acid (n=9, 8), ETI (n=4, 6), ETYA (n=4, 6), and arachidonic acid (n=8, 9) in *Xenopus* oocytes. All values except that of linolelaidic acid/Kv4.3 alone were statistically significant when compared to no fatty acid controls. Differences of all values between Kv4.3 and Kv4.3+ KChIP1 for all fatty acids were statistically insignificant. (B) Percentage inhibition of inactivation time constants ($\tau_{inact}$) of currents in panel A under the same conditions. Values are presented as mean±SEM. All values for Kv4.3 alone were not statistically significant compared to no-fatty acid control. All values for Kv4.3+KChIP1 except that of linolelaidic acid were statistically significant compared to no-fatty acid control. The differences of values between Kv4.3 and Kv4.3+ KChIP1 within every fatty acid treatment except linolelaidic acid were significant.

Certain fatty acids were shown previously to mimic the effects of arachidonic acid on Kv4 current in *Xenopus* oocytes when Kv4 α was expressed alone (Villarroel and Schwarz, J Neurosci 16:2522-32 (1996)). Thus, the fatty acid selectivity for Kv4 current in the presence of KchIPs was investigated. Arachidonic acid is a 20-carbon fatty acid carrying four cis double bonds with the first double bond at C5 (20:4 c5). The following arachidonic acid analogs with distinct structural features were studied: γ-linolenic acid (18:3 c9) has three cis double bonds instead of four double bonds, linolelaidic acid (18:2 t9) has two trans double bonds instead of four cis double bonds, 5,8,11,14-eicosatetraynoic acid (ETYA, 20:4 n5) has four triple bonds instead of double bonds found in arachidonic acid (n indicates position of the first triple bond), and 5,8,11-eicosatriynoic acid (ETI, 20:3 n5) has three triple bonds. FIG. 66A shows that the peak amplitude of Kv4.3 current was inhibited significantly compared with no-fatty acid control by 10 µM of γ-linolenic acid, ETI, ETYA, and arachidonic acid, independent of the presence of KChIP1. The percent inhibition of amplitude of Kv4 alone and Kv4/KChIP was not significantly different for these fatty acids. A small, statistically significant block of Kv4 current amplitude by 10 µM linolelaidic acid was observed in the presence of KChIP1 but not absence of KChIP1 when the values were compared to their respective controls. However, there was no significant difference when comparing Kv4.3 and Kv4.3/KChIP KChIP1.

Figure 66B:
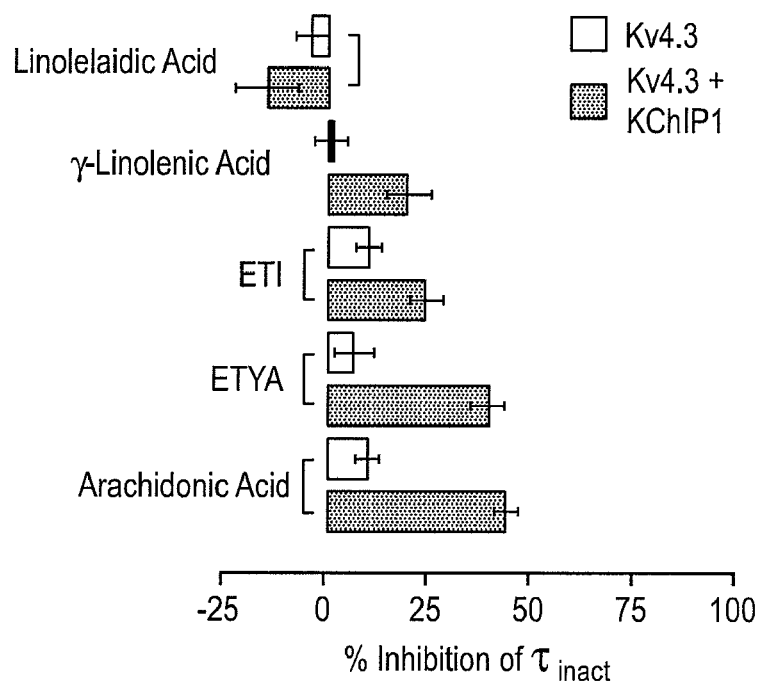

In the absence of KChIP1 none of the fatty acids tested showed a statistically significant effect on Kv4.3 inactivation time constant (FIG. 66B). Only those fatty acids that caused a substantial current block independently of KChIPs (γ-linolenic acid, ETI, ETYA, and arachidonic acid) reduced Kv4.3 inactivation time constant when co-expressed with KChIP1. Linolelaidic acid, which showed only a modest KChIP-dependent Kv4.3 current block, did not affect the Kv4.3 inactivation time constant (FIG. 66B). Therefore, certain long chain fatty acids can imitate arachidonic acid to modulate Kv4 current kinetics in a KChIP-dependent manner. In general, there is good connection in the ability for a given fatty acid to block peak amplitude and modify kinetics of the reconstituted Kv4/KChIP current.

Arachidonic Acid does not Disrupt Association of Kv4 and KChIP

For this experiment, the following assays were used.

In Vitro Binding Assay

The N-terminal domain of rat Kv4.3 was expressed as a GST fusion (GST-Kv4.3N) and purified from *E. coli* essentially following protocols provided by Amersham Pharmacia Biotech (Piscataway, N.J.). Recombinant rat KChIP1 protein was first expressed and purified as a GST-fusion, then the GST moiety was cleaved using PreScission protease (Amersham Pharmacia Biotech) to give rise to the free KChIP1 protein. Both GST-Kv4.3N and KChIP proteins were >95% pure as estimated by coomassie stain of denaturing gels. In vitro binding assays were performed using a Biacore 3000 from Biacore AB in Uppsala, Sweden. The experiments were performed in phosphate buffered saline (PBS), pH 7.4, with 1 mM $CaCl_2$ and 0.05% polysorbate P-20. Anti-GST antibody (Biacore AB) was coupled to 3 flowcells of a CM-5 chip (Biacore AB) at a level of 2000 resonance units (RUs) using amine coupling. The final flowcell was activated and blocked with ethanolamine to use as a reference control surface. The GST-Kv4.3N terminal domain was captured on two of the anti-GST flowcells and GST alone was bound to the third anti-GST flowcell at levels of 150 RUs. Purified KChIP1 at 1 µM in the presence and absence of 10 µM arachidonic acid was then injected over all four flowcells. Arachidonic acid (10 µM) alone was also injected. Data are shown as GST reference-subtracted sensograms.

Yeast 2-Hybrid Strains and Growth Assays

Diploid strains containing bait (the N-terminal domain of Kv4.3 or the empty vector pGBT9) and fish (KChIP1) plasmids were obtained as described in (An, et al., 2000). For synchronization, strains were grown to saturation before they were inoculated at equal OD600 value into 5 ml of synthetic complete-TrpLeuHis drop-out (SC-WLH) medium that selects for interaction-dependent growth or 5 ml of SC-WL medium that is nonselective in the presence or absence of 10 µM ETYA. 5 mM 3-AT (3-amino-1,2,4-triazole) was included in the media to suppress weak self-activating activity from the Kv4.3 N-terminal domain bait. Cultures were grown for 17 hours at 30° C. and OD600 values were read by a spectrophotometer.

Figure 67A:
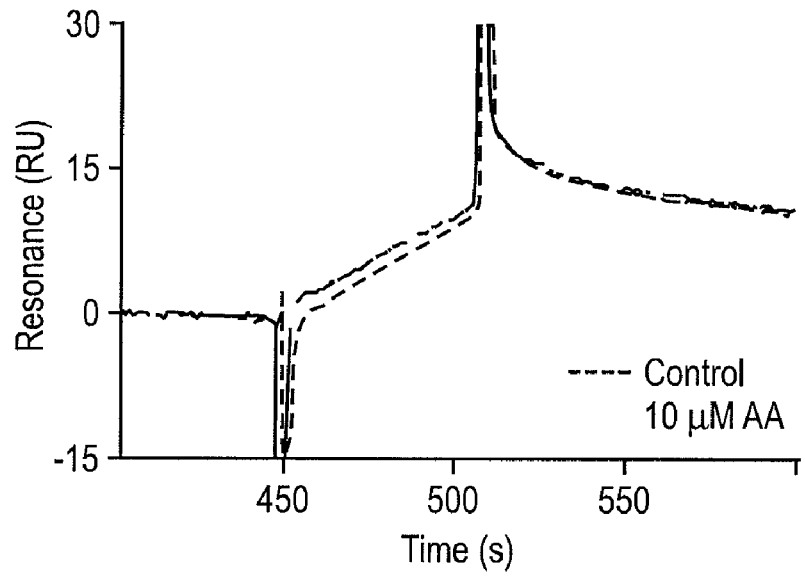
FIG. 67 is a graph indicating that Arachidonic acid does not interfere with association between KChIP1 and the N-terminal domain of Kv4.3. (A) Superimposed sensograms showing that neither the association phase nor the dissociation phase of interaction between the intracellular N-terminal domain of Kv4.3 and KChIP1 was qualitatively changed by 10 μM arachidonic acid in Biosensor assays. (B) N-terminal domain of Kv4.3 and KChIP1 interaction-dependent growth in selective SC-WLH medium was not altered by 10 μM of ETYA. The non-selective medium SC-WL, which allowed strains to grow independently of the interaction between the N-terminal domain of Kv4.3 and KChIP1, was used to control the non-specific effects of ETYA on growth of the strains. Values are presented as mean±SEM. n=4 for each data point.
Figure 67B:
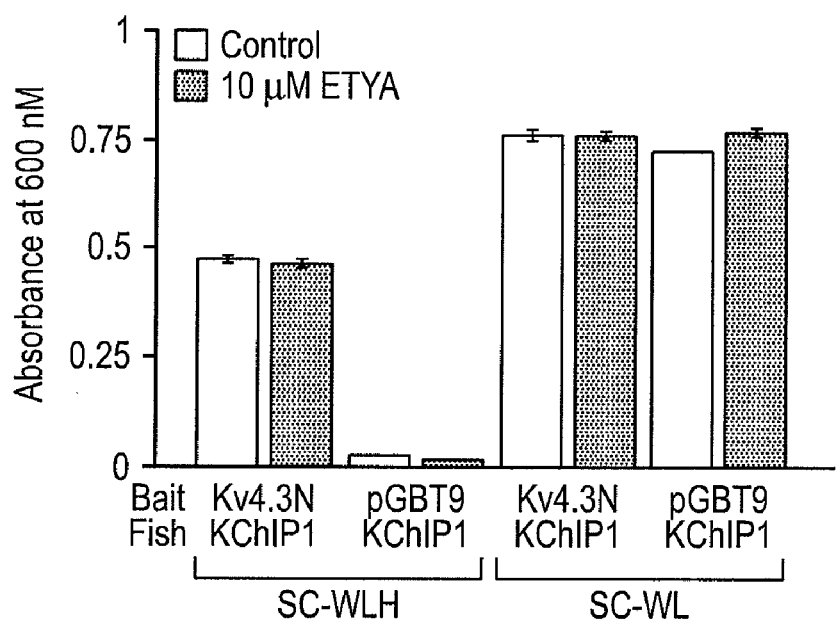

To test the hypothesis that arachidonic acid acts by interfering with the binding between Kv4 and KChIPs, the surface plasmon resonance measurement (Biosensor) was first used to monitor the association and dissociation phases of Kv4-KChIP interaction in the presence and absence of arachidonic acid. The intracellular N-terminal domain of Kv4.3 was expressed as a GST fusion protein (GST-Kv4.3N) and immobilized to the surface of a Biosensor chip. Recombinant KChIP1 protein was passed over the chip surface in the presence and absence of 10 µM arachidonic acid. As shown in FIG. 67A, KChIP1 protein was bound to the GST-Kv4.3N surface but a qualitative difference aws not observed in either the on- or the off-phase of the association of KChIP1 and the Kv4.3 N-terminal domain. The Biosensor results were further confirmed in the yeast 2-hybrid system where Kv4-KChIP interaction-dependent growth in the selective SC-WLH medium was not affected by 10 PM ETYA (FIG. 67B). ETYA instead of arachidonic acid was used in these experiments because, while both ETYA and arachidonic acid affect Kv4 current nearly identically, ETYA is non-metabolizable, and is, thus, better suited for this experiment. Taken together, the results show that the fatty acids tested do not disrupt association between Kv4 and KChIPs.

Kv4/KChIP is More Sensitive to AA Modulation than is Kv1.1/Kvβ1

The pore-forming alpha subunits of ion channels, including those of potassium channels, often do not work alone. They associate with auxiliary subunits and these auxiliary subunits can change channel activities dramatically. Therefore, it is more useful to study alpha subunits in combination with their auxiliary subunits as the physiologically relevant channels are complexes of alpha-auxiliary subunits.

Expressed alone, the recombinant Kv4 alpha subunits were shown to be by far more sensitive to AA inhibition than alpha subunits of several other voltage-gated potassium channels (e.g., Kv1.1) (Villarroel (1996) supra). However, this paper examined AA modulation of only the alpha subunits of the channels. It was not known whether Kv4 current would still be more sensitive to AA modulation than would be other channel currents if all channels were to be tested in the presence of their cognate auxiliary subunits.

In this example, the foregoing was tested by measuring two alpha/auxiliary complexes: Kv4.3/KChIP1 and Kv1.1/Kvβ1. (Kvβ1, which is one of the classic potassium channel beta subunits, dramatically changes Kv1.1 kinetics). Kv4.3/KChIP and Kv1.1/Kvβ1 were expressed respectively in *Xenopus* oocytes and their resulting currents were recorded in the presence or absence of 10 PM AA. The results indicated that the peak amplitude of Kv1.1/Kvβ1 current was not significantly increased in the presence of 10 μM of AA (11±4 to 14±1 μA), whereas the peak amplitude of Kv4.3/KChIP1 was drastically decreased (44±10 to 21±4 μA, Table 4). Kinetically, KvKv4.3/KChIP1 was much more sensitive to AA modulation than was Kv1.1/Kvβ1 (Table 4). While 10 PM AA did not cause a statistically significant decrease of the inactivation time constant of Kv1.1/Kvβ2 (11±1 to 9±1 ms), the same concentration of AA considerably decreased that of Kv4.3/KChIP1 from 104±7 to 55±4 ms). These results indicate that AA more readily modulates both the kinetics and amplitude of Kv4/KChIPs potassium currents in native neurons than the kinetics and amplitude of Kv1.1/Kvβ1.

nal domains that are variable in length, but the core C-terminal domain is sufficient for associating with and modulating Kv4. The human KChIP2 gene spans approximately 18 kb in the q23 region of human chromosome 10 between WI-8488 and WI-6750. This region is syntenic to mouse chromosome 19 between D19Mit40 and D19Mit1. A rat variant discovered by database mining changed the last five amino acids and maintained its ability to associate with and modulate Kv4. Therefore, these multiple variants of KChIP2 appear to function similarly in Kv4 modulation.

Example 27

KChIP1L Function and Expression

RT-PCR was performed to examine tissue expression of the rat KChIP1l (KChIP1long) splice variant. PolyA+ RNA from heart, brain, lung, spleen, liver, skeletal muscle, kidney, and testes were purchased from Clontech. RT-PCR was performed using the One-step RT-PCR kit from Clontech with amplifying 5' primer GGTACCTTCTCGTCCCTGCAGAC-CAAACAAAG (SEQ ID NO: 104) and 3' primer CGG-TAAAGGACTTGCAGTTCTCTC (SEQ ID NO:105) with the modifications on PCR condition: 50° C. for 1 hour; 94° C. for 3 minutes; 50 cycles of 94° C. for 30 seconds, 65° C. for 30 seconds, and 68° C. for 2 minutes. The 5' primer is KChIP1-specific. Both KChIP1 and KChIP1l can be amplified by the same primer set, giving two different sized PCR products that separate into two bands by electrophoresis. A KChIP1l-specific band was only observed in brain, indicating it is specifically expressed in the brain. The same reaction also showed a strong KChIP1-specific signal in the brain and a barely visible band in skeletal muscle. No KChIP1 or KChIP1l signals were observed in any other tissues examined. In summary, KChIP1l expression is brain-specific whereas KChIP1 expression is brain predominant with a very low level of expression in skeletal muscle.

The function of KChIP1l in *Xenopus* oocytes was also examined. Kv4.3 cRNA was injected into *Xenopus* oocytes either with or without KChIP1l cRNA. Similar to KChIP1, KChIP1l increased peak amplitude of Kv4.3 from 15±4± to 55±7 μA and increased inactivation time constant from 56±4

TABLE 4

AA modulation of Kv4, Kv4/KChIP1, Kv1.1, Kv1.1/Kvβ1 currents in Xenopus oocytes.

|  | Kv4.3 0 μM AA | Kv4.3 10 μM AA | KV4.3/KChIP1 0 μM AA | KV4.3/KChIP1 10 μM AA | Kv1.1 0 μM AA | Kv1.1 10 μM AA | KV1.1/Kvβ1 0 μM AA | Kv1.1/Kvβ1 10 μM AA |
|---|---|---|---|---|---|---|---|---|
| Inactivation time constant (ms ± SEM) | 75 ± 7 | 66 ± 6 | 104 ± 7 | 55 ± 4 | N.A. | N.A. | 11 ± 1 | 9 ± 1 |
| Peak amplitude (μA ± SEM) | 30 ± 7 | 13 ± 1 | 44 ± 10 | 21 ± 4 | 19 ± 2 | 21 ± 3 | 11 ± 4 | 14 ± 1 |

Example 26

K-Channel Interacting Protein-2 (KChIP2) Splice Variants, Chromosomal Organization and Localization In the present Example, variants of KChIP2 and their chromosomal organization were identified using standard techniques. KChIP2 genes are highly conserved at the amino acid level among human, rat, and mouse. Multiple human splice variants were identified by database mining and cDNA library screening. Alternative splicing gives rise to N-termito 100±8 ms (Table 5). These data demonstrate that KchiP1l, like KChIP1, modulates peak amplitude and kinetics of Kv4 current in vitro.

Given that the common C-terminal 185 amino acid to both KChIP1 and KChIP1l is responsible for binding to Kv4.3, it is likely that KChIP1l co-associates with Kv4 in the brain. The insertion of extra amino acids in the KChIP1l protein may be important for unknown functions, and the DNA sequence encoding these amino acids may be used as a specific gene marker for detecting cell tissue and/or cell type specific expression of this particular splice variant.

The DNA and protein sequences specific to the KchI11 splice variant are identical between rat and human. So, functional data obtained with KChIP1l molecules from one species also apply to that from the other species.

TABLE 5

Modulation of Kv4.3 by KChIP1l and KChIP1N.

| | Kv4.3 co-expressed with | | | |
|---|---|---|---|---|
| | none | KChIP1l | KChIP1 | KChIP1N |
| Inactivation time constant (ms ± SEM) | 56 ± 4 | 100 ± 8 | 112 ± 3 | 1778 ± 136 |
| Peak amplitude (μA ± SEM) | 15 ± 4 | 55 ± 7 | 59 ± 5 | 18 ± 3 |

Example 28

KChIP1N Function and Expression

Figure 68:
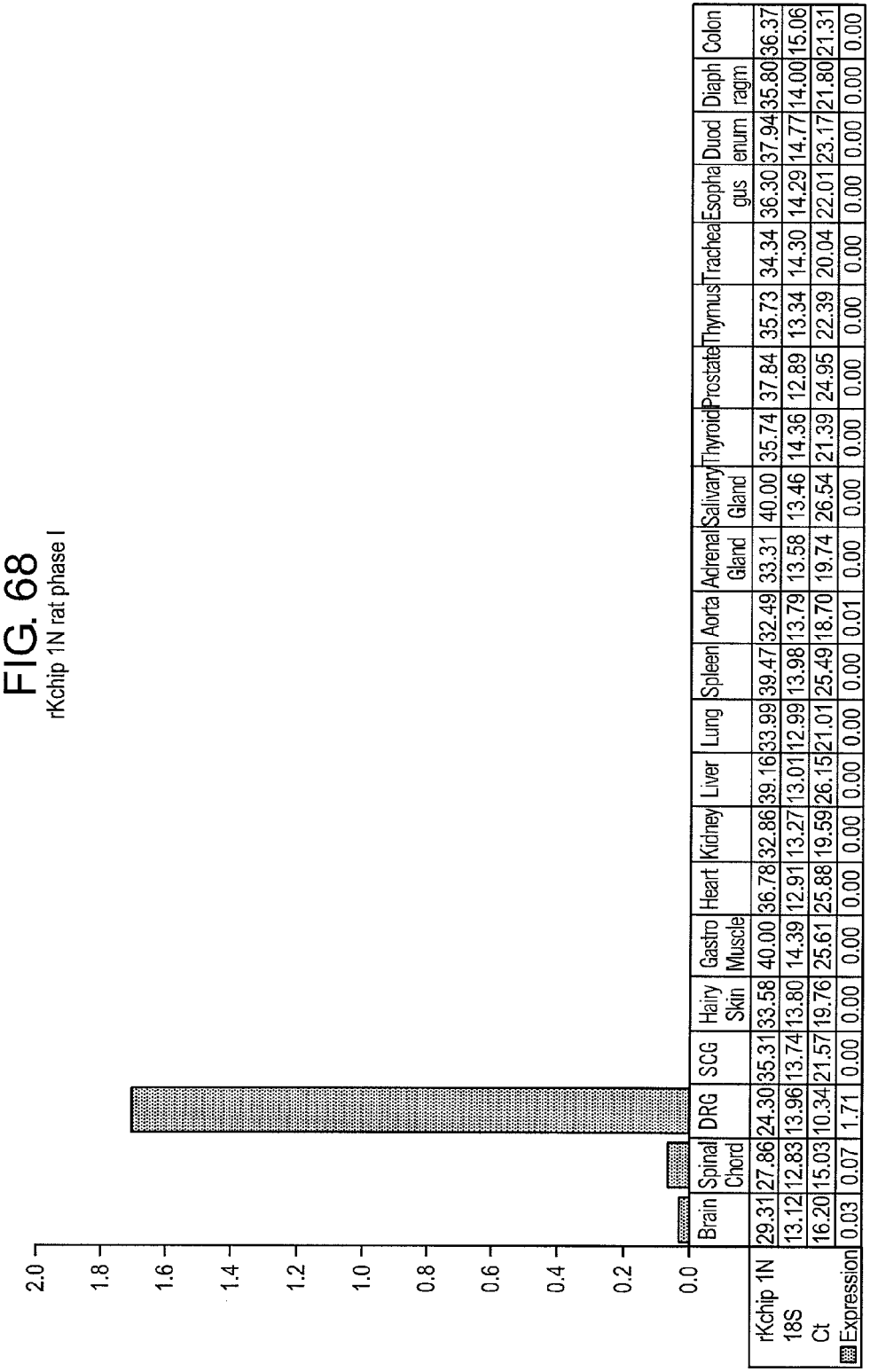
FIG. 68 is a graph depicting the results from a Taqman analysis of rat KChIP1N tissue expression.

The expression of rat KChIP1N was examined using the Taqman technique with the probe GGCAAAGAAGCGC-GATTTT (SEQ ID NO:106), forward primer TCCCGGG-TAGGCAAGCA (SEQ ID NO:107), and reverse primer CCTGCTCAAGCCCAGCACTGCA (SEQ ID NO:108). The probe is specific to KChIP1N. As shown in FIG. 68, KChIP1N is predominantly expressed in dorsal root ganglion (DRG), and at low levels in spinal cord and brain.

The function of KChIP1N in *Xenopus* oocytes was also examined. Kv4.3 cRNA was injected into *Xenopus* oocytes either with or without KChIP1N cRNA. In contrast to KChIP1 and KChIP1l, KChIP1N did not affect peak amplitude of Kv4.3 (15±4 vs. 18±3 without or with KChIP1N, Table 5). Surprisingly, KChIP1N caused a much greater increase of inactivation time constant of Kv4.3 than KChIP1 or KChIP I (32-fold increase by KChIP1N vs. ~2 fold increase by KChIP1 or KChIP1l; Table 5).

The foregoing data demonstrate that KchiP1N modulates Kv4 current in vitro in a manner distinct from KChIP1 or KChIP1l. First, the increase of the inactivation time constant by KChIP1N was considerably bigger as opposed to the increase mediated by KChIP1 or KChIP1l. As a result, KChIP1N was able to change the fast inactivating Kv4.3 current (nearly completely inactivated within 200 ms) to nearly non-inactivating for a 500 ms second+40 volts pulse. Second, KChIP1N, at the particular concentration tested, did not affect peak amplitude of Kv4. Because all KChIP1 splice variants share the C-terminal 196 amino acids, these data point to an important and distinct function of the unique 36-amino acid N-terminal domain of KChIP1N.

Example 29

KChIP2 Splice Variant Function

In this Example, the function of KChIP2 splice variants, rat KChIP2l, human KChIP2s, and rat KChIP2C in *Xenopus* oocytes was examined. The results from the experiments are summarized in the following table.

TABLE 6

Modulation of KV4 current by KChIP2 splice variants.

| | Kv4.3 co-expressed with | | | | |
|---|---|---|---|---|---|
| | KChIP2l | KChIP2m | KChIP2s | KChIP2C | none |
| Peak amplitude (μA ± SEM) | 51 ± 4 | 40 ± 4 | 44 ± 3 | 44 ± 5 | 14 ± 3 |
| Inactivation time constant (ms ± SEM) | 87 ± 4 | 70 ± 2 | 90 ± 3 | 74 ± 4 | 55 ± 4 |

The data demonstrate that these KChIP2 splice variants modulate Kv4 current similar to KChIP2m (Table 6). Since there is an extremely high homology at the amino acid level between the rat and human KChIP2s (>95%), it is believed that the results obtained using KChIP2 molecules from one species will be similar to the results for KChIP2 molecules from other species.

Example 30

KChIP4 Function and Expression

Northern analysis was performed to determine the tissue expression of KChIP4. A probe, taken from the 3'UT region of rat KChIP4 (598-909) common to all of the N-terminal splice variants of KChIP4, was used to probe a rat Clontech MTN Northern blot. Among the tissues represented on the Northern blot (heart, brain, lung, spleen, liver, muscle, kidney, and testes), a predominant band of approximately 2.4 kb was observed only in the brain. A faint band with a slightly faster mobility was present in the kidney. Therefore, it is apparent that the N-terminal splice variants of KChIP4 are predominantly expressed in the brain and at lower levels in the kidney.

The ability of KChIP4 to associate with Kv4 was also examined using a yeast 2-hybrid assay. The H domain of KChIP4 (the C-terminal 185 amino acids) which is common to all N-terminal splice variants of KChIP4 and homologous to other KChIPs, was expressed as "fish" and the N-terminal domains of Kv4.3, Kv4.2 were expressed as "baits" (Kv4.3N, Kv4.2N, respectively) using standard techniques. KChIP4H associated with Kv4.3N and Kv4.2N, but not with Kv1.1N or other control baits both in a growth assay and in a β-galactosidase assay. These results indicate that KChIP4s bind Kv4 channels in a specific manner.

Example 31

Functional Analysis of KChIP4N2

KChIP4N2, unlike KChIP1, kCHIP2, and KChIP3, showed a dose-dependent effect on the peak amplitude of Kv4.3 when these were co-injected into *Xenopus* oocytes (Table 7). At high concentrations (e.g., 5× dilution of stock), KChIP4N2 suppressed Kv4.3 current amplitude, whereas more diluted concentrations of KChIP4N2 either enhanced or had no effect ontKv4 current amplitude (Table 7)

KChIP4N2, unlike KChIP1, kCHIP2, and KChIP3, also showed a dose-dependent effect on the inactivation kinetics of Kv4.3 when these were co-injected into *Xenopus* oocytes (Table 7). At high concentrations, KChIP4 converted the fast-inactivating Kv4.3 current into an almost non-inactivating current (e.g., at 5× dilution of stock the current curve was too slow to decrease over time to fit and obtain an inactivation time constant). When a more diluted KChIP4N2 cRNA was injected, the inactivation time constants gradually decreased toward the value obtained in the absence of KChIP4N2.

TABLE 7

Modulation of peak amplitude and kinetics of Kv4.3 current by different concentrations of KChIP4N2 in Xenopus oocytes.

| Kv4.3 co-expressed with KChIP4N2 diluted by factors of (1x = stock) | 1× | 5× | 30× | 120× | 500× | none |
|---|---|---|---|---|---|---|
| Inactivation time constant (ms ± SEM) | | | 681 ± 28 | 193 ± 13 | 84 ± 5 | 56 ± 4 |
| Peak amplitude (µA ± SEM) | 0 ± 0 | 4 ± 1 | 25 ± 2 | 16 ± 3 | 9 ± 4 | 15 ± 4 |

The N-terminal domain of KChIP4N2 is necessary for the observed action of KChIP4N2. Deletion of the N-terminal domain essentially abolished the effects of the wild type KChIP4N2 on the peak amplitude and the inactivation time constant of Kv4.3 (Table 8).

The action of the N-terminal domain of KChIP4N2 seems to be dominant over other KChIP molecules. We made a chimeric molecule, 4N-1H, where the N-terminal domain of KChIP4N2 was fused to the C-terminal 185 amino acid H domain of KChIP1 (KChIP1H, which is homologous to other KChIPs). When co-expressed with Kv4, KChIP1H modulated Kv4 current almost identically to KChIP1, and produced a modulation profile that is quite different from that produced by KChIP4N2 (previous filing, [An F. et al. (2000) Nature 403:553-556). However, when co-expressed with Kv4.3, 4N-1H produced a modulation profile almost indistinguishable from that of KChIP4N2 instead of that of KChIP1H or KChIP1 (Table 6). This indicates that the N-terminal domain of KChIP4N2 can function as a module, and its modulatory effect is dominant over the modulatory effects of other KChIPs.

TABLE 8

The N-terminal domain of KChIP4N2 is necessary for the effect of KChIP4N2, and is dominant over KChIP1.

| | Kv4.3 co-expressed with | | |
|---|---|---|---|
| | KChIP4 (30× dilution) | KChIP4H | 4N-1H |
| Inactivation time constant (ms ± SEM) | 681 ± 28 | 105 ± 4 | 680 ± 39 |
| Peak amplitude (µA ± SEM) | 25 ± 2 | 19 ± 2 | 26 ± 3 |

Figure 61:
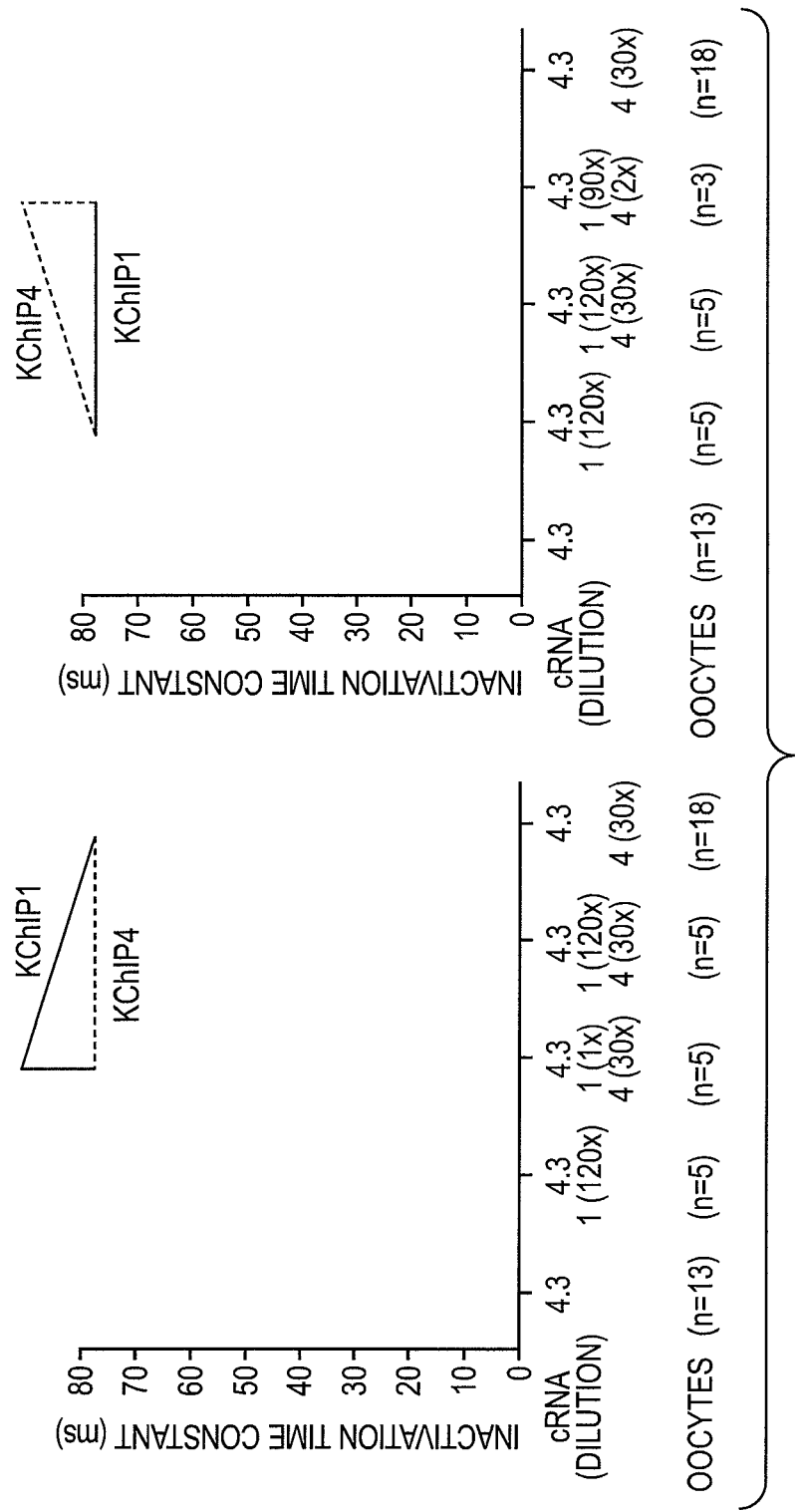
FIG. 61 is a set of graphs depicting the competitive modulation of Kv4.3 inactivation time constant by KChIP4N2 and KChIP1. The cRNA species injected are listed in the cRNA section with 4.3 indicating Kv4.3, 1 indicating KChIP1, and 4 indicating KChIP4. The numbers in the parentheses indicate dilution factors of cRNA injected with 1×=stock solution. The triangles above the bar graphs illustrate combination of fixed amount of KChIP4N2 or KChIP1 and increasing amount of KChIP1 or KChIP4N2, respectively.

Because KChIP4 and other KChIPs associate with the Kv4 N-terminal domain (Kv4N), it is conceivable that these KChIPs bind to the same site on Kv4N. If this is the case, KChIP4N2 and KChIP1 should compete with each other for modulating the Kv4 current when both of them are co-expressed with Kv4. This hypothesis was tested and as indicated in FIG. 61, KChIP4N2 and KChIP1 do indeed compete with each other for modulating the Kv4 current. As the concentration of KChIP4 cRNA injected into the Xenopus oocytes was held constant whereas the concentration of KChIP1 cRNA was gradually increased, the Kv4.3 current profiles changed from those of KChIP4 to those similar to KChIP1. Reciprocally, as the concentration of KChIP1 cRNA was held constant whereas the concentration of KChIP4 cRNA was gradually increased, the current profiles changed from those of KChIP1 to those similar to KChIP4.

These results indicate that KChIP1 and KChIP4 functionally compete with each other, likely through competitive binding to the same site on Kv4.3N. The results also demonstrate that different combinations of KChIP4N2 and other KChIPs will give rise to currents with hybrid profiles that are quantitatively and qualitatively similar or different from the parental profiles. It is conceivable that KChIP4N2 and other KChIPs are co-expressed in certain cell types in vivo (e.g., in the brain). Therefore, depending on the in vivo concentrations in a particular cell type, KChIP4N2 and other KChIPs may produce quite different currents even though the pore-forming alpha subunits are the same Kv4 molecules.

The implications of the foregoing observations with respect to KChIP4N2 are many fold. The data indicate that the N-terminal domain carries a dominant modulatory function that can be separated from the functions of the H domain (binding to Kv4 and modulating Kv4 current amplitude and kinetics as described in An et al., supra, but in a manner that is different from those of the KChIP4N2's N-terminal domain). Consequently, it is conceivable that the N-terminal domain of KChIP4N2 interacts with parts of the potassium channel other than the N-terminal domain of Kv4. These other sites on Kv4 are likely important for controlling the movement of potassium ions through the channel, given KChIP4N2's dramatic effect on inactivation kinetics. It is then possible to use the N-terminal domain of KChIP4N2 as a tool for designing and conducting protein/peptide/compound screens using this distinct activity as a read out. Using these screening assays it is possible to obtain proteins/peptides/compounds that modulate Kv4 activity in a KChIP dependent or independent manner.

As discussed above, KChIP1N and KChIP4N2 share similar Kv4 current modulating characteristics. Both can convert fast-inactivating Kv4 currents into almost non-inactivating currents. Both can have no effect on peak amplitude of Kv4. These are characteristically different from the actions of KChIP1, KChIP2, and KChIP3. Interestingly, when the N-terminal domains of human KChIP1N and monkey KChIP4N2 were aligned (using Megalign, DNA Star), they showed a considerable homology (FIG. 62) suggesting the existence of a protein motif that underlies the distinct modulation by KChIP1N and KChIP4N2. In contrast, the N-terminal domains of human/rat KChIP1 and monkey KChIP4N2 were quite divergent (FIG. 62).

Example 32

Functional Analysis of KChIP4N1 and KChIP4n3

KChIP4N1 and KChIP4N3 were co-injected with Kv4.3 cRNA into Xenopus oocytes. The modulation effects of these proteins on Kv4.3 are summarized in table 9. Both increased the inactivation time constant of Kv4.3. While KChIP4N3 increased the peak amplitude of Kv4.3, KChIP4N1 statistically had no significant (ns) effect on Kv4.3 amplitude.

TABLE 9

Modulation of Kv4 current by KChIP4N1 and KChIP4N3 in *Xenopus* oocytes.

| | Kv4.3 co-expressed with | | |
|---|---|---|---|
| | KChIP4N1 | KChIP4N3 | none |
| Peak amplitude (µA ± SEM) | 6 ± 1 (ns) | 43 ± 4 | 15 ± 4 |
| Inactivation time constant (ms ± SEM) | 112 ± 7 | 85 ± 4 | 56 ± 4 |

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated nucleic acid molecule comprising a nucleotide sequence which is at least 95% identical to the nucleotide sequence of SEQ ID NO:96, or a complement to the full length thereof, wherein said nucleic acid molecule encodes a polypeptide which is capable of binding to and/or modulating a potassium channel.

2. An isolated nucleic acid molecule comprising the nucleotide sequence of SEQ ID NO:96, or a complement to the full length thereof.

3. An isolated nucleic acid molecule consisting of the nucleotide sequence of SEQ ID NO:96, or a complement to the full length thereof.

4. An isolated nucleic acid molecule which encodes a polypeptide comprising the amino acid sequence of SEQ ID NO:97, or a complement to the full length thereof.

5. An isolated nucleic acid molecule which encodes a polypeptide consisting of the amino acid sequence of SEQ ID NO:97, or a complement to the full length thereof.

6. An isolated nucleic acid molecule comprising a nucleotide sequence which encodes for a polypeptide comprising a sequence at least 95% identical to the amino acid sequence of SEQ ID NO:97, wherein said polypeptide is capable of binding to and/or modulating a potassium channel.

7. The isolated nucleic acid molecule of claim 6, wherein the polypeptide further comprises a calcium binding domain comprising the amino acid sequence of SEQ ID NO:43.

8. The isolated nucleic acid molecule of claim 7, wherein said polypeptide comprises the C-terminal 185 amino acids of SEQ ID NO:97.

9. A composition comprising the isolated nucleic acid molecule of any one of claims 1, 2, 3-5, 6 or 7.

10. A kit comprising the isolated nucleic acid molecule of any one of claims 1, 2, 3-5, 6 or 7, and instructions for use.

11. The nucleic acid molecule of any one of claims 1, 4-5, 6 or 7, further comprising vector nucleic acid sequences.

12. An isolated nucleic acid comprising the nucleotide sequence of SEQ ID NO:96 and further comprising vector nucleic acid sequences.

13. The nucleic acid molecule of any one of claims 1, 2, 4, 6 or 7, further comprising nucleic acid sequences encoding a heterologous polypeptide.

14. An isolated nucleic acid comprising the nucleotide sequence of SEQ ID NO:96 and further comprising nucleic acid sequences encoding a heterologous polypeptide.

15. An isolated nucleic acid molecule which comprises a sequence encoding a polypeptide consisting of SEQ ID NO:97, and further comprising nucleic acid sequences encoding a heterologous polypeptide.

16. A cultured, non-human host cell which contains the nucleic acid molecule of any one of claims 1, 2, 3-5, 6 or 7.

17. The host cell of claim 16 which is a mammalian host cell.

18. A method for producing a polypeptide, comprising culturing the host cell of claim 16 under conditions in which the nucleic acid molecule is expressed.

* * * * *

UNITED STATES PATENT AND TRADEMARK OFFICE
CERTIFICATE OF CORRECTION

PATENT NO. : 7,556,938 B1  Page 1 of 1
APPLICATION NO. : 09/703094
DATED : July 7, 2009
INVENTOR(S) : Kenneth Rhodes et al.

It is certified that error appears in the above-identified patent and that said Letters Patent is hereby corrected as shown below:

Col. 332 Claim 12, line 41, after "isolated nucleic acid" add --molecule--.

Col. 332 Claim 14, line 47, after "isolated nucleic acid" add --molecule--.

Signed and Sealed this

Eighth Day of September, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,556,938 B1 | Page 1 of 1 |
| APPLICATION NO. | : 09/703094 | |
| DATED | : July 7, 2009 | |
| INVENTOR(S) | : Rhodes et al. | |

It is certified that error appears in the above-identified patent and that said Letters Patent is hereby corrected as shown below:

On the Title Page

Item [*] Notice: Subject to any disclaimer, the term of this patent is extended or adjusted under 35 USC 154(b) by 689 days Delete the phrase "by 689 days" and insert -- by 481 days --

Signed and Sealed this

Twenty-seventh Day of July, 2010

David J. Kappos
*Director of the United States Patent and Trademark Office*